(12) United States Patent
Raitano et al.

(10) Patent No.: US 7,696,336 B2
(45) Date of Patent: Apr. 13, 2010

(54) NUCLEIC ACIDS AND CORRESPONDING PROTEINS ENTITLED 251P5G2 USEFUL IN TREATMENT AND DETECTION OF CANCER

(75) Inventors: Arthur B. Raitano, Los Angeles, CA (US); Pia M. Challita-Eid, Encino, CA (US); Aya Jakobovits, Beverly Hills, CA (US); Mary Faris, Los Angeles, CA (US); Wangmao Ge, Culver City, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

(21) Appl. No.: 11/549,900

(22) Filed: Oct. 16, 2006

(65) Prior Publication Data

US 2007/0231261 A1    Oct. 4, 2007

Related U.S. Application Data

(63) Continuation of application No. 10/418,972, filed on Apr. 17, 2003, now abandoned.

(60) Provisional application No. 60/404,306, filed on Aug. 16, 2002, provisional application No. 60/423,290, filed on Nov. 1, 2002.

(51) Int. Cl.
C07H 21/02 (2006.01)
C12N 15/00 (2006.01)
C12N 5/00 (2006.01)
C12P 21/06 (2006.01)

(52) U.S. Cl. .................. 536/23.1; 435/320.1; 435/325; 435/69.1

(58) Field of Classification Search ................. None
See application file for complete search history.

(56) References Cited

U.S. PATENT DOCUMENTS

| | | | |
|---|---|---|---|
| 5,539,084 | A | 7/1996 | Geysen |
| 5,614,372 | A | 3/1997 | Lilja et al. |
| 5,785,973 | A | 7/1998 | Bixler et al. |
| 5,840,839 | A | 11/1998 | Wang et al. |
| 6,344,550 | B1 | 2/2002 | Frudakis et al. |
| 6,800,746 | B2 | 10/2004 | Xu et al. |
| 2002/0022248 | A1 | 2/2002 | Xu et al. |
| 2002/0082206 | A1 | 6/2002 | Leach et al. |
| 2002/0132753 | A1 | 9/2002 | Rosen et al. |
| 2002/0165371 | A1 | 11/2002 | Frudakis |
| 2002/0192763 | A1 | 12/2002 | Xu et al. |
| 2003/0134283 | A1 | 7/2003 | Peterson |
| 2003/0157089 | A1 | 8/2003 | Xu et al. |
| 2003/0185830 | A1 | 10/2003 | Xu et al. |
| 2004/0072996 | A1* | 4/2004 | Lal et al. ................ 530/350 |
| 2004/0081653 | A1 | 4/2004 | Raitano et al. |
| 2004/0115629 | A1 | 6/2004 | Panzer et al. |

FOREIGN PATENT DOCUMENTS

| | | |
|---|---|---|
| CN | 1345964 | 4/2002 |
| CN | 1363678 | 8/2002 |
| EP | 1 033 401 | 9/2000 |
| EP | 1 074 617 | 2/2001 |
| EP | 1 396 543 | 3/2004 |
| EP | 1 447 413 | 8/2004 |
| WO | WO-97/25426 | 7/1997 |
| WO | WO-98/45328 | 10/1998 |
| WO | WO-98/45436 | 10/1998 |
| WO | WO-99/06550 | 2/1999 |
| WO | WO-99/31236 | 6/1999 |
| WO | WO-99/38972 | 8/1999 |
| WO | WO-00/04149 | 1/2000 |
| WO | WO-00/21991 | 4/2000 |
| WO | WO-00/61753 | 10/2000 |
| WO | WO-00/73509 | 12/2000 |
| WO | WO-01/25272 | 4/2001 |
| WO | WO-01/34802 | 5/2001 |
| WO | WO-01/51628 | 7/2001 |
| WO | WO-01/51633 | 7/2001 |
| WO | WO-01/51659 | 7/2001 |
| WO | WO-01/55320 | 8/2001 |
| WO | WO-01/55322 | 8/2001 |
| WO | WO-01/55326 | 8/2001 |
| WO | WO-01/57182 | 8/2001 |
| WO | WO-01/57272 | 8/2001 |

(Continued)

OTHER PUBLICATIONS

Overbeek, 1994, "Factors affecting transgenic animal production," Transgenic animal technology, pp. 96-98.*
Wall, 1996 Theriogenology, vol. 45, pp. 57-68.*
Houdebine, 1994, J. Biotech. vol. 34, pp. 269-287, specifically p. 281.*
Kappell, 1992, Current Opinions in Biotechnology, vol. 3, pp. 548-553.*
Cameron, 1997, Mol. Biol. 7, pp. 253-265.*
Mullins, 1993, Hypotension, vol. 22, pp. 630-633.*
Mullins, 1990, Nature, vol. 344, 541-544.*
Hammer, 1990, Cell, vol. 63, 1099-1112.*

(Continued)

Primary Examiner—Christopher H Yaen
Assistant Examiner—Hong Sang
(74) Attorney, Agent, or Firm—Morrison & Foerster LLP

(57) ABSTRACT

A novel gene 251P5G2 and its encoded protein, and variants thereof, are described wherein 251P5G2 exhibits tissue specific expression in normal adult tissue, and is aberrantly expressed in the cancers listed in Table I. Consequently, 251P5G2 provides a diagnostic, prognostic, prophylactic and/or therapeutic target for cancer. The 251P5G2 gene or fragment thereof, or its encoded protein, or variants thereof, or a fragment thereof, can be used to elicit a humoral or cellular immune response; antibodies or T cells reactive with 251P5G2 can be used in active or passive immunization.

5 Claims, 62 Drawing Sheets

FOREIGN PATENT DOCUMENTS

| | | |
|---|---|---|
| WO | WO-01/57273 | 8/2001 |
| WO | WO-01/57274 | 8/2001 |
| WO | WO-01/57275 | 8/2001 |
| WO | WO-01/57276 | 8/2001 |
| WO | WO-01/57277 | 8/2001 |
| WO | WO-01/59063 | 8/2001 |
| WO | WO-01/60860 | 8/2001 |
| WO | WO-01/64834 | 9/2001 |
| WO | WO-01/73032 | 10/2001 |
| WO | WO-01/75067 | 10/2001 |
| WO | WO-01/75171 | 10/2001 |
| WO | WO-01/85791 | 11/2001 |
| WO | WO-01/86003 | 11/2001 |
| WO | WO-01/90152 | 11/2001 |
| WO | WO-01/94629 | 12/2001 |
| WO | WO-01/98351 | 12/2001 |
| WO | WO-02/18632 | 3/2002 |
| WO | WO-02/30268 | 4/2002 |
| WO | WO-02/50105 | 6/2002 |
| WO | WO-02/055700 | 7/2002 |
| WO | WO-02/077013 | 10/2002 |
| WO | WO-02/077186 | 10/2002 |
| WO | WO-02/078516 | 10/2002 |
| WO | WO-02/079448 | 10/2002 |
| WO | WO-02/083876 | 10/2002 |
| WO | WO-02/085298 | 10/2002 |
| WO | WO-02/089747 | 11/2002 |
| WO | WO-02/097031 | 12/2002 |
| WO | WO-03/004623 | 1/2003 |
| WO | WO-03/005888 | 1/2003 |
| WO | WO-03/008583 | 1/2003 |
| WO | WO-03/009814 | 2/2003 |
| WO | WO-03/013431 | 2/2003 |
| WO | WO-03/016478 | 2/2003 |
| WO | WO-03/039443 | 5/2003 |
| WO | WO-03/039484 | 5/2003 |
| WO | WO-03/050236 | 6/2003 |
| WO | WO-03/052049 | 6/2003 |
| WO | WO-03/057146 | 7/2003 |
| WO | WO-03/062376 | 7/2003 |
| WO | WO-03/076586 | 9/2003 |
| WO | WO-03/080795 | 10/2003 |
| WO | WO-2004/016733 | 2/2004 |
| WO | WO-2004/110345 | 12/2004 |

OTHER PUBLICATIONS

Niemann, 1997, Transg. Res. 7, pp. 73-75.*
Mullins, 1989, EMBO J., vol. 8, pp. 4065-4072.*
Taurog, 1988, J. Immunol., vol. 141, pp. 4020-4023.*
Mullins,1996, J. Clin. Invest. vol. 98, pp. S37-S40.*
NCBI AC 060814.*
Thomas et al., Nature Reviews Genetics, 2003, 4: 346-358.*
Bangari et al., Curr. Gene. Ther., 2006, 6:215-226.*
Goncalves et al., Bioessays, 2005, 27: 506-517.*
Riott et al., Immunology, Fourth Edition (1996) Mosby, p. 7.9-7.11.
Jain, Sci. Am. (1994) 171:58-65.
Gura, Science (1997) 278(5340):1041-1042.
MSNBC News Services, "Mixed results on new cancer drug" Nov. 2000.
Greenbaum et al., Genome Biology (2003) 4(9):117.1-117.8.
Alberts et al., Molecular Biology of the Cell, $3^{rd}$ Edition (1994) p. 465.
Mallampalli et al., Biochem. J. (1996) 38:333-341.
Fu et al., EMBO Journal (1996) 15:4392-4401.
International Search Report for PCT/US03/12354, mailed on Jan. 20, 2006, 3 pages.

* cited by examiner

Figure 1: 251P5G2 SSH sequence of 162 nucleotides. (SEQ ID NO: 1)

```
  1 GATCACCCTC CTCAGGTAGA AAGATGCCTC ATATTTGAAG TCATTCTGAA AATTCAGTGA
 61 TTCAAAGAGC TGTGGAGACA AGAACACCAT GGTGAGAAGG ACCACCATGT GGATAAGGGC
121 CACATGACAG ACTGGTAGGT AAGTGCGCTC TGGCCTGAGA TC
```

Figure 2A. The cDNA (SEQ ID. NO. : 2) and amino acid sequence (SEQ ID. NO. : 3) of 251P5G2 v.1 clone 4.7.
The start methionine is underlined. The open reading frame extends from nucleic acid 722-1489 including the stop codon.

```
   1 gttttttttttttttttttttttttttttttatttttaagggattcgtttaataggacttg
  61 tggtaagtggaataatgccatgcaaaggtccccatgtctaaccaccaggttctaggcatg
 121 tattatggtatatgagaaatgggaattcaggctgcagatgaaatcaaggttgataaccag
 181 ctgactctaaaacaaaaacattaacttgaattacagatttgggcctaatgtaattataag
 241 cattcttaaaagtgaaagaaataataagagaaactgagtgctgtgatgtgagtcagttaa
 301 actttttttcaacttttctttaggtgattattttcccttaacataaaatttactttag
 361 ctcaactatacaaacatgtgagttattgttatgtaaccatcactcttcattaagaaatgc
 421 tttgtaaaagtgagccagttttcatatacattcttcaaaatacattctcaacattata
 481 catcaaattatatatacatacatgcacacatacactatatatcaaggatttatatgag
 541 aggattaattaagaaaaaaattagtggaataaaaataatgtttatgataattttggccat
 601 agaatatataatacagatgatgtgaagtacaaaatgttttttatacttcatattttgatg
 661 tacaaagtatgtttgtctttgtaattcagatgattactttgcacttgtgttcccatgaaa
   1  M  P  F  I  S  K  L  V  L  A  S  Q  P  T  L  F  S  F  F  S
 721 aATGCCTTTCATTTCTAAGCTGGTATTGGCATCTCAGCCAACACTTTTCTCCTTCTTTTC
  21  A  S  S  P  F  L  L  F  L  D  L  R  P  E  R  T  Y  L  P  V
 781 TGCGTCTTCTCCTTTTCTGCTTTTTCTGGATCTCAGGCCAGAGCGCACTTACCTACCAGT
  41  C  H  V  A  L  I  H  M  V  V  L  L  T  M  V  F  L  S  P  Q
 841 CTGTCATGTGGCCCTCATCCACATGGTGGTCCTTCTCACCATGGTGTTCTTGTCTCCACA
  61  L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTGAG
  81  R  V  I  R  V  L  S  I  C  T  T  C  L  L  G  M  L  Q  V  V
 961 GAGGGTGATCAGGGTCCTCTCCATTTGTACCACCTGCCTCCTGGGCATGCTGCAGGTCGT
 101  N  I  S  P  S  I  S  W  L  V  R  F  K  W  K  S  T  I  F  T
1021 CAACATCAGCCCCAGCATTTCCTGGTTGGTGAGGTTTAAATGGAAATCCACAATTTTTAC
 121  F  H  L  F  S  W  S  L  S  F  P  V  S  S  S  L  I  F  Y  T
1081 CTTCCATTTGTTCTCATGGTCTCTCAGTTTTCCTGTTAGTAGTAGCCTGATCTTTTACAC
 141  V  A  S  S  N  V  T  Q  I  N  L  H  V  S  K  Y  C  S  L  F
1141 TGTGGCTTCTTCCAATGTGACCCAGATCAATTTGCATGTCAGTAAATACTGTTCACTTTT
 161  P  I  N  S  I  I  R  G  L  F  F  T  L  S  L  F  R  D  V  F
1201 CCCAATAAACTCCATAATCAGAGGACTGTTTTTCACTCTGTCATTATTCAGAGATGTTTT
 181  L  K  Q  I  M  L  F  S  S  V  Y  M  M  T  L  I  Q  E  L  Q
1261 TCTTAAACAAATAATGCTGTTCTCAAGTGTCTACATGATGACTCTCATTCAGGAACTACA
 201  E  I  L  V  P  S  Q  P  Q  P  L  P  K  D  L  C  R  G  K  S
1321 GGAGATCCTGGTACCTTCACAGCCCCAGCCTCTACCTAAGGATCTTTGCAGAGGCAAGAG
```

Figure 2A (Con't)

```
 221  H   Q   H   I   L   L   P   V   S   F   S   V   G   M   Y   K   M   D   F   I
1381  CCATCAGCACATCCTGCTGCCGGTGAGTTTCTCGGTGGGCATGTACAAGATGGACTTCAT
 241  I   S   T   S   S   T   L   P   W   A   Y   D   R   G   V   *
1441  CATCTCAACCTCCTCAACATTGCCATGGGCATATGACCGTGGTGTCTAGaggctagtggg
1501  cagtgtctataccattgtcaggttttggtgctactgagatctgataaaagggtaatcaa
1561  tgtgatgtaaactataagacaaatgtttaaaaggttaattgtatgaatcctgtcatgagt
1621  taaattattcagagtgttcattatagagaataatccaaagttaaaataattggataattt
1681  atttgtatgtaggataaaagtagtaggagattgcttcttgaagatttaaaattatattga
1741  gtgtaattatttgcattaaaataattttaaatgttttgaatagcaagtattgatataatt
1801  aaactttcgaataacttagtgctttgcctttattcctaatgtttatatggaagcatgtgg
1861  tcaatgtttgatgcattacagctctgagcggtccttctgtattaggtggtcatcatttat
1921  atacttctccataaaagattaaggacctggaaatgtaagatacatgaagaaaatctaagt
1981  ggagaggctgtttgtggttaagtgataacagtgttgtaagcgatgcatgaggtaggtgtt
2041  cagtgcatatcctctgcatttttattaataaacactgtaaaatttagaagaaaattgtttc
2101  accaaatgcacataaaactaataaaatagagtggattttgatatgtccctcgtgcc
```

Figure 2B. The cDNA (SEQ ID. NO.: 4) and amino acid sequence (SEQ ID. NO.: 5) of 251P5G2 v.2. The start methionine is underlined. The open reading frame extends from nucleic acid 722-1489 including the stop codon.

```
   1 gttttttttttttttttttttttttttttattttaagggattcgtttaataggacttg
  61 tggtaagtggaataatgccatgcaaaggtccccatgtctaaccaccaggttctaggcatg
 121 tattatggtatatgagaaatgggaattcaggctgcagatgaaatcaaggttgataaccag
 181 ctgactctaaaacaaaaacattaacttgaattacagatttgggcctaatgtaattataag
 241 cattcttaaaagtgaaagaaataataagagaaactgagtgctgtgatgtgagtcagttaa
 301 actttttttcaacttttctttaggtgattattttcccttaacataaaatttactttag
 361 ctcaactatacaaacatgtgagttattgttatgtaaccatcactcttcattaagaaatgc
 421 tttgtaaaaagtgagccagttttcatatacattcttcaaaatacattctcaacattata
 481 catcaaattatatatacatacatgcacacatacactatatatatcaaggatttatatgag
 541 aggattaattaagaaaaaaattagtggaataaaaataatgtttatgataattttggccat
 601 agaatatataatacagatgatgtgaagtacaaaatgttttttatacttcatattttgatg
 661 tacaaagtatgtttgtctttgtaattcagatgattactttgcacttgtgttcccatgaaa
   1  M  P  F  I  S  K  L  V  L  A  S  Q  P  T  L  C  S  F  F  S
 721 aATGCCTTTCATTTCTAAGCTGGTATTGGCATCTCAGCCAACACTTTGCTCCTTCTTTTC
  21  A  S  S  P  F  L  L  F  L  D  L  R  P  E  R  T  Y  L  P  V
 781 TGCGTCTTCTCCTTTTCTGCTTTTTCTGGATCTCAGGCCAGAGCGCACTTACCTACCAGT
  41  C  H  V  A  L  I  H  M  V  V  L  L  T  M  V  F  L  S  P  Q
 841 CTGTCATGTGGCCCTCATCCACATGGTGGTCCTTCTCACCATGGTGTTCTTGTCTCCACA
  61  L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTGAG
  81  R  V  I  R  V  L  S  I  C  T  T  C  L  L  G  M  L  Q  V  V
 961 GAGGGTGATCAGGGTCCTCTCCATTTGTACCACCTGCCTCCTGGGCATGCTGCAGGTCGT
 101  N  I  S  P  S  I  S  W  L  V  R  F  K  W  K  S  T  I  F  T
1021 CAACATCAGCCCCAGCATTTCCTGGTTGGTGAGGTTTAAATGGAAATCCACAATTTTTAC
 121  F  H  L  F  S  W  S  L  S  F  P  V  S  S  S  L  I  F  Y  T
1081 CTTCCATTTGTTCTCATGGTCTCTCAGTTTTCCTGTTAGTAGTAGCCTGATCTTTTACAC
 141  V  A  S  N  V  T  Q  I  N  L  H  V  S  K  Y  C  S  L  F
1141 TGTGGCTTCTTCCAATGTGACCCAGATCAATTTGCATGTCAGTAAATACTGTTCACTTTT
 161  P  I  N  S  I  I  R  G  L  F  F  T  L  S  L  F  R  D  V  F
1201 CCCAATAAACTCCATAATCAGAGGACTGTTTTCACTCTGTCATTATTCAGAGATGTTTT
 181  L  K  Q  I  M  L  F  S  S  V  Y  M  M  T  L  I  Q  E  L  Q
1261 TCTTAAACAAATAATGCTGTTCTCAAGTGTCTACATGATGACTCTCATTCAGGAACTACA
 201  E  I  L  V  P  S  Q  P  Q  P  L  P  K  D  L  C  R  G  K  S
1321 GGAGATCCTGGTACCTTCACAGCCCCAGCCTCTACCTAAGGATCTTTGCAGAGGCAAGAG
```

Figure 2B (Con't)

```
 221  H  Q  H  I  L  L  P  V  S  F  S  V  G  M  Y  K  M  D  F  I
1381  CCATCAGCACATCCTGCTGCCGGTGAGTTTCTCGGTGGGCATGTACAAGATGGACTTCAT
 241  I  S  T  S  S  T  L  P  W  A  Y  D  R  G  V  *
1441  CATCTCAACCTCCTCAACATTGCCATGGGCATATGACCGTGGTGTCTAGaggctagtggg
1501  cagtgtctataccattgtcaggttttggtgctactgagatctgataaaagggtaatcaa
1561  tgtgatgtaaactataagacaaatgtttaaaaggttaattgtatgaatcctgtcatgagt
1621  taaattattcagagtgttcattatagagaataatccaaagttaaaataattggataattt
1681  atttgtatgtaggataaaagtagtaggagattgcttcttgaagatttaaaattatattga
1741  gtgtaattatttgcattaaaataattttaaatgttttgaatagcaagtattgatataatt
1801  aaactttcgaataacttagtgctttgcctttattcctaatgtttatatggaagcatgtgg
1861  tcaatgtttgatgcattacagctctgagcggtccttctgtattaggtggtcatcatttat
1921  atacttctccataaaagattaaggacctggaaatgtaagatacatgaagaaaatctaagt
1981  ggagaggctgtttgtggttaagtgataacagtgttgtaagcgatgcatgaggtaggtgtt
2041  cagtgcatatcctctgcatttattaataaacactgtaaaatttagaagaaaattgtttc
2101  accaaatgcacataaaactaataaaatagagtggattttgatatgtccctcgtgcc
```

Figure 2C. The cDNA (SEQ ID. NO.: 6) and amino acid sequence (SEQ ID. NO.: 7) of 251P5G2 v.3. The start methionine is underlined. The open reading frame extends from nucleic acid 722-1489 including the stop codon.

```
   1 gtttttttttttttttttttttttttttattttaagggattcgtttaataggacttg
  61 tggtaagtggaataatgccatgcaaaggtccccatgtctaaccaccaggttctaggcatg
 121 tattatggtatatgagaaatgggaattcaggctgcagatgaaatcaaggttgataaccag
 181 ctgactctaaaacaaaaacattaacttgaattacagatttggcctaatgtaattataag
 241 cattcttaaaagtgaaagaaataataagagaaactgagtgctgtgatgtgagtcagttaa
 301 acttttttttcaacttttctttaggtgattattttcccttaacataaaatttactttag
 361 ctcaactatacaaacatgtgagttattgttatgtaaccatcactcttcattaagaaatgc
 421 tttgtaaaaagtgagccagttttcatatacattcttcaaaatacattctcaacattata
 481 catcaaattatatatacatacatgcacacatacactatatatatcaaggatttatatgag
 541 aggattaattaagaaaaaaattagtggaataaaaataatgtttatgataattttggccat
 601 agaatatataatacagatgatgtgaagtacaaaatgttttttatacttcatattttgatg
 661 tacaaagtatgtttgtctttgtaattcagatgattactttgcacttgtgttcccatgaaa
```

```
   1   M  P  F  I  S  K  L  V  L  A  S  Q  P  T  L  F  S  F  F  S
 721 aATGCCTTTCATTTCTAAGCTGGTATTGGCATCTCAGCCAACACTTTTCTCCTTCTTTTC
  21   A  S  S  P  F  L  L  F  L  D  L  R  P  E  R  T  Y  L  P  V
 781 TGCGTCTTCTCCTTTTCTGCTTTTTCTGGATCTCAGGCCAGAGCGCACTTACCTACCAGT
  41   C  H  V  A  L  I  H  M  V  V  L  L  T  M  V  F  L  S  P  Q
 841 CTGTCATGTGGCCCTCATCCACATGGTGGTCCTTCTCACCATGGTGTTCTTGTCTCCACA
  61   L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTGAG
  81   R  V  I  R  D  L  S  I  C  T  T  C  L  L  G  M  L  Q  V  V
 961 GAGGGTGATCAGGGACCTCTCCATTTGTACCACCTGCCTCCTGGGCATGCTGCAGGTCGT
 101   N  I  S  P  S  I  S  W  L  V  R  F  K  W  K  S  T  I  F  T
1021 CAACATCAGCCCCAGCATTTCCTGGTTGGTGAGGTTTAAATGGAAATCCACAATTTTTAC
 121   F  H  L  F  S  W  S  L  S  F  P  V  S  S  S  L  I  F  Y  T
1081 CTTCCATTTGTTCTCATGGTCTCTCAGTTTTCCTGTTAGTAGTAGCCTGATCTTTTACAC
 141   V  A  S  S  N  V  T  Q  I  N  L  H  V  S  K  Y  C  S  L  F
1141 TGTGGCTTCTTCCAATGTGACCCAGATCAATTTGCATGTCAGTAAATACTGTTCACTTTT
 161   P  I  N  S  I  I  R  G  L  F  F  T  L  S  L  F  R  D  V  F
1201 CCCAATAAACTCCATAATCAGAGGACTGTTTTTCACTCTGTCATTATTCAGAGATGTTTT
 181   L  K  Q  I  M  L  F  S  S  V  Y  M  M  T  L  I  Q  E  L  Q
1261 TCTTAAACAAATAATGCTGTTCTCAAGTGTCTACATGATGACTCTCATTCAGGAACTACA
 201   E  I  L  V  P  S  Q  P  Q  P  L  P  K  D  L  C  R  G  K  S
1321 GGAGATCCTGGTACCTTCACAGCCCCAGCCTCTACCTAAGGATCTTTGCACAGGCAAGAG
 221   H  Q  H  I  L  L  P  V  S  F  S  V  G  M  Y  K  M  D  F  I
```

Figure 2C (Con't)

```
1381 CCATCAGCACATCCTGCTGCCGGTGAGTTTCTCGGTGGGCATGTACAAGATGGACTTCAT
 241  I  S  T  S  S  T  L  P  W  A  Y  D  R  G  V  *
1441 CATCTCAACCTCCTCAACATTGCCATGGGCATATGACCGTGGTGTCTAGaggctagtggg
1501 cagtgtctataccattgtcaggttttggtgctactgagatctgataaagggtaatcaa
1561 tgtgatgtaaactataagacaaatgtttaaaaggttaattgtatgaatcctgtcatgagt
1621 taaattattcagagtgttcattatagagaataatccaaagttaaaataattggataattt
1681 atttgtatgtaggataaaagtagtaggagattgcttcttgaagatttaaaattatattga
1741 gtgtaattatttgcattaaaataattttaaatgttttgaatagcaagtattgatataatt
1801 aaactttcgaataacttagtgctttgcctttattcctaatgtttatatggaagcatgtgg
1861 tcaatgtttgatgcattacagctctgagcggtccttctgtattaggtggtcatcatttat
1921 atacttctccataaaagattaaggacctggaaatgtaagatacatgaagaaaatctaagt
1981 ggagaggctgtttgtggttaagtgataacagtgttgtaagcgatgcatgaggtaggtgtt
2041 cagtgcatatcctctgcatttttattaataaacactgtaaaatttagaagaaaattgtttc
2101 accaaatgcacataaaactaataaaatagagtggattttgatatgtccctcgtgcc
```

Figure 2D. The cDNA (SEQ ID. NO. : 8) and amino acid sequence (SEQ ID. NO. : 9) of 251P5G2 v.4. The start methionine is underlined. The open reading frame extends from nucleic acid 722-1489 including the stop codon.

```
   1 gtttttttttttttttttttttttttttttattttaagggattcgtttaataggacttg
  61 tggtaagtggaataatgccatgcaaaggtccccatgtctaaccaccaggttctaggcatg
 121 tattatggtatatgagaaatgggaattcaggctgcagatgaaatcaaggttgataaccag
 181 ctgactctaaaacaaaaacattaacttgaattacagatttgggcctaatgtaattataag
 241 cattcttaaaagtgaaagaaataataagagaaactgagtgctgtgatgtgagtcagttaa
 301 acttttttttcaacttttctttaggtgattattttcccttaacataaaatttactttag
 361 ctcaactatacaaacatgtgagttattgttatgtaaccatcactcttcattaagaaatgc
 421 tttgtaaaaagtgagccagttttcatatacattcttcaaaatacattctcaacattata
 481 catcaaattatatacatacatgcacacatacactatatatcaaggatttatatgag
 541 aggattaattaagaaaaaaattagtggaataaaaataatgtttatgataattttggccat
 601 agaatatataatacagatgatgtgaagtacaaaatgttttttatacttcatattttgatg
 661 tacaaagtatgtttgtctttgtaattcagatgattactttgcacttgtgttcccatgaaa
   1  M  P  F  I  S  K  L  V  L  A  S  Q  P  T  L  F  S  F  F  S
 721 aATGCCTTTCATTTCTAAGCTGGTATTCGCATCTCAGCCAACACTTTTCTCCTTCTTTTC
  21  A  S  S  P  F  L  L  F  L  D  L  R  P  E  R  T  Y  L  P  V
 781 TGCGTCTTCTCCTTTTCTGCTTTTTCTGGATCTCAGGCCAGAGCGCACTTACCTACCAGT
  41  C  H  V  A  L  I  H  M  V  V  L  L  T  M  V  F  L  S  P  Q
 841 CTGTCATGTGGCCCTCATCCACATGGTGGTCCTTCTCACCATGGTGTTCTTGTCTCCACA
  61  L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTGAG
  81  R  V  I  R  V  L  S  I  C  T  T  C  L  L  D  M  L  Q  V  V
 961 GAGGGTGATCAGGGTCCTCTCCATTTGTACCACCTGCCTCCTGGACATGCTGCAGGTCGT
 101  N  I  S  P  S  I  S  W  L  V  R  F  K  W  K  S  T  I  F  T
1021 CAACATCAGCCCCAGCATTTCCTGGTTGGTGAGGTTTAAATGGAAATCCACAATTTTTAC
 121  F  H  L  F  S  W  S  L  S  F  P  V  S  S  S  L  I  F  Y  T
1081 CTTCCATTTGTTCTCATGGTCTCTCAGTTTTCCTGTTAGTAGTAGCCTGATCTTTTACAC
 141  V  A  S  S  N  V  T  Q  I  N  L  H  V  S  K  Y  C  S  L  F
1141 TGTGGCTTCTTCCAATGTGACCCAGATCAATTTGCATGTCAGTAAATACTGTTCACTTTT
 161  P  I  N  S  I  I  R  G  L  F  F  T  L  S  L  F  R  D  V  F
1201 CCCAATAAACTCCATAATCAGAGGACTGTTTTTCACTCTGTCATTATTCAGAGATGTTTT
 181  L  K  Q  I  M  L  F  S  S  V  Y  M  M  T  L  I  Q  E  L  Q
1261 TCTTAAACAAATAATGCTGTTCTCAAGTGTCTACATGATGACTCTCATTCAGGAACTACA
 201  E  I  L  V  P  S  Q  P  Q  P  L  P  K  D  L  C  R  G  K  S
1321 GGAGATCCTGGTACCTTCACAGCCCCAGCCTCTACCTAAGGATCTTTGCAGAGGCAAGAG
```

Figure 2D (Con't)

```
 221  H   Q   H   I   L   L   P   V   S   F   S   V   G   M   Y   K   M   D   F   I
1381  CCATCAGCACATCCTGCTGCCGGTGAGTTTCTCGGTGGGCATGTACAAGATGGACTTCAT
 241  I   S   T   S   S   T   L   P   W   A   Y   D   R   G   V   *
1441  CATCTCAACCTCCTCAACATTGCCATGGGCATATGACCGTGGTGTCTAGaggctagtggg
1501  cagtgtctataccattgtcaggttttggtgctactgagatctgataaagggtaatcaa
1561  tgtgatgtaaactataagacaaatgtttaaaaggttaattgtatgaatcctgtcatgagt
1621  taaattattcagagtgttcattatagagaataatccaaagttaaataattggataattt
1681  atttgtatgtaggataaaagtagtaggagattgcttcttgaagatttaaaattatattga
1741  gtgtaattatttgcattaaaataattttaaatgttttgaatagcaagtattgatataatt
1801  aaactttcgaataacttagtgctttgcctttattcctaatgtttatatggaagcatgtgg
1861  tcaatgtttgatgcattacagctctgagcggtccttctgtattaggtggtcatcatttat
1921  atacttctccataaaagattaaggacctggaaatgtaagatacatgaagaaaatctaagt
1981  ggagaggctgtttgtggttaagtgataacagtgttgtaagcgatgcatgaggtaggtgtt
2041  cagtgcatatcctctgcatttattaataaacactgtaaaatttagaagaaaattgtttc
2101  accaaatgcacataaaactaataaaatagagtggattttgatatgtccctcgtgcc
```

Figure 2E. The cDNA (SEQ ID. NO. : 10) and amino acid sequence (SEQ ID. NO. : 11) of 251P5G2 v.5. The start methionine is underlined. The open reading frame extends from nucleic acid 722-1489 including the stop codon.

```
   1 gtttttttttttttttttttttttttttatttttaagggattcgtttaataggacttg
  61 tggtaagtggaataatgccatgcaaaggtccccatgtctaaccaccaggttctaggcatg
 121 tattatggtatatgagaaatgggaattcaggctgcagatgaaatcaaggttgataaccag
 181 ctgactctaaaacaaaaacattaacttgaattacagatttgggcctaatgtaattataag
 241 cattcttaaaagtgaaagaaataataagagaaactgagtgctgtgatgtgagtcagttaa
 301 acttttttttcaacttttctttaggtgattattttcccttaacataaaatttactttag
 361 ctcaactatacaaacatgtgagttattgttatgtaaccatcactcttcattaagaaatgc
 421 tttgtaaaaagtgagccagttttttcatatacattcttcaaaatacattctcaacattata
 481 catcaaattatatatacatacatgcacacatacactatatatatcaaggatttatatgag
 541 aggattaattaagaaaaaaattagtggaataaaaataatgtttatgataatttggccat
 601 agaatatataatacagatgatgtgaagtacaaaatgttttttatacttcatattttgatg
 661 tacaaagtatgtttgtctttgtaattcagatgattactttgcacttgtgttcccatgaaa
   1  M  P  F  I  S  K  L  V  L  A  S  Q  P  T  L  F  S  F  F  S
 721 aATGCCTTTCATTTCTAAGCTGGTATTGGCATCTCAGCCAACACTTTTCTCCTTCTTTTC
  21  A  S  S  P  F  L  L  F  L  D  R  P  E  R  T  Y  L  P  V
 781 TGCGTCTTCTCCTTTTCTGCTTTTTCTGGATCTCAGGCCAGAGCGCACTTACCTACCAGT
  41  C  H  V  A  L  I  H  M  V  V  L  L  T  M  V  F  L  S  P  Q
 841 CTGTCATGTGGCCCTCATCCACATGGTGGTCCTTCTCACCATGGTGTTCTTGTCTCCACA
  61  L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTGAG
  81  R  V  I  R  V  L  S  I  C  T  T  C  L  L  G  M  L  Q  V  V
 961 GAGGGTGATCAGGGTCCTCTCCATTTGTACCACCTGCCTCCTGGGCATGCTGCAGGTCGT
 101  N  I  S  P  S  I  S  W  L  V  R  F  K  W  K  S  T  I  F  T
1021 CAACATCAGCCCCAGCATTTCCTGGTTGGTGAGGTTTAAATGGAAATCCACAATTTTTAC
 121  F  H  L  F  S  W  S  L  S  F  P  V  S  S  L  I  F  Y  T
1081 CTTCCATTTGTTCTCATGGTCTCTCAGTTTTCCTGTTAGTAGTAGCCTGATCTTTTACAC
 141  V  A  S  S  N  V  T  Q  I  N  L  H  V  S  K  Y  C  S  L  F
1141 TGTGGCTTCTTCCAATGTGACCCAGATCAATTTGCATGTCAGTAAATACTGTTCACTTTT
 161  P  I  N  S  I  I  R  G  L  F  F  T  L  S  L  F  R  D  V  F
1201 CCCAATAAACTCCATAATCAGAGGACTGTTTTTCACTCTGTCATTATTCAGAGATGTTTT
 181  L  K  Q  I  M  L  F  S  S  V  Y  M  M  T  L  I  Q  E  L  Q
1261 TCTTAAACACATAATGCTGTTCTCAAGTGTCTACATGATGACTCTCATTCAGGAACTACA
 201  E  I  L  V  P  S  Q  P  Q  P  L  P  K  D  L  C  R  G  K  S
1321 GGAGATCCTGGTACCTTCACAGCCCCAGCCTCTACCTAAGGATCTTTGCAGAGGCAAGAG
```

Figure 2E (Con't)

```
 221  H   Q   H   I   L   L   P   V   S   F   S   V   G   M   Y   K   M   D   F   I
1381  CCATCAGCACATCCTGCTGCCGGTGAGTTTCTCGGTGGGCATGTACAAGATGGACTTCAT
 241  I   S   T   S   S   T   L   P   W   A   Y   D   R   G   V   *
1441  CATCTCAACCTCCTCAACATTGCCATGGGCATATGACCGTGGTGTCTAGaggctagtggg
1501  cagtgtctataccattgtcaggttttggtgctactgagatctgataaagggtaatcaa
1561  tgtgatgtaaactataagacaaatgtttaaaaggttaattgtatgaatcctgtcatgagt
1621  taaattattcagagtgttcattatagagaataatccaaagttaaaataattggataattt
1681  atttgtatgtaggataaaagtagtaggagattgcttcttgaagatttaaaattatattga
1741  gtgtaattatttgcattaaaataatttaaatgttttgaatagcaagtattgatataatt
1801  aaactttcgaataacttagtgctttgcctttattcctaatgtttatatggaagcatgtgg
1861  tcaatgtttgatgcattacagctctgagcggtccttctgtattaggtggtcatcatttat
1921  atacttctccataaaagattaaggacctggaaatgtaagatacatgaagaaaatctaagt
1981  ggagaggctgtttgtggttaagtgataacagtgttgtaagcgatgcatgaggtaggtgtt
2041  cagtgcatatcctctgcatttattaataaacactgtaaaatttagaagaaaattgtttc
2101  accaaatgcacataaaactaataaaatagagtggattttgatatgtccctcgtgcc
```

Figure 2F. The cDNA (SEQ ID. NO. : 12) and amino acid sequence (SEQ ID. NO. : 13) of 251P5G2 v.6. The start methionine is underlined. The open reading frame extends from nucleic acid 722-1489 including the stop codon.

```
   1 gtttttttttttttttttttttttttttattttaagggattcgtttaataggacttg
  61 tggtaagtggaataatgccatgcaaaggtccccatgtctaaccaccaggttctaggcatg
 121 tattatggtatatgagaaatgggaattcaggctgcagatgaaatcaaggttgataaccag
 181 ctgactctaaaacaaaaacattaacttgaattacagatttgggcctaatgtaattataag
 241 cattcttaaaagtgaaagaaataataagagaaactgagtgctgtgatgtgagtcagttaa
 301 actttttttcaacttttctttaggtgattattttcccttaacataaaatttactttag
 361 ctcaactatacaaacatgtgagttattgttatgtaaccatcactcttcattaagaaatgc
 421 tttgtaaaaagtgagccagttttcatatacattcttcaaaatacattctcaacattata
 481 catcaaattatatatacatacatgcacacatacactatatatatcaaggatttatatgag
 541 aggattaattaagaaaaaaattagtggaataaaaataatgtttatgataattttggccat
 601 agaatatataatacagatgatgtgaagtacaaaatgttttttatacttcatattttgatg
 661 tacaaagtatgtttgtctttgtaattcagatgattactttgcacttgtgttcccatgaaa
   1  M  P  F  I  S  K  L  V  L  A  S  Q  P  T  L  F  S  F  F  S
 721 aATGCCTTTCATTTCTAAGCTGGTATTGGCATCTCAGCCAACACTTTTCTCCTTCTTTTC
  21  A  S  S  P  F  L  L  F  L  D  L  R  P  E  R  T  Y  L  P  V
 781 TGCGTCTTCTCCTTTTCTGCTTTTTCTGGATCTCAGGCCAGAGCGCACTTACCTACCAGT
  41  C  H  V  A  L  I  H  M  V  V  L  L  T  M  V  F  L  S  P  Q
 841 CTGTCATGTGGCCCTCATCCACATGGTGGTCCTTCTCACCATGGTGTTCTTGTCTCCACA
  61  L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTGAG
  81  R  V  I  R  V  L  S  I  C  T  T  C  L  L  G  M  L  Q  V  V
 961 GAGGGTGATCAGGGTCCTCTCCATTTGTACCACCTGCCTCCTGGGCATGCTGCAGGTCGT
 101  N  I  S  P  S  I  S  W  L  V  R  F  K  W  K  S  T  I  F  T
1021 CAACATCAGCCCCAGCATTTCCTGGTTGGTGAGGTTTAAATGGAAATCCACAATTTTTAC
 121  F  H  L  F  S  W  S  L  S  F  P  V  S  S  S  L  I  F  Y  T
1081 CTTCCATTTGTTCTCATGGTCTCTCAGTTTTCCTGTTAGTAGTAGCCTGATCTTTTACAC
 141  V  A  S  S  N  V  T  Q  I  N  L  H  V  S  K  Y  C  S  L  F
1141 TGTGGCTTCTTCCAATGTGACCCAGATCAATTTGCATGTCAGTAAATACTGTTCACTTTT
 161  P  I  N  S  I  I  R  G  L  F  F  T  L  S  L  F  R  D  V  F
1201 CCCAATAAACTCCATAATCAGAGGACTGTTTTTCACTCTGTCATTATTCAGAGATGTTTT
 181  L  K  Q  I  M  L  F  S  S  V  Y  M  M  T  L  I  Q  E  L  Q
1261 TCTTAAACAAATAATGCTGTTCTCAAGTGTCTACATGATGACTCTCATTCAGGAACTACA
 201  E  I  L  V  P  S  Q  P  Q  P  L  P  K  D  L  C  R  G  K  S
1321 GGAGATCCTGGTACCTTCACAGCCCCAGCCTCTACCTAAGGATCTTTGCAGAGGCAAGAG
```

Figure 2F (Con't)

```
 221  H  Q  H  I  L  L  P  V  S  F  S  V  G  M  Y  K  M  D  F  I
1381  CCATCAGCACATCCTGCTGCCGGTGAGTTTCTCGGTGGGCATGTACAAGATGGACTTCAT
 241  I  S  T  S  S  T  L  P  W  A  Y  D  R  G  V  *
1441  CATCTCAACCTCCTCAACGTTGCCATGGGCATATGACCGTGGTGTCTAGaggctagtggg
1501  cagtgtctataccattgtcaggttttggtgctactgagatctgataaaagggtaatcaa
1561  tgtgatgtaaactataagacaaatgtttaaaaggttaattgtatgaatcctgtcatgagt
1621  taaattattcagagtgttcattatagagaataatccaaagttaaaataattggataattt
1681  atttgtatgtaggataaaagtagtaggagattgcttcttgaagatttaaaattatattga
1741  gtgtaattatttgcattaaaataattttaaatgttttgaatagcaagtattgatataatt
1801  aaactttcgaataacttagtgctttgcctttattcctaatgtttatatggaagcatgtgg
1861  tcaatgtttgatgcattacagctctgagcggtccttctgtattaggtggtcatcatttat
1921  atacttctccataaaagattaaggacctggaaatgtaagatacatgaagaaaatctaagt
1981  ggagaggctgtttgtggttaagtgataacagtgttgtaagcgatgcatgaggtaggtgtt
2041  cagtgcatatcctctgcatttattaataaacactgtaaaatttagaagaaaattgtttc
2101  accaaatgcacataaaactaataaaatagagtggattttgatatgtccctcgtgcc
```

Figure 2G. The cDNA (SEQ ID. NO.: 14) and amino acid sequence (SEQ ID. NO.: 15) of 251P5G2 v.7. The start methionine is underlined. The open reading frame extends from nucleic acid 722-1489 including the stop codon.

```
   1 gttttttttttttttttttttttttttttattttaagggattcgtttaataggacttg
  61 tggtaagtggaataatgccatgcaaaggtccccatgtctaaccaccaggttctaggcatg
 121 tattatggtatatgagaaatgggaattcaggctgcagatgaaatcaaggttgataaccag
 181 ctgactctaaaacaaaaacattaacttgaattacagatttgggcctaatgtaattataag
 241 cattcttaaaagtgaaagaaataataagagaaactgagtgctgtgatgtgagtcagttaa
 301 actttttttcaacttttctttaggtgattattttcccttaacataaaatttactttag
 361 ctcaactatacaaacatgtgagttattgttatgtaaccatcactcttcattaagaaatgc
 421 tttgtaaaaagtgagccagttttcatatacattcttcaaaatacattctcaacattata
 481 catcaaattatatatacatacatgcacacatacactatatatatcaaggatttatatgag
 541 aggattaattaagaaaaaaattagtggaataaaaataatgtttatgataattttggccat
 601 agaatatataatacagatgatgtgaagtacaaaatgttttttatacttcatattttgatg
 661 tacaaagtatgtttgtctttgtaattcagatgattactttgcacttgtgttcccatgaaa
   1   M  P  F  I  S  K  L  V  L  A  S  Q  P  T  L  F  S  F  F  S
 721 aATGCCTTTCATTTCTAAGCTGGTATTGGCATCTCAGCCAACACTTTTCTCCTTCTTTTC
  21   A  S  S  P  F  L  L  F  L  D  L  R  P  E  R  T  Y  L  P  V
 781 TGCGTCTTCTCCTTTTCTGCTTTTTCTGGATCTCAGGCCAGAGCGCACTTACCTACCAGT
  41   C  H  V  A  L  I  H  M  V  V  L  L  T  M  V  F  L  S  P  Q
 841 CTGTCATGTGGCCCTCATCCACATGGTGGTCCTTCTCACCATGGTGTTCTTGTCTCCACA
  61   L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTGAG
  81   R  V  I  R  V  L  S  I  C  T  T  C  L  L  G  M  L  Q  V  V
 961 GAGGGTGATCAGGGTCCTCTCCATTTGTACCACCTGCCTCCTGGGCATGCTGCAGGTCGT
 101   N  I  S  P  S  I  S  W  L  V  R  F  K  W  K  S  T  I  F  T
1021 CAACATCAGCCCCAGCATTTCCTGGTTGGTGAGGTTTAAATGGAAATCCACAATTTTTAC
 121   F  H  L  F  S  W  S  L  S  F  P  V  S  S  S  L  I  F  Y  T
1081 CTTCCATTTGTTCTCATGGTCTCTCAGTTTTCCTGTTAGTAGTAGCCTGATCTTTTACAC
 141   V  A  S  S  N  V  T  Q  I  N  L  H  V  S  K  Y  C  S  L  F
1141 TGTGGCTTCTTCCAATGTGACCCAGATCAATTTGCATGTCAGTAAATACTGTTCACTTTT
 161   P  I  N  S  I  I  R  G  L  F  F  T  L  S  L  F  R  D  V  F
1201 CCCAATAAACTCCATAATCAGAGGACTGTTTTCACTCTGTCATTATTCAGAGATGTTTT
 181   L  K  Q  I  M  L  F  S  S  V  Y  M  M  T  L  I  Q  E  L  Q
1261 TCTTAAACAAATAATGCTGTTCTCAAGTGTCTACATGATGACTCTCATTCAGGAACTACA
 201   E  I  L  V  P  S  Q  P  Q  P  L  P  K  D  L  C  R  G  K  S
1321 GGAGATCCTGGTACCTTCACAGCCCCAGCCTCTACCTAAGGATCTTTGCAGAGGCAAGAG
```

Figure 2G (Con't)

```
 221  H  Q  H  I  L  L  P  V  S  F  S  V  G  M  Y  K  M  D  F  I
1381  CCATCAGCACATCCTGCTGCCGGTGAGTTTCTCGGTGGGCATGTACAAGATGGACTTCAT
 241  I  S  T  S  S  T  L  P  W  A  Y  D  R  G  V  *
1441  CATCTCAACCTCCTCAACATTGCCATGGGCATATGACCGTGGTGTCTAGaggctagtggg
1501  cagtgtctataccattgtcaggttttggtgctactgagatctgataaaagggtaatcaa
1561  tgtgatgtaaactataagacaaatgtttaaaaggttaattgtatgaatcctgtcatgagt
1621  taaattattcagagtgttcattatagagaataatccaaagttaaaataattggataattt
1681  atttgtatgtaggataaaagtagtaggagattgcttcttgaagatttaaaattatattga
1741  gtgtaattatttgcattaaaataattttaaatgttttgaatagcaagtattgatataatt
1801  aaactttcgaataacttagtgctttgcctttattcctaatgtttatatggaagcatgtgg
1861  tcaatgtttgatgcattacagctctgagcggtccttctgtattaggtggtcatcatttat
1921  gtacttctccataaaagattaaggacctggaaatgtaagatacatgaagaaaatctaagt
1981  ggagaggctgtttgtggttaagtgataacagtgttgtaagcgatgcatgaggtaggtgtt
2041  cagtgcatatcctctgcattttattaataaacactgtaaaatttagaagaaaattgtttc
2101  accaaatgcacataaaactaataaaatagagtggattttgatatgtccctcgtgcc
```

Figure 2H. The cDNA (SEQ ID. NO.: 16) and amino acid sequence (SEQ ID. NO.: 17) of 251P5G2 v.8. The start methionine is underlined. The open reading frame extends from nucleic acid 722-1489 including the stop codon.

```
   1 gttttttttttttttttttttttttttttattttaagggattcgtttaataggacttg
  61 tggtaagtggaataatgccatgcaaggtccccatgtctaaccaccaggttctaggcatg
 121 tattatggtatatgagaaatgggaattcaggctgcagatgaaatcaaggttgataaccag
 181 ctgactctaaaacaaaaacattaacttgaattacagatttgggcctaatgtaattataag
 241 cattcttaaaagtgaaagaaataataagagaaactgagtgctgtgatgtgagtcagttaa
 301 acttttttttcaacttttttctttaggtgattattttcccttaacataaaatttactttag
 361 ctcaactatacaaacatgtgagttattgttatgtaaccatcactcttcattaagaaatgc
 421 tttgtaaaaagtgagccagttttcatatacattcttcaaaatacattctcaacattata
 481 catcaaattatatatacatacatgcacacatacactatatatatcaaggatttatatgat
 541 aggattaattaagaaaaaaattagtggaataaaaataatgtttatgataattttggccat
 601 agaatatataatacagatgatgtgaagtacaaaatgttttttatacttcatattttgatg
 661 tacaaagtatgtttgtctttgtaattcagatgattactttgcacttgtgttcccatgaaa
   1   M  P  F  I  S  K  L  V  L  A  S  Q  P  T  L  F  S  F  F  S
 721 aATGCCTTTCATTTCTAAGCTGGTATTGGCATCTCAGCCAACACTTTTCTCCTTCTTTTC
  21   A  S  S  P  F  L  L  F  L  D  L  R  P  E  R  T  Y  L  P  V
 781 TGCGTCTTCTCCTTTTCTGCTTTTTCTGGATCTCAGGCCAGAGCGCACTTACCTACCAGT
  41   C  H  V  A  L  I  H  M  V  V  L  L  T  M  V  F  L  S  P  Q
 841 CTGTCATGTGGCCCTCATCCACATGGTGGTCCTTCTCACCATGGTGTTCTTGTCTCCACA
  61   L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTGAG
  81   R  V  I  R  V  L  S  I  C  T  T  C  L  L  G  M  L  Q  V  V
 961 GAGGGTGATCAGGGTCCTCTCCATTTGTACCACCTGCCTCCTGGGCATGCTGCAGGTCGT
 101   N  I  S  P  S  I  S  W  L  V  R  F  K  W  K  S  T  I  F  T
1021 CAACATCAGCCCCAGCATTTCCTGGTTGGTGAGGTTTAAATGGAAATCCACAATTTTTAC
 121   F  H  L  F  S  W  S  L  S  F  P  V  S  S  S  L  I  F  Y  T
1081 CTTCCATTTGTTCTCATGGTCTCTCAGTTTTCCTGTTAGTAGTAGCCTGATCTTTTACAC
 141   V  A  S  S  N  V  T  Q  I  N  L  H  V  S  K  Y  C  S  L  F
1141 TGTGGCTTCTTCCAATGTGACCCAGATCAATTTGCATGTCAGTAAATACTGTTCACTTTT
 161   P  I  N  S  I  I  R  G  L  F  F  T  L  S  L  F  R  D  V  F
1201 CCCAATAAACTCCATAATCAGAGGACTGTTTTTCACTCTGTCATTATTCAGAGATGTTTT
 181   L  K  Q  I  M  L  F  S  S  V  Y  M  M  T  L  I  Q  E  L  Q
1261 TCTTAAACAAATAATGCTGTTCTCAAGTGTCTACATGATGACTCTCATTCAGGAACTACA
 201   E  I  L  V  P  S  Q  P  Q  P  L  P  K  D  L  C  R  G  K  S
1321 GGAGATCCTGGTACCTTCACAGCCCCAGCCTCTACCTAAGGATCTTTGCAGAGGCAAGAG
```

Figure 2H (Con't)

```
 221  H  Q  H  I  L  L  P  V  S  F  S  V  G  M  Y  K  M  D  F  I
1381  CCATCAGCACATCCTGCTGCCGGTGAGTTTCTCGGTGGGCATGTACAAGATGGACTTCAT
 241  I  S  T  S  S  T  L  P  W  A  Y  D  R  G  V  *
1441  CATCTCAACCTCCTCAACATTGCCATGGGCATATGACCGTGGTGTCTAGaggctagtggg
1501  cagtgtctataccattgtcaggttttggtgctactgagatctgataaaagggtaatcaa
1561  tgtgatgtaaactataagacaaatgtttaaaaggttaattgtatgaatcctgtcatgagt
1621  taaattattcagagtgttcattatagagaataatccaaagttaaaataattggataattt
1681  atttgtatgtaggataaaagtagtaggagattgcttcttgaagatttaaaattatattga
1741  gtgtaattatttgcattaaaataattttaaatgttttgaatagcaagtattgatataatt
1801  aaactttcgaataacttagtgctttgcctttattcctaatgtttatatggaagcatgtgg
1861  tcaatgtttgatgcattacagctctgagcggtccttctgtattaggtggtcatcatttat
1921  atacttctccataaaagattaaggacctggaaatgtaagatacatgaagaaaatctaagt
1981  ggagaggctgtttgtggttaagtgataacagtgttgtaagcgatgcatgaggtaggtgtt
2041  cagtgcatatcctctgcatttattaataaacactgtaaaatttagaagaaaattgtttc
2101  accaaatgcacataaaactaataaaatagagtggattttgatatgtccctcgtgcc
```

Figure 2I. The cDNA (SEQ ID. NO.: 18) and amino acid sequence (SEQ ID. NO.: 19) of 251P5G2 v.9. The start methionine is underlined. The open reading frame extends from nucleic acid 722-1489 including the stop codon.

```
   1 gtttttttttttttttttttttttttttttatttttaagggattcgtttaataggacttg
  61 tggtaagtggaataatgccatgcaaaggtccccatgtctaaccaccaggttctaggcatg
 121 tattatggtatatgagaaatgggaattcaggctgcagatgaaatcaaggttgataaccag
 181 ctgactctaaaacaaaaacattaacttgaattacagatttgggcctaatgtaattataag
 241 cattcttaaaagtgaaagaaataataagagaaactgagtgctgtgatgtgagtcagttaa
 301 actttttttcaacttttctttaggtgattattttcccttaacataaaatttactttag
 361 ctcaactatacaaacatgtgagttattgttatgtaaccatcactcttcattaagaaatgc
 421 tttgtaaaaagtgagccagttttcatatacattcttcaaaatacattctcaacattata
 481 tatcaaattatatatacatacatgcacacatacactatatatatcaaggatttatatgag
 541 aggattaattaagaaaaaaattagtggaataaaaataatgtttatgataattttggccat
 601 agaatatataatacagatgatgtgaagtacaaaatgttttttatacttcatattttgatg
 661 tacaaagtatgtttgtctttgtaattcagatgattactttgcacttgtgttcccatgaaa
       1   M  P  F  I  S  K  L  V  L  A  S  Q  P  T  L  F  S  F  F  S
 721 aATGCCTTTCATTTCTAAGCTGGTATTGGCATCTCAGCCAACACTTTTCTCCTTCTTTTC
      21   A  S  S  P  F  L  L  F  L  D  L  R  P  E  R  T  Y  L  P  V
 781 TGCGTCTTCTCCTTTTCTGCTTTTTCTGGATCTCAGGCCAGAGCGCACTTACCTACCAGT
      41   C  H  V  A  L  I  H  M  V  V  L  L  T  M  V  F  L  S  P  Q
 841 CTGTCATGTGGCCCTCATCCACATGGTGGTCCTTCTCACCATGGTGTTCTTGTCTCCACA
      61   L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTGAG
      81   R  V  I  R  V  L  S  I  C  T  T  C  L  L  G  M  L  Q  V  V
 961 GAGGGTGATCAGGGTCCTCTCCATTTGTACCACCTGCCTCCTGGGCATGCTGCAGGTCGT
     101   N  I  S  P  S  I  S  W  L  V  R  F  K  W  K  S  T  I  F  T
1021 CAACATCAGCCCCAGCATTTCCTGGTTGGTGAGGTTTAAATGGAAATCCACAATTTTTAC
     121   F  H  L  F  S  W  S  L  S  F  P  V  S  S  S  L  I  F  Y  T
1081 CTTCCATTTGTTCTCATGGTCTCTCAGTTTTCCTGTTAGTAGTAGCCTGATCTTTTACAC
     141   V  A  S  S  N  V  T  Q  I  N  L  H  V  S  K  Y  C  S  L  F
1141 TGTGGCTTCTTCCAATGTGACCCAGATCAATTTGCATGTCAGTAAATACTGTTCACTTTT
     161   P  I  N  S  I  I  R  G  L  F  F  T  L  S  L  F  R  D  V  F
1201 CCCAATAAACTCCATAATCAGAGGACTGTTTTTCACTCTGTCATTATTCAGAGATGTTTT
     181   L  K  Q  I  M  L  F  S  S  V  Y  M  M  T  L  I  Q  E  L  Q
1261 TCTTAAACAAATAATGCTGTTCTCAAGTGTCTACATGATGACTCTCATTCAGGAACTACA
     201   E  I  L  V  P  S  Q  P  Q  P  L  P  K  D  L  C  R  G  K  S
1321 GGAGATCCTGGTACCTTCACAGCCCCAGCCTCTACCTAAGGATCTTTGCAGAGGCAAGAG
```

Figure 2I (Con't)

```
 221  H  Q  H  I  L  L  P  V  S  F  S  V  G  M  Y  K  M  D  F  I
1381  CCATCAGCACATCCTGCTGCCGGTGAGTTTCTCGGTGGGCATGTACAAGATGGACTTCAT
 241  I  S  T  S  S  T  L  P  W  A  Y  D  R  G  V  *
1441  CATCTCAACCTCCTCAACATTGCCATGGGCATATGACCGTGGTGTCTAGaggctagtggg
1501  cagtgtctataccattgtcaggttttggtgctactgagatctgataaagggtaatcaa
1561  tgtgatgtaaactataagacaaatgtttaaaaggttaattgtatgaatcctgtcatgagt
1621  taaattattcagagtgttcattatagagaataatccaaagttaaaataattggataattt
1681  atttgtatgtaggataaaagtagtaggagattgcttcttgaagatttaaaattatattga
1741  gtgtaattatttgcattaaaataattttaaatgttttgaatagcaagtattgatataatt
1801  aaactttcgaataacttagtgctttgcctttattcctaatgtttatatggaagcatgtgg
1861  tcaatgtttgatgcattacagctctgagcggtccttctgtattaggtggtcatcatttat
1921  atacttctccataaaagattaaggacctggaaatgtaagatacatgaagaaaatctaagt
1981  ggagaggctgtttgtggttaagtgataacagtgttgtaagcgatgcatgaggtaggtgtt
2041  cagtgcatatcctctgcatttattaataaacactgtaaatttagaagaaaattgtttc
2101  accaaatgcacataaaactaataaaatagagtggattttgatatgtcctcgtgcc
```

Figure 2J. The cDNA (SEQ ID. NO. : 20) and amino acid sequence (SEQ ID. NO. : 21) of 251P5G2 v.10. The start methionine is underlined. The open reading frame extends from nucleic acid 722-1489 including the stop codon.

```
   1 gtttttttttttttttttttttttttttttatttaagggattcgtttaataggacttg
  61 tggtaagtggaataatgccatgcaaaggtccccatgtctaaccaccaggttctaggcatg
 121 tattatggtatatgagaaatgggaattcaggctgcagatgaaatcaaggttgataaccag
 181 ctgactctaaaacaaaaacattaacttgaattacagatttgggcctaatgtaattataag
 241 cattcttaaaagtgaaagaaataataagagaaactgagtactgtgatgtgagtcagttaa
 301 actttttttcaacttttcctttaggtgattattttcccttaacataaaatttactttag
 361 ctcaactatacaaacatgtgagttattgttatgtaaccatcactcttcattaagaaatgc
 421 tttgtaaaaagtgagccagttttcatatacattcttcaaaatacattctcaacattata
 481 catcaaattatatatacatacatgcacacatacactatatatatcaaggatttatatgag
 541 aggattaattaagaaaaaaattagtggaataaaaataatgtttatgataattttggccat
 601 agaatatataatacagatgatgtgaagtacaaaatgttttttatacttcatatttgatg
 661 tacaaagtatgtttgtctttgtaattcagatgattactttgcacttgtgttcccatgaaa
   1  M  P  F  I  S  K  L  V  L  A  S  Q  P  T  L  F  S  F  F  S
 721 aATGCCTTTCATTTCTAAGCTGGTATTGGCATCTCAGCCAACACTTTTCTCCTTCTTTTC
  21  A  S  S  P  F  L  L  F  L  D  L  R  P  E  R  T  Y  L  P  V
 781 TGCGTCTTCTCCTTTTCTGCTTTTTCTGGATCTCAGGCCAGAGCGCACTTACCTACCAGT
  41  C  H  V  A  L  I  H  M  V  V  L  L  T  M  V  F  L  S  P  Q
 841 CTGTCATCTGGCCCTCATCCACATGGTGGTCCTTCTCACCATGGTGTTCTTGTCTCCACA
  61  L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTGAG
  81  R  V  I  R  V  L  S  I  C  T  T  C  L  L  G  M  L  Q  V  V
 961 GAGGGTGATCAGGGTCCTCTCCATTTGTACCACCTGCCTCCTGGGCATGCTGCAGGTCGT
 101  N  I  S  P  S  I  S  W  L  V  R  F  K  W  K  S  T  I  F  T
1021 CAACATCAGCCCCAGCATTTCCTGGTTGGTGAGGTTTAAATGGAAATCCACAATTTTTAC
 121  F  H  L  F  S  W  S  L  S  F  P  V  S  S  S  L  I  F  Y  T
1081 CTTCCATTTGTTCTCATGGTCTCTCAGTTTTCCTGTTAGTAGTAGCCTGATCTTTTACAC
 141  V  A  S  S  N  V  T  Q  I  N  L  H  V  S  K  Y  C  S  L  F
1141 TGTGGCTTCTTCCAATGTGACCCAGATCAATTTGCATGTCAGTAAATACTGTTCACTTTT
 161  P  I  N  S  I  I  R  G  L  F  F  T  L  S  L  F  R  D  V  F
1201 CCCAATAAACTCCATAATCAGAGGACTGTTTTCACTCTGTCATTATTCAGAGATGTTTT
 181  L  K  Q  I  M  L  F  S  S  V  Y  M  M  T  L  I  Q  E  L  Q
1261 TCTTAAACAAATAATGCTGTTCTCAAGTGTCTACATGATGACTCTCATTCAGGAACTACA
 201  E  I  L  V  P  S  Q  P  Q  P  L  P  K  D  L  C  R  G  K  S
1321 GGAGATCCTGGTACCTTCACAGCCCCAGCCTCTACCTAAGGATCTTTGCAGAGGCAAGAG
```

Figure 2J (Con't)

```
 221 H  Q  H  I  L  L  P  V  S  F  S  V  G  M  Y  K  M  D  F  I
1381 CCATCAGCACATCCTGCTGCCGGTGAGTTTCTCGGTGGGCATGTACAAGATGGACTTCAT
 241 I  S  T  S  S  T  L  P  W  A  Y  D  R  G  V  *
1441 CATCTCAACCTCCTCAACATTGCCATGGGCATATGACCGTGGTGTCTAGaggctagtggg
1501 cagtgtctataccattgtcaggttttggtgctactgagatctgataaagggtaatcaa
1561 tgtgatgtaaactataagacaaatgtttaaaaggttaattgtatgaatcctgtcatgagt
1621 taaattattcagagtgttcattatagagaataatccaaagttaaaataattggataattt
1681 atttgtatgtaggataaaagtagtaggagattgcttcttgaagatttaaaattatattga
1741 gtgtaattatttgcattaaaataattttaaatgttttgaatagcaagtattgatataatt
1801 aaactttcgaataacttagtgctttgcctttattcctaatgtttatatggaagcatgtgg
1861 tcaatgtttgatgcattacagctctgagcggtccttctgtattaggtggtcatcatttat
1921 atacttctccataaaagattaaggacctggaaatgtaagatacatgaagaaaatctaagt
1981 ggagaggctgtttgtggttaagtgataacagtgttgtaagcgatgcatgaggtaggtgtt
2041 cagtgcatatcctctgcattttattaataaacactgtaaaatttagaagaaaattgtttc
2101 accaaatgcacataaaactaataaaatagagtggattttgatatgtccctcgtgcc
```

Figure 2K. The cDNA (SEQ ID. NO.: 22) and amino acid sequence (SEQ ID. NO.: 23) of 251P5G2 v.11. The start methionine is underlined. The open reading frame extends from nucleic acid 722-1489 including the stop codon.

```
   1 gttttttttttttttttttttttttttttatttttaagggattcgtttaataggacttg
  61 tggtaagtggaataatgccatgcaaaggtccccatgtctaaccaccaggttctaggcatg
 121 tattatggtatatgagaaatgggaattcaggctgcagatgatatcaaggttgataaccag
 181 ctgactctaaaacaaaaacattaacttgaattacagatttgggcctaatgtaattataag
 241 cattcttaaaagtgaaagaaataataagagaaactgagtgctgtgatgtgagtcagttaa
 301 actttttttcaacttttctttaggtgattattttcccttaacataaaatttactttag
 361 ctcaactatacaaacatgtgagttattgttatgtaaccatcactcttcattaagaaatgc
 421 tttgtaaaaagtgagccagttttcatatacattcttcaaaatacattctcaacattata
 481 catcaaattatatatacatacatgcacacatacactatatatatcaaggatttatatgag
 541 aggattaattaagaaaaaaattagtggaataaaaataatgtttatgataattttggccat
 601 agaatatataatacagatgatgtgaagtacaaaatgttttttatacttcatattttgatg
 661 tacaaagtatgtttgtctttgtaattcagatgattactttgcacttgtgttcccatgaaa
   1  M  P  F  I  S  K  L  V  L  A  S  Q  P  T  L  F  S  F  F  S
 721 aATGCCTTTCATTTCTAAGCTGGTATTGGCATCTCAGCCAACACTTTTCTCCTTCTTTTC
  21  A  S  S  P  F  L  L  F  L  D  L  R  P  E  R  T  Y  L  P  V
 781 TGCGTCTTCTCCTTTTCTGCTTTTTCTGGATCTCAGGCCAGAGCGCACTTACCTACCAGT
  41  C  H  V  A  L  I  H  M  V  V  L  L  T  M  V  F  L  S  P  Q
 841 CTGTCATGTGGCCCTCATCCACATGGTGGTCCTTCTCACCATGGTGTTCTTGTCTCCACA
  61  L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTCAG
  81  R  V  I  R  V  L  S  I  C  T  T  C  L  L  G  M  L  Q  V  V
 961 GAGGGTGATCAGGGTCCTCTCCATTTGTACCACCTGCCTCCTGGGCATGCTGCAGGTCGT
 101  N  I  S  P  I  S  W  L  V  R  F  K  W  K  S  T  I  F  T
1021 CAACATCAGCCCCAGCATTTCCTGGTTGGTGAGGTTTAAATGGAAATCCACAATTTTTAC
 121  F  H  L  F  S  W  S  L  S  F  P  V  S  S  S  L  I  F  Y  T
1081 CTTCCATTTGTTCTCATGGTCTCTCAGTTTTCCTGTTAGTAGTAGCCTGATCTTTTACAC
 141  V  A  S  S  N  V  T  Q  I  N  L  H  V  S  K  Y  C  S  L  F
1141 TGTGGCTTCTTCCAATGTGACCCAGATCAATTTGCATGTCAGTAAATACTGTTCACTTTT
 161  P  I  N  S  I  I  R  G  L  F  F  T  L  S  L  F  R  D  V  F
1201 CCCAATAAACTCCATAATCAGAGGACTGTTTTTCACTCTGTCATTATTCAGAGATGTTTT
 181  L  K  Q  I  M  L  F  S  S  V  Y  M  M  T  L  I  Q  E  L  Q
1261 TCTTAAACAAATAATGCTGTTCTCAAGTGTCTACATGATGACTCTCATTCAGGAACTACA
 201  E  I  L  V  P  S  Q  P  Q  P  L  P  K  D  L  C  R  G  K  S
1321 GGAGATCCTGGTACCTTCACAGCCCCAGCCTCTACCTAAGGATCTTTGCAGAGGCAAGAG
```

Figure 2K (Con't)

```
 221  H  Q  H  I  L  L  P  V  S  F  S  V  G  M  Y  K  M  D  F  I
1381  CCATCAGCACATCCTGCTGCCGGTGAGTTTCTCGGTGGGCATGTACAAGATGGACTTCAT
 241  I  S  T  S  S  T  L  P  W  A  Y  D  R  G  V  *
1441  CATCTCAACCTCCTCAACATTGCCATGGGCATATGACCGTGGTGTCTAGaggctagtggg
1501  cagtgtctataccattgtcaggttttggtgctactgagatctgataaaagggtaatcaa
1561  tgtgatgtaaactataagacaaatgtttaaaaggttaattgtatgaatcctgtcatgagt
1621  taaattattcagagtgttcattatagagaataatccaaagttaaaataattggataattt
1681  atttgtatgtaggataaaagtagtaggagattgcttcttgaagatttaaaattatattga
1741  gtgtaattatttgcattaaaataattttaaatgttttgaatagcaagtattgatataatt
1801  aaactttcgaataacttagtgctttgcctttattcctaatgtttatatggaagcatgtgg
1861  tcaatgtttgatgcattacagctctgagcggtccttctgtattaggtggtcatcatttat
1921  atacttctccataaaagattaaggacctggaaatgtaagatacatgaagaaaatctaagt
1981  ggagaggctgtttgtggttaagtgataacagtgttgtaagcgatgcatgaggtaggtgtt
2041  cagtgcatatcctctgcatttattaataaacactgtaaaatttagaagaaaattgtttc
2101  accaaatgcacataaaactaataaaatagagtggattttgatatgtccctcgtgcc
```

Figure 2L. The cDNA (SEQ ID. NO. : 24) and amino acid sequence (SEQ ID. NO. : 25) of 251P5G2 v.12.
The start methionine is underlined. The open reading frame extends from nucleic acid 722-4522 including the stop codon.

```
   1 gttttttttttttttttttttttttttttatttttaagggattcgtttaataggacttg
  61 tggtaagtggaataatgccatgcaaaggtccccatgtctaaccaccaggttctaggcatg
 121 tattatggtatatgagaaatggaattcaggctgcagatgaaatcaaggttgataaccag
 181 ctgactctaaaacaaaaacattaacttgaattacagatttgggcctaatgtaattataag
 241 cattcttaaaagtgaaagaaataataagagaaactgagtgctgtgatgtgagtcagttaa
 301 acttttttttcaacttttctttaggtgattattttcccttaacataaaatttactttag
 361 ctcaactatacaaacatgtgagttattgttatgtaaccatcactcttcattaagaaatgc
 421 tttgtaaaaagtgagccagttttcatatacattcttcaaaatacattctcaacattata
 481 catcaaattatatatacatacatgcacacatacactatatatatcaaggatttatatgag
 541 aggattaattaagaaaaaaattagtggaataaaaataatgtttatgataattttggccat
 601 agaatatataatacagatgatgtgaagtacaaaatgttttttatacttcatattttgatg
 661 tacaaagtatgtttgtctttgtaattcagatgattactttgcacttgtgttcccatgaaa
   1  M  P  F  I  S  K  L  V  L  A  S  Q  P  T  L  F  S  F  F  S
 721 aATGCCTTTCATTTCTAAGCTGGTATTGGCATCTCAGCCAACACTTTTCTCCTTCTTTTC
  21  A  S  S  P  F  L  L  F  L  D  L  R  P  E  R  T  Y  L  P  V
 781 TGCGTCTTCTCCTTTTCTGCTTTTTCTGGATCTCAGGCCAGAGCGCACTTACCTACCAGT
  41  C  H  V  A  L  I  H  M  V  V  L  L  T  M  V  F  L  S  P  Q
 841 CTGTCATGTGGCCCTCATCCACATGGTGGTCCTTCTCACCATGGTGTTCTTGTCTCCACA
  61  L  F  E  S  L  N  F  Q  N  D  F  K  Y  E  A  S  F  Y  L  R
 901 GCTCTTTGAATCACTGAATTTTCAGAATGACTTCAAATATGAGGCATCTTTCTACCTGAG
  81  R  V  I  R  V  L  S  I  C  T  T  C  L  L  D  M  L  Q  V  V
 961 GAGGGTGATCAGGGTCCTCTCCATTTGTACCACCTGCCTCCTGGACATGCTGCAGGTCGT
 101  N  I  S  P  S  I  S  W  L  I  M  L  F  S  S  V  Y  M  M  T
1021 CAACATCAGCCCCAGCATTTCCTGGTTGATAATGCTGTTCTCAAGTGTCTACATGATGAC
 121  L  I  Q  E  L  Q  E  I  L  V  P  S  Q  P  Q  P  L  P  K  D
1081 TCTCATTCAGGAACTACAGGAGATCCTGGTACCTTCACAGCCCCAGCCTCTACCTAAGGA
 141  L  C  R  G  K  S  H  Q  H  I  L  L  P  T  Q  A  T  F  A  A
1141 TCTTTGCAGAGGCAAGAGCCATCAGCACATCCTGCTGCCGACTCAAGCAACTTTTGCTGC
 161  A  T  G  L  W  A  A  L  T  T  V  S  N  P  S  R  A  D  P  V
1201 AGCAACTGGACTATGGCTGCACTAACCACCGTATCAAATCCAAGCAGAGCAGATCCTGT
 181  T  W  R  K  E  P  A  V  L  P  C  C  N  L  E  K  G  S  W  L
1261 GACCTGGAGAAAGGAGCCGGCTGTCCTTCCCTGCTGTAACCTAGAGAAAGGAAGCTGGCT
 201  S  F  P  G  T  A  A  R  K  E  F  S  T  T  L  T  G  H  S  A
1321 GTCCTTCCCTGGCACAGCTGCACGCAAGGAATTTTCCACCACGCTCACCGGGCACAGCGC
```

Figure 2L (Con't)

```
 221    L  S  L  S  S  S  R  A  L  P  G  S  L  P  A  F  A  D  L  P
1381   GCTGAGCCTCTCCAGTTCGCGGGCCCTCCCCGGCTCGCTCCCGGCTTTCGCAGACCTCCC
 241    R  S  C  P  E  S  E  Q  S  A  T  P  A  G  A  F  L  L  G  W
1441   CCGCTCCTGCCCTGAGTCCGAGCAGAGCGCAACGCCAGCCGGCGCCTTCCTCCTGGGCTG
 261    E  R  V  V  Q  R  R  L  E  V  P  R  P  Q  A  A  P  A  T  S
1501   GGAGCGAGTGGTGCAGCGGCGGCTCGAAGTCCCCCGGCCTCAAGCAGCCCCCGCGACTAG
 281    A  T  P  S  R  D  P  S  P  P  C  H  Q  R  R  D  A  A  C  L
1561   CGCGACACCCTCGCGGGATCCGAGTCCACCCTGCCACCAGCGCCGGGACGCCGCGTGCCT
 301    R  A  Q  G  L  T  R  A  F  Q  V  V  H  L  A  P  T  A  P  D
1621   CAGAGCCCAAGGGCTGACCCGGGCCTTCCAGGTGGTCCATCTCGCTCCTACGGCTCCCGA
 321    G  G  A  G  C  P  P  S  R  N  S  Y  R  L  T  H  V  R  C  A
1681   CGGTGGCGCTGGGTGTCCCCCATCCCGCAATTCCTACCGGCTGACCCATGTGCGCTGCGC
 341    Q  G  L  E  A  A  S  A  N  L  P  G  A  P  G  R  S  S  S  C
1741   CCAGGGGCTGGAGGCTGCCAGCGCCAACCTTCCCGGCGCTCCGGGGCGGAGCAGCTCCTG
 361    A  L  R  Y  R  S  G  P  S  V  S  S  A  P  S  P  A  E  P  P
1801   CGCCCTGCGCTACCGCAGCGGCCCTTCAGTCAGCTCCGCGCCGTCCCCGCAGAGCCCCC
 381    A  H  Q  R  L  L  F  L  P  R  A  P  Q  A  V  S  G  P  Q  E
1861   GGCGCACCAGCGCCTGCTTTTCCTTCCCCGAGCGCCTCAAGCAGTCTCTGGGCCGCAGGA
 401    Q  P  S  E  E  A  L  G  V  G  S  L  S  V  F  Q  L  H  L  I
1921   ACAGCCCTCTGAAGAGGCGCTTGGTGTAGGAAGCCTCTCAGTTTTCCAGTTACACCTAAT
 421    Q  C  I  P  N  L  S  Y  P  L  V  L  R  H  I  P  E  I  L  K
1981   ACAGTGTATTCCAAATCTAAGTTACCCACTAGTACTTCGGCACATTCCAGAAATTCTGAA
 441    F  S  E  K  E  T  G  G  G  I  L  G  L  E  L  P  A  T  A  A
2041   ATTTTCTGAAAAGGAAACTGGTGGTGGAATTCTAGGCTTAGAATTACCAGCGACAGCTGC
 461    R  L  S  G  L  N  S  I  M  Q  I  K  E  F  E  E  L  V  K  L
2101   TCGCCTCTCAGGATTAAACAGCATAATGCAAATCAAAGAGTTTGAAGAATTGGTAAAACT
 481    H  S  L  S  H  K  V  I  Q  C  V  F  A  K  K  K  N  V  D  K
2161   TCACAGCTTGTCACACAAAGTCATTCAGTGTGTGTTTGCAAAGAAAAAAAATGTAGACAA
 501    W  D  D  F  C  L  S  E  G  Y  H  S  F  L  I  M  K  E  T
2221   ATGGGATGACTTTTGTCTTAGTGAGGGTTATGGACATTCATTCTTAATAATGAAAGAAAC
 521    S  T  K  I  S  G  L  I  Q  E  M  G  S  G  K  S  N  V  G  T
2281   GTCGACTAAAATATCAGGTTTAATTCAGGAGATGGGGAGCGGCAAGAGCAACGTGGGCAC
 541    W  G  D  Y  D  D  S  A  F  M  E  P  R  Y  H  V  R  R  E  D
2341   TTGGGGAGACTACGACGACAGCGCCTTCATGGAGCCGAGGTACCACGTCCGTCGAGAAGA
 561    L  D  K  L  H  R  A  A  W  W  G  K  V  P  R  K  D  L  I  V
2401   TCTGGACAAGCTCCACAGAGCTGCCTGGTGGGGTAAAGTCCCCAGAAAGGATCTCATCGT
```

Figure 2L (Con't)

```
581   M  L  R  D  T  D  M  N  K  R  D  K  Q  K  R  T  A  L  H  L
2461  CATGCTCAGGGACACTGACATGAACAAGAGGGACAAGCAAAAGAGGACTGCTCTACATTT
601   A  S  A  N  G  N  S  E  V  V  Q  L  L  L  D  R  R  C  Q  L
2521  GGCCTCTGCCAATGGAAATTCAGAAGTAGTACAACTCCTGCTGGACAGACGATGTCAACT
621   N  V  L  D  N  K  K  R  T  A  L  I  K  A  V  Q  C  Q  E  D
2581  TAACGTCCTTGACAACAAAAAAAGGACAGCTCTGATAAAGGCCGTACAATGCCAGGAAGA
641   E  C  V  L  M  L  L  E  H  G  A  D  G  N  I  Q  D  E  Y  G
2641  TGAATGTGTGTTAATGTTGCTGGAACATGGCGCTGATGGAAATATTCAAGATGAGTATGG
661   N  T  A  L  H  Y  A  I  Y  N  E  D  K  L  M  A  K  A  L  L
2701  AAATACCGCTCTACACTATGCTATCTACAATGAAGATAAATTAATGGCCAAAGCACTGCT
681   L  Y  G  A  D  I  E  S  K  N  K  C  G  L  T  P  L  L  L  G
2761  CTTATATGGTGCTGATATTGAATCAAAAAACAAGTGTGGCCTCACACCACTTTTGCTTGG
701   V  H  E  Q  K  Q  E  V  V  K  F  L  I  K  K  K  A  N  L  N
2821  CGTACATGAACAAAAACAGGAAGTGGTGAAATTTTTAATCAAGAAAAAAGCTAATTTAAA
721   A  L  D  R  Y  G  R  T  A  L  I  L  A  V  C  C  G  S  A  S
2881  TGCACTTGATAGATATGGAAGAACTGCCCTCATACTTGCTGTATGTTGTGGATCAGCAAG
741   I  V  N  L  L  E  Q  N  V  D  V  S  S  Q  D  L  S  G  Q
2941  TATAGTCAATCTTCTACTTGAGCAAAATGTTGATGTATCTTCTCAAGATCTATCTGGACA
761   T  A  R  E  Y  A  V  S  S  H  H  H  V  I  C  E  L  L  S  D
3001  GACGGCCAGAGAGTATGCTGTTTCTAGTCATCATCATGTAATTTGTGAATTACTTTCTGA
781   Y  K  E  K  Q  M  L  K  I  S  S  E  N  S  N  P  V  I  T  I
3061  CTATAAAGAAAAACAGATGCTAAAAATCTCTTCTGAAAACAGCAATCCAGTGATAACCAT
801   L  N  I  K  L  P  L  K  V  E  E  I  K  K  H  G  S  N  P
3121  CCTTAATATCAAACTTCCACTCAAGGTTGAAGAAGAAATAAAGAAGCATGGAAGTAATCC
821   V  G  L  P  E  N  L  T  N  G  A  S  A  G  N  G  D  D  G  L
3181  TGTGGGATTACCAGAAAACCTGACTAATGGTGCCAGTGCTGGCAATGGTGATGATGGATT
841   I  P  Q  R  K  S  R  K  P  E  N  Q  Q  F  P  D  T  E  N  E
3241  AATTCCACAAAGGAAGAGCAGAAAACCTGAAAATCAGCAATTTCCTGACACTGAGAATGA
861   E  Y  H  S  D  E  Q  N  D  T  Q  K  Q  L  S  E  E  Q  N  T
3301  AGAGTATCACAGTGACGAACAAAATGATACCCAGAAACAACTTTCTGAAGAACAGAACAC
881   G  I  S  Q  D  E  I  L  T  N  K  Q  K  Q  I  E  V  A  E  K
3361  TGGAATATCACAAGATGAGATTCTGACTAATAAACAAAAGCAGATAGAAGTGGCTGAAAA
901   E  M  N  S  E  L  S  L  S  H  K  K  E  E  D  L  L  R  E  N
3421  GGAAATGAATTCTGAGCTTTCTCTTAGTCATAAGAAAGAAGAAGATCTCTTGCGTGAAAA
921   S  M  L  R  E  E  I  A  K  L  R  L  E  L  D  E  T  K  H  Q
3481  CAGCATGTTGCGGGAAGAAATTGCCAAGCTAAGACTGGAACTAGATGAAACAAAACATCA
```

Figure 2L (Con't)

```
 941  N  Q  L  R  E  N  K  I  L  E  E  I  E  S  V  K  E  K  L  L
3541  GAACCAGCTAAGGGAAAATAAAATTTTGGAGGAAATTGAAAGTGTAAAAGAAAAACTTCT
 961  K  T  I  Q  L  N  E  E  A  L  T  K  T  K  V  A  G  F  S  L
3601  AAAGACTATACAACTGAATGAAGAAGCATTAACGAAAACCAAGGTGGCTGGTTTCTCTTT
 981  R  Q  L  G  L  A  Q  H  A  Q  A  S  V  Q  Q  L  C  Y  K  W
3661  GCGCCAGCTTGGCCTTGCCCAGCATGCACAAGCCTCAGTGCAACAGCTGTGCTACAAATG
1001  N  H  T  E  K  T  E  Q  Q  A  Q  E  Q  E  V  A  G  F  S  L
3721  GAACCACACAGAGAAAACAGAGCAGCAGGCTCAGGAGCAGGAGGTGGCTGGTTTCTCTTT
1021  R  Q  L  G  L  A  Q  H  A  Q  A  S  V  Q  Q  L  C  Y  K  W
3781  GCGCCAGCTTGGCCTTGCCCAGCATGCACAAGCCTCAGTACAACAACTGTGCTACAAATG
1041  G  H  T  E  K  T  E  Q  Q  A  Q  E  Q  G  A  A  L  R  S  Q
3841  GGGCCACACAGAGAAAACAGAGCAGCAGGCTCAGGAGCAGGGAGCTGCGCTGAGGTCCCA
1061  I  G  D  P  G  G  V  P  L  S  E  G  G  T  A  A  G  D  Q  G
3901  GATAGGCGACCCTGGCGGGGTGCCCCTGAGCGAAGGGGGGACAGCAGCAGGAGACCAGGG
1081  P  G  T  H  L  P  P  R  E  P  R  A  S  P  G  T  P  S  L  V
3961  TCCAGGGACCCACCTCCCACCGAGGGAACCTCGAGCCTCCCCTGGCACCCCTAGCTTGGT
1101  R  L  A  S  G  A  R  A  A  A  L  P  P  P  T  G  K  N  G  R
4021  CCGCCTGGCCTCCGGAGCCCGAGCTGCTGCGCTTCCCCCACCCACAGGGAAAAACGGCCG
1121  S  P  T  K  Q  K  S  V  C  D  S  S  G  W  I  L  P  V  P  T
4081  ATCTCCAACCAAACAGAAATCTGTGTGTGACTCCTCTGGTTGGATACTGCCAGTCCCCAC
1141  F  S  S  G  S  F  L  G  R  R  C  P  M  F  D  V  S  P  A  M
4141  ATTTTCTTCCGGGAGTTTTCTTGGCAGAAGGTGCCCAATGTTTGATGTTTCGCCAGCCAT
1161  R  L  K  S  D  S  N  R  E  T  H  Q  A  F  R  D  K  D  D  L
4201  GAGGCTGAAAAGTGACAGCAATAGAGAAACACATCAGGCTTTCCGCGACAAAGATGACCT
1181  P  F  F  K  T  Q  Q  S  P  R  H  T  K  D  L  G  Q  D  D  R
4261  TCCCTTCTTCAAAACTCAGCAATCTCCACGGCACACAAAGGACTTAGGACAAGATGACCG
1201  A  G  V  L  A  P  K  C  R  P  G  T  L  C  H  T  D  T  P  P
4321  AGCTGGAGTGCTCGCCCCAAAATGCAGGCCCGGAACACTCTGCCACACGGACACACCACC
1221  H  R  N  A  D  T  P  P  H  R  H  T  T  T  L  P  H  R  D  T
4381  ACACAGAAATGCGGACACACCACCACACAGACACACCACCACGCTGCCACACAGAGACAC
1241  T  T  S  L  P  H  F  H  V  S  A  G  G  V  G  P  T  T  L  G
4441  CACCACATCGTTGCCACACTTTCATGTGTCAGCTGGCGGTGTGGGCCCCACGACTCTGGG
1261  S  N  R  E  I  T  *
4501  CTCTAATAGAGAAATTACTTAG
```

Figure 2M. The cDNA (SEQ ID. NO. : 26) and amino acid sequence (SEQ ID. NO. : 27) of 251P5G2 v.13. The start methionine is underlined. The open reading frame extends from nucleic acid 1-3801 including the stop codon.

```
  1 M   P   F   I   S   K   L   V   L   A   S   Q   P   T   L   F   S   F   F   S
  1 ATGCCTTTCATTTCTAAGCTGGTATTGGCATCTCAGCCAACACTTTTCTCCTTCTTTTCT
 21 A   S   S   P   F   L   L   F   L   D   L   R   P   E   R   T   Y   L   P   V
 61 GCGTCTTCTCCTTTTCTGCTTTTTCTGGATCTCAGGCCAGAGCGCACTTACCTACCAGTC
 41 C   H   V   A   L   I   H   M   V   V   L   L   T   M   V   F   L   S   P   Q
121 TGTCATGTGGCCCTCATCCACATGGTGGTCCTTCTCACCATGGTGTTCTTGTCTCCACAG
 61 L   F   E   S   L   N   F   Q   N   D   F   K   Y   E   A   S   F   Y   L   R
181 CTCTTTGAATCACTGAATTTTCAGAATGACTTCAAATATGAGGCATCTTTCTACCTGAGG
 81 R   V   I   R   V   L   S   I   C   T   T   C   L   L   D   M   L   Q   V   V
241 AGGGTGATCAGGGTCCTCTCCATTTGTACCACCTGCCTCCTGGACATGCTGCAGGTCGTC
101 N   I   S   P   S   I   S   W   L   I   M   L   F   S   S   V   Y   M   M   T
301 AACATCAGCCCCAGCATTTCCTGGTTGATAATGCTGTTCTCAAGTGTCTACATGATGACT
121 L   I   Q   E   L   Q   E   I   L   V   P   S   Q   P   Q   P   L   P   K   D
361 CTCATTCAGGAACTACAGGAGATCCTGGTACCTTCACAGCCCCAGCCTCTACCTAAGGAT
141 L   C   R   G   K   S   H   Q   H   I   L   L   P   T   Q   A   T   F   A   A
421 CTTTGCAGAGGCAAGAGCCATCAGCACATCCTGCTGCCGACTCAAGCAACTTTTGCTGCA
161 A   T   G   L   W   A   A   L   T   T   V   S   N   P   S   R   A   D   P   V
481 GCAACTGGACTATGGGCTGCACTAACCACCGTATCAAATCCAAGCAGAGCAGATCCTGTG
181 T   W   R   K   E   P   A   V   L   P   C   C   N   L   E   K   G   S   W   L
541 ACCTGGAGAAAGGAGCCGGCTGTCCTTCCCTGCTGTAACCTAGAGAAAGGAAGCTGGCTG
201 S   F   P   G   T   A   A   R   K   E   F   S   T   T   L   T   G   H   S   A
601 TCCTTCCCTGGCACAGCTGCACGCAAGGAATTTTCCACCACGCTCACCGGGCACAGCGCG
221 L   S   L   S   S   R   A   L   P   G   S   L   P   A   F   A   D   L   P
661 CTGAGCCTCTCCAGTTCGCGGGCCCTCCCCGGCTCGCTCCCGGCTTTCGCAGACCTCCCC
241 R   S   C   P   E   S   E   Q   S   A   T   P   A   G   A   F   L   L   G   W
721 CGCTCCTGCCCTGAGTCCGAGCAGAGCGCAACGCCAGCCGGCGCCTTCCTCCTGGGCTGG
261 E   R   V   V   Q   R   R   L   E   V   P   R   P   Q   A   A   P   A   T   S
781 GAGCGAGTGGTGCAGCGGCGGCTCGAAGTCCCCCGGCCTCAAGCAGCCCCCGCGACTAGC
281 A   T   P   S   R   D   P   S   P   P   C   H   Q   R   R   D   A   A   C   L
841 GCGACACCCTCGCGGGATCCGAGTCCACCCTGCCACCAGCGCCGGGACGCCGCGTGCCTC
301 R   A   Q   G   L   T   R   A   F   Q   V   V   H   L   A   P   T   A   P   D
901 AGAGCCCAAGGGCTGACCCGGGCCTTCCAGGTGGTCCATCTCGCTCCTACGGCTCCCGAC
321 G   G   A   G   C   P   P   S   R   N   S   Y   R   L   T   H   V   R   C   A
961 GGTGGCGCTGGGTGTCCCCCATCCCGCAATTCCTACCGGCTGACCCATGTGCGCTGCGCC
```

Figure 2M (Con't)

```
 341 Q  G  L  E  A  A  S  A  N  L  P  G  A  P  G  R  S  S  S  C
1021 CAGGGGCTGGAGGCTGCCAGCGCCAACCTTCCCGGCGCTCCGGGGCGGAGCAGCTCCTGC
 361 A  L  R  Y  R  S  G  P  S  V  S  S  A  P  S  P  A  E  P  P
1081 GCCCTGCGCTACCGCAGCGGCCCTTCAGTCAGCTCCGCGCCGTCCCCCGCAGAGCCCCCG
 381 A  H  Q  R  L  L  F  L  P  R  A  P  Q  A  V  S  G  P  Q  E
1141 GCGCACCAGCGCCTGCTTTTCCTTCCCCGAGCGCCTCAAGCAGTCTCTGGGCCGCAGGAA
 401 Q  P  S  E  E  A  L  G  V  G  S  L  S  V  F  Q  L  H  L  I
1201 CAGCCCTCTGAAGAGGCGCTTGGTGTAGGAAGCCTCTCAGTTTTCCAGTTACACCTAATA
 421 Q  C  I  P  N  L  S  Y  P  L  V  L  R  E  I  P  E  I  L  K
1261 CAGTGTATTCCAAATCTAAGTTACCCACTAGTACTTCGGCACATTCCAGAAATTCTGAAA
 441 F  S  E  K  E  T  G  G  G  I  L  G  L  E  L  P  A  T  A  A
1321 TTTTCTGAAAAGGAAACTGGTGGTGGAATTCTAGGCTTAGAATTACCAGCGACAGCTGCT
 461 R  L  S  G  L  N  S  I  M  Q  I  K  E  F  E  E  L  V  K  L
1381 CGCCTCTCAGGATTAAACAGCATAATGCAAATCAAAGAGTTTGAAGAATTGGTAAAACTT
 481 H  S  L  S  H  K  V  I  Q  C  V  F  A  K  K  K  N  V  D  K
1441 CACAGCTTGTCACACAAAGTCATTCAGTGTGTGTTTGCAAAGAAAAAAAATGTAGACAAA
 501 W  D  D  F  C  L  S  E  G  Y  G  H  S  F  L  I  M  K  E  T
1501 TGGGATGACTTTTGTCTTAGTGAGGGTTATGGACATTCATTCTTAATAATGAAAGAAACG
 521 S  T  K  I  S  G  L  I  Q  E  M  G  S  G  K  S  N  V  G  T
1561 TCGACTAAAATATCAGGTTTAATTCAGGAGATGGGGAGCGGCAAGAGCAACGTGGGCACT
 541 W  G  D  Y  D  D  S  A  F  M  E  P  R  Y  H  V  R  R  E  D
1621 TGGGGAGACTACGACGACAGCGCCTTCATGGAGCCGAGGTACCACGTCCGTCGAGAAGAT
 561 L  D  K  L  H  R  A  A  W  W  G  K  V  P  R  K  D  L  I  V
1681 CTGGACAAGCTCCACAGAGCTGCCTGGTGGGGTAAAGTCCCCAGAAAGGATCTCATCGTC
 581 M  L  R  D  T  D  M  N  K  R  D  K  Q  K  R  T  A  L  H  L
1741 ATGCTCAGGGACACTGACATGAACAAGAGGGACAAGCAAAAGAGGACTGCTCTACATTTG
 601 A  S  A  N  G  N  S  E  V  V  Q  L  L  L  D  R  R  C  Q  L
1801 GCCTCTGCCAATGGAAATTCAGAAGTAGTACAACTCCTGCTGGACAGACGATGTCAACTT
 621 N  V  L  D  N  K  K  R  T  A  L  I  K  A  V  Q  C  Q  E  D
1861 AACGTCCTTGACAACAAAAAAAGGACAGCTCTGATAAAGGCCGTACAATGCCAGGAAGAT
 641 E  C  V  L  M  L  L  E  H  G  A  D  G  N  I  Q  D  E  Y  G
1921 GAATGTGTGTTAATGTTGCTGGAACATGGCGCTGATGGAAATATTCAAGATGAGTATGGA
 661 N  T  A  L  H  Y  A  I  Y  N  E  D  K  L  M  A  K  A  L  L
1981 AATACCGCTCTACACTATGCTATCTACAATGAAGATAAATTAATGGCCAAAGCACTGCTC
 681 L  Y  G  A  D  I  E  S  K  N  C  G  L  T  P  L  L  L  G
2041 TTATATGGTGCTGATATTGAATCAAAAAACAAGTGTGGCCTCACACCACTTTTGCTTGGC
```

Figure 2M (Con't)

```
 701 V  H  E  Q  K  Q  E  V  V  K  F  L  I  K  K  K  A  N  L  N
2101 GTACATGAACAAAAACAGGAAGTGGTGAAATTTTTAATCAAGAAAAAGCTAATTTAAAT
 721 A  L  D  R  Y  G  R  T  A  L  I  L  A  V  C  C  G  S  A  S
2161 GCACTTGATAGATATGGAAGAACTGCCCTCATACTTGCTGTATGTTGTGGATCAGCAAGT
 741 I  V  N  L  L  E  Q  N  V  D  V  S  S  Q  D  L  S  G  Q
2221 ATAGTCAATCTTCTACTTGAGCAAAATGTTGATGTATCTTCTCAAGATCTATCTGGACAG
 761 T  A  R  E  Y  A  V  S  S  H  H  H  V  I  C  E  L  L  S  D
2281 ACGGCCAGAGAGTATGCTGTTTCTAGTCATCATCATGTAATTTGTGAATTACTTTCTGAC
 781 Y  K  E  K  Q  M  L  K  I  S  S  E  N  S  N  P  V  I  T  I
2341 TATAAAGAAAAACAGATGCTAAAAATCTCTTCTGAAAACAGCAATCCAGTGATAACCATC
 801 L  N  I  K  L  P  L  K  V  E  E  E  I  K  K  H  G  S  N  P
2401 CTTAATATCAAACTTCCACTCAAGGTTGAAGAAGAAATAAAGAAGCATGGAAGTAATCCT
 821 V  G  L  P  E  N  L  T  N  G  A  S  A  G  N  G  D  D  G  L
2461 GTGGGATTACCAGAAAACCTGACTAATGGTGCCAGTGCTGGCAATGGTGATGATGGATTA
 841 I  P  Q  R  K  S  R  K  P  E  N  Q  Q  F  P  D  T  E  N  E
2521 ATTCCACAAAGGAAGAGCAGAAAACCTGAAAATCAGCAATTTCCTGACACTGAGAATGAA
 861 E  Y  H  S  D  E  Q  N  D  T  Q  K  Q  L  S  E  E  Q  N  T
2581 GAGTATCACAGTGACGAACAAAATGATACCCAGAAACAACTTTCTGAAGAACAGAACACT
 881 G  I  S  Q  D  E  I  L  T  N  K  Q  K  Q  I  E  V  A  E  K
2641 GGAATATCACAAGATGAGATTCTGACTAATAAACAAAAGCAGATAGAAGTGGCTGAAAAG
 901 E  M  N  S  E  L  S  L  S  H  K  K  E  E  D  L  L  R  E  N
2701 GAAATGAATTCTGAGCTTTCTCTTAGTCATAAGAAAGAAGAAGATCTCTTGCGTGAAAAC
 921 S  M  L  R  E  E  I  A  K  L  R  L  E  L  D  E  T  K  H  Q
2761 AGCATGTTGCGGGAAGAAATTGCCAAGCTAAGACTGGAACTAGATGAAACAAAACATCAG
 941 N  Q  L  R  E  N  K  I  L  E  E  I  E  S  V  K  E  K  L  L
2821 AACCAGCTAAGGGAAAATAAAATTTTGGAGGAAATTGAAAGTGTAAAAGAAAAACTTCTA
 961 K  T  I  Q  L  N  E  E  A  L  T  K  T  K  V  A  G  F  S  L
2881 AAGACTATACAACTGAATGAAGAAGCATTAACGAAAACCAAGGTGGCTGGTTTCTCTTTG
 981 R  Q  L  G  L  A  Q  H  A  Q  A  S  V  Q  Q  L  C  Y  K  W
2941 CGCCAGCTTGGCCTTGCCCAGCATGCACAAGCCTCAGTGCAACAGCTGTGCTACAAATGG
1001 N  H  T  E  K  T  E  Q  Q  A  Q  E  Q  E  V  A  G  F  S  L
3001 AACCACACAGAGAAAACAGAGCAGCAGGCTCAGGAGCAGGAGGTGGCTGGTTTCTCTTTG
1021 R  Q  L  G  L  A  Q  H  A  Q  A  S  V  Q  Q  L  C  Y  K  W
3061 CGCCAGCTTGGCCTTGCCCAGCATGCACAAGCCTCAGTACAACAACTGTGCTACAAATGG
1041 G  H  T  E  K  T  E  Q  Q  A  Q  E  Q  G  A  A  L  R  S  Q
3121 GGCCACACAGAGAAAACAGAGCAGCAGGCTCAGGAGCAGGGAGCTGCGCTGAGGTCCCAG
```

Figure 2M (Con't)

```
1061 I   G   D   P   G   G   V   P   L   S   E   G   G   T   A   A   G   D   Q   G
3181 ATAGGCGACCCTGGCGGGGTGCCCCTGAGCGAAGGGGGGACAGCAGCAGGAGACCAGGGT

1081 P   G   T   H   L   P   P   R   E   P   R   A   S   P   G   T   P   S   L   V
3241 CCAGGGACCCACCTCCCACCGAGGGAACCTCGAGCCTCCCCTGGCACCCCTAGCTTGGTC

1101 R   L   A   S   G   A   R   A   A   A   L   P   P   P   T   G   K   N   G   R
3301 CGCCTGGCCTCCGGAGCCCGAGCTGCTGCGCTTCCCCCACCCACAGGGAAAAACGGCCGA

1121 S   P   T   K   Q   K   S   V   C   D   S   S   G   W   I   L   P   V   P   T
3361 TCTCCAACCAAACAGAAATCTGTGTGTGACTCCTCTGGTTGGATACTGCCAGTCCCCACA

1141 F   S   S   G   S   F   L   G   R   R   C   P   M   F   D   V   S   P   A   M
3421 TTTTCTTCCGGGAGTTTTCTTGGCAGAAGGTGCCCAATGTTTGATGTTTCGCCAGCCATG

1161 R   L   K   S   D   S   N   R   E   T   H   Q   A   F   R   D   K   D   D   L
3481 AGGCTGAAAAGTGACAGCAATAGAGAAACACATCAGGCTTTCCGCGACAAAGATGACCTT

1181 P   F   F   K   T   Q   Q   S   P   R   H   T   K   D   L   G   Q   D   D   R
3541 CCCTTCTTCAAAACTCAGCAATCTCCACGGCACACAAAGGACTTAGGACAAGATGACCGA

1201 A   G   V   L   A   P   K   C   R   P   G   T   L   C   H   T   D   T   P   P
3601 GCTGGAGTGCTCGCCCCAAAATGCAGGCCCGGAACACTCTGCCACACGGACACACCACCA

1221 H   R   N   A   D   T   P   P   H   R   H   T   T   T   L   P   H   R   D   T
3661 CACAGAAATGCGGACACACCACCACACAGACACACCACCACGCTGCCACACAGAGACACC

1241 T   T   S   L   P   H   F   H   V   S   A   G   G   V   G   P   T   T   L   G
3721 ACCACATCGTTGCCACACTTTCATGTGTCAGCTGGCGGTGTGGGCCCCACGACTCTGGGC

1261 S   N   R   E   I   T   *
3781 TCTAATAGAGAAATTACTTAG
```

Figure 3A. Amino acid sequence of 251P5G2 v.1 clone 4.7 (SEQ ID. NO. : 28). The 251P5G2 v.1 protein has 255 amino acids.

```
  1 MPFISKLVLA SQPTLFSFFS ASSPFLLFLD LRPERTYLPV CHVALIHMVV LLTMVFLSPQ
 61 LFESLNFQND FKYEASFYLR RVIRVLSICT TCLLGMLQVV NISPSISWLV RFKWKSTIFT
121 FHLFSWSLSF PVSSSLIFYT VASSNVTQIN LHVSKYCSLF PINSIIRGLF FTLSLFRDVF
181 LKQIMLFSSV YMMTLIQELQ EILVPSQPQP LPKDLCRGKS HQHILLPVSF SVGMYKMDFI
241 ISTSSTLPWA YDRGV
```

Figure 3B. Amino acid sequence of 251P5G2 v.2 (SEQ ID. NO. : 29). The 251P5G2 v.2 protein has 255 amino acids.

```
  1 MPFISKLVLA SQPTLCSFFS ASSPFLLFLD LRPERTYLPV CHVALIHMVV LLTMVFLSPQ
 61 LFESLNFQND FKYEASFYLR RVIRVLSICT TCLLGMLQVV NISPSISWLV RFKWKSTIFT
121 FHLFSWSLSF PVSSSLIFYT VASSNVTQIN LHVSKYCSLF PINSIIRGLF FTLSLFRDVF
181 LKQIMLFSSV YMMTLIQELQ EILVPSQPQP LPKDLCRGKS HQHILLPVSF SVGMYKMDFI
241 ISTSSTLPWA YDRGV
```

Figure 3C. Amino acid sequence of 251P5G2 v.3 (SEQ ID. NO. : 30). The 251P5G2 v.3 protein has 255 amino acids.

```
  1 MPFISKLVLA SQPTLFSFFS ASSPFLLFLD LRPERTYLPV CHVALIHMVV LLTMVFLSPQ
 61 LFESLNFQND FKYEASFYLR RVIRDLSICT TCLLGMLQVV NISPSISWLV RFKWKSTIFT
121 FHLFSWSLSF PVSSSLIFYT VASSNVTQIN LHVSKYCSLF PINSIIRGLF FTLSLFRDVF
181 LKQIMLFSSV YMMTLIQELQ EILVPSQPQP LPKDLCRGKS HQHILLPVSF SVGMYKMDFI
241 ISTSSTLPWA YDRGV
```

Figure 3D. Amino acid sequence of 251P5G2 v.4 (SEQ ID. NO. : 31). The 251P5G2 v.4 protein has 255 amino acids.

```
  1 MPFISKLVLA SQPTLFSFFS ASSPFLLFLD LRPERTYLPV CHVALIHMVV LLTMVFLSPQ
 61 LFESLNFQND FKYEASFYLR RVIRVLSICT TCLLDMLQVV NISPSISWLV RFKWKSTIFT
121 FHLFSWSLSF PVSSSLIFYT VASSNVTQIN LHVSKYCSLF PINSIIRGLF FTLSLFRDVF
181 LKQIMLFSSV YMMTLIQELQ EILVPSQPQP LPKDLCRGKS HQHILLPVSF SVGMYKMDFI
241 ISTSSTLPWA YDRGV
```

Figure 3E. Amino acid sequence of 251P5G2 v.12 (SEQ ID. NO. : 32). The 251P5G2 v.12 protein has 1266 amino acids.

```
   1 MPFISKLVLA SQPTLFSFFS ASSPFLLFLD LRPERTYLPV CHVALIHMVV LLTMVFLSPQ
  61 LFESLNFQND FKYEASFYLR RVIRVLSICT TCLLDMLQVV NISPSISWLI MLFSSVYMMT
 121 LIQELQEILV PSQPQPLPKD LCRGKSHQHI LLPTQATFAA ATGLWAALTT VSNPSRADPV
 181 TWRKEPAVLP CCNLEKGSWL SFPGTAARKE FSTTLTGHSA LSLSSSRALP GSLPAFADLP
 241 RSCPESEQSA TPAGAFLLGW ERVVQRRLEV PRPQAAPATS ATPSRDPSPP CHQRRDAACL
 301 RAQGLTRAFQ VVHLAPTAPD GGAGCPPSRN SYRLTHVRCA QGLEAASANL PGAPGRSSSC
 361 ALRYRSGPSV SSAPSPAEPP AHQRLLFLPR APQAVSGPQE QPSEEALGVG SLSVFQLHLI
 421 QCIPNLSYPL VLRHIPEILK FSEKETGGGI LGLELPATAA RLSGLNSIMQ IKEFEELVKL
 481 HSLSHKVIQC VFAKKKNVDK WDDFCLSEGY GHSFLIMKET STKISGLIQE MGSGKSNVGT
 541 WGDYDDSAFM EPRYHVRRED LDKLHRAAWW GKVPRKDLIV MLRDTDMNKR DKQKRTALHL
 601 ASANGNSEVV QLLLDRRCQL NVLDNKKRTA LIKAVQCQED ECVLMLLEHG ADGNIQDEYG
 661 NTALHYAIYN EDKLMAKALL LYGADIESKN KCGLTPLLLG VHEQKQEVVK FLIKKKANLN
 721 ALDRYGRTAL ILAVCCGSAS IVNLLLEQNV DVSSQDLSGQ TAREYAVSSH HHVICELLSD
 781 YKEKQMLKIS SENSNPVITI LNIKLPLKVE EEIKKHGSNP VGLPENLTNG ASAGNGDDGL
 841 IPQRKSRKPE NQQFPDTENE EYHSDEQNDT QKQLSEEQNT GISQDEILTN KQKQIEVAEK
 901 EMNSELSLSH KKEEDLLREN SMLREEIAKL RLELDETKHQ NQLRENKILE EIESVKEKLL
 961 KTIQLNEEAL TKTKVAGFSL RQLGLAQHAQ ASVQQLCYKW NHTEKTEQQA QEQEVAGFSL
1021 RQLGLAQHAQ ASVQQLCYKW GHTEKTEQQA QEQGAALRSQ IGDPGGVPLS EGGTAAGDQG
1081 PGTHLPPREP RASPGTPSLV RLASGARAAA LPPPTGKNGR SPTKQKSVCD SSGWILPVPT
1141 FSSGSFLGRR CPMFDVSPAM RLKSDSNRET HQAFRDKDDL PFFKTQQSPR HTKDLGQDDR
1201 AGVLAPKCRP GTLCHTDTPP HRNADTPPHR HTTTLPHRDT TTSLPHFHVS AGGVGPTTLG
1261 SNREIT
```

Figure 4A. Alignment of 251P5G2 v.1 (SEQ ID NO: 33) with the mouse vomeronasal 1 receptor C3. (SEQ ID NO: 34)

>gi|20821692|ref|XP_124715.1| (XM_124715) vomeronasal 1 receptor, C3 [Mus musculus]
    Length = 299

Score = 144 bits (362), Expect = 1e-33
Identities = 103/234 (44%), Positives = 141/234 (60%), Gaps = 6/234 (2%)

```
Query:  25  FLLFLDL--RPERTYLPVCHVALIHMVVLLTM-VFLSPQLFESLNFQNDFKYEASFYLRR  81
            F +F+ L  RP+    L  C   IH+++ T    L  +FES+N +NDFK + +FY+ R
Sbjct:  25  FYIFIILGHRPKPMDLISCQQTFIHIMLFFTAGDILHTDIFESMNIENDFKCKTTFYICR  84

Query:  82  VIRVLSICTTCLLGMLQVVNISPSISWLVRFKWKSTIFTFHLF--SWSLSFPVSSSLIFY  139
            V+R LSICTTCLL + Q V ISP+ S L +FK K   +T + F   WS +   SS+LIFY
Sbjct:  85  VMRGLSICTTCLLSVFQAVTISPNTSLLAKFKHKLKKYTINAFFYIWSFNLSFSSNLIFY  144

Query: 140  TVASSNVTQIN-LHVSKYCSLFPINSIIRGLFFTLSLFRDVFLKQIMLFSSVYMMTLIQE  198
              A +NV++ N + V+KYCSLFP+N IIRGL  T++  RDVFL  +ML +S YM+ ++
Sbjct: 145  VGAYTNVSETNQMKVTKYCSLFPMNYIIRGLILTVTTSRDVFLVGVMLITSTYMVIILFR  204

Query: 199  LQEILVPSQPQPLPKDLCRGKSHQHILLPVSFSVGMYKMDFIISTSSTLPWAYD  252
             Q        +       K+ Q ILL V F V MY +DFIIS++S L W YD
Sbjct: 205  HQRQCKHLHSIRHLRASPEKKATQTILLLVVFFVVMYWVDFIISSTSVLLWMYD  258
```

Figure 4B. Amino acid alignment of 251P5G2 v.12 (SEQ ID NO: 35) with the protein XM_063686 predicted from GenomeScan. (SEQ ID NO: 36)

```
>gi|20552217|ref|XP_063686.5| (XM_063686) similar to bA255A11.3 (novel protein similar to KIAA1074)
    [Homo sapiens]
    Length = 1213

Score = 2387 bits (6186), Expect = 0.0
 Identities = 1213/1213 (100%), Positives = 1213/1213 (100%)

Query: 54   MVFLSPQLFESLNFQNDFKYEASFYLRRVIRVLSICTTCLLDMLQVVNISPSISWLIMLF 113
            MVFLSPQLFESLNFQNDFKYEASFYLRRVIRVLSICTTCLLDMLQVVNISPSISWLIMLF
Sbjct: 1    MVFLSPQLFESLNFQNDFKYEASFYLRRVIRVLSICTTCLLDMLQVVNISPSISWLIMLF 60

Query: 114  SSVYMMTLIQELQEILVPSQPQPLPKDLCRGKSHQHILLPTQATFAAATGLWAALTTVSN 173
            SSVYMMTLIQELQEILVPSQPQPLPKDLCRGKSHQHILLPTQATFAAATGLWAALTTVSN
Sbjct: 61   SSVYMMTLIQELQEILVPSQPQPLPKDLCRGKSHQHILLPTQATFAAATGLWAALTTVSN 120

Query: 174  PSRADPVTWRKEPAVLPCCNLEKGSWLSFPGTAARKEFSTTLTGHSALSLSSSRALPGSL 233
            PSRADPVTWRKEPAVLPCCNLEKGSWLSFPGTAARKEFSTTLTGHSALSLSSSRALPGSL
Sbjct: 121  PSRADPVTWRKEPAVLPCCNLEKGSWLSFPGTAARKEFSTTLTGHSALSLSSSRALPGSL 180

Query: 234  PAFADLPRSCPESEQSATPAGAFLLGWERVVQRRLEVPRPQAAPATSATPSRDPSPPCHQ 293
            PAFADLPRSCPESEQSATPAGAFLLGWERVVQRRLEVPRPQAAPATSATPSRDPSPPCHQ
Sbjct: 181  PAFADLPRSCPESEQSATPAGAFLLGWERVVQRRLEVPRPQAAPATSATPSRDPSPPCHQ 240

Query: 294  RRDAACLRAQGLTRAFQVVHLAPTAPDGGAGCPPSRNSYRLTHVRCAQGLEAASANLPGA 353
            RRDAACLRAQGLTRAFQVVHLAPTAPDGGAGCPPSRNSYRLTHVRCAQGLEAASANLPGA
Sbjct: 241  RRDAACLRAQGLTRAFQVVHLAPTAPDGGAGCPPSRNSYRLTHVRCAQGLEAASANLPGA 300

Query: 354  PGRSSSCALRYRSGPSVSSAPSPAEPPAHQRLLFLPRAPQAVSGPQEQPSEEALGVGSLS 413
            PGRSSSCALRYRSGPSVSSAPSPAEPPAHQRLLFLPRAPQAVSGPQEQPSEEALGVGSLS
Sbjct: 301  PGRSSSCALRYRSGPSVSSAPSPAEPPAHQRLLFLPRAPQAVSGPQEQPSEEALGVGSLS 360

Query: 414  VFQLHLIQCIPNLSYPLVLRHIPEILKFSEKETGGGILGLELPATAARLSGLNSIMQIKE 473
            VFQLHLIQCIPNLSYPLVLRHIPEILKFSEKETGGGILGLELPATAARLSGLNSIMQIKE
Sbjct: 361  VFQLHLIQCIPNLSYPLVLRHIPEILKFSEKETGGGILGLELPATAARLSGLNSIMQIKE 420

Query: 474  FEELVKLHSLSHKVIQCVFAKKKNVDKWDDFCLSEGYGHSFLIMKETSTKISGLIQEMGS 533
            FEELVKLHSLSHKVIQCVFAKKKNVDKWDDFCLSEGYGHSFLIMKETSTKISGLIQEMGS
Sbjct: 421  FEELVKLHSLSHKVIQCVFAKKKNVDKWDDFCLSEGYGHSFLIMKETSTKISGLIQEMGS 480

Query: 534  GKSNVGTWGDYDDSAFMEPRYHVRREDLDKLHRAAWWGKVPRKDLIVMLRDTDMNKRDKQ 593
            GKSNVGTWGDYDDSAFMEPRYHVRREDLDKLHRAAWWGKVPRKDLIVMLRDTDMNKRDKQ
Sbjct: 481  GKSNVGTWGDYDDSAFMEPRYHVRREDLDKLHRAAWWGKVPRKDLIVMLRDTDMNKRDKQ 540

Query: 594  KRTALHLASANGNSEVVQLLLDRRCQLNVLDNKKRTALIKAVQCQEDECVLMLLEHGADG 653
            KRTALHLASANGNSEVVQLLLDRRCQLNVLDNKKRTALIKAVQCQEDECVLMLLEHGADG
Sbjct: 541  KRTALHLASANGNSEVVQLLLDRRCQLNVLDNKKRTALIKAVQCQEDECVLMLLEHGADG 600

Query: 654  NIQDEYGNTALHYAIYNEDKLMAKALLLYGADIESKNKCGLTPLLLGVHEQKQEVVKFLI 713
            NIQDEYGNTALHYAIYNEDKLMAKALLLYGADIESKNKCGLTPLLLGVHEQKQEVVKFLI
Sbjct: 601  NIQDEYGNTALHYAIYNEDKLMAKALLLYGADIESKNKCGLTPLLLGVHEQKQEVVKFLI 660

Query: 714  KKKANLNALDRYGRTALILAVCCGSASIVNLLLEQNVDVSSQDLSGQTAREYAVSSHHHV 773
            KKKANLNALDRYGRTALILAVCCGSASIVNLLLEQNVDVSSQDLSGQTAREYAVSSHHHV
Sbjct: 661  KKKANLNALDRYGRTALILAVCCGSASIVNLLLEQNVDVSSQDLSGQTAREYAVSSHHHV 720

Query: 774  ICELLSDYKEKQMLKISSENSNPVITILNIKLPLKVEEEIKKHGSNPVGLPENLTNGASA 833
            ICELLSDYKEKQMLKISSENSNPVITILNIKLPLKVEEEIKKHGSNPVGLPENLTNGASA
Sbjct: 721  ICELLSDYKEKQMLKISSENSNPVITILNIKLPLKVEEEIKKHGSNPVGLPENLTNGASA 780

Query: 834  GNGDDGLIPQRKSRKPENQQFPDTENEEYHSDEQNDTQKQLSEEQNTGISQDEILTNKQK 893
            GNGDDGLIPQRKSRKPENQQFPDTENEEYHSDEQNDTQKQLSEEQNTGISQDEILTNKQK
```

Figure 4B (Con't)

```
Sbjct:  781  GNGDDGLIPQRKSRKPENQQFPDTENEEYHSDEQNDTQKQLSEEQNTGISQDEILTNKQK  840

Query:  894  QIEVAEKEMNSELSLSHKKEEDLLRENSMLREEIAKLRLELDETKHQNQLRENKILEEIE  953
             QIEVAEKEMNSELSLSHKKEEDLLRENSMLREEIAKLRLELDETKHQNQLRENKILEEIE
Sbjct:  841  QIEVAEKEMNSELSLSHKKEEDLLRENSMLREEIAKLRLELDETKHQNQLRENKILEEIE  900

Query:  954  SVKEKLLKTIQLNEEALTKTKVAGFSLRQLGLAQHAQASVQQLCYKWNHTEKTEQQAQEQ  1013
             SVKEKLLKTIQLNEEALTKTKVAGFSLRQLGLAQHAQASVQQLCYKWNHTEKTEQQAQEQ
Sbjct:  901  SVKEKLLKTIQLNEEALTKTKVAGFSLRQLGLAQHAQASVQQLCYKWNHTEKTEQQAQEQ  960

Query: 1014  EVAGFSLRQLGLAQHAQASVQQLCYKWGHTEKTEQQAQEQGAALRSQIGDPGGVPLSEGG  1073
             EVAGFSLRQLGLAQHAQASVQQLCYKWGHTEKTEQQAQEQGAALRSQIGDPGGVPLSEGG
Sbjct:  961  EVAGFSLRQLGLAQHAQASVQQLCYKWGHTEKTEQQAQEQGAALRSQIGDPGGVPLSEGG  1020

Query: 1074  TAAGDQGPGTHLPPREPRASPGTPSLVRLASGARAAALPPPTGKNGRSPTKQKSVCDSSG  1133
             TAAGDQGPGTHLPPREPRASPGTPSLVRLASGARAAALPPPTGKNGRSPTKQKSVCDSSG
Sbjct: 1021  TAAGDQGPGTHLPPREPRASPGTPSLVRLASGARAAALPPPTGKNGRSPTKQKSVCDSSG  1080

Query: 1134  WILPVPTFSSGSFLGRRCPMFDVSPAMRLKSDSNRETHQAFRDKDDLPFFKTQQSPRHTK  1193
             WILPVPTFSSGSFLGRRCPMFDVSPAMRLKSDSNRETHQAFRDKDDLPFFKTQQSPRHTK
Sbjct: 1081  WILPVPTFSSGSFLGRRCPMFDVSPAMRLKSDSNRETHQAFRDKDDLPFFKTQQSPRHTK  1140

Query: 1194  DLGQDDRAGVLAPKCRPGTLCHTDTPPHRNADTPPHRHTTTLPHRDTTTSLPHFHVSAGG  1253
             DLGQDDRAGVLAPKCRPGTLCHTDTPPHRNADTPPHRHTTTLPHRDTTTSLPHFHVSAGG
Sbjct: 1141  DLGQDDRAGVLAPKCRPGTLCHTDTPPHRNADTPPHRHTTTLPHRDTTTSLPHFHVSAGG  1200

Query: 1254  VGPTTLGSNREIT  1266
             VGPTTLGSNREIT
Sbjct: 1201  VGPTTLGSNREIT  1213
```

Figure 5: 251P5G2 variant 1
Hydrophilicity profile
(Hopp T.P., Woods K.R., 1981. Proc. Natl. Acad. Sci. U.S.A. 78:3824-3828)
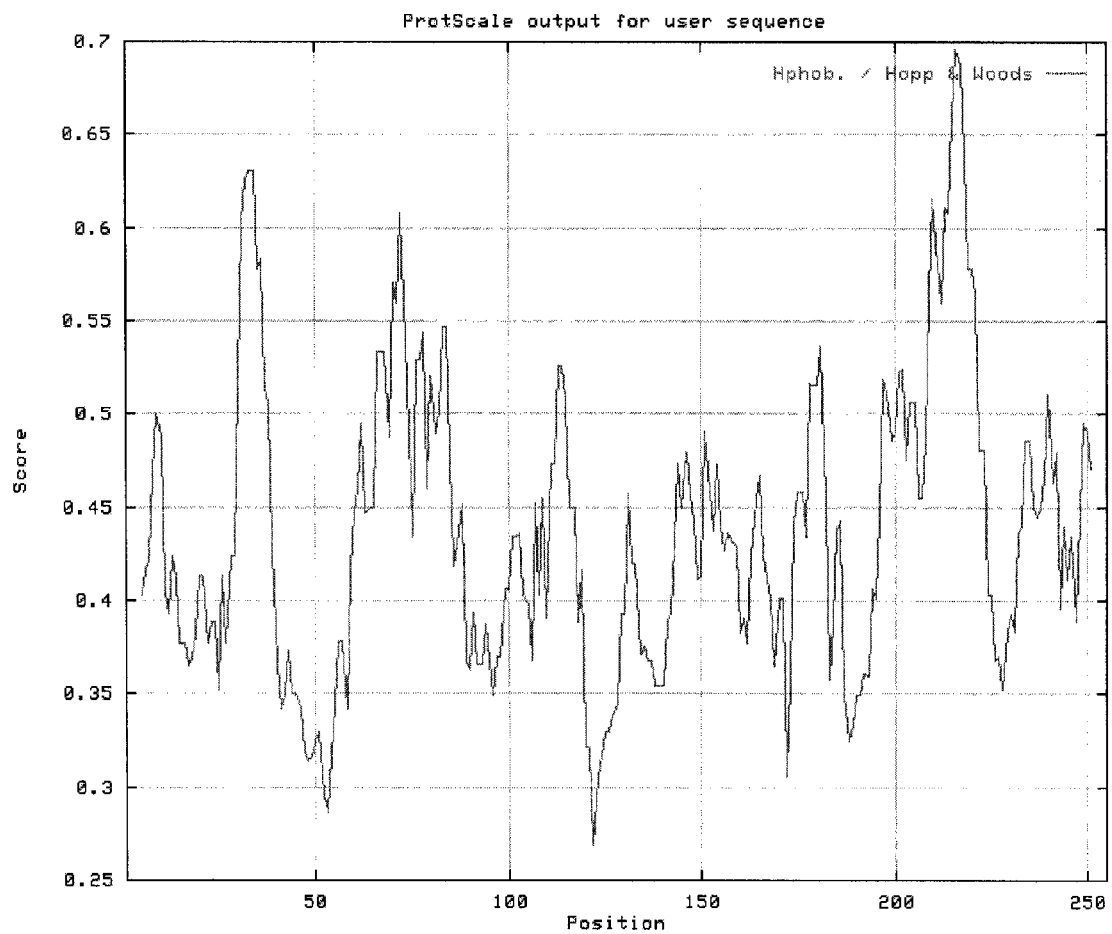

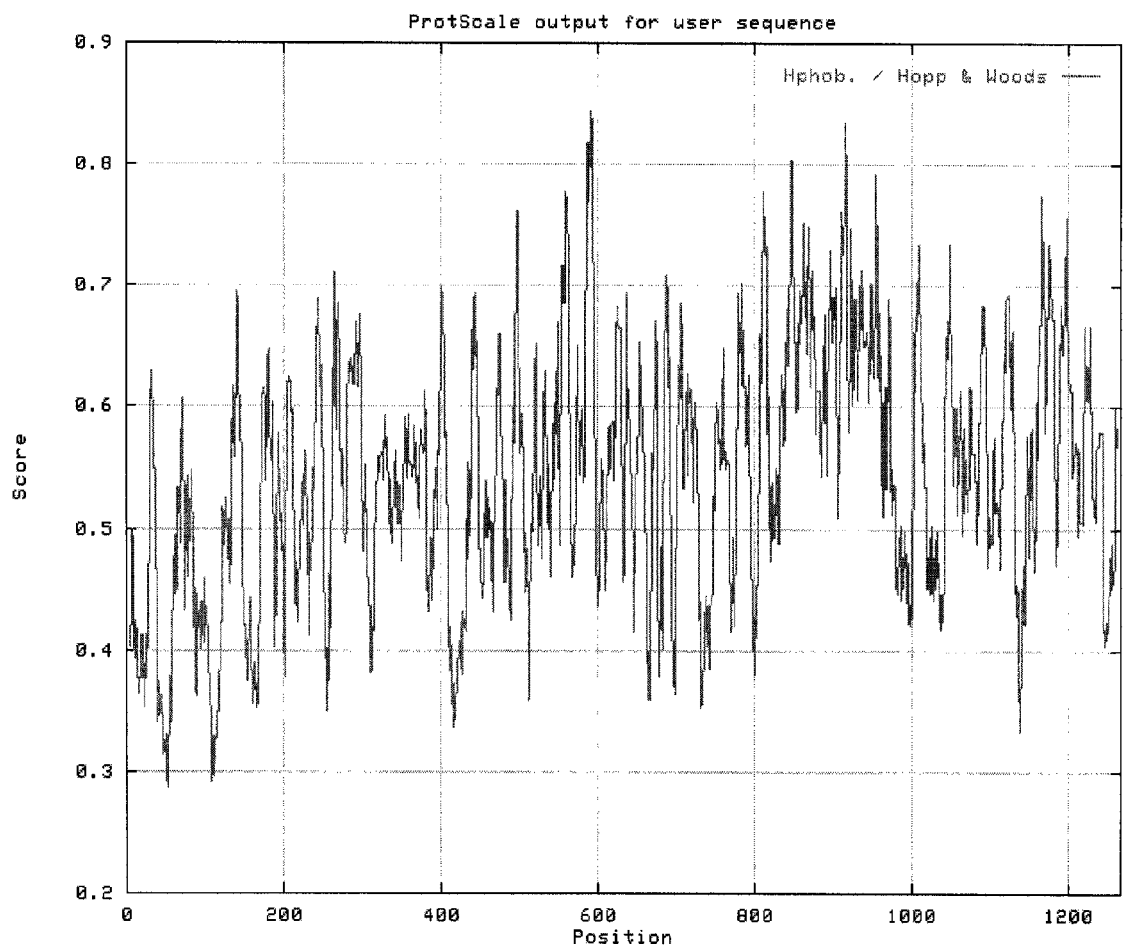
Figure 5A: 251P5G2 variant 12
Hydrophilicity profile
(Hopp T.P., Woods K.R., 1981. Proc. Natl. Acad. Sci. U.S.A. 78:3824-3828)

Figure 6: 251P5G2 variant 1
Hydropathicity Profile
(Kyte J., Doolittle R.F., 1982. J. Mol. Biol. 157:105-132)
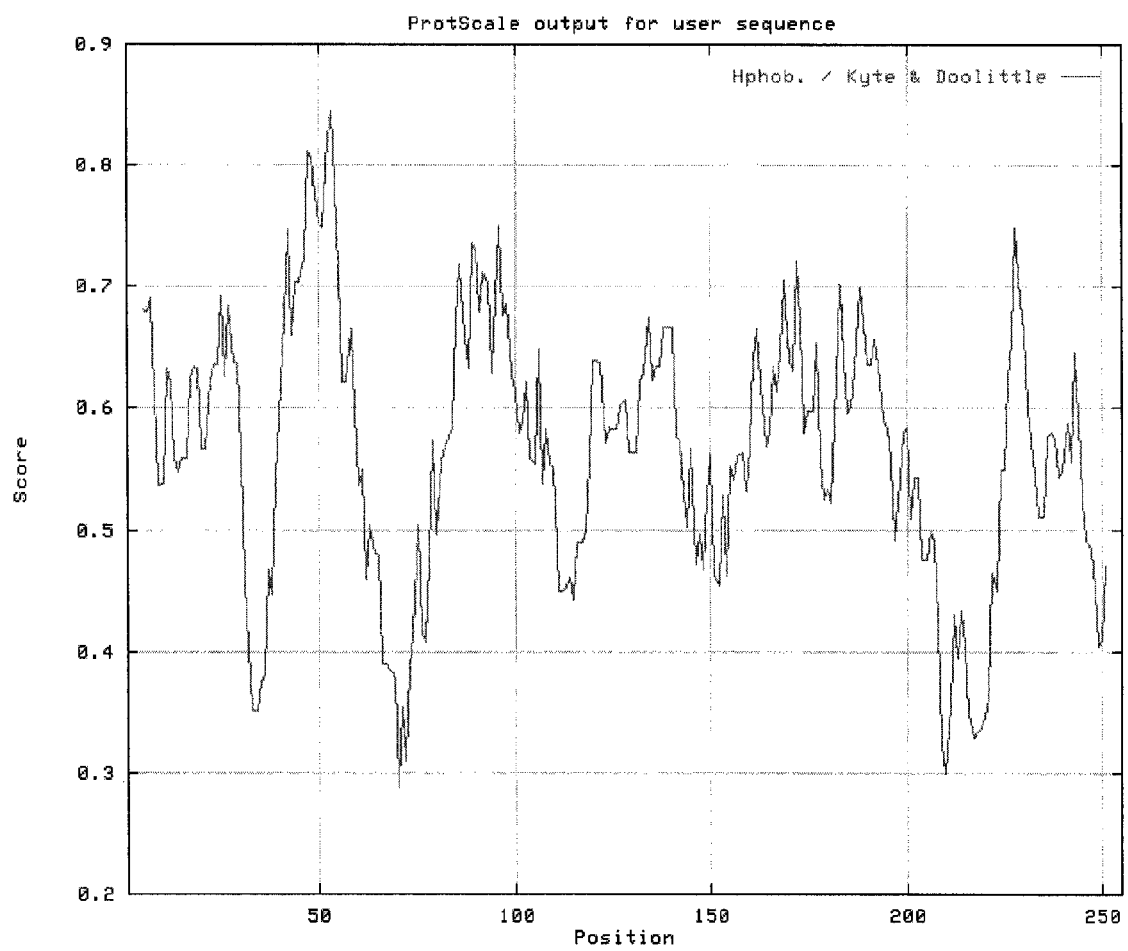

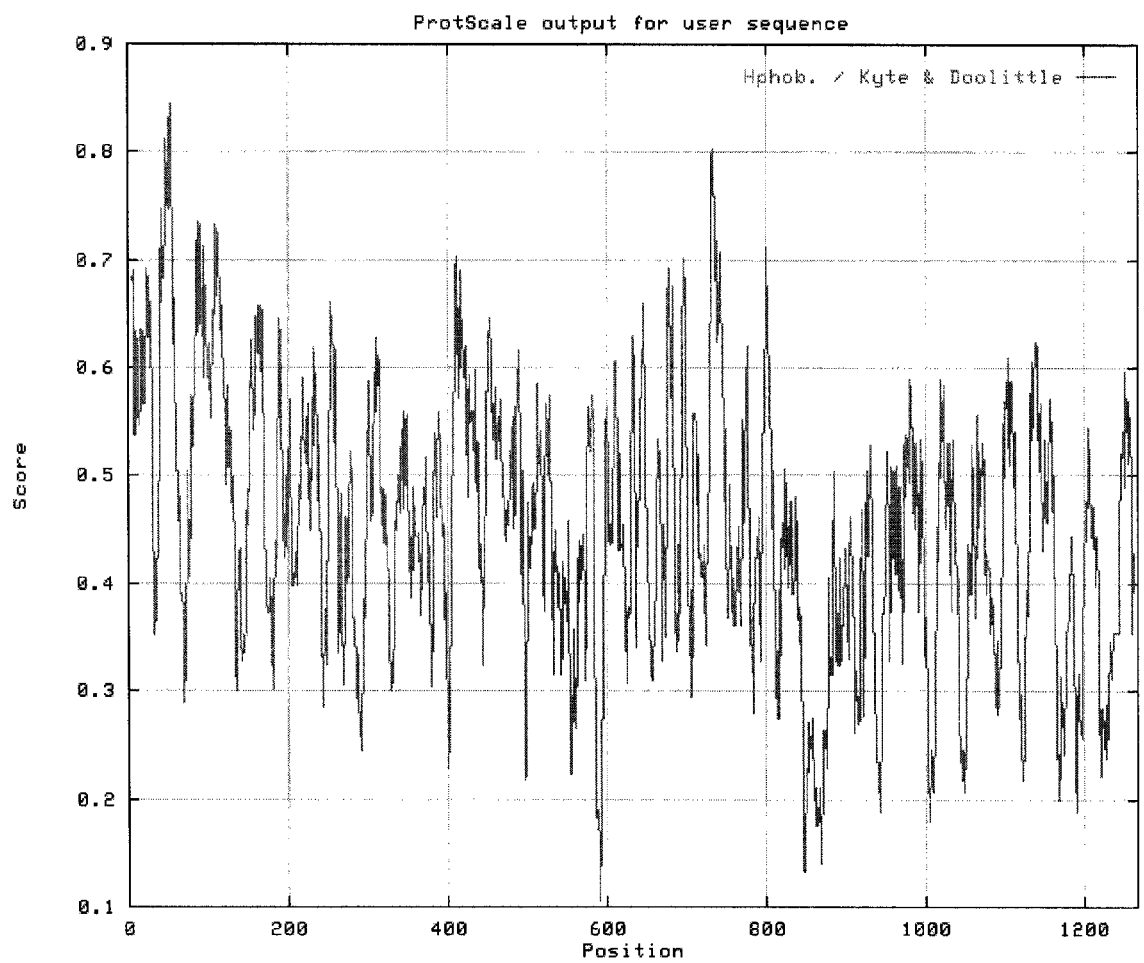
Figure 6A: 251P5G2 variant 12
Hydropathicity Profile
(Kyte J., Doolittle R.F., 1982. J. Mol. Biol. 157:105-132)

Figure 7: 251P5G2 variant 1
% Accessible Residues Profile
(Janin J., 1979. Nature 277:491-492)
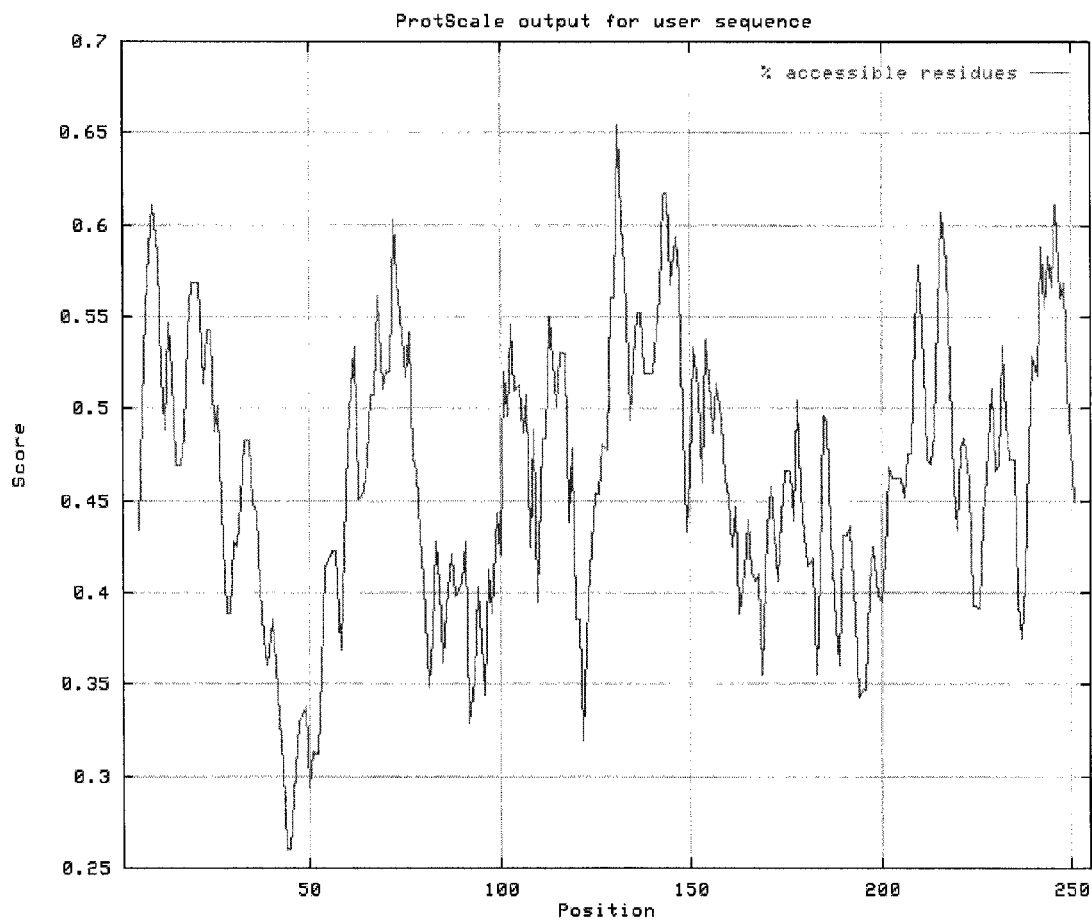

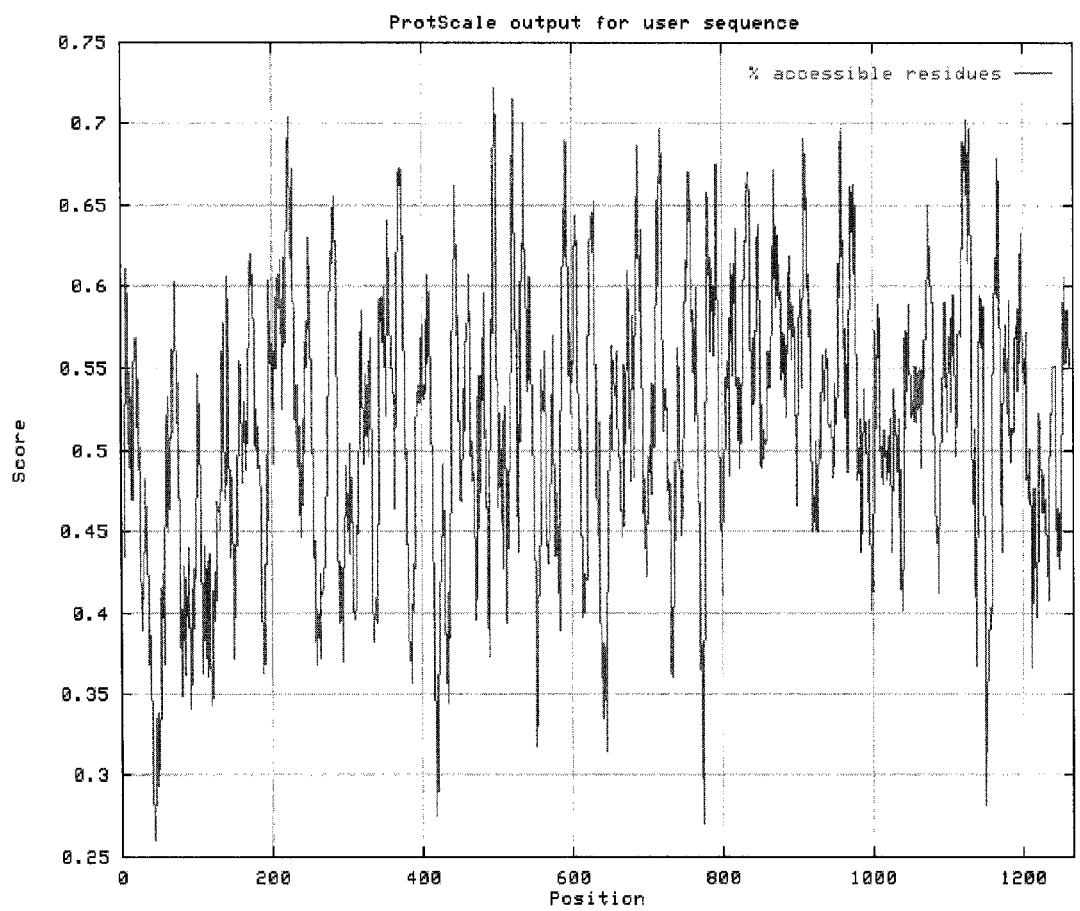
Figure 7A: 251P5G2 variant 12
% Accessible Residues Profile
(Janin J., 1979. Nature 277:491-492)

Figure 8: 251P5G2 variant 1
Average Flexibility Profile
(Bhaskaran R., Ponnuswamy P.K., 1988.
Int. J. Pept. Protein Res. 32:242-255)
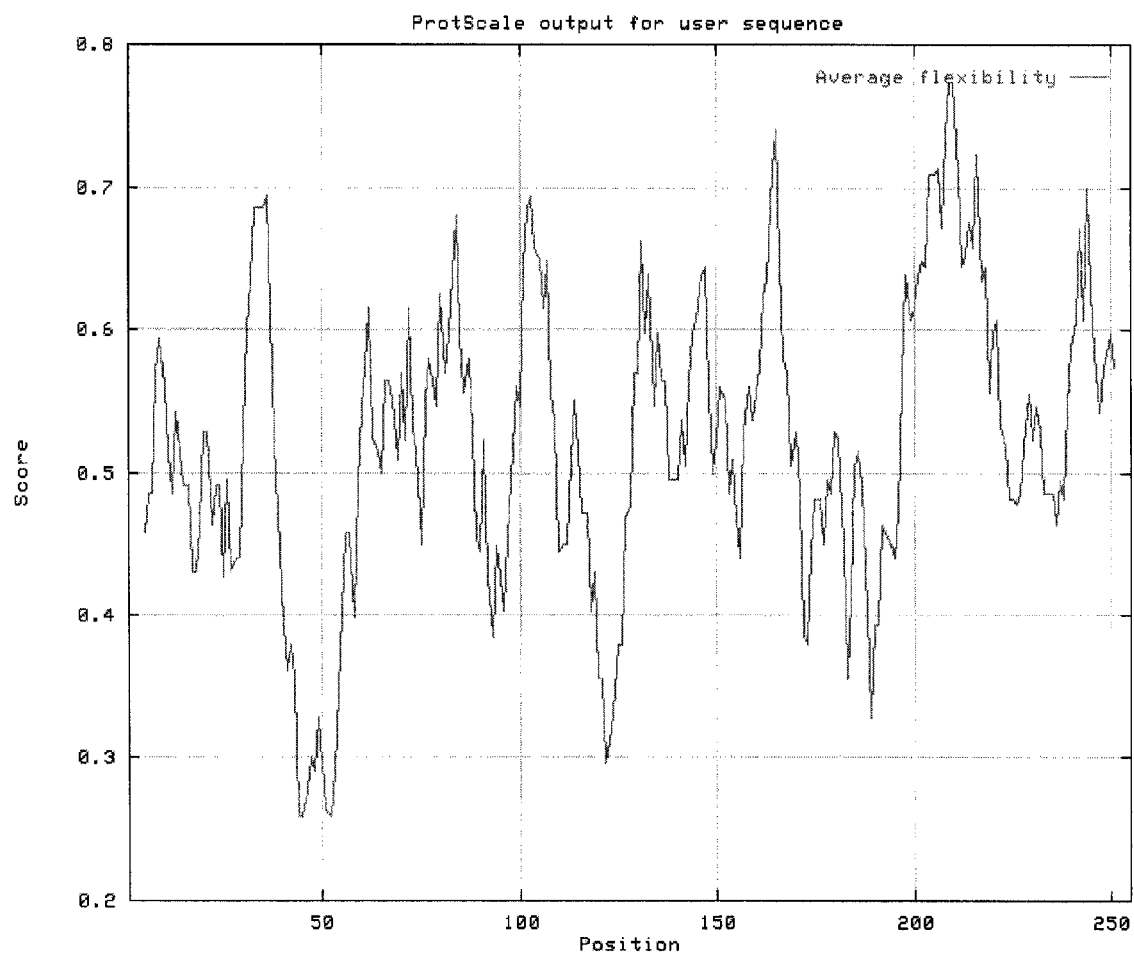

Figure 8A: 251P5G2 variant 12
Average Flexibility Profile
(Bhaskaran R., Ponnuswamy P.K., 1988.
Int. J. Pept. Protein Res. 32:242-255)
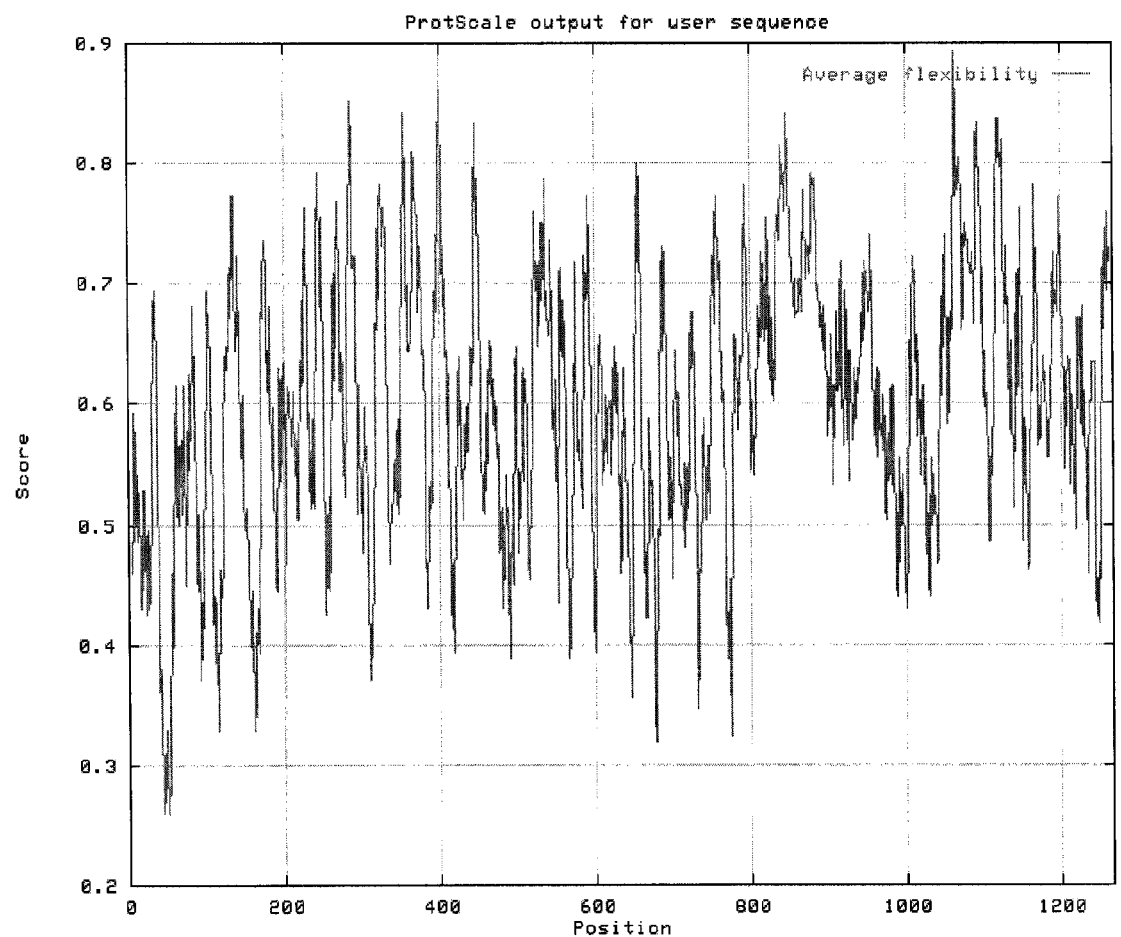

Figure 9: 251P5G2 variant 1
Beta-turn Profile
(Deleage, G., Roux B. 1987. Protein Engineering 1:289-294)
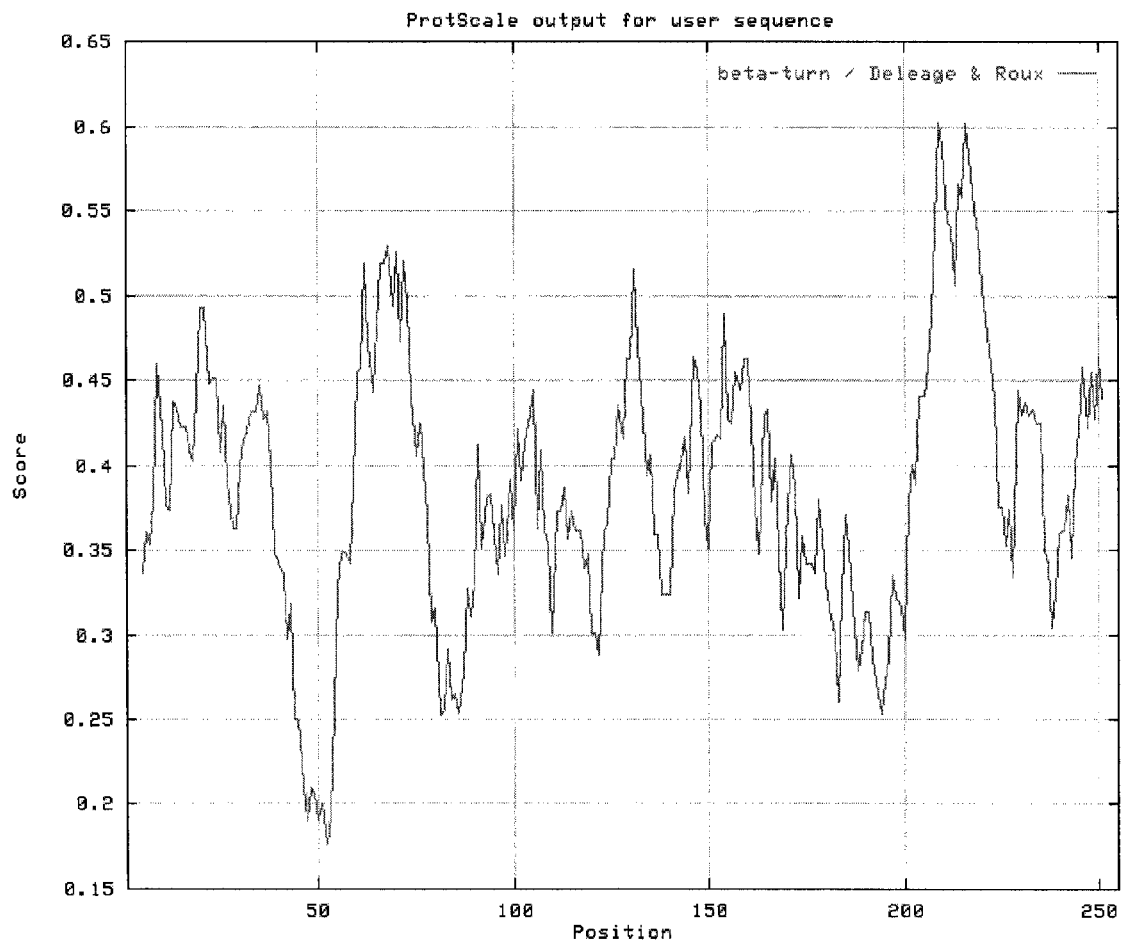

Figure 9A: 251P5G2 variant 12
Beta-turn Profile
(Deleage, G., Roux B. 1987. Protein Engineering 1:289-294)
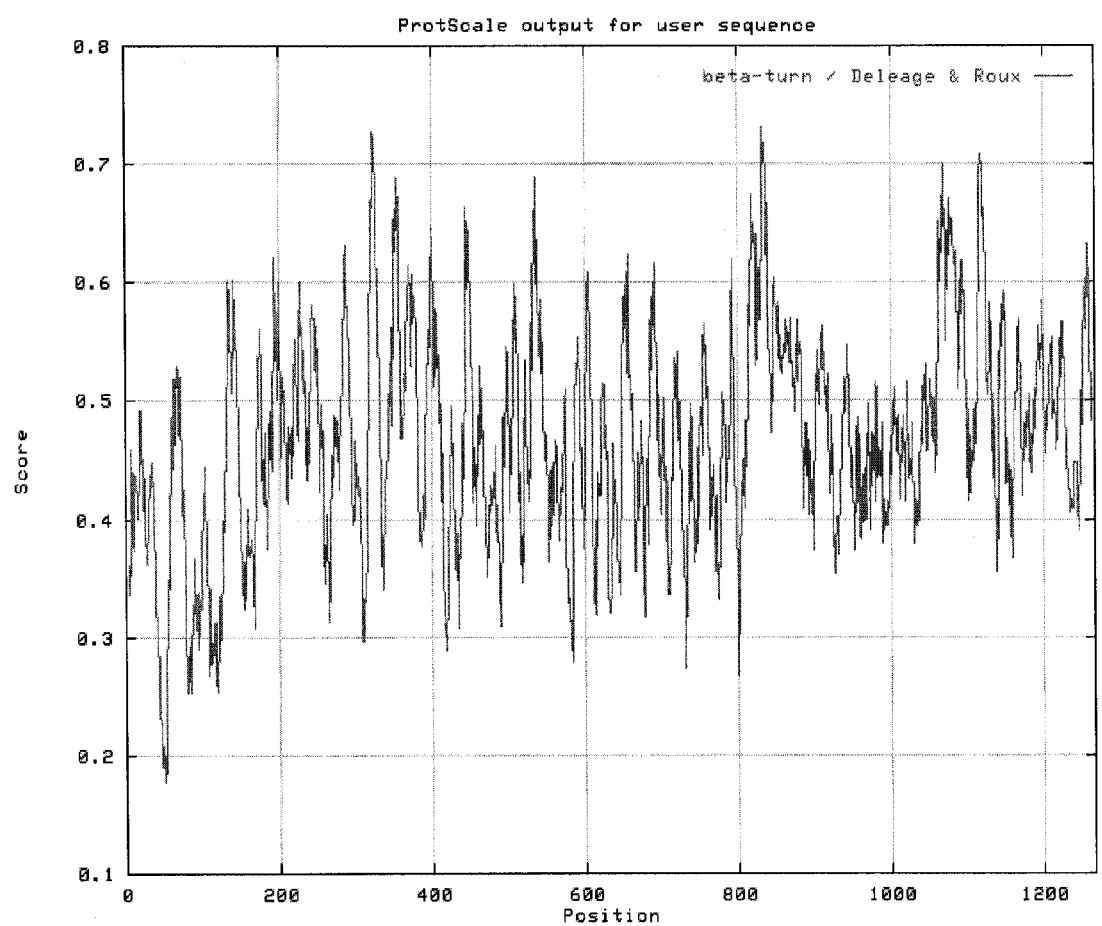

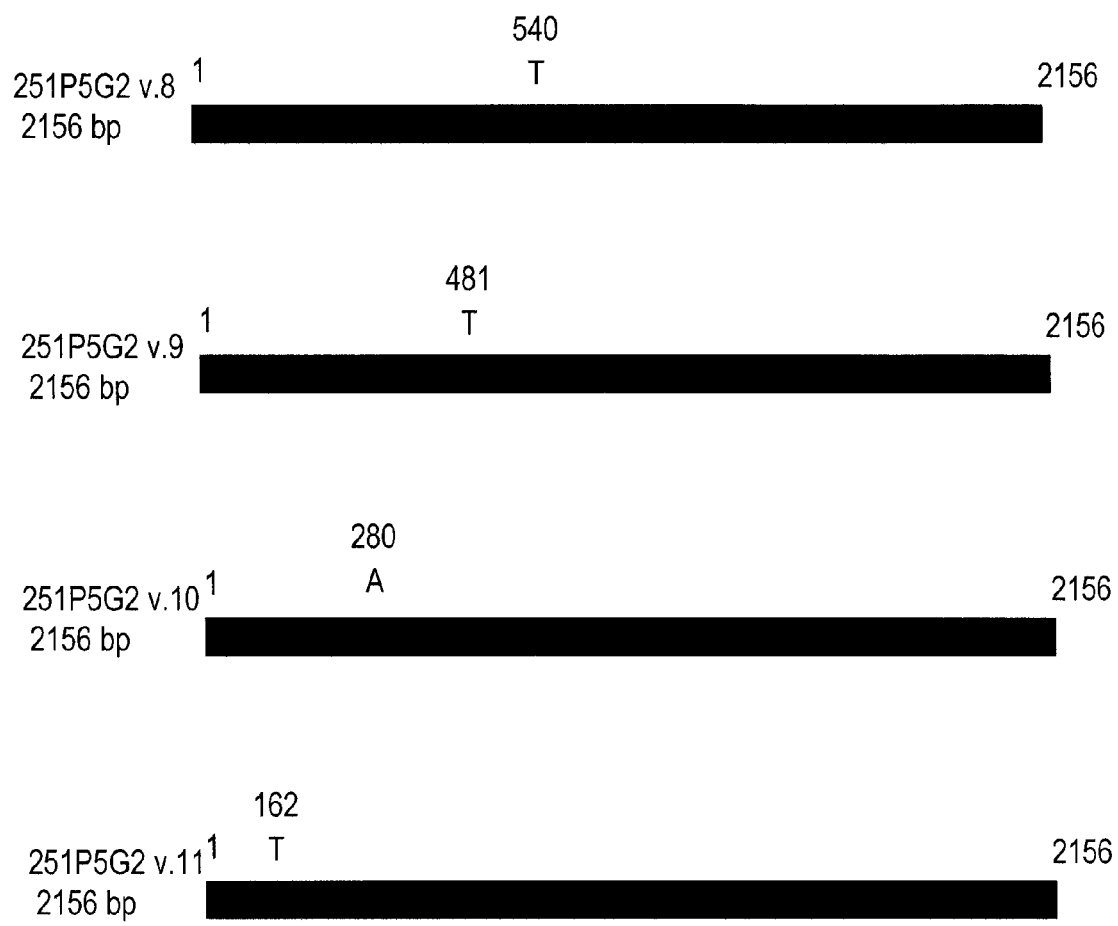
Figure 10 (con't)

Figure 13A: Secondary structure prediction of 251P5G2 variant 1

```
         10        20        30        40        50        60        70
         |         |         |         |         |         |         |
MPFISKLVLASQPTLFSFFSASSPFLLFLDLRPERTYLPVCHVALIHMVLLTMVFLSPQLFESLNFQND
cchhheeeecccccceeeecccccccheeeecccccccccchhhhhhhhhhhhcccchhcccccc
FKYEASFYLRRVIRVLSICTTCLLGMLQVVNISPSISWLVRFKWKSTIFTFHLFSWSLSFPVSSSLIFYT
chhhhhhhhhhhhhhhhhhhhhcceeeeecccchhhhhcccheeeeeeeeecccccccceeeee
VASSNVTQINLHVSKYCSLFPINSIIRGLFFTLSLFRDVFLKQIMLFSSVYMMTLIQELQEILVPSQPQP
ecccccheeeehhccccchhhhhhhhhhhhhhhhhhhhhhhhhhhhhhheccccccc
LPKDLCRGKSHQHILLPVSFSVGMYKMDFIISTSSTLPWAYDRGV
ccccccccccceeeeeccccceeeccccccccccccccc
```

Alpha helix (h): 40.39%
Extended strand (e): 18.82%
Random coil (c): 40.78%

Figure 13B: Secondary structure prediction of 251P5G2 variant 12

```
         10         20         30         40         50         60         70
          |          |          |          |          |          |          |
MPFISKIVLASQPTLFSFFSASSPFLLFLDLRPERTYLPVCHVALIHMVLLTMVFLSPQLFESLNFQND
cchhheeecccccceeeccccceeeecccccccccccccchhhhhhhhhhhhhccchhccccccc
FKYEASFYLRRVIRVLSICTTCLLDMLQVVNISPSISWLIMLFSSVYMMTLIQELQEIIVPSQPQPLPKD
chhhhhhhhhhhhhhhhhhhhhhhhhhhhheeccccchhhhhhhhhhhhhhhhhheccccccccccc
LCRGKSHQHILLPTQATFAAATGLWAALTTVSNPSRADPVTWRKEPAVLPCCNLEKGSWLSFPGTAARKE
cccccccceeeccchhhhhhhhhhhhhhhhhhheccccccccccccccccccccccccccccc
FSTTLTGHSALSLSSSRALPGSLPAFADLPRSCPESEQSATPAGAFLLGWERVVQRRLEVPRPQAAPATS
cccccccceeecccccccccccccccccchccccccccccccchhhhhhhhhhhhccccccccccc
ATPSRDPSPPCHQRRDAACLRAQGLTRAFQVVHLAPTAPDGGAGCPPSRNSYRLTHVRCAQGLEAASANL
ccccccccccccccchhhhhhhhhhhhhheeeccccccccccccccccceeehhccchhhhhhcc
PGAPGRSSSCALRYRSGPSVSSAPSPAEPPAHQRLLFLPRAPQAVSGPQEQPSEEALGVGSLSVFQLHLI
cccccccccceeeccccccccccccccccccccccccccccccccccchhcccchhhhhhhhhh
QCIPNLSYPLVLRHIPEILKFSEKETGGILGLELPATAARLSGLNSIMQIKEFEELVKLHSLSHKVIQC
hhhccccccehhhhhhhhheeecccccccccccccccccceeeehhhhhhhhhcchhhhhhhhhhh
VFAKKKNVDKWDDFCLSEGYGHSFLIMKETSTKISGLIQEMGSGKSNVGTWGDYDDSAFMEPRYHVRRED
hhhcccccccccccccceeeeccccccceeehhhhhhhhcccchhhhhhhcccccccccccccchh
LDKLHRAAWWGKVPRKDLIVMLRDTDMNKRDKQKRTALHLASANGNSEVVQLLLDRRCQLNVLDNKKRTA
hhhhhhhhhccccccceeeeeeeccccchhhhhhcccccchhhhhhhhhhccchhhhhhhhhhhhh
```

Alpha helix (h): 42.28%
Extended strand (e): 8.33%
Random coil (c) : 49.39%

Figure 13B (con't)

Secondary structure prediction of 251P5G2 variant 12

```
         640       650       660       670       680       690       700
          |         |         |         |         |         |         |
LIKAVQCQEDECVIMLLEHGADGNIQDEYGNTALHYAIYNEDKLMAKALLLYGADIESKNKCGLTPLLIG
hhhhhhhchhhhhheeehhcccccchcccchhhhhhhhhhhhhhcccchccccccccccceee
VHEQKQEVVKELIKKKANLNALDRYGRTALILAVCCGSASIVNLLLEQNVDVSSQDLSGQTAREYAVSSH
hhhhhhhhhhhhhhhhhcccceeeeeeccchhhhhcccccccchhhhhhhcc
HHVICELLSDYKEKQMLKISSENSNPVITILNIKLPLKVEEEIKKHGSNPVGLPENLTNGASAGNGDDGL
chhhhhhhchhhcheeeeeccccceeeeccccccchhhccccccccccccccccccccc
IPQRKSRKPENQQFPDTENEEYHSDEQNDTQKQLSEEQNTGISQDEILTNKQKQIEVAEKEMNSELSLSH
cccccccccccccccccccccccccchhhhhccccchhhcchhhccccccc
KKEEDLIRENSMLREEIAKLRLELDETKHQNQLRENKILEEIESVKEKLLKTIQLNEEALTKTKVAGFSL
chhhhhhhhchhhhhhhhhhhhhhhcccccccchhhhhhhhhchhhhhhhhchhhhhhhcchh
RQLGLAQHAQASVQQLCYKWNHTEKTEQQAQEFEVAGFSLRQLGLAQHAQASVQQLCYKWGHTEKTEQQA
hhhhhhhhhhhhhhhhhhhhhccccccchhhhhhhhhhhhchhhhhhhhhhhhhhhcccccccchhh
QEQGAALRSQIGDPGGVPLSEGGTAAGDQGPGTHLPPREPRASPGTPSLVRLASGARAAALPPPTGKNGR
hhhhhhhhhhcccccccccccccccccccccccccccccccccccchhehhccccccccccccccccc
SPTKQKSVCDSSGWILPVPT
cccccceeccccccccccc
```

6 transmembrane domains predicted 5 transmembrane domains predicted 6 transmembrane domains predicted Transmembrane domains 3 transmembrane domains predicted

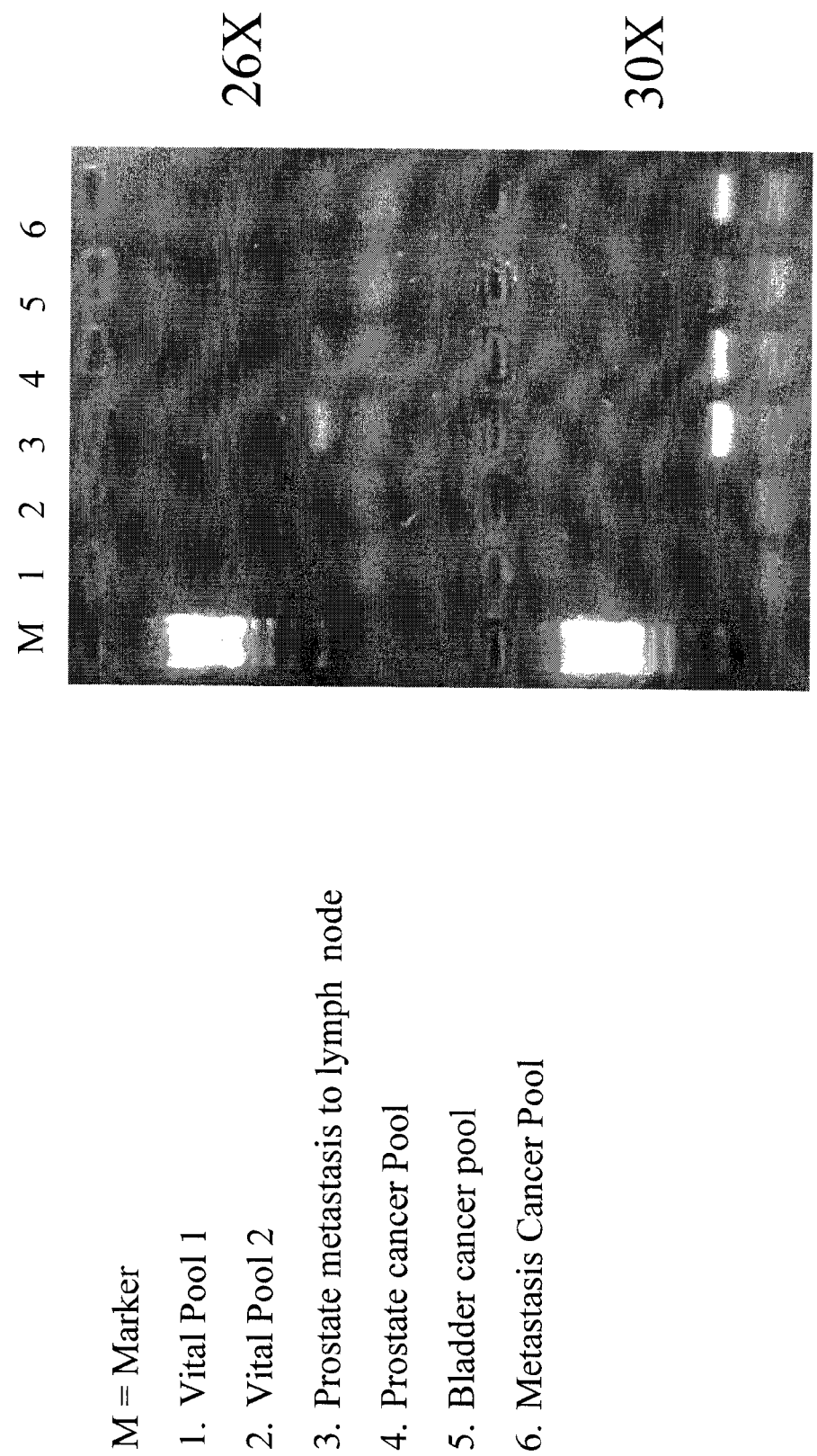
Figure 14   Expression of 251P5G2 by RT-PCR
M = Marker
1. Vital Pool 1
2. Vital Pool 2
3. Prostate metastasis to lymph node
4. Prostate cancer Pool
5. Bladder cancer pool
6. Metastasis Cancer Pool

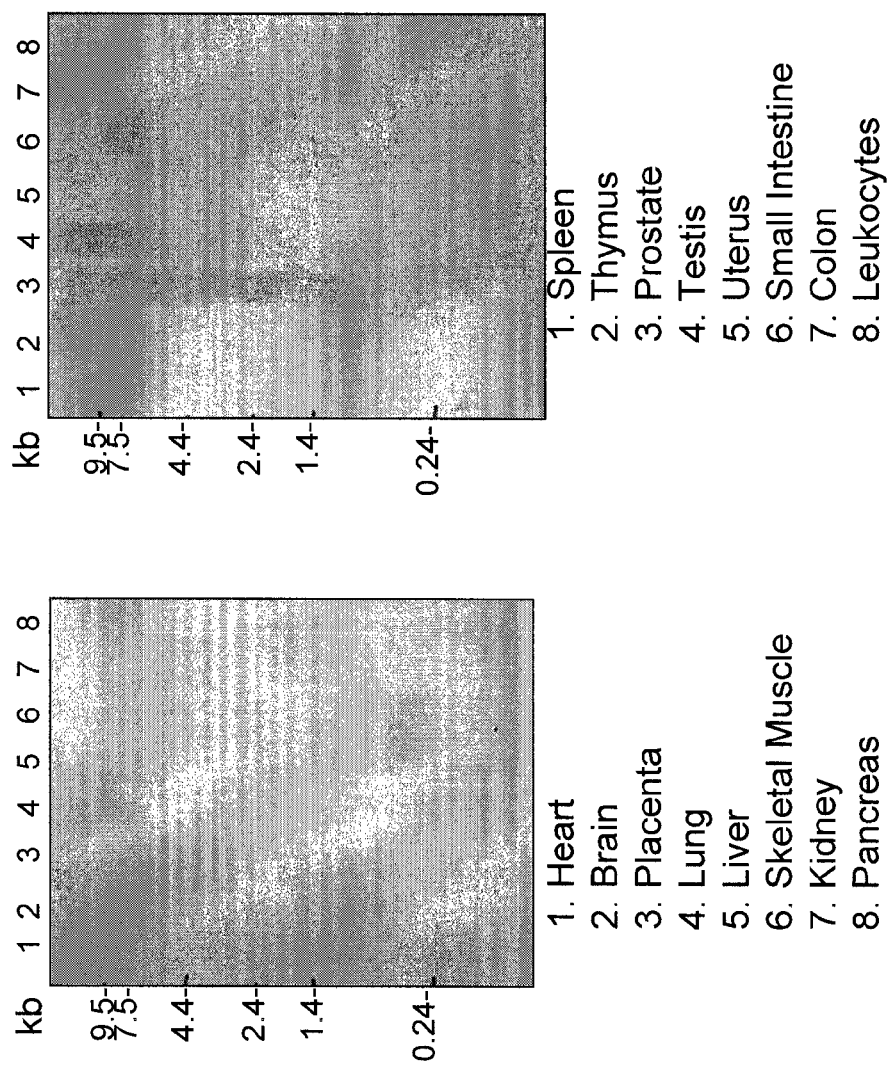
Figure 15  251P5G2 Expression in Normal Tissues

Figure 16 Expression of 251P5G2 in Prostate Cancer Metastasis Specimens
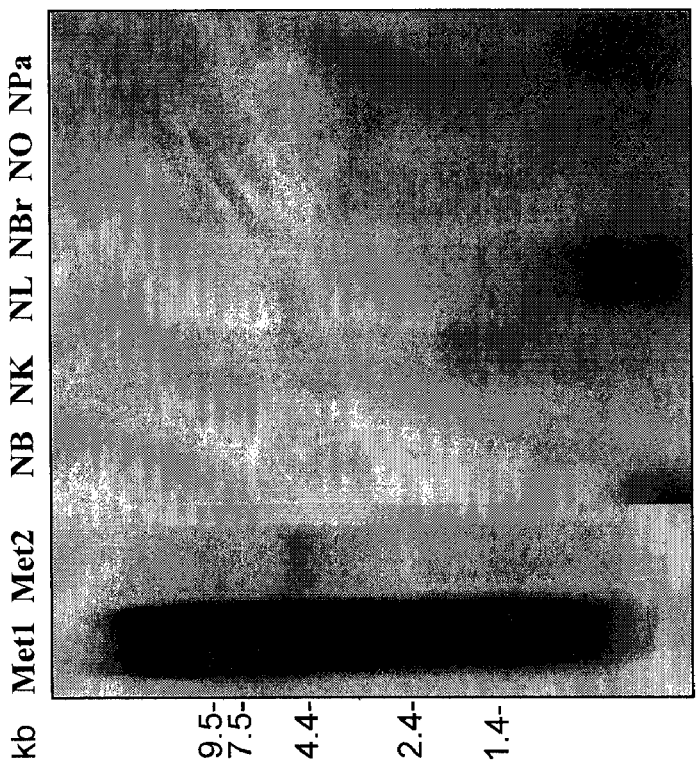
Met1 = Prostate cancer metastasis to lymph node from patient 1
Met2 = Prostate cancer metastasis to lymph node from patient 2
NB = normal bladder
NK = normal kidney
NL = normal lung
NBr = normal breast
NO = normal ovary
NPa = normal pancreas

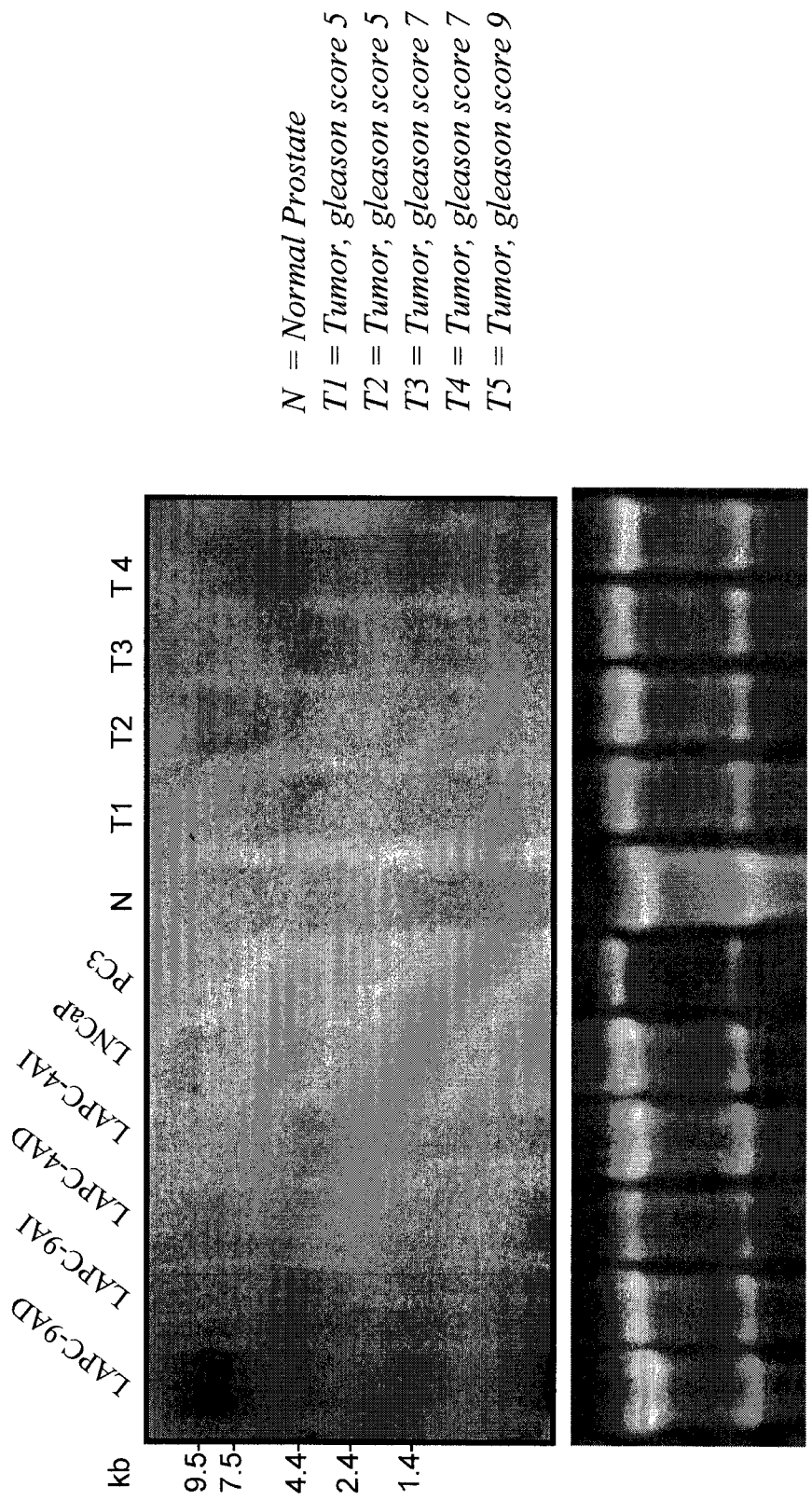
Figure 17 Expression of 251P5G2 in Prostate Cancer Patient Specimens
N = Normal Prostate
T1 = Tumor, gleason score 5
T2 = Tumor, gleason score 5
T3 = Tumor, gleason score 7
T4 = Tumor, gleason score 7
T5 = Tumor, gleason score 9

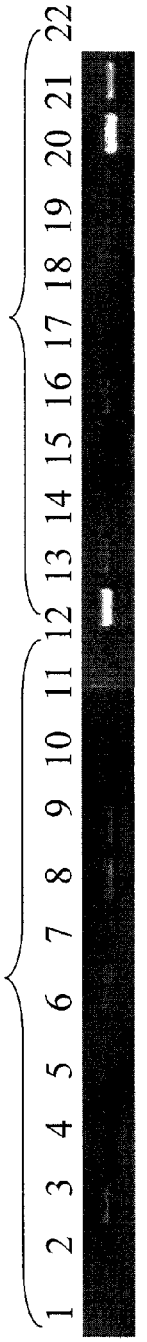
Figure 18: Expression of 251P5G2 in Human Normal and Cancer Tissues

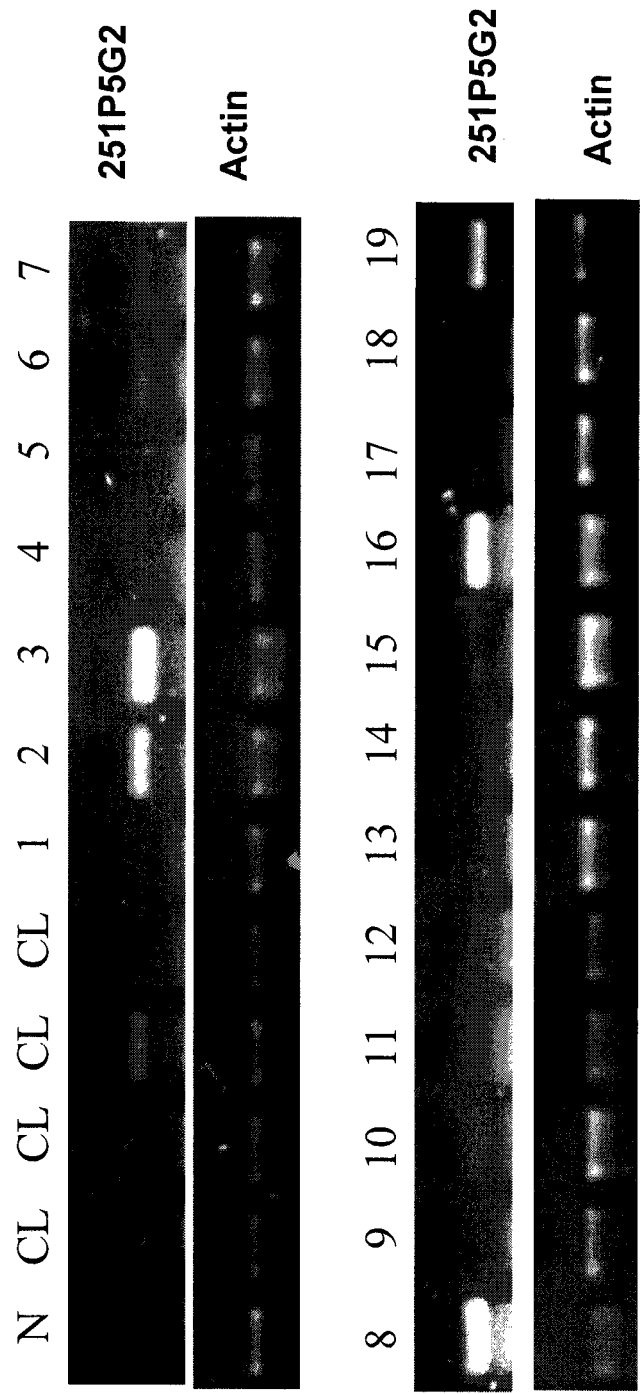
Figure 19: 251P5G2 Expression in Prostate Cancer Patient Specimens
N = Normal Prostate
CL (in order from left to right): PC3, DU145, LNCaP, 293T

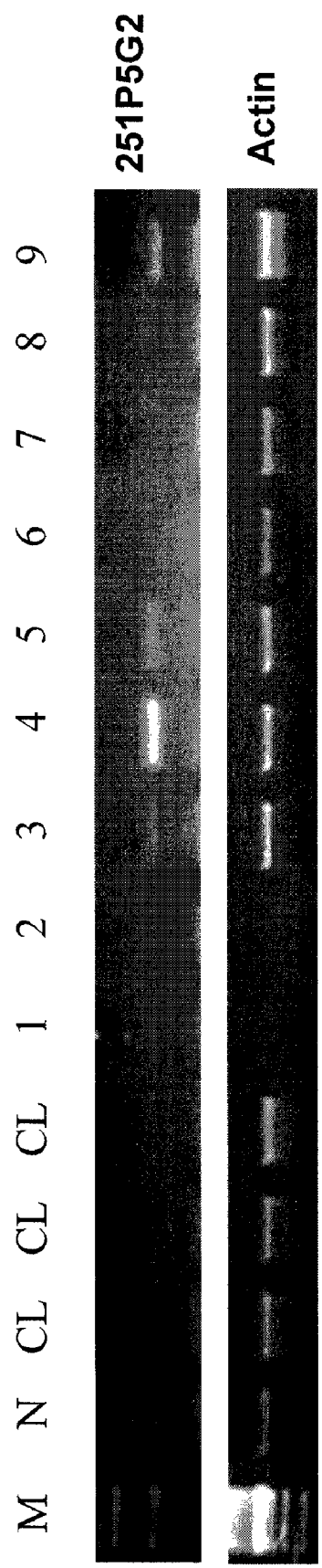
Figure 20: 251P5G2 Expression in Bladder Cancer Patient Specimens
N = Normal Bladder
CL (in order from left to right) = UM-UC-3, TCCSUP, J82

NUCLEIC ACIDS AND CORRESPONDING PROTEINS ENTITLED 251P5G2 USEFUL IN TREATMENT AND DETECTION OF CANCER

CROSS-REFERENCE TO RELATED APPLICATIONS

This application is a continuation of U.S. Ser. No. 10/418,972 filed 17 Apr. 2003 which is a non-provisional utility patent application, now abandoned, that claims priority from U.S. Provisional Patent Application U.S. Ser. No. 60/404,306, filed 16 Aug. 2002 and this application claims priority from U.S. Provisional Patent Application U.S. Ser. No. 60/423,290, filed 1 Nov. 2002. The contents of the applications listed in this paragraph are fully incorporated by reference herein.

STATEMENT OF RIGHTS TO INVENTIONS MADE UNDER FEDERALLY SPONSORED RESEARCH

Not applicable.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 511582007801Seqlist.txt | Oct. 16, 2006 | 264,665 bytes |

FIELD OF THE INVENTION

The invention described herein relates to genes and their encoded proteins, termed 251P5G2, expressed in certain cancers, and to diagnostic and therapeutic methods and compositions useful in the management of cancers that express 251P5G2.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93:7252), prostate-specific membrane (PSM) antigen (Pinto et al., Clin Cancer Res 1996 September 2 (9): 1445-51), STEAP (Hubert, et al., Proc Natl Acad Sci USA. 1999 Dec. 7; 96(25): 14523-8) and prostate stem cell antigen (PSCA) (Reiter et al., 1998, Proc. Natl. Acad. Sci. USA 95:1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, con-current with an increasing older population. In 1998, there was an estimated 54,500 cases, including 39,500 in men and 15,000 in women. The age-adjusted incidence in the United States is 32 per 100,000 for men and eight per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

SUMMARY OF THE INVENTION

The present invention relates to a gene, designated 251P5G2, that has now been found to be over-expressed in the cancer(s) listed in Table I. Northern blot expression analysis of 251P5G2 gene expression in normal tissues shows a restricted expression pattern in adult tissues. The nucleotide (FIG. 2) and amino acid (FIG. 2, and FIG. 3) sequences of 251P5G2 are provided. The tissue-related profile of 251P5G2 in normal adult tissues, combined with the over-expression observed in the tissues listed in Table I, shows that 251P5G2 is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the 251P5G2 genes, mRNAs, and/or coding sequences, preferably in isolated form, including polynucleotides encoding 251P5G2-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a 251P5G2-related protein, as well as the peptides/proteins themselves; DNA, RNA, DNA/RNA hybrids, and related molecules, polynucleotides or oligonucleotides complementary or having at least a 90% homology to the 251P5G2 genes or mRNA sequences or parts thereof, and polynucleotides or oligonucleotides that hybridize to the 251P5G2 genes, mRNAs, or to 251P5G2-encoding polynucleotides. Also provided are means for isolating cDNAs and the genes encoding 251P5G2. Recombinant DNA molecules containing 251P5G2 polynucleotides, cells transformed or transduced with such molecules, and host-vector systems for the expression of 251P5G2 gene products are also provided. The invention further provides antibodies that bind to 251P5G2 proteins and polypeptide fragments thereof, including polyclonal and monoclonal antibodies, murine and other mammalian antibodies, chimeric antibodies, humanized and fully human antibodies, and antibodies labeled with a detectable marker or therapeutic agent. In certain embodiments, there is a proviso that the entire nucleic acid sequence of FIG. 2 is not encoded and/or the entire amino acid sequence of FIG. 2 is not prepared. In certain embodiments, the entire nucleic acid sequence of FIG. 2 is encoded and/or the entire amino acid sequence of FIG. 2 is prepared, either of which are in respective human unit dose forms.

The invention further provides methods for detecting the presence and status of 251P5G2 polynucleotides and proteins in various biological samples, as well as methods for identifying cells that express 251P5G2. A typical embodiment of this invention provides methods for monitoring 251P5G2 gene products in a tissue or hematology sample having or suspected of having some form of growth dysregulation such as cancer.

The invention further provides various immunogenic or therapeutic compositions and strategies for treating cancers that express 251P5G2 such as cancers of tissues listed in Table I, including therapies aimed at inhibiting the transcription, translation, processing or function of 251P5G2 as well as cancer vaccines. In one aspect, the invention provides compositions, and methods comprising them, for treating a cancer that expresses 251P5G2 in a human subject wherein the composition comprises a carrier suitable for human use and a human unit dose of one or more than one agent that inhibits the production or function of 251P5G2. Preferably, the carrier is a uniquely human carrier. In another aspect of the invention, the agent is a moiety that is immunoreactive with 251P5G2 protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

In another aspect, the agent comprises one or more than one peptide which comprises a cytotoxic T lymphocyte (CTL) epitope that binds an HLA class I molecule in a human to elicit a CTL response to 251P5G2 and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with 251P5G2 as described above. The one or more than one nucleic acid molecule may also be, or encodes, a molecule that inhibits production of 251P5G2. Non-limiting examples of such molecules include, but are not limited to, those complementary to a nucleotide sequence essential for production of 251P5G2 (e.g. antisense sequences or molecules that form a triple helix with a nucleotide double helix essential for 251P5G2 production) or a ribozyme effective to lyse 251P5G2 mRNA.

Note that to determine the starting position of any peptide set forth in Tables VIII-XXI and XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides in Table VII. Generally, a unique Search Peptide is used to obtain HLA peptides of a particular for a particular variant. The position of each Search Peptide relative to its respective parent molecule is listed in Table VII. Accordingly, if a Search Peptide begins at position "X", one must add the value "X−1" to each position in Tables VIII-XXI and XXII to XLIX to obtain the actual position of the HLA peptides in their parental molecule. For example, if a particular Search Peptide begins at position 150 of its parental molecule, one must add 150−1, i.e., 149 to each HLA peptide amino acid position to calculate the position of that amino acid in the parent molecule.

One embodiment of the invention comprises an HLA peptide, that occurs at least twice in Tables VIII-XXI and XXII to XLIX collectively, or an oligonucleotide that encodes the HLA peptide. Another embodiment of the invention comprises an HLA peptide that occurs at least once in Tables VII I-XXI and at least once in tables XXII to XLIX, or an oligonucleotide that encodes the HLA peptide.

Another embodiment of the invention is antibody epitopes, which comprise a peptide regions, or an oligonucleotide encoding the peptide region, that has one two, three, four, or five of the following characteristics:

i) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a peptide region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or v) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9.

BRIEF DESCRIPTION OF THE FIGURES

FIG. 1. The 251P5G2 SSH sequence of 162 nucleotides.
FIG. 2.

Figure 10:
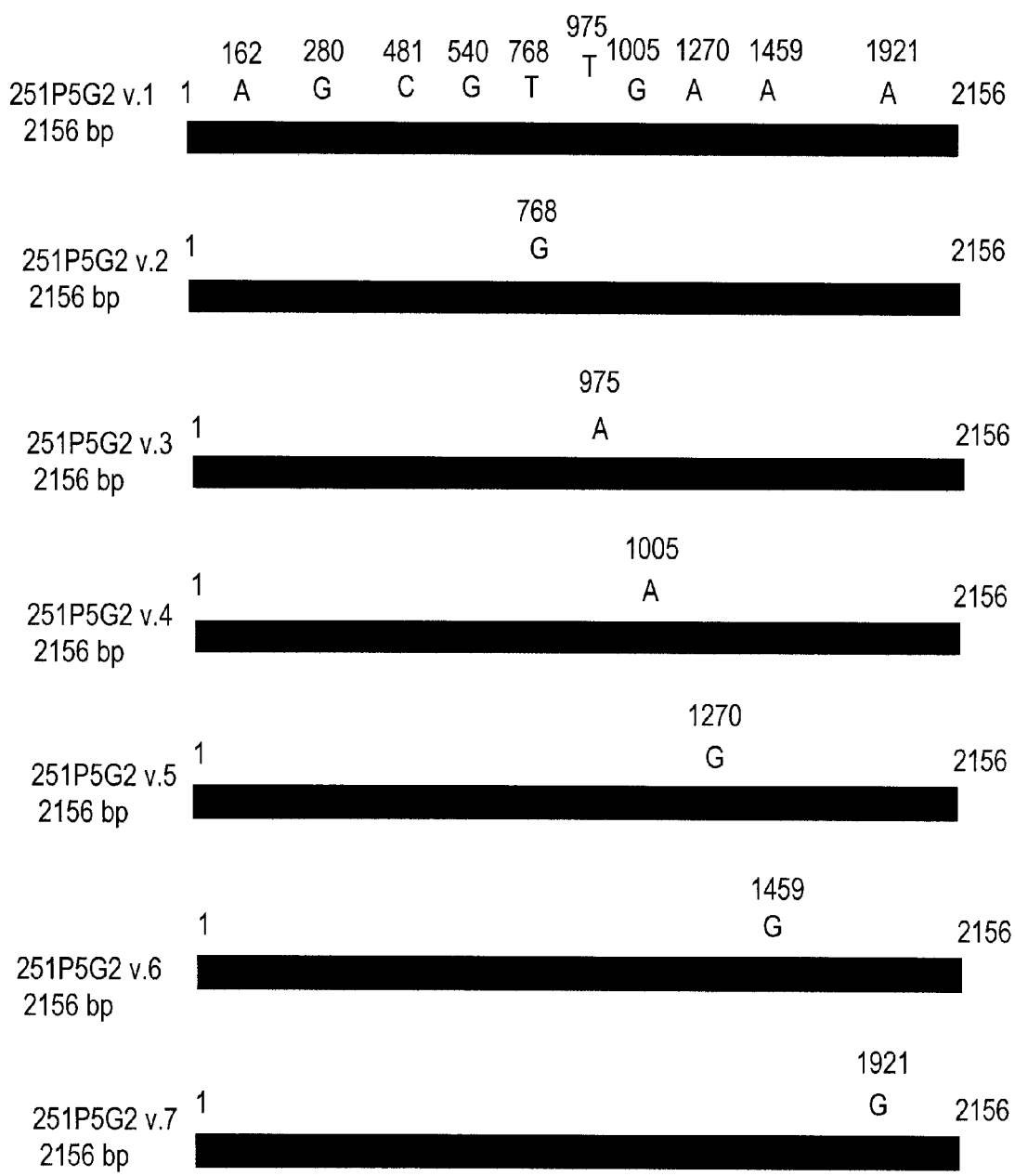

A) The cDNA and amino acid sequence of 251P5G2 variant 1 (also called "251P5G2 v.1" or "251P5G2 variant 1") is shown in FIG. 2A. The start methionine is underlined. The open reading frame extends from nucleic acid 722-1489 including the stop codon.

B) The cDNA and amino acid sequence of 251P5G2 variant 2 (also called "251P5G2 v.2") is shown in FIG. 2B. The codon for the start methionine is underlined. The open reading frame extends from nucleic acid 722-1489 including the stop codon.

C) The cDNA and amino acid sequence of 251P5G2 variant 3 (also called "251P5G2 v.3") is shown in FIG. 2C. The codon for the start methionine is underlined. The open reading frame extends from nucleic acid 722-1489 including the stop codon.

D) The cDNA and amino acid sequence of 251P5G2 variant 4 (also called "251P5G2 v.4") is shown in FIG. 2D. The codon for the start methionine is underlined. The open reading frame extends from nucleic acid 722-1489 including the stop codon.

E) The cDNA and amino acid sequence of 251P5G2 variant 5 (also called "251P5G2 v.5") is shown in FIG. 2E. The codon for the start methionine is underlined. The open reading frame extends from nucleic acid 722-1489 including the stop codon.

F) The cDNA and amino acid sequence of 251P5G2 variant 6 (also called "251P5G2 v.6") is shown in FIG. 2F. The codon for the start methionine is underlined. The open reading frame extends from nucleic acid 722-1489 including the stop codon.

G) The cDNA and amino acid sequence of 251P5G2 variant 7 (also called "251P5G2 v.7") is shown in FIG. 2G. The codon for the start methionine is underlined. The open reading frame extends from nucleic acid 722-1489 including the stop codon.

H) The cDNA and amino acid sequence of 251P5G2 variant 8 (also called "251P5G2 v.8") is shown in FIG. 2H. The codon for the start methionine is underlined. The open reading frame extends from nucleic acid 722-1489 including the stop codon.

I) The cDNA and amino acid sequence of 251P5G2 variant 9 (also called "251P5G2 v.9") is shown in FIG. 2I. The codon for the start methionine is underlined. The open reading frame extends from nucleic acid 722-1489 including the stop codon.

J) The cDNA and amino acid sequence of 251P5G2 variant 10 (also called "251P5G2 v.10") is shown in FIG. 2J. The codon for the start methionine is underlined. The open reading frame extends from nucleic acid 722-1489 including the stop codon.

K) The cDNA and amino acid sequence of 251P5G2 variant 11 (also called "251P5G2 v.11") is shown in FIG. 2K. The codon for the start methionine is underlined. The open reading frame extends from nucleic acid 722-1489 including the stop codon.

L) The cDNA and amino acid sequence of 251P5G2 variant 12 (also called "251P5G2 v.12") is shown in FIG. 2L. The codon for the start methionine is underlined. The open reading frame extends from nucleic acid 722-4522 including the stop codon.

M) The cDNA and amino acid sequence of 251P5G2 variant 13 (also called "251P5G2 v.13") is shown in FIG. 2M. The codon for the start methionine is underlined. The open reading frame extends from nucleic acid 1-3801 including the stop codon.

FIG. 3.
A) The amino acid sequence of 251P5G2 v.1 is shown in FIG. 3A; it has 255 amino acids.
B) The amino acid sequence of 251P5G2 v.2 is shown in FIG. 3B; it has 255 amino acids.
C) The amino acid sequence of 251P5G2 v.3 is shown in FIG. 3C; it has 255 amino acids.
D) The amino acid sequence of 251P5G2 v.4 is shown in FIG. 3D; it has 255 amino acids.
E) The amino acid sequence of 251P5G2 v.12 is shown in FIG. 3E; it has 1266 amino acids.

As used herein, a reference to 251P5G2 includes all variants thereof, including those shown in FIGS. 2, 3, 10, and 11, unless the context clearly indicates otherwise.

FIG. 4. FIG. 4A. Alignment of 251P5G2 v.1 with the mouse vomeronasal 1 receptor C3. FIG. 4B. Amino acid alignment of 251P5G2 v.12 with the protein XM_063686 predicted from GenomeScan.

FIG. 5. Hydrophilicity amino acid profile of 251P5G2 v.1 and v.12 determined by computer algorithm sequence analysis using the method of Hopp and Woods (Hopp T. P., Woods K. R., 1981. Proc. Natl. Acad. Sci. U.S.A. 78:3824-3828) accessed on the Protscale website located on the World Wide Web at through the ExPasy molecular biology server.

FIG. 6. Hydropathicity amino acid profile of 251P5G2 v.1 and v.12 determined by computer algorithm sequence analysis using the method of Kyte and Doolittle (Kyte J., Doolittle R. F., 1982. J. Mol. Biol. 157:105-132) accessed on the ProtScale website located on the World Wide Web at through the ExPasy molecular biology server.

FIG. 7. Percent accessible residues amino acid profile of 251P5G2 v.1 and v.12 determined by computer algorithm sequence analysis using the method of Janin (Janin J., 1979 Nature 277:491-492) accessed on the ProtScale website located on the World Wide Web through the ExPasy molecular biology server.

FIG. 8. Average flexibility amino acid profile of 251P5G2 v.1 and v.12 determined by computer algorithm sequence analysis using the method of Bhaskaran and Ponnuswamy (Bhaskaran R., and Ponnuswamy P. K., 1988. Int. J. Pept. Protein Res. 32:242-255) accessed on the ProtScale website located on the World Wide Web through the ExPasy molecular biology server.

FIG. 9. Beta-turn amino acid profile of 251P5G2 v.1 and v.12 determined by computer algorithm sequence analysis using the method of Deleage and Roux (Deleage, G., Roux B. 1987 Protein Engineering 1:289-294) accessed on the ProtScale website located on the World Wide Web through the ExPasy molecular biology server.

FIG. 10. Schematic alignment of SNP variants of 251P5G2. Variants 251P5G2 v.2 through v.11 are variants with single nucleotide differences. Though these SNP variants are shown separately, they could also occur in any combinations and in any transcript variants that contains the base pairs. Numbers correspond to those of 251P5G2 v.1. Black box shows the same sequence as 251P5G2 v.1. SNPs are indicated above the box.

Figure 11:
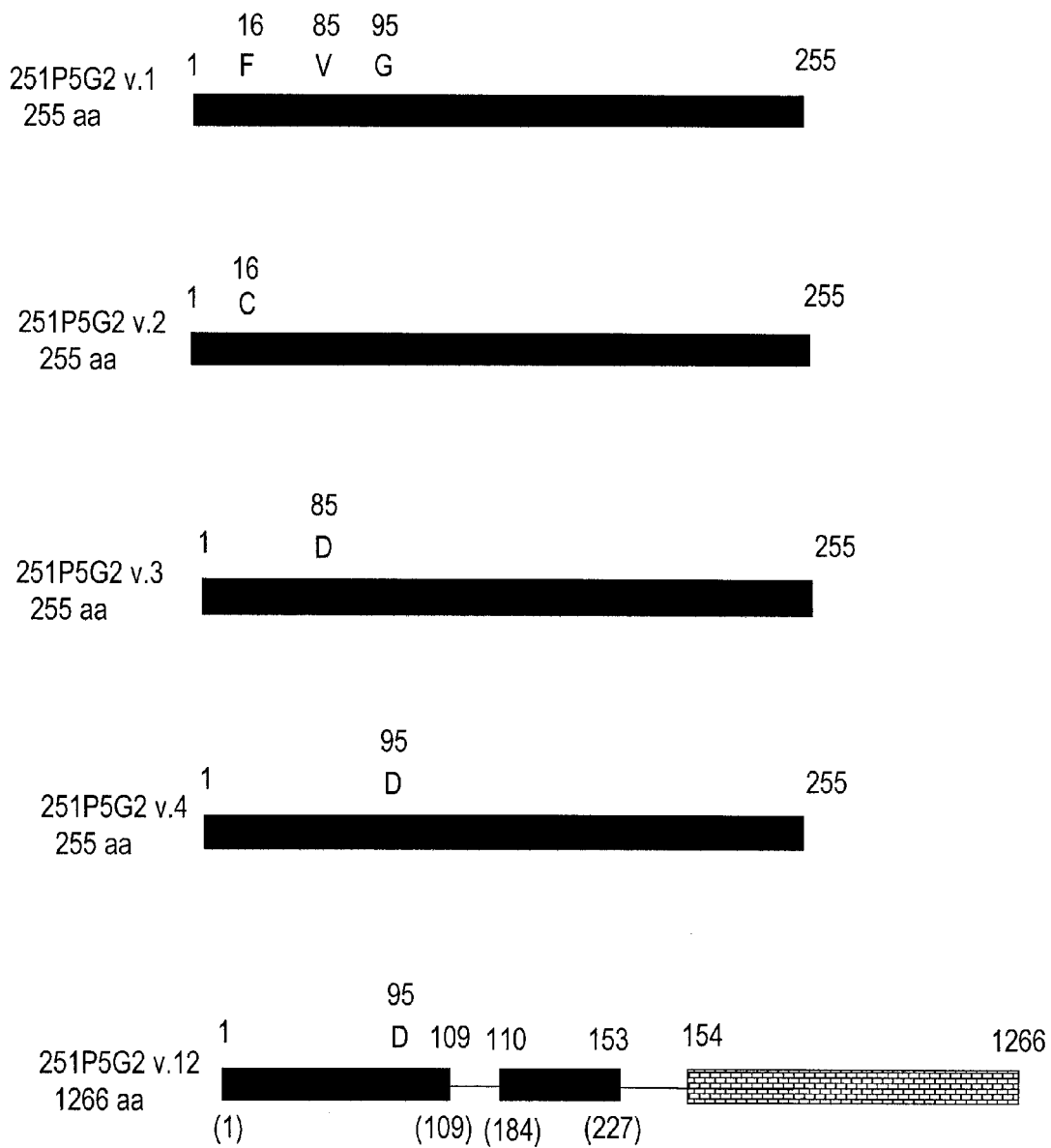
Figure 12:
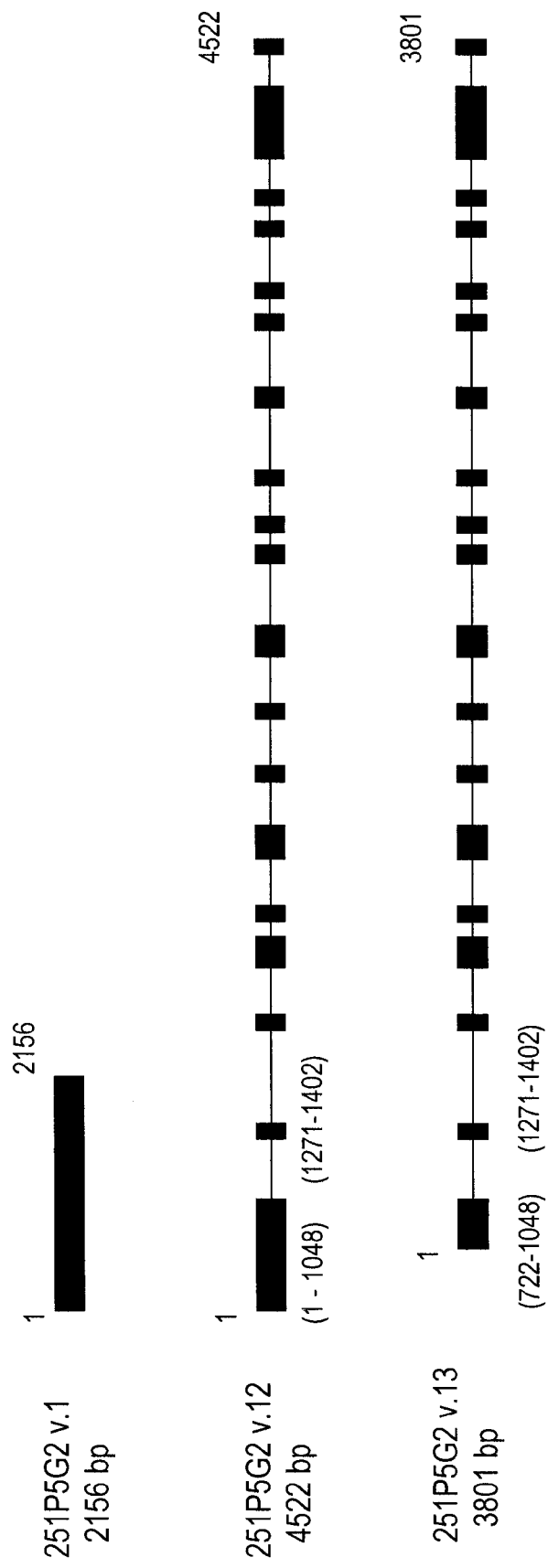

FIG. 11. Schematic alignment of protein variants of 251P5G2. Protein variants correspond to nucleotide variants. Nucleotide variants 251P5G2 v.5 through v.11 in FIG. 10 code for the same protein as 251P5G2 v.1. Nucleotide variants 251P5G2 v.12 and v.13 as shown in FIG. 12 code the same protein. Single amino acid differences were indicated above the boxes. Black boxes represent the same sequence as 251P5G2 v.1. Numbers underneath the box correspond to 251P5G2 v.1.

FIG. 12. Exon compositions of transcript variants of 251P5G2. Variant 251P5G2 v.12 and v.13 are transcript variants each with 19 exons. The first two exons of variants 251P5G2 v.12 and v.13 matches part of variant 251P5G2 v.1. Compared with 251P5G2 v.12, 251P5G2 v.13 has a shorter first exon (starting at base 722) but the other 18 exons are the same. Numbers in "( )" underneath the boxes correspond to those of 251P5G2 v.1. Lengths of introns and exons are not proportional.

Figure 13:
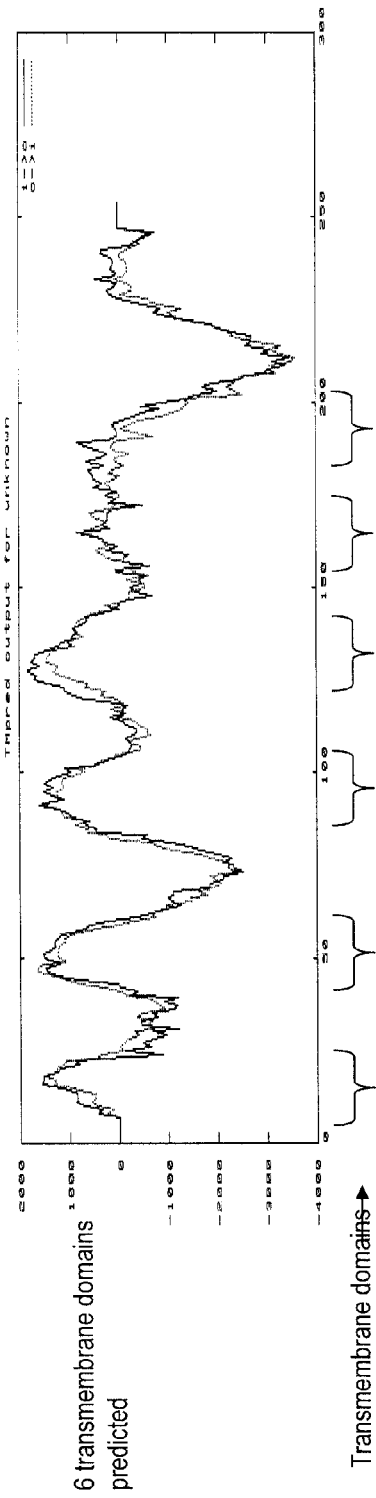
Figure 13:
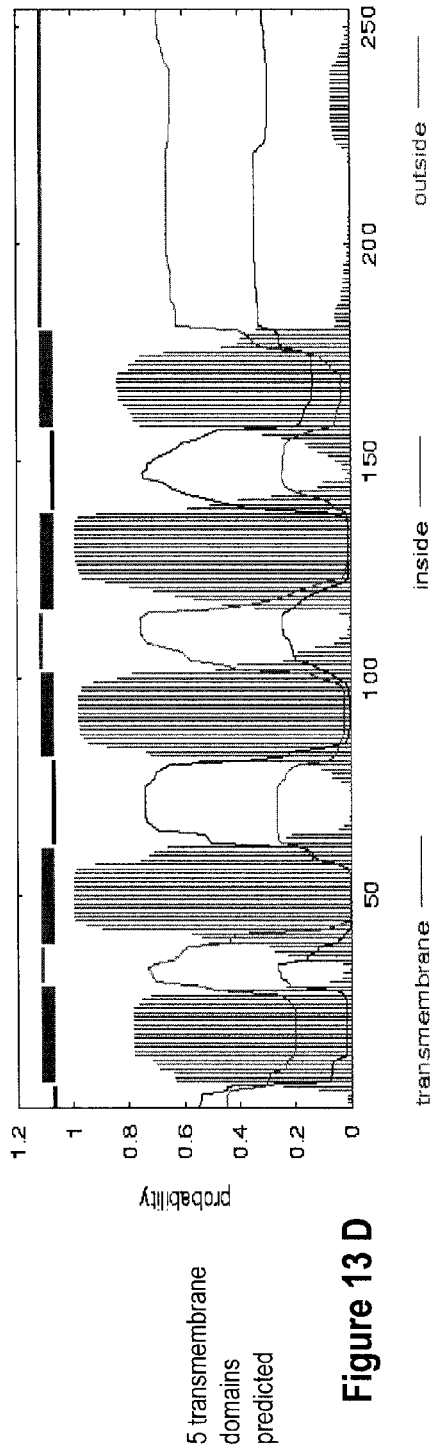
Figure 13:
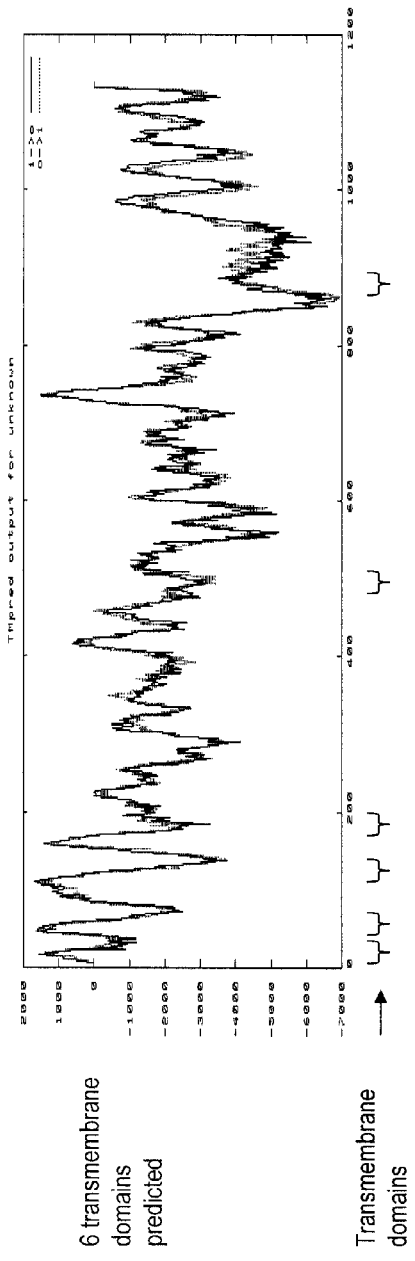
Figure 13:
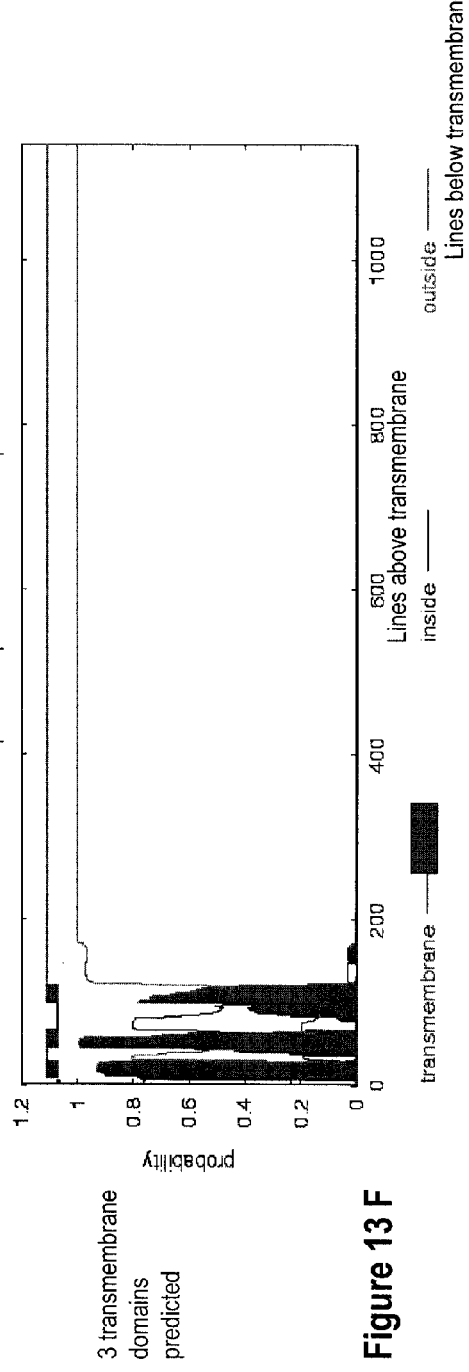

FIG. 13. FIGS. 13(A) (SEQ ID NO: 82) and 13(B) (SEQ ID NO: 83) Secondary structure and transmembrane domains prediction for 251P5G2 protein variants.

The secondary structure of 251P5G2 protein variants 1 and 12 (FIGS. 31A and 13B, respectively) were predicted using the HNN—Hierarchical Neural Network method (Guermeur, 1997), accessed from the ExPasy molecular biology server located on the World Wide Web at (.expasy.ch/tools/). This method predicts the presence and location of alpha helices, extended strands, and random coils from the primary protein sequence. The percent of the protein in a given secondary structure is also listed.

FIGS. 13(C) and 13(E): Schematic representations of the probability of existence of transmembrane regions and orientation of 251P5G2 variants 1 and 12, respectively, based on the TMpred algorithm of Hofmann and Stoffel which utilizes TMBASE (K. Hofmann, W. Stoffel. TMBASE—A database of membrane spanning protein segments Biol. Chem. Hoppe-Seyler 374:166, 1993). FIGS. 13(D) and (F): Schematic representations of the probability of the existence of transmembrane regions and the extracellular and intracellular orientation of 251P5G2 variants 1 and 12, respectively, based on the TMHMM algorithm of Sonnhammer, von Heijne, and Krogh (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998). The TMpred and TMHMM algorithms are accessed FIG. 14. Expression of 251P5G2 by RT-PCR. First strand cDNA was prepared from vital pool 1 (liver, lung and kidney), vital pool 2 (pancreas, colon and stomach), prostate cancer metastasis to lymph node, prostate cancer pool, bladder cancer pool, and cancer metastasis pool. Normalization was performed by PCR using primers to actin and GAPDH. Semi-quantitative PCR, using primers to 251P5G2, was performed at 26 and 30 cycles of amplification. Results show strong expression of 251P5G2 in prostate cancer metastasis, prostate cancer pool, and cancer metastasis pool. Expression of 251P5G2 was also detected in bladder cancer pool, but not in vital pool 1 and vital pool 2.

FIG. 15. Expression of 251P5G2 in normal tissues. Two multiple tissue northern blots (Clontech) both with 2 ug of mRNA/lane were probed with the 251P5G2 sequence. Size standards in kilobases (kb) are indicated on the side. Results show weak expression of 251P5G2 in prostate and testis, but not in any other normal tissue tested.

FIG. 16. Expression of 251P5G2 in Patient Cancer Specimens and Normal Tissues. RNA was extracted from two prostate cancer metastasis to lymph node isolated from two different patients (Met1 and Met2), as well as from normal bladder (NB), normal kidney (NK), normal lung (NL) and normal breast (NBr), normal ovary (NO), and normal pancreas (NPa). Northern blot with 10 μg of total RNA/lane was probed with 251P5G2 SSH sequence. Size standards in kilobases (kb) are indicated on the side. The 251P5G2 transcript was detected in the prostate cancer metastasis specimens, but not in the normal tissues tested.

FIG. 17. Expression of 251P5G2 in Prostate Cancer Patient Specimens. RNA was extracted from prostate cancer xenografts (LAPC-4AD, LAPC-4AI, LAPC-9AD, LAPC-9AI), prostate cancer cell lines (LNCaP and PC3), normal prostate (N), and prostate cancer patient tumors (T). Northern blots with 10 ug of total RNA were probed with the 251P5G2 SSH fragment. Size standards in kilobases are on the side. Results show expression of 251P5G2 in the LAPC-9AD xenograft and in prostate tumor tissues. Lower level expression was detected in the other xenograft tissues and LNCaP cell line but not in PC3. The lower panel represents ethidium-bromide staining of the gel confirming the quality of the RNA.

FIG. 18. Expression of 251P5G2 in Human Normal and Cancer Tissues. First strand cDNA was prepared from a panel of 13 normal tissues, prostate cancer pool, bladder cancer pool, kidney cancer pool, colon cancer pool, lung cancer pool, ovary cancer pool, breast cancer pool, pancreas cancer pool, 2 different prostate cancer metastasis specimens to lymph node, and a pool of prostate cancer LAPC xenografts (LAPC-4AD, LAPC-4AI, LAPC-9AD, and LAPC-9AI). Normalization was performed by PCR using primers to actin and GAPDH. Semi-quantitative PCR, using primers to 251P5G2, was performed at 26 and 30 cycles of amplification. A standard curve was generated using plasmid DNA containing 251P5G2 of known copy number. The experiment was performed in duplicate. Results show strong expression of 251P5G2 in prostate cancer metastasis, prostate cancer pool, and cancer metastasis pool. Expression of 251P5G2 was also detected in bladder cancer pool. Amongst normal tissues, very weak expression was detected in hear, prostate, skeletal muscle and testis but not in any other normal tissue tested.

FIG. 19. Expression of 251P5G2 in Prostate Cancer Patient Specimens. First strand cDNA was prepared from normal prostate, prostate cancer cell lines (PC3, DU145, LNCaP, 293T), and a panel of prostate cancer patient specimens. Normalization was performed by PCR using primers to actin and GAPDH. Semi-quantitative PCR, using primers to 251P5G2, was performed at 26 and 30 cycles of amplification. Results show expression of 251P5G2 in 10 out of 19 patient specimens. Very strong expression was detected in 5 out of the 10 expressing tumors. Expression was also detected in LNCaP but not in the other cell lines tested nor in normal prostate.

FIG. 20. Expression of 251P5G2 in BladderCancer Patient Specimens. First strand cDNA was prepared from normal bladder, bladder cancer cell lines (UM-UC-3, TCCSUP, J82), and a panel of bladder cancer patient specimens. Normalization was performed by PCR using primers to actin and GAPDH. Semi-quantitative PCR, using primers to 251P5G2, was performed at 26 and 30 cycles of amplification. Results show expression of 251P5G2 in 5 out of 9 patient specimens, but not in the cell lines tested nor in normal bladder.

DETAILED DESCRIPTION OF THE INVENTION

Outline of Sections
I.) Definitions
II.) 251P5G2 Polynucleotides
II.A.) Uses of 251P5G2 Polynucleotides
II.A.1.) Monitoring of Genetic Abnormalities
II.A.2.) Antisense Embodiments
II.A.3.) Primers and Primer Pairs
II.A.4.) Isolation of 251P5G2-Encoding Nucleic Acid Molecules
II.A.5.) Recombinant Nucleic Acid Molecules and Host-Vector Systems
III.) 251P5G2-related Proteins
III.A.) Motif-bearing Protein Embodiments
III.B.) Expression of 251P5G2-related Proteins
III.C.) Modifications of 251P5G2-related Proteins
III.D.) Uses of 251P5G2-related Proteins
IV.) 251P5G2 Antibodies
V.) 251P5G2 Cellular Immune Responses
VI.) 251P5G2 Transgenic Animals
VII.) Methods for the Detection of 251P5G2
VIII.) Methods for Monitoring the Status of 251P5G2-related Genes and Their Products
IX.) Identification of Molecules That Interact With 251P5G2
X.) Therapeutic Methods and Compositions
X.A.) Anti-Cancer Vaccines
X.B.) 251P5G2 as a Target for Antibody-based Therapy
X.C.) 251P5G2 as a Target for Cellular Immune Responses
X.C.1. Minigene Vaccines
X.C.2. Combinations of CTL Peptides with Helper Peptides
X.C.3. Combinations of CTL Peptides with T Cell Priming Agents
X.C.4. Vaccine Compositions Comprising DC Pulsed with CTL and/or HTL Peptides
X.D.) Adoptive Immunotherapy
X.E.) Administration of Vaccines for Therapeutic or Prophylactic Purposes
XI.) Diagnostic and Prognostic Embodiments of 251P5G2.
XII.) Inhibition of 251P5G2 Protein Function
XII.A.) Inhibition of 251P5G2 With Intracellular Antibodies
XII.B.) Inhibition of 251P5G2 with Recombinant Proteins
XII.C.) Inhibition of 251P5G2 Transcription or Translation
XII.D.) General Considerations for Therapeutic Strategies
XIII.) Identification, Characterization and Use of Modulators of 251P5G2
XIV.) KITS/Articles of Manufacture
I.) Definitions:

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 251P5G2 (either by removing the underlying glycosylation site or by deleting the glycosylation by chemical and/or enzymatic means), and/or adding one or more glycosylation sites that are not present in the native sequence 251P5G2. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 251P5G2-related protein). For example, an analog of a 251P5G2 protein can be specifically bound by an antibody or T cell that specifically binds to 251P5G2.

The term "antibody" is used in the broadest sense. Therefore, an "antibody" can be naturally occurring or man-made such as monoclonal antibodies produced by conventional hybridoma technology. Anti-251P5G2 antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment it specifically covers single anti-251P5G2 antibodies and clones thereof (including agonist, antagonist and neutralizing antibodies) and anti-251P5G2 antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

A "combinatorial library" is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Numerous chemical compounds are synthesized through such combinatorial mixing of chemical building blocks (Gallop et al., J. Med. Chem. 37(9): 1233-1251 (1994)).

Preparation and screening of combinatorial libraries is well known to those of skill in the art. Such combinatorial chemical libraries include, but are not limited to, peptide libraries (see, e.g., U.S. Pat. No. 5,010,175, Furka, Pept. Prot. Res. 37:487-493 (1991), Houghton et al., Nature, 354:84-88 (1991)), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with a Beta-D-Glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho, et al., Science 261: 1303 (1993)), and/or peptidyl phosphonates (Campbell et al., J. Org. Chem. 59:658 (1994)). See, generally, Gordon et al., J. Med. Chem. 37:1385 (1994), nucleic acid libraries (see, e.g., Stratagene, Corp.), peptide nucleic acid libraries (see, e.g., U.S. Pat. No. 5,539,083), antibody libraries (see, e.g., Vaughn et al., Nature Biotechnology 14(3): 309-314 (1996), and PCT/US96/10287), carbohydrate libraries (see, e.g., Liang et al., Science 274:1520-1522 (1996), and U.S. Pat. No. 5,593,853), and small organic molecule libraries (see, e.g., benzodiazepines, Baum, C&EN, January 18, page 33 (1993); isoprenoids, U.S. Pat. No. 5,569,588; thiazolidinones and methathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288, 514; and the like).

Devices for the preparation of combinatorial libraries are commercially available (see, e.g., 357 NIPS, 390 NIPS, Advanced Chem Tech, Louisville Ky.; Symphony, Rainin, Woburn, Mass.; 433A, Applied Biosystems, Foster City, Calif.; 9050, Plus, Millipore, Bedford, NIA). A number of well-known robotic systems have also been developed for solution phase chemistries. These systems include automated workstations such as the automated synthesis apparatus developed by Takeda Chemical Industries, LTD. (Osaka, Japan) and many robotic systems utilizing robotic arms (Zymate H, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Asinex, Moscow, RU; Tripos, Inc., St. Louis, Mo.; ChemStar, Ltd, Moscow, RU; 3D Pharmaceuticals, Exton, Pa.; Martek Biosciences, Columbia, Md.; etc.).

The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to auristatins, auromycins, maytansinoids, yttrium, bismuth, ricin, ricin A-chain, combrestatin, duocarmycins, dolostatins, doxorubicin, daunorubicin, taxol, cisplatin, cc1065, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, restrictocin, phenomycin, enomycin, curicin, crotin, calicheamicin, Sapaonaria officinalis inhibitor, and glucocorticoid and other chemotherapeutic agents, as well as radioisotopes such as $At^{211}, I^{131}, I^{125}, Y^{90}, Re^{186}, Re^{188}, Sm^{153}, Bi^{212\ or\ 213}, P^{32}$ and radioactive isotopes of Lu including $Lu^{177}$. Antibodies may also be conjugated to an anti-cancer pro-drug activating enzyme capable of converting the pro-drug to its active form.

The "gene product" is sometimes referred to herein as a protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 2. The cancer protein can be a fragment, or alternatively, be the full-length protein to the fragment encoded by the nucleic acids of FIG. 2. In one embodiment, a cancer amino acid sequence is used to determine sequence identity or similarity. In another embodiment, the sequences are naturally occurring allelic variants of a protein encoded by a nucleic acid of FIG. 2. In another embodiment, the sequences are sequence variants as further described herein.

"High throughput screening" assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins; U.S. Pat. No. 5,585,639 discloses high throughput screening methods for nucleic acid binding (i.e., in arrays); while U.S. Pat. Nos. 5,576,220 and 5,541,061 disclose high throughput methods of screening for ligand/antibody binding.

In addition, high throughput screening systems are commercially available (see, e.g., Amersham Biosciences, Piscataway, N.J.; Zymark Corp., Hopkinton, Mass.; Air Technical Industries, Mentor, Ohio; Beckman Instruments, Inc. Fullerton, Calif.; Precision Systems, Inc., Natick, Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., IMMUNOLOGY, $8^{TH}$ ED., Lange Publishing, Los Altos, Calif. (1994).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 251P5G2 genes or that encode polypeptides other than 251P5G2 gene product or fragments thereof. A skilled artisan can readily employ nucleic acid isolation procedures to obtain an isolated 251P5G2 polynucleotide. A protein is said to be "isolated," for example, when physical, mechanical or chemical methods are employed to remove the 251P5G2 proteins from cellular constituents that are normally associated with the protein. A skilled artisan can readily employ standard purification methods to obtain an isolated 251P5G2 protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage T×N×M+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

Modulators of cancer can also be nucleic acids. Nucleic acid modulating agents can be naturally occurring nucleic acids, random nucleic acids, or "biased" random nucleic acids. For example, digests of prokaryotic or eukaryotic genomes can be used in an approach analogous to that outlined above for proteins.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of a 251P5G2-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 2, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. Alternatively, in another embodiment, the primary anchor residues of a peptide binds an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

"Radioisotopes" include, but are not limited to the following (non-limiting exemplary uses are also set forth):

Examples of Medical Isotopes:

| Isotope | Description of use |
| --- | --- |
| Actinium-225 (AC-225) | See Thorium-229 (Th-229) |
| Actinium-227 (AC-227) | Parent of Radium-223 (Ra-223) which is an alpha emitter used to treat metastases in the skeleton resulting from cancer (i.e., breast and prostate cancers), and cancer radioimmunotherapy |
| Bismuth-212 (Bi-212) | See Thorium-228 (Th-228) |
| Bismuth-213 (Bi-213) | See Thorium-229 (Th-229) |
| Cadmium-109 (Cd-109) | Cancer detection |
| Cobalt-60 (Co-60) | Radiation source for radiotherapy of cancer, for food irradiators, and for sterilization of medical supplies |
| Copper-64 (Cu-64) | A positron emitter used for cancer therapy and SPECT imaging |
| Copper-67 (Cu-67) | Beta/gamma emitter used in cancer radioimmunotherapy and diagnostic studies (i.e., breast and colon cancers, and lymphoma) |

-continued

| Isotope | Description of use |
|---|---|
| Dysprosium-166 (Dy-166) | Cancer radioimmunotherapy |
| Erbium-169 (Er-169) | Rheumatoid arthritis treatment, particularly for the small joints associated with fingers and toes |
| Europium-152 (Eu-152) | Radiation source for food irradiation and for sterilization of medical supplies |
| Europium-154 (Eu-154) | Radiation source for food irradiation and for sterilization of medical supplies |
| Gadolinium-153 (Gd-153) | Osteoporosis detection and nuclear medical quality assurance devices |
| Gold-198 (Au-198) | Implant and intracavity therapy of ovarian, prostate, and brain cancers |
| Holmium-166 (Ho-166) | Multiple myeloma treatment in targeted skeletal therapy, cancer radioimmunotherapy, bone marrow ablation, and rheumatoid arthritis treatment |
| Iodine-125 (I-125) | Osteoporosis detection, diagnostic imaging, tracer drugs, brain cancer treatment, radiolabeling, tumor imaging, mapping of receptors in the brain, interstitial radiation therapy, brachytherapy for treatment of prostate cancer, determination of glomerular filtration rate (GFR), determination of plasma volume, detection of deep vein thrombosis of the legs |
| Iodine-131 (I-131) | Thyroid function evaluation, thyroid disease detection, treatment of thyroid cancer as well as other non-malignant thyroid diseases (i.e., Graves disease, goiters, and hyperthyroidism), treatment of leukemia, lymphoma, and other forms of cancer (e.g., breast cancer) using radioimmunotherapy |
| Iridium-192 (Ir-192) | Brachytherapy, brain and spinal cord tumor treatment, treatment of blocked arteries (i.e., arteriosclerosis and restenosis), and implants for breast and prostate tumors |
| Lutetium-177 (Lu-177) | Cancer radioimmunotherapy and treatment of blocked arteries (i.e., arteriosclerosis and restenosis) |
| Molybdenum-99 (Mo-99) | Parent of Technetium-99 m (Tc-99 m) which is used for imaging the brain, liver, lungs, heart, and other organs. Currently, Tc-99 m is the most widely used radioisotope used for diagnostic imaging of various cancers and diseases involving the brain, heart, liver, lungs; also used in detection of deep vein thrombosis of the legs |
| Osmium-194 (Os-194) | Cancer radioimmunotherapy |
| Palladium-103 (Pd-103) | Prostate cancer treatment |
| Platinum-195 m (Pt-195 m) | Studies on biodistribution and metabolism of cisplatin, a chemotherapeutic drug |
| Phosphorus-32 (P-32) | Polycythemia rubra vera (blood cell disease) and leukemia treatment, bone cancer diagnosis/treatment; colon, pancreatic, and liver cancer treatment; radiolabeling nucleic acids for in vitro research, diagnosis of superficial tumors, treatment of blocked arteries (i.e., arteriosclerosis and restenosis), and intracavity therapy |
| Phosphorus-33 (P-33) | Leukemia treatment, bone disease diagnosis/treatment, radiolabeling, and treatment of blocked arteries (i.e., arteriosclerosis and restenosis) |
| Radium-223 (Ra-223) | See Actinium-227 (Ac-227) |
| Rhenium-186 (Re-186) | Bone cancer pain relief, rheumatoid arthritis treatment, and diagnosis and treatment of lymphoma and bone, breast, colon, and liver cancers using radioimmunotherapy |
| Rhenium-188 (Re-188) | Cancer diagnosis and treatment using radioimmunotherapy, bone cancer pain relief, treatment of rheumatoid arthritis, and treatment of prostate cancer |
| Rhodium-105 (Rh-105) | Cancer radioimmunotherapy |
| Samarium-145 (Sm-145) | Ocular cancer treatment |
| Samarium-153 (Sm-153) | Cancer radioimmunotherapy and bone cancer pain relief |
| Scandium-47 (Sc-47) | Cancer radioimmunotherapy and bone cancer pain relief |
| Selenium-75 (Se-75) | Radiotracer used in brain studies, imaging of adrenal cortex by gamma-scintigraphy, lateral locations of steroid secreting tumors, pancreatic scanning, detection of hyperactive parathyroid glands, measure rate of bile acid loss from the endogenous pool |
| Strontium-85 (Sr-85) | Bone cancer detection and brain scans |
| Strontium-89 (Sr-89) | Bone cancer pain relief, multiple myeloma treatment, and osteoblastic therapy |
| Technetium-99 m (Tc-99 m) | See Molybdenum-99 (Mo-99) |
| Thorium-228 (Th-228) | Parent of Bismuth-212 (Bi-212) which is an alpha emitter used in cancer radioimmunotherapy |
| Thorium-229 (Th-229) | Parent of Actinium-225 (Ac-225) and grandparent of Bismuth-213 (Bi-213) which are alpha emitters used in cancer radioimmunotherapy |
| Thulium-170 (Tm-170) | Gamma source for blood irradiators, energy source for implanted medical devices |
| Tin-117 m (Sn-117 m) | Cancer immunotherapy and bone cancer pain relief |
| Tungsten-188 (W-188) | Parent for Rhenium-188 (Re-188) which is used for cancer diagnostics/treatment, bone cancer pain relief, rheumatoid arthritis treatment, and treatment of blocked arteries (i.e., arteriosclerosis and restenosis) |
| Xenon-127 | Neuroimaging of brain disorders, high resolution SPECT studies, pulmonary function tests, |

-continued

| Isotope | Description of use |
| --- | --- |
| (Xe-127) | and cerebral blood flow studies |
| Ytterbium-175 (Yb-175) | Cancer radioimmunotherapy |
| Yttrium-90 (Y-90) | Microseeds obtained from irradiating Yttrium-89 (Y-89) for liver cancer treatment |
| Yttrium-91 (Y-91) | A gamma-emitting label for Yttrium-90 (Y-90) which is used for cancer radioimmunotherapy (i.e., lymphoma, breast, colon, kidney, lung, ovarian, prostate, pancreatic, and inoperable liver cancers) |

By "randomized" or grammatical equivalents as herein applied to nucleic acids and proteins is meant that each nucleic acid and peptide consists of essentially random nucleotides and amino acids, respectively. These random peptides (or nucleic acids, discussed herein) can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, a library is "fully randomized," with no sequence preferences or constants at any position. In another embodiment, the library is a "biased random" library. That is, some positions within the sequence either are held constant, or are selected from a limited number of possibilities. For example, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

A "recombinant" DNA or RNA molecule is a DNA or RNA molecule that has been subjected to molecular manipulation in vitro.

Non-limiting examples of small molecules include compounds that bind or interact with 251P5G2, ligands including hormones, neuropeptides, chemokines, odorants, phospholipids, and functional equivalents thereof that bind and preferably inhibit 251P5G2 protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, 251P5G2 protein; are not found in naturally occurring metabolic pathways; and/or are more soluble in aqueous than non-aqueous solutions "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles. Overall phenotypic frequencies of HLA-supertypes in different ethnic populations are set forth in Table IV (F). The non-limiting constituents of various supertypes are as follows:

A2: A*0201, A*0202, A*0203, A*0204, A*0205, A*0206, A*6802, A*6901, A*0207

A3: A3, A11, A31, A*3301, A*6801, A*0301, A*1101, A*3101

B7: B7, B*3501-03, B*51, B*5301, B*5401, B*5501, B*5502, B*5601, B*6701, B*7801, B*0702, B*5101, B*5602

B44: B*3701, B*4402, B*4403, B*60 (B*4001), B61 (B*4006)

A1: A*0102, A*2604, A*3601, A*4301, A*8001

A24: A*24, A*30, A*2403, A*2404, A*3002, A*3003

B27: B*1401-02, B*1503, B*1509, B*1510, B*1518, B*3801-02, B*3901, B*3902, B*3903-04, B*4801-02, B*7301, B*2701-08

B58: B*1516, B*1517, B*5701, B*5702, B58

B62: B*4601, B52, B*1501 (B62), B*1502 (B75), B*1513 (B77)

Calculated population coverage afforded by different HLA-supertype combinations are set forth in Table IV (G).

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 251P5G2 protein shown in FIG. 2 or FIG. 3. An analog is an example of a variant protein. Splice isoforms and single nucleotides polymorphisms (SNPs) are further examples of variants.

The "251P5G2-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 251P5G2 proteins or fragments thereof, as well as fusion proteins of a 251P5G2 protein and a heterologous polypeptide are also included. Such 251P5G2 proteins are collectively referred to as the 251P5G2-related proteins, the proteins of the invention, or 251P5G2. The term "251P5G2-related protein" refers to a polypeptide fragment or a 251P5G2 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, or 576 or more amino acids.

II.) 251P5G2 Polynucleotides

One aspect of the invention provides polynucleotides corresponding or complementary to all or part of a 251P5G2 gene, mRNA, and/or coding sequence, preferably in isolated form, including polynucleotides encoding a 251P5G2-related protein and fragments thereof, DNA, RNA, DNA/RNA hybrid, and related molecules, polynucleotides or oligonucleotides complementary to a 251P5G2 gene or mRNA sequence or a part thereof, and polynucleotides or oligonucleotides that hybridize to a 251P5G2 gene, mRNA, or to a 251P5G2 encoding polynucleotide (collectively, "251P5G2 polynucleotides"). In all instances when referred to in this section, T can also be U in FIG. 2.

Embodiments of a 251P5G2 polynucleotide include: a 251P5G2 polynucleotide having the sequence shown in FIG. 2, the nucleotide sequence of 251P5G2 as shown in FIG. 2 wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of 251P5G2 nucleotides comprise, without limitation:

(I) a polynucleotide comprising, consisting essentially of, or consisting of a sequence as shown in FIG. 2, wherein T can also be U;

(II) a polynucleotide comprising, consisting essentially of, or consisting of the sequence as shown in FIG. 2A, from nucleotide residue number 722 through nucleotide residue number 1489, including the stop codon, wherein T can also be U;

(III) a polynucleotide comprising, consisting essentially of, or consisting of the sequence as shown in FIG. 2B, from nucleotide residue number 722 through nucleotide residue number 1489, including the stop codon, wherein T can also be U;

(IV) a polynucleotide comprising, consisting essentially of, or consisting of the sequence as shown in FIG. 2C, from nucleotide residue number 722 through nucleotide residue number 1489, including the a stop codon, wherein T can also be U;

(V) a polynucleotide comprising, consisting essentially of, or consisting of the sequence as shown in FIG. 2D, from nucleotide residue number 722 through nucleotide residue number 1489, including the stop codon, wherein T can also be U;

(VI) a polynucleotide comprising, consisting essentially of, or consisting of the sequence as shown in FIG. 2E, from nucleotide residue number 722 through nucleotide residue number 1489, including the stop codon, wherein T can also be U;

(VII) a polynucleotide comprising, consisting essentially of, or consisting of the sequence as shown in FIG. 2F, from nucleotide residue number 722 through nucleotide residue number 1489, including the stop codon, wherein T can also be U;

(VIII) a polynucleotide comprising, consisting essentially of, or consisting of the sequence as shown in FIG. 2G, from nucleotide residue number 722 through nucleotide residue number 1489, including the stop codon, wherein T can also be U;

(IX) a polynucleotide comprising, consisting essentially of, or consisting of the sequence as shown in FIG. 2H, from nucleotide residue number 722 through nucleotide residue number 1489, including the stop codon, wherein T can also be U;

(X) a polynucleotide comprising, consisting essentially of, or consisting of the sequence as shown in FIG. 2I, from nucleotide residue number 722 through nucleotide residue number 1489, including the stop codon, wherein T can also be U;

(XI) a polynucleotide comprising, consisting essentially of, or consisting of the sequence as shown in FIG. 2J, from nucleotide residue number 722 through nucleotide residue number 1489, including the stop codon, wherein T can also be U;

(XII) a polynucleotide comprising, consisting essentially of, or consisting of the sequence as shown in FIG. 2K, from nucleotide residue number 722 through nucleotide residue number 1489, including the stop codon, wherein T can also be U;

(XIII) a polynucleotide comprising, consisting essentially of, or consisting of the sequence as shown in FIG. 2L, from nucleotide residue number 722 through nucleotide residue number 4522, including the stop codon, wherein T can also be U;

(XIV) a polynucleotide comprising, consisting essentially of, or consisting of the sequence as shown in FIG. 2M, from nucleotide residue number 1 through nucleotide residue number 3801, including the stop codon, wherein T can also be U;

(XV) a polynucleotide that encodes a 251P5G2-related protein that is at least 90, 91, 92, 93, 94, 95, 96, 97, 98, 99 or 100% homologous to an entire amino acid sequence shown in FIG. 2A-M;

(XVI) a polynucleotide that encodes a 251P5G2-related protein that is at least 90, 91, 92, 93, 94, 95, 96, 97, 98, 99 or 100% identical to an entire amino acid sequence shown in FIG. 2A-M;

(XVII) a polynucleotide that encodes at least one peptide set forth in Tables VIII-XXI and XXII-XLIX;

(XVIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A-D in any whole number increment up to 255 that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XIX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A-D in any whole number increment up to 255 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A-D in any whole number increment up to 255 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A-D in any whole number increment up to 255 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A-D in any whole number increment up to 255 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XXIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 1266 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XXIV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 1266 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XXV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 1266 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXVI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 1266 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXVII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 1266 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9

(XXVIII) a polynucleotide that is fully complementary to a polynucleotide of any one of (I)-(XXVII).

(XXIX) a peptide that is encoded by any of (I) to (XXVIII); and (XXX) a composition comprising a polynucleotide of any of (I)-(XXVIII) or peptide of (XXIX) together with a pharmaceutical excipient and/or in a human unit dose form.

(XXXI) a method of using a polynucleotide of any (I)-(XXVIII) or peptide of (XXIX) or a composition of (XXX) in a method to modulate a cell expressing 251P5G2, (XXXII) a method of using a polynucleotide of any (I)-(XXVIII) or peptide of (XXIX) or a composition of (XXX) in a method to diagnose, prophylax, prognose, or treat an individual who bears a cell expressing 251P5G2

(XXXIII) a method of using a polynucleotide of any (I)-(XXVIII) or peptide of (XXIX) or a composition of (XXX) in a method to diagnose, prophylax, prognose, or treat an individual who bears a cell expressing 251P5G2, said cell from a cancer of a tissue listed in Table I;

(XXIV) a method of using a polynucleotide of any (I)-(XXVIII) or peptide of (XXIX) or a composition of (XXX) in a method to diagnose, prophylax, prognose, or treat a cancer;

(XXXV) a method of using a polynucleotide of any (I)-(XXVIII) or peptide of (XXIX) or a composition of (XXX) in a method to diagnose, prophylax, prognose, or treat a cancer of a tissue listed in Table I; and, (XXXVI) a method of using a polynucleotide of any (I)-(XXVIII) or peptide of (XXIX) or a composition of (XXX) in a method to identify or characterize a modulator of a cell expressing 251P5G2.

As used herein, a range is understood to disclose specifically all whole unit positions thereof.

Typical embodiments of the invention disclosed herein include 251P5G2 polynucleotides that encode specific portions of 251P5G2 mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, or 255 or more contiguous amino acids of 251P5G2 variant 1; the maximal lengths relevant for other variants are: variant 2, 255 amino acids; variant 3, 255 amino acids, variant 4, 255 amino acids, and variant 12, 1266 amino acids.

For example, representative embodiments of the invention disclosed herein include: polynucleotides and their encoded peptides themselves encoding about amino acid 1 to about amino acid 10 of the 251P5G2 protein shown in FIG. 2 or FIG. 3, polynucleotides encoding about amino acid 10 to about amino acid 20 of the 251P5G2 protein shown in FIG. 2 or FIG. 3, polynucleotides encoding about amino acid 20 to about amino acid 30 of the 251P5G2 protein shown in FIG. 2 or FIG. 3, polynucleotides encoding about amino acid 30 to about amino acid 40 of the 251P5G2 protein shown in FIG. 2 or FIG. 3, polynucleotides encoding about amino acid 40 to about amino acid 50 of the 251P5G2 protein shown in FIG. 2 or FIG. 3, polynucleotides encoding about amino acid 50 to about amino acid 60 of the 251P5G2 protein shown in FIG. 2 or FIG. 3, polynucleotides encoding about amino acid 60 to about amino acid 70 of the 251P5G2 protein shown in FIG. 2 or FIG. 3, polynucleotides encoding about amino acid 70 to about amino acid 80 of the 251P5G2 protein shown in FIG. 2 or FIG. 3, polynucleotides encoding about amino acid 80 to about amino acid 90 of the 251P5G2 protein shown in FIG. 2 or FIG. 3, polynucleotides encoding about amino acid 90 to about amino acid 100 of the 251P5G2 protein shown in FIG. 2 or FIG. 3, in increments of about 10 amino acids, ending at the carboxyl terminal amino acid set forth in FIG. 2 or FIG. 3. Accordingly, polynucleotides encoding portions of the amino acid sequence (of about 10 amino acids), of amino acids, 100 through the carboxyl terminal amino acid of the 251P5G2 protein are embodiments of the invention. Wherein it is understood that each particular amino acid position discloses that position plus or minus five amino acid residues.

Polynucleotides encoding relatively long portions of a 251P5G2 protein are also within the scope of the invention. For example, polynucleotides encoding from about amino acid 1 (or 20 or 30 or 40 etc.) to about amino acid 20, (or 30, or 40 or 50 etc.) of the 251P5G2 protein "or variant" shown in FIG. 2 or FIG. 3 can be generated by a variety of techniques well known in the art. These polynucleotide fragments can include any portion of the 251P5G2 sequence as shown in FIG. 2.

Additional illustrative embodiments of the invention disclosed herein include 251P5G2 polynucleotide fragments encoding one or more of the biological motifs contained within a 251P5G2 protein "or variant" sequence, including one or more of the motif-bearing subsequences of a 251P5G2 protein "or variant" set forth in Tables VIII-XXI and XXII-XLIX. In another embodiment, typical polynucleotide fragments of the invention encode one or more of the regions of 251P5G2 protein or variant that exhibit homology to a known molecule. In another embodiment of the invention, typical polynucleotide fragments can encode one or more of the 251P5G2 protein or variant N-glycosylation sites, cAMP and cGMP-dependent protein kinase phosphorylation sites, casein kinase II phosphorylation sites or N-myristoylation site and amidation sites.

Note that to determine the starting position of any peptide set forth in Tables VIII-XXI and Tables XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides listed in Table VII. Generally, a unique Search Peptide is used to obtain HLA peptides for a particular variant. The position of each Search Peptide relative to its respective parent molecule is listed in Table VII. Accordingly, if a Search Peptide begins at position "X", one must add the value "X minus 1" to each position in Tables VIII-XXI and Tables XXII-IL to obtain the actual position of the HLA peptides in their parental molecule. For example if a particular Search Peptide begins at position 150 of its parental molecule, one must add 150−1, i.e., 149 to each HLA peptide amino acid position to calculate the position of that amino acid in the parent molecule.

II.A.) Uses of 251P5G2 Polynucleotides

II.A.1.) Monitoring of Genetic Abnormalities

The polynucleotides of the preceding paragraphs have a number of different specific uses. The human 251P5G2 gene maps to the chromosomal location set forth in the Example entitled "Chromosomal Mapping of 251P5G2." For example, because the 251P5G2 gene maps to this chromosome, polynucleotides that encode different regions of the 251P5G2 proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83 (1998); Johansson et al., Blood 86(10): 3905-3914 (1995) and Finger et al., P.N.A.S. 85(23): 9158-9162 (1988)). Thus, polynucleotides encoding specific regions of the 251P5G2 proteins provide new tools that can be used to delineate, with greater precision than previously possible, cytogenetic abnormalities in the chromosomal region that encodes 251P5G2 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as 251P5G2 was shown to be highly expressed in prostate and other cancers, 251P5G2 polynucleotides are used in methods assessing the status of 251P5G2 gene products in normal versus cancerous tissues. Typically, polynucleotides that encode specific regions of the 251P5G2 proteins are used to assess the presence of perturbations (such as deletions, insertions, point mutations, or alterations resulting in a loss of an antigen etc.) in specific regions of the 251P5G2 gene, such as regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 251P5G2. For example, antisense molecules can be RNAs or other molecules, including peptide nucleic acids (PNAs) or non-nucleic acid molecules such as phosphorothioate derivatives that specifically bind DNA or RNA in a base pair-dependent manner. A skilled artisan can readily obtain these classes of nucleic acid molecules using the 251P5G2 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 251P5G2. See for example, Jack Cohen, Oligodeoxynucleotides, Antisense Inhibitors of Gene Expression, CRC Press, 1989; and Synthesis 1:1-5 (1988). The 251P5G2 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693-4698 (1990); and Iyer, R. P. et al., J. Am. Chem. Soc. 112:1253-1254 (1990). Additional 251P5G2 antisense oligonucleotides of the present invention include morpholino antisense oligonucleotides known in the art (see, e.g., Partridge et al., 1996, Antisense & Nucleic Acid Drug Development 6: 169-175).

The 251P5G2 antisense oligonucleotides of the present invention typically can be RNA or DNA that is complementary to and stably hybridizes with the first 100 5' codons or last 100 3' codons of a 251P5G2 genomic sequence or the corresponding mRNA. Absolute complementarity is not required, although high degrees of complementarity are preferred. Use of an oligonucleotide complementary to this region allows for the selective hybridization to 251P5G2 mRNA and not to mRNA specifying other regulatory subunits of protein kinase. In one embodiment, 251P5G2 antisense oligonucleotides of the present invention are 15 to 30-mer fragments of the antisense DNA molecule that have a sequence that hybridizes to 251P5G2 mRNA. Optionally, 251P5G2 antisense oligonucleotide is a 30-mer oligonucleotide that is complementary to a region in the first 10 5' codons or last 10 3' codons of 251P5G2. Alternatively, the antisense molecules are modified to employ ribozymes in the inhibition of 251P5G2 expression, see, e.g., L. A. Couture & D. T. Stinchcomb; Trends Genet 12: 510-515 (1996).

II.A.3.) Primers and Primer Pairs

Further specific embodiments of these nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 251P5G2 polynucleotide in a sample and as a means for detecting a cell expressing a 251P5G2 protein.

Examples of such probes include polypeptides comprising all or part of the human 251P5G2 cDNA sequence shown in FIG. 2. Examples of primer pairs capable of specifically amplifying 251P5G2 mRNAs are also described in the Examples. As will be understood by the skilled artisan, a great many different primers and probes can be prepared based on the sequences provided herein and used effectively to amplify and/or detect a 251P5G2 mRNA.

The 251P5G2 polynucleotides of the invention are useful for a variety of purposes, including but not limited to their use as probes and primers for the amplification and/or detection of the 251P5G2 gene(s), mRNA(s), or fragments thereof; as reagents for the diagnosis and/or prognosis of prostate cancer and other cancers; as coding sequences capable of directing the expression of 251P5G2 polypeptides; as tools for modulating or inhibiting the expression of the 251P5G2 gene(s) and/or translation of the 251P5G2 transcript(s); and as therapeutic agents.

The present invention includes the use of any probe as described herein to identify and isolate a 251P5G2 or 251P5G2 related nucleic acid sequence from a naturally occurring source, such as humans or other mammals, as well as the isolated nucleic acid sequence per se, which would comprise all or most of the sequences found in the probe used.

II.A.4.) Isolation of 251P5G2-Encoding Nucleic Acid Molecules

The 251P5G2 cDNA sequences described herein enable the isolation of other polynucleotides encoding 251P5G2 gene product(s), as well as the isolation of polynucleotides encoding 251P5G2 gene product homologs, alternatively spliced isoforms, allelic variants, and mutant forms of a 251P5G2 gene product as well as polynucleotides that encode analogs of 251P5G2-related proteins. Various molecular cloning methods that can be employed to isolate full length cDNAs encoding a 251P5G2 gene are well known (see, for example, Sambrook, J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 251P5G2 gene cDNAs can be identified by probing with a labeled 251P5G2 cDNA or a fragment thereof. For example, in one embodiment, a 251P5G2 cDNA (e.g., FIG. 2) or a portion thereof can be synthesized and used as a probe to retrieve overlapping and full-length cDNAs corresponding to a 251P5G2 gene. A 251P5G2 gene itself can be isolated by screening genomic DNA libraries, bacterial artificial chromosome libraries (BACs), yeast artificial chromosome libraries (YACs), and the like, with 251P5G2 DNA probes or primers.

II.A.5.) Recombinant Nucleic Acid Molecules and Host-Vector Systems

The invention also provides recombinant DNA or RNA molecules containing a 251P5G2 polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a 251P5G2 polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 251P5G2 or a fragment, analog or homolog thereof can be used to generate 251P5G2 proteins or fragments thereof using any number of host-vector systems routinely used and widely known in the art.

A wide range of host-vector systems suitable for the expression of 251P5G2 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 251P5G2 can be expressed in several prostate cancer and non-prostate cell lines, including for example 293, 293T, rat-1, NIH 3T3 and TsuPr1. The host-vector systems of the invention are useful for the production of a 251P5G2 protein or fragment thereof. Such host-vector systems can be employed to study the functional properties of 251P5G2 and 251P5G2 mutations or analogs.

Recombinant human 251P5G2 protein or an analog or homolog or fragment thereof can be produced by mammalian cells transfected with a construct encoding a 251P5G2-related nucleotide. For example, 293T cells can be transfected with an expression plasmid encoding 251P5G2 or fragment, analog or homolog thereof, a 251P5G2-related protein is expressed in the 293T cells, and the recombinant 251P5G2 protein is isolated using standard purification methods (e.g., affinity purification using anti-251P5G2 antibodies). In another embodiment, a 251P5G2 coding sequence is subcloned into the retroviral vector pSRαMSVtkneo and used to infect various mammalian cell lines, such as NIH 3T3, TsuPr1, 293 and rat-1 in order to establish 251P5G2 expressing cell lines. Various other expression systems well known in the art can also be employed. Expression constructs encoding a leader peptide joined in frame to a 251P5G2 coding sequence can be used for the generation of a secreted form of recombinant 251P5G2 protein.

As discussed herein, redundancy in the genetic code permits variation in 251P5G2 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at URL dna.affrc.go.jp/~nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell. Biol.*, 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) 251P5G2-related Proteins

Another aspect of the present invention provides 251P5G2-related proteins. Specific embodiments of 251P5G2 proteins comprise a polypeptide having all or part of the amino acid sequence of human 251P5G2 as shown in FIG. 2 or FIG. 3. Alternatively, embodiments of 251P5G2 proteins comprise variant, homolog or analog polypeptides that have alterations in the amino acid sequence of 251P5G2 shown in FIG. 2 or FIG. 3.

Embodiments of a 251P5G2 polypeptide include: a 251P5G2 polypeptide having a sequence shown in FIG. 2, a peptide sequence of a 251P5G2 as shown in FIG. 2 wherein T is U; at least 10 contiguous nucleotides of a polypeptide having the sequence as shown in FIG. 2; or, at least 10 contiguous peptides of a polypeptide having the sequence as shown in FIG. 2 where T is U. For example, embodiments of 251P5G2 peptides comprise, without limitation:

(I) a protein comprising, consisting essentially of, or consisting of an amino acid sequence as shown in FIG. 2A-M or FIG. 3A-E;

(II) a 251P5G2-related protein that is at least 90, 91, 92, 93, 94, 95, 96, 97, 98, 99 or 100% homologous to an entire amino acid sequence shown in FIG. 2A-M or 3A-E;

(III) a 251P5G2-related protein that is at least 90, 91, 92, 93, 94, 95, 96, 97, 98, 99 or 100% identical to an entire amino acid sequence shown in FIG. 2A-M or 3A-E;

(IV) a protein that comprises at least one peptide set forth in Tables VIII to XLIX, optionally with a proviso that it is not an entire protein of FIG. 2;

(V) a protein that comprises at least one peptide set forth in Tables VIII-XXI, collectively, which peptide is also set forth in Tables XXII to XLIX, collectively, optionally with a proviso that it is not an entire protein of FIG. 2;

(VI) a protein that comprises at least two peptides selected from the peptides set forth in Tables VIII-XLIX, optionally with a proviso that it is not an entire protein of FIG. 2;

(VII) a protein that comprises at least two peptides selected from the peptides set forth in Tables VIII to XLIX collectively, with a proviso that the protein is not a contiguous sequence from an amino acid sequence of FIG. 2;

(VIII) a protein that comprises at least one peptide selected from the peptides set forth in Tables VIII-XXI; and at least one peptide selected from the peptides set forth in Tables XXII to XLIX, with a proviso that the protein is not a contiguous sequence from an amino acid sequence of FIG. 2;

(IX) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A-D or 3E, in any whole number increment up to 255 or 1266 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(X) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A-D or 3E, in any whole number increment up to 255 or 1266 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XI) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A-D, or 3E, in any whole number increment up to 255 or 1266 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A-D or 3E, in any whole number increment up to 255 or 1266 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XIII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, amino acids of a protein of FIG. 3A-D or 3E in any whole number increment up to 255 or 1266 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIV) a peptide that occurs at least twice in Tables VIII-XXI and XXII to XLIX, collectively;

(XV) a peptide that occurs at least three times in Tables VIII-XXI and XXII to XLIX, collectively;

(XVI) a peptide that occurs at least four times in Tables VIII-XXI and XXII to XLIX, collectively;

(XVII) a peptide that occurs at least five times in Tables VIII-XXI and XXII to XLIX, collectively;

(XVIII) a peptide that occurs at least once in Tables VIII-XXI, and at least once in tables XXII to XLIX;

(XIX) a peptide that occurs at least once in Tables VIII-XXI, and at least twice in tables XXII to XLIX;

(XX) a peptide that occurs at least twice in Tables VIII-XXI, and at least once in tables XXII to XLIX;

(XXI) a peptide that occurs at least twice in Tables VIII-XXI, and at least twice in tables XXII to XLIX;

(XXII) a peptide which comprises one two, three, four, or five of the following characteristics, or an oligonucleotide encoding such peptide:

i) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or, v) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9;

(XXIII) a composition comprising a peptide of (I)-(XXII) or an antibody or binding region thereof together with a pharmaceutical excipient and/or in a human unit dose form.

(XXIV) a method of using a peptide of (I)-(XXII), or an antibody or binding region thereof or a composition of (XXIII) in a method to modulate a cell expressing 251P5G2, (XXV) a method of using a peptide of (I)-(XXII) or an antibody or binding region thereof or a composition of (XXIII) in a method to diagnose, prophylax, prognose, or treat an individual who bears a cell expressing 251P5G2

(XXVI) a method of using a peptide of (I)-(XXII) or an antibody or binding region thereof or a composition (XXIII) in a method to diagnose, prophylax, prognose, or treat an individual who bears a cell expressing 251P5G2, said cell from a cancer of a tissue listed in Table I;

(XXVII) a method of using a peptide of (I)-(XXII) or an antibody or binding region thereof or a composition of (XXIII) in a method to diagnose, prophylax, prognose, or treat a cancer;

(XXVIII) a method of using a peptide of (I)-(XXII) or an antibody or binding region thereof or a composition of (XXIII) in a method to diagnose, prophylax, prognose, or treat a cancer of a tissue listed in Table I; and, (XXIX) a method of using a peptide of (I)-(XXII) or an antibody or binding region thereof or a composition (XXIII) in a method to identify or characterize a modulator of a cell expressing 251P5G2.

As used herein, a range is understood to specifically disclose all whole unit positions thereof.

Typical embodiments of the invention disclosed herein include 251P5G2 polynucleotides that encode specific portions of 251P5G2 mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, or 255 or more contiguous amino acids of 251P5G2 variant 1; the maximal lengths relevant for other variants are: variant 2, 255 amino acids; variant 3, 255 amino acids, variant 4, 255 amino acids, and variant 12, 1266 amino acids.

In general, naturally occurring allelic variants of human 251P5G2 share a high degree of structural identity and homology (e.g., 90% or more homology). Typically, allelic variants of a 251P5G2 protein contain conservative amino acid substitutions within the 251P5G2 sequences described herein or contain a substitution of an amino acid from a corresponding position in a homologue of 251P5G2. One class of 251P5G2 allelic variants are proteins that share a high degree of homology with at least a small region of a particular 251P5G2 amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" $2^{nd}$ ED. Lubert Stryer ed (Stanford University); Henikoff et al., PNAS 1992 Vol 89 10915-10919; Lei et al., J Biol Chem 1995 May 19; 270(20):11882-6).

Embodiments of the invention disclosed herein include a wide variety of art-accepted variants or analogs of 251P5G2 proteins such as polypeptides having amino acid insertions, deletions and substitutions. 251P5G2 variants can be made using methods known in the art such as site-directed mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., Gene, 34:315 (1985)), restriction selection mutagenesis (Wells et al., *Philos. Trans. R. Soc. London SerA*, 317:415 (1986)) or other known techniques can be performed on the cloned DNA to produce the 251P5G2 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

As defined herein, 251P5G2 variants, analogs or homologs, have the distinguishing attribute of having at least one epitope that is "cross reactive" with a 251P5G2 protein having an amino acid sequence of FIG. 3. As used in this sentence, "cross reactive" means that an antibody or T cell that specifically binds to a 251P5G2 variant also specifically binds to a 251P5G2 protein having an amino acid sequence set forth in FIG. 3. A polypeptide ceases to be a variant of a protein shown in FIG. 3, when it no longer contains any epitope capable of being recognized by an antibody or T cell that specifically binds to the starting 251P5G2 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol. 2000 165(12): 6949-6955; Hebbes et al., Mol Immunol (1989) 26(9):865-73; Schwartz et al., J Immunol (1985) 135(4):2598-608.

Other classes of 251P5G2-related protein variants share 70%, 75%, 80%, 85% or 90% or more similarity with an amino acid sequence of FIG. 3, or a fragment thereof. Another specific class of 251P5G2 protein variants or analogs comprises one or more of the 251P5G2 biological motifs described herein or presently known in the art. Thus, encompassed by the present invention are analogs of 251P5G2 fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of a 251P5G2 protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of a 251P5G2 protein shown in FIG. 2 or FIG. 3.

Moreover, representative embodiments of the invention disclosed herein include polypeptides consisting of about amino acid 1 to about amino acid 10 of a 251P5G2 protein shown in FIG. 2 or FIG. 3, polypeptides consisting of about amino acid 10 to about amino acid 20 of a 251P5G2 protein shown in FIG. 2 or FIG. 3, polypeptides consisting of about amino acid 20 to about amino acid 30 of a 251P5G2 protein shown in FIG. 2 or FIG. 3, polypeptides consisting of about amino acid 30 to about amino acid 40 of a 251P5G2 protein shown in FIG. 2 or FIG. 3, polypeptides consisting of about amino acid 40 to about amino acid 50 of a 251P5G2 protein shown in FIG. 2 or FIG. 3, polypeptides consisting of about amino acid 50 to about amino acid 60 of a 251P5G2 protein shown in FIG. 2 or FIG. 3, polypeptides consisting of about amino acid 60 to about amino acid 70 of a 251P5G2 protein shown in FIG. 2 or FIG. 3, polypeptides consisting of about amino acid 70 to about amino acid 80 of a 251P5G2 protein shown in FIG. 2 or FIG. 3, polypeptides consisting of about amino acid 80 to about amino acid 90 of a 251P5G2 protein shown in FIG. 2 or FIG. 3, polypeptides consisting of about amino acid 90 to about amino acid 100 of a 251P5G2 protein shown in FIG. 2 or FIG. 3, etc. throughout the entirety of a 251P5G2 amino acid sequence. Moreover, polypeptides consisting of about amino acid 1 (or 20 or 30 or 40 etc.) to about amino acid 20, (or 130, or 140 or 150 etc.) of a 251P5G2 protein shown in FIG. 2 or FIG. 3 are embodiments of the invention. It is to be appreciated that the starting and stopping positions in this paragraph refer to the specified position as well as that position plus or minus 5 residues.

251P5G2-related proteins are generated using standard peptide synthesis technology or using chemical cleavage methods well known in the art. Alternatively, recombinant methods can be used to generate nucleic acid molecules that encode a 251P5G2-related protein. In one embodiment, nucleic acid molecules provide a means to generate defined fragments of a 251P5G2 protein (or variants, homologs or analogs thereof).

III.A.) Motif-bearing Protein Embodiments

Additional illustrative embodiments of the invention disclosed herein include 251P5G2 polypeptides comprising the amino acid residues of one or more of the biological motifs contained within a 251P5G2 polypeptide sequence set forth in FIG. 2 or FIG. 3. Various motifs are known in the art, and a protein can be evaluated for the presence of such motifs by a number of publicly available Internet sites (see, e.g., URL addresses: pfam.wustl.edu/; searchlauncher.bcm.tmc.edu/seq-search/struc-predict.html; psort.ims.u-tokyo.ac.jp/; cbs.dtu.dk/; ebi.ac.uk/interpro/scan.html; expasy.ch/tools/scnpsit1.html; Epimatrix™ and Epimer™, Brown University, brown.edu/Research/TB-HIV_Lab/epimatrix/epimatrix.html; and BIMAS, bimas.dcrt.nih.gov/.).

Motif bearing subsequences of all 251P5G2 variant proteins are set forth and identified in Tables VIII-XXI and XXII-XLIX.

Table V sets forth several frequently occurring motifs based on pfam searches (see URL address pfam.wustl.edu/). The columns of Table V list (1) motif name abbreviation, (2) percent identity found amongst the different member of the motif family, (3) motif name or description and (4) most common function; location information is included if the motif is relevant for location.

Polypeptides comprising one or more of the 251P5G2 motifs discussed above are useful in elucidating the specific characteristics of a malignant phenotype in view of the observation that the 251P5G2 motifs discussed above are associated with growth dysregulation and because 251P5G2 is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); Hall et al., Nucleic Acids Research 24(6): 1119-1126 (1996); Peterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997)). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides set forth in Tables VIII-XXI and XXII-XLIX. CTL epitopes can be determined using specific algorithms to identify peptides within a 251P5G2 protein that are capable of optimally binding to specified HLA alleles (e.g., Table IV; Epimatrix™ and Epimer™, Brown University, URL brown.edu/Research/TB-HIV_Lab/epimatrix/epimatrix.html; and BIMAS, URL bimas.dcrt.nih.gov/.) Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermotifs of Table IV). The epitope is analoged by substituting out an amino acid at one of the specified positions, and replacing it with another amino acid specified for that position. For example, on the basis of residues defined in Table IV, one can substitute out a deleterious residue in favor of any other residue, such as a preferred residue; substitute a less-preferred residue with a preferred residue; or substitute an originally-occurring preferred residue with another preferred residue. Substitutions can occur at primary anchor positions or at other positions in a peptide; see, e.g., Table IV.

A variety of references reflect the art regarding the identification and generation of epitopes in a protein of interest as well as analogs thereof. See, for example, WO 97/33602 to Chesnut et al.; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 199745(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8): 2663-2669; Alexander et al., Immunity 19941(9): 751-761 and Alexander et al., Immunol. Res. 1998 18(2): 79-92.

Related embodiments of the invention include polypeptides comprising combinations of the different motifs set forth in Table VI, and/or, one or more of the predicted CTL epitopes of Tables VIII-XXI and XXII-XLIX, and/or, one or more of the predicted HTL epitopes of Tables XLVI-XLIX, and/or, one or more of the T cell binding motifs known in the art. Preferred embodiments contain no insertions, deletions or substitutions either within the motifs or within the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically, the number of N-terminal and/or C-terminal amino acid residues on either side of a motif is between about 1 to about 100 amino acid residues, preferably 5 to about 50 amino acid residues.

251P5G2-related proteins are embodied in many forms, preferably in isolated form. A purified 251P5G2 protein molecule will be substantially free of other proteins or molecules that impair the binding of 251P5G2 to antibody, T cell or other ligand. The nature and degree of isolation and purification will depend on the intended use. Embodiments of a 251P5G2-related proteins include purified 251P5G2-related proteins and functional, soluble 251P5G2-related proteins. In one embodiment, a functional, soluble 251P5G2 protein or fragment thereof retains the ability to be bound by antibody, T cell or other ligand.

The invention also provides 251P5G2 proteins comprising biologically active fragments of a 251P5G2 amino acid sequence shown in FIG. 2 or FIG. 3. Such proteins exhibit properties of the starting 251P5G2 protein, such as the ability to elicit the generation of antibodies that specifically bind an epitope associated with the starting 251P5G2 protein; to be bound by such antibodies; to elicit the activation of HTL or CTL; and/or, to be recognized by HTL or CTL that also specifically bind to the starting protein.

251P5G2-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or based on immunogenicity. Fragments that contain such structures are particularly useful in generating subunit-specific anti-251P5G2 antibodies or T cells or in identifying cellular factors that bind to 251P5G2. For example, hydrophilicity profiles can be generated, and immunogenic peptide fragments identified, using the method of Hopp, T. P. and Woods, K. R., 1981, Proc. Natl. Acad. Sci. U.S.A. 78:3824-3828. Hydropathicity profiles can be generated, and immunogenic peptide fragments identified, using the method of Kyte, J. and Doolittle, R. F., 1982, J. Mol. Biol. 157:105-132. Percent (%) Accessible Residues profiles can be generated, and immunogenic peptide fragments identified, using the method of Janin J., 1979, Nature 277:491-492. Average Flexibility profiles can be generated, and immunogenic peptide fragments identified, using the method of Bhaskaran R., Ponnuswamy P. K., 1988, Int. J. Pept. Protein Res. 32:242-255. Beta-turn profiles can be generated, and immunogenic peptide fragments identified, using the method of Deleage, G., Roux B., 1987, Protein Engineering 1:289-294.

CTL epitopes can be determined using specific algorithms to identify peptides within a 251P5G2 protein that are capable of optimally binding to specified HLA alleles (e.g., by using the SYFPEITHI site at World Wide Web URL syfpeithi.bmi-heidelberg.com/; the listings in Table IV (A)-(E); Epimatrix™ and Epimer™, Brown University, URL (brown.edu/Research/TB-HIV_Lab/epimatrix/epimatrix.html); and BIMAS, URL bimas.dcrt.nih.gov/). Illustrating this, peptide epitopes from 251P5G2 that are presented in the context of human MHC Class I molecules, e.g., HLA-A1, A2, A3, A11, A24, B7 and B35 were predicted (see, e.g., Tables VIII-XXI, XXII-XLIX). Specifically, the complete amino acid sequence of the 251P5G2 protein and relevant portions of other variants, i.e., for HLA Class I predictions 9 flanking residues on either side of a point mutation or exon junction, and for HLA Class II predictions 14 flanking residues on either side of a point mutation or exon junction corresponding to that variant, were entered into the HLA Peptide Motif Search algorithm found in the Bioinformatics and Molecular Analysis Section (BIMAS) web site listed above; in addition to the site SYFPEITHI, at URL syfpeithi.bmi-heidelberg.com/.

The HLA peptide motif search algorithm was developed by Dr. Ken Parker based on binding of specific peptide sequences in the groove of HLA Class I molecules, in particular HLA-A2 (see, e.g., Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for Class I HLA-A2, the epitopes preferably contain a leucine (L) or methionine (M) at position 2 and a valine (V) or leucine (L) at the C-terminus (see, e.g., Parker et al., J. Immunol. 149: 3580-7 (1992)). Selected results of 251P5G2 predicted binding peptides are shown in Tables VIII-XXI and XXII-XLIX herein. In Tables VIII-XXI and XXII-XLVII, selected candidates, 9-mers and 10-mers, for each family member are shown along with their location, the amino acid sequence of each specific peptide, and an estimated binding score. In Tables XLVI-XLIX, selected candidates, 15-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV (or determined using World Wide Web site URL syfpeithi.bmi-heidelberg.com/, or BIMAS, bimas.dcrt.nih.gov/) are to be "applied" to a 251P5G2 protein in accordance with the invention. As used in this context "applied" means that a 251P5G2 protein is evaluated, e.g., visually or by computer-based patterns finding methods, as appreciated by those of skill in the relevant art. Every subsequence of a 251P5G2 protein of 8, 9, 10, or 11 amino acid residues that bears an HLA Class I motif, or a subsequence of 9 or more amino acid residues that bear an HLA Class II motif are within the scope of the invention.

III.B.) Expression of 251P5G2-related Proteins

In an embodiment described in the examples that follow, 251P5G2 can be conveniently expressed in cells (such as 293T cells) transfected with a commercially available expression vector such as a CMV-driven expression vector encoding 251P5G2 with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 251P5G2 protein in transfected cells. The secreted HIS-tagged 251P5G2 in the culture media can be purified, e.g., using a nickel column using standard techniques.

III.C.) Modifications of 251P5G2-related Proteins

Modifications of 251P5G2-related proteins such as covalent modifications are included within the scope of this invention. One type of covalent modification includes reacting targeted amino acid residues of a 251P5G2 polypeptide with an organic derivatizing agent that is capable of reacting with selected side chains or the N- or C-terminal residues of a 251P5G2 protein. Another type of covalent modification of a 251P5G2 polypeptide included within the scope of this invention comprises altering the native glycosylation pattern of a protein of the invention. Another type of covalent modification of 251P5G2 comprises linking a 251P5G2 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 251P5G2-related proteins of the present invention can also be modified to form a chimeric molecule comprising 251P5G2 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a 251P5G2 sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of 251P5G2. A chimeric molecule can comprise a fusion of a 251P5G2-related protein with a polyhistidine epitope tag, which provides an epitope to which immobilized nickel can selectively bind, with cytokines or with growth factors. The epitope tag is generally placed at the amino- or carboxyl-terminus of a 251P5G2 protein. In an alternative embodiment, the chimeric molecule can comprise a fusion of a 251P5G2-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 251P5G2 polypeptide in place of at least one variable region within an Ig molecule. In a preferred embodiment, the immunoglobulin fusion includes the hinge, CH2 and CH3, or the hinge, CHI, CH2 and CH3 regions of an IgGI molecule. For the production of immunoglobulin fusions see, e.g., U.S. Pat. No. 5,428, 130 issued Jun. 27, 1995.

III.D.) Uses of 251P5G2-related Proteins

The proteins of the invention have a number of different specific uses. As 251P5G2 is highly expressed in prostate and other cancers, 251P5G2-related proteins are used in methods that assess the status of 251P5G2 gene products in normal versus cancerous tissues, thereby elucidating the malignant phenotype. Typically, polypeptides from specific regions of a 251P5G2 protein are used to assess the presence of perturbations (such as deletions, insertions, point mutations etc.) in those regions (such as regions containing one or more motifs). Exemplary assays utilize antibodies or T cells targeting 251P5G2-related proteins comprising the amino acid residues of one or more of the biological motifs contained within a 251P5G2 polypeptide sequence in order to evaluate the characteristics of this region in normal versus cancerous tissues or to elicit an immune response to the epitope. Alternatively, 251P5G2-related proteins that contain the amino acid residues of one or more of the biological motifs in a 251P5G2 protein are used to screen for factors that interact with that region of 251P5G2.

251P5G2 protein fragments/subsequences are particularly useful in generating and characterizing domain-specific antibodies (e.g., antibodies recognizing an extracellular or intracellular epitope of a 251P5G2 protein), for identifying agents or cellular factors that bind to 251P5G2 or a particular structural domain thereof, and in various therapeutic and diagnostic contexts, including but not limited to diagnostic assays, cancer vaccines and methods of preparing such vaccines.

Proteins encoded by the 251P5G2 genes, or by analogs, homologs or fragments thereof, have a variety of uses, including but not limited to generating antibodies and in methods for identifying ligands and other agents and cellular constituents that bind to a 251P5G2 gene product. Antibodies raised against a 251P5G2 protein or fragment thereof are useful in diagnostic and prognostic assays, and imaging methodologies in the management of human cancers characterized by expression of 251P5G2 protein, such as those listed in Table I. Such antibodies can be expressed intracellularly and used in methods of treating patients with such cancers. 251P5G2-related nucleic acids or proteins are also used in generating HTL or CTL responses.

Various immunological assays useful for the detection of 251P5G2 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 251P5G2-expressing cells (e.g., in radioscintigraphic imaging methods). 251P5G2 proteins are also particularly useful in generating cancer vaccines, as further described herein.

IV.) 251P5G2 Antibodies

Another aspect of the invention provides antibodies that bind to 251P5G2-related proteins. Preferred antibodies specifically bind to a 251P5G2-related protein and do not bind (or bind weakly) to peptides or proteins that are not 251P5G2-related proteins under physiological conditions. In this context, examples of physiological conditions include: 1) phosphate buffered saline; 2) Tris-buffered saline containing 25 mM Tris and 150 mM NaCl; or normal saline (0.9% NaCl); 4) animal serum such as human serum; or, 5) a combination of any of 1) through 4); these reactions preferably taking place at pH 7.5, alternatively in a range of pH 7.0 to 8.0, or alternatively in a range of pH 6.5 to 8.5; also, these reactions taking place at a temperature between 4° C. to 37° C. For example, antibodies that bind 251P5G2 can bind 251P5G2-related proteins such as the homologs or analogs thereof.

251P5G2 antibodies of the invention are particularly useful in cancer (see, e.g., Table I) diagnostic and prognostic assays, and imaging methodologies. Similarly, such antibodies are useful in the treatment, diagnosis, and/or prognosis of other cancers, to the extent 251P5G2 is also expressed or overexpressed in these other cancers. Moreover, intracellularly expressed antibodies (e.g., single chain antibodies) are therapeutically useful in treating cancers in which the expression of 251P5G2 is involved, such as advanced or metastatic prostate cancers.

The invention also provides various immunological assays useful for the detection and quantification of 251P5G2 and mutant 251P5G2-related proteins. Such assays can comprise one or more 251P5G2 antibodies capable of recognizing and binding a 251P5G2-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing 251P5G2 are also provided by the invention, including but not limited to radioscintigraphic imaging methods using labeled 251P5G2 antibodies. Such assays are clinically useful in the detection, monitoring, and prognosis of 251P5G2 expressing cancers such as prostate cancer.

251P5G2 antibodies are also used in methods for purifying a 251P5G2-related protein and for isolating 251P5G2 homologues and related molecules. For example, a method of purifying a 251P5G2-related protein comprises incubating a 251P5G2 antibody, which has been coupled to a solid matrix, with a lysate or other solution containing a 251P5G2-related protein under conditions that permit the 251P5G2 antibody to bind to the 251P5G2-related protein; washing the solid matrix to eliminate impurities; and eluting the 251P5G2-related protein from the coupled antibody. Other uses of 251P5G2 antibodies in accordance with the invention include generating anti-idiotypic antibodies that mimic a 251P5G2 protein.

Various methods for the preparation of antibodies are well known in the art. For example, antibodies can be prepared by immunizing a suitable mammalian host using a 251P5G2-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 251P5G2 can also be used, such as a 251P5G2 GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 251P5G2-related protein is synthesized and used as an immunogen.

In addition, naked DNA immunization techniques known in the art are used (with or without purified 251P5G2-related protein or 251P5G2 expressing cells) to generate an immune response to the encoded immunogen (for review, see Donnelly et al., 1997, Ann. Rev. Immunol. 15: 617-648).

The amino acid sequence of a 251P5G2 protein as shown in FIG. 2 or FIG. 3 can be analyzed to select specific regions of the 251P5G2 protein for generating antibodies. For example, hydrophobicity and hydrophilicity analyses of a 251P5G2 amino acid sequence are used to identify hydrophilic regions in the 251P5G2 structure. Regions of a 251P5G2 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Methods for the generation of 251P5G2 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 251P5G2 immunogen is often conducted by injection over a suitable time period and with use of a suitable adjuvant, as is understood in the art. During the immunization schedule, titers of antibodies can be taken to determine adequacy of antibody formation.

251P5G2 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 251P5G2-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a 251P5G2 protein can also be produced in the context of chimeric or complementarity-determining region (CDR) grafted antibodies of multiple species origin. Humanized or human 251P5G2 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535-539). Fully human 251P5G2 monoclonal antibodies can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human 251P5G2 monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614; U.S. Pat. Nos. 6,162,963 issued 19 Dec. 2000; 6,150,584 issued 12 Nov. 2000; and, 6,114,598 issued 5 Sep. 2000). This method avoids the in vitro manipulation required with phage display technology and efficiently produces high affinity authentic human antibodies.

Reactivity of 251P5G2 antibodies with a 251P5G2-related protein can be established by a number of well known means, including Western blot, immunoprecipitation, ELISA, and FACS analyses using, as appropriate, 251P5G2-related proteins, 251P5G2-expressing cells or extracts thereof. A 251P5G2 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 251P5G2 epitopes are generated using methods generally known in the art. Homodimeric antibodies can also be generated by cross-linking techniques known in the art (e.g., Wolff et al., Cancer Res. 53: 2560-2565).

V.) 251P5G2 Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., Cell 47:1071, 1986; Babbitt, B. P. et al., Nature 317: 359, 1985; Townsend, A. and Bodmer, H., Annu. Rev. Immunol. 7:601, 1989; Germain, R. N., Annu. Rev. Immunol. 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., J. Immunol. 160: 3363, 1998; Rammensee, et al., Immunogenetics 41:178, 1995; Rammensee et al., SYFPEITHI, access via World Wide Web at URL (134.2.96.221/scripts.hlaserver.dll/home.htm); Sette, A. and Sidney, J. Curr. Opin. Immunol. 10:478, 1998; Engelhard, V. H., Curr. Opin. Immunol. 6:13, 1994; Sette, A. and Grey, H. M., Curr. Opin. Immunol. 4:79, 1992; Sinigaglia, F. and Hammer, J. Curr. Biol. 6:52, 1994; Ruppert et al., Cell 74:929-937, 1993; Kondo et al., J. Immunol. 155: 4307-4312, 1995; Sidney et al., J. Immunol. 157:3480-3490, 1996; Sidney et al., Human Immunol. 45:79-93, 1996; Sette, A. and Sidney, J. Immunogenetics 1999 November; 50(3-4): 201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. Annu. Rev. Immunol. 13:587, 1995; Smith, et al., Immunity 4:203, 1996; Fremont et al., Immunity 8:305, 1998; Stern et al., Structure 2:245, 1994; Jones, E. Y. Curr. Opin. Immunol. 9:75, 1997; Brown, J. H. et al., Nature 364:33, 1993; Guo, H. C. et al., Proc. Natl. Acad. Sci. USA 90:8053, 1993; Guo, H. C. et al., Nature 360:364, 1992; Silver, M. L. et al., Nature 360:367, 1992; Matsumura, M. et al., Science 257:927, 1992; Madden et al., Cell 70:1035, 1992; Fremont, D. H. et al., Science 257:919, 1992; Saper, M. A., Bjorkman, P. J. and Wiley, D.C., J. Mol. Biol. 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., Mol. Immunol. 32:603, 1995; Celis, E. et al., Proc. Natl. Acad. Sci. USA 91:2105, 1994; Tsai, V. et al., J. Immunol. 158:1796, 1997; Kawashima, I. et al., Human Immunol. 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., J. Immunol. 26:97, 1996; Wentworth, P. A. et al., Int. Immunol. 8:651, 1996; Alexander, J. et al., J. Immunol. 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., J. Exp. Med. 181:1047, 1995; Doolan, D. L. et al., Immunity 7:97, 1997; Bertoni, R. et al., J. Clin. Invest. 100:503, 1997; Threlkeld, S. C. et al., J. Immunol. 159:1648, 1997; Diepolder, H. M. et al., J. Virol. 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

VI.) 251P5G2 Transgenic Animals

Nucleic acids that encode a 251P5G2-related protein can also be used to generate either transgenic animals or "knock out" animals that, in turn, are useful in the development and screening of therapeutically useful reagents. In accordance with established techniques, cDNA encoding 251P5G2 can be used to clone genomic DNA that encodes 251P5G2. The cloned genomic sequences can then be used to generate transgenic animals containing cells that express DNA that encode 251P5G2. Methods for generating transgenic animals, particularly animals such as mice or rats, have become conventional in the art and are described, for example, in U.S. Pat. Nos. 4,736,866 issued 12 Apr. 1988, and 4,870,009 issued 26 Sep. 1989. Typically, particular cells would be targeted for 251P5G2 transgene incorporation with tissue-specific enhancers.

Transgenic animals that include a copy of a transgene encoding 251P5G2 can be used to examine the effect of increased expression of DNA that encodes 251P5G2. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 251P5G2 can be used to construct a 251P5G2 "knock out" animal that has a defective or altered gene encoding 251P5G2 as a result of homologous recombination between the endogenous gene encoding 251P5G2 and altered genomic DNA encoding 251P5G2 introduced into an embryonic cell of the animal. For example, cDNA that encodes 251P5G2 can be used to clone genomic DNA encoding 251P5G2 in accordance with established techniques. A portion of the genomic DNA encoding 251P5G2 can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell*, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell*, 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a 251P5G2 polypeptide.

VII.) Methods for the Detection of 251P5G2

Another aspect of the present invention relates to methods for detecting 251P5G2 polynucleotides and 251P5G2-related proteins, as well as methods for identifying a cell that expresses 251P5G2. The expression profile of 251P5G2 makes it a diagnostic marker for metastasized disease. Accordingly, the status of 251P5G2 gene products provides information useful for predicting a variety of factors including susceptibility to advanced stage disease, rate of progression, and/or tumor aggressiveness. As discussed in detail herein, the status of 251P5G2 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 251P5G2 polynucleotides in a biological sample, such as serum, bone, prostate, and other tissues, urine, semen, cell preparations, and the like. Detectable 251P5G2 polynucleotides include, for example, a 251P5G2 gene or fragment thereof, 251P5G2 mRNA, alternative splice variant 251P5G2 mRNAs, and recombinant DNA or RNA molecules that contain a 251P5G2 polynucleotide. A number of methods for amplifying and/or detecting the presence of 251P5G2 polynucleotides are well known in the art and can be employed in the practice of this aspect of the invention.

In one embodiment, a method for detecting a 251P5G2 mRNA in a biological sample comprises producing cDNA from the sample by reverse transcription using at least one primer; amplifying the cDNA so produced using a 251P5G2 polynucleotides as sense and antisense primers to amplify 251P5G2 cDNAs therein; and detecting the presence of the amplified 251P5G2 cDNA. Optionally, the sequence of the amplified 251P5G2 cDNA can be determined.

In another embodiment, a method of detecting a 251P5G2 gene in a biological sample comprises first isolating genomic DNA from the sample; amplifying the isolated genomic DNA using 251P5G2 polynucleotides as sense and antisense primers; and detecting the presence of the amplified 251P5G2 gene. Any number of appropriate sense and antisense probe combinations can be designed from a 251P5G2 nucleotide sequence (see, e.g., FIG. 2) and used for this purpose.

The invention also provides assays for detecting the presence of a 251P5G2 protein in a tissue or other biological sample such as serum, semen, bone, prostate, urine, cell preparations, and the like. Methods for detecting a 251P5G2-related protein are also well known and include, for example, immunoprecipitation, immunohistochemical analysis, Western blot analysis, molecular binding assays, ELISA, ELIFA and the like. For example, a method of detecting the presence of a 251P5G2-related protein in a biological sample comprises first contacting the sample with a 251P5G2 antibody, a 251P5G2-reactive fragment thereof, or a recombinant protein containing an antigen-binding region of a 251P5G2 antibody; and then detecting the binding of 251P5G2-related protein in the sample.

Methods for identifying a cell that expresses 251P5G2 are also within the scope of the invention. In one embodiment, an assay for identifying a cell that expresses a 251P5G2 gene comprises detecting the presence of 251P5G2 mRNA in the cell. Methods for the detection of particular mRNAs in cells are well known and include, for example, hybridization assays using complementary DNA probes (such as in situ hybridization using labeled 251P5G2 riboprobes, Northern blot and related techniques) and various nucleic acid amplification assays (such as RT-PCR using complementary primers specific for 251P5G2, and other amplification type detection methods, such as, for example, branched DNA, SISBA, TMA and the like). Alternatively, an assay for identifying a cell that expresses a 251P5G2 gene comprises detecting the presence of 251P5G2-related protein in the cell or secreted by the cell. Various methods for the detection of proteins are well known in the art and are employed for the detection of 251P5G2-related proteins and cells that express 251P5G2-related proteins.

251P5G2 expression analysis is also useful as a tool for identifying and evaluating agents that modulate 251P5G2 gene expression. For example, 251P5G2 expression is significantly upregulated in prostate cancer, and is expressed in cancers of the tissues listed in Table I. Identification of a molecule or biological agent that inhibits 251P5G2 expression or over-expression in cancer cells is of therapeutic value. For example, such an agent can be identified by using a screen that quantifies 251P5G2 expression by RT-PCR, nucleic acid hybridization or antibody binding.

VIII.) Methods for Monitoring the Status of 251P5G2-related Genes and their Products Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., *Cancer Surv.* 23: 19-32 (1995)). In this context, examining a biological sample for evidence of dysregulated cell growth (such as aberrant 251P5G2 expression in cancers) allows for early detection of such aberrant physiology, before a pathologic state such as cancer has progressed to a stage that therapeutic options are more limited and or the prognosis is worse. In such examinations, the status of 251P5G2 in a biological sample of interest can be compared, for example, to the status of 251P5G2 in a corresponding normal sample (e.g. a sample from that individual or alternatively another individual that is not affected by a pathology). An alteration in the status of 251P5G2 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2): 306-14 and U.S. Pat. No. 5,837,501) to compare 251P5G2 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 251P5G2 expressing cells) as well as the level, and biological activity of expressed gene products (such as 251P5G2 mRNA, polynucleotides and polypeptides). Typically, an alteration in the status of 251P5G2 comprises a change in the location of 251P5G2 and/or 251P5G2 expressing cells and/or an increase in 251P5G2 mRNA and/or protein expression.

251P5G2 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a 251P5G2 gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 251P5G2 in a biological sample is evaluated by various methods utilized by skilled artisans including, but not limited to genomic Southern analysis (to examine, for example perturbations in a 251P5G2 gene), Northern analysis and/or PCR analysis of 251P5G2 mRNA (to examine, for example alterations in the polynucleotide sequences or expression levels of 251P5G2 mRNAs), and, Western and/or immunohistochemical analysis (to examine, for example alterations in polypeptide sequences, alterations in polypeptide localization within a sample, alterations in expression levels of 251P5G2 proteins and/or associations of 251P5G2 proteins with polypeptide binding partners). Detectable 251P5G2 polynucleotides include, for example, a 251P5G2 gene or fragment thereof, 251P5G2 mRNA, alternative splice variants, 251P5G2 mRNAs, and recombinant DNA or RNA molecules containing a 251P5G2 polynucleotide.

The expression profile of 251P5G2 makes it a diagnostic marker for local and/or metastasized disease, and provides information on the growth or oncogenic potential of a biological sample. In particular, the status of 251P5G2 provides information useful for predicting susceptibility to particular disease stages, progression, and/or tumor aggressiveness. The invention provides methods and assays for determining 251P5G2 status and diagnosing cancers that express 251P5G2, such as cancers of the tissues listed in Table I. For example, because 251P5G2 mRNA is so highly expressed in prostate and other cancers relative to normal prostate tissue, assays that evaluate the levels of 251P5G2 mRNA transcripts or proteins in a biological sample can be used to diagnose a disease associated with 251P5G2 dysregulation, and can provide prognostic information useful in defining appropriate therapeutic options.

The expression status of 251P5G2 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 251P5G2 in biological samples such as those from individuals suffering from, or suspected of suffering from a pathology characterized by dysregulated cellular growth, such as cancer.

As described above, the status of 251P5G2 in a biological sample can be examined by a number of well-known procedures in the art. For example, the status of 251P5G2 in a biological sample taken from a specific location in the body can be examined by evaluating the sample for the presence or absence of 251P5G2 expressing cells (e.g. those that express 251P5G2 mRNAs or proteins). This examination can provide evidence of dysregulated cellular growth, for example, when 251P5G2-expressing cells are found in a biological sample that does not normally contain such cells (such as a lymph node), because such alterations in the status of 251P5G2 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000);Su et al., Semin. Surg. Oncol. 18(1): 17-28 (2000) and Freeman et al., J Urol 1995 August 154(2 Pt 1):474-8).

In one aspect, the invention provides methods for monitoring 251P5G2 gene products by determining the status of 251P5G2 gene products expressed by cells from an individual suspected of having a disease associated with dysregulated cell growth (such as hyperplasia or cancer) and then comparing the status so determined to the status of 251P5G2 gene products in a corresponding normal sample. The presence of aberrant 251P5G2 gene products in the test sample relative to the normal sample provides an indication of the presence of dysregulated cell growth within the cells of the individual.

In another aspect, the invention provides assays useful in determining the presence of cancer in an individual, comprising detecting a significant increase in 251P5G2 mRNA or protein expression in a test cell or tissue sample relative to expression levels in the corresponding normal cell or tissue. The presence of 251P5G2 mRNA can, for example, be evaluated in tissues including but not limited to those listed in Table I. The presence of significant 251P5G2 expression in any of these tissues is useful to indicate the emergence, presence and/or severity of a cancer, since the corresponding normal tissues do not express 251P5G2 mRNA or express it at lower levels.

In a related embodiment, 251P5G2 status is determined at the protein level rather than at the nucleic acid level. For example, such a method comprises determining the level of 251P5G2 protein expressed by cells in a test tissue sample and comparing the level so determined to the level of 251P5G2 expressed in a corresponding normal sample. In one embodiment, the presence of 251P5G2 protein is evaluated, for example, using immunohistochemical methods. 251P5G2 antibodies or binding partners capable of detecting 251P5G2 protein expression are used in a variety of assay formats well known in the art for this purpose.

In a further embodiment, one can evaluate the status of 251P5G2 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of 251P5G2 may be indicative of the presence or promotion of a tumor. Such assays therefore have diagnostic and predictive value where a mutation in 251P5G2 indicates a potential loss of function or increase in tumor growth.

A wide variety of assays for observing perturbations in nucleotide and amino acid sequences are well known in the art. For example, the size and structure of nucleic acid or amino acid sequences of 251P5G2 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 issued 7 Sep. 1999, and 5,952,170 issued 17 Jan. 1995).

Additionally, one can examine the methylation status of a 251P5G2 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al., Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of 251P5G2. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 251P5G2 expression. The presence of RT-PCR amplifiable 251P5G2 mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 251P5G2 mRNA or 251P5G2 protein in a tissue sample, its presence indicating susceptibility to cancer, wherein the degree of 251P5G2 mRNA expression correlates to the degree of susceptibility. In a specific embodiment, the presence of 251P5G2 in prostate or other tissue is examined, with the presence of 251P5G2 in the sample providing an indication of prostate cancer susceptibility (or the emergence or existence of a prostate tumor). Similarly, one can evaluate the integrity 251P5G2 nucleotide and amino acid sequences in a biological sample, in order to identify perturbations in the structure of these molecules such as insertions, deletions, substitutions and the like. The presence of one or more perturbations in 251P5G2 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 251P5G2 mRNA or 251P5G2 protein expressed by tumor cells, comparing the level so determined to the level of 251P5G2 mRNA or 251P5G2 protein expressed in a corresponding normal tissue taken from the same individual or a normal tissue reference sample, wherein the degree of 251P5G2 mRNA or 251P5G2 protein expression in the tumor sample relative to the normal sample indicates the degree of aggressiveness. In a specific embodiment, aggressiveness of a tumor is evaluated by determining the extent to which 251P5G2 is expressed in the tumor cells, with higher expression levels indicating more aggressive tumors. Another embodiment is the evaluation of the integrity of 251P5G2 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 251P5G2 mRNA or 251P5G2 protein expressed by cells in a sample of the tumor, comparing the level so determined to the level of 251P5G2 mRNA or 251P5G2 protein expressed in an equivalent tissue sample taken from the same individual at a different time, wherein the degree of 251P5G2 mRNA or 251P5G2 protein expression in the tumor sample over time provides information on the progression of the cancer. In a specific embodiment, the progression of a cancer is evaluated by determining 251P5G2 expression in the tumor cells over time, where increased expression over time indicates a progression of the cancer. Also, one can evaluate the integrity 251P5G2 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 251P5G2 gene and 251P5G2 gene products (or perturbations in 251P5G2 gene and 251P5G2 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74-88; Epstein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of 251P5G2 gene and 251P5G2 gene products (or perturbations in 251P5G2 gene and 251P5G2 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 251P5G2 gene and 251P5G2 gene products (or perturbations in 251P5G2 gene and 251P5G2 gene products) and another factor associated with malignancy entails detecting the overexpression of 251P5G2 mRNA or protein in a tissue sample, detecting the overexpression of PSA mRNA or protein in a tissue sample (or PSCA or PSM expression), and observing a coincidence of 251P5G2 mRNA or protein and PSA mRNA or protein overexpression (or PSCA or PSM expression). In a specific embodiment, the expression of 251P5G2 and PSA mRNA in prostate tissue is examined, where the coincidence of 251P5G2 and PSA mRNA overexpression in the sample indicates the existence of prostate cancer, prostate cancer susceptibility or the emergence or status of a prostate tumor.

Methods for detecting and quantifying the expression of 251P5G2 mRNA or protein are described herein, and standard nucleic acid and protein detection and quantification technologies are well known in the art. Standard methods for the detection and quantification of 251P5G2 mRNA include in situ hybridization using labeled 251P5G2 riboprobes, Northern blot and related techniques using 251P5G2 polynucleotide probes, RT-PCR analysis using primers specific for 251P5G2, and other amplification type detection methods, such as, for example, branched DNA, SISBA, TMA and the like. In a specific embodiment, semi-quantitative RT-PCR is used to detect and quantify 251P5G2 mRNA expression. Any number of primers capable of amplifying 251P5G2 can be used for this purpose, including but not limited to the various primer sets specifically described herein. In a specific embodiment, polyclonal or monoclonal antibodies specifically reactive with the wild-type 251P5G2 protein can be used in an immunohistochemical assay of biopsied tissue.

IX.) Identification of Molecules that Interact with 251P5G2

The 251P5G2 protein and nucleic acid sequences disclosed herein allow a skilled artisan to identify proteins, small molecules and other agents that interact with 251P5G2, as well as pathways activated by 251P5G2 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. Nos. 5,955,280 issued 21 Sep. 1999, 5,925,523 issued 20 Jul. 1999, 5,846,722 issued 8 Dec. 1998 and 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with 251P5G2 protein sequences. In such methods, peptides that bind to 251P5G2 are identified by screening libraries that encode a random or controlled collection of amino acids. Peptides encoded by the libraries are expressed as fusion proteins of bacteriophage coat proteins, the bacteriophage particles are then screened against the 251P5G2 protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 251P5G2 protein sequences are disclosed for example in U.S. Pat. Nos. 5,723,286 issued 3 Mar. 1998 and 5,733,731 issued 31 Mar. 1998.

Alternatively, cell lines that express 251P5G2 are used to identify protein-protein interactions mediated by 251P5G2. Such interactions can be examined using immunoprecipitation techniques (see, e.g., Hamilton B. J., et al. Biochem. Biophys. Res. Commun. 1999, 261:646-51). 251P5G2 protein can be immunoprecipitated from 251P5G2-expressing cell lines using anti-251P5G2 antibodies. Alternatively, antibodies against His-tag can be used in a cell line engineered to express fusions of 251P5G2 and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 251P5G2 can be identified through related embodiments of such screening assays. For example, small molecules can be identified that interfere with protein function, including molecules that interfere with 251P5G2's ability to mediate phosphorylation and de-phosphorylation, interaction with DNA or RNA molecules as an indication of regulation of cell cycles, second messenger signaling or tumorigenesis. Similarly, small molecules that modulate 251P5G2-related ion channel, protein pump, or cell communication functions are identified and used to treat patients that have a cancer that expresses 251P5G2 (see, e.g., Hille, B., Ionic Channels of Excitable Membranes $2^{nd}$ Ed., Sinauer Assoc., Sunderland, Mass., 1992). Moreover, ligands that regulate 251P5G2 function can be identified based on their ability to bind 251P5G2 and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 251P5G2 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators, which activate or inhibit 251P5G2.

An embodiment of this invention comprises a method of screening for a molecule that interacts with a 251P5G2 amino acid sequence shown in FIG. 2 or FIG. 3, comprising the steps of contacting a population of molecules with a 251P5G2 amino acid sequence, allowing the population of molecules and the 251P5G2 amino acid sequence to interact under conditions that facilitate an interaction, determining the presence of a molecule that interacts with the 251P5G2 amino acid sequence, and then separating molecules that do not interact with the 251P5G2 amino acid sequence from molecules that do. In a specific embodiment, the method further comprises purifying, characterizing and identifying a molecule that interacts with the 251P5G2 amino acid sequence. The identified molecule can be used to modulate a function performed by 251P5G2. In a preferred embodiment, the 251P5G2 amino acid sequence is contacted with a library of peptides.

X.) Therapeutic Methods and Compositions

The identification of 251P5G2 as a protein that is normally expressed in a restricted set of tissues, but which is also expressed in cancers such as those listed in Table I, opens a number of therapeutic approaches to the treatment of such cancers.

Of note, targeted antitumor therapies have been useful even when the targeted protein is expressed on normal tissues, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

For example, Herceptin® is an FDA approved pharmaceutical that has as its active ingredient an antibody which is immunoreactive with the protein variously known as HER2, HER2/neu, and erb-b-2. It is marketed by Genentech and has been a commercially successful antitumor agent. Herceptin sales reached almost $400 million in 2002. Herceptin is a treatment for HER2 positive metastatic breast cancer. However, the expression of HER2 is not limited to such tumors. The same protein is expressed in a number of normal tissues. In particular, it is known that HER2/neu is present in normal kidney and heart, thus these tissues are present in all human recipients of Herceptin. The presence of HER2/neu in normal kidney is also confirmed by Latif, Z., et al., *B.J.U. International* (2002) 89:5-9. As shown in this article (which evaluated whether renal cell carcinoma should be a preferred indication for anti-HER2 antibodies such as Herceptin) both protein and mRNA are produced in benign renal tissues. Notably, HER2/neu protein was strongly overexpressed in benign renal tissue. Despite the fact that HER2/neu is expressed in such vital tissues as heart and kidney, Herceptin is a very useful, FDA approved, and commercially successful drug. The effect of Herceptin on cardiac tissue, i.e., "cardiotoxicity," has merely been a side effect to treatment. When patients were treated with Herceptin alone, significant cardiotoxicity occurred in a very low percentage of patients.

Of particular note, although kidney tissue is indicated to exhibit normal expression, possibly even higher expression than cardiac tissue, kidney has no appreciable Herceptin side effect whatsoever. Moreover, of the diverse array of normal tissues in which HER2 is expressed, there is very little occurrence of any side effect. Only cardiac tissue has manifested any appreciable side effect at all. A tissue such as kidney, where HER2/neu expression is especially notable, has not been the basis for any side effect.

Furthermore, favorable therapeutic effects have been found for antitumor therapies that target epidermal growth factor receptor (EGFR). EGFR is also expressed in numerous normal tissues. There have been very limited side effects in normal tissues following use of anti-EGFR therapeutics.

Thus, expression of a target protein in normal tissue, even vital normal tissue, does not defeat the utility of a targeting agent for the protein as a therapeutic for certain tumors in which the protein is also overexpressed.

Accordingly, therapeutic approaches that inhibit the activity of a 251P5G2 protein are useful for patients suffering from a cancer that expresses 251P5G2. These therapeutic approaches generally fall into two classes. One class comprises various methods for inhibiting the binding or association of a 251P5G2 protein with its binding partner or with other proteins. Another class comprises a variety of methods for inhibiting the transcription of a 251P5G2 gene or translation of 251P5G2 mRNA.

X.A.) Anti-Cancer Vaccines

The invention provides cancer vaccines comprising a 251P5G2-related protein or 251P5G2-related nucleic acid. In view of the expression of 251P5G2, cancer vaccines prevent and/or treat 251P5G2-expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Such methods can be readily practiced by employing a 251P5G2-related protein, or a 251P5G2-encoding nucleic acid molecule and recombinant vectors capable of expressing and presenting the 251P5G2 immunogen (which typically comprises a number of antibody or T cell epitopes). Skilled artisans understand that a wide variety of vaccine systems for delivery of immunoreactive epitopes are known in the art (see, e.g., Heryln et al., Ann Med 1999 February 31(11):66-78; Maruyama et al., Cancer Immunol Immunother 2000 June 49(3):123-32) Briefly, such methods of generating an immune response (e.g. humoral and/or cell-mediated) in a mammal, comprise the steps of: exposing the mammal's immune system to an immunoreactive epitope (e.g. an epitope present in a 251P5G2 protein shown in FIG. 3 or analog or homolog thereof) so that the mammal generates an immune response that is specific for that epitope (e.g. generates antibodies that specifically recognize that epitope). In a preferred method, a 251P5G2 immunogen contains a biological motif, see e.g., Tables VIII-XXI and XXII-XLIX, or a peptide of a size range from 251P5G2 indicated in FIG. 5, FIG. 6, FIG. 7, FIG. 8, and FIG. 9.

The entire 251P5G2 protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones et al., *Vaccine* 13:675-681, 1995), peptide compositions contained in immune stimulating complexes (ISCOMS) (see, e.g., Takahashi et al., *Nature* 344:873-875, 1990; Hu et al., *Clin Exp Immunol.* 113:235-243, 1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.* 30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148: 1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with 251P5G2-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 251P5G2 protein that bind corresponding HLA alleles (see e.g., Table IV; Epimer™ and Epimatrix™, Brown University (URL brown.edu/Research/TB-HIV_Lab/epimatrix/epimatrix.html); and, BIMAS, (URL bimas.dcrt.nih.gov/; SYFPEITHI at URL syfpeithi.bmi-heidelberg.com/). In a preferred embodiment, a 251P5G2 immunogen contains one or more amino acid sequences identified using techniques well known in the art, such as the sequences shown in Tables VIII-XXI and XXII-XLIX or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a 251P5G2 protein) so that an immune response is generated. A typical embodiment consists of a method for generating an immune response to 251P5G2 in a host, by contacting the host with a sufficient amount of at least one 251P5G2 B cell or cytotoxic T-cell epitope or analog thereof; and at least one periodic interval thereafter re-contacting the host with the 251P5G2 B cell or cytotoxic T-cell epitope or analog thereof. A specific embodiment consists of a method of generating an immune response against a 251P5G2-related protein or a man-made multiepitopic peptide comprising: administering 251P5G2 immunogen (e.g. a 251P5G2 protein or a peptide fragment thereof, a 251P5G2 fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a 251P5G2 immunogen by: administering in vivo to muscle or skin of the individual's body a DNA molecule that comprises a DNA sequence that encodes a 251P5G2 immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics 251P5G2, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 251P5G2. Constructs comprising DNA encoding a 251P5G2-related protein/immunogen and appropriate regulatory sequences can be injected directly into muscle or skin of an individual, such that the cells of the muscle or skin take-up the construct and express the encoded 251P5G2 protein/immunogen. Alternatively, a vaccine comprises a 251P5G2-related protein. Expression of the 251P5G2-related protein immunogen results in the generation of prophylactic or therapeutic humoral and cellular immunity against cells that bear a 251P5G2 protein. Various prophylactic and therapeutic genetic immunization techniques known in the art can be used (for review, see information and references published at Internet address genweb.com). Nucleic acid-based delivery is described, for instance, in Wolff et. al., Science 247:1465

(1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658-663; Tsang et al. *J. Natl. Cancer Inst.* 87:982-990 (1995)). Non-viral delivery systems can also be employed by introducing naked DNA encoding a 251P5G2-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 251P5G2-related nucleic acid molecule. In one embodiment, the full-length human 251P5G2 cDNA is employed. In another embodiment, 251P5G2 nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 251P5G2 antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present 251P5G2 peptides to T cells in the context of MHC class I or II molecules. In one embodiment, autologous dendritic cells are pulsed with 251P5G2 peptides capable of binding to MHC class I and/or class II molecules. In another embodiment, dendritic cells are pulsed with the complete 251P5G2 protein. Yet another embodiment involves engineering the overexpression of a 251P5G2 gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186: 1177-1182). Cells that express 251P5G2 can also be engineered to express immune modulators, such as GM-CSF, and used as immunizing agents.

X.B.) 251P5G2 as a Target for Antibody-based Therapy

251P5G2 is an attractive target for antibody-based therapeutic strategies. A number of antibody strategies are known in the art for targeting both extracellular and intracellular molecules (see, e.g., complement and ADCC mediated killing as well as the use of intrabodies). Because 251P5G2 is expressed by cancer cells of various lineages relative to corresponding normal cells, systemic administration of 251P5G2-immunoreactive compositions are prepared that exhibit excellent sensitivity without toxic, non-specific and/or non-target effects caused by binding of the immunoreactive composition to non-target organs and tissues. Antibodies specifically reactive with domains of 251P5G2 are useful to treat 251P5G2-expressing cancers systemically, either as conjugates with a toxin or therapeutic agent, or as naked antibodies capable of inhibiting cell proliferation or function.

251P5G2 antibodies can be introduced into a patient such that the antibody binds to 251P5G2 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 251P5G2, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of a 251P5G2 sequence shown in FIG. 2 or FIG. 3. In addition, skilled artisans understand that it is routine to conjugate antibodies to cytotoxic agents (see, e.g., Slevers et al. *Blood* 93:11 3678-3684 (Jun. 1, 1999)). When cytotoxic and/or therapeutic agents are delivered directly to cells, such as by conjugating them to antibodies specific for a molecule expressed by that cell (e.g. 251P5G2), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-251P5G2 antibody) that binds to a marker (e.g. 251P5G2) expressed, accessible to binding or localized on the cell surfaces. A typical embodiment is a method of delivering a cytotoxic and/or therapeutic agent to a cell expressing 251P5G2, comprising conjugating the cytotoxic agent to an antibody that immunospecifically binds to a 251P5G2 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-251P5G2 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as Herceptin™ (trastuzumab) with paclitaxel (Genentech, Inc.). The antibodies can be conjugated to a therapeutic agent. To treat prostate cancer, for example, 251P5G2 antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized $IgG_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064).

Although 251P5G2 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

Although 251P5G2 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 251P5G2 expression, preferably using immunohistochemical assessments of tumor tissue, quantitative 251P5G2 imaging, or other techniques that reliably indicate the presence and degree of 251P5G2 expression. Immunohistochemical analysis of tumor biopsies or surgical specimens is preferred for this purpose. Methods for immunohistochemical analysis of tumor tissues are well known in the art.

Anti-251P5G2 monoclonal antibodies that treat prostate and other cancers include those that initiate a potent immune response against the tumor or those that are directly cytotoxic. In this regard, anti-251P5G2 monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-251P5G2 mAbs that exert a direct biological effect on tumor growth are useful to treat cancers that express 251P5G2. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-251P5G2 mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 251P5G2 antigen with high affinity but exhibit low or no antigenicity in the patient.

Therapeutic methods of the invention contemplate the administration of single anti-251P5G2 mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-251P5G2 mAbs can be administered concomitantly with other therapeutic modalities, including but not limited to various chemotherapeutic agents, androgen-blockers, immune modulators (e.g., IL-2, GM-CSF), surgery or radiation. The anti-251P5G2 mAbs are administered in their "naked" or unconjugated form, or can have a therapeutic agent(s) conjugated to them.

Anti-251P5G2 antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-251P5G2 antibody preparation, via an acceptable route of administration such as intravenous injection (IV), typically at a dose in the range of about 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg mAb per week are effective and well tolerated.

Based on clinical experience with the Herceptin™ mAb in the treatment of metastatic breast cancer, an initial loading dose of approximately 4 mg/kg patient body weight IV, followed by weekly doses of about 2 mg/kg IV of the anti-251P5G2 mAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 251P5G2 expression in the patient, the extent of circulating shed 251P5G2 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 251P5G2 in a given sample (e.g. the levels of circulating 251P5G2 antigen and/or 251P5G2 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-251P5G2 antibodies can also be used in anti-cancer therapy as a vaccine for inducing an immune response to cells expressing a 251P5G2-related protein. In particular, the generation of anti-idiotypic antibodies is well known in the art; this methodology can readily be adapted to generate anti-idiotypic anti-251P5G2 antibodies that mimic an epitope on a 251P5G2-related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

X.C.) 251P5G2 as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold. (see, e.g. Davila and Celis, J. Immunol. 165:539-547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress 251P5G2 antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA). For HLA Class II a similar rationale is employed; again 3-4 epitopes are selected from at least one TAA (see, e.g., Rosenberg et al., *Science* 278:1447-1450). Epitopes from one TAA may be used in combination with epitopes from one or more additional TAAs to produce a vaccine that targets tumors with varying expression patterns of frequently-expressed TMs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., *J. Immunol.* 162:3915-3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived 251P5G2, the PADRE® universal helper T cell epitope or multiple HTL epitopes from 251P5G2 (see e.g., Tables VIII-XXI and XXII to XLIX), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830-843 (QYIKANSKFIGITE; SEQ ID NO: 37), *Plasmodium falciparum* circumsporozoite (CS) protein at positions 378-398 (DIEKKIAKMEKASSVFNVVNS; SEQ ID NO: 38), and *Streptococcus* 18 kD protein at positions 116-131 (GAVDSILGGVATYGAA; SEQ ID NO: 39). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed, most preferably, to bind most HLA-DR (human HLA class II) molecules. For instance, a pan-DR-binding epitope peptide having the formula: XKXVAAWTLKAAX (SEQ ID NO: 40), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the $\epsilon$- and $\alpha$-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to $\epsilon$- and $\alpha$-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to prime specifically an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 251P5G2. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 251P5G2.

X.D. Adoptive Immunotherapy

Antigenic 251P5G2-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses 251P5G2. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 251P5G2. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 251P5G2-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 251P5G2, a vaccine comprising 251P5G2-specific CTL may be more efficacious in killing tumor cells in patient with advanced disease than alternative embodiments.

It is generally important to provide an amount of the peptide epitope delivered by a mode of administration sufficient to stimulate effectively a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 µg and the higher value is about 10,000; 20,000; 30,000; or 50,000 µg. Dosage values for a human typically range from about 500 µg to about 50,000 µg per 70 kilogram patient. Boosting dosages of between about 1.0 µg to about 50,000 µg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, 17$^{th}$ Edition, A. Gennaro, Editor, Mack Publishing Co., Easton, Pa., 1985). For example a peptide dose for initial immunization can be from about 1 to about 50,000 µg, generally 100-5,000 µg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5\text{-}10^7$ to $5\times10^9$ pfu.

For antibodies, a treatment generally involves repeated administration of the anti-251P5G2 antibody preparation, via an acceptable route of administration such as intravenous injection (IV), typically at a dose in the range of about 0.1 to about 10 mg/kg body weight. In general, doses in the range of 10-500 mg mAb per week are effective and well tolerated. Moreover, an initial loading dose of approximately 4 mg/kg patient body weight IV, followed by weekly doses of about 2 mg/kg IV of the anti-251P5G2 mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 251P5G2 expression in the patient, the extent of circulating shed 251P5G2 antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 µg-1 mg, 1 mg-50 mg, 50 mg-100 mg, 100 mg-200 mg, 200 mg-300 mg, 400 mg-500 mg, 500 mg-600 mg, 600 mg-700 mg, 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 6, 7, 8, 9, 10 mg/kg body weight followed, e.g., in two, three or four weeks by weekly doses; 0.5-10 mg/kg body weight, e.g., followed in two, three or four weeks by weekly doses; 225, 250, 275, 300, 325, 350, 375, 400 mg m$^2$ of body area weekly; 1-600 mg m$^2$ of body area weekly; 225-400 mg m$^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5 \times 10^{10}$ cells. A dose may also about $10^6$ cells/m$^2$ to about $10^{10}$ cells/m$^2$, or about $10^6$ cells/m$^2$ to about $10^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid liability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) Diagnostic and Prognostic Embodiments of 251P5G2.

As disclosed herein, 251P5G2 polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in the Example entitled "Expression analysis of 251P5G2 in normal tissues, and patient specimens").

251P5G2 can be analogized to a prostate associated antigen PSA, the archetypal marker that has been used by medical practitioners for years to identify and monitor the presence of prostate cancer (see, e.g., Merrill et al., J. Urol. 163(2): 503-5120 (2000); Polascik et al., J. Urol. August; 162(2):293-306 (1999) and Fortier et al., J. Nat. Cancer Inst. 91(19): 1635-1640 (1999)). A variety of other diagnostic markers are also used in similar contexts including p53 and K-ras (see, e.g., Tulchinsky et al., Int J Mol Med 1999 July 4(1):99-102 and Minimoto et al., Cancer Detect Prev 2000; 24(1):1-12). Therefore, this disclosure of 251P5G2 polynucleotides and polypeptides (as well as 251P5G2 polynucleotide probes and anti-251P5G2 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 251P5G2 polynucleotides, polypeptides, reactive T cells and antibodies are analogous to those methods from well-established diagnostic assays, which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567-74 (1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 251P5G2 polynucleotides described herein can be utilized in the same way to detect 251P5G2 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the 251P5G2 polypeptides described herein can be utilized to generate antibodies for use in detecting 251P5G2 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 251P5G2 polynucleotides and/or polypeptides can be used to provide evidence of metastasis. For example, when a biological sample from tissue that does not normally contain 251P5G2-expressing cells (lymph node) is found to contain 251P5G2-expressing cells such as the 251P5G2 expression seen in LAPC4 and LAPC9, xenografts isolated from lymph node and bone metastasis, respectively, this finding is indicative of metastasis.

Alternatively 251P5G2 polynucleotides and/or polypeptides can be used to provide evidence of cancer, for example, when cells in a biological sample that do not normally express 251P5G2 or express 251P5G2 at a different level are found to express 251P5G2 or have an increased expression of 251P5G2 (see, e.g., the 251P5G2 expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 251P5G2) such as PSA, PSCA etc. (see, e.g., Alanen et al., Pathol. Res. Pract. 192(3): 233-237 (1996)).

Just as PSA polynucleotide fragments and polynucleotide variants are employed by skilled artisans for use in methods of monitoring PSA, 251P5G2 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson et al., Methods Mol. Biol. 98:121-154 (1998)). An additional illustration of the use of such fragments is provided in the Example entitled "Expression analysis of 251P5G2 in normal tissues, and patient specimens," where a 251P5G2 polynucleotide fragment is used as a probe to show the expression of 251P5G2 RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November-December 11(6):407-13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g., a 251P5G2 polynucleotide shown in FIG. 2 or variant thereof) under conditions of high stringency.

Furthermore, PSA polypeptides which contain an epitope that can be recognized by an antibody or T cell that specifically binds to that epitope are used in methods of monitoring PSA. 251P5G2 polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. Nos. 5,840,501 and 5,939,533). For example it may be preferable to utilize a polypeptide comprising one of the 251P5G2 biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. a 251P5G2 polypeptide shown in FIG. 3).

As shown herein, the 251P5G2 polynucleotides and polypeptides (as well as the 251P5G2 polynucleotide probes and anti-251P5G2 antibodies or T cells used to identify the presence of these molecules) exhibit specific properties that make them useful in diagnosing cancers such as those listed in Table I. Diagnostic assays that measure the presence of 251P5G2 gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and consequently, materials such as 251P5G2 polynucleotides and polypeptides (as well as the 251P5G2 polynucleotide probes and anti-251P5G2 antibodies used to identify the presence of these molecules) need to be employed to confirm a metastases of prostatic origin.

Finally, in addition to their use in diagnostic assays, the 251P5G2 polynucleotides disclosed herein have a number of other utilities such as their use in the identification of oncogenetic associated chromosomal abnormalities in the chromosomal region to which the 251P5G2 gene maps (see the Example entitled "Chromosomal Mapping of 251P5G2" below). Moreover, in addition to their use in diagnostic assays, the 251P5G2-related proteins and polynucleotides disclosed herein have other utilities such as their use in the forensic analysis of tissues of unknown origin (see, e.g., Takahama K Forensic Sci Int 1996 Jun. 28; 80(1-2): 63-9).

Additionally, 251P5G2-related proteins or polynucleotides of the invention can be used to treat a pathologic condition characterized by the over-expression of 251P5G2. For example, the amino acid or nucleic acid sequence of FIG. 2 or FIG. 3, or fragments of either, can be used to generate an immune response to a 251P5G2 antigen. Antibodies or other molecules that react with 251P5G2 can be used to modulate the function of this molecule, and thereby provide a therapeutic benefit.

XII.) Inhibition of 251P5G2 Protein Function

The invention includes various methods and compositions for inhibiting the binding of 251P5G2 to its binding partner or its association with other protein(s) as well as methods for inhibiting 251P5G2 function.

XII.A.) Inhibition of 251P5G2 with Intracellular Antibodies

In one approach, a recombinant vector that encodes single chain antibodies that specifically bind to 251P5G2 are introduced into 251P5G2 expressing cells via gene transfer technologies. Accordingly, the encoded single chain anti-251P5G2 antibody is expressed intracellularly, binds to 251P5G2 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92:3137-3141; Beerli et al., 1994, J. Biol. Chem. 289: 23931-23936; Deshane et al., 1994, Gene Ther. 1:332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to target precisely the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 251P5G2 in the nucleus, thereby preventing its activity within the nucleus. Nuclear targeting signals are engineered into such 251P5G2 intrabodies in order to achieve the desired targeting. Such 251P5G2 intrabodies are designed to bind specifically to a particular 251P5G2 domain. In another embodiment, cytosolic intrabodies that specifically bind to a 251P5G2 protein are used to prevent 251P5G2 from gaining access to the nucleus, thereby preventing it from exerting any biological activity within the nucleus (e.g., preventing 251P5G2 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of 251P5G2 with Recombinant Proteins

In another approach, recombinant molecules bind to 251P5G2 and thereby inhibit 251P5G2 function. For example, these recombinant molecules prevent or inhibit 251P5G2 from accessing/binding to its binding partner(s) or associating with other protein(s). Such recombinant molecules can, for example, contain the reactive part(s) of a 251P5G2 specific antibody molecule. In a particular embodiment, the 251P5G2 binding domain of a 251P5G2 binding partner is engineered into a dimeric fusion protein, whereby the fusion protein comprises two 251P5G2 ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 251P5G2, whereby the dimeric fusion protein specifically binds to 251P5G2 and blocks 251P5G2 interaction with a binding partner. Such dimeric fusion proteins are further combined into multimeric proteins using known antibody linking technologies.

XII.C.) Inhibition of 251P5G2 Transcription or Translation

The present invention also comprises various methods and compositions for inhibiting the transcription of the 251P5G2 gene. Similarly, the invention also provides methods and compositions for inhibiting the translation of 251P5G2 mRNA into protein.

In one approach, a method of inhibiting the transcription of the 251P5G2 gene comprises contacting the 251P5G2 gene with a 251P5G2 antisense polynucleotide. In another approach, a method of inhibiting 251P5G2 mRNA translation comprises contacting a 251P5G2 mRNA with an antisense polynucleotide. In another approach, a 251P5G2 specific ribozyme is used to cleave a 251P5G2 message, thereby inhibiting translation. Such antisense and ribozyme based methods can also be directed to the regulatory regions of the 251P5G2 gene, such as 251P5G2 promoter and/or enhancer elements. Similarly, proteins capable of inhibiting a 251P5G2 gene transcription factor are used to inhibit 251P5G2 mRNA transcription. The various polynucleotides and compositions useful in the aforementioned methods have been described above. The use of antisense and ribozyme molecules to inhibit transcription and translation is well known in the art.

Other factors that inhibit the transcription of 251P5G2 by interfering with 251P5G2 transcriptional activation are also useful to treat cancers expressing 251P5G2. Similarly, factors that interfere with 251P5G2 processing are useful to treat cancers that express 251P5G2. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 251P5G2 (i.e., antisense, ribozyme, polynucleotides encoding intrabodies and other 251P5G2 inhibitory molecules). A number of gene therapy approaches are known in the art. Recombinant vectors encoding 251P5G2 antisense polynucleotides, ribozymes, factors capable of interfering with 251P5G2 transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 251P5G2 to a binding partner, etc.

In vivo, the effect of a 251P5G2 therapeutic composition can be evaluated in a suitable animal model. For example, xenogeneic prostate cancer models can be used, wherein human prostate cancer explants or passaged xenograft tissues are introduced into immune compromised animals, such as nude or SCID mice (Klein et al., 1997, Nature Medicine 3:402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Identification, Characterization and Use of Modulators of 251P5G2

Methods to Identify and Use Modulators

In one embodiment, screening is performed to identify modulators that induce or suppress a particular expression profile, suppress or induce specific pathways, preferably generating the associated phenotype thereby. In another embodiment, having identified differentially expressed genes important in a particular state; screens are performed to identify modulators that alter expression of individual genes, either increase or decrease. In another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition, screens are done for genes that are induced in response to a candidate agent. After identifying a modulator (one that suppresses a cancer expression pattern leading to a normal expression pattern, or a modulator of a cancer gene that leads to expression of the gene as in normal tissue) a screen is performed to identify genes that are specifically modulated in response to the agent. Comparing expression profiles between normal tissue and agent-treated cancer tissue reveals genes that are not expressed in normal tissue or cancer tissue, but are expressed in agent treated tissue, and vice versa. These agent-specific sequences are identified and used by methods described herein for cancer genes or proteins. In particular these sequences and the proteins they encode are used in marking or identifying agent-treated cells. In addition, antibodies are raised against the agent-induced proteins and used to target novel therapeutics to the treated cancer tissue sample.

Modulator-related Identification and Screening Assays: Gene Expression-related Assays Proteins, nucleic acids, and antibodies of the invention are used in screening assays. The cancer-associated proteins, antibodies, nucleic acids, modified proteins and cells containing these sequences are used in screening assays, such as evaluating the effect of drug candidates on a "gene expression profile," expression profile of polypeptides or alteration of biological function. In one embodiment, the expression profiles are used, preferably in conjunction with high throughput screening techniques to allow monitoring for expression profile genes after treatment with a candidate agent (e.g., Davis, G F, et al, J Biol Screen 7:69 (2002); Zlokarnik, et al., Science 279:84-8 (1998); Heid, Genome Res 6:986-94, 1996).

The cancer proteins, antibodies, nucleic acids, modified proteins and cells containing the native or modified cancer proteins or genes are used in screening assays. That is, the present invention comprises methods for screening for compositions which modulate the cancer phenotype or a physiological function of a cancer protein of the invention. This is done on a gene itself or by evaluating the effect of drug candidates on a "gene expression profile" or biological function. In one embodiment, expression profiles are used, preferably in conjunction with high throughput screening techniques to allow monitoring after treatment with a candidate agent, see Zlokarnik, supra.

A variety of assays are executed directed to the genes and proteins of the invention. Assays are run on an individual nucleic acid or protein level. That is, having identified a particular gene as up regulated in cancer, test compounds are screened for the ability to modulate gene expression or for binding to the cancer protein of the invention. "Modulation" in this context includes an increase or a decrease in gene expression. The preferred amount of modulation will depend on the original change of the gene expression in normal versus tissue undergoing cancer, with changes of at least 10%, preferably 50%, more preferably 100-300%, and in some embodiments 300-1000% or greater. Thus, if a gene exhibits a 4-fold increase in cancer tissue compared to normal tissue, a decrease of about four-fold is often desired; similarly, a 10-fold decrease in cancer tissue compared to normal tissue a target value of a 10-fold increase in expression by the test compound is often desired. Modulators that exacerbate the type of gene expression seen in cancer are also useful, e.g., as an upregulated target in further analyses.

The amount of gene expression is monitored using nucleic acid probes and the quantification of gene expression levels, or, alternatively, a gene product itself is monitored, e.g., through the use of antibodies to the cancer protein and standard immunoassays. Proteomics and separation techniques also allow for quantification of expression.

Expression Monitoring to Identify Compounds that Modify Gene Expression

In one embodiment, gene expression monitoring, i.e., an expression profile, is monitored simultaneously for a number of entities. Such profiles will typically involve one or more of the genes of FIG. 2. In this embodiment, e.g., cancer nucleic acid probes are attached to biochips to detect and quantify cancer sequences in a particular cell. Alternatively, PCR can be used. Thus, a series, e.g., wells of a microtiter plate, can be used with dispensed primers in desired wells. A PCR reaction can then be performed and analyzed for each well.

Expression monitoring is performed to identify compounds that modify the expression of one or more cancer-associated sequences, e.g., a polynucleotide sequence set out in FIG. 2. Generally, a test modulator is added to the cells prior to analysis. Moreover, screens are also provided to identify agents that modulate cancer, modulate cancer proteins of the invention, bind to a cancer protein of the invention, or interfere with the binding of a cancer protein of the invention and an antibody or other binding partner.

In one embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds," as compounds for screening, or as therapeutics.

In certain embodiments, combinatorial libraries of potential modulators are screened for an ability to bind to a cancer polypeptide or to modulate activity. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

As noted above, gene expression monitoring is conveniently used to test candidate modulators (e.g., protein, nucleic acid or small molecule). After the candidate agent has been added and the cells allowed to incubate for a period, the sample containing a target sequence to be analyzed is, e.g., added to a biochip.

If required, the target sequence is prepared using known techniques. For example, a sample is treated to lyse the cells, using known lysis buffers, electroporation, etc., with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

The target sequence can be labeled with, e.g., a fluorescent, a chemiluminescent, a chemical, or a radioactive signal, to provide a means of detecting the target sequence's specific binding to a probe. The label also can be an enzyme, such as alkaline phosphatase or horseradish peroxidase, which when provided with an appropriate substrate produces a product that is detected. Alternatively, the label is a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697. In this embodiment, in general, the target nucleic acid is prepared as outlined above, and then added to the biochip comprising a plurality of nucleic acid probes, under conditions that allow the formation of a hybridization complex.

A variety of hybridization conditions are used in the present invention, including high, moderate and low stringency conditions as outlined above. The assays are generally run under stringency conditions which allow formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc. These parameters may also be used to control non-specific binding, as is generally outlined in U.S. Pat. No. 5,681,697. Thus, it can be desirable to perform certain steps at higher stringency conditions to reduce non-specific binding.

The reactions outlined herein can be accomplished in a variety of ways. Components of the reaction can be added simultaneously, or sequentially, in different orders, with preferred embodiments outlined below. In addition, the reaction may include a variety of other reagents. These include salts, buffers, neutral proteins, e.g. albumin, detergents, etc. which can be used to facilitate optimal hybridization and detection, and/or reduce nonspecific or background interactions. Reagents that otherwise improve the efficiency of the assay, such as protease inhibitors, nuclease inhibitors, anti-microbial agents, etc., may also be used as appropriate, depending on the sample preparation methods and purity of the target. The assay data are analyzed to determine the expression levels of individual genes, and changes in expression levels as between states, forming a gene expression profile.

Biological Activity-related Assays

The invention provides methods identify or screen for a compound that modulates the activity of a cancer-related gene or protein of the invention. The methods comprise adding a test compound, as defined above, to a cell comprising a cancer protein of the invention. The cells contain a recombinant nucleic acid that encodes a cancer protein of the invention. In another embodiment, a library of candidate agents is tested on a plurality of cells.

In one aspect, the assays are evaluated in the presence or absence or previous or subsequent exposure of physiological signals, e.g. hormones, antibodies, peptides, antigens, cytokines, growth factors, action potentials, pharmacological agents including chemotherapeutics, radiation, carcinogenics, or other cells (i.e., cell-cell contacts). In another example, the determinations are made at different stages of the cell cycle process. In this way, compounds that modulate genes or proteins of the invention are identified. Compounds with pharmacological activity are able to enhance or interfere with the activity of the cancer protein of the invention. Once identified, similar structures are evaluated to identify critical structural features of the compound.

In one embodiment, a method of modulating (e.g., inhibiting) cancer cell division is provided; the method comprises administration of a cancer modulator. In another embodiment, a method of modulating (e.g., inhibiting) cancer is provided; the method comprises administration of a cancer modulator. In a further embodiment, methods of treating cells or individuals with cancer are provided; the method comprises administration of a cancer modulator.

In one embodiment, a method for modulating the status of a cell that expresses a gene of the invention is provided. As used herein status comprises such art-accepted parameters such as growth, proliferation, survival, function, apoptosis, senescence, location, enzymatic activity, signal transduction, etc. of a cell. In one embodiment, a cancer inhibitor is an antibody as discussed above. In another embodiment, the cancer inhibitor is an antisense molecule. A variety of cell growth, proliferation, and metastasis assays are known to those of skill in the art, as described herein.

High Throughput Screening to Identify Modulators

The assays to identify suitable modulators are amenable to high throughput screening. Preferred assays thus detect enhancement or inhibition of cancer gene transcription, inhibition or enhancement of polypeptide expression, and inhibition or enhancement of polypeptide activity.

In one embodiment, modulators evaluated in high throughput screening methods are proteins, often naturally occurring proteins or fragments of naturally occurring proteins. Thus, e.g., cellular extracts containing proteins, or random or directed digests of proteinaceous cellular extracts, are used. In this way, libraries of proteins are made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes, or ligands and receptors.

Use of Soft Agar Growth and Colony Formation to Identify and Characterize Modulators Normal cells require a solid substrate to attach and grow. When cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, can regenerate normal phenotype and once again require a solid substrate to attach to and grow. Soft agar growth or colony formation in assays are used to identify modulators of cancer sequences, which when expressed in host cells, inhibit abnormal cellular proliferation and transformation. A modulator reduces or eliminates the host cells' ability to grow suspended in solid or semisolid media, such as agar.

Techniques for soft agar growth or colony formation in suspension assays are described in Freshney, Culture of Animal Cells a Manual of Basic Technique (3rd ed., 1994). See also, the methods section of Garkavtsev et al. (1996), supra.

Evaluation of Contact Inhibition and Growth Density Limitation to Identify and Characterize Modulators Normal cells typically grow in a flat and organized pattern in cell culture until they touch other cells. When the cells touch one another, they are contact inhibited and stop growing. Transformed cells, however, are not contact inhibited and continue to grow to high densities in disorganized foci. Thus, transformed cells grow to a higher saturation density than corresponding normal cells. This is detected morphologically by the formation of a disoriented monolayer of cells or cells in foci. Alternatively, labeling index with ($^3$H)-thymidine at saturation density is used to measure density limitation of growth, similarly an MTT or Alamar blue assay will reveal proliferation capacity of cells and the ability of modulators to affect same. See Freshney (1994), supra. Transformed cells, when transfected with tumor suppressor genes, can regenerate a normal phenotype and become contact inhibited and would grow to a lower density.

In this assay, labeling index with $^3$H-thymidine at saturation density is a preferred method of measuring density limitation of growth. Transformed host cells are transfected with a cancer-associated sequence and are grown for 24 hours at saturation density in non-limiting medium conditions. The percentage of cells labeling with (3H)-thymidine is determined by incorporated cpm.

Contact independent growth is used to identify modulators of cancer sequences, which had led to abnormal cellular proliferation and transformation. A modulator reduces or eliminates contact independent growth, and returns the cells to a normal phenotype.

Evaluation of Growth Factor or Serum Dependence to Identify and Characterize Modulators Transformed cells have lower serum dependence than their normal counterparts (see, e.g., Temin, J. Natl. Cancer Inst. 37:167-175 (1966); Eagle et al., J. Exp. Med 131:836-879 (1970)); Freshney, supra. This is in part due to release of various growth factors by the transformed cells. The degree of growth factor or serum dependence of transformed host cells can be compared with that of control. For example, growth factor or serum dependence of a cell is monitored in methods to identify and characterize compounds that modulate cancer-associated sequences of the invention.

Use of Tumor-specific Marker Levels to Identify and Characterize Modulators

Tumor cells release an increased amount of certain factors (hereinafter "tumor specific markers") than their normal counterparts. For example, plasminogen activator (PA) is released from human glioma at a higher level than from normal brain cells (see, e.g., Gullino, Angiogenesis, Tumor Vascularization, and Potential Interference with Tumor Growth, in Biological Responses in Cancer, pp. 178-184 (Mihich (ed.) 1985)). Similarly, Tumor Angiogenesis Factor (TAF) is released at a higher level in tumor cells than their normal counterparts. See, e.g., Folkman, Angiogenesis and Cancer, Sem Cancer Biol. (1992)), while bFGF is released from endothelial tumors (Ensoli, B et al).

Various techniques which measure the release of these factors are described in Freshney (1994), supra. Also, see, Unkless et al., J. Biol. Chem. 249:4295-4305 (1974); Strickland & Beers, J. Biol. Chem. 251:5694-5702 (1976); Whur et al., Br. J. Cancer 42:305 312 (1980); Gullino, Angiogenesis, Tumor Vascularization, and Potential Interference with Tumor Growth, in Biological Responses in Cancer, pp. 178-184 (Mihich (ed.) 1985); Freshney, Anticancer Res. 5:111-130 (1985). For example, tumor specific marker levels are monitored in methods to identify and characterize compounds that modulate cancer-associated sequences of the invention.

Invasiveness into Matrigel to Identify and Characterize Modulators

The degree of invasiveness into Matrigel or an extracellular matrix constituent can be used as an assay to identify and characterize compounds that modulate cancer associated sequences. Tumor cells exhibit a positive correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells. Techniques described in Cancer Res. 1999; 59:6010; Freshney (1994), supra, can be used. Briefly, the level of invasion of host cells is measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Evaluation of Tumor Growth In Vivo to Identify and Characterize Modulators

Effects of cancer-associated sequences on cell growth are tested in transgenic or immune-suppressed organisms. Transgenic organisms are prepared in a variety of art-accepted ways. For example, knock-out transgenic organisms, e.g., mammals such as mice, are made, in which a cancer gene is disrupted or in which a cancer gene is inserted. Knock-out transgenic mice are made by insertion of a marker gene or other heterologous gene into the endogenous cancer gene site in the mouse genome via homologous recombination. Such mice can also be made by substituting the endogenous cancer gene with a mutated version of the cancer gene, or by mutating the endogenous cancer gene, e.g., by exposure to carcinogens.

To prepare transgenic chimeric animals, e.g., mice, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells some of which are derived from the mutant cell line. Therefore, by breeding the chimeric mice it is possible to obtain a new line of mice containing the introduced genetic lesion (see, e.g., Capecchi et al., Science 244:1288 (1989)). Chimeric mice can be derived according to U.S. Pat. No. 6,365,797, issued 2 Apr. 2002; U.S. Pat. No. 6,107,540 issued 22 Aug. 2000; Hogan et al., Manipulating the Mouse Embryo: A laboratory Manual, Cold Spring Harbor Laboratory (1988) and Teratocarcinomas and Embryonic Stem Cells: A Practical Approach, Robertson, ed., IRL Press, Washington, D.C., (1987).

Alternatively, various immune-suppressed or immune-deficient host animals can be used. For example, a genetically athymic "nude" mouse (see, e.g., Giovanella et al., J. Natl. Cancer Inst. 52:921 (1974)), a SCID mouse, a thymectornized mouse, or an irradiated mouse (see, e.g., Bradley et al., Br. J. Cancer 38:263 (1978); Selby et al., Br. J. Cancer 41:52 (1980)) can be used as a host. Transplantable tumor cells (typically about $10^6$ cells) injected into isogenic hosts produce invasive tumors in a high proportion of cases, while normal cells of similar origin will not. In hosts which developed invasive tumors, cells expressing cancer-associated sequences are injected subcutaneously or orthotopically. Mice are then separated into groups, including control groups and treated experimental groups) e.g. treated with a modulator). After a suitable length of time, preferably 4-8 weeks, tumor growth is measured (e.g., by volume or by its two largest dimensions, or weight) and compared to the control. Tumors that have statistically significant reduction (using, e.g., Student's T test) are said to have inhibited growth.

In Vitro Assays to Identify and Characterize Modulators

Assays to identify compounds with modulating activity can be performed in vitro. For example, a cancer polypeptide is first contacted with a potential modulator and incubated for a suitable amount of time, e.g., from 0.5 to 48 hours. In one embodiment, the cancer polypeptide levels are determined in vitro by measuring the level of protein or mRNA. The level of protein is measured using immunoassays such as Western blotting, ELISA and the like with an antibody that selectively binds to the cancer polypeptide or a fragment thereof. For measurement of mRNA, amplification, e.g., using PCR, LCR, or hybridization assays, e.g., Northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using a cancer protein promoter operably linked to a reporter gene such as luciferase, green fluorescent protein, CAT, or P-gal. The reporter construct is typically transfected into a cell. After treatment with a potential modulator, the amount of reporter gene transcription, translation, or activity is measured according to standard techniques known to those of skill in the art (Davis G F, supra; Gonzalez, J. & Negulescu, P. Curr. Opin. Biotechnol. 1998: 9:624).

As outlined above, in vitro screens are done on individual genes and gene products. That is, having identified a particular differentially expressed gene as important in a particular state, screening of modulators of the expression of the gene or the gene product itself is performed.

In one embodiment, screening for modulators of expression of specific gene(s) is performed. Typically, the expression of only one or a few genes is evaluated. In another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships.

Binding Assays to Identify and Characterize Modulators

In binding assays in accordance with the invention, a purified or isolated gene product of the invention is generally used. For example, antibodies are generated to a protein of the invention, and immunoassays are run to determine the amount and/or location of protein. Alternatively, cells comprising the cancer proteins are used in the assays.

Thus, the methods comprise combining a cancer protein of the invention and a candidate compound such as a ligand, and determining the binding of the compound to the cancer protein of the invention. Preferred embodiments utilize the human cancer protein; animal models of human disease of can also be developed and used. Also, other analogous mammalian proteins also can be used as appreciated by those of skill in the art. Moreover, in some embodiments variant or derivative cancer proteins are used.

Generally, the cancer protein of the invention, or the ligand, is non-diffusibly bound to an insoluble support. The support can, e.g., be one having isolated sample receiving areas (a microtiter plate, an array, etc.). The insoluble supports can be made of any composition to which the compositions can be bound, is readily separated from soluble material, and is otherwise compatible with the overall method of screening. The surface of such supports can be solid or porous and of any convenient shape.

Examples of suitable insoluble supports include microtiter plates, arrays, membranes and beads. These are typically made of glass, plastic (e.g., polystyrene), polysaccharide, nylon, nitrocellulose, or Teflon™, etc. Microtiter plates and arrays are especially convenient because a large number of assays can be carried out simultaneously, using small amounts of reagents and samples. The particular manner of binding of the composition to the support is not crucial so long as it is compatible with the reagents and overall methods of the invention, maintains the activity of the composition and is nondiffusable. Preferred methods of binding include the use of antibodies which do not sterically block either the ligand binding site or activation sequence when attaching the protein to the support, direct binding to "sticky" or ionic supports, chemical crosslinking, the synthesis of the protein or agent on the surface, etc. Following binding of the protein or ligand/binding agent to the support, excess unbound material is removed by washing. The sample receiving areas may then be blocked through incubation with bovine serum albumin (BSA), casein or other innocuous protein or other moiety.

Once a cancer protein of the invention is bound to the support, and a test compound is added to the assay. Alternatively, the candidate binding agent is bound to the support and the cancer protein of the invention is then added. Binding agents include specific antibodies, non-natural binding agents identified in screens of chemical libraries, peptide analogs, etc.

Of particular interest are assays to identify agents that have a low toxicity for human cells. A wide variety of assays can be used for this purpose, including proliferation assays, cAMP assays, labeled in vita protein-protein binding assays, electrophoretic mobility shift assays, immunoassays for protein binding, functional assays (phosphorylation assays, etc.) and the like.

A determination of binding of the test compound (ligand, binding agent, modulator, etc.) to a cancer protein of the invention can be done in a number of ways. The test compound can be labeled, and binding determined directly, e.g., by attaching all or a portion of the cancer protein of the invention to a solid support, adding a labeled candidate compound (e.g., a fluorescent label), washing off excess reagent, and determining whether the label is present on the solid support. Various blocking and washing steps can be utilized as appropriate.

In certain embodiments, only one of the components is labeled, e.g., a protein of the invention or ligands labeled. Alternatively, more than one component is labeled with different labels, e.g., $I^{125}$, for the proteins and a fluorophor for the compound. Proximity reagents, e.g., quenching or energy transfer reagents are also useful.

Competitive Binding to Identify and Characterize Modulators

In one embodiment, the binding of the "test compound" is determined by competitive binding assay with a "competitor." The competitor is a binding moiety that binds to the target molecule (e.g., a cancer protein of the invention). Competitors include compounds such as antibodies, peptides, binding partners, ligands, etc. Under certain circumstances, the competitive binding between the test compound and the competitor displaces the test compound. In one embodiment, the test compound is labeled. Either the test compound, the competitor, or both, is added to the protein for a time sufficient to allow binding. Incubations are performed at a temperature that facilitates optimal activity, typically between four and 40° C. Incubation periods are typically optimized, e.g., to facilitate rapid high throughput screening; typically between zero and one hour will be sufficient. Excess reagent is generally removed or washed away. The second component is then added, and the presence or absence of the labeled component is followed, to indicate binding.

In one embodiment, the competitor is added first, followed by the test compound. Displacement of the competitor is an indication that the test compound is binding to the cancer protein and thus is capable of binding to, and potentially modulating, the activity of the cancer protein. In this embodiment, either component can be labeled. Thus, e.g., if the competitor is labeled, the presence of label in the post-test compound wash solution indicates displacement by the test compound. Alternatively, if the test compound is labeled, the presence of the label on the support indicates displacement.

In an alternative embodiment, the test compound is added first, with incubation and washing, followed by the competitor. The absence of binding by the competitor indicates that the test compound binds to the cancer protein with higher affinity than the competitor. Thus, if the test compound is labeled, the presence of the label on the support, coupled with a lack of competitor binding, indicates that the test compound binds to and thus potentially modulates the cancer protein of the invention.

Accordingly, the competitive binding methods comprise differential screening to identity agents that are capable of modulating the activity of the cancer proteins of the invention. In this embodiment, the methods comprise combining a cancer protein and a competitor in a first sample. A second sample comprises a test compound, the cancer protein, and a competitor. The binding of the competitor is determined for both samples, and a change, or difference in binding between the two samples indicates the presence of an agent capable of binding to the cancer protein and potentially modulating its activity. That is, if the binding of the competitor is different in the second sample relative to the first sample, the agent is capable of binding to the cancer protein.

Alternatively, differential screening is used to identify drug candidates that bind to the native cancer protein, but cannot bind to modified cancer proteins. For example the structure of the cancer protein is modeled and used in rational drug design to synthesize agents that interact with that site, agents which generally do not bind to site-modified proteins. Moreover, such drug candidates that affect the activity of a native cancer protein are also identified by screening drugs for the ability to either enhance or reduce the activity of such proteins.

Positive controls and negative controls can be used in the assays. Preferably control and test samples are performed in at least triplicate to obtain statistically significant results. Incubation of all samples occurs for a time sufficient to allow for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g. albumin, detergents, etc. which are used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components is added in an order that provides for the requisite binding.

Use of Polynucleotides to Down-Regulate or Inhibit a Protein of the Invention.

Polynucleotide modulators of cancer can be introduced into a cell containing the target nucleotide sequence by formation of a conjugate with a ligand-binding molecule, as described in WO 91/04753. Suitable ligand-binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of cancer can be introduced into a cell containing the target nucleic acid sequence, e.g., by formation of a polynucleotide-lipid complex, as described in WO 90/10448. It is understood that the use of antisense molecules or knock out and knock in models may also be used in screening assays as discussed above, in addition to methods of treatment.

Inhibitory and Antisense Nucleotides

In certain embodiments, the activity of a cancer-associated protein is down-regulated, or entirely inhibited, by the use of antisense polynucleotide or inhibitory small nuclear RNA (snRNA), i.e., a nucleic acid complementary to, and which can preferably hybridize specifically to, a coding mRNA nucleic acid sequence, e.g., a cancer protein of the invention, mRNA, or a subsequence thereof. Binding of the antisense polynucleotide to the mRNA reduces the translation and/or stability of the mRNA.

In the context of this invention, antisense polynucleotides can comprise naturally occurring nucleotides, or synthetic species formed from naturally occurring subunits or their close homologs. Antisense polynucleotides may also have altered sugar moieties or inter-sugar linkages. Exemplary among these are the phosphorothioate and other sulfur containing species which are known for use in the art. Analogs are comprised by this invention so long as they function effectively to hybridize with nucleotides of the invention. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Antisense molecules as used herein include antisense or sense oligonucleotides. Sense oligonucleotides can, e.g., be employed to block transcription by binding to the anti-sense strand. The antisense and sense oligonucleotide comprise a single stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 12 nucleotides, preferably from about 12 to 30 nucleotides. The ability to derive an antisense or a sense oligonucleotide, based upon a cDNA sequence encoding a given protein is described in, e.g., Stein &Cohen (Cancer Res. 48:2659 (1988 and van der Krol et al. (BioTechniques 6:958 (1988)).

Ribozymes

In addition to antisense polynucleotides, ribozymes can be used to target and inhibit transcription of cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto et al., Adv. in Pharmacology 25: 289-317 (1994) for a general review of the properties of different ribozymes).

The general features of hairpin ribozymes are described, e.g., in Hampel et al., Nucl. Acids Res. 18:299-304 (1990); European Patent Publication No. 0360257; U.S. Pat. No. 5,254,678. Methods of preparing are well known to those of skill in the art (see, e.g., WO 94/26877; Ojwang et al., Proc. Natl. Acad. Sci. USA 90:6340-6344 (1993); Yamada et al., Human Gene Therapy 1:39-45 (1994); Leavitt et al., Proc. Natl. Acad. Sci. USA 92:699-703 (1995); Leavitt et al., Human Gene Therapy 5:1151-120 (1994); and Yamada et al., Virology 205:121-126 (1994)).

Use of Modulators in Phenotypic Screening

In one embodiment, a test compound is administered to a population of cancer cells, which have an associated cancer expression profile. By "administration" or "contacting" herein is meant that the modulator is added to the cells in such a manner as to allow the modulator to act upon the cell, whether by uptake and intracellular action, or by action at the cell surface. In some embodiments, a nucleic acid encoding a proteinaceous agent (i.e., a peptide) is put into a viral construct such as an adenoviral or retroviral construct, and added to the cell, such that expression of the peptide agent is accomplished, e.g., PCT US97/01019. Regulatable gene therapy systems can also be used. Once the modulator has been administered to the cells, the cells are washed if desired and are allowed to incubate under preferably physiological conditions for some period. The cells are then harvested and a new gene expression profile is generated. Thus, e.g., cancer tissue is screened for agents that modulate, e.g., induce or suppress, the cancer phenotype. A change in at least one gene, preferably many, of the expression profile indicates that the agent has an effect on cancer activity. Similarly, altering a biological function or a signaling pathway is indicative of modulator activity. By defining such a signature for the cancer phenotype, screens for new drugs that alter the phenotype are devised. With this approach, the drug target need not be known and need not be represented in the original gene/protein expression screening platform, nor does the level of transcript for the target protein need to change. The modulator inhibiting function will serve as a surrogate marker As outlined above, screens are done to assess genes or gene products. That is, having identified a particular differentially expressed gene as important in a particular state, screening of modulators of either the expression of the gene or the gene product itself is performed.

Use of Modulators to Affect Peptides of the Invention

Measurements of cancer polypeptide activity, or of the cancer phenotype are performed using a variety of assays. For example, the effects of modulators upon the function of a cancer polypeptide(s) are measured by examining parameters described above. A physiological change that affects activity is used to assess the influence of a test compound on the polypeptides of this invention. When the functional outcomes are determined using intact cells or animals, a variety of effects can be assesses such as, in the case of a cancer associated with solid tumors, tumor growth, tumor metastasis, neovascularization, hormone release, transcriptional changes to both known and uncharacterized genetic markers (e.g., by Northern blots), changes in cell metabolism such as cell growth or pH changes, and changes in intracellular second messengers such as cGNIP.

Methods of Identifying Characterizing Cancer-associated Sequences

Expression of various gene sequences is correlated with cancer. Accordingly, disorders based on mutant or variant cancer genes are determined. In one embodiment, the invention provides methods for identifying cells containing variant cancer genes, e.g., determining the presence of, all or part, the sequence of at least one endogenous cancer gene in a cell. This is accomplished using any number of sequencing techniques. The invention comprises methods of identifying the cancer genotype of an individual, e.g., determining all or part of the sequence of at least one gene of the invention in the individual. This is generally done in at least one tissue of the individual, e.g., a tissue set forth in Table I, and may include the evaluation of a number of tissues or different samples of the same tissue. The method may include comparing the sequence of the sequenced gene to a known cancer gene, i.e., a wild-type gene to determine the presence of family members, homologies, mutations or variants. The sequence of all or part of the gene can then be compared to the sequence of a known cancer gene to determine if any differences exist. This is done using any number of known homology programs, such as BLAST, Bestfit, etc. The presence of a difference in the sequence between the cancer gene of the patient and the known cancer gene correlates with a disease state or a propensity for a disease state, as outlined herein.

In a preferred embodiment, the cancer genes are used as probes to determine the number of copies of the cancer gene in the genome. The cancer genes are used as probes to determine the chromosomal localization of the cancer genes. Information such as chromosomal localization finds use in providing a diagnosis or prognosis in particular when chromosomal abnormalities such as translocations, and the like are identified in the cancer gene locus.

XIV.) Kits/Articles of Manufacture

For use in the diagnostic and therapeutic applications described herein, kits are also within the scope of the invention. Such kits can comprise a carrier, package, or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a FIG. 2-*related* protein or a FIG. 2 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequences in FIG. 2 or FIG. 3 or analogs thereof, or a nucleic acid molecules that encodes such amino acid sequences.

The kit of the invention will typically comprise the container described above and one or more other containers comprising materials desirable from a commercial and user standpoint, including buffers, diluents, filters, needles, syringes; carrier, package, container, vial and/or tube labels listing contents and/or instructions for use, and package inserts with instructions for use.

A label can be present on the container to indicate that the composition is used for a specific therapy or non-therapeutic application, such as a diagnostic or laboratory application, and can also indicate directions for either in vivo or in vita use, such as those described herein. Directions and or other information can also be included on an insert(s) or label(s) which is included with or on the kit.

The terms "kit" and "article of manufacture" can be used as synonyms.

In another embodiment of the invention, an article(s) of manufacture containing compositions, such as amino acid sequence(s), small molecule(s), nucleic acid sequence(s), and/or antibody(s), e.g., materials useful for the diagnosis, prognosis, prophylaxis and/or treatment of neoplasias of tissues such as those set forth in Table I is provided. The article of manufacture typically comprises at least one container and at least one label. Suitable containers include, for example, bottles, vials, syringes, and test tubes. The containers can be formed from a variety of materials such as glass or plastic. The container can hold amino acid sequence(s), small molecule(s), nucleic acid sequence(s), and/or antibody(s), in one embodiment the container holds a polynucleotide for use in examining the mRNA expression profile of a cell, together with reagents used for this purpose.

The container can alternatively hold a composition which is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding 251P5G2 and modulating the function of 251P5G2.

The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a neoplasia of a tissue set forth in Table I. The article of manufacture can further comprise a second container comprising a pharmaceutically-acceptable buffer, such as phosphate-buffered saline, Ringers solution and/ordextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which are intended to limit the scope of the invention.

Example 1

SSH-Generated Isolation of cDNA Fragment of the 251P5G2 Gene

To isolate genes that are over-expressed in prostate cancer we used the Suppression Subtractive Hybridization (SSH) procedure using cDNA derived from prostate cancer tissues. The 251P5G2 SSH cDNA sequence was derived from a prostate cancer metastasis minus cDNAs derived from a pool of 9 normal tissues. The 251P5G2 cDNA was identified as highly expressed in the prostate cancer metastasis.

Materials and Methods

Human Tissues:

The patient cancer and normal tissues were purchased from different sources such as the NDRI (Philadelphia, Pa.). mRNA for some normal tissues were purchased from Clontech, Palo Alto, Calif.

RNA Isolation:

Tissues were homogenized in Trizol reagent (Life Technologies, Gibco BRL) using 10 ml/g tissue isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

```
DPNCDN (cDNA synthesis primer):
5'TTTTGATCAAGCTT₃₀3'                          (SEQ ID NO: 41)

Adaptor 1:
5'CTAATACGACTCACTATAGGGCTCGAGCGGCC            (SEQ ID NO: 42)

GCCCGGGCAG3'

3'GGCCCGTCCCTAG5'                              (SEQ ID NO: 43)

Adaptor 2:
5'GTAATACGACTCACTATAGGGCAGCGTGGTCG            (SEQ ID NO: 44)

CGGCCGAG3'
```

```
                                 -continued
3'CGGCTCCTAG5'                                    (SEQ ID NO: 45)

PCR primer 1:
5'CTAATACGACTCACTATAGGGC3'                        (SEQ ID NO: 46)

Nested primer (NP)1:
5'TCGAGCGGCCGCCCGGGCAGGA3'                        (SEQ ID NO: 47)

Nested primer (NP)2:
5'AGCGTGGTCGCGGCCGAGGA3'                          (SEQ ID NO: 48)
```

Suppression Subtractive Hybridization:

Suppression Subtractive Hybridization (SSH) was used to identify cDNAs corresponding to genes that may be differentially expressed in prostate cancer. The SSH reaction utilized cDNA from prostate cancer and normal tissues.

The gene 251P5G2 sequence was derived from a prostate cancer metastasis minus normal tissue cDNA subtraction. The SSH DNA sequence (FIG. 1) was identified.

The cDNA derived from of pool of normal tissues was used as the source of the "driver" cDNA, while the cDNA from prostate cancer metastasis was used as the source of the "tester" cDNA. Double stranded cDNAs corresponding to tester and driver cDNAs were synthesized from 2 µg of poly (A)$^+$ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Driver cDNA was generated by combining in a 1:1 ratio Dpn II digested cDNA from the relevant tissue source (see above) with a mix of digested cDNAs derived from the nine normal tissues: stomach, skeletal muscle, lung, brain, liver, kidney, pancreas, small intestine, and heart.

Tester cDNA was generated by diluting 1 µl of Dpn II digested cDNA from the relevant tissue source (see above) (400 ng) in 5 µl of water. The diluted cDNA (2 µl, 160 ng) was then ligated to 2 µl of Adaptor 1 and Adaptor 2 (10 µM), in separate ligation reactions, in a total volume of 10 µl at 16° C. overnight, using 400 u of T4 DNA ligase (CLONTECH). Ligation was terminated with 1 µl of 0.2 M EDTA and heating at 72° C. for 5 min.

The first hybridization was performed by adding 1.5 µl (600 ng) of driver cDNA to each of two tubes containing 1.5 µl (20 ng) Adaptor 1- and Adaptor 2-ligated tester cDNA. In a final volume of 4 µl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 µl of fresh denatured driver cDNA and were allowed to hybridize overnight at 68° C. The second hybridization was then diluted in 200 µl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 µl of the diluted final hybridization mix was added to 1 µl of PCR primer 1 (10 µM), 0.5 µl dNTP mix (10 µM), 2.5 µl 10× reaction buffer (CLONTECH) and 0.5 µl 50× Advantage cDNA polymerase Mix (CLONTECH) in a final volume of 25 µl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10-12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 ul of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs can be generated from 1 µg of mRNA with oligo (dT) 12-18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 µl with water prior to normalization. First strand cDNAs from 16 different normal human tissues can be obtained from Clontech.

Normalization of the first strand cDNAs from multiple tissues was performed by using the primers 5'atatcgccgcgctcgtcgtcgacaa3' (SEQ ID NO: 49) and 5'agccacacgcagctcattgtagaagg 3' (SEQ ID NO: 50) to amplify β-actin. First strand cDNA (5 µl) were amplified in a total volume of 50 µl containing 0.4 µM primers, 0.2 µM each dNTPs, 1×PCR buffer (Clontech, 10 mM Tris-HCL, 1.5 mM MgCl$_2$, 50 mM KCl, pH8.3) and 1× Klentaq DNA polymerase (Clontech). Five µl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 b.p. β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 251P5G2 gene, 5 µl of normalized first strand cDNA were analyzed by PCR using 26, and 30 cycles of amplification. Semi-quantitative expression analysis can be achieved by comparing the PCR products at cycle numbers that give light band intensities. The primers used for RT-PCR were designed using the 251P5G2 SSH sequence and are listed below:

```
251P5G2.1
5'-AGTGATTCAAAGAGCTGTGGAGA-3'                    (SEQ ID NO: 51)

251P5G2.2
5'-GGCCAGAGCGCACTTACCTACC-3'                     (SEQ ID NO: 52)
```

A typical RT-PCR expression analysis is shown in FIG. 14. First strand cDNA was prepared from vital pool 1 (liver, lung and kidney), vital pool 2 (pancreas, colon and stomach), prostate cancer metastasis to lymph node, prostate cancer pool, bladder cancer pool, and cancer metastasis pool. Normalization was performed by PCR using primers to actin and GAPDH. Semi-quantitative PCR, using primers to 251P5G2, was performed at 26 and 30 cycles of amplification. Results show strong expression of 251P5G2 in prostate cancer metastasis, prostate cancer pool, and cancer metastasis pool. Expression of 251P5G2 was also detected in bladder cancer pool, but not in vital pool 1 and vital pool 2.

Example 2

Isolation of Full Length 251P5G2 Encoding cDNA

The 251P5G2 SSH cDNA sequence was derived from a subtraction consisting of prostate cancer metastasis to lymph node minus a mixture of 9 normal tissues: stomach, skeletal muscle, lung, brain, liver, kidney, pancreas, small intestine and heart. The SSH cDNA sequence (FIG. 1) was designated 251P5G2.

The 251P5G2 SSH DNA sequence of 162 bp (FIG. 1) was novel and did not show homology to any known gene. 251P5G2 v.1 (clone 4.7) of 2157 bp was cloned from prostate cancer cDNA library, revealing an ORF of 255 amino acids (FIG. 2 and FIG. 3). Other variants of 251P5G2 were also identified and these are listed in FIGS. 2 and 3.

251P5G2 v.1, v.2, v.3, and v.4 proteins are 255 amino acids in length and differ from each other by one amino acid as shown in FIG. 11. 251P5G2 v.5, v.6, v.7, v.8, v.9, and v.10 code for the same protein as 251P5G2 v.1. 251P5G2 v.12 codes for a protein of 1266 amino acids in length. 251P5G2 v.13 codes for the same protein as 251P5G2 v.12.

251P5G2 v.1 and variants v.2 through v.11 are novel, and did not show significant homology to known human genes. The 251P5G2 v.1 protein showed homology to the mouse vomeronasal 1 receptor C3, 44% identity and 60% homology over 234 amino acids (FIG. 4A). 251P5G2 v.12 protein aligns with the protein XM_063686 at 100% identity over 1213 amino acids, ranging from position 54 to 1266 of 251P5G2 v.12 protein (FIG. 4B). XM_063686 protein is a hypothetical protein predicted by automated computational analysis using GenomeScan.

Example 3

Chromosomal Mapping of 251P5G2

Chromosomal localization can implicate genes in disease pathogenesis. Several chromosome mapping approaches are available including fluorescent in situ hybridization (FISH), human/hamster radiation hybrid (RH) panels (Walter et al., 1994; Nature Genetics 7:22; Research Genetics, Huntsville Ala.), human-rodent somatic cell hybrid panels such as is available from the Cornell Institute (Camden, N.J.), and genomic viewers utilizing BLAST homologies to sequenced and mapped genomic clones (NCBI, Bethesda, Md.).

251P5G2 maps to chromosome 15q11.2 using 251P5G2 sequence and the NCBI BLAST tool located on the World Wide Web at (.ncbi.nlm.nih.gov/genome/seq/page.cgi?F=HsBlast.html&&ORG=Hs).

Example 4

Expression Analysis of 251P5G2 in Normal Tissues and Patient Specimens

Expression analysis by RT-PCR demonstrated that 251P5G2 is strongly expressed in prostate cancer patient specimens (FIG. 14). First strand cDNA was prepared from vital pool 1 (liver, lung and kidney), vital pool 2 (pancreas, colon and stomach), prostate cancer metastasis to lymph node, prostate cancer pool, bladder cancer pool, and cancer metastasis pool. Normalization was performed by PCR using primers to actin and GAPDH. Semi-quantitative PCR, using primers to 251P5G2, was performed at 26 and 30 cycles of amplification. Results show strong expression of 251P5G2 in prostate cancer metastasis, prostate cancer pool, and cancer metastasis pool. Expression of 251P5G2 was also detected in bladder cancer pool, but not in vital pool 1 and vital pool 2.

Northern blot analysis of 251P5G2 is a technique known to those skilled in the art to detect 251P5G2 protein production. Northern blotting detects relative levels of mRNA expressed from a 251P5G2 gene. Specific mRNA is measured using a nucleic acid hybridization technique and the signal is detected on an autoradiogram. The stronger the signal, the more abundant is the mRNA. For 251P5G2 genes that produce mRNA that contains an open reading frame flanked by a good Kozak translation initiation site and a stop codon, in the vast majority of cases the synthesized mRNA is expressed as a protein.

The level of expression of the 251P5G2 gene is determined in various normal tissues and in various tumor tissues and tumor cell lines using the technique of Northern blotting, which detects production of messenger RNA. It is well known in the art that the production of messenger RNA, that encodes the protein, is a necessary step in the production of the protein itself. Thus, detection of high levels of messenger RNA by, for example, Northern blot, is a way of determining that the protein itself is produced. The Northern blot technique is used as a routine procedure because it does not require the time delays (as compared to Western blotting, immunoblotting or immunohistochemistry) involved in isolating or synthesizing the protein, preparing an immunological composition of the protein, eliciting a humoral immune response, harvesting the antibodies, and verifying the specificity thereof.

The Kozak consensus sequence for translation initiation CCACC<u>ATG</u>G, where the ATG start codon is noted, is the sequence with the highest established probability of initiating translation. This was confirmed by Peri and Pandey *Trends in Genetics* (2001) 17:685-687. The conclusion is consistent with the general knowledge in the art that, with rare exceptions, expression of an mRNA is predictive of expression of its encoded protein. This is particularly true for mRNA with an open reading frame and a Kozak consensus sequence for translation initiation.

It is understood in the art that the absolute levels of messenger RNA present and the amounts of protein produced do not always provide a 1:1 correlation. In those instances where the Northern blot has shown mRNA to be present, it is almost always possible to detect the presence of the corresponding protein in the tissue which provided a positive result in the Northern blot. The levels of the protein compared to the levels of the mRNA may be differential, but generally, cells that exhibit detectable mRNA also exhibit detectable corresponding protein and vice versa. This is particularly true where the mRNA has an open reading frame and a good Kozak sequence (See, Peri and Pandey, supra.).

Occasionally those skilled in the art encounter a rare occurrence where there is no detectable protein in the presence of corresponding mRNA. (See, Fu, L., et al., Embo. Journal, 15:4392-4401 (1996)). In many cases, a reported lack of protein expression is due to technical limitations of the protein detection assay. These limitations are readily known to those skilled in the art. These limitations include but are not limited to, available antibodies that only detect denatured protein and not native protein present in a cell and unstable proteins with very short half-life. Short-lived proteins are still functional and have been previously described to induce tumor formation. (See, e.g., Reinstein, et al., Oncogene, 19:5944-5950). In such situations, when more sensitive detection techniques are performed and/or other antibodies are generated, protein expression is detected. When studies fail to take these principles into account, they are likely to report artifactually lowered correlations of mRNA to protein. Outside of these rare exceptions the use of Northern blot analysis is recognized to those skilled in the art to be predictive and indicative of the detection of 251P5G2 protein production.

Extensive northern blot analysis of 251P5G2 in multiple human normal tissues is shown in FIG. 15. Two multiple tissue northern blots (Clontech) both with 2 µg of mRNA/lane were probed with the 251P5G2 SSH sequence. Expression of 251P5G2 was detected in normal prostate and testis but not in any other normal tissues tested.

Expression of 251P5G2 in prostate cancer metastasis patient specimens and human normal tissues is shown in FIG. 16. RNA was extracted from two prostate cancer metastasis to lymph node isolated from two different patients (Met1 and Met2), as well as from normal bladder (NB), normal kidney (NK), normal lung (NL), normal breast (NBr), normal ovary (NO), and normal pancreas (NPa). Northern blot with 10 µg of total RNA/lane was probed with 251P5G2 SSH sequence. Results show strong expression of 251P5G2 in the prostate cancer metastasis specimens but not in the normal tissues tested.

Expression of 251P5G2 was also detected in prostate cancer patient specimens and prostate cancer xenograft tissues (FIG. 17). RNA was extracted from prostate cancer xenografts (LAPC-4AD, LAPC-4AI, LAPC-9AD, LAPC-9AI), prostate cancer cell lines (LNCaP and PC3), normal prostate (N), and prostate cancer patient tumors (T). Northern blots with 10 µg of total RNA were probed with the 251P5G2 SSH fragment. Results show expression of 251P5G2 in the LAPC-9AD xenograft and in prostate tumor tissues. Lower level expression was detected in the other xenograft tissues and LNCaP cell line but not in PC3. The lower panel represents ethidium-bromide staining of the gel confirming the quality of the RNA.

FIG. 18 shows expression of 251p5g2 in human normal and cancer tissues. First strand cDNA was prepared from a panel of 13 normal tissues, prostate cancer pool, bladder cancer pool, kidney cancer pool, colon cancer pool, lung cancer pool, ovary cancer pool, breast cancer pool, pancreas cancer pool, 2 different prostate cancer metastasis specimens to lymph node, and a pool of prostate cancer LAPC xenografts (LAPC-4AD, LAPC-4AI, LAPC-9AD, and LAPC-9AI). Normalization was performed by PCR using primers to actin and GAPDH. Semi-quantitative PCR, using primers to 251P5G2, was performed at 26 and 30 cycles of amplification. A standard curve was generated using plasmid DNA containing 251P5G2 of known copy number. The experiment was performed in duplicate. Results show strong expression of 251P5G2 in prostate cancer metastasis, prostate cancer pool, and cancer metastasis pool. Expression of 251P5G2 was also detected in bladder cancer pool. Amongst normal tissues, very weak expression was detected in hear, prostate, skeletal muscle and testis but not in any other normal tissue tested.

FIG. 19 shows expression of 251P5G2 in prostate cancer patient specimens. First strand cDNA was prepared from normal prostate, prostate cancer cell lines (PC3, DU145, LNCaP, 293T), and a panel of prostate cancer patient specimens. Normalization was performed by PCR using primers to actin and GAPDH. Semi-quantitative PCR, using primers to 251P5G2, was performed at 26 and 30 cycles of amplification. Results show expression of 251P5G2 in 10 out of 19 patient specimens. Very strong expression was detected in 5 out of the 10 expressing tumors. Expression was also detected in LNCaP but not in the other cell lines tested nor in normal prostate.

Expression of 251P5G2 in bladder cancer patient specimens is shown in FIG. 20. First strand cDNA was prepared from normal bladder, bladder cancer cell lines (UM-UC-3, TCCSUP, J82), and a panel of bladder cancer patient specimens. Normalization was performed by PCR using primers to actin and GAPDH. Semi-quantitative PCR, using primers to 251P5G2, was performed at 26 and 30 cycles of amplification. Results show expression of 251P5G2 in 5 out of 9 patient specimens, but not in the cell lines tested nor in normal bladder.

The restricted expression of 251P5G2 in normal tissues and the expression detected in prostate cancer, prostate cancer metastasis, and bladder cancer suggest that 251P5G2 is a potential therapeutic target and a diagnostic marker for human cancers.

Example 5

Transcript Variants of 251P5G2

Transcript variants are variants of mature mRNA from the same gene which arise by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for similar or different proteins with the same or a similar function or can encode proteins with different functions, and can be expressed in the same tissue at the same time, or in different tissues at the same time, or in the same tissue at different times, or in different tissues at different times. Proteins encoded by transcript variants can have similar or different cellular or extracellular localizations, e.g., secreted versus intracellular.

Transcript variants are identified by a variety of art-accepted methods. For example, alternative transcripts and splice variants are identified by full-length cloning experiment, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene. Even when a variant is identified that is not a full-length clone, that portion of the variant is very useful for antigen generation and for further cloning of the full-length splice variant, using techniques known in the art.

Moreover, computer programs are available in the art that identify transcript variants based on genomic sequences. Genomic-based transcript variant identification programs include FgenesH (A. Salamov and V. Solovyev, "Ab initio gene finding in *Drosophila* genomic DNA," Genome Research. 2000 April; 10(4):516-22); Grail (URL compbio.oml.gov/Grail-bin/EmptyGrailForm) and GenScan (URL genes.mit.edu/GENSCAN.html). For a general discussion of splice variant identification protocols see., e.g., Southan, C., A genomic perspective on human proteases, FEBS Lett. 2001 Jun. 8; 498(2-3):214-8; de Souza, S. J., et al., Identification of human chromosome 22 transcribed sequences with ORF expressed sequence tags, Proc. Natl. Acad Sci USA. 2000 Nov. 7; 97(23):12690-3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., et al., Albumin banks peninsula: a new termination variant characterized by electrospray mass spectrometry, Biochem Biophys Acta. 1999 Aug. 17; 1433(1-2): 321-6; Ferranti P, et al., Differential splicing of pre-messenger RNA produces multiple forms of mature caprine alpha(s1)-casein, Eur J. Biochem. 1997 Oct. 1; 249(1):1-7. For PCR-based Validation: Wellmann S, et al., Specific reverse transcription-PCR quantification of vascular endothelial growth factor (VEGF) splice variants by LightCycler technology, Clin Chem. 2001 April; 47(4):654-60; Jia, H. P., et al., Discovery of new human beta-defensins using a genomics-based approach, Gene. 2001 Jan. 24; 263(1-2): 211-8. For PCR-based and 5' RACE Validation: Brigle, K. E., et al., Organization of the murine reduced folate carrier gene and identification of variant splice forms, Biochem Biophys Acta. 1997 Aug. 7; 1353(2): 191-8).

It is known in the art that genomic regions are modulated in cancers. When the genomic region to which a gene maps is modulated in a particular cancer, the alternative transcripts or splice variants of the gene are modulated as well. Disclosed herein is that 251P5G2 has a particular expression profile related to cancer. Alternative transcripts and splice variants of 251P5G2 may also be involved in cancers in the same or different tissues, thus serving as tumor-associated markers/antigens.

The exon composition of the original transcript, designated as 251P5G2 v.1, is shown in Table LI. Using the full-length gene and EST sequences, two transcript variants were identified, designated as 251P5G2 v.12 and v.13. Compared with 251P5G2 v.1, transcript variant 251P5G2 v.12 has spliced out two fragments from variant 251P5G2 v.1, as shown in FIG. 12. Theoretically, each different combination of exons in spatial order, e.g. exons 2 and 3, is a potential splice variant. FIG. 12 shows the schematic alignment of exons of the two transcript variants. Tables LII (a) and (b) through LV (a) and (b) are set forth on a variant by variant basis. LII (a) and (b) shows nucleotide sequence of the transcript variant. Table LIII (a) and (b) shows the alignment of the transcript variant with nucleic acid sequence of 251P5G2 v.1. Table LIV (a) and (b) lays out amino acid translation of the transcript variant for the identified reading frame orientation. Table LV (a) and (b) displays alignments of the amino acid sequence encoded by the splice variant with that of 251P5G2 v.1.

Example 6

Single Nucleotide Polymorphisms of 251P5G2

A Single Nucleotide Polymorphism (SNP) is a single base pair variation in a nucleotide sequence at a specific location. At any given point of the genome, there are four possible nucleotide base pairs: A/T, C/G, G/C and T/A. Genotype refers to the specific base pair sequence of one or more locations in the genome of an individual. Haplotype refers to the base pair sequence of more than one location on the same DNA molecule (or the same chromosome in higher organisms), often in the context of one gene or in the context of several tightly linked genes. SNPs that occur on a cDNA are called cSNPs. These cSNPs may change amino acids of the protein encoded by the gene and thus change the functions of the protein. Some SNPs cause inherited diseases; others contribute to quantitative variations in phenotype and reactions to environmental factors including diet and drugs among individuals. Therefore, SNPs and/or combinations of alleles (called haplotypes) have many applications, including diagnosis of inherited diseases, determination of drug reactions and dosage, identification of genes responsible for diseases, and analysis of the genetic relationship between individuals (P. Nowotny, J. M. Kwon and A. M. Goate, "SNP analysis to dissect human traits," Curr. Opin. Neurobiol. 2001 October; 11 (5):637-641; M. Pirmohamed and B. K. Park, "Genetic susceptibility to adverse drug reactions," Trends Pharmacol. Sci. 2001 June; 22(6):298-305; J. H. Riley, C. J. Allan, E. Lai and A. Roses, "The use of single nucleotide polymorphisms in the isolation of common disease genes," Pharmacogenomics. 2000 February; 1(1):39-47; R. Judson, J. C. Stephens and A. Windemuth, "The predictive power of haplotypes in clinical response," Pharmacogenomics. 2000 February; 1(1):15-26).

SNPs are identified by a variety of art-accepted methods (P. Bean, "The promising voyage of SNP target discovery," Am. Clin. Lab. 2001 October-November; 20(9):18-20; K. M. Weiss, "In search of human variation," Genome Res. 1998 July; 8(7):691-697; M. M. She, "Enabling large-scale pharmacogenetic studies by high-throughput mutation detection and genotyping technologies," Clin. Chem. 2001 February; 47(2):164-172). For example, SNPs are identified by sequencing DNA fragments that show polymorphism by gel-based methods such as restriction fragment length polymorphism (RFLP) and denaturing gradient gel electrophoresis (DGGE). They can also be discovered by direct sequencing of DNA samples pooled from different individuals or by comparing sequences from different DNA samples. With the rapid accumulation of sequence data in public and private databases, one can discover SNPs by comparing sequences using computer programs (Z. Gu, L. Hillier and P. Y. Kwok, "Single nucleotide polymorphism hunting in cyberspace," Hum. Mutat. 1998; 12(4):221-225). SNPs can be verified and genotype or haplotype of an individual can be determined by a variety of methods including direct sequencing and high throughput microarrays (P. Y. Kwok, "Methods for genotyping single nucleotide polymorphisms," Annu. Rev. Genomics Hum. Genet. 2001; 2:235-258; M. Kokoris, K. Dix, K. Moynihan, J. Mathis, B. Erwin, P. Grass, B. Hines and A. Duesterhoeft, "High-throughput SNP genotyping with the Masscode system," Mol. Diagn. 2000 December; 5(4):329-340). Using the methods described above, ten SNPs were identified in the original transcript, 251P5G2 v.1, at positions 768 (T/G), 975 (T/A), 1005 (G/A), 1270 (A/G), 1459 (A/G), 1921 (A/G), 540 (G/T), 481 (C/T), 280 (G/A) and 162 (A/T). The transcripts or proteins with alternative alleles were designated as variants 251P5G2 v.2, v.3, v.4, v.5, v.6, v.7, v.8, v.9, v.10 and v.11, respectively. FIG. 10 shows the schematic alignment of the SNP variants. FIG. 11 shows the schematic alignment of protein variants, corresponding to nucleotide variants. Nucleotide variants that code for the same amino acid sequence as variant 1 are not shown in FIG. 11. These alleles of the SNPs, though shown separately here, can occur in different combinations (haplotypes) and in any one of the transcript variants (such as 251P5G2 v.12) that contains the sequence context of the SNPs.

Example 7

Production of Recombinant 251P5G2 in Prokaryotic Systems

To express recombinant 251P5G2 and 251P5G2 variants in prokaryotic cells, the full or partial length 251P5G2 and 251P5G2 variant cDNA sequences are cloned into any one of a variety of expression vectors known in the art. One or more of the following regions of 251P5G2 variants are expressed: the full length sequence presented in FIGS. 2 and 3, or any 8, 9, 10, 11, 12, 13, 14, 15, 16, 17, 18, 19, 20, 21, 22, 23, 24, 25, 26, 27, 28, 29, 30 or more contiguous amino acids from 251P5G2, variants, or analogs thereof.

A. In Vitro Transcription and Translation Constructs:

pCRII: To generate 251P5G2 sense and anti-sense RNA probes for RNA in situ investigations, pCRII constructs (Invitrogen, Carlsbad Calif.) are generated encoding either all or fragments of the 251P5G2 cDNA. The pCRII vector has Sp6 and T7 promoters flanking the insert to drive the transcription of 251P5G2 RNA for use as probes in RNA in situ hybridization experiments. These probes are used to analyze the cell and tissue expression of 251P5G2 at the RNA level. Transcribed 251P5G2 RNA representing the cDNA amino acid coding region of the 251P5G2 gene is used in in vitro translation systems such as the TnT™ Coupled Reticulolysate System (Promega, Corp., Madison, Wis.) to synthesize 251P5G2 protein.

B. Bacterial Constructs:

pGEX Constructs: To generate recombinant 251P5G2 proteins in bacteria that are fused to the Glutathione S-transferase (GST) protein, all or parts of the 251P5G2 cDNA protein coding sequence are cloned into the pGEX family of GST-fusion vectors (Amersham Pharmacia Biotech, Piscataway, N.J.). These constructs allow controlled expression of recombinant 251P5G2 protein sequences with GST fused at the amino-terminus and a six histidine epitope (6xHis) at the carboxyl-terminus. The GST and 6xHis tags permit purification of the recombinant fusion protein from induced bacteria with the appropriate affinity matrix and allow recognition of the fusion protein with anti-GST and anti-His antibodies. The 6xHis tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 251P5G2-related protein. The ampicillin resistance gene and pBR322 origin permits selection and maintenance of the pGEX plasmids in *E. coli*.

pMAL Constructs: To generate, in bacteria, recombinant 251P5G2 proteins that are fused to maltose-binding protein (MBP), all or parts of the 251P5G2 cDNA protein coding sequence are fused to the MBP gene by cloning into the pMAL-c2X and pMAL-p2X vectors (New England Biolabs, Beverly, Mass.). These constructs allow controlled expression of recombinant 251P5G2 protein sequences with MBP fused at the amino-terminus and a 6xHis epitope tag at the carboxyl-terminus. The MBP and 6xHis tags permit purification of the recombinant protein from induced bacteria with the appropriate affinity matrix and allow recognition of the fusion protein with anti-MBP and anti-His antibodies. The 6xHis epitope tag is generated by adding 6 histidine codons to the 3' cloning primer. A Factor Xa recognition site permits cleavage of the pMAL tag from 251P5G2. The pMAL-c2X and pMAL-p2X vectors are optimized to express the recombinant protein in the cytoplasm or periplasm respectively. Periplasm expression enhances folding of proteins with disulfide bonds.

pET Constructs: To express 251P5G2 in bacterial cells, all or parts of the 251P5G2 cDNA protein coding sequence are cloned into the pET family of vectors (Novagen, Madison, Wis.). These vectors allow tightly controlled expression of recombinant 251P5G2 protein in bacteria with and without fusion to proteins that enhance solubility, such as NusA and thioredoxin (Trx), and epitope tags, such as 6xHis and S-Tag™ that aid purification and detection of the recombinant protein. For example, constructs are made utilizing pET NusA fusion system 43.1 such that regions of the 251P5G2 protein are expressed as amino-terminal fusions to NusA.

C. Yeast Constructs:

pESC Constructs: To express 251P5G2 in the yeast species *Saccharomyces cerevisiae* for generation of recombinant protein and functional studies, all or parts of the 251P5G2 cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of 251P5G2. In addition, expression in yeast yields similar post-translational modifications, such as glycosylations and phosphorylations that are found when expressed in eukaryotic cells.

pESP Constructs: To express 251P5G2 in the yeast species *Sacchammyces pombe*, all or parts of the 251P5G2 cDNA protein coding sequence are cloned into the pESP family of vectors. These vectors allow controlled high level of expression of a 251P5G2 protein sequence that is fused at either the amino terminus or at the carboxyl terminus to GST which aids purification of the recombinant protein. A Flag™ epitope tag allows detection of the recombinant protein with anti-Flag™ antibody.

Example 8

Production of Recombinant 251P5G2 in Higher Eukaryotic Systems

A. Mammalian Constructs:

To express recombinant 251P5G2 in eukaryotic cells, the full or partial length 251P5G2 cDNA sequences can be cloned into any one of a variety of expression vectors known in the art. One or more of the following regions of 251P5G2 are expressed in these constructs, amino acids 1 to 255, or any 8, 9, 10, 11, 12, 13, 14, 15, 16, 17, 18, 19, 20, 21, 22, 23, 24, 25, 26, 27, 28, 29, 30 or more contiguous amino acids from 251P5G2 v.1 through v.11;amino acids 1 to 1266, or any 8, 9, 10, 11, 12, 13, 14, 15, 16, 17, 18, 19, 20, 21, 22, 23, 24, 25, 26, 27, 28, 29, 30 or more contiguous amino acids from 251P5G2 v.12 and v.13, variants, or analogs thereof.

The constructs can be transfected into any one of a wide variety of mammalian cells such as 293T cells. Transfected 293T cell lysates can be probed with the anti-251P5G2 polyclonal serum, described herein.

pcDNA4/HisMax Constructs: To express 251P5G2 in mammalian cells, a 251P5G2 ORF, or portions thereof, of 251P5G2 are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6×His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli*.

pcDNA3.1/MycHis Constructs: To express 251P5G2 in mammalian cells, a 251P5G2 ORF, or portions thereof, of 251P5G2 with a consensus Kozak translation initiation site was cloned into pcDNA3.1/MycHis Version A (Invitrogen, Carlsbad, Calif.). Protein expression is driven from the cytomegalovirus (CMV) promoter. The recombinant proteins have the myc epitope and 6×His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli*.

pcDNA3.1/CT-GFP-TOPO Construct: To express 251P5G2 in mammalian cells and to allow detection of the recombinant proteins using fluorescence, a 251P5G2 ORF, or portions thereof, with a consensus Kozak translation initiation site are cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in *E. coli*. Additional constructs with an amino-terminal GFP fusion are made in pcDNA3.1/NT-GFP-TOPO spanning the entire length of a 251P5G2 protein.

PAPtag: A 251P5G2 ORF, or portions thereof, is cloned into pAPtag-5 (GenHunter Corp. Nashville, Tenn.). This construct generates an alkaline phosphatase fusion at the carboxyl-terminus of a 251P5G2 protein while fusing the IgGK signal sequence to the amino-terminus. Constructs are also generated in which alkaline phosphatase with an amino-terminal IgGK signal sequence is fused to the amino-terminus of a 251P5G2 protein. The resulting recombinant 251P5G2 proteins are optimized for secretion into the media of transfected mammalian cells and can be used to identify proteins such as ligands or receptors that interact with 251P5G2 proteins. Protein expression is driven from the CMV promoter and the recombinant proteins also contain myc and 6×His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in *E. coli*.

pTag5: A 251P5G2 ORF, or portions thereof, is cloned into pTag-5. This vector is similar to pAPtag but without the alkaline phosphatase fusion. This construct generates 251P5G2 protein with an amino-terminal IgGK signal sequence and myc and 6×His epitope tags at the carboxyl-terminus that facilitate detection and affinity purification. The resulting recombinant 251P5G2 protein is optimized for secretion into the media of transfected mammalian cells, and is used as immunogen or ligand to identify proteins such as ligands or receptors that interact with the 251P5G2 proteins. Protein expression is driven from the CMV promoter. The Zeocin resistance gene present in the vector allows for selection of mammalian cells expressing the protein, and the ampicillin resistance gene permits selection of the plasmid in *E. coli*.

PsecFc: A 251P5G2 ORF, or portions thereof, is also cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of the 251P5G2 proteins, while fusing the IgGK signal sequence to N-terminus. 251P5G2 fusions utilizing the murine IgG1 Fc region are also used. The resulting recombinant 251P5G2 proteins are optimized for secretion into the media of transfected mammalian cells, and can be used as immunogens or to identify proteins such as ligands or receptors that interact with 251P5G2 protein. Protein expression is driven from the CMV promoter. The hygromycin resistance gene present in the vector allows for selection of mammalian cells that express the recombinant protein, and the ampicillin resistance gene permits selection of the plasmid in *E. coli*.

pSRα Constructs: To generate mammalian cell lines that express 251P5G2 constitutively, 251P5G2 ORF, or portions thereof, of 251P5G2 were cloned into pSRα constructs. Amphotropic and ecotropic retroviruses were generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, 251P5G2, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in *E. coli*. The retroviral vectors can thereafter be used for infection and generation of various cell lines using, for example, PC3, NIH 3T3, TsuPr1, 293 or rat-1 cells.

Additional pSRα constructs are made that fuse an epitope tag such as the FLAG™ tag to the carboxyl-terminus of 251P5G2 sequences to allow detection using anti-Flag antibodies. For example, the FLAG™ sequence 5' gat tac aag gat gac gac gat aag 3' (SEQ ID NO: 53) is added to cloning primer at the 3' end of the ORF. Additional pSRα constructs are made to produce both amino-terminal and carboxyl-terminal GFP and myc/6×His fusion proteins of the full-length 251P5G2 proteins.

Additional Viral Vectors: Additional constructs are made for viral-mediated delivery and expression of 251P5G2. High virus titer leading to high level expression of 251P5G2 is achieved in viral delivery systems such as adenoviral vectors and herpes amplicon vectors. A 251P5G2 coding sequences or fragments thereof are amplified by PCR and subcloned into the AdEasy shuttle vector (Stratagene). Recombination and virus packaging are performed according to the manufacturer's instructions to generate adenoviral vectors. Alternatively, 251P5G2 coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of 251P5G2 in mammalian cells, coding sequences of 251P5G2, or portions thereof, are cloned into regulated mammalian expression systems such as the T-Rex System (Invitrogen), the GeneSwitch System (Invitrogen) and the tightly-regulated Ecdysone System (Stratagene). These systems allow the study of the temporal and concentration dependent effects of recombinant 251P5G2. These vectors are thereafter used to control expression of 251P5G2 in various cell lines such as PC3, NIH 3T3, 293 or rat-1 cells.

B. Baculovirus Expression Systems

To generate recombinant 251P5G2 proteins in a baculovirus expression system, 251P5G2 ORF, or portions thereof, are cloned into the baculovirus transfer vector pBlueBac 4.5 (Invitrogen), which provides a His-tag at the N-terminus. Specifically, pBlueBac-251P5G2 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 251P5G2 protein is then generated by infection of HighFive insect cells (Invitrogen) with purified baculovirus. Recombinant 251P5G2 protein can be detected using anti-251P5G2 or anti-His-tag antibody. 251P5G2 protein can be purified and used in various cell-based assays or as immunogen to generate polyclonal and monoclonal antibodies specific for 251P5G2.

Example 9

Antigenicity Profiles and Secondary Structure

FIG. 5(A & B), FIG. 6(A & B), FIG. 7(A & B), FIG. 8(A & B), and FIG. 9(A & B) depict graphically five amino acid profiles of 251P5G2 variants 1 and 12, each assessment available by accessing the ProtScale website located on the World Wide Web at (.expasy.ch/cgi-bin/protscale.pl) on the ExPasy molecular biology server.

These profiles: FIG. 5, Hydrophilicity, (Hopp T. P., Woods K. R., 1981. Proc. Natl. Acad. Sci. U.S.A. 78:3824-3828); FIG. 6, Hydropathicity, (Kyte J., Doolittle R. F., 1982. J. Mol. Biol. 157:105-132); FIG. 7, Percentage Accessible Residues (Janin J., 1979 Nature 277:491-492); FIG. 8, Average Flexibility, (Bhaskaran R., and Ponnuswamy P. K., 1988. Int. J. Pept. Protein Res. 32:242-255); FIG. 9, Beta-turn (Deleage, G., Roux B. 1987 Protein Engineering 1:289-294); and optionally others available in the art, such as on the ProtScale website, were used to identify antigenic regions of the 251P5G2 protein. Each of the above amino acid profiles of 251P5G2 were generated using the following ProtScale parameters for analysis: 1) A window size of 9; 2) 100% weight of the window edges compared to the window center; and, 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the 251P5G2 variant proteins indicated, e.g., by the profiles set forth in FIG. 5(A & B), FIG. 6(A & B), FIG. 7(A & B), FIG. 8(A & B), and/or FIG. 9(A & B) are used to prepare immunogens, either peptides or nucleic acids that encode them, to generate therapeutic and diagnostic anti-251P5G2 antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the 251P5G2 protein variants 1 and 12 listed in FIGS. 2 and 3. In particular, peptide immunogens of the invention can comprise, a peptide region of at least 5 amino acids of FIGS. 2 and 3 in any whole number increment that includes an amino acid position having a value greater than 0.5 in the Hydrophilicity profiles of FIG. 5; a peptide region of at least 5 amino acids of FIGS. 2 and 3 in any whole number increment that includes an amino acid position having a value less than 0.5 in the Hydropathicity profile of FIG. 6; a peptide region of at least 5 amino acids of FIGS. 2 and 3 in any whole number increment that includes an amino acid position having a value greater than 0.5 in the Percent Accessible Residues profiles of FIG. 7; a peptide region of at least 5 amino acids of FIGS. 2 and 3 in any whole number increment that includes an amino acid position having a value greater than 0.5 in the Average Flexibility profiles on FIG. 8; and, a peptide region of at least 5 amino acids of FIGS. 2 and 3 in any whole number increment that includes an amino acid position having a value greater than 0.5 in the Beta-turn profile of FIG. 9. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 251P5G2 protein variants 1 and 12, namely the predicted presence and location of alpha helices, extended strands, and random coils, is predicted from the primary amino acid sequence using the HNN-Hierarchical Neural Network method (Guermeur, 1997, accessed from the ExPasy molecular biology server located on the World Wide Web at (.expasy.ch/tools/). The analysis indicates that 251P5G2 variant 1 is composed of 40.39% alpha helix, 18.82% extended strand, and 40.78% random coil (FIG. 13A). Variant 12 is composed of 42.28% alpha helix, 8.33% extended strand, and 49.39% random coil (FIG. 13B).

Analysis for the potential presence of transmembrane domains in the 251P5G2 variant proteins was carried out using a variety of transmembrane prediction algorithms accessed from the ExPasy molecular biology server located on the World Wide Web at (.expasy.ch/tools/). Shown graphically in FIGS. 13C and 13D are the results of analysis of variant 1 depicting the presence and location of 6 transmembrane domains using the TMpred program (FIG. 13C) and 5 transmembrane domains using the TMHMM program (FIG. 13D). Shown graphically in FIGS. 13E and 13F are the results of analysis of variant 12 depicting the presence and location of 6 transmembrane domains using the TMpred program (FIG. 13E) and 3 transmembrane domains using the TMHMM program (FIG. 13F). The results of each program, namely the amino acids encoding the transmembrane domains are summarized in Table VI.

Example 10

Generation of 251P5G2 Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with a full length 251P5G2 protein variant, computer algorithms are employed in design of immunogens that, based on amino acid sequence analysis contain characteristics of being antigenic and available for recognition by the immune system of the immunized host (see the Example entitled "Antigenicity Profiles and Secondary Structure"). Such regions would be predicted to be hydrophilic, flexible, in beta-turn conformations, and be exposed on the surface of the protein (see, e.g., FIG. 5(A & B), FIG. 6(A & B), FIG. 7(A & B), FIG. 8(A & B), or FIG. 9(A & B) for amino acid profiles that indicate such regions of 251P5G2 protein variants).

For example, recombinant bacterial fusion proteins or peptides containing hydrophilic, flexible, beta-turn regions of 251P5G2 protein variants are used as antigens to generate polyclonal antibodies in New Zealand White rabbits. For example, in 251P5G2 variant 1, such regions include, but are not limited to, amino acids 28-40, amino acids 65-85, and amino acids 200-222. In sequence specific for variant 12, such regions include, but are not limited to, amino acids 236-251, amino acids 540-598, amino acids 832-978, and amino acids 1151-1242 It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 65-85 of 251P5G2 variant 1 is conjugated to KLH and used to immunize the rabbit. Alternatively the immunizing agent may include all or portions of the 251P5G2 variant proteins, analogs or fusion proteins thereof. For example, the 251P5G2 variant 1 amino acid sequence can be fused using recombinant DNA techniques to any one of a variety of fusion protein partners that are well known in the art, such as glutathione-S-transferase (GST) and HIS tagged fusion proteins. Such fusion proteins are purified from induced bacteria using the appropriate affinity matrix.

In one embodiment, a GST-fusion protein encoding the whole cDNA of 251P5G2 variant 1, amino acids 1-255 fused to GST, is produced and purified and used as immunogen. Other recombinant bacterial fusion proteins that may be employed include maltose binding protein, LacZ, thioredoxin, NusA, or an immunoglobulin constant region (see the section entitled "Production of Recombinant 251P5G2 in Prokaryotic Systems" and Current Protocols In Molecular Biology, Volume 2, Unit 16, Frederick M. Ausubul et al. eds., 1995; Linsley, P. S., Brady, W., Umes, M., Grosmaire, L., Damle, N., and Ledbetter, L. (1991) J. Exp. Med. 174, 561-566).

In addition to bacterial derived fusion proteins, mammalian expressed protein antigens are also used. These antigens are expressed from mammalian expression vectors such as the Tag5 and Fc-fusion vectors (see the section entitled "Production of Recombinant 251P5G2 in Eukaryotic Systems"), and retain post-translational modifications such as glycosylations found in native protein. In one embodiment, amino acids 60-85 of variant 1, encoding a loop between transmembrane domains, is cloned into the Tag5 mammalian secretion vector. The recombinant protein is purified by metal chelate chromatography from tissue culture supernatants of 293T cells stably expressing the recombinant vector. The purified Tag5 251P5G2 protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 μg, typically 100-200 μg, of fusion protein or peptide conjugated to KLH mixed in complete Freund's adjuvant (CFA). Rabbits are then injected subcutaneously every two weeks with up to 200 μg, typically 100-200 μg, of the immunogen in incomplete Freund's adjuvant (IFA). Test bleeds are taken approximately 7-10 days following each immunization and used to monitor the titer of the antiserum by ELISA.

To test reactivity and specificity of immune serum, such as the rabbit serum derived from immunization with the Tag5-251P5G2 variant 1 protein, the full-length 251P5G2 variant 1 cDNA is cloned into pcDNA 3.1 myc-his expression vector (Invitrogen, see the Example entitled "Production of Recombinant 251P5G2 in Eukaryotic Systems"). After transfection of the constructs into 293T cells, cell lysates are probed with the anti-251P5G2 serum and with anti-His antibody (Santa Cruz Biotechnologies, Santa Cruz, Calif.) to determine specific reactivity to denatured 251P5G2 protein using the Western blot technique. In addition, the immune serum is tested by fluorescence microscopy, flow cytometry and immunoprecipitation against 293T and other recombinant 251P5G2-expressing cells to determine specific recognition of native protein. Western blot, immunoprecipitation, fluorescent microscopy, and flow cytometric techniques using cells that endogenously express 251P5G2 are also carried out to test reactivity and specificity.

Anti-serum from rabbits immunized with 251P5G2 variant fusion proteins, such as GST and MBP fusion proteins, are purified by depletion of antibodies reactive to the fusion partner sequence by passage over an affinity column containing the fusion partner either alone or in the context of an irrelevant fusion protein. For example, antiserum derived from a GST-251P5G2 variant 1 fusion protein is first purified by passage over a column of GST protein covalently coupled to AffiGel matrix (BioRad, Hercules, Calif.). The antiserum is then affinity purified by passage over a column composed of a MBP-251P5G2 fusion protein covalently coupled to Affigel matrix. The serum is then further purified by protein G affinity chromatography to isolate the IgG fraction. Sera from other His-tagged antigens and peptide immunized rabbits as well as fusion partner depleted sera are affinity purified by passage over a column matrix composed of the original protein immunogen or free peptide.

Example 11

Generation of 251P5G2 Monoclonal Antibodies (mAbs)

In one embodiment, therapeutic mAbs to 251P5G2 variants comprise those that react with epitopes specific for each variant protein or specific to sequences in common between the variants that would disrupt or modulate the biological function of the 251P5G2 variants, for example those that would disrupt the interaction with ligands and binding partners. Immunogens for generation of such mAbs include those designed to encode or contain the entire 251P5G2 protein variant sequence, regions of the 251P5G2 protein variants predicted to be antigenic from computer analysis of the amino acid sequence (see, e.g., FIG. 5(A & B), FIG. 6(A & B), FIG. 7(A & B), FIG. 8(A & B), or FIG. 9(A & B), and the Example entitled "Antigenicity Profiles"). Immunogens include peptides, recombinant bacterial proteins, and mammalian expressed Tag 5 proteins and human and murine IgG FC fusion proteins. In addition, cells engineered to express high levels of a respective 251P5G2 variant, such as 293T-251P5G2 variant 1 or 300.19-251P5G2 variant 1 murine Pre-B cells, are used to immunize mice.

To generate mAbs to a 251P5G2 variant, mice are first immunized intraperitoneally (IP) with, typically, 10-50 µg of protein immunogen or $10^7$ 251P5G2-expressing cells mixed in complete Freund's adjuvant. Mice are then subsequently immunized IP every 2-4 weeks with, typically, 10-50 µg of protein immunogen or $10^7$ cells mixed in incomplete Freund's adjuvant. Alternatively, MPL-TDM adjuvant is used in immunizations. In addition to the above protein and cell-based immunization strategies, a DNA-based immunization protocol is employed in which a mammalian expression vector encoding a 251P5G2 variant sequence is used to immunize mice by direct injection of the plasmid DNA. For example, amino acids 60-85 is cloned into the Tag5 mammalian secretion vector and the recombinant vector is used as immunogen. In another example the same amino acids are cloned into an Fc-fusion secretion vector in which the 251P5G2 variant 1 sequence is fused at the amino-terminus to an IgK leader sequence and at the carboxyl-terminus to the coding sequence of the human or murine IgG Fc region. This recombinant vector is then used as immunogen. The plasmid immunization protocols are used in combination with purified proteins expressed from the same vector and with cells expressing the respective 251P5G2 variant.

During the immunization protocol, test bleeds are taken 7-10 days following an injection to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Harlow and Lane, 1988).

In one embodiment for generating 251P5G2 monoclonal antibodies, a Tag5-251P5G2 variant 1 antigen encoding amino acids 60-85, is expressed and purified from stably transfected 293T cells. Balb C mice are initially immunized intraperitoneally with 25 μg of the Tag5-251P5G2 variant 1 protein mixed in complete Freund's adjuvant. Mice are subsequently immunized every two weeks with 25 μg of the antigen mixed in incomplete Freund's adjuvant for a total of three immunizations. ELISA using the Tag5 antigen determines the titer of serum from immunized mice. Reactivity and specificity of serum to full length 251P5G2 variant 1 protein is monitored by Western blotting, immunoprecipitation and flow cytometry using 293T cells transfected with an expression vector encoding the 251P5G2 variant 1 cDNA (see e.g., the Example entitled "Production of Recombinant 251P5G2 in Eukaryotic Systems" and FIG. 20. Other recombinant 251P5G2 variant 1-expressing cells or cells endogenously expressing 251P5G2 variant 1 are also used. Mice showing the strongest reactivity are rested and given a final injection of Tag5 antigen in PBS and then sacrificed four days later. The spleens of the sacrificed mice are harvested and fused to SPO/2 myeloma cells using standard procedures (Harlow and Lane, 1988). Supernatants from HAT selected growth wells are screened by ELISA, Western blot, immunoprecipitation, fluorescent microscopy, and flow cytometry to identify 251P5G2 specific antibody-producing clones.

In another embodiment, a Tag5 antigen encoding amino acids 800-1266 of variant 12 is produced, purified and used as immunogen to derive monoclonal antibodies specific to 251P5G2 variant 12. Hybridoma supernatants are then screened on both 251P5G2 variant 1- and 251P5G2 variant 12-expressing cells to identify specific anti-251P5G2 variant 12 monoclonal antibodies.

The binding affinity of a 251P5G2 monoclonal antibody is determined using standard technologies. Affinity measurements quantify the strength of antibody to epitope binding and are used to help define which 251P5G2 monoclonal antibodies preferred for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 12

HLA Class I and Class II Binding Assays

HLA class I and class II binding assays using purified HLA molecules are performed in accordance with disclosed protocols (e.g., PCT publications WO 94/20127 and WO 94/03205; Sidney et al., *Current Protocols in Immunology* 18.3.1 (1998); Sidney, et al., *J. Immunol.* 154:247 (1995); Sette, et al., *Mol. Immunol.* 31:813 (1994)). Briefly, purified MHC molecules (5 to 500 nM) are incubated with various unlabeled peptide inhibitors and 1-10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and $IC_{50} \geqq$ [HLA], the measured $IC_{50}$ values are reasonable approximations of the true $K_D$ values. Peptide inhibitors are typically tested at concentrations ranging from 120 μg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides (see Table IV).

Example 13

Identification of HLA Supermotif- and Motif-bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-bearing Epitopes The searches performed to identify the motif-bearing peptide sequences in the Example entitled "Antigenicity Profiles" and Tables VIII-XXI and XXII-XLIX employ the protein sequence data from the gene product of 251P5G2 set forth in FIGS. 2 and 3, the specific search peptides used to generate the tables are listed in Table VII.

Computer searches for epitopes bearing HLA Class I or Class II supermotifs or motifs are performed as follows. All translated 251P5G2 protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or $\Delta G$) of peptide-HLA molecule interactions can be approximated as a linear polynomial function of the type:

$$\text{"}\Delta G\text{"} = a_{1i} \times a_{2i} \times a_{3i} \ldots \times a_{ni}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount $j_i$ to the free energy of binding of the peptide irrespective of the sequence of the rest of the peptide.

The method of derivation of specific algorithm coefficients has been described in Gulukota et al., *J. Mol. Biol* 267:1258-126, 1997; (see also Sidney et al., *Human Immunol.* 45:79-93, 1996; and Southwood et al., *J. Immunol.* 160:3363-3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-reactive Peptides

Protein sequences from 251P5G2 are scanned utilizing motif identification software, to identify 8-, 9-10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-bearing Epitopes

The 251P5G2 protein sequence(s) scanned above is also examined for the presence of peptides with the HLA-A3-supermotif primary anchors. Peptides corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of ≦500 nM, often ≦200 nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 Supermotif Bearing Epitopes

The 251P5G2 protein(s) scanned above is also analyzed for the presence of 8-, 9-10-, or 11-mer peptides with the HLA-B7-supermotif. Corresponding peptides are synthesized and tested for binding to HLA-B*0702, the molecule encoded by the most common B7-supertype allele (i.e., the prototype B7 supertype allele). Peptides binding B*0702 with $IC_{50}$ of ≦500 nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-bearing Epitopes

To further increase population coverage, HLA-A1 and -A24 epitopes can also be incorporated into vaccine compositions. An analysis of the 251P5G2 protein can also be performed to identify HLA-A1- and A24-motif-containing sequences.

High affinity and/or cross-reactive binding epitopes that bear other motif and/or supermotifs are identified using analogous methodology.

Example 14

Confirmation of Immunogenicity

Cross-reactive candidate CTL A2-supermotif-bearing peptides that are identified as described herein are selected to confirm in vitro immunogenicity. Confirmation is performed using the following methodology:

Target Cell Lines for Cellular Screening:

The 0.221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC): PBMCs are thawed in RPMI with 30 µg/ml DNAse, washed twice and resuspended in complete medium (RPMI-1640 plus 5% AB human serum, non-essential amino acids, sodium pyruvate, L-glutamine and penicillin/streptomycin). The monocytes are purified by plating $10\times10^6$ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide: CD8+ T-cells are isolated by positive selection with Dynal immunomagnetic beads (Dynabeads® M-450) and the detacha-bead® reagent. Typically about $200\text{-}250\times10^6$ PBMC are processed to obtain $24\times10^6$ CD8+ T-cells (enough for a 48-well plate culture). Briefly, the PBMCs are thawed in RPMI with 30 µg/ml DNAse, washed once with PBS containing 1% human AB serum and resuspended in PBS/1% AB serum at a concentration of $20\times10^6$ cells/ml. The magnetic beads are washed 3 times with PBS/AB serum, added to the cells (140 µl beads/ $20\times10^6$ cells) and incubated for 1 hour at 4° C. with continuous mixing. The beads and cells are washed 4× with PBS/AB serum to remove the nonadherent cells and resuspended at $100\times10^6$ cells/ml (based on the original cell number) in PBS/AB serum containing 100 µl/ml detacha-bead® reagent and 30 µg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5-7 minutes, washed once with PBS with 1% BSA, counted and pulsed with 40 µg/ml of peptide at a cell concentration of $1\text{-}2\times10^6$/ml in the presence of 3 µg/ml $\beta_2$-microglobulin for 4 hours at 20° C. The DC are then irradiated (4,200 rads), washed 1 time with medium and counted again.

Setting up induction cultures: 0.25 ml cytokine-generated DC (at $1\times10^5$ cells/ml) are co-cultured with 0.25 ml of CD8+ T-cells (at $2\times10^6$ cell/ml) in each well of a 48-well plate in the presence of 10 ng/ml of IL-7. Recombinant human IL-10 is added the next day at a final concentration of 10 ng/ml and rhuman IL-2 is added 48 hours later at 10 IU/ml.

Restimulation of the induction cultures with peptide-pulsed adherent cells: Seven and fourteen days after the primary induction, the cells are restimulated with peptide-pulsed adherent cells. The PBMCs are thawed and washed twice with RPMI and DNAse. The cells are resuspended at $5\times10^6$ cells/ml and irradiated at –4200 rads. The PBMCs are plated at $2\times10^6$ in 0.5 ml complete medium per well and incubated for 2 hours at 37° C. The plates are washed twice with RPMI by tapping the plate gently to remove the nonadherent cells and the adherent cells pulsed with 10 µg/ml of peptide in the presence of 3 µg/ml $\beta_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2-3 days later at 50 IU/ml (Tsai et al., Critical Reviews in Immunology 18(1-2):65-75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 µg/ml peptide overnight at 37° C.

Adherent target cells are removed from culture flasks with trypsin-EDTA. Target cells are labeled with 200 µCi of $^{51}$Cr sodium chromate (Dupont, Wilmington, Del.) for 1 hour at 37° C. Labeled target cells are resuspended at $10^6$ per ml and diluted 1:10 with K562 cells at a concentration of $3.3\times10^6$/ml (an NK-sensitive erythroblastoma cell line used to reduce non-specific lysis). Target cells (100 µl) and effectors (100 µl) are plated in 96 well round-bottom plates and incubated for 5 hours at 37° C. At that time, 100 µl of supernatant are collected from each well and percent lysis is determined according to the formula:

[(cpm of the test sample–cpm of the spontaneous $^{51}$Cr release sample)/(cpm of the maximal $^{51}$Cr release sample–cpm of the spontaneous $^{51}$Cr release sample)]×100.

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-specific and Endogenous Recognition Immulon 2 plates are coated with mouse anti-human IFNγ monoclonal antibody (4 µg/ml 0.1 M NaHCO$_3$, pH8.2) overnight at 4° C. The plates are washed with Ca$^{2+}$, Mg$^{2+}$-free PBS/0.05% Tween 20 and blocked with PBS/10% FCS for two hours, after which the CTLs (100 µl/well) and targets (100 µl/well) are added to each well, leaving empty wells for the standards and blanks (which received media only). The target cells, either peptide-pulsed or endogenous targets, are used at a concentration of $1\times10^6$ cells/ml. The plates are incubated for 48 hours at 37° C. with 5% CO$_2$.

Recombinant human IFN-gamma is added to the standard wells starting at 400 pg or 1200 pg/100 microliter/well and the plate incubated for two hours at 37° C. The plates are washed and 100 µl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5-15 minutes. The reaction is stopped with 50 microliter/well 1 M H$_3$PO$_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, $5\times10^4$ CD8+ cells are added to a T25 flask containing the following: $1\times10^6$ irradiated (4,200 rad) PBMC (autologous or allogeneic) per ml, $2\times10^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 µM 2-mercaptoethanol, L-glutamine and penicillin/streptomycin. Recombinant human IL2 is added 24 hours later at a final concentration of 200 IU/ml and every three days thereafter with fresh media at 50 IU/ml. The cells are split if the cell concentration exceeds $1\times10^6$/ml and the cultures are assayed between days 13 and 15 at E:T ratios of 30, 10, 3 and 1:1 in the $^{51}$Cr release assay or at $1\times10^6$/ml in the in situ IFNγ assay using the same targets as before the expansion.

Cultures are expanded in the absence of anti-CD3+ as follows. Those cultures that demonstrate specific lytic activity against peptide and endogenous targets are selected and $5\times10^4$ CD8+ cells are added to a T25 flask containing the following: $1\times10^6$ autologous PBMC per ml which have been peptide-pulsed with 10 µg/ml peptide for two hours at 37° C. and irradiated (4,200 rad); $2\times10^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 251P5G2. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2- and A3-supermotif-bearing peptides.

Peptides bearing other supermotifs/motifs, e.g., HLA-A1, HLA-A24 etc. are also confirmed using similar methodology Example 15

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analoged to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an $IC_{50}$ of 500 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., *J. Immunol.* 157:2539, 1996; and Pogue et al., *Proc. Natl. Acad. Sci. USA* 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-supermotif-bearing Peptides

Analogs of HLA-A3 supermotif-bearing epitopes are generated using strategies similar to those employed in analoging HLA-A2 supermotif-bearing peptides. For example, peptides binding to 3/5 of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate $\leq$500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et al. (*J. Immunol.* 157:3480-3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analoged peptides are additionally tested for the ability to stimulate a recall response using PBMC from patients with 251P5G2-expressing tumors.

Other Analoging Strategies

Another form of peptide analoging, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitution of α-amino butyric acid for cysteine not only alleviates this problem, but has been shown to improve binding and crossbinding capabilities in some instances (see, e.g., the review by Sette et al., In: Persistent Viral Infections, Eds. R. Ahmed and 1. Chen, John Wiley & Sons, England, 1999).

Thus, by the use of single amino acid substitutions, the binding properties and/or cross-reactivity of peptide ligands for HLA supertype molecules can be modulated.

Example 16

Identification and Confirmation of 251P5G2-derived Sequences with HLA-DR Binding Motifs Peptide epitopes bearing an HLA class II supermotif or motif are identified and confirmed as outlined below using methodology similar to that described for HLA Class I peptides.

Selection of HLA-DR-supermotif-bearing Epitopes.

To identify 251P5G2-derived, HLA class II HTL epitopes, a 251P5G2 antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood et al., *J. Immunol.* 160: 3363-3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but additionally evaluates sequences for the presence of secondary anchors. Using allele-specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 251P5G2-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 β1, DR2w2 β2, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 251P5G2-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 251P5G2 antigens are analyzed for sequences carrying one of the two DR3-specific binding motifs reported by Geluk et al. (*J. Immunol.* 152:5742-5748, 1994). The corresponding peptides are then synthesized and confirmed as having the ability to bind DR3 with an affinity of 1 μM or better, i.e., less than 1 μM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 17

Immunogenicity of 251P5G2-Derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have 251P5G2-expressing tumors.

Example 18

Calculation of Phenotypic Frequencies of HLA-Supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf=1−(SQRT(1−af)) (see, e.g., Sidney et al., *Human Immunol* 45:79-93, 1996). To obtain overall phenotypic frequencies, cumulative gene frequencies are calculated, and the cumulative antigen frequencies derived by the use of the inverse formula $[af=1-(1-Cgf)^2]$.

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1-A)). Confirmed members of the A3-like supertype are A3, A11, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%, see, e.g., Table IV (G). An analogous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 19

CTL Recognition of Endogenously Processed Antigens after Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/$K^b$ target cells in the absence or presence of peptide, and also tested on $^{51}$Cr labeled target cells bearing the endogenously synthesized antigen, i.e. cells that are stably transfected with 251P5G2 expression vectors.

The results demonstrate that CTL lines obtained from animals primed with peptide epitope recognize endogenously synthesized 251P5G2 antigen. The choice of transgenic mouse model to be used for such an analysis depends upon the epitope(s) that are being evaluated. In addition to HLA-A*0201/$K^b$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 20

Activity of CTL-HTL Conjugated Epitopes in Transgenic Mice

This example illustrates the induction of CTLs and HTLs in transgenic mice, by use of a 251P5G2-derived CTL and HTL peptide vaccine compositions. The vaccine composition used herein comprise peptides to be administered to a patient with a 251P5G2-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization procedures: Immunization of transgenic mice is performed as described (Alexander et al., *J. Immunol.* 159:4753-4761, 1997). For example, A2/$K^b$ mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are Jurkat cells transfected with the HLA-A2.1/$K^b$ chimeric gene (e.g., Vitiello et al., *J. Exp. Med.* 173:1007, 1991)

In vitro CTL activation: One week after priming, spleen cells ($30 \times 10^6$ cells/flask) are co-cultured at 37° C. with syngeneic, irradiated (3000 rads), peptide coated lymphoblasts ($10 \times 10^6$ cells/flask) in 10 ml of culture medium/T25 flask. After six days, effector cells are harvested and assayed for cytotoxic activity.

Assay for cytotoxic activity: Target cells (1.0 to $1.5 \times 10^6$) are incubated at 37° C. in the presence of 200 µl of $^{51}$Cr. After 60 minutes, cells are washed three times and resuspended in R10 medium. Peptide is added where required at a concentration of 1 µg/ml. For the assay, $10^{4}$ $^{51}$Cr-labeled target cells are added to different concentrations of effector cells (final volume of 200 µl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/(maximum release−spontaneous release). To facilitate comparison between separate CTL assays run under the same conditions, % $^{51}$Cr release data is expressed as lytic units/$10^6$ cells. One lytic unit is arbitrarily defined as the number of effector cells required to achieve 30% lysis of 10,000 target cells in a six hour $^{51}$Cr release assay. To obtain specific lytic units/$10^6$, the lytic units/$10^6$ obtained in the absence of peptide is subtracted from the lytic units/$10^6$ obtained in the presence of peptide. For example, if 30% $^{51}$Cr release is obtained at the effector (E): target (T) ratio of 50:1 (i.e., $5 \times 10^5$ effector cells for 10,000 targets) in the absence of peptide and 5:1 (i.e., $5 \times 10^4$ effector cells for 10,000 targets) in the presence of peptide, the specific lytic units would be: $[(1/50,000)-(1/500,000)] \times 10^6 = 18$ LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity." Analyses similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 21

Selection of CTL and HTL Epitopes for Inclusion in a 251P5G2-specific Vaccine

This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with 251P5G2 clearance. The number of epitopes used depends on observations of patients who spontaneously clear 251P5G2. For example, if it has been observed that patients who spontaneously clear 251P5G2-expressing cells generate an immune response to at least three (3) epitopes from 251P5G2 antigen, then at least three epitopes should be included for HLA class I. A similar rationale is used to determine HLA class II epitopes.

Epitopes are often selected that have a binding affinity of an $IC_{50}$ of 500 nM or less for an HLA class I molecule, or for class II, an $IC_{50}$ of 1000 nM or less; or HLA Class I peptides with high binding scores from the BIMAS web site, at URL bimas.dcrt.nih.gov/.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art, can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 251P5G2, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected peptides, when administered, is safe, efficacious, and elicits an immune response similar in magnitude to an immune response that controls or clears cells that bear or overexpress 251P5G2.

Example 22

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived 251P5G2, are selected such that multiple supermotifs/motifs are represented to ensure broad population coverage. Similarly, HLA class II epitopes are selected from 251P5G2 to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and H is antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 µg of each of two oligonucleotides are annealed and extended: In an example using eight oligonucleotides, i.e., four pairs of primers, oligonucleotides 1+2, 3+4, 5+6, and 7+8 are combined in 100 µl reactions containing Pfu polymerase buffer (1x=10 mM KCL, 10 mM $(NH4)_2SO_4$, 20 mM Tris-chloride, pH 8.75, 2 mM $MgSO_4$, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 23

The Plasmid Construct and the Degree to which it Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683-692, 1996; Demotz et al., *Nature* 342:682-684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama et al., *J. Immunol.* 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., *Immunity* 1:751-761, 1994.

For example, to confirm the capacity of a DNA minigene construct containing at least one HLA-A2 supermotif peptide to induce CTLs in vivo, HLA-A2.1/$K^b$ transgenic mice, for example, are immunized intramuscularly with 100 µg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}Cr$ release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-$A^b$-restricted mice, for example, are immunized intramuscularly with 100 µg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3H$-thymidine incorporation proliferation assay, (see, e.g., Alexander et al. Immunity 1:751-761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., *Aids Res. and Human Retroviruses* 14, Supplement 3:S299-S309, 1998) or recombinant vaccinia, for example, expressing a minigene or DNA encoding the complete protein of interest (see, e.g., Hanke et al., *Vaccine* 16:439-445, 1998; Sedegah et al., *Proc. Natl. Acad. Sci. USA* 95:7648-53, 1998; Hanke and McMichael, *Immunol. Letters* 66:177-181, 1999; and Robinson et al., *Nature Med.* 5:526-34, 1999).

For example, the efficacy of the DNA minigene used in a prime boost protocol is initially evaluated in transgenic mice. In this example, A2.1/K$^b$ transgenic mice are immunized IM with 100 µg of a DNA minigene encoding the immunogenic peptides including at least one HLA-A2 supermotif-bearing peptide. After an incubation period (ranging from 3-9 weeks), the mice are boosted IP with 10$^7$ pfu/mouse of a recombinant vaccinia virus expressing the same sequence encoded by the DNA minigene. Control mice are immunized with 100 µg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 24

Peptide Compositions for Prophylactic Uses

Vaccine compositions of the present invention can be used to prevent 251P5G2 expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 251P5G2-associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 µg, generally 100-5,000 µg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 251P5G2-associated disease.

Alternatively, a composition typically comprising transfecting agents is used for the administration of a nucleic acid-based vaccine in accordance with methodologies known in the art and disclosed herein.

Example 25

Polyepitopic Vaccine Compositions Derived from Native 251P5G2 Sequences

A native 251P5G2 polyprotein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested" epitopes can be used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10-mer epitope can be present in a 10 amino acid peptide. Such a vaccine composition is administered for therapeutic or prophylactic purposes.

The vaccine composition will include, for example, multiple CTL epitopes from 251P5G2 antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally, such an embodiment provides for the possibility of motif-bearing epitopes for an HLA makeup(s) that is presently unknown. Furthermore, this embodiment (excluding an analoged embodiment) directs the immune response to multiple peptide sequences that are actually present in native 251P5G2, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 26

Polyepitopic Vaccine Compositions from Multiple Antigens

The 251P5G2 peptide epitopes of the present invention are used in conjunction with epitopes from other target tumor-associated antigens, to create a vaccine composition that is useful for the prevention or treatment of cancer that expresses 251P5G2 and such other antigens. For example, a vaccine composition can be provided as a single polypeptide that incorporates multiple epitopes from 251P5G2 as well as tumor-associated antigens that are often expressed with a target cancer associated with 251P5G2 expression, or can be administered as a composition comprising a cocktail of one or more discrete epitopes. Alternatively, the vaccine can be administered as a minigene construct or as dendritic cells which have been loaded with the peptide epitopes in vitro.

Example 27

Use of Peptides to Evaluate an Immune Response

Peptides of the invention may be used to analyze an immune response for the presence of specific antibodies, CTL or HTL directed to 251P5G2. Such an analysis can be performed in a manner described by Ogg et al., *Science* 279: 2103-2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, 251P5G2 HLA-A*0201-specific CTL frequencies from HLA A*0201-positive individuals at different stages of disease or following immunization comprising a 251P5G2 peptide containing an A*0201 motif. Tetrameric complexes are synthesized as described (Musey et al., *N. Engl. J. Med.* 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 µl of cold phosphate-buffered saline. Tricolor analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the 251P5G2 epitope, and thus the status of exposure to 251P5G2, or exposure to a vaccine that elicits a protective or therapeutic response.

Example 28

Use of Peptide Epitopes to Evaluate Recall Responses

The peptide epitopes of the invention are used as reagents to evaluate T cell responses, such as acute or recall responses, in patients. Such an analysis may be performed on patients who have recovered from 251P5G2-associated disease or who have been vaccinated with a 251P5G2 vaccine.

For example, the class I restricted CTL response of persons who have been vaccinated may be analyzed. The vaccine may be any 251P5G2 vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 μg/ml), and Hepes (10 mM) containing 10% heat-inactivated human AB serum (complete RPMI) and plated using microculture formats. A synthetic peptide comprising an epitope of the invention is added at 10 μg/ml to each well and HBV core 128-140 epitope is added at 1 μg/ml to each well as a source of T cell help during the first week of stimulation.

In the microculture format, $4\times10^5$ PBMC are stimulated with peptide in 8 replicate cultures in 96-well round bottom plate in 100 μl/well of complete RPMI. On days 3 and 10,100 μl of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}Cr$ release, based on comparison with non-diseased control subjects as previously described (Rehermann, et al., *Nature Med.* 2:1104, 1108, 1996; Rehermann et al., *J. Clin. Invest.* 97:1655-1665, 1996; and Rehermann et al. *J. Clin. Invest.* 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol* 66:2670-2678, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 μM, and labeled with 100 μCi of $^{51}Cr$ (Amersham Corp., Arlington Heights, Ill.) for 1 hour after which they are washed four times with HBSS.

Cytolytic activity is determined in a standard 4-h, split well $^{51}Cr$ release assay using U-bottomed 96 well plates containing 3,000 targets/well. Stimulated PBMC are tested at effector/target (E/T) ratios of 20-50:1 on day 14. Percent cytotoxicity is determined from the formula: 100×[(experimental release−spontaneous release)/maximum release−spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to 251P5G2 or a 251P5G2 vaccine.

Similarly, Class II restricted HTL responses may also be analyzed. Purified PBMC are cultured in a 96-well flat bottom plate at a density of $1.5\times10^5$ cells/well and are stimulated with 10 μg/ml synthetic peptide of the invention, whole 251P5G2 antigen, or PHA. Cells are routinely plated in replicates of 4-6 wells for each condition. After seven days of culture, the medium is removed and replaced with fresh medium containing 10 U/ml IL-2. Two days later, 1 µCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 29

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 µg of peptide composition;

Group II: 3 subjects are injected with placebo and 6 subjects are injected with 50 µg peptide composition;

Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 30

Phase II Trials in Patients Expressing 251P5G2

Phase II trials are performed to study the effect of administering the CTL-HTL peptide compositions to patients having cancer that expresses 251P5G2. The main objectives of the trial are to determine an effective dose and regimen for inducing CTLs in cancer patients that express 251P5G2, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-65 and represent diverse ethnic backgrounds. All of them have a tumor that expresses 251P5G2.

Clinical manifestations or antigen-specific T-cell responses are monitored to assess the effects of administering the peptide compositions. The vaccine composition is found to be both safe and efficacious in the treatment of 251P5G2-associated disease.

Example 31

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of "Minigene" Multi-Epitope DNA Plasmids" in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5 \times 10^7$ to $5 \times 10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against 251P5G2 is generated.

Example 32

Administration of Vaccine Compositions Using Dendritic Cells (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction, respectively, of the target cells that bear the 251P5G2 protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g., *Nature Med.* 4:328, 1998; *Nature Med.* 2:52, 1996 and *Prostate* 32:272, 1997). Although 2-50×$10^6$ DC per patient are typically administered, larger number of DC, such as $10^7$ or $10^8$ can also be provided. Such cell populations typically contain between 50-90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive 5×$10^6$ DC, then the patient will be injected with a total of 2.5×$10^8$ peptide-loaded PBMC. The percent DC mobilized by an agent such as Progenipoietin™ is typically estimated to be between 2-10%, but can vary as appreciated by one of skill in the art.

Ex Vivo Activation of CTL/HTL Responses

Alternatively, ex vivo CTL or HTL responses to 251P5G2 antigens can be induced by incubating, in tissue culture, the patient's, or genetically compatible, CTL or HTL precursor cells together with a source of APC, such as DC, and immunogenic peptides. After an appropriate incubation time (typically about 7-28 days), in which the precursor cells are activated and expanded into effector cells, the cells are infused into the patient, where they will destroy (CTL) or facilitate destruction (HTL) of their specific target cells, i.e., tumor cells.

Example 33

An Alternative Method of Identifying and Confirming Motif-Bearing Peptides

Another method of identifying and confirming motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be transfected with nucleic acids that express the antigen of interest, e.g. 251P5G2. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et al., *J. Immunol.* 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 251P5G2 to isolate peptides corresponding to 251P5G2 that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 34

Complementary Polynucleotides

Sequences complementary to the 251P5G2-encoding sequences, or any parts thereof, are used to detect, decrease, or inhibit expression of naturally occurring 251P5G2. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of 251P5G2. To inhibit transcription, a complementary oligonucleotide is designed from the most unique 5' sequence and used to prevent promoter binding to the coding sequence. To inhibit translation, a complementary oligonucleotide is designed to prevent ribosomal binding to a 251P5G2-encoding transcript.

Example 35

Purification of Naturally-occurring or Recombinant 251P5G2 Using 251P5G2-Specific Antibodies Naturally occurring or recombinant 251P5G2 is substantially purified by immunoaffinity chromatography using antibodies specific for 251P5G2. An immunoaffinity column is constructed by covalently coupling anti-251P5G2 antibody to an activated chromatographic resin, such as CNBr-activated SEPHAROSE (Amersham Pharmacia Biotech). After the coupling, the resin is blocked and washed according to the manufacturers instructions.

Media containing 251P5G2 are passed over the immunoaffinity column, and the column is washed under conditions that allow the preferential absorbance of 251P5G2 (e.g., high ionic strength buffers in the presence of detergent). The column is eluted under conditions that disrupt antibody/251P5G2 binding (e.g., a buffer of pH 2 to pH 3, or a high concentration of a chaotrope, such as urea or thiocyanate ion), and GCR.P is collected.

Example 36

Identification of Molecules which Interact with 251P5G2

251P5G2, or biologically active fragments thereof, are labeled with 121 1 Bolton-Hunter reagent. (See, e.g., Bolton et al. (1973) Biochem. J. 133:529.) Candidate molecules previously arrayed in the wells of a multi-well plate are incubated with the labeled 251P5G2, washed, and any wells with labeled 251P5G2 complex are assayed. Data obtained using different concentrations of 251P5G2 are used to calculate values for the number, affinity, and association of 251P5G2 with the candidate molecules.

Example 37

In Vivo Assay for 251P5G2 Tumor Growth Promotion

The effect of the 251P5G2 protein on tumor cell growth is evaluated in vivo by evaluating tumor development and growth of cells expressing or lacking 251P5G2. For example, SCID mice are injected subcutaneously on each flank with $1 \times 10^6$ of either 3T3, prostate or bladder cancer cell lines (e.g. PC3 or J82 cells) containing tkNeo empty vector or 251P5G2. At least two strategies may be used: (1) Constitutive 251P5G2 expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tetracycline, etc., provided such promoters are compatible with the host cell systems. Tumor volume is then monitored by caliper measurement at the appearance of palpable tumors and followed over time to determine if 251P5G2-expressing cells grow at a faster rate and whether tumors produced by 251P5G2-expressing cells demonstrate characteristics of altered aggressiveness (e.g. enhanced metastasis, vascularization, reduced responsiveness to chemotherapeutic drugs).

Additionally, mice can be implanted with $1 \times 10^5$ of the same cells orthotopically to determine if 251P5G2 has an effect on local growth in the bladder or prostate, and whether 251P5G2 affects the ability of the cells to metastasize, specifically to lymph nodes and bone (Fu. X. et al Int J. Cancer. 1992, 52:987; Fu. X. et al, Int J. Cancer. 1991, 49:938). The assay is also useful to determine the 251P5G2 inhibitory effect of candidate therapeutic compositions, such as for example, 251P5G2 intrabodies, 251P5G2 antisense molecules and ribozymes.

Example 38

251P5G2 Monoclonal Antibody-mediated Inhibition of Bladder, and Prostate Tumors In Vivo The significant expression of 251P5G2 in cancer tissues, together with its restrictive expression in normal tissues makes 251P5G2 a good target for antibody therapy. Similarly, 251P5G2 is a target for T cell-based immunotherapy. Thus, the therapeutic efficacy of anti-251P5G2 mAbs in human prostate cancer xenograft mouse models is evaluated by using recombinant cell lines such as PC3-251P5G2, and 3T3-251P5G2 (see, e.g., Kaighn, M. E., et al., Invest Urol, 1979. 17(1): p. 16-23), as well as human prostate xenograft models such as LAPC9 (Saffran et al, Proc Natl Acad Sci USA. 2001, 98:2658). Similarly, anti-251P5G2 mAbs are evaluated in human bladder cancer xenograft models using recombinant cell lines such as J82-251P5G2.

Antibody efficacy on tumor growth and metastasis formation is studied, e.g., in a mouse orthotopic bladder cancer xenograft model, and a mouse prostate cancer xenograft model. The antibodies can be unconjugated, as discussed in this Example, or can be conjugated to a therapeutic modality, as appreciated in the art. Anti-251P5G2 mAbs inhibit formation of prostate and bladder xenografts. Anti-251P5G2 mAbs also retard the growth of established orthotopic tumors and prolonged survival of tumor-bearing mice. These results indicate the utility of anti-251P5G2 mAbs in the treatment of local and advanced stages of prostate and bladder cancer. (See, e.g., Saffran, D., et al., PNAS 10:1073-1078 or on the World Wide Web at (.pnas.org/cgi/doi/10.1073/pnas.051624698).

Administration of the anti-251P5G2 mAbs led to retardation of established orthotopic tumor growth and inhibition of metastasis to distant sites, resulting in a significant prolongation in the survival of tumor-bearing mice. These studies indicate that 251P5G2 as an attractive target for immunotherapy and demonstrate the therapeutic potential of anti-251P5G2 mAbs for the treatment of local and metastatic cancer. This example demonstrates that unconjugated 251P5G2 monoclonal antibodies are effective to inhibit the growth of human bladder and prostate tumor xenografts grown in SCID mice; accordingly a combination of such efficacious monoclonal antibodies is also effective.

Tumor Inhibition Using Multiple Unconjugated 251P5G2 mAbs

Materials and Methods

251P5G2 Monoclonal Antibodies:

Monoclonal antibodies are raised against 251P5G2 as described in the Example entitled "Generation of 251P5G2 Monoclonal Antibodies (mAbs)." The antibodies are characterized by ELISA, Western blot, FACS, and immunoprecipitation for their capacity to bind 251P5G2. Epitope mapping data for the anti-251P5G2 mAbs, as determined by ELISA and Western analysis, recognize epitopes on the 251P5G2 protein. Immunohistochemical analysis of prostate cancer tissues and cells with these antibodies is performed.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of SCABER, J82, A498, 769P, CaOv1 or PA1 tumor xenografts.

Cell Lines

The bladder and prostate carcinoma cell lines, J82 and PC3 as well as the fibroblast line NIH 3T3 (American Type Culture Collection) are maintained in media supplemented with L-glutamine and 10% FBS.

A J82-251P5G2, PC3-251P5G2 and 3T3-251P5G2 cell populations are generated by retroviral gene transfer as described in Hubert, R. S., et al., Proc Natl Acad Sci USA, 1999. 96(25): 14523.

Xenograft Mouse Models.

Subcutaneous (s.c.) tumors are generated by injection of $1 \times 10^6$ cancer cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. Tumor sizes are determined by caliper measurements, and the tumor volume is calculated as: Length×Width×Height. Mice with s.c. tumors greater than 1.5 cm in diameter are sacrificed.

Orthotopic injections are performed under anesthesia by using ketamine/xylazine. For bladder orthotopic studies, an incision is made through the abdomen to expose the bladder, and tumor cells ($5 \times 10^5$) mixed with Matrigel are injected into the bladder wall in a 10-µl volume. To monitor tumor growth, mice are palpated and blood is collected on a weekly basis to measure BTA levels. For prostate orthopotic models, an incision is made through the abdominal muscles to expose the bladder and seminal vesicles, which then are delivered through the incision to expose the dorsal prostate. Tumor cells e.g. LAPC-9 cells ($5 \times 10^5$) mixed with Matrigel are injected into the prostate in a 10-µl volume (Yoshida Y et al, Anticancer Res. 1998, 18:327; Ahn et al, Tumour Biol. 2001, 22:146). To monitor tumor growth, blood is collected on a weekly basis measuring PSA levels. The mice are segregated into groups for the appropriate treatments, with anti-251P5G2 or control mAbs being injected i.p.

Anti-251P5G2 mAbs Inhibit Growth of 251P5G2-Expressing Xenograft-Cancer Tumors

The effect of anti-251P5G2 mAbs on tumor formation is tested on the growth and progression of bladder, and prostate cancer xenografts using J82-251P5G2, and PC3-251P5G2 orthotopic models. As compared with the s.c. tumor model, the orthotopic model, which requires injection of tumor cells directly in the mouse bladder, and prostate, respectively, results in a local tumor growth, development of metastasis in distal sites, deterioration of mouse health, and subsequent death (Saffran, D., et al., PNAS supra; Fu, X., et al., Int J Cancer, 1992. 52(6): p. 987-90; Kubota, T., J Cell Biochem, 1994. 56(1): p. 4-8). The features make the orthotopic model more representative of human disease progression and allowed us to follow the therapeutic effect of mAbs on clinically relevant end points.

Accordingly, tumor cells are injected into the mouse bladder, or prostate, and 2 days later, the mice are segregated into two groups and treated with either: a) 200-500 µg, of anti-251P5G2 Ab, or b) PBS three times per week for two to five weeks.

A major advantage of the orthotopic cancer models is the ability to study the development of metastases. Formation of metastasis in mice bearing established orthotopic tumors is studies by IHC analysis on lung sections using an antibody against a tumor-specific cell-surface protein such as anti-CK20 for bladder cancer, anti-STEAP-1 for prostate cancer models (Lin S et al, Cancer Detect Prev. 2001; 25:202; Saffran, D., et al., PNAS supra).

Mice bearing established orthotopic tumors are administered 1000 µg injections of either anti-251P5G2 mAb or PBS over a 4-week period. Mice in both groups are allowed to establish a high tumor burden, to ensure a high frequency of metastasis formation in mouse lungs. Mice then are killed and their bladders, livers, bone and lungs are analyzed for the presence of tumor cells by IHC analysis.

These studies demonstrate a broad anti-tumor efficacy of anti-251P5G2 antibodies on initiation and progression of prostate and kidney cancer in xenograft mouse models. Anti-251P5G2 antibodies inhibit tumor formation of tumors as well as retarding the growth of already established tumors and prolong the survival of treated mice. Moreover, anti-251P5G2 mAbs demonstrate a dramatic inhibitory effect on the spread of local bladder and prostate tumor to distal sites, even in the presence of a large tumor burden. Thus, anti-251P5G2 mAbs are efficacious on major clinically relevant end points (tumor growth), prolongation of survival, and health.

Example 39

Therapeutic and Diagnostic Use of Anti-251P5G2 Antibodies in Humans

Anti-251P5G2 monoclonal antibodies are safely and effectively used for diagnostic, prophylactic, prognostic and/or therapeutic purposes in humans. Western blot and immunohistochemical analysis of cancer tissues and cancer xenografts with anti-251P5G2 mAb show strong extensive staining in carcinoma but significantly lower or undetectable levels in normal tissues. Detection of 251P5G2 in carcinoma and in metastatic disease demonstrates the usefulness of the mAb as a diagnostic and/or prognostic indicator. Anti-251P5G2 antibodies are therefore used in diagnostic applications such as immunohistochemistry of kidney biopsy specimens to detect cancer from suspect patients.

As determined by flow cytometry, anti-251P5G2 mAb specifically binds to carcinoma cells. Thus, anti-251P5G2 antibodies are used in diagnostic whole body imaging applications, such as radioimmunoscintigraphy and radioimmunotherapy, (see, e.g., Potamianos S., et. al. Anticancer Res 20(2A):925-948 (2000)) for the detection of localized and metastatic cancers that exhibit expression of 251P5G2. Shedding or release of an extracellular domain of 251P5G2 into the extracellular milieu, such as that seen for alkaline phosphodiesterase B10 (Meerson, N. R., Hepatology 27:563-568 (1998)), allows diagnostic detection of 251P5G2 by anti-251P5G2 antibodies in serum and/or urine samples from suspect patients.

Anti-251P5G2 antibodies that specifically bind 251P5G2 are used in therapeutic applications for the treatment of cancers that express 251P5G2. Anti-251P5G2 antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-251P5G2 antibodies are tested for efficacy of tumor prevention and growth inhibition in the SCID mouse cancer xenograft models, e.g., kidney cancer models AGS-K3 and AGS-K6, (see, e.g., the Example entitled "251P5G2 Monoclonal Antibody-mediated Inhibition of Bladder and Lung Tumors In Vivo"). Either conjugated and unconjugated anti-251P5G2 antibodies are used as a therapeutic modality in human clinical trials either alone or in combination with other treatments as described in following Examples.

Example 40

Human Clinical Trials for the Treatment and Diagnosis of Human Carcinomas Through Use of Human Anti-251P5G2 Antibodies In Vivo Antibodies are used in accordance with the present invention which recognize an epitope on 251P5G2, and are used in the treatment of certain tumors such as those listed in Table I. Based upon a number of factors, including 251P5G2 expression levels, tumors such as those listed in Table I are presently preferred indications. In connection with each of these indications, three clinical approaches are successfully pursued.

I.) Adjunctive therapy: In adjunctive therapy, patients are treated with anti-251P5G2 antibodies in combination with a chemotherapeutic or antineoplastic agent and/or radiation therapy. Primary cancer targets, such as those listed in Table I, are treated under standard protocols by the addition anti-251P5G2 antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-251P5G2 antibodies are utilized in several adjunctive clinical trials in combination with the chemotherapeutic or antineoplastic agents adriamycin (advanced prostate carcinoma), cisplatin (advanced head and neck and lung carcinomas), taxol (breast cancer), and doxorubicin (preclinical).

II.) Monotherapy: In connection with the use of the anti-251P5G2 antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-251P5G2 antibodies, the radiolabeled antibodies are utilized as a diagnostic and/or imaging agent. In such a role, the labeled antibodies localize to both solid tumors, as well as, metastatic lesions of cells expressing 251P5G2. In connection with the use of the anti-251P5G2 antibodies as imaging agents, the antibodies are used as an adjunct to surgical treatment of solid tumors, as both a pre-surgical screen as well as a post-operative follow-up to determine what tumor remains and/or returns. In one embodiment, a ($^{111}$In)-251P5G2 antibody is used as an imaging agent in a Phase I human clinical trial in patients having a carcinoma that expresses 251P5G2 (by analogy see, e.g., Divgi et al. *J. Natl. Cancer Inst.* 83:97-104 (1991)). Patients are followed with standard anterior and posterior gamma camera. The results indicate that primary lesions and metastatic lesions are identified.

Dose and Route of Administration

As appreciated by those of ordinary skill in the art, dosing considerations can be determined through comparison with the analogous products that are in the clinic. Thus, anti-251P5G2 antibodies can be administered with doses in the range of 5 to 400 mg/m$^2$, with the lower doses used, e.g., in connection with safety studies. The affinity of anti-251P5G2 antibodies relative to the affinity of a known antibody for its target is one parameter used by those of skill in the art for determining analogous dose regimens. Further, anti-251P5G2 antibodies that are fully human antibodies, as compared to the chimeric antibody, have slower clearance; accordingly, dosing in patients with such fully human anti-251P5G2 antibodies can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are useful for delivery of anti-251P5G2 antibodies. Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-251P5G2 antibodies in connection with adjunctive therapy, monotherapy, and as an imaging agent. Trials initially demonstrate safety and thereafter confirm efficacy in repeat doses. Trails are open label comparing standard chemotherapy with standard therapy plus anti-251P5G2 antibodies. As will be appreciated, one criteria that can be utilized in connection with enrollment of patients is 251P5G2 expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 251P5G2. Standard tests and follow-up are utilized to monitor each of these safety concerns. Anti-251P5G2 antibodies are found to be safe upon human administration.

Example 41

Human Clinical Trial Adjunctive Therapy with Human Anti-251P5G2 Antibody and Chemotherapeutic Agent A phase I human clinical trial is initiated to assess the safety of six intravenous doses of a human anti-251P5G2 antibody in connection with the treatment of a solid tumor, e.g., a cancer of a tissue listed in Table I. In the study, the safety of single doses of anti-251P5G2 antibodies when utilized as an adjunctive therapy to an antineoplastic or chemotherapeutic agent as defined herein, such as, without limitation: cisplatin, topotecan, doxorubicin, adriamycin, taxol, or the like, is assessed. The trial design includes delivery of six single doses of an anti-251P5G2 antibody with dosage of antibody escalating from approximately about 25 mg/m$^2$ to about 275 mg/m$^2$ over the course of the treatment in accordance with the following schedule:

|  | Day 0 | Day 7 | Day 14 | Day 21 | Day 28 | Day 35 |
| --- | --- | --- | --- | --- | --- | --- |
| mAb Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients are closely followed for one-week following each administration of antibody and chemotherapy. In particular, patients are assessed for the safety concerns mentioned above: (i) cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express 251P5G2. Standard tests and follow-up are utilized to monitor each of these safety concerns. Patients are also assessed for clinical outcome, and particularly reduction in tumor mass as evidenced by MRI or other imaging.

The anti-251P5G2 antibodies are demonstrated to be safe and efficacious, Phase II trials confirm the efficacy and refine optimum dosing.

Example 42

Human Clinical Trial: Monotherapy with Human Anti-251P5G2 Antibody

Anti-251P5G2 antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-251P5G2 antibodies.

Example 43

Human Clinical Trial: Diagnostic Imaging with Anti-251P5G2 Antibody

Once again, as the adjunctive therapy discussed above is safe within the safety criteria discussed above, a human clinical trial is conducted concerning the use of anti-251P5G2 antibodies as a diagnostic imaging agent. The protocol is designed in a substantially similar manner to those described in the art, such as in Divgi et al. *J. Natl. Cancer Inst.* 83:97-104 (1991). The antibodies are found to be both safe and efficacious when used as a diagnostic modality.

Example 44

Homology Comparison of 251P5G2 to Known Sequences

The 251P5G2 protein of FIG. 3 has 255 amino acids with calculated molecular weight of 29.3 kDa, and pI of 9.4. Three variants of 251P5G2 have been identified, 251P5G2 v.1, v.2 and v 3, which differ from variant 1 by 1 amino acid each at aa positions 16 and 95 respectively. The 251P5G2 protein exhibits homology to a previously cloned murine gene, namely vomeronasal 1 receptor, C3 (gi 20821692), and shows 44% identity and 60% homology to that gene over the length of the protein (FIG. 4). 251P5G2 is a multi-transmembrane protein, predicted to carry 5 or 6 transmembrane domains. Bioinformatic analysis indicates that the 251P5G2 protein may localize to the endoplasmic reticulum or peroxisome (see Table L). However, based on it topology and similarity to vomeronasal receptor suggest that 251P5G2 may also localize to the plasma membrane. Motif analysis revealed the presence of a vomeronasal organ pheromone receptor family signature, a rhodopsin-like GPCR superfamily signature, and iodothyronine deiodinase motif (see Table VI).

The vomeronasal receptors share sequence homology to other families of G protein-coupled receptors, and are distantly related to the T2R bitter taste receptors and rhodopsin-like GPCRs. G-protein coupled receptors are seven-transmembrane receptors that exhibit an extracellular amino-terminus, three extracellular loops, three intracellular loops and an intracellular carboxyl terminus. G-protein coupled receptors are stimulated by a variety of stimuli, including polypeptide hormones, neurotransmitters, chemokines and phospholipids (Civelli O et al, Trends Neurosci. 2001, 24:230; Vrecl M et al Mol Endocrinol. 1998, 12:1818). Ligand binding traditionally occurs between the first and second extracellular loops of the GPCR. Upon ligand binding GPCRs transduce signals across the cell surface membrane by associating with trimeric G proteins. Vomeronasal receptors are expressed in the apical regions of the vomeranasal organs, often in neurons expressing Gi2 subunits of G proteins. Vomeronasal receptors are activated by pheromones and signal by activating the ERK-MAPK and inositol trisphosphate pathways (Dudley C A et al, Brain Res. 2001, 915:32; Wekesa K S et al, Endocrinology. 1997, 138:3497). Although the function of vomeronasal receptors is not well understood, they appear to be associated with motility, cell proliferation and programmed cell death (Riccardi D. Cell Calcium. 1999, 26:77) all of which have a direct effect on tumor growth and progression. This is further supported by recent studies associating GPCRs with cellular transformation. In particular, KSHV G protein-coupled receptor was found to transform NIH 3T3 cells in vitro and induces multifocal KS-like lesions in KSHV-GPCR-transgenic mice (Schwarz M, Murphy P M. J Immunol 2001, 167:505). KSHV-GPCR was capable of producing its effect on endothelial cells and fibroblasts by activating defined signaling pathways, including the AKT survival pathway (Montaner S et al, Cancer Res 2001, 61:2641). In addition, KSHV-GPCR induced the activation of mitogenic pathways such as AP-1 and NFk$\beta$, resulting in the expression of pro-inflammatory genes (Schwarz M, Murphy P M. J Immunol 2001, 167:505).

Accordingly, when 251P5G2 functions as a regulator of tumor formation, cell proliferation, invasion or cell signaling, 251P5G2 is used for therapeutic, diagnostic, prognostic and/or preventative purposes.

Example 45

Identification and Confirmation of Potential Signal Transduction Pathways

Many mammalian proteins have been reported to interact with signaling molecules and to participate in regulating signaling pathways. (J Neurochem. 2001; 76:217-223). In particular, GPCRs have been reported to activate MAK cascades as well as G proteins, and been associated with the EGFR pathway in epithelial cells (Naor, Z., et al, Trends Endocrinol Metab. 2000, 11:91; Vacate F et al, Cancer Res. 2000, 60:5310; Della Rocca G. J., et al, J Biol Chem. 1999, 274: 13978). In addition, GPCRs transmit their signals by activating the protein kinase A or the phospholipase C pathways, generating inositol 1,4,5-trisphosphate (IP3) and diacyl-glycerol (DAG) (Breer, 1993, Ciba Found Symp 179: 97; Bruch, 1996, Comp Biochem Physiol B Biochem Mol Biol 113: 451).

Using immunoprecipitation and Western blotting techniques, proteins are identified that associate with 251P5G2 and mediate signaling events. Several pathways known to play a role in cancer biology can be regulated by 251P5G2, including phospholipid pathways such as PI3K, AKT, etc, adhesion and migration pathways, including FAK, Rho, Rac-1, etc, as well as mitogenic/survival cascades such as ERK, p38, etc (Cell Growth Differ. 2000, 11:279; J Biol Chem. 1999, 274:801; Oncogene. 2000, 19:3003; J. Cell Biol. 1997, 138:913). Using Western blotting and other techniques, the ability of 251P5G2 to regulate these pathways is confirmed. Cells expressing or lacking 251P5G2 are either left untreated or stimulated with cytokines, androgen and anti-integrin antibodies. Cell lysates are analyzed using anti-phospho-specific antibodies (Cell Signaling, Santa Cruz Biotechnology) in order to detect phosphorylation and regulation of ERK, p38, AKT, PI3K, PLC and other signaling molecules.

To confirm that 251P5G2 directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress
7. TCF-luc, TCF/Lef; |-catenin, Adhesion/invasion Gene-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer.

Signaling pathways activated by 251P5G2 are mapped and used for the identification and validation of therapeutic targets. When 251P5G2 is involved in cell signaling, it is used as target for diagnostic, prognostic, preventative and/or therapeutic purposes.

Example 46

251P5G2 Functions as a GPCR Inhibitors

Sequence and homology analysis of 251P5G2 indicated that 251P5G2 is a member of the pheromone GPCR family. Vomeronasal receptors are known to regulate biological responses by activating PLC. In order to confirm that 251P5G2 functions as a GPCR and mediates the activation PLC, phosphorylation of PLC is investigated in PC3 and PC3-251P5G2 cells. Control PC3 and PC3-251P5G2 cells are grown in a low concentration of fetal bovine serum (FBS) and stimulated with 10% FBS, pheromones and LPA. PLC phosphorylation is investigated by western blotting.

GPCRs are activated by ligand binding to the extracellular loops, resulting in the binding of trimeric G proteins to GPCR and their activation. Using this information, several therapeutic and small molecule strategies are utilized to inhibit GPCR activation or downstream signaling events.

One strategy inhibits receptor and ligand binding. Recent studies using several types of GPCRs, have demonstrated the effectiveness of this strategy (Fawzi A B, et al. 2001, Mol. Pharmacol., 59:30). Using a compound named SCH-202676, they inhibited agonist and antagonist binding to GPCRs by allosterically hindering ligand-GPCR interaction. Using this and even more specific allosteric (small molecule) inhibitors, signal transduction through 251P5G2 can be inhibited, thereby providing therapeutic, prognostic, diagnostic and/or prophylactic benefit.

A second approach is to inhibit G alpha subunit activation. Activation of GPCRs results in the exchange of GTP for GDP on the G alpha subunit of the trimeric G protein. Inhibition of Gα activation prevents the activation of downstream signaling cascades and therefore biological effects of GPCR. One molecule used to inhibit GDP exchange on Gα subunits is Suranim (Freissmuth M et al, 1996, Mol. Pharmacol, 49:602). Since suranim functions as a universal Gα inhibitor, it prevents the activation of most Gα subunits.

A third approach is to inhibit Gα subunit association with GPCR. In order for trimeric G proteins to be activated following GPCR/ligand interaction, it is necessary for them to associate with their corresponding GPCR. Mutational analysis has mapped the interaction of Gα to the first and third intracellular loops of GPCRs (Heller R at al. 1996, Biochem. Biophys. Res. Commun). Several studies have used synthetic (small molecule) peptides corresponding to the intracellular sequence of loops 1 and 3 as inhibitors (Mukherjee, S., et al. 1999, J. Biol. Chem.). Using such short peptides that serve as receptor mimics, they are used to compete for binding of Ga subunits to 251P5G2 and thereby provide therapeutic, prognostic, diagnostic and/or prophylactic benefit.

Thus, compounds and small molecules designed to inhibit 251P5G2 function and downstream signaling events are used for therapeutic diagnostic, prognostic and/or preventative purposes.

Example 47

Regulation of Transcription

The cell surface localization of 251P5G2 and its similarity to GPCRs indicate that it is effectively used as a modulator of the transcriptional regulation of eukaryotic genes. Regulation of gene expression is confirmed, e.g., by studying gene expression in cells expressing or lacking 251P5G2. For this purpose, two types of experiments are performed.

In the first set of experiments, RNA from parental and 251P5G2-expressing cells are extracted and hybridized to commercially available gene arrays (Clontech) (Smid-Koopman E et al. Br J Cancer. 2000. 83:246). Resting cells as well as cells treated with FBS, pheromones, or growth factors are compared. Differentially expressed genes are identified in accordance with procedures known in the art. The differentially expressed genes are then mapped to biological pathways (Chen K et al. Thyroid. 2001. 11:41.).

In the second set of experiments, specific transcriptional pathway activation is evaluated using commercially available (Stratagene) luciferase reporter constructs including: NFkB-luc, SRE-luc, ELK1-luc, ARE-luc, p53-luc, and CRE-luc. These transcriptional reporters contain consensus binding sites for known transcription factors that lie downstream of well-characterized signal transduction pathways, and represent a good tool to ascertain pathway activation and screen for positive and negative modulators of pathway activation.

Thus, 251P5G2 plays a role in gene regulation, and it is used as a target for diagnostic, prognostic, preventative and/or therapeutic purposes.

Example 48

Involvement in Tumor Progression

The 251P5G2 gene can contribute to the growth of cancer cells. The role of 251P5G2 in tumor growth is confirmed in a variety of primary and transfected cell lines including prostate, and bladder cell lines, as well as NIH 3T3 cells engineered to stably express 251P5G2. Parental cells lacking 251P5G2 and cells expressing 251P5G2 are evaluated for cell growth using a well-documented proliferation assay (Fraser S P, et al., Prostate 2000; 44:61, Johnson D E, Ochieng J, Evans S L. Anticancer Drugs. 1996, 7:288). The effect of 251P5G2 can also observed on cell cycle progression. Control and 251P5G2-expressing cells are grown in low serum overnight, and treated with 10% FBS for 48 and 72 hrs. Cells are analyzed for BrdU and propidium iodide incorporation by FACS analysis.

To confirm the role of 251P5G2 in the transformation process, its effect in colony forming assays is investigated. Parental NIH-3T3 cells lacking 251P5G2 are compared to NIH-3T3 cells expressing 251P5G2, using a soft agar assay under stringent and more permissive conditions (Song Z. et al. Cancer Res. 2000; 60:6730).

To confirm the role of 251P5G2 in invasion and metastasis of cancer cells, a well-established assay is used. A non-limiting example is the use of an assay which provides a basement membrane or an analog thereof used to detect whether cells are invasive (e.g., a Transwell Insert System assay (Becton Dickinson) (Cancer Res. 1999; 59:6010)). Control cells, including prostate, and bladder cell lines lacking 251P5G2 are compared to cells expressing 251P5G2. Cells are loaded with the fluorescent dye, calcein, and plated in the top well of a support structure coated with a basement membrane analog (e.g. the Transwell insert) and used in the assay. Invasion is determined by fluorescence of cells in the lower chamber relative to the fluorescence of the entire cell population.

251P5G2 can also play a role in cell cycle and apoptosis. Parental cells and cells expressing 251P5G2 are compared for differences in cell cycle regulation using a well-established BrdU assay (Abdel-Malek Z A. J Cell Physiol. 1988, 136: 247). In short, cells are grown under both optimal (full serum) and limiting (low serum) conditions are labeled with BrdU and stained with anti-BrdU Ab and propidium iodide. Cells are analyzed for entry into the G1, S, and G2M phases of the cell cycle. Alternatively, the effect of stress on apoptosis is evaluated in control parental cells and cells expressing 251P5G2, including normal and tumor prostate, colon and lung cells. Engineered and parental cells are treated with various chemotherapeutic agents, such as etoposide, flutamide, etc, and protein synthesis inhibitors, such as cycloheximide. Cells are stained with annexin V-FITC and cell death is measured by FACS analysis. The modulation of cell death by 251P5G2 can play a critical role in regulating tumor progression and tumor load.

When 251P5G2 plays a role in cell growth, transformation, invasion or apoptosis, it is used as a target for diagnostic, prognostic, preventative and/or therapeutic purposes.

Example 49

Involvement in Angiogenesis

Angiogenesis or new capillary blood vessel formation is necessary for tumor growth (Hanahan D, Folkman J. Cell. 1996, 86:353; Folkman J. Endocrinology. 1998 139:441). Based on the effect of phsophodieseterase inhibitors on endothelial cells, 251P5G2 plays a role in angiogenesis (DeFouw L et al, Microvasc Res 2001, 62:263). Several assays have been developed to measure angiogenesis in vitro and in vivo, such as the tissue culture assays endothelial cell tube formation and endothelial cell proliferation. Using these assays as well as in vitro neo-vascularization, the role of 251P5G2 in angiogenesis, enhancement or inhibition, is confirmed.

For example, endothelial cells engineered to express 251P5G2 are evaluated using tube formation and proliferation assays. The effect of 251P5G2 is also confirmed in animal models in vivo. For example, cells either expressing or lacking 251P5G2 are implanted subcutaneously in immunocompromised mice. Endothelial cell migration and angiogenesis are evaluated 5-15 days later using immunohistochemistry techniques. 251P5G2 affects angiogenesis, and it is used as a target for diagnostic, prognostic, preventative and/or therapeutic purposes.

Example 50

Involvement in Protein-Protein Interactions

Several GPCRs have been shown to interact with other proteins, thereby regulating signal transduction, gene transcription, transformation and cell adhesion (Sexton P M et al, Cell Signal. 2001, 13:73; Turner C E, J Cell Sci. 2000, 23:4139). Using immunoprecipitation techniques as well as two yeast hybrid systems, proteins are identified that associate with 251P5G2. Immunoprecipitates from cells expressing 251P5G2 and cells lacking 251P5G2 are compared for specific protein-protein associations.

Studies are performed to confirm the extent of association of 251P5G2 with effector molecules, such as nuclear proteins, transcription factors, kinases, phosphates etc. Studies comparing 251P5G2 positive and 251P5G2 negative cells as well as studies comparing unstimulated/resting cells and cells treated with epithelial cell activators, such as cytokines, growth factors and anti-integrin Ab reveal unique interactions.

In addition, protein-protein interactions are confirmed using two yeast hybrid methodology (Curr Opin Chem. Biol. 1999, 3:64). A vector carrying a library of proteins fused to the activation domain of a transcription factor is introduced into yeast expressing a 251P5G2-DNA-binding domain fusion protein and a reporter construct. Protein-protein interaction is detected by colorimetric reporter activity. Specific association with effector molecules and transcription factors directs one of skill to the mode of action of 251P5G2, and thus identifies therapeutic, prognostic, preventative and/or diagnostic targets for cancer. This and similar assays are also used to identify and screen for small molecules that interact with 251P5G2.

Thus it is found that 251P5G2 associates with proteins and small molecules. Accordingly, 251P5G2 and these proteins and small molecules are used for diagnostic, prognostic, preventative and/or therapeutic purposes.

Example 51

Involvement in Adhesion

Cell adhesion plays a critical role in tissue colonization and metastasis. The presence of link motif in 251P5G2 is indicative of its role in cell adhesion. To confirm that 251P5G2 plays a role in cell adhesion, control cells lacking 251P5G2 are compared to cells expressing 251P5G2, using techniques previously described (see, e.g., Haier et al, Br. J. Cancer. 1999, 80:1867; Lehr and Pienta, J. Natl. Cancer Inst. 1998, 90:118). Briefly, in one embodiment, cells labeled with a fluorescent indicator, such as calcein, are incubated on tissue culture wells coated with media alone or with matrix proteins. Adherent cells are detected by fluorimetric analysis and percent adhesion is calculated. This experimental system can be used to identify proteins, antibodies and/or small molecules that modulate cell adhesion to extracellular matrix and cell-cell interaction. Since cell adhesion plays a critical role in tumor growth, progression, and, colonization, the gene involved in this process can serves as a diagnostic, preventative and therapeutic modality.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables:

TABLE I

Tissues that Express 251P5G2:

a. Malignant Tissues
Prostate
Bladder

TABLE II

Amino Acid Abbreviations

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix
Adapted from the GCG Software 9.0 BLOSUM62 amino acid substitution matrix (block substitution matrix). The higher the value, the more likely a substitution is found in related, natural proteins. (See world wide web URL ikp.unibe.ch/manual/blosum62.html)

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | -2 | -1 | -2 | 0 | -2 | -1 | -1 | -1 | -1 | -2 | -1 | -1 | -1 | 1 | 0 | 0 | -3 | -2 | A |
|   | 9 | -3 | -4 | -2 | -3 | -3 | -1 | -3 | -1 | -1 | -3 | -3 | -3 | -3 | -1 | -1 | -1 | -2 | -2 | C |
|   |   | 6 | 2 | -3 | -1 | -1 | -3 | -1 | -4 | -3 | 1 | -1 | 0 | -2 | 0 | -1 | -3 | -4 | -3 | D |
|   |   |   | 5 | -3 | -2 | 0 | -3 | 1 | -3 | -2 | 0 | -1 | 2 | 0 | 0 | -1 | -2 | -3 | -2 | E |
|   |   |   |   | 6 | -3 | -1 | 0 | -3 | 0 | 0 | -3 | -4 | -3 | -3 | -2 | -2 | -1 | 1 | 3 | F |
|   |   |   |   |   | 6 | -2 | -4 | -2 | -4 | -3 | 0 | -2 | -2 | -2 | 0 | -2 | -3 | -2 | -3 | G |
|   |   |   |   |   |   | 8 | -3 | -1 | -3 | -2 | 1 | -2 | 0 | 0 | -1 | -2 | -3 | -2 | 2 | H |
|   |   |   |   |   |   |   | 4 | -3 | 2 | 1 | -3 | -3 | -3 | -3 | -2 | -1 | 3 | -3 | -1 | I |
|   |   |   |   |   |   |   |   | 5 | -2 | -1 | 0 | -1 | 1 | 2 | 0 | -1 | -2 | -3 | -2 | K |
|   |   |   |   |   |   |   |   |   | 4 | 2 | -3 | -3 | -2 | -2 | -2 | -1 | 1 | -2 | -1 | L |
|   |   |   |   |   |   |   |   |   |   | 5 | -2 | -2 | 0 | -1 | -1 | -1 | 1 | -1 | -1 | M |
|   |   |   |   |   |   |   |   |   |   |   | 6 | -2 | 0 | 0 | 1 | 0 | -3 | -4 | -2 | N |
|   |   |   |   |   |   |   |   |   |   |   |   | 7 | -1 | -2 | -1 | -1 | -2 | -4 | -3 | P |
|   |   |   |   |   |   |   |   |   |   |   |   |   | 5 | 1 | 0 | -1 | -2 | -2 | -1 | Q |
|   |   |   |   |   |   |   |   |   |   |   |   |   |   | 5 | -1 | -1 | -3 | -3 | -2 | R |
|   |   |   |   |   |   |   |   |   |   |   |   |   |   |   | 4 | 1 | -2 | -3 | -2 | S |
|   |   |   |   |   |   |   |   |   |   |   |   |   |   |   |   | 5 | 0 | -2 | -2 | T |
|   |   |   |   |   |   |   |   |   |   |   |   |   |   |   |   |   | 4 | -3 | -1 | V |
|   |   |   |   |   |   |   |   |   |   |   |   |   |   |   |   |   |   | 11 | 2 | W |
|   |   |   |   |   |   |   |   |   |   |   |   |   |   |   |   |   |   |   | 7 | Y |

Table IV:

HLA Class I/II Motifs/Supermotifs

TABLE IV (A)

| | HLA Class I Supermotifs/Motifs | | |
|---|---|---|---|
| | POSITION 2 (Primary Anchor) | POSITION 3 (Primary Anchor) | POSITION C Terminus (Primary Anchor) |
| SUPERMOTIF | | | |
| A1 | T*ILVMS* | | FWY |
| A2 | LIVM*ATQ* | | IV*MATL* |
| A3 | VSM*ATLI* | | RK |
| A24 | YF*WIVLMT* | | FI*YWLM* |
| B7 | P | | VILF*MWYA* |
| B27 | RHK | | FYL*WMIVA* |
| B44 | ED | | FWYLIMVA |
| B58 | ATS | | FWY*LIVMA* |
| B62 | QL*IVMP* | | FWY*MIVLA* |
| MOTIFS | | | |
| A1 | TSM | | Y |
| A1 | | DE*AS* | Y |
| A2.1 | LM*VQIAT* | | V*LIMAT* |
| A3 | LMVISATF*CGD* | | KYR*HFA* |
| A11 | VTMLISAGN*CDF* | | K*RYH* |
| A24 | YFW*M* | | FLIW |

TABLE IV (A)-continued

| | HLA Class I Supermotifs/Motifs | | |
|---|---|---|---|
| | POSITION 2 (Primary Anchor) | POSITION 3 (Primary Anchor) | POSITION C Terminus (Primary Anchor) |
| A*3101 | MVT*ALIS* | | R*K* |
| A*3301 | MVALF*IST* | | RK |
| A*6801 | AVT*MSLI* | | RK |
| B*0702 | P | | LMF*WYAIV* |
| B*3501 | P | | LMFWY*IVA* |
| B51 | P | | LIVF*WYAM* |
| B*5301 | P | | IMFWY*ALV* |
| B*5401 | P | | ATIV*LMFWY* |

Bolded residues are preferred, italicized residues are less preferred: A peptide is considered motif-bearing if it has primary anchors at each primary anchor position for a motif or supermotif as specified in the above table.

TABLE IV (B)

| HLA Class II Supermotif | | |
|---|---|---|
| 1 | 6 | 9 |
| W, F, Y, V, .I, L | A, V, I, L, P, C, S, T | A, V, I, L, C, S, T, M, Y |

TABLE IV (C)

| | | HLA Class II Motifs | | | | | | | | |
|---|---|---|---|---|---|---|---|---|---|---|
| MOTIFS | | 1° anchor 1 | 2 | 3 | 4 | 5 | 1° anchor 6 | 7 | 8 | 9 |
| DR4 | preferred | FMY*LIVW* | M | T | | I | VST*CPALIM* | MH R | | MH WDE |
| | deleterious | | | | W | | | | | |
| DR1 | preferred | MF*LIVWY* | | | PAMQ | | VMAT*SPLIC* | M GDE | D | AVM |
| | deleterious | | C | CH | FD | CWD | | | | |
| DR7 | preferred | MF*LIVWY* | M | W | A | | IVMSA*CTPL* | M GRD | N | IV G |
| | deleterious | | C | | G | | | | | |

| DR3 | MOTIFS | 1° anchor 1 | 2 | 3 | 1° anchor 4 | 5 | 1° anchor 6 |
|---|---|---|---|---|---|---|---|
| Motif a preferred | | LIVMFY | | | D | | |
| Motif b preferred | | LIVMFAY | | | DNQEST | | KRH |
| DR Supermotif | | MF*LIVWY* | | | | | VMSTA*CPLI* |

Italicized residues indicate less preferred or "tolerated" residues

TABLE IV (D)

| | | HLA Class I Supermotifs | | | | | | | |
|---|---|---|---|---|---|---|---|---|---|
| SUPER-MOTIFS | POSITION: | 1 | 2 | 3 | 4 | 5 | 6 | 7 | 8 | C-terminus |
| A1 | | | 1° Anchor TI*LVMS* | | | | | | | 1° Anchor FWY |
| A2 | | | 1° Anchor LIVM*ATQ* | | | | | | | 1° Anchor LIVMAT |
| A3 | Preferred | | 1° Anchor VSMA*TLI* | YFW (4/5) | | | YFW (3/5) | YFW (4/5) | P (4/5) | 1° Anchor RK |
| | deleterious | DE (3/5); P (5/5) | | DE (4/5) | | | | | | |
| A24 | | | 1° Anchor YF*WIVLMT* | | | | | | | 1° Anchor FI*YWLM* |
| B7 | Preferred | FWY (5/5) LIVM (3/5) | 1° Anchor P | FWY (4/5) | | | | | FWY (3/5) | 1°Anchor VILF*MWYA* |
| | deleterious | DE (3/5); P(5/5); G(4/5); A(3/5); QN(3/5) | | | | DE (3/5) | G (4/5) | QN (4/5) | DE (4/5) | |

TABLE IV (D)-continued

HLA Class I Supermotifs

| SUPER-MOTIFS | POSITION: | 1 | 2 | 3 | 4 | 5 | 6 | 7 | 8 | C-terminus |
|---|---|---|---|---|---|---|---|---|---|---|
| B27 | | | 1° Anchor RHK | | | | | | | 1° Anchor FYL*WMIVA* |
| B44 | | | 1° Anchor ED | | | | | | | 1° Anchor FWYLIMVA |
| B58 | | | 1° Anchor ATS | | | | | | | 1° Anchor FWY*LIVMA* |
| B62 | | | 1° Anchor QL*IVMP* | | | | | | | 1° Anchor FWY*MIVLA* |

Italicized residues indicate less preferred or "tolerated" residues

TABLE IV (E)

HLA Class I Motifs

| | POSITION | 1 | 2 | 3 | 4 | 5 |
|---|---|---|---|---|---|---|
| A1 9-mer | preferred | GFYW | 1° Anchor STM | DEA | | YFW |
| | deleterious | DE | | RHKLIVMP | A | G |
| A1 9-mer | preferred | GRHK | ASTCLIVM | 1° Anchor DEAS | GSTC | |
| | deleterious | A | RHKDEPYFW | | DE | PQN |
| A1 10-mer | preferred | YFW | 1° Anchor STM | DEAQN | A | YFWQN |
| | deleterious | GP | | RHKGLIVM | DE | RHK |
| A1 10-mer | preferred | YFW | STCLIVM | 1° Anchor DEAS | A | YFW |
| | deleterious | RHK | RHKDEPYFW | | | P |
| A2.1 9-mer | preferred | YFW | 1° Anchor LM*IVQAT* | YFW | STC | YFW |
| | deleterious | DEP | | DERKH | | |
| A2.1 10-mer | preferred | AYFW | 1° Anchor LM*IVQAT* | LVIM | G | |
| | deleterious | DEP | | DE | RKHA | P |
| A3 | preferred | RHK | 1° Anchor LMVISATFCGD | YFW | PRHKYFW | A |
| | deleterious | DEP | | DE | | |
| A11 | preferred | A | 1° Anchor VTLMISAGN*CDF* | YFW | YFW | A |
| | deleterious | DEP | | | STC | |
| A24 9-mer | preferred | YFWRHK | 1° Anchor YF*WM* | | STC | |
| | deleterious | DEG | | DE | G | QNP |
| A24 10-mer | Preferred | | 1° Anchor YF*WM* | | P | YFWP |
| | Deleterious | | | GDE | QN | RHK |
| A3101 | Preferred | RHK | 1° Anchor MVT*ALIS* | YFW | P | RHK |
| | Deleterious | DEP | | DE | | ADE |
| A3301 | Preferred | | 1° Anchor MVALF*IST* | YFW | | |
| | Deleterious | GP | | DE | | |
| A6801 | Preferred | YFWSTC | 1° Anchor AVT*MSLI* | | | YFWLIVM |
| | deleterious | GP | | DEG | | RHK |
| B0702 | Preferred | RHKFWY | 1° Anchor P | RHK | | RHK |
| | deleterious | DEQNP | | DEP | DE | DE |
| A1 9-mer | preferred | GFYW | 1° Anchor STM | DEA | | YFW |
| | deleterious | DE | | RHKLIVMP | A | G |
| A1 9-mer | preferred | GRHK | ASTCLIVM | 1° Anchor DEAS | GSTC | |
| | deleterious | A | RHKDEPYFW | | DE | PQN |
| B3501 | Preferred | FWYLIVM | 1° Anchor P | FWY | | |
| | deleterious | AGP | | | | G |
| B51 | Preferred | LIVMFWY | 1° Anchor P | FWY | STC | FWY |
| | deleterious | AGPDERHKSTC | | | | DE |

TABLE IV (E)-continued

HLA Class I Motifs

| | | | | | | | |
|---|---|---|---|---|---|---|---|
| B5301 | preferred | LIVMFWY | 1° Anchor P | | FWY | STC | FWY |
| | deleterious | AGPQN | | | | | |
| B5401 | preferred | FWY | 1° Anchor P | | FWYLIVM | | LIVM |
| | deleterious | GPQNDE | | | | GDESTC | RHKDE |

| | POSITION | 6 | 7 | 8 | 9 or C-terminus | C-terminus |
|---|---|---|---|---|---|---|
| A1 9-mer | preferred | P | DEQN | YFW | 1° Anchor Y | |
| | deleterious | A | | | | |
| A1 9-mer | preferred | ASTC | LIVM | DE | 1° Anchor Y | |
| | deleterious | RHK | PG | GP | | |
| A1 10-mer | preferred | | PASTC | GDE | P | 1° Anchor Y |
| | deleterious | QNA | RHKYFW | RHK | A | |
| A1 10-mer | preferred | | PG | G | YFW | 1° Anchor Y |
| | deleterious | G | | PRHK | QN | |
| A2.1 9-mer | preferred | | A | P | 1° Anchor V*LIMAT* | |
| | deleterious | RKH | DERKH | | | |
| A2.1 10-mer | preferred | G | | FYWLVIM | | 1° Anchor V*LIMAT* |
| | deleterious | | RKH | DERKHRKH | | |
| A3 | preferred | YFW | | P | 1° Anchor KYR*HFA* | |
| | deleterious | | | | | |
| A11 | preferred | YFW | YFW | P | 1° Anchor K*RYH* | |
| | deleterious | | A | G | | |
| A24 9-mer | preferred | | YFW | YFW | 1° Anchor FLIW | |
| | deleterious | DERHKG | | AQN | | |
| A24 10-mer | Preferred | | P | | | 1° Anchor FLIW |
| | Deleterious | DE | A | QN | DEA | |
| A3101 | Preferred | YFW | YFW | AP | 1° Anchor R*K* | |
| | Deleterious | DE | DE | DE | | |
| A3301 | Preferred | | AYFW | | 1° Anchor RK | |
| | Deleterious | | | | | |
| A6801 | Preferred | | YFW | P | 1° Anchor RK | |
| | deleterious | | | A | | |
| B0702 | Preferred | RHK | RHK | PA | 1° Anchor LMF*WYAIV* | |
| | deleterious | GDE | QN | DE | | |
| A1 9-mer | preferred | P | DEQN | YFW | 1° Anchor Y | |
| | deleterious | A | | | | |
| A1 9-mer | preferred | ASTC | LIVM | DE | 1° Anchor Y | |
| | deleterious | RHK | PG | GP | | |
| B3501 | Preferred | | FWY | | 1° Anchor LMFWY*IVA* | |
| | deleterious | G | | | | |
| B51 | Preferred | | G | FWY | 1° Anchor LIVF*WYAM* | |
| | deleterious | G | DEQN | GDE | | |
| B5301 | preferred | | LIVMFWY | FWY | 1° Anchor IMFWY*ALV* | |
| | deleterious | G | RHKQN | DE | | |
| B5401 | preferred | | ALIVM | FWYAP | 1° Anchor ATIV*LMFWY* | |
| | deleterious | DE | QNDGE | DE | | |

TABLE IV (F)

Summary of HLA-supertypes
Overall phenotypic frequencies of HLA-supertypes in different ethnic populations

| | Specificity | | Phenotypic frequency | | | | | |
|---|---|---|---|---|---|---|---|---|
| Supertype | Position 2 | C-Terminus | Caucasian | N.A. Black | Japanese | Chinese | Hispanic | Average |
| B7 | P | AILMVFWY | 43.2 | 55.1 | 57.1 | 43.0 | 49.3 | 49.5 |
| A3 | AILMVST | RK | 37.5 | 42.1 | 45.8 | 52.7 | 43.1 | 44.2 |
| A2 | AILMVT | AILMVT | 45.8 | 39.0 | 42.4 | 45.9 | 43.0 | 42.2 |
| A24 | YF (WIVLMT) | FI (YWLM) | 23.9 | 38.9 | 58.6 | 40.1 | 38.3 | 40.0 |
| B44 | E (D) | FWYLIMVA | 43.0 | 21.2 | 42.9 | 39.1 | 39.0 | 37.0 |
| A1 | TI (LVMS) | FWY | 47.1 | 16.1 | 21.8 | 14.7 | 26.3 | 25.2 |
| B27 | RHK | FYL (WMI) | 28.4 | 26.1 | 13.3 | 13.9 | 35.3 | 23.4 |
| B62 | QL (IVMP) | FMY (MIV) | 12.6 | 4.8 | 36.5 | 25.4 | 11.1 | 18.1 |
| B58 | ATS | FWY (LIV) | 10.0 | 25.1 | 1.6 | 9.0 | 5.9 | 10.3 |

TABLE IV (G)

Calculated population coverage afforded by different HLA-supertype combinations

| | Phenotypic frequency | | | | | |
|---|---|---|---|---|---|---|
| HLA-supertypes | Caucasian | N.A Blacks | Japanese | Chinese | Hispanic | Average |
| A2, A3 and B7 | 83.0 | 86.1 | 87.5 | 88.4 | 86.3 | 86.2 |
| A2, A3, B7, A24, B44 and A1 | 99.5 | 98.1 | 100.0 | 99.5 | 99.4 | 99.3 |
| A2, A3, B7, A24, B44, A1, B27, B62, and B 58 | 99.9 | 99.6 | 100.0 | 99.8 | 99.9 | 99.8 |

Motifs indicate the residues defining supertype specificites. The motifs incorporate residues determined on the basis of published data to be recognized by multiple alleles within the supertype. Residues within brackets are additional residues also predicted to be tolerated by multiple alleles within the supertype.

TABLE V

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| Ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |

TABLE V-continued

Frequently Occurring Motifs

| Name | avrg. % identity | Description | Potential Function |
| --- | --- | --- | --- |
| Oxidored_q1 | 32% | NADH-Ubiquinone/plastoquinone (complex I), various chains | membrane associated. Involved in proton translocation across the membrane |
| Efhand | 24% | EF hand | calcium-binding domain, consists of a 12 residue loop flanked on both sides by a 12 residue alpha-helical domain |
| Rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| Fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE VI

Motifs and Post-translational Modifications of 251P5G2

N-glycosylation site
145-148 NVTQ                                   (SEQ ID NO: 54)

N-myristoylation site
168-173 GLFFTL                                 (SEQ ID NO: 55)

Leucine zipper pattern
31-52 LRPERTYLPVCHVALIHMVVLL                   (SEQ ID NO: 56)

TABLE VII

Search Peptides

251P5G2 Variant 1, original sequence, nonamers,
decamers (SEQ ID NO: 57).
MPFISKLVLA SQPTLFSFFS ASSPFLLFLD LRPERTYLPV
CHVALIHMVV LLTMVFLSPQ LFESLNFQND FKYEASFYLR
RVIRVLSICT TCLLGMLQVV NISPSISWLV RFKWKSTIFT
FHLFSWSLSF PVSSSLIFYT VASSNVTQIN LHVSKYCSLF
PINSIIRGLF FTLSLFRDVF LKQIMLFSSV YMMTLIQELQ
EILVPSQPQP LPKDLCRGKS HQHILLPVSF SVGMYKMDFI
ISTSSTLPWA YDRGV 251P5G2 Variant 2
nonamers
VLA SQPTLCSFFS ASSP.                           (SEQ ID NO: 58)

decamers
LVLA SQPTLCSFFS ASSPF.                         (SEQ ID NO: 59)

251P5G2 Variant 3
nonamers
FYLR RVIRDLSICT TCL.                           (SEQ ID NO: 60)

decamers
SFYLR RVIRDLSICT TCLL.                         (SEQ ID NO: 61)

251P5G2 Variant 4
nonamers

TABLE VII-continued

Search Peptides

SICT TCLLDMLQVV NIS.                           (SEQ ID NO: 62)

decamers
LSICT TCLLDMLQVV NISP.                         (SEQ ID NO: 63)

251P5G2 Variant 12
251P5G2 Variant 12a
Nonamers
ISPSISWLIMLFSSVY.                              (SEQ ID NO: 64)

Decamers
NISPSISWLIMLFSSVYM.                            (SEQ ID NO: 65)

15-mers
MLQVVNISPSISWLIMLFSSVYMMTLIQ.                  (SEQ ID NO: 66)

251P5G2 Variant 12b Nonamers (SEQ ID NO: 67).
SHQHILLPTQATFAAATGLWAALTTVSNPSRADPVTWRKEPAVLPCCNLE
KGSWLSFPGTAARKEFSTTLTGHSALSLSSSRALPGSLPAFADLPRSCPE
SEQSATPAGAFLLGWERVVQRRLEVPRPQAAPATSATPSRDPSPPCHQRR
DAACLRAQGLTRAFQVVHLAPTAPDGGAGCPPSRNSYRLTHVRCAQGLEA
ASANLPGAPGRSSSCALRYRSGPSVSSAPSPAEPPAHQRLLFLPRAPQAV
SGPQEQPSEEALGVGSLSVFQLHLIQCIPNLSYPLVLRHIPEILKFSEKE
TGGGILGLELPATAARLSGLNSIMQIKEFEELVKLHSLSHKVIQCVFAKK
KNVDKWDDFCLSEGYGHSFLIMKETSTKISGLIQEMGSGKSNVGTWGDYD
DSAFMEPRYHVRREDLDKLHRAAWWGKVPRKDLIVMLRDTDMNKRDKQKR
TALHLASANGNSEVVQLLLDRRCQLNVLDNKKRTALIKAVQCQEDECVLM
LLEHGADGNIQDEYGNTALHYAIYNEDKLMAKALLLYGADIESKNKCGLT
PLLLGVHEQKQEVVKFLIKKKANLNALDRYGRTALILAVCCGSASIVNLL
LEQNVDVSSQDLSGQTAREYAVSSHHHVICELLSDYKEKQMLKISSENSN
PVITILNIKLPLKVEEEIKKHGSNPVGLPENLTNGASAGNGDDGLIPQRK
SRKPENQQFPDTENEEYHSDEQNDTQKQLSEEQNTGISQDEILTNKQKQI
EVAEKEMNSELSLSHKKEEDLLRENSMLREEIAKLRLELDETKHQNQLRE
NKILEEIESVKEKLLKTIQLNEEALTKTKVAGFSLRQLGLAQHAQASVQQ
LCYKWNHTEKTEQQAQEQEVAGFSLRQLGLAQHAQASVQQLCYKWGHTEK
TEQQAQEQGAALRSQIGDPGGVPLSEGGTAAGDQGPGTHLPPREPRASPG
TPSLVRLASGARAAALPPPTGKNGRSPTKQKSVCDSSGWILPVPTFSSGS
FLGRRCPMFDVSPAMRLKSDSNRETHQAFRDKDDLPFFKTQQSPRHTKDL
GQDDRAGVLAPKCRPGTLCHTDTPPHRNADTPPHRHTTTLPHRDTTTSLP
HFHVSAGGVGPTTLGSNREIT Decamers: (SEQ ID NO: 68).
KSHQHILLPTQATFAAATGLWAALTTVSNPSRADPVTWRKEPAVLPCCNL
EKGSWLSFPGTAARKEFSTTLTGHSALSLSSSRALPGSLPAFADLPRSCP

TABLE VII-continued

Search Peptides

ESEQSATPAGAFLLGWERVVQRRLEVPRPQAAPATSATPSRDPSPPCHQR
RDAACLRAQGLTRAFQVVHLAPTAPDGGAGCPPSRNSYRLTHVRCAQGLE
AASANLPGAPGRSSSCALRYRSGPSVSSAPSPAEPPAHQRLLFLPRAPQA
VSGPQEQPSEEALGVGSLSVFQLHLIQCIPNLSYPLVLRHIPEILKFSEK
ETGGGILGLELPATAARLSGLNSIMQIKEFEELVKLHSLSHKVIQCVFAK
KKNVDKWDDFCLSEGYGHSFLIMKETSTKISGLIQEMGSGKSNVGTWGDY
DDSAFMEPRYHVRREDLDKLHRAAWWGKVPRKDLIVMLRDTDMNKRDKQK
RTALHLASANGNSEVVQLLLDRRCQLNVLDNKKRTALIKAVQCQEDECVL
MLLEHGADGNIQDEYGNTALHYAIYNEDKLMAKALLLYGADIESKNKCGL
TPLLLGVHEQKQEVVKFLIKKKANLNALDRYGRTALILAVCCGSASIVNL
LLEQNVDVSSQDLSGQTAREYAVSSHHHVICELLSDYKEKQMLKISSENS
NPVITILNIKLPLKVEEEIKKHGSNPVGLPENLTNGASAGNGDDGLIPQR
KSRKPENQQFPDTENEEYHSDEQNDTQKQLSEEQNTGISQDEILTNKQKQ
IEVAEKEMNSELSLSHKKEEDLLRENSMLREEIAKLRLELDETKHQNQLR
ENKILEEIESVKEKLLKTIQLNEEALTKTKVAGFSLRQLGLAQHAQASVQ
QLCYKWNHTEKTEQQAQEQEVAGFSLRQLGLAQHAQASVQQLCYKWGHTE
KTEQQAQEQGAALRSQIGDPGGVPLSEGGTAAGDQGPGTHLPPREPRASP
GTPSLVRLASGARAAALPPPTGKNGRSPTKQKSVCDSSGWILPVPTFSSG
SFLGRRCPMFDVSPAMRLKSDSNRETHQAFRDKDDLPFFKTQQSPRHTKD
LGQDDRAGVLAPKCRPGTLCHTDTPPHRNADTPPHRHTTTLPHRDTTTSL
PHFHVSAGGVGPTTLGSNREITDLCRGKSHQHILLPTQATFAAATGLWAA
LTTVSNPSRADPVTWRKEPAVLPCCNLEKGSWLSFPGTAARKEFSTTLTG
HSALSLSSSRALPGSLPAFADLPRSCPESEQSATPAGAFLLGWERVVQRR
LEVPRPQAAPATSATPSRDPSPPCHQRRDAACLRAQGLTRAFQVVHLAPT
APDGGAGCPPSRNSYRLTHVRCAQGLEAASANLPGAPGRSSSCALRYRSG
PSVSSAPSPAEPPAHQRLLFLPRAPQAVSGPQEQPSEEALGVGSLSVFQL
HLIQCIPNLSYPLVLRHIPEILKFSEKETGGGILGLELPATAARLSGLNS
IMQIKEFEELVKLHSLSHKVIQCVFAKKKNVDKWDDFCLSEGYGHSFLIM
KETSTKISGLIQEMGSGKSNVGTWGDYDDSAFMEPRYHVRREDLDKLHRA
AWWGKVPRKDLIVMLRDTDMNKRDKQKRTALHLASANGNSEVVQLLLDRR
CQLNVLDNKKRTALIKAVQCQEDECVLMLLEHGADGNIQDEYGNTALHYA
IYNEDKLMAKALLLYGADIESKNKCGLTPLLLGVHEQKQEVVKFLIKKKA
NLNALDRYGRTALILAVCCGSASIVNLLLEQNVDVSSQDLSGQTAREYAV
SSHHHVICELLSDYKEKQMLKISSENSNPVITILNIKLPLKVEEEIKKHG
SNPVGLPENLTNGASAGNGDDGLIPQRKSRKPENQQFPDTENEEYHSDEQ
NDTQKQLSEEQNTGISQDEILTNKQKQIEVAEKEMNSELSLSHKKEEDLL
RENSMLREEIAKLRLELDETKHQNQLRENKILEEIESVKEKLLKTIQLNE
EALTKTKVAGFSLRQLGLAQHAQASVQQLCYKWNHTEKTEQQAQEQEVAG
FSLRQLGLAQHAQASVQQLCYKWGHTEKTEQQAQEQGAALRSQIGDPGGV
PLSEGGTAAGDQGPGTHLPPREPRASPGTPSLVRLASGARAAALPPPTGK
NGRSPTKQKSVCDSSGWILPVPTFSSGSFLGRRCPMFDVSPAMRLKSDSN
RETHQAFRDKDDLPFFKTQQSPRHTKDLGQDDRAGVLAPKCRPGTLCHTD
TPPHRNADTPPHRHTTTLPHRDTTTSLPHFHVSAGGVGPTTLGSNREIT

Tables VIII-XXI:

TABLE VIII

| Pos | 123456789 | Score |
|---|---|---|
| V1-A1-9mers:251P5G2 Each peptide is a portion of SEQ ID NO: 3; each start position is specified, the length of peptide is 9 amino acids, and the end position for each peptide is the start position plus eight. | | |
| 10 | ASQPTLFSF | 7.500 |
| 245 | STLPWAYDR | 5.000 |
| 205 | PSQPQPLPK | 1.500 |
| 228 | VSFSVGMYK | 1.500 |
| 209 | QPLPKDLCR | 1.250 |
| 72 | KYEASFYLR | 0.900 |
| 243 | TSSTLPWAY | 0.750 |
| 163 | NSIIRGLFF | 0.750 |

TABLE VIII-continued

| Pos | 123456789 | Score |
|---|---|---|
| 21 | ASSPFLLFL | 0.750 |
| 196 | IQELQEILV | 0.675 |
| 65 | LNFQNDFKY | 0.625 |
| 48 | MVVLLTMVF | 0.500 |
| 28 | FLDLRPERT | 0.500 |
| 148 | QINLHVSKY | 0.500 |
| 56 | FLSPQLFES | 0.500 |
| 122 | HLFSWSLSF | 0.500 |
| 231 | SVGMYKMDF | 0.500 |
| 224 | ILLPVSFSV | 0.500 |
| 183 | QIMLFSSVY | 0.500 |
| 20 | SASSPFLLF | 0.500 |
| 199 | LQEILVPSQ | 0.270 |
| 131 | PVSSSLIFY | 0.250 |
| 236 | KMDFIISTS | 0.250 |
| 116 | STIFTFHLF | 0.250 |
| 61 | LFESLNFQN | 0.225 |
| 105 | SISWLVRFK | 0.200 |
| 64 | SLNFQNDFK | 0.200 |
| 128 | LSFPVSSSL | 0.150 |
| 63 | ESLNFQNDF | 0.150 |
| 90 | TTCLLGMLQ | 0.125 |
| 68 | QNDFKYEAS | 0.125 |
| 103 | SPSISWLVR | 0.125 |
| 130 | FPVSSSLIF | 0.125 |
| 32 | RPERTYLPV | 0.113 |
| 54 | MVFLSPQLF | 0.100 |
| 168 | GLFFTLSLF | 0.100 |
| 172 | TLSLFRDVF | 0.100 |
| 174 | SLFRDVFLK | 0.100 |
| 101 | NISPSISWL | 0.100 |
| 158 | SLFPINSII | 0.100 |
| 8 | VLASQPTLF | 0.100 |
| 115 | KSTIFTFHL | 0.075 |
| 132 | VSSSLIFYT | 0.075 |
| 187 | FSSVYMMTL | 0.075 |
| 19 | FSASSPFLL | 0.075 |
| 241 | ISTSSTLPW | 0.075 |

TABLE VIII-continued

| Pos | 123456789 | Score |
|---|---|---|
| 143 | SSNVTQINL | 0.075 |
| 147 | TQINLHVSK | 0.060 |
| 40 | VCHVALIHM | 0.050 |
| 42 | HVALIHMVV | 0.050 |
| 117 | TIFTFHLFS | 0.050 |
| 9 | LASQPTLFS | 0.050 |
| 156 | YCSLFPINS | 0.050 |
| 242 | STSSTLPWA | 0.050 |
| 189 | SVYMMTLIQ | 0.050 |
| 88 | ICTTCLLGM | 0.050 |
| 87 | SICTTCLLG | 0.050 |
| 145 | NVTQINLHV | 0.050 |
| 227 | PVSFSVGMY | 0.050 |
| 178 | DVFLKQIML | 0.050 |
| 91 | TCLLGMLQV | 0.050 |
| 45 | LIHMVVLLT | 0.050 |
| 50 | VLLTMVFLS | 0.050 |
| 104 | PSISWLVRF | 0.030 |
| 173 | LSLFRDVFL | 0.030 |
| 133 | SSSLIFYTV | 0.030 |
| 126 | WSLSFPVSS | 0.030 |
| 159 | LFPINSIIR | 0.025 |
| 35 | RTYLPVCHV | 0.025 |
| 52 | LTMVFLSPQ | 0.025 |
| 73 | YEASFYLRR | 0.025 |
| 146 | VTQINLHVS | 0.025 |
| 162 | INSIIRGLF | 0.025 |
| 207 | QPQPLPKDL | 0.025 |
| 176 | FRDVFLKQI | 0.025 |
| 119 | FTFHLFSWS | 0.025 |
| 89 | CTTCLLGML | 0.025 |
| 139 | YTVASSNVT | 0.025 |
| 169 | LFFTLSLFR | 0.025 |
| 171 | FTLSLFRDV | 0.025 |
| 7 | LVLASQPTL | 0.020 |
| 140 | TVASSNVTQ | 0.020 |
| 136 | LIFYTVASS | 0.020 |
| 185 | MLFSSVYMM | 0.020 |
| 43 | VALIHMVVL | 0.020 |

TABLE VIII-continued

| Pos | 123456789 | Score |
|---|---|---|
| 93 | LLGMLQVVN | 0.020 |
| 150 | NLHVSKYCS | 0.020 |
| 202 | ILVPSQPQP | 0.020 |
| 98 | QVVNISPSI | 0.020 |
| 37 | YLPVCHVAL | 0.020 |
| 44 | ALIHMVVLL | 0.020 |
| 135 | SLIFYTVAS | 0.020 |
| 49 | VVLLTMVFL | 0.020 |
| 198 | ELQEILVPS | 0.020 |
| 188 | SSVYMMTLI | 0.015 |
| 86 | LSICTTCLL | 0.015 |
| 142 | ASSNVTQIN | 0.015 |
| 102 | ISPSISWLV | 0.015 |
| 57 | LSPQLFESL | 0.015 |
| 157 | CSLFPINSI | 0.015 |

V2-A1-
9mers:251P5G2
Each peptide is a portion of SEQ ID NO: 5; each start position is specified, the length of peptide is 9 amino acids, and the end position for each peptide is the start position plus eight.

| Pos | 123456789 | Score |
|---|---|---|
| 3 | ASQPTLCSF | 1.500 |
| 2 | LASQPTLCS | 0.050 |
| 8 | LCSFFSASS | 0.020 |
| 4 | SQPTLCSFF | 0.015 |
| 5 | QPTLCSFFS | 0.013 |
| 6 | PTLCSFFSA | 0.013 |
| 7 | TLCSFFSAS | 0.010 |
| 1 | VLASQPTLC | 0.010 |
| 9 | CSFFSASSP | 0.002 |

V3-A1-
9mers:251P5G2
Each peptide is a portion of SEQ ID NO: 7; each start position is specified, the length of peptide is 9 amino acids, and the end position for each peptide is the start position plus eight.

| Pos | 123456789 | Score |
|---|---|---|
| 7 | IRDLSICTT | 0.025 |
| 9 | DLSICTTCL | 0.010 |
| 6 | VIRDLSICT | 0.005 |
| 4 | RRVIRDLSI | 0.003 |

TABLE VIII-continued

| Pos | 123456789 | Score |
|---|---|---|
| 5 | RVIRDLSIC | 0.001 |
| 8 | RDLSICTTC | 0.001 |
| 2 | YLRRVIRDL | 0.000 |
| 3 | LRRVIRDLS | 0.000 |
| 1 | FYLRRVIRD | 0.000 |

V4-A1-
9mers:251P5G2
Each peptide is a portion of SEQ ID NO: 9; each start position is specified, the length of peptide is 9 amino acids, and the end position for each peptide is the start position plus eight.

| Pos | 123456789 | Score |
|---|---|---|
| 7 | LLDMLQVVN | 1.000 |
| 4 | TTCLLDMLQ | 0.125 |
| 5 | TCLLDMLQV | 0.050 |
| 2 | ICTTCLLDM | 0.050 |
| 3 | CTTCLLDML | 0.025 |
| 6 | CLLDMLQVV | 0.010 |
| 9 | DMLQVVNIS | 0.005 |
| 1 | SICTTCLLD | 0.005 |
| 8 | LDMLQVVNI | 0.001 |

V12A-A1-
9mers:251P5G2
Each peptide is a portion of SEQ ID NO: 25; each start position is specified, the length of peptide is 9 amino acids, and the end position for each peptide is the start position plus eight.

| Pos | 123456789 | Score |
|---|---|---|
| 8 | LIMLFSSVY | 0.500 |
| 4 | SISWLIMLF | 0.500 |
| 1 | ISPSISWLI | 0.015 |
| 2 | SPSISWLIM | 0.013 |
| 7 | WLIMLFSSV | 0.010 |
| 3 | PSISWLIML | 0.008 |
| 5 | ISWLIMLFS | 0.008 |
| 6 | SWLIMLFSS | 0.003 |

V12B-A1-
9mers:251P5G2
Each peptide is a portion of SEQ ID NO: 25; each start position is specified, the length of peptide is 9 amino acids, and the end position for each peptide is the start position plus eight.

| Pos | 123456789 | Score |
|---|---|---|
| 31 | RADPVTWRK | 100.000 |
| 404 | FMEPRYHVR | 45.000 |
| 758 | NSELSLSHK | 27.000 |
| 439 | DTDMNKRDK | 25.000 |
| 524 | YNEDKLMAK | 22.500 |
| 629 | ICELLSDYK | 18.000 |
| 803 | ILEEIESVK | 18.000 |
| 361 | LSEGYGHSF | 13.500 |
| 538 | GADIESKNK | 10.000 |
| 231 | PAEPPAHQR | 9.000 |
| 461 | NSEVVQLLL | 6.750 |
| 709 | FPDTENEEY | 6.250 |
| 179 | GCPPSRNSY | 5.000 |
| 711 | DTENEEYHS | 4.500 |
| 326 | IKEFEELVK | 4.500 |
| 211 | RSSSCALRY | 3.750 |
| 55 | LSFPGTAAR | 3.000 |
| 905 | AQEQGAALR | 2.700 |
| 865 | AQEQEVAGF | 2.700 |
| 645 | SSENSNPVI | 2.700 |
| 924 | LSEGGTAAG | 2.700 |
| 916 | IGDPGGVPL | 2.500 |
| 845 | QASVQQLCY | 2.500 |
| 1031 | DKDDLPFFK | 2.500 |
| 885 | QASVQQLCY | 2.500 |
| 516 | NTALHYAIY | 2.500 |
| 860 | KTEQQAQEQ | 2.250 |
| 38 | RKEPAVLPC | 2.250 |
| 900 | KTEQQAQEQ | 2.250 |
| 964 | AALPPPTGK | 2.000 |
| 5 | ILLPTQATF | 2.000 |
| 1010 | DVSPAMRLK | 2.000 |
| 197 | GLEAASANL | 1.800 |
| 122 | RLEVPRPQA | 1.800 |
| 738 | SQDEILTNK | 1.500 |
| 401 | DSAFMEPRY | 1.500 |
| 729 | LSEEQNTGI | 1.350 |
| 100 | ESEQSATPA | 1.350 |
| 430 | RKDLIVMLR | 1.250 |
| 413 | REDLDKLHR | 1.250 |

TABLE VIII-continued

| Pos | 123456789 | Score |
|---|---|---|
| 1070 | HTDTPPHRN | 1.250 |
| 396 | WGDYDDSAF | 1.250 |
| 819 | QLNEEALTK | 1.000 |
| 43 | VLPCCNLEK | 1.000 |
| 341 | KVIQCVFAK | 1.000 |
| 694 | GLIPQRKSR | 1.000 |
| 540 | DIESKNKCG | 0.900 |
| 719 | SDEQNDTQK | 0.900 |
| 663 | KVEEEIKKH | 0.900 |
| 1022 | NRETHQAFR | 0.900 |
| 786 | RLELDETKH | 0.900 |
| 501 | LLEHGADGN | 0.900 |
| 821 | NEEALTKTK | 0.900 |
| 749 | QIEVAEKEM | 0.900 |
| 806 | EIESVKEKL | 0.900 |
| 600 | LLEQNVDVS | 0.900 |
| 307 | GLELPATAA | 0.900 |
| 1018 | KSDSNRETH | 0.750 |
| 612 | LSGQTAREY | 0.750 |
| 281 | LSYPLVLRH | 0.750 |
| 718 | HSDEQNDTQ | 0.750 |
| 996 | FSSGSFLGR | 0.750 |
| 633 | LSDYKEKQM | 0.750 |
| 867 | EQEVAGFSL | 0.675 |
| 560 | KQEVVKFLI | 0.675 |
| 690 | NGDDGLIPQ | 0.625 |
| 82 | RALPGSLPA | 0.500 |
| 23 | LTTVSNPSR | 0.500 |
| 691 | GDDGLIPQR | 0.500 |
| 1108 | GVGPTTLGS | 0.500 |
| 548 | GLTPLLLGV | 0.500 |
| 139 | SRDPSPPCH | 0.500 |
| 1094 | DTTTSLPHF | 0.500 |
| 1078 | NADTPPHRH | 0.500 |
| 604 | NVDVSSQDL | 0.500 |
| 983 | VCDSSGWIL | 0.500 |

TABLE IX

| Pos | 1234567890 | Score |
|---|---|---|
| | V1-A1-10mers:251P5G2 Each peptide is a portion of SEQ ID NO: 3; each start position is specified, the length of peptide is 10 amino acids, and the end position for each peptide is the start position plus nine. | |
| 28 | FLDLRPERTY | 25.000 |
| 158 | SLFPINSIIR | 5.000 |
| 64 | SLNFQNDFKY | 2.500 |
| 68 | QNDFKYEASF | 2.500 |
| 72 | KYEASFYLRR | 2.250 |
| 173 | LSLFRDVFLK | 1.500 |
| 10 | ASQPTLFSFF | 1.500 |
| 242 | STSSTLPWAY | 1.250 |
| 146 | VTQINLHVSK | 1.000 |
| 230 | FSVGMYKMDF | 0.750 |
| 19 | FSASSPFLLF | 0.750 |
| 102 | ISPSISWLVR | 0.750 |
| 130 | FPVSSSLIFY | 0.625 |
| 168 | GLFFTLSLFR | 0.500 |
| 178 | DVFLKQIMLF | 0.500 |
| 9 | LASQPTLFSF | 0.500 |
| 244 | SSTLPWAYDR | 0.300 |
| 75 | ASFYLRRVIR | 0.300 |
| 63 | ESLNFQNDFK | 0.300 |
| 171 | FTLSLFRDVF | 0.250 |
| 245 | STLPWAYDRG | 0.250 |
| 236 | KMDFIISTSS | 0.250 |
| 204 | VPSQPQPLPK | 0.250 |
| 47 | HMVVLLTMVF | 0.250 |
| 26 | LLFLDLRPER | 0.200 |
| 128 | LSFPVSSSLI | 0.150 |
| 115 | KSTIFTFHLF | 0.150 |
| 16 | FSFFSASSPF | 0.150 |
| 90 | TTCLLGMLQV | 0.125 |
| 116 | STIFTFHLFS | 0.125 |
| 162 | INSIIRGLFF | 0.125 |
| 89 | CTTCLLGMLQ | 0.125 |

TABLE IX-continued

| Pos | 1234567890 | Score |
|---|---|---|
| 58 | SPQLFESLNF | 0.125 |
| 226 | LPVSFSVGMY | 0.125 |
| 56 | FLSPQLFESL | 0.100 |
| 224 | ILLPVSFSVG | 0.100 |
| 7 | LVLASQPTLF | 0.100 |
| 202 | ILVPSQPQPL | 0.100 |
| 101 | NISPSISWLV | 0.100 |
| 227 | PVSFSVGMYK | 0.100 |
| 219 | KSHQHILLPV | 0.075 |
| 188 | SSVYMMTLIQ | 0.075 |
| 163 | NSIIRGLFFT | 0.075 |
| 22 | SSPFLLFLDL | 0.075 |
| 21 | ASSPFLLFLD | 0.075 |
| 142 | ASSNVTQINL | 0.075 |
| 182 | KQIMLFSSVY | 0.075 |
| 147 | TQINLHVSKY | 0.075 |
| 86 | LSICTTCLLG | 0.075 |
| 196 | IQELQEILVP | 0.068 |
| 53 | TMVFLSPQLF | 0.050 |
| 185 | MLFSSVYMMT | 0.050 |
| 87 | SICTTCLLGM | 0.050 |
| 49 | VVLLTMVFLS | 0.050 |
| 105 | SISWLVRFKW | 0.050 |
| 60 | QLFESLNFQN | 0.050 |
| 117 | TIFTFHLFSW | 0.050 |
| 8 | VLASQPTLFS | 0.050 |
| 240 | IISTSSTLPW | 0.050 |
| 45 | LIHMVVLLTM | 0.050 |
| 52 | LTMVFLSPQL | 0.050 |
| 103 | SPSISWLVRF | 0.050 |
| 44 | ALIHMVVLLT | 0.050 |
| 99 | VVNISPSISW | 0.050 |
| 195 | LIQELQEILV | 0.050 |
| 139 | YTVASSNVTQ | 0.050 |
| 223 | HILLPVSFSV | 0.050 |
| 20 | SASSPFLLFL | 0.050 |
| 32 | RPERTYLPVC | 0.045 |
| 104 | PSISWLVRFK | 0.030 |
| 106 | ISWLVRFKWK | 0.030 |
| 221 | HQHILLPVSF | 0.030 |
| 241 | ISTSSTLPWA | 0.030 |
| 132 | VSSSLIFYTV | 0.030 |
| 228 | VSFSVGMYKM | 0.030 |
| 134 | SSLIFYTVAS | 0.030 |
| 167 | RGLFFTLSLF | 0.025 |
| 23 | SPFLLFLDLR | 0.025 |
| 129 | SFPVSSSLIF | 0.025 |
| 209 | QPLPKDLCRG | 0.025 |
| 207 | QPQPLPKDLC | 0.025 |
| 193 | MTLIQELQEI | 0.025 |
| 119 | FTFHLFSWSL | 0.025 |
| 35 | RTYLPVCHVA | 0.025 |
| 176 | FRDVFLKQIM | 0.025 |
| 121 | FHLFSWSLSF | 0.025 |
| 14 | TLFSFFSASS | 0.020 |
| 42 | HVALIHMVVL | 0.020 |
| 198 | ELQEILVPSQ | 0.020 |
| 6 | KLVLASQPTL | 0.020 |
| 93 | LLGMLQVVNI | 0.020 |
| 135 | SLIFYTVASS | 0.020 |
| 225 | LLPVSFSVGM | 0.020 |
| 43 | VALIHMVLL | 0.020 |
| 92 | CLLGMLQVVN | 0.020 |
| 48 | MVVLLTMVFL | 0.020 |
| 37 | YLPVCHVALI | 0.020 |
| 183 | QIMLFSSVYM | 0.020 |
| 172 | TLSLFRDVFL | 0.020 |
| 57 | LSPQLFESLN | 0.015 |

V2-A1-10mers:251P5G2
Each peptide is a portion of SEQ ID NO: 5; each start position is specified, the length of peptide is 10 amino acids, and the end position for each peptide is the start position plus nine.

| Pos | 1234567890 | Score |
|---|---|---|
| 4 | ASQPTLCSFF | 1.500 |
| 10 | CSFFSASSPF | 0.150 |
| 3 | LASQPTLCSF | 0.100 |

TABLE IX-continued

| Pos | 1234567890 | Score |
|---|---|---|
| 2 | VLASQPTLCS | 0.050 |
| 8 | TLCSFFSASS | 0.020 |
| 6 | QPTLCSFFSA | 0.013 |
| 1 | LVLASQPTLC | 0.010 |
| 5 | SQPTLCSFFS | 0.007 |
| 7 | PTLCSFFSAS | 0.003 |
| 9 | LCSFFSASSP | 0.001 |

V3-A1-10mers:251P5G2
Each peptide is a portion of SEQ ID NO: 7; each start position is specified, the length of peptide is 10 amino acids, and the end position for each peptide is the start position plus nine.

| Pos | 1234567890 | Score |
|---|---|---|
| 8 | IRDLSICTTC | 0.025 |
| 10 | DLSICTTCLL | 0.010 |
| 6 | RVIRDLSICT | 0.005 |
| 7 | VIRDLSICTT | 0.001 |
| 9 | RDLSICTTCL | 0.001 |
| 5 | RRVIRDLSIC | 0.001 |
| 4 | LRRVIRDLSI | 0.000 |
| 1 | SFYLRRVIRD | 0.000 |
| 3 | YLRRVIRDLS | 0.000 |
| 2 | FYLRRVIRDL | 0.000 |

V4-A1-10mers:251P5G2
Each peptide is a portion of SEQ ID NO: 9; each start position is specified the length of peptide is 10 amino acids, and the end position for each peptide is the start position plus nine.

| Pos | 1234567890 | Score |
|---|---|---|
| 8 | LLDMLQVVNI | 1.000 |
| 5 | TTCLLDMLQV | 0.125 |
| 4 | CTTCLLDMLQ | 0.125 |
| 2 | SICTTCLLDM | 0.050 |
| 7 | CLLDMLQVVN | 0.020 |
| 3 | ICTTCLLDML | 0.010 |
| 6 | TCLLDMLQVV | 0.010 |
| 1 | LSICTTCLLD | 0.007 |
| 10 | DMLQVVNISP | 0.003 |
| 9 | LDMLQVVNIS | 0.001 |

TABLE IX-continued

| Pos | 1234567890 | Score |
|---|---|---|

V12A-A1-10mers:251P5G2
Each peptide is a portion of SEQ ID NO: 25; each start position is specified the length of peptide is 10 amino acids, and the end position for each peptide is the start position plus nine.

| Pos | 1234567890 | Score |
|---|---|---|
| 8 | WLIMLFSSVY | 0.500 |
| 1 | NISPSISWLI | 0.100 |
| 4 | PSISWLIMLF | 0.075 |
| 2 | ISPSISWLIM | 0.075 |
| 5 | SISWLIMLFS | 0.050 |
| 9 | LIMLFSSVYM | 0.020 |
| 3 | SPSISWLIML | 0.013 |
| 6 | ISWLIMLFSS | 0.008 |
| 7 | SWLIMLFSSV | 0.001 |

V12B-A1-10mers:251P5G2
Each peptide is a portion of SEQ ID NO: 25; each start position is specified, the length of peptide is 10 amino acids, and the end position for each peptide is the start position plus nine.

| Pos | 1234567890 | Score |
|---|---|---|
| 405 | FMEPRYHVRR | 90.000 |
| 759 | NSELSLSHKK | 27.000 |
| 506 | GADGNIQDEY | 25.000 |
| 308 | GLELPATAAR | 18.000 |
| 719 | HSDEQNDTQK | 15.000 |
| 561 | KQEVVKFLIK | 13.500 |
| 43 | AVLPCCNLEK | 10.000 |
| 56 | LSFPGTAARK | 6.000 |
| 821 | LNEEALTKTK | 4.500 |
| 291 | IPEILKFSEK | 4.500 |
| 49 | NLEKGSWLSF | 4.500 |
| 101 | ESEQSATPAG | 2.700 |
| 646 | SSENSNPVIT | 2.700 |
| 529 | KLMAKALLLY | 2.500 |
| 691 | NGDDGLIPQR | 2.500 |
| 917 | IGDPGGVPLS | 2.500 |
| 275 | LIQCIPNLSY | 2.500 |
| 413 | RREDLDKLHR | 2.250 |
| 901 | KTEQQAQEQG | 2.250 |
| 695 | GLIPQRKSRK | 2.000 |

TABLE IX-continued

| Pos | 1234567890 | Score |
|---|---|---|
| 83 | RALPGSLPAF | 2.000 |
| 601 | LLEQNVDVSS | 1.800 |
| 557 | VHEQKQEVVK | 1.800 |
| 776 | NSMLREEIAK | 1.500 |
| 362 | LSEGYGHSFL | 1.350 |
| 868 | EQEVAGFSLR | 1.350 |
| 730 | LSEEQNTGIS | 1.350 |
| 1071 | HTDTPPHRNA | 1.250 |
| 357 | WDDFCLSEGY | 1.250 |
| 440 | DTDMNKRDKQ | 1.250 |
| 179 | AGCPPSRNSY | 1.250 |
| 180 | GCPPSRNSYR | 1.000 |
| 787 | RLELDETKHQ | 0.900 |
| 502 | LLEHGADGNI | 0.900 |
| 805 | LEEIESVKEK | 0.900 |
| 740 | QDEILTNKQK | 0.900 |
| 664 | KVEEEIKKHG | 0.900 |
| 807 | EIESVKEKLL | 0.900 |
| 232 | PAEPPAHQRL | 0.900 |
| 39 | RKEPAVLPCC | 0.900 |
| 750 | QIEVAEKEMN | 0.900 |
| 541 | DIESKNKCGL | 0.900 |
| 123 | RLEVPRPQAA | 0.900 |
| 391 | KSNVGTWGDY | 0.750 |
| 948 | ASPGTPSLVR | 0.750 |
| 610 | SQDLSGQTAR | 0.750 |
| 649 | NSNPVITILN | 0.750 |
| 634 | LSDYKEKQML | 0.750 |
| 1019 | KSDSNRETHQ | 0.750 |
| 462 | NSEVVQLLLD | 0.675 |
| 906 | AQEQGAALRS | 0.675 |
| 493 | CQEDECVLML | 0.675 |
| 628 | HVICELLSDY | 0.500 |
| 990 | WILPVPTFSS | 0.500 |
| 105 | SATPAGAFLL | 0.500 |
| 605 | NVDVSSQDLS | 0.500 |
| 32 | RADPVTWRKE | 0.500 |
| 789 | ELDETKHQNQ | 0.500 |

TABLE IX-continued

| Pos | 1234567890 | Score |
|---|---|---|
| 572 | KANLNALDRY | 0.500 |
| 1011 | DVSPAMRLKS | 0.500 |
| 1040 | KTQQSPRHTK | 0.500 |
| 612 | DLSGQTAREY | 0.500 |
| 88 | SLPAFADLPR | 0.500 |
| 692 | GDDGLIPQRK | 0.500 |
| 478 | VLDNKKRTAL | 0.500 |
| 1073 | DTPPHRNADT | 0.500 |
| 1079 | NADTPPHRHT | 0.500 |
| 539 | GADIESKNKC | 0.500 |
| 704 | KPENQQFPDT | 0.450 |
| 525 | YNEDKLMAKA | 0.450 |
| 342 | KVIQCVFAKK | 0.400 |
| 655 | TILNIKLPLK | 0.400 |
| 845 | AQASVQQLCY | 0.375 |
| 885 | AQASVQQLCY | 0.375 |
| 1098 | TSLPHFHVSA | 0.300 |
| 673 | GSNPVGLPEN | 0.300 |
| 738 | ISQDEILTNK | 0.300 |
| 258 | PSEEALGVGS | 0.270 |
| 925 | LSEGGTAAGD | 0.270 |
| 397 | WGDYDDSAFM | 0.250 |
| 967 | LPPPTGKNGR | 0.250 |
| 1089 | TTLPHRDTTT | 0.250 |
| 1081 | DTPPHRHTTT | 0.250 |
| 984 | VCDSSGWILP | 0.250 |
| 516 | GNTALHYAIY | 0.250 |
| 142 | DPSPPCHQRR | 0.250 |
| 938 | GTHLPPREPR | 0.250 |
| 400 | YDDSAFMEPR | 0.250 |
| 353 | NVDKWDDFCL | 0.250 |
| 140 | SRDPSPPCHQ | 0.250 |
| 469 | LLDRRCQLNV | 0.250 |
| 712 | DTENEEYHSD | 0.225 |
| 679 | LPENLTNGAS | 0.225 |
| 299 | EKETGGGILG | 0.225 |
| 329 | EFEELVKLHS | 0.225 |
| 373 | MKETSTKISG | 0.225 |
| 861 | KTEQQAQEQE | 0.225 |

TABLE IX-continued

| Pos | 1234567890 | Score |
|---|---|---|
| 779 | LREEIAKLRL | 0.225 |
| 858 | HTEKTEQQAQ | 0.225 |
| 731 | SEEQNTGISQ | 0.225 |

TABLE X

| Pos | 123456789 | Score |
|---|---|---|

V1-A2-9mers:251P5G2
Each peptide is a portion of SEQ ID NO: 3; each start position is specified, the length of peptide is 9 amino acids, and the end position for each peptide is the start position plus eight.

| Pos | 123456789 | Score |
|---|---|---|
| 224 | ILLPVSFSV | 2537.396 |
| 191 | YMMTLIQEL | 603.960 |
| 92 | CLLGMLQVV | 242.674 |
| 49 | VVLLTMVFL | 148.730 |
| 184 | IMLFSSVYM | 124.127 |
| 124 | FSWSLSFPV | 100.540 |
| 37 | YLPVCHVAL | 98.267 |
| 164 | SIIRGLFFT | 75.179 |
| 185 | MLFSSVYMM | 71.872 |
| 233 | GMYKMDFII | 57.337 |
| 71 | FKYEASFYL | 57.122 |
| 44 | ALIHMVVLL | 49.134 |
| 182 | KQIMLFSSV | 46.894 |
| 101 | NISPSISWL | 37.157 |
| 85 | VLSICTTCL | 36.316 |
| 67 | FQNDFKYEA | 36.099 |
| 6 | KLVLASQPT | 26.082 |
| 194 | TLIQELQEI | 23.995 |
| 158 | SLFPINSII | 15.827 |
| 53 | TMVFLSPQL | 15.428 |
| 239 | FIISTSSTL | 13.512 |
| 7 | LVLASQPTL | 11.757 |
| 115 | KSTIFTPHL | 10.757 |
| 108 | WLVRFKWKS | 9.770 |
| 35 | RTYLPCHV | 7.110 |
| 28 | FLDLRPERT | 6.719 |
| 21 | ASSPFLLFL | 6.703 |

TABLE X-continued

| Pos | 123456789 | Score |
|---|---|---|
| 235 | YKMDFIIST | 6.312 |
| 50 | VLLTMVFLS | 6.253 |
| 171 | FTLSLFRDV | 6.248 |
| 145 | NVTQINLHV | 6.086 |
| 132 | VSSSLIFYT | 6.067 |
| 102 | ISPSISWLV | 5.789 |
| 173 | LSLFRDVFL | 4.824 |
| 56 | FLSPQLFES | 4.573 |
| 165 | IIRGLFFTL | 4.182 |
| 195 | LIQELQEIL | 4.113 |
| 45 | LIHMVVLLT | 4.006 |
| 47 | HMVVLLTMV | 3.928 |
| 91 | TCLLGMLQV | 3.864 |
| 19 | FSASSPFLL | 3.720 |
| 203 | LVPSQPQPL | 3.178 |
| 60 | QLFESLNFQ | 2.860 |
| 232 | VGMYKMDFI | 2.655 |
| 112 | FKWKSTIFT | 2.173 |
| 14 | TLFSFFSAS | 1.991 |
| 167 | RGLFFTLSL | 1.961 |
| 43 | VALIHMVVL | 1.760 |
| 84 | RVLSICTTC | 1.608 |
| 187 | FSSVYMMTL | 1.475 |
| 78 | YLRRVIRVL | 1.409 |
| 247 | LPWAYDRGV | 1.281 |
| 149 | INLHVSKYC | 1.122 |
| 94 | LGMLQVVNI | 0.985 |
| 23 | SPFLLFLDL | 0.980 |
| 98 | QVVNISPSI | 0.913 |
| 128 | LSFPVSSSL | 0.877 |
| 242 | STSSTLPWA | 0.873 |
| 133 | SSSLIFYTV | 0.863 |
| 117 | TIFTFHLFS | 0.792 |
| 196 | IQELQEILV | 0.767 |
| 174 | SLFRDVFLK | 0.736 |
| 30 | DLRPERTYL | 0.670 |
| 168 | GLFFTLSLF | 0.634 |
| 154 | SKYCSLFPI | 0.619 |

TABLE X-continued

| Pos | 123456789 | Score |
|---|---|---|
| 157 | CSLFPINSI | 0.580 |
| 141 | VASSNVTQI | 0.567 |
| 178 | DVFLKQIML | 0.519 |
| 120 | TFHLFSWSL | 0.423 |
| 81 | RVIRVLSIC | 0.410 |
| 77 | FYLRRVIRV | 0.378 |
| 18 | FFSASSPFL | 0.375 |
| 1 | MPFISKLVL | 0.360 |
| 134 | SSLIFYTVA | 0.280 |
| 38 | LPVCHVALI | 0.266 |
| 25 | FLLFLDLRP | 0.254 |
| 86 | LSICTTCLL | 0.237 |
| 57 | LSPQLFESL | 0.221 |
| 226 | LPVSFSVGM | 0.209 |
| 139 | YTVASSNVT | 0.195 |
| 95 | GMLQVVNIS | 0.188 |
| 119 | FTFHLFSWS | 0.184 |
| 236 | KMDFIISTS | 0.173 |
| 127 | SLSFPVSSS | 0.171 |
| 188 | SSVYMMTLI | 0.157 |
| 180 | FLKQIMLFS | 0.152 |
| 136 | LIFYTVASS | 0.148 |
| 109 | LVRFKWKST | 0.143 |
| 207 | QPQPLPKDL | 0.139 |
| 143 | SSNVTQINL | 0.139 |
| 82 | VIRVLSICT | 0.132 |
| 88 | ICTTCLLGM | 0.127 |
| 40 | VCHVALIHM | 0.127 |
| 8 | VLASQPTLF | 0.127 |
| 220 | SHQHILLPV | 0.111 |
| 41 | CHVALIHMV | 0.111 |
| 3 | FISKLVLAS | 0.108 |
| 225 | LLPVSFSVG | 0.099 |
| 89 | CTTCLLGML | 0.089 |
| 42 | HVALIHMVV | 0.085 |

TABLE X-continued

| Pos | 123456789 | Score |
|---|---|---|

V2-A2-
9mers:251P5G2
Each peptide is a portion of
SEQ ID NO: 5; each start
position is specified, the
length of peptide is 9 amino
acids, and the end position
for each peptide is the start
position plus eight.

| Pos | 123456789 | Score |
|---|---|---|
| 1 | VLASQPTLC | 8.446 |
| 7 | TLCSFFSAS | 0.538 |
| 6 | PTLCSFFSA | 0.062 |
| 4 | SQPTLCSFF | 0.042 |
| 5 | QPTLCSFFS | 0.016 |
| 8 | LCSFFSASS | 0.003 |
| 2 | LASQPTLCS | 0.002 |
| 3 | ASQPTLCSF | 0.001 |
| 9 | CSFFSASSP | 0.000 |

V3-A2-
9mers:251P5G2
Each peptide is a portion of
SEQ ID NO: 7; each start
position is specified, the
length of peptide is 9 amino
acids, and the end position
for each peptide is the start
position plus eight.

| Pos | 123456789 | Score |
|---|---|---|
| 2 | YLRRVIRDL | 3.435 |
| 9 | DLSICTTCL | 1.602 |
| 6 | VIRDLSICT | 0.543 |
| 5 | RVIRDLSIC | 0.410 |
| 8 | RDLSICTTC | 0.026 |
| 7 | IRDLSICTT | 0.002 |
| 4 | RRVIRDLSI | 0.001 |
| 1 | FYLRRVIRD | 0.000 |
| 3 | LRRVIRDLS | 0.000 |

V4-A2-
9mers:251P5G2
Each peptide is a portion of
SEQ ID NO: 9; each start
position is specified, the
length of peptide is 9 amino
acids, and the end position
for each peptide is the start
position plus eight.

| Pos | 123456789 | Score |
|---|---|---|
| 6 | CLLDMLQVV | 994.963 |
| 5 | TCLLDMLQV | 3.864 |
| 3 | CTTCLLDML | 0.334 |
| 8 | LDMLQVVNI | 0.210 |
| 2 | ICTTCLLDM | 0.127 |
| 7 | LLDMLQVVN | 0.021 |

TABLE X-continued

| Pos | 123456789 | Score |
|---|---|---|
| 9 | DMLQVVNIS | 0.014 |
| 1 | SICTTCLLD | 0.002 |
| 4 | TTCLLDMLQ | 0.000 |

V12A-A2-
9mers:251P5G2
Each peptide is a portion of SEQ ID NO: 25; each start position is specified, the length of peptide is 9 amino acids, and the end position for each peptide is the start position plus eight.

| Pos | 123456789 | Score |
|---|---|---|
| 7 | WLIMLFSSV | 607.884 |
| 1 | ISPSISWLI | 0.868 |
| 8 | LIMLFSSVY | 0.100 |
| 5 | ISWLIMLFS | 0.087 |
| 4 | SISWLIMLF | 0.024 |
| 2 | SPSISWLIM | 0.023 |
| 3 | PSISWLIML | 0.007 |
| 6 | SWLIMLFSS | 0.001 |

V12B-A2-
9mers:251P5G2
Each peptide is a portion of SEQ ID NO: 25; each start position is specified, the length of peptide is 9 amino acids, and the end position for each peptide is the start position plus eight.

| Pos | 123456789 | Score |
|---|---|---|
| 599 | LLLEQNVDV | 1793.677 |
| 18 | GLWAALTTV | 1327.748 |
| 802 | KILEEIESV | 572.255 |
| 467 | LLLDRRCQL | 550.915 |
| 242 | FLPRAPQAV | 319.939 |
| 528 | KLMAKALLL | 276.643 |
| 334 | KLHSLSHKV | 243.432 |
| 548 | GLTPLLLGV | 159.970 |
| 566 | FLIKKKANL | 98.267 |
| 111 | FLLGWERVV | 97.070 |
| 266 | SLSVFQLHL | 81.177 |
| 261 | ALGVGSLSV | 69.552 |
| 159 | GLTRAFQVV | 54.181 |
| 327 | KEFEELVKL | 50.726 |
| 6 | LLPTQATFA | 46.451 |
| 270 | FQLHLIQCI | 41.407 |
| 533 | ALLLYGADI | 38.601 |
| 369 | FLIMKETST | 34.279 |
| 498 | VLMLLEHGA | 31.249 |
| 305 | ILGLELPAT | 29.137 |
| 777 | MLREEIAKL | 26.027 |
| 555 | GVHEQKQEV | 24.952 |
| 54 | WLSFPGTAA | 22.853 |
| 345 | CVFAKKKNV | 22.517 |
| 1098 | SLPHFHVSA | 18.878 |
| 742 | ILTNKQKQI | 17.736 |
| 35 | VTWRKEPAV | 13.630 |
| 285 | LVLRHIPEI | 13.206 |
| 850 | QLCYKWNHT | 12.668 |
| 47 | CNLEKGSWL | 11.635 |
| 337 | SLSHKVIQC | 11.426 |
| 654 | TILNIKLPL | 10.868 |
| 418 | KLHRAAWWG | 10.759 |
| 476 | NVLDNKKRT | 9.892 |
| 727 | KQLSEEQNT | 9.784 |
| 158 | QGLTRAFQV | 9.743 |
| 427 | KVPRKDLIV | 8.733 |
| 164 | FQVVHLAPT | 7.994 |
| 1089 | TLPHRDTTT | 7.452 |
| 614 | GQTAREYAV | 7.052 |
| 117 | RVVQRRLEV | 6.086 |
| 770 | DLLRENSML | 5.928 |
| 490 | VQCQEDECV | 5.874 |
| 1096 | TTSLPHFHV | 5.603 |
| 378 | KISGLIQEM | 5.499 |
| 755 | KEMNSELSL | 5.379 |
| 652 | VITILNIKL | 4.993 |
| 953 | SLVRLASGA | 4.968 |
| 75 | ALSLSSSRA | 4.968 |
| 818 | IQLNEEALT | 4.752 |
| 620 | YAVSSHHHV | 4.444 |
| 385 | EMGSGKSNV | 3.767 |
| 324 | MQIKEFEEL | 3.428 |
| 796 | NQLRENKIL | 3.286 |
| 644 | ISSENSNPV | 3.165 |
| 1050 | LGQDDRAGV | 3.165 |

TABLE X-continued

| Pos | 123456789 | Score |
|---|---|---|
| 264 | VGSLSVFQL | 3.162 |
| 277 | CIPNLSYPL | 2.937 |
| 9 | TQATFAAAT | 2.871 |
| 597 | VNLLLEQNV | 2.856 |
| 434 | IVMLRDTDM | 2.734 |
| 982 | SVCDSSGWI | 2.676 |
| 325 | QIKEFEELV | 2.555 |
| 304 | GILGLELPA | 2.527 |
| 362 | SEGYGHSFL | 2.285 |
| 784 | KLRLELDET | 2.234 |
| 813 | KLLKTIQLN | 2.220 |
| 522 | AIYNEDKLM | 2.186 |
| 316 | RLSGLNSIM | 2.037 |
| 500 | MLLEHGADG | 1.922 |
| 514 | YGNTALHYA | 1.887 |
| 836 | RQLGLAQHA | 1.864 |
| 876 | RQLGLAQHA | 1.864 |
| 256 | QPSEEALGV | 1.861 |
| 371 | IMKETSTKI | 1.838 |
| 338 | LSHKVIQCV | 1.775 |
| 13 | FAAATGLWA | 1.746 |
| 105 | ATPAGAFLL | 1.721 |
| 273 | HLIQCIPNL | 1.671 |
| 890 | QLCYKWGHT | 1.647 |
| 840 | LAQHAQASV | 1.642 |
| 880 | LAQHAQASV | 1.642 |
| 104 | SATPAGAFL | 1.632 |
| 309 | ELPATAARL | 1.602 |
| 493 | QEDECVLML | 1.567 |
| 559 | QKQEVVKFL | 1.539 |
| 1113 | TLGSNREIT | 1.497 |
| 817 | TIQLNEEAL | 1.439 |
| 510 | IQDEYGNTA | 1.404 |
| 560 | KQEVVKFLI | 1.374 |
| 197 | GLEAASANL | 1.367 |
| 460 | GNSEVVQLL | 1.315 |
| 904 | QAQEQGAAL | 1.216 |
| 1007 | PMFDVSPAM | 1.197 |

TABLE X-continued

| Pos | 123456789 | Score |
|---|---|---|
| 14 | AAATGLWAA | 1.190 |
| 278 | IPNLSYPLV | 1.158 |
| 586 | ILAVCCGSA | 1.098 |
| 68 | TTLTGHSAL | 1.098 |
| 11 | ATFAAATGL | 1.098 |
| 184 | RNSYRLTHV | 1.044 |

TABLE XI

| Pos | 123456789 | Score |
|---|---|---|

V1-A2-
10mers:251P5G2
Each peptide is a portion of SEQ ID NO: 3; each start position is specified, the length of peptide is 10 amino acids, and the end position for each peptide is the start position plus nine.

| Pos | 123456789 | Score |
|---|---|---|
| 119 | FTFHLFSWSL | 143.920 |
| 172 | TLSLFRDVFL | 117.493 |
| 37 | YLPVCHVALI | 110.379 |
| 56 | FLSPQLFESL | 91.487 |
| 6 | KLVLASQPTL | 74.768 |
| 101 | NISPSISWLV | 71.726 |
| 185 | MLFSSVYMMT | 70.310 |
| 195 | LIQELQEILV | 66.657 |
| 108 | WLVRFKWKST | 58.275 |
| 184 | IMLFSSVYMM | 51.908 |
| 93 | LLGMLQVVNI | 40.792 |
| 48 | MVVLLTMVFL | 40.197 |
| 85 | VLSICTTCLL | 36.316 |
| 202 | ILVPSQPQPL | 36.316 |
| 164 | SIIRGLFFTL | 32.369 |
| 225 | LLPVSFSVGM | 32.093 |
| 150 | NLHVSKYCSL | 32.044 |
| 127 | SLSFPVSSSL | 21.362 |
| 44 | ALIHMVVLLT | 17.140 |
| 20 | SASSPFLLFL | 14.262 |
| 246 | TLPWAYDRGV | 13.910 |
| 183 | QIMLFSSVYM | 13.901 |
| 223 | HILLPVSFSV | 6.978 |
| 84 | RVLSICTTCL | 6.916 |
| 60 | QLFESLNFQN | 6.557 |
| 231 | SVGMYKMDFI | 5.658 |

TABLE XI-continued

| Pos | 123456789 | Score |
|---|---|---|
| 43 | VALIHMVVLL | 4.292 |
| 194 | TLIQELQEIL | 4.292 |
| 148 | QINLHVSKYC | 3.757 |
| 219 | KSHQHILLPV | 3.655 |
| 163 | NSIIRGLFFT | 3.569 |
| 114 | WKSTIFTFHL | 3.008 |
| 100 | VNISPSISWL | 2.999 |
| 73 | YEASFYLRRV | 2.862 |
| 45 | LIHMVVLLTM | 2.671 |
| 90 | TTCLLGMLQV | 2.222 |
| 206 | SQPQPLPKDL | 2.166 |
| 140 | TVASSNVTQI | 2.100 |
| 193 | MTLIQELQEI | 2.096 |
| 52 | LTMVFLSPQL | 1.866 |
| 97 | LQVVNISPSI | 1.798 |
| 40 | VCHVALIHMV | 1.775 |
| 91 | TCLLGMLQVV | 1.584 |
| 87 | SICTTCLLGM | 1.571 |
| 132 | VSSSLIFYTV | 1.466 |
| 131 | PVSSSLIFYT | 1.052 |
| 14 | TLFSFFSASS | 1.048 |
| 29 | LDLRPERTYL | 1.026 |
| 232 | VGMYKMDFII | 1.019 |
| 11 | SQPTLFSFFS | 0.916 |
| 187 | FSSVYMMTLI | 0.721 |
| 156 | YCSLFPINSI | 0.721 |
| 46 | IHMVVLLTMV | 0.699 |
| 241 | ISTSSTLPWA | 0.697 |
| 8 | VLASQPTLFS | 0.697 |
| 81 | RVIRVLSICT | 0.652 |
| 49 | VVLLTMVFLS | 0.547 |
| 117 | TIFTFHLFSW | 0.506 |
| 123 | LFSWSLSFPV | 0.476 |
| 1 | MPFISKLVLA | 0.469 |
| 228 | VSFSVGMYKM | 0.469 |
| 144 | SNVTQINLHV | 0.454 |
| 64 | SLNFQNDFKY | 0.432 |
| 128 | LSFPVSSSLI | 0.428 |

TABLE XI-continued

| Pos | 123456789 | Score |
|---|---|---|
| 18 | FFSASSPFLL | 0.396 |
| 224 | ILLPVSFSVG | 0.365 |
| 12 | QPTLFSFFSA | 0.357 |
| 76 | SFYLRRVIRV | 0.355 |
| 181 | LKQIMLFSSV | 0.312 |
| 82 | VIRVLSICTT | 0.304 |
| 168 | GLFFTLSLFR | 0.303 |
| 17 | SFFSASSPFL | 0.302 |
| 160 | FPINSIIRGL | 0.295 |
| 96 | MLQVVNISPS | 0.291 |
| 22 | SSPFLLFLDL | 0.265 |
| 137 | IFYTVASSNV | 0.263 |
| 51 | LLTMVFLSPQ | 0.221 |
| 50 | VLLTMVFLSP | 0.178 |
| 135 | SLIFYTVASS | 0.171 |
| 180 | FLKQIMLFSS | 0.160 |
| 142 | ASSNVTQINL | 0.139 |
| 233 | GMYKMDFIIS | 0.134 |
| 109 | LVRFKWKSTI | 0.118 |
| 25 | FLLFLDLRPE | 0.117 |
| 92 | CLLGMLQVVN | 0.113 |
| 174 | SLFRDVFLKQ | 0.105 |
| 67 | FQNDFKYEAS | 0.105 |
| 157 | CSLFPINSII | 0.103 |
| 31 | LRPERTYLPV | 0.101 |
| 26 | LLFLDLRPER | 0.094 |
| 35 | RTYLPVCHVA | 0.091 |
| 191 | YMMTLIQELQ | 0.090 |
| 170 | FFTLSLFRDV | 0.084 |
| 133 | SSSLIFYTVA | 0.076 |
| 236 | KMDFIISTSS | 0.075 |
| 88 | ICTTCLLGML | 0.071 |
| 27 | LFLDLRPERT | 0.065 |
| 237 | MDFIISTSST | 0.065 |
| 136 | LIFYTVASSN | 0.064 |
| 42 | HVALIHMVVL | 0.060 |

TABLE XI-continued

V2-A2-10mers:251P5G2

Each peptide is a portion of SEQ ID NO: 5; each start position is specified, the length of peptide is 10 amino acids, and the end position for each peptide is the start position plus nine.

| Pos | 123456789 | Score |
|---|---|---|
| 1 | LVLASQPTLC | 2.734 |
| 6 | QPTLCSFFSA | 0.357 |
| 8 | TLCSFFSASS | 0.283 |
| 5 | SQPTLCSFFS | 0.241 |
| 2 | VLASQPTLCS | 0.127 |
| 3 | LASQPTLCSF | 0.004 |
| 4 | ASQPTLCSFF | 0.003 |
| 10 | CSFFSASSPF | 0.002 |
| 7 | PTLCSFFSAS | 0.001 |
| 9 | LCSFFSASSP | 0.000 |

V3-A2-10mers:251P5G2

Each peptide is a portion of SEQ ID NO: 7; each start position is specified, the length of peptide is 10 amino acids, and the end position for each peptide is the start position plus nine.

| Pos | 123456789 | Score |
|---|---|---|
| 10 | DLSICTTCLL | 1.602 |
| 7 | VIRDLSICTT | 1.248 |
| 6 | RVIRDLSICT | 0.652 |
| 9 | RDLSICTTCL | 0.110 |
| 2 | FYLRRVIRDL | 0.023 |
| 3 | YLRRVIRDLS | 0.013 |
| 5 | RRVIRDLSIC | 0.001 |
| 8 | IRDLSICTTC | 0.000 |
| 4 | LRRVIRDLSI | 0.000 |
| 1 | SFYLRRVIRD | 0.000 |

V4-A2-10mers:251P5G2

Each peptide is a portion of SEQ ID NO: 9; each start position is specified, the length of peptide is 10 amino acids, and the end position for each peptide is the start position plus nine.

| Pos | 123456789 | Score |
|---|---|---|
| 8 | LLDMLQVVNI | 16.317 |
| 5 | TTCLLDMLQV | 2.222 |
| 6 | TCLLDMLQVV | 1.584 |
| 2 | SICTTCLLDM | 1.571 |
| 7 | CLLDMLQVVN | 0.463 |
| 3 | ICTTCLLDML | 0.267 |
| 10 | DMLQVVNISP | 0.003 |
| 9 | LDMLQVVNIS | 0.001 |
| 4 | CTTCLLDMLQ | 0.000 |
| 1 | LSICTTCLLD | 0.000 |

V12A-A2-10mers:251P5G2

Each peptide is a portion of SEQ ID NO: 25; each start position is specified, the length of peptide is 10 amino acids, and the end position for each peptide is the start position plus nine.

| Pos | 123456789 | Score |
|---|---|---|
| 9 | LIMLFSSVYM | 23.632 |
| 1 | NISPSISWLI | 10.759 |
| 8 | WLIMLFSSVY | 0.534 |
| 3 | SPSISWLIML | 0.321 |
| 5 | SISWLIMLFS | 0.130 |
| 6 | ISWLIMLFSS | 0.092 |
| 7 | SWLIMLFSSV | 0.068 |
| 2 | ISPSISWLIM | 0.038 |
| 4 | PSISWLIMLF | 0.000 |

V12B-A2-10mers:251P5G2

Each peptide is a portion of SEQ ID NO: 25; each start position is specified, the length of peptide is 10 amino acids, and the end position for each peptide is the start position plus nine.

| Pos | 123456789 | Score |
|---|---|---|
| 599 | NLLLEQNVDV | 257.342 |
| 6 | ILLPTQATFA | 171.868 |
| 338 | SLSHKVIQCV | 159.970 |
| 777 | SMLREEIAKL | 131.296 |
| 656 | ILNIKLPLKV | 118.238 |
| 467 | QLLLDRRCQL | 79.041 |
| 820 | QLNEEALTKT | 70.272 |
| 880 | GLAQHAQASV | 69.552 |
| 840 | GLAQHAQASV | 69.552 |
| 7 | LLPTQATFAA | 48.984 |
| 469 | LLDRRCQLNV | 47.295 |
| 729 | QLSEEQNTGI | 42.774 |
| 158 | AQGLTRAFQV | 40.900 |
| 633 | LLSDYKEKQM | 34.627 |
| 644 | KISSENSNPV | 33.472 |
| 241 | LLFLPRAPQA | 31.249 |
| 84 | ALPGSLPAFA | 27.324 |
| 264 | GVGSLSVFQL | 24.935 |
| 324 | IMQIKEFEEL | 24.419 |
| 267 | SLSVFQLHLI | 23.995 |
| 983 | SVCDSSGWIL | 23.566 |

TABLE XI-continued

| Pos | 123456789 | Score |
|---|---|---|
| 325 | MQIKEFEELV | 22.322 |
| 70 | TLTGHSALSL | 21.362 |
| 678 | GLPENLTNGA | 20.369 |
| 660 | KLPLKVEEEI | 17.892 |
| 335 | KLHSLSHKVI | 14.971 |
| 478 | VLDNKKRTAL | 14.526 |
| 278 | CIPNLSYPLV | 14.345 |
| 1059 | VLAPKCRPGT | 12.668 |
| 916 | QIGDPGGVPL | 12.043 |
| 763 | SLSHKKEEDL | 10.468 |
| 597 | IVNLLLEQNV | 10.346 |
| 867 | QEQEVAGFSL | 9.878 |
| 371 | LIMKETSTKI | 9.023 |
| 305 | GILGLELPAT | 8.720 |
| 577 | ALDRYGRTAL | 8.545 |
| 306 | ILGLELPATA | 8.446 |
| 749 | KQIEVAEKEM | 7.228 |
| 511 | IQDEYGNTAL | 6.039 |
| 1096 | TTTSLPHFHV | 5.603 |
| 14 | FAAATGLWAA | 5.475 |
| 217 | ALRYRSGPSV | 5.286 |
| 1050 | DLGQDDRAGV | 5.216 |
| 556 | GVHEQKQEVV | 5.013 |
| 385 | QEMGSGKSNV | 5.004 |
| 878 | QLGLAQHAQA | 4.968 |
| 957 | RLASGARAAA | 4.968 |
| 838 | QLGLAQHAQA | 4.968 |
| 850 | QQLCYKWNHT | 4.752 |
| 353 | NVDKWDDFCL | 4.337 |
| 76 | ALSLSSSRAL | 4.272 |
| 18 | TGLWAALTTV | 3.864 |
| 548 | CGLTPLLLGV | 3.864 |
| 269 | SVFQLHLIQC | 3.699 |
| 403 | SAFMEPRYHV | 3.574 |
| 300 | KETGGGILGL | 3.344 |
| 374 | KETSTKISGL | 3.344 |
| 830 | KVAGFSLRQL | 3.009 |
| 490 | AVQCQEDECV | 2.982 |
| 110 | GAFLLQWERV | 2.977 |
| 510 | NIQDEYGNTA | 2.801 |
| 309 | LELPATAARL | 2.613 |
| 589 | AVCCGSASIV | 2.495 |
| 286 | LVLRHIPEIL | 2.362 |
| 165 | FQVVHLAPTA | 2.317 |
| 529 | KLMAKALLLY | 2.220 |
| 523 | AIYNEDKLMA | 2.186 |
| 904 | QQAQEQGAAL | 2.166 |
| 1042 | QQSPRHTKDL | 2.166 |
| 197 | QGLEAASANL | 2.115 |
| 266 | GSLSVFQLHL | 1.961 |
| 468 | LLLDRRCQLN | 1.922 |
| 533 | KALLLYGADI | 1.876 |
| 105 | SATPAGAFLL | 1.721 |
| 36 | VTWRKEPAVL | 1.716 |
| 744 | LTNKQKQIEV | 1.642 |
| 456 | LASANGNSEV | 1.642 |
| 498 | CVLMLLEHGA | 1.608 |
| 494 | QEDECVLMLL | 1.567 |
| 491 | VQCQEDECVL | 1.510 |
| 428 | KVPRKDLIVM | 1.435 |
| 862 | TEQQAQEQEV | 1.352 |
| 477 | NVLDNKKRTA | 1.319 |
| 159 | QGLTRAFQVV | 1.309 |
| 493 | CQEDECVLML | 1.307 |
| 994 | VPTFSSGSFL | 1.304 |
| 352 | KNVDKWDDFC | 1.254 |
| 363 | SEGYGHSFLI | 1.177 |
| 434 | LIVMLRDTDM | 1.161 |
| 530 | LMAKALLLYG | 1.157 |
| 818 | TIQLNEEALT | 1.025 |
| 990 | WILPVPTFSS | 1.011 |
| 947 | RASPGTPSLV | 0.966 |
| 501 | MLLEHGADGN | 0.942 |
| 600 | LLLEQNVDVS | 0.888 |
| 155 | CLRAQGLTRA | 0.868 |
| 307 | LGLELPATAA | 0.836 |
| 1052 | GQDDRAGVLA | 0.826 |

TABLE XI-continued

| Pos | 123456789 | Score |
|---|---|---|
| 1003 | LGRRCPMFDV | 0.783 |
| 555 | LGVHEQKQEV | 0.772 |

TABLE XII

| Pos | 123456789 | Score |
|---|---|---|

V1-A3-9mers:251P5G2
Each peptide is a portion of SEQ ID NO: 3; each start position is specified, the length of peptide is 9 amino acids, and the end position for each peptide is the start position plus eight.

| Pos | 123456789 | Score |
|---|---|---|
| 174 | SLFRDVFLK | 900.000 |
| 122 | HLFSWSLSF | 60.000 |
| 168 | GLFFTLSLF | 45.000 |
| 233 | GMYKMDFII | 27.000 |
| 64 | SLNFQNDFK | 20.000 |
| 185 | MLFSSVYMM | 9.000 |
| 158 | SLFPINSII | 6.750 |
| 172 | TLSLFRDVF | 6.000 |
| 245 | STLPWAYDR | 4.050 |
| 44 | ALIHMVVLL | 2.700 |
| 224 | ILLPVSFSV | 2.025 |
| 8 | VLASQPTLF | 2.000 |
| 183 | QIMLFSSVY | 1.800 |
| 14 | TLFSFFSAS | 1.800 |
| 228 | VSFSVGMYK | 1.500 |
| 191 | YMMTLIQEL | 1.350 |
| 194 | TLIQELQEI | 1.350 |
| 148 | QINLHVSKY | 1.200 |
| 231 | SVGMYKMDF | 1.200 |
| 54 | MVFLSPQLF | 1.000 |
| 147 | TQINLHVSK | 0.900 |
| 53 | TMVFLSPQL | 0.900 |
| 165 | IIRGLFFTL | 0.810 |
| 95 | GMLQVVNIS | 0.810 |
| 92 | CLLGMLQVV | 0.675 |
| 152 | HVSKYCSLF | 0.600 |
| 37 | YLPVCHVAL | 0.600 |
| 105 | SISWLVRFK | 0.600 |
| 85 | VLSICTTCL | 0.600 |

TABLE XII-continued

| Pos | 123456789 | Score |
|---|---|---|
| 48 | MVVLLTMVF | 0.600 |
| 108 | WLVRKWKS | 0.540 |
| 50 | VLLTMVFLS | 0.540 |
| 47 | HMVVLLTMV | 0.450 |
| 116 | STIFTFHLF | 0.450 |
| 6 | KLVLASQPT | 0.450 |
| 184 | IMLFSSVYM | 0.300 |
| 56 | FLSPQLFES | 0.270 |
| 236 | KMDFIISTS | 0.270 |
| 30 | DLRPERTYL | 0.270 |
| 60 | QLFESLNFQ | 0.225 |
| 35 | RTYLPVCHV | 0.225 |
| 178 | DVFLKQIML | 0.180 |
| 23 | SPFLLFLDL | 0.180 |
| 20 | SASSPFLLF | 0.180 |
| 180 | FLKQIMLFS | 0.180 |
| 135 | SLIFYTVAS | 0.180 |
| 127 | SLSFPVSSS | 0.180 |
| 51 | LLTMVFLSP | 0.180 |
| 11 | SQPTLFSFF | 0.180 |
| 209 | QPLPKDLCR | 0.180 |
| 78 | YLRRVIRVL | 0.135 |
| 101 | NISPISWL | 0.135 |
| 49 | VVLLTMVFL | 0.135 |
| 98 | QVVNISPSI | 0.135 |
| 117 | TIFTFHLFS | 0.120 |
| 131 | PVSSSLIFY | 0.120 |
| 65 | LNFQNDFKY | 0.120 |
| 150 | NLHVSKYCS | 0.120 |
| 72 | KYEASFYLR | 0.108 |
| 28 | FLDLRPERT | 0.100 |
| 239 | FIISTSSTL | 0.090 |
| 7 | LVLASQPTL | 0.090 |
| 195 | LIQELQEIL | 0.090 |
| 45 | LIHNVVLLT | 0.090 |
| 115 | KSTIFTFHL | 0.081 |
| 182 | KQIMLFSSV | 0.081 |
| 103 | SPSISWLVR | 0.080 |
| 73 | YEASFYLRR | 0.072 |

TABLE XII-continued

| Pos | 123456789 | Score |
|---|---|---|
| 164 | SIIRGLFFT | 0.068 |
| 81 | RVIRVLSIC | 0.068 |
| 10 | ASQPTLFSF | 0.068 |
| 42 | HVALIHMVV | 0.060 |
| 145 | NVTQINLHV | 0.060 |
| 1 | MPFISKLVL | 0.060 |
| 136 | LIFYTVASS | 0.060 |
| 130 | FPVSSSLIF | 0.060 |
| 225 | LLPVSFSVG | 0.060 |
| 243 | TSSTLPWAY | 0.060 |
| 25 | FLLFLDLRP | 0.060 |
| 96 | MLQVVNISP | 0.060 |
| 203 | LVPSQPQPL | 0.060 |
| 67 | FQNDFKYEA | 0.054 |
| 107 | SWLVRFKWK | 0.045 |
| 84 | RVLSICTTC | 0.045 |
| 202 | ILVPSQPQP | 0.045 |
| 198 | ELQEILVPS | 0.041 |
| 21 | ASSPFLLFL | 0.041 |
| 169 | LFFTLSLFR | 0.040 |
| 227 | PVSFSVGMY | 0.036 |
| 128 | LSFPVSSSL | 0.034 |
| 205 | PSQPQPLPK | 0.030 |
| 119 | FTFHLFSWS | 0.030 |
| 192 | MMTLIQELQ | 0.030 |
| 163 | NSIIRGLFF | 0.030 |
| 69 | NDFKYEASF | 0.030 |
| 113 | KWKSTIFTF | 0.027 |
| 223 | HILLPVSFS | 0.027 |
| 187 | FSSVYMMTL | 0.027 |
| 38 | LPVCHVALI | 0.027 |
| 3 | FISKLVLAS | 0.024 |

V2-A3-
9mers:251P5G2
Each peptide is a portion of SEQ ID NO: 5; each start position is specified, the length of peptide is 9 amino acids, and the end position for each peptide is the start position plus eight.

| Pos | 123456789 | Score |
|---|---|---|
| 7 | TLCSFFSAS | 0.360 |
| 1 | VLASQPTLC | 0.200 |
| 4 | SQPTLCSFF | 0.060 |
| 3 | ASQPTLCSF | 0.022 |
| 6 | PTLCSFFSA | 0.013 |
| 8 | LCSFFSASS | 0.001 |
| 5 | QPTLCSFFS | 0.001 |
| 2 | LASQPTLCS | 0.001 |
| 9 | CSFFSASSP | 0.001 |

V3-A3-
9mers:251P5G2
Each peptide is a portion of SEQ ID NO: 5; each start position is specified, the length of peptide is 9 amino acids, and the end position for each peptide is the start position plus eight.

| Pos | 123456789 | Score |
|---|---|---|
| 9 | DLSICTTCL | 0.180 |
| 2 | YLRRVIRDL | 0.135 |
| 5 | RVIRDLSIC | 0.045 |
| 6 | VIRDLSICT | 0.020 |
| 4 | RRVIRDLSI | 0.002 |
| 8 | RDLSICTTC | 0.000 |
| 1 | FYLRRVIRD | 0.000 |
| 7 | IRDLSICTT | 0.000 |
| 3 | LRRVIRDLS | 0.000 |

V4-A3-
9mers:251P5G2
Each peptide is a portion of SEQ ID NO: 7; each start position is specified, the length of peptide is 9 amino acids, and the end position for each peptide is the start position plus eight.

| Pos | 123456789 | Score |
|---|---|---|
| 6 | CLLDMLQVV | 0.450 |
| 9 | DMLQVVNIS | 0.081 |
| 3 | CTTCLLDML | 0.045 |
| 7 | LLDMLQVVN | 0.020 |
| 5 | TCLLDMLQV | 0.009 |
| 2 | ICTTCLLDM | 0.006 |
| 1 | SICTTCLLD | 0.004 |
| 8 | LDMLQVVNI | 0.003 |
| 4 | TTCLLDMLQ | 0.002 |

V12A-A3-
9mers:251P5G2
Each peptide is a portion of SEQ ID NO: 25; each start position is specified, the length of peptide is 9 amino acids, and the end position for each peptide is the start position plus eight.

| Pos | 123456789 | Score |
|---|---|---|
| 8 | LIMLFSSVY | 1.800 |
| 7 | WLIMLFSSV | 0.900 |
| 4 | SISWLIMLF | 0.600 |
| 1 | ISPSISWLI | 0.013 |

TABLE XII-continued

| Pos | 123456789 | Score |
|---|---|---|
| 5 | ISWLIMLFS | 0.005 |
| 3 | PSISWLIML | 0.004 |
| 2 | SPSISWLIM | 0.004 |
| 6 | SWLIMLFSS | 0.000 |

V12B-A3-
9mers:251P5G2
Each peptide is a portion of SEQ ID NO: 25; each start position is specified, the length of peptide is 9 amino acids, and the end position for each peptide is the start position plus eight.

| Pos | 123456789 | Score |
|---|---|---|
| 319 | GLNSIMQIK | 135.000 |
| 341 | KVIQCVFAK | 81.000 |
| 552 | LLLGVHEQK | 67.500 |
| 819 | QLNEEALTK | 60.000 |
| 776 | SMLREEIAK | 60.000 |
| 803 | ILEEIESVK | 45.000 |
| 436 | MLRDTDMNK | 40.000 |
| 43 | VLPCCNLEK | 40.000 |
| 655 | ILNIKLPLK | 30.000 |
| 474 | QLNVLDNKK | 20.000 |
| 694 | GLIPQRKSR | 13.500 |
| 771 | LLRENSMLR | 12.000 |
| 529 | LMAKALLLY | 12.000 |
| 342 | VIQCVFAKK | 9.000 |
| 280 | NLSYPLVLR | 9.000 |
| 562 | EVVKFLIKK | 8.100 |
| 154 | CLRAQGLTR | 8.000 |
| 404 | FMEPRYHVR | 6.000 |
| 528 | KLMAKALLL | 5.400 |
| 5 | ILLPTQATF | 4.500 |
| 631 | ELLSDYKEK | 4.500 |
| 83 | ALPGSLPAF | 4.500 |
| 18 | GLWAALTTV | 4.500 |
| 410 | HVRREDLDK | 4.000 |
| 266 | SLSVFQLHL | 3.600 |
| 441 | DMNKRDKQK | 3.000 |
| 382 | LIQEMGSGK | 3.000 |
| 370 | LIMKETSTK | 3.000 |
| 533 | ALLLYGADI | 2.700 |
| 548 | GLTPLLLGV | 2.700 |
| 473 | CQLNVLDNK | 2.025 |

TABLE XII-continued

| Pos | 123456789 | Score |
|---|---|---|
| 738 | SQDEILTNK | 2.025 |
| 695 | LIPQRKSRK | 2.000 |
| 1001 | FLGRRCPMF | 2.000 |
| 661 | PLKVEEEIK | 2.000 |
| 159 | GLTRAFQVV | 1.800 |
| 197 | GLEAASANL | 1.800 |
| 109 | GAFLLGWER | 1.800 |
| 563 | VVKFLIKKK | 1.500 |
| 273 | HLIQCIPNL | 1.350 |
| 31 | RADPVTWRK | 1.350 |
| 777 | MLREEIAKL | 1.350 |
| 337 | SLSHKVIQC | 1.200 |
| 307 | GLELPATAA | 0.900 |
| 467 | LLLDRRCQL | 0.900 |
| 286 | VLRHIPEIL | 0.900 |
| 566 | FLIKKKANL | 0.900 |
| 104 | TQQSPRHTK | 0.900 |
| 628 | VICELLSDY | 0.900 |
| 371 | IMKETSTKI | 0.900 |
| 343 | IQCVFAKKK | 0.900 |
| 237 | HQRLLFLPR | 0.720 |
| 651 | PVITILNIK | 0.675 |
| 964 | AALPPPTGK | 0.675 |
| 535 | LLYGADIES | 0.600 |
| 1098 | SLPHFHVSA | 0.600 |
| 794 | HQNQLRENK | 0.600 |
| 464 | VVQLLLDRR | 0.600 |
| 334 | KLHSLSHKV | 0.600 |
| 463 | EVVQLLLDR | 0.540 |
| 561 | QEVVKFLIK | 0.540 |
| 599 | LLLEQNVDV | 0.450 |
| 784 | KLRLELDET | 0.450 |
| 423 | AWWGKVPRK | 0.450 |
| 261 | ALGVGSLSV | 0.400 |
| 275 | IQCIPNLSY | 0.360 |
| 939 | HLPPREPRA | 0.300 |
| 825 | LTKTKVAGF | 0.300 |
| 498 | VLMLLEHGA | 0.300 |

TABLE XII-continued

| Pos | 123456789 | Score |
|---|---|---|
| 538 | GADIESKNK | 0.300 |
| 316 | RLSGLNSIM | 0.300 |
| 54 | WLSFPGTAA | 0.300 |
| 742 | ILTNKQKQI | 0.300 |
| 122 | RLEVPRPQA | 0.300 |
| 953 | SLVRLASGA | 0.300 |
| 304 | GILGLELPA | 0.270 |
| 770 | DLLRENSML | 0.270 |
| 827 | KTKVAGFSL | 0.270 |
| 654 | TILNIKLPL | 0.270 |
| 560 | KQEVVKFLI | 0.243 |
| 571 | KANLNALDR | 0.240 |
| 886 | ASVQQLCYK | 0.225 |
| 846 | ASVQQLCYK | 0.225 |
| 802 | KILEEIESV | 0.203 |
| 422 | AAWWGKVPR | 0.200 |
| 516 | NTALHYAIY | 0.200 |
| 75 | ALSLSSSRA | 0.200 |
| 23 | LTTVSNPSR | 0.200 |
| 786 | RLELDETKH | 0.200 |
| 242 | FLPRAPQAV | 0.200 |
| 347 | FAKKKNVDK | 0.200 |
| 6 | LLPTQATFA | 0.200 |
| 629 | ICELLSDYK | 0.200 |
| 365 | YGHSFLIMK | 0.180 |
| 418 | KLHRAAWWG | 0.180 |
| 990 | ILPVPTFSS | 0.180 |
| 309 | ELPARAARL | 0.180 |
| 659 | KLPLKVEEE | 0.180 |
| 935 | GPGTHLPPR | 0.180 |
| 179 | GCPPSRNSY | 0.180 |

TABLE XIII

| Pos | 1234567890 | Score |
|---|---|---|
| | V1-A3-10mers:251P5G2 | |

Each peptide is a portion of SEQ ID NO: 3; each start position is specified, the length of peptide is 10 amino acids, and the end position for each peptide is the start position plus nine.

| Pos | 1234567890 | Score |
|---|---|---|
| 168 | GLFFTLSLFR | 120.000 |
| 158 | SLFPINSIIR | 60.000 |
| 26 | LLFLDLRPER | 20.000 |
| 64 | SLNFQNDFKY | 12.000 |
| 47 | HMVVLLTMVF | 6.000 |
| 233 | GMYKMDFIIS | 3.600 |
| 53 | TMVFLSPQLF | 3.000 |
| 184 | IMLFSSVYMM | 2.700 |
| 56 | FLSPQLFESL | 2.700 |
| 6 | KLVLASQPTL | 2.700 |
| 37 | YLPVCHVALI | 1.800 |
| 93 | LLGMLQVVNI | 1.800 |
| 182 | KQIMLFSSVY | 1.620 |
| 185 | MLFSSVYMMT | 1.500 |
| 44 | ALIHMVVLLT | 1.350 |
| 119 | FTFHLFSWSL | 1.350 |
| 202 | ILVPSQPQPL | 1.350 |
| 173 | LSLFRDVFLK | 1.350 |
| 146 | VTQINLHVSK | 1.000 |
| 178 | DVFLKQIMLF | 0.900 |
| 127 | SLSFPVSSSL | 0.900 |
| 194 | TLIQELQEIL | 0.900 |
| 23 | SPFLLFLDLR | 0.900 |
| 174 | SLFRDVFLKQ | 0.900 |
| 164 | SIIRGLFFTL | 0.810 |
| 106 | ISWLVRFKWK | 0.750 |
| 85 | VLSICTTCLL | 0.600 |
| 242 | STSSTLPWAY | 0.600 |
| 28 | FLDLRPERTY | 0.600 |
| 150 | NLHVSKYCSL | 0.600 |
| 225 | LLPVSFSVGM | 0.600 |
| 172 | TLSLFRDVFL | 0.600 |
| 227 | PVSFSVGMYK | 0.600 |
| 14 | TLFSFFSASS | 0.600 |
| 147 | TQINLHVSKY | 0.540 |

TABLE XIII-continued

| Pos | 1234567890 | Score |
|---|---|---|
| 117 | TIFTFHLFSW | 0.450 |
| 171 | FTLSLFRDVF | 0.450 |
| 60 | QLFESLNFQN | 0.450 |
| 204 | VPSQPQPLPK | 0.400 |
| 7 | LVLASQPTLF | 0.300 |
| 95 | GMLQVVNSIP | 0.270 |
| 50 | VLLTMVFLSP | 0.270 |
| 71 | FKYEASFYLR | 0.270 |
| 210 | PLPKDLCRGK | 0.200 |
| 236 | KMDFIISTSS | 0.180 |
| 135 | SLIFYTVASS | 0.180 |
| 180 | FLKQIMLFSS | 0.180 |
| 244 | SSTLPWAYDR | 0.180 |
| 140 | TVASSNVTQI | 0.180 |
| 109 | LVRFKWKSTI | 0.180 |
| 130 | FPVSSSLIFY | 0.180 |
| 122 | HLFSWSLSFP | 0.150 |
| 223 | HILLPVSFSV | 0.135 |
| 224 | ILLPVSFSVG | 0.135 |
| 230 | FSVGMYKMDF | 0.135 |
| 48 | MVVLLTMVFL | 0.135 |
| 101 | NISPSISWLV | 0.135 |
| 8 | VLASQPTLFS | 0.120 |
| 75 | ASFYLRRVIR | 0.100 |
| 115 | KSTIFTFHLF | 0.090 |
| 9 | LASQPTLFSF | 0.090 |
| 231 | SVGMYKMDFI | 0.090 |
| 19 | FSASSPFLLF | 0.090 |
| 84 | RVLSICTTCL | 0.090 |
| 42 | HVALIHMVVL | 0.090 |
| 103 | SPSISWLVRF | 0.090 |
| 51 | LLTMVFLSPQ | 0.090 |
| 105 | SISWLVRFKW | 0.090 |
| 45 | LIHMVVLLTM | 0.090 |
| 35 | RTYLPVCHVA | 0.075 |
| 108 | WLVRFKWKST | 0.075 |
| 72 | KYEASFYLRR | 0.072 |
| 193 | MTLIQELQEI | 0.068 |
| 195 | LIQELQEILV | 0.060 |

TABLE XIII-continued

| Pos | 1234567890 | Score |
|---|---|---|
| 96 | MLQVVNISPS | 0.060 |
| 87 | SICTTCLLGM | 0.060 |

V2-A3-10mers:251P5G2
Each peptide is a portion of SEQ ID NO: 5; each start position is specified, the length of peptide is 10 amino acids, and the end position for each peptide is the start position plus nine.

| Pos | 1234567890 | Score |
|---|---|---|
| 2 | VLASQPTLCS | 0.120 |
| 8 | TLCSFFSASS | 0.120 |
| 10 | CSFFSASSPF | 0.050 |
| 1 | LVLASQPTLC | 0.030 |
| 3 | LASQPTLCSF | 0.030 |
| 6 | QPTLCSFFSA | 0.018 |
| 4 | ASQPTLCSFF | 0.015 |
| 5 | SQPTLCSFFS | 0.004 |
| 7 | PTLCSFFSAS | 0.003 |
| 9 | LCSFFSASSP | 0.000 |

V3-A3-10mers:251P5G2
Each peptide is a portion of SEQ ID NO: 7; each start position is specified, the length of peptide is 10 amino acids, and the end position for each peptide is the start position plus nine.

| Pos | 1234567890 | Score |
|---|---|---|
| 10 | DLSICTTCLL | 0.180 |
| 3 | YLRRVIRDLS | 0.060 |
| 6 | RVIRDLSICT | 0.030 |
| 7 | VIRDLSICTT | 0.015 |
| 4 | LRRVIRDLSI | 0.001 |
| 9 | RDLSICTTCL | 0.001 |
| 1 | SFYLRRVIRD | 0.001 |
| 5 | RRVIRDLSIC | 0.000 |
| 8 | IRDLSICTTC | 0.000 |
| 2 | FYLRRVIRDL | 0.000 |

V4-A3-10mers:251P5G2
Each peptide is a portion of SEQ ID NO: 9; each start position is specified, the length of peptide is 10 amino acids, and the end position for each peptide is the start position plus nine.

| Pos | 1234567890 | Score |
|---|---|---|
| 8 | LLDMLQVVNI | 1.800 |
| 2 | SICTTCLLDM | 0.060 |
| 5 | TTCLLDMLQV | 0.030 |
| 7 | CLLDMLQVVN | 0.030 |
| 10 | DMLQVVNISP | 0.027 |
| 3 | ICTTCLLDML | 0.009 |

TABLE XIII-continued

| Pos | 1234567890 | Score |
|---|---|---|
| 6 | TCLLDMLQVV | 0.005 |
| 4 | CTTCLLDMLQ | 0.002 |
| 1 | LSICTTCLLD | 0.000 |
| 9 | LDMLQVVNIS | 0.000 |

V12A-A3-
10mers:251P5G2
Each peptide is a portion of SEQ ID NO: 25; each start position is specified, the length of peptide is 10 amino acids, and the end position for each peptide is the start position plus nine.

| Pos | 1234567890 | Score |
|---|---|---|
| 8 | WLIMLFSSVY | 18.000 |
| 1 | NISPSISWLI | 0.405 |
| 3 | SPSISWLIML | 0.054 |
| 9 | LIMLFSSVYM | 0.030 |
| 5 | SISWLIMLFS | 0.018 |
| 4 | PSISWLIMLF | 0.005 |
| 6 | ISWLIMLFSS | 0.005 |
| 2 | ISPSISWLIM | 0.002 |
| 7 | SWLIMLFSSV | 0.001 |

V12B-A3-
10mers:251P5G2
Each peptide is a portion of SEQ ID NO: 25; each start position is specified, the length of peptide is 10 amino acids, and the end position for each peptide is the start position plus nine.

| Pos | 1234567890 | Score |
|---|---|---|
| 536 | LLYGADIESK | 225.000 |
| 419 | KLHRAAWWGK | 180.000 |
| 695 | GLIPQRKSRK | 135.000 |
| 382 | GLIQEMGSGK | 90.000 |
| 785 | KLRLELDETK | 60.000 |
| 436 | VMLRDTDMNK | 60.000 |
| 287 | VLRHIPEILK | 60.000 |
| 529 | KLMAKALLLY | 54.000 |
| 342 | KVIQCKFAKK | 40.500 |
| 370 | FLIMKETSTK | 30.000 |
| 803 | KILEEIESVK | 20.250 |
| 405 | FMEPRYHVRR | 18.000 |
| 113 | LLGWERVVQR | 12.000 |
| 308 | GLELPATAAR | 12.000 |
| 574 | NLNALDRYGR | 12.000 |
| 561 | KQEVVKFLIK | 10.800 |
| 43 | AVLPCCNLEK | 9.000 |
| 361 | CLSEGYGHSF | 9.000 |
| 88 | SLPAFADLPR | 8.000 |
| 825 | ALTKTKVAGF | 6.000 |
| 326 | QIKEFEELVK | 6.000 |
| 437 | MLRDTDMNKR | 6.000 |
| 747 | KQKQIEVAEK | 5.400 |
| 1040 | KTQQSPRHTK | 4.500 |
| 655 | TILNIKLPLK | 4.500 |
| 552 | PLLLGVHEQK | 4.500 |
| 778 | MLREEIAKLR | 4.500 |
| 49 | NLEKGSWLSF | 4.000 |
| 55 | WLSFPGTAAR | 4.000 |
| 662 | PLKVEEEIKK | 4.000 |
| 1015 | AMRLKSDSNR | 4.000 |
| 23 | ALTTVSNPSR | 4.000 |
| 771 | DLLRENSMLR | 3.600 |
| 629 | VICELLSDYK | 3.000 |
| 262 | ALFVGSLSVF | 3.000 |
| 423 | AAWWGKVPRK | 3.000 |
| 333 | LVKLHSLSHK | 3.000 |
| 343 | VIQCVFAKKK | 3.000 |
| 660 | KLPLKVEEEI | 2.700 |
| 1008 | PMFDVSPAMR | 2.000 |
| 475 | QLNVLDNKKR | 2.000 |
| 954 | SLVRLASGAR | 1.800 |
| 324 | IMQIKEFEEL | 1.800 |
| 70 | TLTGHSALSL | 1.800 |
| 828 | KTKVAGFSLR | 1.800 |
| 160 | GLTRAFQVVH | 1.800 |
| 819 | IQLNEEALTK | 1.800 |
| 264 | GVGSLSVFQL | 1.620 |
| 777 | SMLREEIAKL | 1.350 |
| 275 | LIQCIPNLSY | 1.200 |
| 281 | NLSYPLVLRH | 1.200 |
| 442 | DMNKRDKQKR | 1.200 |
| 852 | LCYKWNHTEK | 1.000 |
| 892 | LCYKWGHTEK | 1.000 |
| 241 | LLFLPRAPQA | 1.000 |
| 729 | QLSEEQNTGI | 0.900 |
| 678 | GLPENLTNGA | 0.900 |

TABLE XIII-continued

| Pos | 1234567890 | Score |
|---|---|---|
| 938 | GTHLPPREPR | 0.900 |
| 628 | HVICELLSDY | 0.900 |
| 335 | KLHSLSHKVI | 0.900 |
| 267 | SLSVFQLHLI | 0.900 |
| 474 | CQLNVLDNKK | 0.900 |
| 467 | QLLLDRRCQL | 0.900 |
| 562 | QEVVKFLIKK | 0.810 |
| 56 | LSFPGTAARK | 0.750 |
| 563 | EVVKFLIKKK | 0.675 |
| 651 | NPVITILNIK | 0.675 |
| 395 | GTWGDYDDSA | 0.675 |
| 840 | GLAQHAQASV | 0.600 |
| 291 | IPEILKFSEK | 0.600 |
| 7 | LLPTQATFAA | 0.600 |
| 478 | VLDNKKRTAL | 0.600 |
| 880 | GLAQHAQASV | 0.600 |
| 19 | GLWAALTTVS | 0.600 |
| 577 | ALDRYGRTAL | 0.600 |
| 763 | SLSHKKEEDL | 0.600 |
| 365 | GYGHSFLIMK | 0.540 |
| 473 | RCQLNVLDNK | 0.450 |
| 6 | ILLPTQATFA | 0.450 |
| 338 | SLSHKVIQCV | 0.450 |
| 549 | GLTPLLLGVH | 0.405 |
| 469 | LLDRRCQLNV | 0.400 |
| 656 | ILNIKLPLKV | 0.400 |
| 119 | VVQRRLEVPR | 0.400 |
| 520 | LHYAIYNEDK | 0.300 |
| 84 | ALPGSLPAFA | 0.300 |
| 875 | SLRQLGLQH | 0.300 |
| 155 | CLRAQGLTRA | 0.300 |
| 776 | NSMLREEIAK | 0.300 |
| 5 | HILLPTQATF | 0.300 |
| 661 | LPLKVEEEIK | 0.300 |
| 964 | AAALPPPTGK | 0.300 |
| 886 | QASVQQLCYK | 0.300 |
| 599 | NLLLEQNVDV | 0.300 |
| 846 | QASVQQLCYK | 0.300 |

TABLE XIII-continued

| Pos | 1234567890 | Score |
|---|---|---|
| 835 | SLRQLGLAQH | 0.300 |
| 269 | SVFQLHLIQC | 0.300 |
| 341 | HKVIQCVFAK | 0.270 |
| 506 | GADGNIQDEY | 0.270 |
| 464 | EVVQLLLDRR | 0.270 |

TABLE XIV

| Pos | 123456789 | Score |
|---|---|---|
| V1-A11- 9mers:251P5G2 Each peptide is a portion of SEQ ID NO: 3; each start position is specified, the length of peptide is 9 amino acids, and the end position for each peptide is the start position plus eight. | | |
| 174 | SLFRDVFLK | 2.400 |
| 147 | TQINLHVSK | 0.900 |
| 245 | STLPWAYDR | 0.600 |
| 72 | KYEASFYLR | 0.480 |
| 64 | SLNFQNDFK | 0.400 |
| 169 | LFFTLSLFR | 0.160 |
| 209 | QPLPKDLCR | 0.120 |
| 159 | LFPINSIIR | 0.080 |
| 103 | SPSISWLVR | 0.080 |
| 76 | SFYLRRVIR | 0.080 |
| 228 | VSFSVGMYK | 0.080 |
| 233 | GMYKMDFII | 0.072 |
| 35 | RTYLPVCHV | 0.060 |
| 27 | LFLDLRPER | 0.060 |
| 48 | MVVLLTMVF | 0.060 |
| 231 | SVGMYKMDF | 0.040 |
| 54 | MVFLSPQLF | 0.040 |
| 42 | HVALIHMVV | 0.040 |
| 105 | SISWLVRFK | 0.040 |
| 145 | NVTQINLHV | 0.040 |
| 98 | QVVNISPSI | 0.030 |
| 49 | VVLLTMVFL | 0.030 |
| 7 | LVLASQPTL | 0.030 |
| 182 | KQIMLFSSV | 0.027 |
| 178 | DVFLKQIML | 0.024 |
| 168 | GLFFTLSLF | 0.024 |
| 73 | YEASFYLRR | 0.024 |

TABLE XIV-continued

| Pos | 123456789 | Score |
|---|---|---|
| 203 | LVPSQPQPL | 0.020 |
| 152 | HVSKYCSLF | 0.020 |
| 211 | LPKDLCRGK | 0.020 |
| 224 | ILLPVSFSV | 0.018 |
| 122 | HLFSWSLSF | 0.016 |
| 185 | MLFSSVYMM | 0.016 |
| 107 | SWLVRFKWK | 0.015 |
| 116 | STIFTFHLF | 0.015 |
| 165 | IIRGLFFTL | 0.012 |
| 77 | FYLRRVIRV | 0.012 |
| 67 | FQNDFKYEA | 0.012 |
| 196 | IQELQEILV | 0.012 |
| 32 | RPERTYLPV | 0.012 |
| 242 | STSSTLPWA | 0.010 |
| 89 | CTTCLLGML | 0.010 |
| 81 | RVIRVLSIC | 0.009 |
| 84 | RVLSICTTC | 0.009 |
| 23 | SPFLLFLDL | 0.008 |
| 158 | SLFPINSII | 0.008 |
| 189 | SVYMMTLIQ | 0.008 |
| 183 | QIMLFSSVY | 0.008 |
| 1 | MPFISKLVL | 0.008 |
| 191 | YMMTLIQEL | 0.008 |
| 24 | PFLLFLDLR | 0.006 |
| 92 | CLLGMLQVV | 0.006 |
| 44 | ALIHMVVLL | 0.006 |
| 184 | IMLFSSVYM | 0.006 |
| 118 | IFTFHLFSW | 0.006 |
| 36 | TYLPVCHVA | 0.006 |
| 194 | TLIQELQEI | 0.006 |
| 91 | TCLLGMLQV | 0.006 |
| 239 | FIISTSSTL | 0.006 |
| 111 | RFKWKSTIF | 0.006 |
| 11 | SQPTLFSFF | 0.006 |
| 47 | HMVVLLTMV | 0.006 |
| 179 | VFLKQIMLF | 0.006 |
| 130 | FPVSSSLIF | 0.006 |
| 53 | TMVFLSPQL | 0.006 |

TABLE XIV-continued

| Pos | 123456789 | Score |
|---|---|---|
| 13 | PTLFSFFSA | 0.005 |
| 205 | PSQPQPLPK | 0.004 |
| 148 | QINLHVSKY | 0.004 |
| 40 | VCHVALIHM | 0.004 |
| 39 | PVCHVALIH | 0.004 |
| 172 | TLSLFRDVF | 0.004 |
| 131 | PVSSSLIFY | 0.004 |
| 229 | SFSVGMYKM | 0.004 |
| 120 | TFHLFSWSL | 0.004 |
| 37 | YLPVCHVAL | 0.004 |
| 88 | ICTTCLLGM | 0.004 |
| 8 | VLASQPTLF | 0.004 |
| 195 | LIQELQEIL | 0.004 |
| 138 | FYTVASSNV | 0.004 |
| 85 | VLSICTTCL | 0.004 |
| 17 | SFFSASSPF | 0.004 |
| 20 | SASSPFLLF | 0.004 |
| 101 | NISPSISWL | 0.004 |
| 226 | LPVSVSVGM | 0.003 |
| 38 | LPVCHVALI | 0.003 |
| 43 | VALIHMVVL | 0.003 |
| 193 | MTLIQELQE | 0.003 |
| 65 | LNFQNDFKY | 0.002 |
| 99 | VVNISPSIS | 0.002 |
| 52 | LTMVFLSPQ | 0.002 |
| 90 | TTCLLGMLQ | 0.002 |
| 119 | FTFHLFSWS | 0.002 |
| 141 | VASSNVTQI | 0.002 |
| 215 | LCRGKSHQH | 0.002 |
| 140 | TVASSNVTQ | 0.002 |
| 18 | FFSASSPFL | 0.002 |
| 227 | PVSFSVGMY | 0.002 |
| 129 | SFPVSSSLI | 0.002 |
| 80 | RRVIRVLSI | 0.002 |
| 59 | PQLFESLNF | 0.002 |

TABLE XIV-continued

| Pos | 123456789 | Score |
|---|---|---|
| V2-A11-9mers:251P5G2 Each peptide is a portion of SEQ ID NO: 5; each start position is specified, the length of peptide is 9 amino acids, and the end position for each peptide is the start position plus eight. | | |
| 4 | SQPTLCSFF | 0.006 |
| 6 | PTLCSFFSA | 0.005 |
| 5 | QPTLCSFFS | 0.001 |
| 7 | TLCSFFSAS | 0.000 |
| 1 | VLASQPTLC | 0.000 |
| 2 | LASQPTLCS | 0.000 |
| 8 | LCSFFSASS | 0.000 |
| 3 | ASQPTLCSF | 0.000 |
| 9 | CSFFSASSP | 0.000 |
| V3-A11-9mers:251P5G2 Each peptide is a portion of SEQ ID NO: 7; each start position is specified, the length of peptide is 9 amino acids, and the end position for each peptide is the start position plus eight. | | |
| 5 | RVIRDLSIC | 0.009 |
| 4 | RRVIRDLSI | 0.002 |
| 1 | FYLRRVIRD | 0.001 |
| 9 | DLSICTTCL | 0.001 |
| 6 | VIRDLSICT | 0.001 |
| 2 | YLRRVIRDL | 0.000 |
| 8 | RDLSICTTC | 0.000 |
| 7 | IRDLSICTT | 0.000 |
| 3 | LRRIVRDLS | 0.000 |
| V4-A11-9mers:251P5G2 Each peptide is a portion of SEQ ID NO: 9; each start position is specified, the length of peptide is 9 amino acids, and the end position for each peptide is the start position plus eight. | | |
| 3 | CTTCLLDML | 0.010 |
| 5 | TCLLDMLQV | 0.006 |
| 6 | CLLDMLQVV | 0.006 |
| 2 | ICTTCLLDM | 0.004 |
| 4 | TTCLLDMLQ | 0.002 |
| 1 | SICTTCLLD | 0.001 |
| 7 | LLDMLQVVN | 0.000 |
| 8 | LDMLQVVNI | 0.000 |
| 9 | DMLQVVNIS | 0.000 |

TABLE XIV-continued

| Pos | 123456789 | Score |
|---|---|---|
| V12A-A11-9mers:251P5G2 Each peptide is a portion of SEQ ID NO: 25; each start position is specified, the length of peptide is 9 amino acids, and the end position for each peptide is the start position plus eight. | | |
| 8 | LIMLFSSVY | 0.008 |
| 4 | SISWLIMLF | 0.008 |
| 7 | WLIMLFSSV | 0.006 |
| 2 | SPSISWLIM | 0.004 |
| 1 | ISPSISWLI | 0.000 |
| 6 | SWLIMLFSS | 0.000 |
| 5 | ISWLIMLFS | 0.000 |
| 3 | PSISWLIML | 0.000 |
| V12B-A11-9mers:251P5G2 Each peptide is a portion SEQ ID NO: 25; each start position is specified, the length of peptide is 9 amino acids, and the end position for each peptide is the start position plus eight. | | |
| 341 | KVIQCVFAK | 27.000 |
| 410 | HVRREDLDK | 4.000 |
| 562 | EVVKFLIKK | 1.800 |
| 31 | RADPVTWRK | 1.200 |
| 776 | SMLREEIAK | 1.200 |
| 319 | GLNSIMQIK | 1.200 |
| 563 | VVKFLIKKK | 1.000 |
| 473 | CQLNVLDNK | 0.900 |
| 370 | LIMKETSTK | 0.800 |
| 436 | MLRDTDMNK | 0.800 |
| 819 | QLNEEALTK | 0.800 |
| 43 | VLPCCNLEK | 0.800 |
| 738 | SQDEILTNK | 0.600 |
| 794 | HQNQLRENK | 0.600 |
| 1040 | TQQSPRHTK | 0.600 |
| 552 | LLLGVHEQK | 0.600 |
| 109 | GAFLLGWER | 0.480 |
| 803 | ILEEIESVK | 0.400 |
| 852 | CYKWNHTEK | 0.400 |
| 474 | QLNVLDNKK | 0.400 |
| 464 | VVQLLLDRR | 0.400 |

TABLE XIV-continued

| Pos | 123456789 | Score |
|---|---|---|
| 954 | LVRLASGAR | 0.400 |
| 382 | LIQEMGSGK | 0.400 |
| 695 | LIPQRKSRK | 0.400 |
| 342 | VIQCVFAKK | 0.400 |
| 520 | HYAIYNEDK | 0.400 |
| 655 | ILNIKLPLK | 0.400 |
| 892 | CYKWGHTEK | 0.400 |
| 536 | LYGADIESK | 0.400 |
| 463 | EVVQLLLDR | 0.360 |
| 651 | PVITILNIK | 0.300 |
| 343 | IQCVFAKKK | 0.300 |
| 964 | AALPPPTGK | 0.300 |
| 538 | GADIESKNK | 0.300 |
| 237 | HQRLLFLPR | 0.240 |
| 571 | KANLNALDR | 0.240 |
| 635 | DYKEKQMLK | 0.240 |
| 23 | LTTVSNPSR | 0.200 |
| 347 | FAKKKNVDK | 0.200 |
| 56 | SFPGTAARK | 0.200 |
| 629 | ICELLSDYK | 0.200 |
| 117 | RVVQRRLEV | 0.180 |
| 694 | GLIPQRKSR | 0.180 |
| 561 | QEVVKFLIK | 0.180 |
| 154 | CLRAQGLTR | 0.160 |
| 771 | LLRENSMLR | 0.160 |
| 935 | GPGTHLPPR | 0.120 |
| 119 | VQRRLEVPR | 0.120 |
| 1110 | GPTTLGSNR | 0.120 |
| 905 | AQEQGAALR | 0.120 |
| 427 | KVPRKDLIV | 0.120 |
| 827 | KTKVAGFSL | 0.090 |
| 631 | ELLSDYKEK | 0.090 |
| 759 | SELSLSHKK | 0.090 |
| 422 | AAWGKVPR | 0.080 |
| 404 | FMEPRYHVR | 0.080 |
| 948 | SPGTPSLVR | 0.080 |
| 88 | LPAFADLPR | 0.080 |
| 280 | NLSYPLVLR | 0.080 |

TABLE XIV-continued

| Pos | 123456789 | Score |
|---|---|---|
| 524 | YNEDKLMAK | 0.080 |
| 413 | REDLDKLHR | 0.072 |
| 662 | LKVEEEIKK | 0.060 |
| 971 | GKNGRSPTK | 0.060 |
| 1010 | DVSPAMRLK | 0.060 |
| 441 | DMNKRDKQK | 0.060 |
| 74 | SALSLSSSR | 0.060 |
| 555 | GVHEQKQEV | 0.060 |
| 557 | HEQKQEVVK | 0.060 |
| 791 | ETKHQNQLR | 0.060 |
| 560 | KQEVVKFLI | 0.054 |
| 528 | KLMAKALLL | 0.048 |
| 816 | KTIQLNEEA | 0.045 |
| 887 | SVQQLCYKW | 0.040 |
| 423 | AWWGKVPRK | 0.040 |
| 332 | LVKLHSLSH | 0.040 |
| 326 | IKEFEELVK | 0.040 |
| 1008 | MFDVSPAMR | 0.040 |
| 480 | NKKRTALIK | 0.040 |
| 180 | CPPSRNSYR | 0.040 |
| 847 | SVQQLCYKW | 0.040 |
| 287 | LRHIPEILK | 0.040 |
| 1037 | FFKTQQSPR | 0.040 |
| 434 | IVMLRDTDM | 0.040 |
| 419 | LHRAAWWGK | 0.040 |
| 661 | PLKVEEEIK | 0.040 |
| 365 | YGHSFLIMK | 0.040 |
| 614 | GQTAREYAV | 0.036 |
| 447 | KQKRTALHL | 0.036 |
| 304 | GILGLELPA | 0.036 |
| 785 | LRLELDETK | 0.030 |
| 886 | ASVQQLCYK | 0.030 |
| 1024 | ETHQAFRDK | 0.030 |
| 439 | DTDMNKRDK | 0.030 |
| 333 | VKLHSLSHK | 0.030 |
| 846 | ASVQQLCYK | 0.030 |
| 1096 | TTSLPHFHV | 0.030 |
| 105 | ATPAGAFLL | 0.030 |
| 663 | KVEEEIKKH | 0.030 |

TABLE XIV-continued

| Pos | 123456789 | Score |
|---|---|---|
| 821 | NEEALTKTK | 0.030 |
| 450 | RTALHLASA | 0.030 |

TABLE XV

| Pos | 1234567890 | Score |
|---|---|---|
| \multicolumn{3}{c}{V1-A11-10mers:251P5G2 Each peptide is a portion of SEQ ID NO: 3; each start position is specified, the length of peptide is 10 amino acids, and the end position for each peptide is the start position plus nine.} | | |
| 146 | VTQINLHVSK | 1.000 |
| 168 | GLFFTLSLFR | 0.960 |
| 72 | KYEASFYLRR | 0.480 |
| 204 | VPSQPQPLPK | 0.400 |
| 227 | PVSFSVGMYK | 0.400 |
| 158 | SLEPINSIIR | 0.320 |
| 26 | LLFLDLRPER | 0.160 |
| 173 | LSLFRDVFLK | 0.090 |
| 84 | RVLSICTTCL | 0.090 |
| 23 | SPFLLFLDLR | 0.080 |
| 35 | RTYLPVCHVA | 0.060 |
| 99 | VVNISPSISW | 0.040 |
| 119 | FTFHLFSWSL | 0.040 |
| 7 | LVLASQPTLF | 0.030 |
| 48 | MVVLLTMVFL | 0.030 |
| 182 | KQIMLFSSVY | 0.027 |
| 208 | PQPLPKDLCR | 0.024 |
| 117 | TIFTFHLFSW | 0.024 |
| 178 | DVFLKQIMLF | 0.024 |
| 109 | LVRFKWKSTI | 0.020 |
| 140 | TVASSNVTQI | 0.020 |
| 231 | SVGMYKMDFI | 0.020 |
| 242 | STSSTLPWAY | 0.020 |
| 90 | TTCLLGMLQV | 0.020 |
| 42 | HVALIHMVVL | 0.020 |
| 106 | ISWLVRFKWK | 0.020 |
| 52 | LTMVFLSPQL | 0.020 |
| 164 | SIIRGLFFTL | 0.018 |

TABLE XV-continued

| Pos | 1234567890 | Score |
|---|---|---|
| 6 | KLVLASQPTL | 0.018 |
| 81 | RVIRVLSICT | 0.018 |
| 223 | HILLPVSFSV | 0.018 |
| 71 | FKYEASFYLR | 0.016 |
| 171 | FTLSLFRDVF | 0.015 |
| 193 | MTLIQELQEI | 0.015 |
| 47 | HMVVLLTMVF | 0.012 |
| 64 | SLNFQNDFKY | 0.012 |
| 184 | IMLFSSVYMM | 0.012 |
| 105 | SISWLVRFKW | 0.012 |
| 63 | ESLNFQNDFK | 0.009 |
| 49 | VVLLTMVFLS | 0.009 |
| 97 | LQVVNISPSI | 0.009 |
| 147 | TQINLHVSKY | 0.009 |
| 190 | VYMMTLIQEL | 0.008 |
| 87 | SICTTCLLGM | 0.008 |
| 240 | IISTSSTLPW | 0.008 |
| 183 | QIMLFSSVYM | 0.008 |
| 101 | NISPSISWLV | 0.008 |
| 244 | SSTLPWAYDR | 0.008 |
| 54 | MVFLSPQLFE | 0.008 |
| 45 | LIHMVVLLTM | 0.008 |
| 189 | SVYMMTLIQE | 0.008 |
| 75 | ASFYLRRVIR | 0.008 |
| 102 | ISPSISWLVR | 0.008 |
| 195 | LIQELQEILV | 0.008 |
| 76 | SFYLRRVIRV | 0.008 |
| 202 | ILVPSQPQPL | 0.006 |
| 9 | LASQPTLFSF | 0.006 |
| 53 | TMVFLSPQLF | 0.006 |
| 130 | FPVSSSLIFY | 0.006 |
| 36 | TYLPVCHVAL | 0.006 |
| 221 | HQHILLPVSF | 0.006 |
| 194 | TLIQELQEIL | 0.006 |
| 38 | LPVCHVALIH | 0.006 |
| 123 | LFSWSLSFPV | 0.006 |
| 18 | FFSASSPFLL | 0.006 |
| 12 | QPTLFSFFSA | 0.006 |

TABLE XV-continued

| Pos | 1234567890 | Score |
|---|---|---|
| 233 | GMYKMDFIIS | 0.005 |
| 210 | PLPKDLCRGK | 0.004 |
| 1 | MPFISKLVLA | 0.004 |
| 66 | NFQNDFKYEA | 0.004 |
| 172 | TLSLFRDVFL | 0.004 |
| 152 | HVSKYCSLFP | 0.004 |
| 129 | SFPVSSSLIF | 0.004 |
| 56 | FLSPQLFESL | 0.004 |
| 93 | LLGMLQVVNI | 0.004 |
| 17 | SFFSASSPFL | 0.004 |
| 37 | YLPVCHVALI | 0.004 |
| 39 | PVCHVALIHM | 0.004 |
| 20 | SASSPFLLFL | 0.004 |
| 85 | VLSICTTCLL | 0.004 |
| 127 | SLSFPVSSSL | 0.004 |
| 58 | SPQLFESLNF | 0.004 |
| 225 | LLPVSFSVGM | 0.004 |
| 150 | NLHVSKYCSL | 0.004 |
| 186 | LFSSVYMMTL | 0.004 |
| 137 | IFYTVASSNV | 0.004 |
| 95 | GMLQVVNISP | 0.004 |
| 116 | STIFTFHLFS | 0.003 |
| 226 | LPVSFSVGMY | 0.003 |
| 43 | VALIHMVVLL | 0.003 |
| 91 | TCLLGMLQVV | 0.003 |
| 206 | SQPQPLPKDL | 0.003 |
| 98 | QVVNISPSIS | 0.003 |
| 60 | QLFESLNFQN | 0.002 |
| 155 | KYCSLFPINS | 0.002 |
| 156 | YCSLFPINSI | 0.002 |
| 88 | ICTTCLLGML | 0.002 |
| 40 | VCHVALIHMV | 0.002 |
| 215 | LCRGKSHQHI | 0.002 |
| 203 | LVPSQPQPLP | 0.002 |

TABLE XV-continued

| Pos | 1234567890 | Score |
|---|---|---|

V2-A11-
10mers:251P5G2
Each peptide is a portion of
SEQ ID NO: 5; each start
position is specified, the
length of peptide is 10 amino
acids, and the end position
for each peptide is the start
position plus nine.

| 6 | QPTLCSFFSA | 0.006 |
|---|---|---|
| 1 | LVLASQPTLC | 0.003 |
| 3 | LASQPTLCSF | 0.002 |
| 5 | SQPTLCSFFS | 0.002 |
| 2 | VLASQPTLCS | 0.001 |
| 10 | CSFFSASSPF | 0.000 |
| 8 | TLCSFFSASS | 0.000 |
| 9 | LCSFFSASSP | 0.000 |
| 4 | ASQPTLCSFF | 0.000 |
| 7 | PTLCSFFSAS | 0.000 |

V3-A11-
10mers:251P5G2
Each peptide is a portion of
SEQ ID NO: 7; each start
position is specified, the
length of peptide is 10 amino
acids, and the end position
for each peptide is the start
position plus nine.

| 6 | RVIRDLSICT | 0.018 |
|---|---|---|
| 10 | DLSICTTCLL | 0.001 |
| 9 | RDLSICTTCL | 0.001 |
| 1 | SFYLRRVIRD | 0.001 |
| 2 | FYLRRVIRDL | 0.001 |
| 7 | VIRDLSICTT | 0.000 |
| 4 | LRRVIRDLSI | 0.000 |
| 3 | YLRRVIRDLS | 0.000 |
| 5 | RRVIRDLSIC | 0.000 |
| 8 | IRDLSICTTC | 0.000 |

V4-A11-
10mers:251P5G2
Each peptide is a portion of
SEQ ID NO: 9; each start
position is specified, the
length of peptide is 10 amino
acids, and the end position
for each peptide is the start
position plus nine.

| 5 | TTCLLDMLQV | 0.020 |
|---|---|---|
| 2 | SICTTCLLDM | 0.008 |
| 8 | LLDMLQVVNI | 0.004 |
| 6 | TCLLDMLQVV | 0.003 |

TABLE XV-continued

| Pos | 1234567890 | Score |
|---|---|---|
| 3 | ICTTCLLDML | 0.002 |
| 4 | CTTCLLDMLQ | 0.002 |
| 7 | CLLDMLQVVN | 0.001 |
| 10 | DMLQVVNISP | 0.000 |
| 1 | LSICTTCLLD | 0.000 |
| 9 | LDMLQVVNIS | 0.000 |

V12A-A11-10mers:251P5G2
Each peptide is a portion of SEQ ID NO: 25; each start position is specified, the length of peptide is 10 amino acids, and the end position for each peptide is the start position plus nine.

| Pos | 1234567890 | Score |
|---|---|---|
| 9 | LIMLFSSVYM | 0.008 |
| 1 | NISPSISWLI | 0.008 |
| 8 | WLIMLFSSVY | 0.006 |
| 3 | SPSISWLIML | 0.004 |
| 5 | SISWLIMLFS | 0.001 |
| 2 | ISPSISWLIM | 0.000 |
| 7 | SWLIMLFSSV | 0.000 |
| 6 | ISWLIMLFSS | 0.000 |
| 4 | PSISWLIMLF | 0.000 |

V12B-A11-10mers:251P5G2
Each peptide is a portion of SEQ ID NO: 25; each start position is specified, the length of peptide is 10 amino acids, and the end position for each peptide is the start position plus nine.

| Pos | 1234567890 | Score |
|---|---|---|
| 342 | KVIQCVFAKK | 9.000 |
| 43 | AVLPCCNLEK | 6.000 |
| 561 | KQEVVKFLIK | 3.600 |
| 1040 | KTQQSPRHTK | 3.000 |
| 365 | GYGHSFLIMK | 2.400 |
| 419 | KLHRAAWWGK | 2.400 |
| 333 | LVKLHSLSHK | 2.000 |
| 819 | IQLNEEALTK | 1.800 |
| 695 | GLIPQRKSRK | 1.800 |
| 803 | KILEEIESVK | 1.800 |
| 747 | KQKQIEVAEK | 1.800 |
| 382 | GLIQEMGSGK | 1.800 |
| 785 | KLRLELDETK | 1.200 |
| 436 | VMLRDTDMNK | 1.200 |
| 474 | CQLNVLDNKK | 0.900 |
| 287 | VLRHIPEILK | 0.800 |
| 524 | IYNEDKLMAK | 0.800 |
| 536 | LLYGADIESK | 0.800 |
| 326 | QIKEFEELVK | 0.800 |
| 828 | KTKVAGFSLR | 0.600 |
| 655 | TILNIKLPLK | 0.600 |
| 370 | FLIMKETSTK | 0.600 |
| 473 | RCQLNVLDNK | 0.600 |
| 938 | GTHLPPREPR | 0.600 |
| 563 | EVVKFLIKKK | 0.450 |
| 852 | LCYKWNHTEK | 0.400 |
| 119 | VVQRRLEVPR | 0.400 |
| 629 | VICELLSDYK | 0.400 |
| 423 | AAWWGKVPRK | 0.400 |
| 892 | LCYKWGHTEK | 0.400 |
| 661 | LPLKVEEEIK | 0.300 |
| 651 | NPVITILNIK | 0.300 |
| 308 | GLELPATAAR | 0.240 |
| 964 | AAALPPPTGK | 0.200 |
| 291 | IPEILKFSEK | 0.200 |
| 1047 | HTKDLGQDDR | 0.200 |
| 343 | VIQCVFAKKK | 0.200 |
| 347 | VFAKKKNVDK | 0.200 |
| 886 | QASVQQLCYK | 0.200 |
| 846 | QASVQQLCYK | 0.200 |
| 1031 | RDKDDLPFFK | 0.180 |
| 464 | EVVQLLLDRR | 0.180 |
| 264 | GVGSLSVFQL | 0.180 |
| 562 | QEVVKFLIKK | 0.180 |
| 88 | SLPAFADLPR | 0.160 |
| 574 | NLNALDRYGR | 0.160 |
| 154 | ACLRAQGLTR | 0.120 |
| 610 | SQDLSGQTAR | 0.120 |
| 422 | RAAWWGKVPR | 0.120 |
| 954 | SLVRLASGAR | 0.120 |
| 148 | HQRRDAACLR | 0.120 |
| 180 | GCPPSRNSYR | 0.120 |

TABLE XV-continued

| Pos | 1234567890 | Score |
|---|---|---|
| 428 | KVPRKDLIVM | 0.120 |
| 808 | IESVKEKLLK | 0.120 |
| 341 | HKVIQCVFAK | 0.090 |
| 635 | SDYKEKQMLK | 0.080 |
| 405 | FMEPRYHVRR | 0.080 |
| 23 | ALTTVSNPSR | 0.080 |
| 55 | WLSFPGTAAR | 0.080 |
| 404 | AFMEPRYHVR | 0.080 |
| 662 | PLKVEEEIKK | 0.080 |
| 1015 | AMRLKSDSNR | 0.080 |
| 113 | LLGWERVVQR | 0.080 |
| 996 | TFSSGSFLGR | 0.080 |
| 437 | MLRDTDMNKR | 0.080 |
| 776 | NSMLREEIAK | 0.080 |
| 771 | DLLRENSMLR | 0.072 |
| 794 | KHQNQLRENK | 0.060 |
| 973 | KNGRSPTKQK | 0.060 |
| 692 | GDDGLIPQRK | 0.060 |
| 410 | YHVRREDLDK | 0.060 |
| 552 | PLLLGVHEQK | 0.060 |
| 1056 | RAGVLAPKCR | 0.060 |
| 353 | NVDKWDDFCL | 0.060 |
| 395 | GTWGDYDDSA | 0.060 |
| 556 | GVHEQKQEVV | 0.060 |

TABLE XVI

| Pos | 123456789 | Score |
|---|---|---|
| \multicolumn{3}{|c|}{V1-A24-9mers:251P5G2 Each peptide is a portion of SEQ ID NO: 3; each start position is specified, the length of peptide is 9 amino acids, and the end position for each peptide is the start position plus eight.} | | |
| 120 | TFHLFSWSL | 20.000 |
| 111 | RFKWKSTIF | 20.000 |
| 18 | FFSASSPFL | 20.000 |
| 179 | VFLKQIMLF | 15.000 |
| 155 | KYCSLFPIN | 14.400 |
| 36 | TYLPVCHVA | 12.600 |

TABLE XVI-continued

| Pos | 123456789 | Score |
|---|---|---|
| 167 | RGLFFTLSL | 12.000 |
| 17 | SFFSASSPF | 10.000 |
| 191 | YMMTLIQEL | 9.504 |
| 207 | QPQPLPKDL | 8.640 |
| 57 | LSPQLFESL | 8.640 |
| 195 | LIQELQEIL | 8.640 |
| 115 | KSTIFTPHL | 8.000 |
| 217 | RGKSHQHIL | 8.000 |
| 77 | FYLRRVIRV | 7.500 |
| 129 | SFPVSSSLI | 7.500 |
| 203 | LVPSQPQPL | 7.200 |
| 53 | TMVFLSPQL | 7.200 |
| 128 | LSFPVSSSL | 6.720 |
| 37 | YLPVCHVAL | 6.000 |
| 44 | ALIHMVVLL | 6.000 |
| 49 | VVLLTMVFL | 6.000 |
| 86 | LSICTTCLL | 6.000 |
| 173 | LSLFRDVFL | 6.000 |
| 7 | LVLASQPTL | 6.000 |
| 239 | FIISTSSTL | 6.000 |
| 143 | SSNVTQINL | 6.000 |
| 234 | MYKMDFIIS | 6.000 |
| 43 | VALIHMVVL | 6.000 |
| 165 | IIRGLFFTL | 5.760 |
| 23 | SPFLLFLDL | 5.760 |
| 78 | YLRRVIRVL | 5.600 |
| 138 | FYTVASSNV | 5.000 |
| 30 | DLRPERTYL | 4.800 |
| 89 | CTTCLLGML | 4.800 |
| 101 | NISPSISWL | 4.800 |
| 21 | ASSPFLLFL | 4.800 |
| 11 | SQPTLFSFF | 4.320 |
| 113 | KWKSTIFTF | 4.000 |
| 19 | FSASSPFLL | 4.000 |
| 85 | VLSICTTCL | 4.000 |
| 187 | FSSVYMMTL | 4.000 |
| 178 | DVFLKQIML | 4.000 |
| 1 | MPFISKLVL | 4.000 |

TABLE XVI-continued

| Pos | 123456789 | Score |
|-----|-----------|-------|
| 116 | STIFTFHLF | 3.600 |
| 63  | ESLNFQNDF | 3.600 |
| 10  | ASQPTLFSF | 3.600 |
| 48  | MVVLLTMVF | 3.600 |
| 163 | NSIIRGLFF | 3.000 |
| 130 | FPVSSSLIF | 3.000 |
| 162 | INSIIRGLF | 2.800 |
| 229 | SFSVGMYKM | 2.750 |
| 20  | SASSPFLLF | 2.400 |
| 54  | MVFLSPQLF | 2.400 |
| 98  | QVVNISPSI | 2.100 |
| 168 | GLFFTLSLF | 2.000 |
| 172 | TLSLFRDVF | 2.000 |
| 231 | SVGMYKMDF | 2.000 |
| 8   | VLASQPTLF | 2.000 |
| 122 | HLFSWSLSF | 2.000 |
| 152 | HVSKYCSLF | 2.000 |
| 194 | TLIQELQEI | 1.980 |
| 72  | KYEASFYLR | 1.800 |
| 157 | CSLFPINSI | 1.800 |
| 158 | SLFPINSII | 1.680 |
| 188 | SSVYMMTLI | 1.500 |
| 94  | LGMLQVVNI | 1.500 |
| 232 | VGMYKMDFI | 1.500 |
| 38  | LPVCHVALI | 1.500 |
| 75  | ASFYLRRVI | 1.200 |
| 141 | VASSNVTQI | 1.000 |
| 233 | GMYKMDFII | 1.000 |
| 61  | LFESLNFQN | 0.900 |
| 161 | PINSIIRGL | 0.840 |
| 238 | DFIISTSST | 0.750 |
| 184 | IMLFSSVYM | 0.750 |
| 190 | VYMMTLIQE | 0.750 |
| 226 | LPVSFSVGM | 0.750 |
| 137 | IFYTVASSN | 0.700 |
| 186 | LFSSVYMMT | 0.700 |
| 151 | LHVSKYCSL | 0.600 |
| 70  | DFKYEASFY | 0.500 |
| 185 | MLFSSVYMM | 0.500 |

TABLE XVI-continued

| Pos | 123456789 | Score |
|-----|-----------|-------|
| 88  | ICTTCLLGM | 0.500 |
| 40  | VCHVALIHM | 0.500 |
| 118 | IFTFHLFSW | 0.500 |
| 15  | LFSFFSASS | 0.500 |
| 71  | FKYEASFYL | 0.480 |
| 182 | KQIMLFSSV | 0.432 |
| 84  | RVLSICTTC | 0.420 |
| 81  | RVIRVLSIC | 0.420 |
| 218 | GKSHQHILL | 0.400 |
| 222 | QHILLPVSF | 0.360 |
| 6   | KLVLASQPT | 0.360 |
| 59  | PQLFESLNF | 0.300 |
| 80  | RRVIRVLSI | 0.300 |
| 32  | RPERTYLPV | 0.300 |
| 104 | PSISWLVRF | 0.300 |
| 236 | KMDFIISTS | 0.280 |
| 95  | GMLQVVNIS | 0.252 |

V2-A24-
9mers:251P5G2
Each peptide is a portion of
SEQ ID NO: 5; each start
position is specified, the
length of peptide is 9 amino
acids, and the end position
for each peptide is the start
position plus eight.

| Pos | 123456789 | Score |
|-----|-----------|-------|
| 3 | ASQPTLCSF | 3.600 |
| 4 | SQPTLCSFF | 3.600 |
| 7 | TLCSFFSAS | 0.120 |
| 8 | LCSFFSASS | 0.100 |
| 1 | VLASQPTLC | 0.100 |
| 5 | QPTLCSFFS | 0.100 |
| 2 | LASQPTLCS | 0.100 |
| 6 | PTLCSFFSA | 0.018 |
| 9 | CSFFSASSP | 0.010 |

V3-A24-
9mers:251P5G2
Each peptide is a portion of
SEQ ID NO: 7; each start
position is specified, the
length of peptide is 9 amino
acids, and the end position
for each peptide is the start
position plus eight.

| Pos | 123456789 | Score |
|-----|-----------|-------|
| 2 | YLRRVIRDL | 5.600 |
| 9 | DLSICTTCL | 4.000 |

TABLE XVI-continued

| Pos | 123456789 | Score |
|---|---|---|
| 1 | FYLRRVIRD | 0.750 |
| 5 | RVIRDLSIC | 0.300 |
| 4 | RRVIRDLSI | 0.300 |
| 6 | VIRDLSICT | 0.144 |
| 8 | RDLSICTTC | 0.042 |
| 3 | LRRVIRDLS | 0.014 |
| 7 | IRDLSICTT | 0.010 |

V4-A24-9mers:251P5G2
Each peptide is a portion of SEQ ID NO: 9; each start position is specified, the length of peptide is 9 amino acids, and the end position for each peptide is the start position plus eight.

| Pos | 123456789 | Score |
|---|---|---|
| 3 | CTTCLLDML | 4.800 |
| 2 | ICTTCLLDM | 0.500 |
| 9 | DMLQVVNIS | 0.252 |
| 6 | CLLDMLQVV | 0.216 |
| 8 | LDMLQVVNI | 0.150 |
| 5 | TCLLDMLQV | 0.150 |
| 7 | LLDMLQVVN | 0.120 |
| 4 | TTCLLDMLQ | 0.012 |
| 1 | SICTTCLLD | 0.010 |

V12A-A24-9mers:251P5G2
Each peptide is a portion of SEQ ID NO: 25; each start position is specified, the length of peptide is 9 amino acids, and the end position for each peptide is the start position plus eight.

| Pos | 123456789 | Score |
|---|---|---|
| 4 | SISWLIMLF | 2.400 |
| 1 | ISPSISWLI | 2.100 |
| 3 | PSISWLIML | 0.600 |
| 2 | SPSISWLIM | 0.500 |
| 7 | WLIMLFSSV | 0.216 |
| 6 | SWLIMLFSS | 0.150 |
| 8 | LIMLFSSVY | 0.150 |
| 5 | ISWLIMLFS | 0.140 |

TABLE XVI-continued

V12B-A24-9mers:251P5G2
Each peptide is a portion of SEQ ID NO: 25; each start position is specified, the length of peptide is 9 amino acids, and the end position for each peptide is the start position plus eight.

| Pos | 123456789 | Score |
|---|---|---|
| 579 | RYGRTALIL | 400.000 |
| 408 | RYHVRREDL | 400.000 |
| 282 | SYPLVLRHI | 105.000 |
| 364 | GYGHSFLIM | 30.000 |
| 872 | GFSLRQLGL | 20.000 |
| 832 | GFSLRQLGL | 20.000 |
| 528 | KLMAKALLL | 12.000 |
| 648 | NSNPVITIL | 10.080 |
| 218 | RYRSGPSVS | 10.000 |
| 946 | RASPGTPSL | 9.600 |
| 806 | EIESVKEKL | 9.240 |
| 523 | IYNEDKLMA | 9.000 |
| 86 | GSLPAFADL | 8.640 |
| 654 | TILNIKLPL | 8.400 |
| 461 | NSEVVQLLL | 8.400 |
| 460 | GNSEVVQLL | 8.064 |
| 447 | KQKRTALHL | 8.000 |
| 544 | KNKCGLTPL | 8.000 |
| 827 | KTKVAGFSL | 8.000 |
| 546 | KCGLTPLLL | 8.000 |
| 324 | MQIKEFEEL | 7.920 |
| 491 | QCQEDECVL | 7.200 |
| 883 | HAQASVQQL | 7.200 |
| 904 | QAQEQGAAL | 7.200 |
| 351 | KNVDKWDDF | 7.200 |
| 674 | NPVGLPENL | 7.200 |
| 277 | CIPNLSYPL | 7.200 |
| 843 | HAQASVQQL | 7.200 |
| 467 | LLLDRRCQL | 7.200 |
| 156 | RAQGLTRAF | 7.200 |
| 47 | CNLEKGSWL | 7.200 |
| 721 | EQNDTQKQL | 7.200 |
| 592 | GSASIVNLL | 6.720 |
| 521 | YAIYNEDKL | 6.600 |

TABLE XVI-continued

| Pos | 123456789 | Score |
|---|---|---|
| 566 | FLIKKKANL | 6.000 |
| 309 | ELPATAARL | 6.000 |
| 796 | NQLRENKIL | 6.000 |
| 735 | TGISQDEIL | 6.000 |
| 105 | ATPAGAFLL | 6.000 |
| 273 | HLIQCIPNL | 6.000 |
| 68 | TTLTGHSAL | 6.000 |
| 76 | LSLSSSRAL | 6.000 |
| 233 | EPPAHQRLL | 6.000 |
| 867 | EQEVAGFSL | 6.000 |
| 459 | NGNSEVVQL | 6.000 |
| 770 | DLLRENSML | 6.000 |
| 817 | TIQLNEEAL | 6.000 |
| 1042 | QSPRHTKDL | 6.000 |
| 197 | GLEAASANL | 6.000 |
| 286 | VLRHIPEIL | 5.600 |
| 593 | SASIVNLLL | 5.600 |
| 652 | VITILNIKL | 5.280 |
| 781 | EIAKLRLEL | 5.280 |
| 777 | MLREEIAKL | 5.280 |
| 302 | GGGILGLEL | 5.280 |
| 186 | SYRLTHVRC | 5.000 |
| 513 | EYGNTALHY | 5.000 |
| 916 | IGDPGGVPL | 4.800 |
| 80 | SSRALPGSL | 4.800 |
| 1051 | GQDDRAGVL | 4.800 |
| 152 | AACLRAQGL | 4.800 |
| 15 | AATGLWAAL | 4.800 |
| 104 | SATPAGAFL | 4.800 |
| 604 | NVDVSSQDL | 4.800 |
| 560 | KQEVVKFLI | 4.200 |
| 36 | TWRKEPAVL | 4.000 |
| 425 | WGKVPRKDL | 4.000 |
| 1106 | AGGVGPTTL | 4.000 |
| 958 | ASGARAAAL | 4.000 |
| 870 | VAGFSLRQL | 4.000 |
| 687 | SAGNGDDGL | 4.000 |
| 312 | ATAARLSGL | 4.000 |

TABLE XVI-continued

| Pos | 123456789 | Score |
|---|---|---|
| 266 | SLSVFQLHL | 4.000 |
| 147 | HQRRDAACL | 4.000 |
| 983 | VCDSSGWIL | 4.000 |
| 830 | VAGFSLRQL | 4.000 |
| 1060 | APKCRPGTL | 4.000 |
| 264 | VGSLSVFQL | 4.000 |
| 11 | ATFAAATGL | 4.000 |
| 763 | LSHKKEEDL | 4.000 |
| 591 | CGSASIVNL | 4.000 |
| 374 | ETSTKISGL | 4.000 |
| 300 | ETGGGILGL | 4.000 |
| 70 | LTGHSALSL | 4.000 |
| 5 | ILLPTQATF | 3.600 |
| 321 | NSIMQIKEF | 3.300 |
| 262 | LGVGSLSVF | 3.000 |
| 361 | LSEGYGHSF | 3.000 |
| 865 | AQEQEVAGF | 3.000 |
| 988 | GWILPVPTF | 3.000 |
| 83 | ALPGSLPAF | 3.000 |
| 1021 | SNRETHQAF | 2.880 |
| 660 | LPLKVEEEI | 2.310 |
| 558 | EQKQEVVKF | 2.200 |
| 270 | FQLHLIQCI | 2.160 |
| 825 | LTKTKVAGF | 2.000 |
| 396 | WGDYDDSAF | 2.000 |
| 1001 | FLGRRCPMF | 2.000 |

TABLE XVII

| Pos | 1234567890 | Score |
|---|---|---|
| V1-A-24-10mers:251P5G2 Each peptide is a portion of SEQ ID NO: 3; each start position is specified, the length of peptide is 10 amino acids, and the end position for each peptide is the start position plus nine. | | |
| 190 | VYMMTLIQEL | 475.200 |
| 77 | FYLRRVIRVL | 420.000 |
| 36 | TYLPVCHVAL | 360.000 |
| 238 | DFIISTSSTL | 30.000 |

TABLE XVII-continued

| Pos | 1234567890 | Score |
|---|---|---|
| 17 | SFFSASSPFL | 20.000 |
| 186 | LFSSVYMMTL | 20.000 |
| 18 | FFSASSPFLL | 20.000 |
| 70 | DFKYEASFYL | 20.000 |
| 129 | SFPVSSSLIF | 15.000 |
| 84 | RVLSICTTCL | 12.00 |
| 6 | KLVLASQPTL | 12.00 |
| 155 | KYCSLFPINS | 10.000 |
| 202 | ILVPSQPQPL | 8.640 |
| 22 | SSPFLLFLDL | 8.640 |
| 164 | SIIRGLFFTL | 8.640 |
| 160 | FPINSIIRGL | 8.400 |
| 217 | RGKSHQHILL | 8.000 |
| 206 | SQPQPLPKDL | 7.200 |
| 194 | TLIQELQEIL | 7.200 |
| 52 | LTMVFLSPQL | 7.200 |
| 56 | FLSPQLFESL | 6.912 |
| 43 | VALIHMVVLL | 6.000 |
| 48 | MVVLLTMVFL | 6.000 |
| 167 | RGLFFTLSLF | 6.000 |
| 138 | FYTVASSNVT | 6.000 |
| 175 | LFRDVFLKQI | 6.000 |
| 100 | VNISPSISWL | 6.000 |
| 127 | SLSFPVSSSL | 5.600 |
| 10 | ASQPTLFSFF | 5.184 |
| 234 | MYKMDFIIST | 5.000 |
| 88 | ICTTCLLGML | 4.800 |
| 115 | KSTIFTFHLF | 4.800 |
| 85 | VLSICTTCLL | 4.000 |
| 20 | SASSPFLLFL | 4.000 |
| 172 | TLSLFRDVFL | 4.000 |
| 142 | ASSNVTQINL | 4.000 |
| 42 | HVALIHMVVL | 4.000 |
| 150 | NLHVSKYCSL | 4.000 |
| 119 | FTFHLFSWSL | 4.000 |
| 47 | HMVVLLTMVF | 3.600 |
| 53 | TMVFLSPQLF | 3.600 |
| 58 | SPQLFESLNF | 3.000 |
| 230 | FSVGMYKMDF | 3.000 |

TABLE XVII-continued

| Pos | 1234567890 | Score |
|---|---|---|
| 7 | LVLASQPTLF | 3.000 |
| 171 | FTLSLFRDVF | 3.000 |
| 19 | FSASSPFLLF | 2.400 |
| 221 | HQHILLPVSF | 2.400 |
| 97 | LQVVNISPSI | 2.100 |
| 157 | CSLFPINSII | 2.100 |
| 68 | QNDFKYEASF | 2.000 |
| 178 | DVFLKQIMLF | 2.000 |
| 9 | LASQPTLFSF | 2.000 |
| 162 | INSIIRGLFF | 2.000 |
| 103 | SPSISWLVRF | 2.000 |
| 16 | FSFFSASSPF | 2.000 |
| 193 | MTLIQELQEI | 1.980 |
| 37 | YLPVCHVALI | 1.500 |
| 72 | KYEASFYLRR | 1.500 |
| 232 | VGMYKMDFII | 1.500 |
| 177 | RDVFLKQIML | 1.200 |
| 156 | YCSLFPINSI | 1.200 |
| 215 | LCRGKSHQHI | 1.200 |
| 128 | LSFPVSSSLI | 1.200 |
| 74 | EASFYLRRVI | 1.200 |
| 179 | VFLKQIMLFS | 1.050 |
| 93 | LLGMLQVVNI | 1.000 |
| 153 | VSKYCSLFPI | 1.000 |
| 140 | TVASSNVTQI | 1.000 |
| 187 | FSSVYMMTLI | 1.000 |
| 231 | SVGMYKMDFI | 1.000 |
| 111 | RFKWKSTIFT | 1.000 |
| 109 | LVRFKWKSTI | 1.000 |
| 27 | LFLDLRPERT | 0.900 |
| 55 | VFLSPQLFES | 0.825 |
| 66 | NFQNDFKYEA | 0.825 |
| 184 | IMLFSSVYMM | 0.750 |
| 183 | QIMLFSSVYM | 0.750 |
| 225 | LLPVSFSVGM | 0.750 |
| 118 | IFTFHLFSWS | 0.720 |
| 170 | FFTLSLFRDV | 0.720 |
| 45 | LIHMVVLLTM | 0.700 |

TABLE XVII-continued

| Pos | 1234567890 | Score |
|-----|------------|-------|
| 123 | LFSWSLSFPV | 0.600 |
| 29  | LDLRPERTYL | 0.600 |
| 228 | VSFSVGMYKM | 0.550 |
| 137 | IFYTVASSNV | 0.500 |
| 120 | TFHLFSWSLS | 0.500 |
| 76  | SFYLRRVIRV | 0.500 |
| 87  | SICTTCLLGM | 0.500 |
| 161 | PINSIIRGLF | 0.420 |
| 166 | IRGLFFTLSL | 0.400 |
| 216 | CRGKSHQHIL | 0.400 |
| 114 | WKSTIFTFHL | 0.400 |
| 81  | RVIRVLSICT | 0.360 |
| 182 | KQIMLFSSVY | 0.300 |
| 32  | RPERTYLPVC | 0.300 |
| 151 | LHVSKYCSLF | 0.300 |
| 121 | FHLFSWSLSF | 0.300 |
| 219 | KSHQHILLPV | 0.280 |
| 35  | RTYLPVCHVA | 0.280 |
| 236 | KMDFIISTSS | 0.280 |

V2-A24-10mers:251P5G2
Each peptide is a portion of SEQ ID NO: 5; each start position is specified, the length of peptide is 10 amino acids, and the end position for each peptide is the start position plus nine.

| Pos | 1234567890 | Score |
|-----|------------|-------|
| 4   | ASQPTLCSFF | 4.320 |
| 3   | LASQPTLCSF | 2.000 |
| 10  | CSFFSASSPF | 2.000 |
| 1   | LVLASQPTLC | 0.150 |
| 5   | SQPTLCSFFS | 0.150 |
| 6   | QPTLCSFFSA | 0.120 |
| 8   | TLCSFFSASS | 0.100 |
| 2   | VLASQPTLCS | 0.100 |
| 7   | PTLCSFFSAS | 0.018 |
| 9   | LCSFFSASSP | 0.010 |

TABLE XVII-continued

V3-A24-10mers:251P5G2
Each peptide is a portion of SEQ ID NO: 7; each start position is specified, the length of peptide is 10 amino acids, and the end position for each peptide is the start position plus nine.

| Pos | 1234567890 | Score |
|-----|------------|-------|
| 2   | FYLRRVIRDL | 420.000 |
| 10  | DLSICTTCLL | 4.000 |
| 9   | RDLSICTTCL | 1.200 |
| 6   | RVIRDLSICT | 0.360 |
| 3   | YLRRVIRDLS | 0.140 |
| 7   | VIRDLSICTT | 0.120 |
| 4   | LRRVIRDLSI | 0.100 |
| 1   | SFYLRRVIRD | 0.050 |
| 5   | RRVIRDLSIC | 0.030 |
| 8   | IRDLSICTTC | 0.014 |

V4-A24-10mers:251P5G2
Each peptide is a portion of SEQ ID NO: 9; each start position is specified, the length of peptide is 10 amino acids, and the end position for each peptide is the start position plus nine.

| Pos | 1234567890 | Score |
|-----|------------|-------|
| 3   | ICTTCLLDML | 4.800 |
| 8   | LLDMLQVVNI | 1.000 |
| 2   | SICTTCLLDM | 0.500 |
| 7   | CLLDMLQVVN | 0.216 |
| 6   | TCLLDMLQVV | 0.180 |
| 5   | TTCLLDMLQV | 0.100 |
| 9   | LDMLQVVNIS | 0.025 |
| 10  | DMLQVVNISP | 0.021 |
| 1   | LSICTTCLLD | 0.015 |
| 4   | CTTCLLDMLQ | 0.012 |

V12A-A24-10mers:251P5G2
Each peptide is a portion of SEQ ID NO: 25; each start position is specified, the length of peptide is 10 amino acids, and the end position for each peptide is the start position plus nine.

| Pos | 1234567890 | Score |
|-----|------------|-------|
| 3   | SPSISWLIML | 4.000 |
| 1   | NISPSISWLI | 1.680 |
| 9   | LIMLFSSVYM | 0.750 |
| 2   | ISPSISWLIM | 0.750 |

TABLE XVII-continued

| Pos | 1234567890 | Score |
|---|---|---|
| 4 | PSISWLIMLF | 0.360 |
| 7 | SWLIMLFSSV | 0.216 |
| 8 | WLIMLFSSVY | 0.150 |
| 5 | SISWLIMLFS | 0.140 |
| 6 | ISWLIMLFSS | 0.100 |

V12B-A24-10mers:251P5G2
Each peptide is a portion of SEQ ID NO: 25; each start position is specified, the length of peptide is 10 amino acids, and the end position for each peptide is the start position plus nine.

| Pos | 1234567890 | Score |
|---|---|---|
| 521 | HYAIYNEDKL | 220.000 |
| 636 | DYKEKQMLKI | 66.000 |
| 566 | KFLIKKKANL | 60.000 |
| 1009 | MFDVSPAMRL | 20.000 |
| 1001 | SFLGRRCPMF | 15.000 |
| 1029 | AFRDKDDLPF | 12.000 |
| 817 | KTIQLNEEAL | 12.000 |
| 270 | VFQLHLIQCI | 10.800 |
| 460 | NGNSEVVQLL | 10.080 |
| 219 | RYRSGPSVSS | 10.000 |
| 580 | RYGRTALILA | 10.000 |
| 545 | KNKCGLTPLL | 9.600 |
| 604 | QNVDVSSQDL | 8.640 |
| 277 | QCIPNLSYPL | 8.640 |
| 286 | LVLRHIPEIL | 8.400 |
| 115 | GWERVVQRRL | 8.400 |
| 654 | ITILNIKLPL | 8.400 |
| 830 | KVAGFSLRQL | 8.000 |
| 324 | IMQIKEFEEL | 7.920 |
| 537 | LYGADIESKN | 7.700 |
| 493 | CQEDECVLML | 7.200 |
| 83 | RALPGSLPAF | 7.200 |
| 674 | SNPVGLPENL | 7.200 |
| 197 | QGLEAASANL | 7.200 |
| 1051 | LGQDDRAGVL | 7.200 |
| 461 | GNSEVVQLLL | 6.720 |
| 592 | CGSASIVNLL | 6.720 |
| 777 | SMLREEIAKL | 6.600 |

TABLE XVII-continued

| Pos | 1234567890 | Score |
|---|---|---|
| 753 | VAEKEMNSEL | 6.600 |
| 624 | SSHHHVICEL | 6.160 |
| 1082 | TPPHRHTTTL | 6.000 |
| 807 | EIESVKEKLL | 6.000 |
| 717 | EYHSDEQNDT | 6.000 |
| 541 | DIESKNKCGL | 6.000 |
| 1060 | LAPKCRPGTL | 6.000 |
| 362 | LSEGYGHSFL | 6.000 |
| 266 | GSLSVFQLHL | 6.000 |
| 796 | QNQLRENKIL | 6.000 |
| 279 | IPNLSYPLVL | 6.000 |
| 181 | CPPSRNSYRL | 6.000 |
| 467 | QLLLDRRCQL | 6.000 |
| 47 | CCNLEKGSWL | 6.000 |
| 559 | EQKQEVVKFL | 5.600 |
| 648 | ENSNPVITIL | 5.600 |
| 593 | GSASIVNLLL | 5.600 |
| 853 | CYKWNHTEKT | 5.500 |
| 893 | CYKWGHTEKT | 5.500 |
| 302 | TGGGILGLEL | 5.280 |
| 187 | SYRLTHVRCA | 5.000 |
| 514 | EYGNTALHYA | 5.000 |
| 620 | EYAVSSHHHV | 5.000 |
| 429 | VPRKDLIVML | 4.800 |
| 15 | AAATGLWAAL | 4.800 |
| 701 | KSRKPENQQF | 4.800 |
| 80 | SSSRALPGSL | 4.800 |
| 983 | SVCDSSGWIL | 4.800 |
| 916 | QIGDPGGVPL | 4.800 |
| 1042 | QQSPRHTKDL | 4.800 |
| 152 | DAACLRAQGL | 4.800 |
| 634 | LSDYKEKQML | 4.800 |
| 511 | IQDEYGNTAL | 4.800 |
| 105 | SATPAGAFLL | 4.800 |
| 190 | LTHVRCAQGL | 4.800 |
| 660 | KLPLKVEEEI | 4.620 |
| 411 | HVRREDLDKL | 4.400 |
| 904 | QQAQEQGAAL | 4.000 |
| 425 | WWGKVPRKDL | 4.000 |

TABLE XVII-continued

| Pos | 1234567890 | Score |
|---|---|---|
| 687 | ASAGNGDDGL | 4.000 |
| 491 | VQCQEDECVL | 4.000 |
| 1091 | LPHRDTTTSL | 4.000 |
| 994 | VPTFSSGSFL | 4.000 |
| 932 | AGDQGPGTHL | 4.000 |
| 11 | QATFAAATGL | 4.000 |
| 459 | ANGNSEVVQL | 4.000 |
| 949 | SPGTPSLVRL | 4.000 |
| 763 | SLSHKKEEDL | 4.000 |
| 353 | NVDKWDDFCL | 4.000 |
| 41 | EPAVLPCCNL | 4.000 |
| 764 | LSHKKEEDLL | 4.000 |
| 62 | AARKEFSTTL | 4.000 |
| 161 | LTRAFQVVHL | 4.000 |
| 870 | EVAGFSLRQL | 4.000 |
| 209 | APGRSSSCAL | 4.000 |
| 478 | VLDNKKRTAL | 4.000 |
| 1027 | HQAFRDKDDL | 4.000 |
| 832 | AGFSLRQLGL | 4.000 |
| 1106 | SAGGVGPTTL | 4.000 |
| 70 | TLTGHSALSL | 4.000 |
| 68 | STTLTGHSAL | 4.000 |
| 735 | NTGISQDEIL | 4.000 |
| 958 | LASGARAAAL | 4.000 |
| 36 | VTWRKEPAVL | 4.000 |
| 872 | AGFSLRQLGL | 4.000 |
| 591 | CCGSASIVNL | 4.000 |
| 577 | ALDRYGRTAL | 4.000 |
| 76 | ALSLSSSRAL | 4.000 |
| 104 | QSATPAGAFL | 4.000 |
| 264 | GVGSLSVFQL | 4.000 |
| 865 | QAQEQEVAGF | 3.600 |
| 1021 | DSNRETHQAF | 3.600 |

TABLE XVIII

| Pos | 123456789 | Score |
|---|---|---|
| \multicolumn{3}{c}{V1-B7-9mers:251P5G2} | | |

Each peptide is a portion of SEQ ID NO: 3; each start position is specified, the length of peptide is 9 amino acids, and the end position for each peptide is the start position plus eight.

| Pos | 123456789 | Score |
|---|---|---|
| 207 | QPQPLPKDL | 80.00 |
| 23 | SPFLLFLDL | 80.00 |
| 1 | MPFISKLVL | 80.00 |
| 30 | DLRPERTYL | 60.00 |
| 78 | YLRRVIRVL | 40.00 |
| 165 | IIRGLFFTL | 40.00 |
| 178 | DVFLKQIML | 20.00 |
| 203 | LVPSQPQPL | 20.00 |
| 7 | LVLASQPTL | 20.00 |
| 49 | VVLLTMVFL | 20.00 |
| 226 | LPVSFSVGM | 20.00 |
| 191 | YMMTLIQEL | 12.00 |
| 44 | ALIHMVVLL | 12.00 |
| 21 | ASSPFLLFL | 12.00 |
| 43 | VALIHMVVL | 12.00 |
| 38 | LPVCHVALI | 8.000 |
| 109 | LVRFKWKST | 5.000 |
| 195 | LIQELQEIL | 4.000 |
| 53 | TMVFLSPQL | 4.000 |
| 217 | RGKSHQHIL | 4.000 |
| 57 | LSPQLFESL | 4.000 |
| 86 | LSICTTCLL | 4.000 |
| 173 | LSLFRDVFL | 4.000 |
| 239 | FIISTSSTL | 4.000 |
| 115 | KSTIFTFHL | 4.000 |
| 85 | VLSICTTCL | 4.000 |
| 101 | NISPSISWL | 4.000 |
| 128 | LSFPVSSSL | 4.000 |
| 37 | YLPVCHVAL | 4.000 |
| 247 | LPWAYDRGV | 4.000 |
| 143 | SSNVTQINL | 4.000 |
| 19 | FSASSPFLL | 4.000 |
| 89 | CTTCLLGML | 4.000 |
| 167 | RGLFFTLSL | 4.000 |

TABLE XVIII-continued

| Pos | 123456789 | Score |
|---|---|---|
| 187 | FSSVYMMTL | 4.000 |
| 98 | QVVNISPSI | 2.000 |
| 75 | ASFYLRRVI | 1.800 |
| 141 | VASSNVTQI | 1.200 |
| 232 | VGMYKMDFI | 1.200 |
| 32 | RPERTYLPV | 1.200 |
| 94 | LGMLQVVNI | 1.200 |
| 185 | MLFSSVYMM | 1.000 |
| 82 | VIRVLSICT | 1.000 |
| 88 | ICTTCLLGM | 1.000 |
| 40 | VCHVALIHM | 1.000 |
| 184 | IMLFSSVYM | 1.000 |
| 145 | NVTQINLHV | 1.000 |
| 42 | HVALIHMVV | 1.000 |
| 157 | CSLFPINSI | 0.600 |
| 74 | EASFYLRRV | 0.600 |
| 84 | RVLSICTTC | 0.500 |
| 81 | RVIRVLSIC | 0.500 |
| 12 | QPTLFSFFS | 0.400 |
| 151 | LHVSKYCSL | 0.400 |
| 18 | FFSASSPFL | 0.400 |
| 161 | PINSIIRGL | 0.400 |
| 58 | SPQLFESLN | 0.400 |
| 233 | GMYKMDFII | 0.400 |
| 120 | TFHLFSWSL | 0.400 |
| 194 | TLIQELQEI | 0.400 |
| 188 | SSVYMMTLI | 0.400 |
| 130 | FPVSSSLIF | 0.400 |
| 71 | FKYEASFYL | 0.400 |
| 158 | SLFPINSII | 0.400 |
| 218 | GKSHQHILL | 0.400 |
| 46 | IHMVVLLTM | 0.300 |
| 204 | VPSQPQPLP | 0.300 |
| 35 | RTYLPVCHV | 0.300 |
| 124 | FSWSLSFPV | 0.200 |
| 182 | KQIMLFSSV | 0.200 |
| 91 | TCLLGMLQV | 0.200 |
| 102 | ISPSISWLV | 0.200 |
| 171 | FTLSLFRDV | 0.200 |
| 133 | SSSLIFYTV | 0.200 |
| 103 | SPSISWLVR | 0.200 |
| 47 | HMVVLLTMV | 0.200 |
| 160 | FPINSIIRG | 0.200 |
| 209 | QPLPKDLCR | 0.200 |
| 211 | LPKDLCRGK | 0.200 |
| 224 | ILLPVSFSV | 0.200 |
| 92 | CLLGMLQVV | 0.200 |
| 231 | SVGMYKMDF | 0.100 |
| 6 | KLVLASQPT | 0.100 |
| 139 | YTVASSNVT | 0.100 |
| 229 | SFSVGMYKM | 0.100 |
| 45 | LIHMVVLLT | 0.100 |
| 99 | VVNISPSIS | 0.100 |
| 215 | LCRGKSHQH | 0.100 |
| 242 | STSSTLPWA | 0.100 |
| 149 | INLHVSKYC | 0.100 |
| 152 | HVSKYCSLF | 0.100 |
| 164 | SIIRGLFFT | 0.100 |
| 177 | RDVFLKQIM | 0.100 |
| 67 | FQNDFKYEA | 0.100 |
| 54 | MVFLSPQLF | 0.100 |
| 132 | VSSSLIFYT | 0.100 |
| 48 | MVVLLTMVF | 0.100 |
| 134 | SSLIFYTVA | 0.100 |
| 9 | LASQPTLFS | 0.090 |
| 20 | SASSPFLLF | 0.090 |

V2-B7-
9mers:251P5G2
Each peptide is a portion of
SEQ ID NO: 5; each start
position is specified, the
length of peptide is 9 amino
acids, and the end position
for each peptide is the start
position plus eight.

| Pos | 123456789 | Score |
|---|---|---|
| 5 | QPTLCSFFS | 0.400 |
| 1 | VLASQPTLC | 0.100 |
| 2 | LASQPTLCS | 0.090 |
| 3 | ASQPTLCSF | 0.060 |
| 7 | TLCSFFSAS | 0.020 |
| 8 | LCSFFSASS | 0.020 |

TABLE XVIII-continued

| Pos | 123456789 | Score |
|---|---|---|
| 4 | SQPTLCSFF | 0.020 |
| 6 | PTLCSFFSA | 0.010 |
| 9 | CSFFSASSP | 0.010 |

V3-B7-
9mers:251P5G2
Each peptide is a portion of SEQ ID NO: 7; each start position is specified, the length of peptide is 9 amino acids, and the end position for each peptide is the start position plus eight.

| Pos | 123456789 | Score |
|---|---|---|
| 2 | YLRRVIRDL | 40.00 |
| 9 | DLSICTTCL | 4.000 |
| 6 | VIRDLSICT | 1.000 |
| 5 | RVIRDLSIC | 0.500 |
| 4 | RRVIRDLSI | 0.040 |
| 3 | LRRVIRDLS | 0.030 |
| 8 | RDLSICTTC | 0.010 |
| 7 | IRDLSICTT | 0.003 |
| 1 | FYLRRVIRD | 0.001 |

V4-B7-
9mers:251P5G2
Each peptide is a portion of SEQ ID NO: 9; each start position is specified, the length of peptide is 9 amino acids, and the end position for each peptide is the start position plus eight.

| Pos | 123456789 | Score |
|---|---|---|
| 3 | CTTCLLDML | 4.000 |
| 2 | ICTTCLLDM | 1.000 |
| 6 | CLLDMLQVV | 0.200 |
| 5 | TCLLDMLQV | 0.200 |
| 8 | LDMLQVVNI | 0.120 |
| 9 | DMLQVVNIS | 0.020 |
| 4 | TTCLLDMLQ | 0.010 |
| 1 | SICTTCLLD | 0.010 |
| 7 | LLDMLQVVN | 0.006 |

V12A-B7-
9mers:251P5G2
Each peptide is a portion of SEQ ID NO: 25; each start position is specified, the length of peptide is 9 amino acids, and the end position for each peptide is the start position plus eight.

| Pos | 123456789 | Score |
|---|---|---|
| 2 | SPSISWLIM | 20.000 |
| 1 | ISPSISWLI | 0.400 |

TABLE XVIII-continued

| Pos | 123456789 | Score |
|---|---|---|
| 3 | PSISWLIML | 0.400 |
| 7 | WLIMLFSSV | 0.200 |
| 8 | LIMLFSSVY | 0.060 |
| 4 | SISWLIMLF | 0.020 |
| 5 | ISWLIMLFS | 0.020 |
| 6 | SWLIMLFSS | 0.002 |

V12B-B7-
9mers:251P5G2
Each peptide is a portion of SEQ ID NO: 25; each start position is specified, the length of peptide is 9 amino acids, and the end position for each peptide is the start position plus eight.

| Pos | 123456789 | Score |
|---|---|---|
| 1060 | APKCRPGTL | 240.000 |
| 428 | VPRKDLIVM | 200.000 |
| 233 | EPPAHQRLL | 80.000 |
| 674 | NPVGLPENL | 80.000 |
| 286 | VLRHIPEIL | 40.0 |
| 147 | HQRRDAACL | 40.000 |
| 777 | MLREEIAKL | 40.000 |
| 152 | AACLRAQGL | 36.000 |
| 15 | AATGLWAAL | 36.000 |
| 125 | VPRPQAAPA | 20.000 |
| 434 | IVMLRDTDM | 15.000 |
| 104 | SATPAGAFL | 12.000 |
| 830 | VAGFSLRQL | 12.000 |
| 958 | ASGARAAAL | 12.000 |
| 946 | RASPGTPSL | 12.000 |
| 687 | SAGNGDDGL | 12.000 |
| 312 | ATAARLSGL | 12.000 |
| 521 | YAIYNEDKL | 12.000 |
| 1106 | AGGVGPTTL | 12.000 |
| 883 | HAQASVQQL | 12.000 |
| 11 | ATFAAATGL | 12.000 |
| 870 | VAGFSLRQL | 12.000 |
| 843 | HAQASVQQL | 12.000 |
| 528 | KLMAKALLL | 12.000 |
| 904 | QAQEQGAAL | 12.000 |
| 593 | SASIVNLLL | 12.000 |
| 1027 | QAFRDKDDL | 12.00 |
| 105 | ATPAGAFLL | 12.000 |

TABLE XVIII-continued

| Pos | 123456789 | Score |
|---|---|---|
| 61 | AARKEFSTT | 9.000 |
| 170 | APTAPDGGA | 9.000 |
| 425 | WGKVPRKDL | 9.000 |
| 1082 | PPHRHTTTL | 8.000 |
| 660 | LPLKVEEEI | 8.000 |
| 181 | PPSRNSYRL | 8.000 |
| 650 | NPVITILNI | 8.000 |
| 208 | APGRSSSCA | 6.000 |
| 621 | AVSSHHHVI | 6.000 |
| 604 | NVDVSSQDL | 6.000 |
| 781 | EIAKLRLEL | 6.000 |
| 1006 | CPMFDVSPA | 6.000 |
| 228 | APSPAEPPA | 6.000 |
| 467 | LLLDRRCQL | 6.000 |
| 588 | AVCCGSASI | 6.000 |
| 577 | LDRYGRTAL | 6.000 |
| 243 | LPRAPQAVS | 6.000 |
| 591 | CGSASIVNL | 4.000 |
| 76 | LSLSSSRAL | 4.000 |
| 817 | TIQLNEEAL | 4.000 |
| 309 | ELPATAARL | 4.000 |
| 544 | KNKCGLTPL | 4.000 |
| 491 | QCQEDECVL | 4.000 |
| 86 | GSLPAFADL | 4.000 |
| 735 | TGISQDEIL | 4.000 |
| 1042 | QSPRHTKDL | 4.000 |
| 592 | GSASIVNLL | 4.000 |
| 278 | IPNLSYPLV | 4.000 |
| 266 | SLSVFQLHL | 4.000 |
| 648 | NSNPVITIL | 4.000 |
| 36 | TWRKEPAVL | 4.000 |
| 460 | GNSEVVQLL | 4.000 |
| 256 | QPSEEALGV | 4.000 |
| 374 | ETSTKISGL | 4.000 |
| 566 | FLIKKKANL | 4.000 |
| 277 | CIPNLSYPL | 4.000 |
| 411 | VRREDLDKL | 4.000 |
| 302 | GGGILGLEL | 4.000 |

TABLE XVIII-continued

| Pos | 123456789 | Score |
|---|---|---|
| 47 | CNLEKGSWL | 4.000 |
| 796 | NQLRENKIL | 4.000 |
| 264 | VGSLSVFQL | 4.000 |
| 447 | KQKRTALHL | 4.000 |
| 300 | ETGGGILGL | 4.000 |
| 324 | MQIKEFEEL | 4.000 |
| 827 | KTKVAGFSL | 4.000 |
| 68 | TTLTGHSAL | 4.000 |
| 654 | TILNIKLPL | 4.000 |
| 546 | KCGLTPLLL | 4.000 |
| 652 | VITILNIKL | 4.000 |
| 115 | WERVVQRRL | 4.000 |
| 763 | LSHKKEEDL | 4.000 |
| 721 | EQNDTQKQL | 4.000 |
| 770 | DLLRENSML | 4.000 |
| 459 | NGNSEVVQL | 4.000 |
| 209 | PGRSSSCAL | 4.000 |
| 273 | HLIQCIPNL | 4.000 |
| 470 | DRRCQLNVL | 4.000 |
| 70 | LTGHSALSL | 4.000 |
| 522 | AIYNEDKLM | 3.000 |
| 84 | LPGSLPAFA | 2.000 |
| 7 | LPTQATFAA | 2.000 |
| 285 | LVLRHIPEI | 2.000 |
| 944 | EPRASPGTP | 2.000 |
| 1073 | TPPHRNADT | 2.000 |
| 28 | NPSRADPVT | 2.000 |
| 1043 | SPRHTKDLG | 2.000 |
| 976 | SPTKQKSVC | 2.000 |
| 922 | VPLSEGGTA | 2.000 |
| 94 | LPRSCPESE | 2.000 |
| 1081 | TPPHRHTTT | 2.000 |
| 982 | SVCDSSGWI | 2.000 |

TABLE XIX

| Pos | 1234567890 | Score |
|---|---|---|
| | V1-B7-10mers:251P5G2 Each peptide is a portion of SEQ ID NO: 3; each start position is specified, the length of peptide is 10 amino acids, and the end position for each peptide is the start position plus nine. | |
| 160 | FPINSIIRGL | 80.000 |
| 48 | MVVLLTMVFL | 20.000 |
| 42 | HVALIHMVVL | 20.000 |
| 84 | RVLSICTTCL | 20.000 |
| 109 | LVRFKWKSTI | 20.000 |
| 142 | ASSNVTQINL | 12.000 |
| 20 | SASSPFLLFL | 12.000 |
| 43 | VALIHMVVLL | 12.000 |
| 52 | LTMVFLSPQL | 12.000 |
| 88 | ICTTCLLGML | 4.000 |
| 172 | TLSLFRDVFL | 4.000 |
| 119 | FTFHLFSWSL | 4.000 |
| 127 | SLSFPVSSSL | 4.000 |
| 85 | VLSICTTCLL | 4.000 |
| 22 | SSPFLLFLDL | 4.000 |
| 217 | RGKSHQHILL | 4.000 |
| 202 | ILVPSQPQPL | 4.000 |
| 100 | VNISPSISWL | 4.000 |
| 194 | TLIQELQEIL | 4.000 |
| 206 | SQPQPLPKDL | 4.000 |
| 6 | KLVLASQPTL | 4.000 |
| 150 | NLHVSKYCSL | 4.000 |
| 56 | FLSPQLFESL | 4.000 |
| 164 | SIIRGLFFTL | 4.000 |
| 215 | LCRGKSHQHI | 4.000 |
| 207 | QPQPLPKDLC | 3.000 |
| 183 | QIMLFSSVYM | 3.000 |
| 140 | TVASSNVTQI | 2.000 |
| 1 | MPFISKLVLA | 2.000 |
| 12 | QPTLFSFFSA | 2.000 |
| 231 | SVGMYKMDFI | 2.000 |
| 74 | EASFYLRRVI | 1.800 |
| 190 | VYMMTLIQEL | 1.200 |
| 232 | VGMYKMDFII | 1.200 |
| 184 | IMLFSSVYMM | 1.000 |
| 82 | VIRVLSICTT | 1.000 |
| 225 | LLPVSFSVGM | 1.000 |
| 87 | SICTTCLLGM | 1.000 |
| 45 | LIHMVVLLTM | 1.000 |
| 228 | VSFSVGMYKM | 1.000 |
| 29 | LDLRPERTYL | 0.600 |
| 156 | YCSLFPINSI | 0.600 |
| 32 | RPERTYLPVC | 0.600 |
| 211 | LPKDLCRGKS | 0.600 |
| 39 | PVCHVALIHM | 0.500 |
| 81 | RVIRVLSICT | 0.500 |
| 36 | TYLPVCHVAL | 0.400 |
| 70 | DFKYEASFYL | 0.400 |
| 18 | FFSASSPFLL | 0.400 |
| 97 | LQVVNISPSI | 0.400 |
| 186 | LFSSVYMMTL | 0.400 |
| 128 | LSFPVSSSLI | 0.400 |
| 77 | FYLRRVIRVL | 0.400 |
| 103 | SPSISWLVRF | 0.400 |
| 187 | FSSVYMMTLI | 0.400 |
| 193 | MTLIQELQEI | 0.400 |
| 238 | DFIISTSSTL | 0.400 |
| 175 | LFRDVFLKQI | 0.400 |
| 17 | SFFSASSPFL | 0.400 |
| 79 | LRRVIRVLSI | 0.400 |
| 216 | CRGKSHQHIL | 0.400 |
| 177 | RDVFLKQIML | 0.400 |
| 226 | LPVSFSVGMY | 0.400 |
| 166 | IRGLFFTLSL | 0.400 |
| 37 | YLPVCHVALI | 0.400 |
| 93 | LLGMLQVVNI | 0.400 |
| 153 | VSKYCSLFPI | 0.400 |
| 157 | CSLFPINSII | 0.400 |
| 114 | WKSTIFTFHL | 0.400 |
| 130 | FPVSSSLIFY | 0.400 |
| 58 | SPQLFESLNF | 0.400 |
| 44 | ALIHMVVLLT | 0.300 |

TABLE XIX-continued

| Pos | 1234567890 | Score |
|---|---|---|
| 78 | YLRRVIRVLS | 0.300 |
| 91 | TCLLGMLQVV | 0.200 |
| 195 | LIQELQEILV | 0.200 |
| 90 | TTCLLGMLQV | 0.200 |
| 101 | NISPSISWLV | 0.200 |
| 219 | KSHQHILLPV | 0.200 |
| 40 | VCHVALIHMV | 0.200 |
| 209 | QPLPKDLCRG | 0.200 |
| 132 | VSSSLIFYTV | 0.200 |
| 144 | SNVTQINLHV | 0.200 |
| 165 | IIRGLFFTLS | 0.200 |
| 38 | LPVCHVALIH | 0.200 |
| 246 | TLPWAYDRGV | 0.200 |
| 204 | VPSQPQPLPK | 0.200 |
| 23 | SPFLLFLDLR | 0.200 |
| 223 | HILLPVSFSV | 0.200 |
| 99 | VVNISPSISW | 0.150 |
| 163 | NSIIRGLFFT | 0.100 |
| 98 | QVVNISPSIS | 0.100 |
| 241 | ISTSSTLPWA | 0.100 |
| 178 | DVFLKQIMLF | 0.100 |
| 35 | RTYLPVCHVA | 0.100 |
| 133 | SSSLIFYTVA | 0.100 |
| 49 | VVLLTMVFLS | 0.100 |
| 148 | QINLHVSKYC | 0.100 |
| 30 | DLRPERTYLP | 0.100 |
| 185 | MLFSSVYMMT | 0.100 |
| 7 | LVLASQPTLF | 0.100 |

V2-B7-
10mers:251P5G2
Each peptide is a portion of
SEQ ID NO: 5; each start
position is specified, the
length of peptide is 10 amino
acids, and the end position
for each peptide is the start
position plus nine.

| Pos | 1234567890 | Score |
|---|---|---|
| 6 | QPTLCSFFSA | 2.000 |
| 1 | LVLASQPTLC | 0.500 |
| 3 | LASQPTLCSF | 0.060 |
| 4 | ASQPTLCSFF | 0.060 |
| 2 | VLASQPTLCS | 0.030 |
| 10 | CSFFSASSPF | 0.020 |

TABLE XIX-continued

| Pos | 1234567890 | Score |
|---|---|---|
| 8 | TLCSFFSASS | 0.020 |
| 5 | SQPTLCSFFS | 0.020 |
| 9 | LCSFFSASSP | 0.010 |
| 7 | PTLCSFFSAS | 0.002 |

V3-B7-
10mers:251P5G2
Each peptide is a portion of
SEQ ID NO: 7; each start
position is specified, the
length of peptide is 10 amino
acids, and the end position
for each peptide is the start
position plus nine.

| Pos | 1234567890 | Score |
|---|---|---|
| 10 | DLSICTTCLL | 4.000 |
| 7 | VIRDLSICTT | 1.000 |
| 6 | RVIRDLSICT | 0.500 |
| 2 | FYLRRVIRDL | 0.400 |
| 9 | RDLSICTTCL | 0.400 |
| 4 | LRRVIRDLSI | 0.400 |
| 3 | YLRRVIRDLS | 0.300 |
| 5 | RRVIRDLSIC | 0.010 |
| 8 | IRDLSICTTC | 0.003 |
| 1 | SFYLRRVIRD | 0.001 |

V4-B7-
10mers:251P5G2
Each peptide is a portion of
SEQ ID NO: 9; each start
position is specified, the
length of peptide is 10 amino
acids, and the end position
for each peptide is the start
position plus nine.

| Pos | 1234567890 | Score |
|---|---|---|
| 3 | ICTTCLLDML | 4.000 |
| 2 | SICTTCLLDM | 1.000 |
| 5 | TTCLLDMLQV | 0.200 |
| 6 | TCLLDMLQVV | 0.200 |
| 8 | LLDMLQVVNI | 0.120 |
| 7 | CLLDMLQVVN | 0.020 |
| 4 | CTTCLLDMLQ | 0.010 |
| 10 | DMLQVVNISP | 0.010 |
| 1 | LSICTTCLLD | 0.010 |
| 9 | LDMLQVVNIS | 0.006 |

TABLE XIX-continued

| Pos | 1234567890 | Score |
|---|---|---|
| \multicolumn{3}{c}{V12A-B7-10mers:251P5G2 Each peptide is a portion of SEQ ID NO: 25; each start position is specified, the length of peptide is 10 amino acids, and the end position for each peptide is the start position plus nine.} | | |
| 3 | SPSISWLIML | 80.000 |
| 9 | LIMLFSSVYM | 3.000 |
| 2 | ISPSISWLIM | 1.000 |
| 1 | NISPSISWLI | 0.400 |
| 6 | ISWLIMLFSS | 0.020 |
| 7 | SWLIMLFSSV | 0.020 |
| 5 | SISWLIMLFS | 0.020 |
| 8 | WLIMLFSSVY | 0.020 |
| 4 | PSISWLIMLF | 0.002 |
| \multicolumn{3}{c}{V12B-B7-10mers:251P5G2 Each peptide is a portion of SEQ ID NO: 25; each start position is specified, the length of peptide is 10 amino acids, and the end position for each peptide is the start position plus nine.} | | |
| 429 | VPRKDLIVML | 800.000 |
| 62 | AARKEFSTTL | 360.000 |
| 209 | APGRSSSCAL | 240.000 |
| 411 | HVRREDLDKL | 200.000 |
| 41 | EPAVLPCCNL | 120.000 |
| 994 | VPTFSSGSFL | 80.000 |
| 279 | IPNLSYPLVL | 80.000 |
| 1091 | LPHRDTTTSL | 80.000 |
| 1082 | TPPHRHTTTL | 80.000 |
| 949 | SPGTPSLVRL | 80.000 |
| 181 | CPPSRNSYRL | 80.000 |
| 1007 | CPMFDVSPAM | 60.000 |
| 161 | LTRAFQVVHL | 40.000 |
| 315 | AARLSGLNSI | 36.000 |
| 15 | AAATGLWAAL | 36.000 |
| 983 | SVCDSSGWIL | 20.000 |
| 830 | KVAGFSLRQL | 20.000 |
| 126 | VPRPQAAPAT | 20.000 |
| 264 | GVGSLSVFQL | 20.000 |
| 286 | LVLRHIPEIL | 20.000 |
| 870 | EVAGFSLRQL | 20.000 |
| 1060 | LAPKCRPGTL | 12.000 |
| 958 | LASGARAAAL | 12.000 |
| 105 | SATPAGAFLL | 12.000 |
| 152 | DAACLRAQGL | 12.000 |
| 872 | AGFSLRQLGL | 12.000 |
| 76 | ALSLSSSRAL | 12.000 |
| 459 | ANGNSEVVQL | 12.000 |
| 1106 | SAGGVGPTTL | 12.000 |
| 832 | AGFSLRQLGL | 12.000 |
| 11 | QATFAAATGL | 12.000 |
| 687 | ASAGNGDDGL | 12.000 |
| 1061 | APKCRPGTLC | 9.000 |
| 235 | PPAHQRLLFL | 8.000 |
| 217 | ALRYRSGPSV | 6.000 |
| 945 | EPRASPGTPS | 6.000 |
| 353 | NVDKWDDFCL | 6.000 |
| 467 | QLLLDRRCQL | 6.000 |
| 577 | ALDRYGRTAL | 5.400 |
| 932 | AGDQGPGTHL | 5.400 |
| 955 | LVRLASGARA | 5.000 |
| 192 | HVRCAQGLEA | 5.000 |
| 428 | KVPRKDLIVM | 5.000 |
| 796 | QNQLRENKIL | 4.000 |
| 266 | GSLSVFQLHL | 4.000 |
| 559 | EQKQEVVKFL | 4.000 |
| 1027 | HQAFRDKDDL | 4.000 |
| 545 | KNKCGLTPLL | 4.000 |
| 916 | QIGDPGGVPL | 4.000 |
| 624 | SSHHVICEL | 4.000 |
| 593 | GSASIVNLLL | 4.000 |
| 197 | QGLEAASANL | 4.000 |
| 654 | ITILNIKLPL | 4.000 |
| 70 | TLTGHSALSL | 4.000 |
| 68 | STTLTGHSAL | 4.000 |
| 1051 | LGQDDRAGVL | 4.000 |
| 460 | NGNSEVVQLL | 4.000 |
| 904 | QQAQEQGAAL | 4.000 |

TABLE XIX-continued

| Pos | 1234567890 | Score |
|---|---|---|
| 777 | SMLREEIAKL | 4.000 |
| 104 | QSATPAGAFL | 4.000 |
| 763 | SLSHKKEEDL | 4.000 |
| 302 | TGGGILGLEL | 4.000 |
| 277 | QCIPNLSYPL | 4.000 |
| 591 | CCGSASIVNL | 4.000 |
| 190 | LTHVRCAQGL | 4.000 |
| 461 | GNSEVVQLLL | 4.000 |
| 470 | LDRRCQLNVL | 4.000 |
| 47 | CCNLEKGSWL | 4.000 |
| 604 | QNVDVSSQDL | 4.000 |
| 36 | VTWRKEPAVL | 4.000 |
| 817 | KTIQLNEEAL | 4.000 |
| 674 | SNPVGLPENL | 4.000 |
| 491 | VQCQEDECVL | 4.000 |
| 324 | IMQIKEFEEL | 4.000 |
| 592 | CGSASIVNLL | 4.000 |
| 80 | SSSRALPGSL | 4.000 |
| 1042 | QQSPRHTKDL | 4.000 |
| 648 | ENSNPVITIL | 4.000 |
| 735 | NTGISQDEIL | 4.000 |
| 764 | LSHKKEEDLL | 4.000 |
| 753 | VAEKEMNSEL | 3.600 |
| 253 | GPQEQPSEEA | 3.000 |
| 1003 | LGRRCPMFDV | 3.000 |
| 490 | AVQCQEDECV | 3.000 |
| 522 | YAIYNEDKLM | 3.000 |
| 675 | NPVGLPENLT | 3.000 |
| 95 | LPRSCPESEQ | 3.000 |
| 407 | EPRYHVRRED | 3.000 |
| 589 | AVCCGSASIV | 3.000 |
| 144 | SPPCHQRRDA | 3.000 |
| 128 | RPQAAPATSA | 3.000 |
| 138 | TPSRDPSPPC | 3.000 |
| 244 | LPRAPQAVSG | 2.000 |
| 8 | LPTQATFAAA | 2.000 |
| 652 | PVITILNIKL | 2.000 |
| 1065 | RPGTLCHTDT | 2.000 |
| 34 | DPVTWRKEPA | 2.000 |
| 923 | VPLSEGGTAA | 2.000 |
| 581 | YGRTALILAV | 2.000 |
| 1044 | SPRHTKDLGQ | 2.000 |

TABLE XX

| Pos | 123456789 | Score |
|---|---|---|
| \multicolumn{3}{c}{V1-B35-9mers:251P5G2 Each peptide is a portion of SEQ ID NO: 3; each start position is specified, the length of peptide is 9 amino acids, and the end position for each peptide is the start position plus eight.} | | |
| 226 | LPVSFSVGM | 40.000 |
| 1 | MPFISKLVL | 20.000 |
| 207 | QPQPLPKDL | 20.000 |
| 23 | SPFLLFLDL | 20.000 |
| 130 | FPVSSSLIF | 20.000 |
| 115 | KSTIFTFHL | 10.000 |
| 243 | TSSTLPWAY | 10.000 |
| 38 | LPVCHVALI | 8.000 |
| 217 | RGKSHQHIL | 6.000 |
| 187 | FSSVYMMTL | 5.000 |
| 21 | ASSPFLLFL | 5.000 |
| 19 | FSASSPFLL | 5.000 |
| 10 | ASQPTLFSF | 5.000 |
| 173 | LSLFRDVFL | 5.000 |
| 86 | LSICTTCLL | 5.000 |
| 128 | LSFPVSSSL | 5.000 |
| 143 | SSNVTQINL | 5.000 |
| 63 | ESLNFQNDF | 5.000 |
| 163 | NSIIRGLFF | 5.000 |
| 57 | LSPQLFESL | 5.000 |
| 30 | DLRPERTYL | 4.500 |
| 247 | LPWAYDRGV | 4.000 |
| 20 | SASSPFLLF | 3.000 |
| 165 | IIRGLFFTL | 3.000 |
| 43 | VALIHMVVL | 3.000 |
| 78 | YLRRVIRVL | 3.000 |
| 106 | ISWLVRFKW | 2.500 |

TABLE XX-continued

| Pos | 123456789 | Score |
|---|---|---|
| 241 | ISTSSTLPW | 2.500 |
| 32 | RPERTYLPV | 2.400 |
| 184 | IMLFSSVYM | 2.000 |
| 12 | QPTLFSFFS | 2.000 |
| 157 | CSLFPINSI | 2.000 |
| 188 | SSVYMMTLI | 2.000 |
| 183 | QIMLFSSVY | 2.000 |
| 185 | MLFSSVYMM | 2.000 |
| 65 | LNFQNDFKY | 2.000 |
| 167 | RGLFFTLSL | 2.000 |
| 195 | LIQELQEIL | 2.000 |
| 58 | SPQLFESLN | 2.000 |
| 40 | VCHVALIHM | 2.000 |
| 75 | ASFYLRRVI | 2.000 |
| 148 | QINLHVSKY | 2.000 |
| 88 | ICTTCLLGM | 2.000 |
| 141 | VASSNVTQI | 1.200 |
| 211 | LPKDLCRGK | 1.200 |
| 116 | STIFTFHLF | 1.000 |
| 53 | TMVFLSPQL | 1.000 |
| 37 | YLPVCHVAL | 1.000 |
| 124 | FSWSLSFPV | 1.000 |
| 7 | LVLASQPTL | 1.000 |
| 49 | VVLLTMVFL | 1.000 |
| 85 | VLSICTTCL | 1.000 |
| 44 | ALIHMVVLL | 1.000 |
| 203 | LVPSQPQPL | 1.000 |
| 178 | DVFLKQIML | 1.000 |
| 239 | FIISTSSTL | 1.000 |
| 133 | SSSLIFYTV | 1.000 |
| 8 | VLASQPTLF | 1.000 |
| 101 | NISPSISWL | 1.000 |
| 162 | INSIIRGLF | 1.000 |
| 172 | TLSLFRDVF | 1.000 |
| 11 | SQPTLFSFF | 1.000 |
| 191 | YMMTLIQEL | 1.000 |
| 54 | MVFLSPQLF | 1.000 |
| 168 | GLFFTLSLF | 1.000 |

TABLE XX-continued

| Pos | 123456789 | Score |
|---|---|---|
| 231 | SVGMYKMDF | 1.000 |
| 48 | MVVLLTMVF | 1.000 |
| 89 | CTTCLLGML | 1.000 |
| 102 | ISPSISWLV | 1.000 |
| 152 | HVSKYCSLF | 1.000 |
| 122 | HLFSWSLSF | 1.000 |
| 70 | DFKYEASFY | 0.900 |
| 194 | TLIQELQEI | 0.600 |
| 111 | RFKWKSTIF | 0.600 |
| 74 | EASFYLRRV | 0.600 |
| 113 | KWKSTIFTF | 0.600 |
| 142 | ASSNVTQIN | 0.500 |
| 134 | SSLIFYTVA | 0.500 |
| 132 | VSSSLIFYT | 0.500 |
| 100 | VNISPSISW | 0.500 |
| 104 | PSISWLVRF | 0.500 |
| 126 | WSLSFPVSS | 0.500 |
| 98 | QVVNISPSI | 0.400 |
| 233 | GMYKMDFII | 0.400 |
| 182 | KQIMLFSSV | 0.400 |
| 35 | RTYLPVCHV | 0.400 |
| 177 | RDVFLKQIM | 0.400 |
| 158 | SLFPINSII | 0.400 |
| 94 | LGMLQVVNI | 0.400 |
| 232 | VGMYKMDFI | 0.400 |
| 82 | VIRVLSICT | 0.300 |
| 9 | LASQPTLFS | 0.300 |
| 180 | FLKQIMLFS | 0.300 |
| 109 | LVRFKWKST | 0.300 |
| 145 | NVTQINLHV | 0.200 |
| 171 | FTLSLFRDV | 0.200 |
| 29 | LDLRPERTY | 0.200 |
| 131 | PVSSSLIFY | 0.200 |
| 160 | FPINSIIRG | 0.200 |
| 209 | QPLPKDLCR | 0.200 |

TABLE XX-continued

| Pos | 123456789 | Score |
|---|---|---|

V2-B35-
9mers:251P5G2
Each peptide is a portion of
SEQ ID NO: 5; each start
position is specified, the
length of peptide is 9 amino
acids, and the end position
for each peptide is the start
position plus eight.

| Pos | 123456789 | Score |
|---|---|---|
| 3 | ASQPTLCSF | 5.000 |
| 5 | QPTLCSFFS | 2.000 |
| 4 | SQPTLCSFF | 1.000 |
| 2 | LASQPTLCS | 0.300 |
| 8 | LCSFFSASS | 0.100 |
| 7 | TLCSFFSAS | 0.100 |
| 1 | VLASQPTLC | 0.100 |
| 9 | CSFFSASSP | 0.050 |
| 6 | PTLCSFFSA | 0.010 |

V3-B35-
9mers:251P5G2
Each peptide is a portion of
SEQ ID NO: 7; each start
position is specified, the
length of peptide is 9 amino
acids, and the end position
for each peptide is the start
position plus eight.

| Pos | 123456789 | Score |
|---|---|---|
| 2 | YLRRVIRDL | 3.000 |
| 9 | DLSICTTCL | 1.000 |
| 6 | VIRDLSICT | 0.600 |
| 5 | RVIRDLSIC | 0.300 |
| 4 | RRVIRDLSI | 0.080 |
| 3 | LRRVIRDLS | 0.030 |
| 8 | RDLSICTTC | 0.020 |
| 7 | IRDLSICTT | 0.003 |
| 1 | FYLRRVIRD | 0.001 |

V4-B35-
9mers:251P5G2
Each peptide is a portion of
SEQ ID NO: 9; each start
position is specified, the
length of peptide is 9 amino
acids, and the end position
for each peptide is the start
position plus eight.

| Pos | 123456789 | Score |
|---|---|---|
| 2 | ICTTCLLDM | 2.000 |
| 3 | CTTCLLDML | 1.000 |
| 6 | CLLDMLQVV | 0.400 |
| 5 | TCLLDMLQV | 0.300 |
| 9 | DMLQVVNIS | 0.100 |
| 8 | LDMLQVVNI | 0.040 |
| 7 | LLDMLQVVN | 0.030 |
| 4 | TTCLLDMLQ | 0.010 |
| 1 | SICTTCLLD | 0.010 |

V12A-B35-
9mers:251P5G2
Each peptide is a portion of
SEQ ID NO: 25; each start
position is specified, the
length of peptide is 9 amino
acids, and the end position
for each peptide is the start
position plus eight.

| Pos | 123456789 | Score |
|---|---|---|
| 2 | SPSISWLIM | 40.000 |
| 8 | LIMLFSSVY | 2.000 |
| 1 | ISPSISWLI | 2.000 |
| 4 | SISWLIMLF | 1.000 |
| 3 | PSISWLIML | 0.500 |
| 5 | ISWLIMLFS | 0.500 |
| 7 | WLIMLFSSV | 0.200 |
| 6 | SWLIMLFSS | 0.010 |

V12B-B35-
9mers:251P5G2
Each peptide is a portion of
SEQ ID NO: 25; each start
position is specified, the
length of peptide is 9 amino
acids, and the end position
for each peptide is the start
position plus eight.

| Pos | 123456789 | Score |
|---|---|---|
| 428 | VPRKDLIVM | 180.000 |
| 1060 | APKCRPGTL | 60.000 |
| 674 | NPVGLPENL | 20.000 |
| 993 | VPTFSSGSF | 20.000 |
| 233 | EPPAHQRLL | 20.000 |
| 211 | RSSSCALRY | 20.000 |
| 709 | FPDTENEEY | 18.000 |
| 80 | SSRALPGSL | 15.000 |
| 256 | QPSEEALGV | 12.000 |
| 612 | LSGQTAREY | 10.000 |
| 401 | DSAFMEPRY | 10.000 |
| 777 | MLREEIAKL | 9.000 |
| 650 | NPVITILNI | 8.000 |
| 660 | LPLKVEEEI | 8.000 |
| 981 | KSVCDSSGW | 7.500 |
| 946 | RASPGTPSL | 6.000 |
| 544 | KNKCGLTPL | 6.000 |

TABLE XX-continued

| Pos | 123456789 | Score |
|---|---|---|
| 125 | VPRPQAAPA | 6.000 |
| 885 | QASVQQLCY | 6.000 |
| 447 | KQKRTALHL | 6.000 |
| 1021 | SNRETHQAF | 6.000 |
| 243 | LPRAPQAVS | 6.000 |
| 845 | QASVQQLCY | 6.000 |
| 156 | RAQGLTRAF | 6.000 |
| 827 | KTKVAGFSL | 6.000 |
| 904 | QAQEQGAAL | 6.000 |
| 1042 | QSPRHTKDL | 5.000 |
| 321 | NSIMQIKEF | 5.000 |
| 958 | ASGARAAAL | 5.000 |
| 103 | QSATPAGAF | 5.000 |
| 76 | LSLSSSRAL | 5.000 |
| 648 | NSNPVITIL | 5.000 |
| 86 | GSLPAFADL | 5.000 |
| 763 | LSHKKEEDL | 5.000 |
| 592 | GSASIVNLL | 5.000 |
| 1027 | QAFRDKDDL | 4.500 |
| 558 | EQKQEVVKF | 4.500 |
| 147 | HQRRDAACL | 4.500 |
| 628 | VICELLSDY | 4.000 |
| 316 | RLSGLNSIM | 4.000 |
| 278 | IPNLSYPLV | 4.000 |
| 351 | KNVDKWDDF | 4.000 |
| 127 | RPQAAPATS | 4.000 |
| 378 | KISGLIQEM | 4.000 |
| 687 | SAGNGDDGL | 3.000 |
| 491 | QCQEDECVL | 3.000 |
| 1006 | CPMFDVSPA | 3.000 |
| 522 | AIYNEDKLM | 3.000 |
| 870 | VAGFSLRQL | 3.000 |
| 1090 | LPHRDTTTS | 3.000 |
| 593 | SASIVNLLL | 3.000 |
| 830 | VAGFSLRQL | 3.000 |
| 521 | YAIYNEDKL | 3.000 |
| 633 | LSDYKEKQM | 3.000 |
| 922 | VPLSEGGTA | 3.000 |
| 825 | LTKTKVAGF | 3.000 |
| 15 | AATGLWAAL | 3.000 |
| 286 | VLRHIPEIL | 3.000 |
| 104 | SATPAGAFL | 3.000 |
| 940 | LPPREPRAS | 3.000 |
| 152 | AACLRAQGL | 3.000 |
| 883 | HAQASVQQL | 3.000 |
| 425 | WGKVPRKDL | 3.000 |
| 843 | HAQASVQQL | 3.000 |
| 371 | IMKETSTKI | 2.400 |
| 546 | KCGLTPLLL | 2.000 |
| 375 | TSTKISGLI | 2.000 |
| 228 | APSPAEPPA | 2.000 |
| 170 | APTAPDGGA | 2.000 |
| 275 | IQCIPNLSY | 2.000 |
| 208 | APGRSSSCA | 2.000 |
| 179 | GCPPSRNSY | 2.000 |
| 1035 | LPFFKTQQS | 2.000 |
| 391 | SNVGTWGDY | 2.000 |
| 1081 | TPPHRHTTT | 2.000 |
| 951 | TPSLVRLAS | 2.000 |
| 7 | LPTQATFAA | 2.000 |
| 84 | LPGSLPAFA | 2.000 |
| 234 | PPAHQRLLF | 2.000 |
| 516 | NTALHYAIY | 2.000 |
| 644 | ISSENSNPV | 2.000 |
| 434 | IVMLRDTDM | 2.000 |
| 40 | EPAVLPCCN | 2.000 |
| 267 | LSVFQLHLI | 2.000 |
| 1082 | PPHRHTTTL | 2.000 |
| 976 | SPTKQKSVC | 2.000 |
| 310 | LPATAARLS | 2.000 |
| 131 | APATSATPS | 2.000 |
| 28 | NPSRADPVT | 2.000 |
| 572 | ANLNALDRY | 2.000 |
| 460 | GNSEVVQLL | 2.000 |
| 467 | LLLDRRCQL | 2.000 |
| 1073 | TPPHRNADT | 2.000 |
| 181 | PPSRNSYRL | 2.000 |

TABLE XX-continued

| Pos | 123456789 | Score |
|---|---|---|
| 205 | LPGAPGRSS | 2.000 |
| 529 | LMAKALLLY | 2.000 |
| 528 | KLMAKALLL | 2.000 |
| 721 | EQNDTQKQL | 2.000 |
| 47 | CNLEKGSWL | 2.000 |
| 222 | GPSVSSAPS | 2.000 |

TABLE XXI

| Pos | 1234567890 | Score |
|---|---|---|
| | V1-B35-10mers:251P5G2 Each peptide is a portion of SEQ ID NO: 3; each start position is specified, the length of peptide is 10 amino acids, and the end position for each peptide is the start position plus nine. | |
| 226 | LPVSFSVGMY | 40.000 |
| 130 | FPVSSSLIFY | 40.000 |
| 58 | SPQLFESLNF | 30.000 |
| 103 | SPSISWLVRF | 20.000 |
| 160 | FPINSIIRGL | 20.000 |
| 211 | LPKDLCRGKS | 12.000 |
| 228 | VSFSVGMYKM | 10.000 |
| 115 | KSTIFTFHLF | 10.000 |
| 217 | RGKSHQHILL | 6.000 |
| 153 | VSKYCSLFPI | 6.000 |
| 230 | FSVGMYKMDF | 5.000 |
| 19 | FSASSPFLLF | 5.000 |
| 16 | FSFFSASSPF | 5.000 |
| 22 | SSPFLLFLDL | 5.000 |
| 142 | ASSNVTQINL | 5.000 |
| 10 | ASQPTLFSFF | 5.000 |
| 182 | KQIMLFSSVY | 4.000 |
| 43 | VALIHMVVLL | 3.000 |
| 9 | LASQPTLFSF | 3.000 |
| 20 | SASSPFLLFL | 3.000 |
| 167 | RGLFFTLSLF | 2.000 |
| 184 | IMLFSSVYMM | 2.000 |
| 147 | TQINLHVSKY | 2.000 |
| 12 | QPTLFSFFSA | 2.000 |

TABLE XXI-continued

| Pos | 1234567890 | Score |
|---|---|---|
| 128 | LSFPVSSSLI | 2.000 |
| 187 | FSSVYMMTLI | 2.000 |
| 87 | SICTTCLLGM | 2.000 |
| 84 | RVLSICTTCL | 2.000 |
| 207 | QPQPLPKDLC | 2.000 |
| 1 | MPFISKLVLA | 2.000 |
| 157 | CSLFPINSII | 2.000 |
| 6 | KLVLASQPTL | 2.000 |
| 242 | STSSTLPWAY | 2.000 |
| 183 | QIMLFSSVYM | 2.000 |
| 225 | LLPVSFSVGM | 2.000 |
| 219 | KSHQHILLPV | 2.000 |
| 45 | LIHMVVLLTM | 2.000 |
| 64 | SLNFQNDFKY | 2.000 |
| 32 | RPERTYLPVC | 1.200 |
| 109 | LVRFKWKSTI | 1.200 |
| 74 | EASFYLRRVI | 1.200 |
| 215 | LCRGKSHQHI | 1.200 |
| 171 | FTLSLFRDVF | 1.000 |
| 202 | ILVPSQPQPL | 1.000 |
| 221 | HQHILLPVSF | 1.000 |
| 132 | VSSSLIFYTV | 1.000 |
| 164 | SIIRGLFFTL | 1.000 |
| 178 | DVFLKQIMLF | 1.000 |
| 7 | LVLASQPTLF | 1.000 |
| 42 | HVALIHMVVL | 1.000 |
| 119 | FTFHLFSWSL | 1.000 |
| 150 | NLHVSKYCSL | 1.000 |
| 172 | TLSLFRDVFL | 1.000 |
| 88 | ICTTCLLGML | 1.000 |
| 48 | MVVLLTMVFL | 1.000 |
| 100 | VNISPSISWL | 1.000 |
| 47 | HMVVLLTMVF | 1.000 |
| 194 | TLIQELQEIL | 1.000 |
| 206 | SQPQPLPKDL | 1.000 |
| 162 | INSIIRGLFF | 1.000 |
| 127 | SLSFPVSSSL | 1.000 |
| 56 | FLSPQLFESL | 1.000 |
| 53 | TMVFLSPQLF | 1.000 |

TABLE XXI-continued

| Pos | 1234567890 | Score |
|-----|------------|-------|
| 85  | VLSICTTCLL | 1.000 |
| 52  | LTMVFLSPQL | 1.000 |
| 193 | MTLIQELQEI | 0.600 |
| 28  | FLDLRPERTY | 0.600 |
| 105 | SISWLVRFKW | 0.500 |
| 241 | ISTSSTLPWA | 0.500 |
| 124 | FSWSLSFPVS | 0.500 |
| 240 | IISTSSTLPW | 0.500 |
| 57  | LSPQLFESLN | 0.500 |
| 163 | NSIIRGLFFT | 0.500 |
| 99  | VVNISPSISW | 0.500 |
| 134 | SSLIFYTVAS | 0.500 |
| 117 | TIFTPHLFSW | 0.500 |
| 133 | SSSLIFYTVA | 0.500 |
| 126 | WSLSFPVSSS | 0.500 |
| 97  | LQVVNISPSI | 0.400 |
| 231 | SVGMYKMDFI | 0.400 |
| 93  | LLGMLQVVNI | 0.400 |
| 232 | VGMYKMDFII | 0.400 |
| 195 | LIQELQEILV | 0.400 |
| 140 | TVASSNVTQI | 0.400 |
| 37  | YLPVCHVALI | 0.400 |
| 156 | YCSLFPINSI | 0.400 |
| 69  | NDFKYEASFY | 0.300 |
| 68  | QNDFKYEASF | 0.300 |
| 180 | FLKQIMLFSS | 0.300 |
| 165 | IIRGLFFTLS | 0.300 |
| 82  | VIRVLSICTT | 0.300 |
| 78  | YLRRVIRVLS | 0.300 |
| 141 | VASSNVTQIN | 0.300 |
| 209 | QPLPKDLCRG | 0.300 |
| 70  | DFKYEASFYL | 0.300 |
| 175 | LFRDVFLKQI | 0.240 |
| 177 | RDVFLKQIML | 0.200 |
| 144 | SNVTQINLHV | 0.200 |
| 38  | LPVCHVALIH | 0.200 |
| 39  | PVCHVALIHM | 0.200 |

TABLE XXI-continued

| Pos | 1234567890 | Score |
|-----|------------|-------|

V2-B35-
10mers:251P5G2
Each peptide is a portion of
SEQ ID NO: 5; each start
position is specified, the
length of peptide is 10 amino
acids, and the end position
for each peptide is the start
position plus nine.

| Pos | 1234567890 | Score |
|-----|------------|-------|
| 4   | ASQPTLCSFF | 5.000 |
| 10  | CSFFSASSPF | 5.000 |
| 3   | LASQPTLCSF | 3.000 |
| 6   | QPTLCSFFSA | 2.000 |
| 8   | TLCSFFSASS | 0.100 |
| 1   | LVLASQPTLC | 0.100 |
| 5   | SQPTLCSFFS | 0.100 |
| 2   | VLASQPTLCS | 0.100 |
| 7   | PTLCSFFSAS | 0.010 |
| 9   | LCSFFSASSP | 0.010 |

V3-B35-
10mers:251P5G2
Each peptide is a portion of
SEQ ID NO: 7; each start
position is specified, the
length of peptide is 10 amino
acids, and the end position
for each peptide is the start
position plus nine.

| Pos | 1234567890 | Score |
|-----|------------|-------|
| 10  | DLSICTTCLL | 1.000 |
| 7   | VIRDLSICTT | 0.600 |
| 3   | YLRRVIRDLS | 0.300 |
| 9   | RDLSICTTCL | 0.200 |
| 6   | RVIRDLSICT | 0.200 |
| 4   | LRRVIRDLSI | 0.120 |
| 2   | FYLRRVIRDL | 0.100 |
| 5   | RRVIRDLSIC | 0.030 |
| 8   | IRDLSICTTC | 0.003 |
| 1   | SFYLRRVIRD | 0.001 |

V4-B35-
10mers:251P5G2
Each peptide is a portion of
SEQ ID NO: 9; each start
position is specified, the
length of peptide is 10 amino
acids, and the end position
for each peptide is the start
position plus nine.

| Pos | 1234567890 | Score |
|-----|------------|-------|
| 2   | SICTTCLLDM | 2.000 |
| 3   | ICTTCLLDML | 1.000 |
| 5   | TTCLLDMLQV | 0.300 |
| 6   | TCLLDMLQVV | 0.200 |

TABLE XXI-continued

| Pos | 1234567890 | Score |
|---|---|---|
| 7 | CLLDMLQVVN | 0.200 |
| 8 | LLDMLQVVNI | 0.120 |
| 1 | LSICTTCLLD | 0.050 |
| 4 | CTTCLLDMLQ | 0.010 |
| 10 | DMLQVVNISP | 0.010 |
| 9 | LDMLQVVNIS | 0.010 |

V12A-B35-10mers:251P5G2
Each peptide is a portion of SEQ ID NO: 25; each start position is specified, the length of peptide is 10 amino acids, and the end position for each peptide is the start position plus nine.

| Pos | 1234567890 | Score |
|---|---|---|
| 3 | SPSISWLIML | 20.000 |
| 2 | ISPSISWLIM | 10.000 |
| 8 | WLIMLFSSVY | 2.000 |
| 9 | LIMLFSSVYM | 2.000 |
| 6 | ISWLIMLFSS | 0.500 |
| 4 | PSISWLIMLF | 0.500 |
| 1 | NISPSISWLI | 0.400 |
| 5 | SISWLIMLFS | 0.100 |
| 7 | SWLIMLFSSV | 0.020 |

V12B-B35-10mers:251P5G2
Each peptide is a portion of SEQ ID NO: 25; each start position is specified, the length of peptide is 10 amino acids, and the end position for each peptide is the start position plus nine.

| Pos | 1234567890 | Score |
|---|---|---|
| 429 | VPRKDLIVML | 60.000 |
| 701 | KSRKPENQQF | 45.000 |
| 1007 | CPMFDVSPAM | 40.000 |
| 994 | VPTFSSGSFL | 20.000 |
| 234 | EPPAHQRLLF | 20.000 |
| 279 | IPNLSYPLVL | 20.000 |
| 181 | CPPSRNSYRL | 20.000 |
| 209 | APGRSSSCAL | 20.000 |
| 58 | FPGTAARKEF | 20.000 |
| 949 | SPGTPSLVRL | 20.000 |
| 1082 | TPPHRHTTTL | 20.000 |
| 391 | KSNVGTWGDY | 20.000 |
| 41 | EPAVLPCCNL | 20.000 |
| 1091 | LPHRDTTTSL | 20.000 |
| 29 | NPSRADPVTW | 15.000 |
| 572 | KANLNALDRY | 12.000 |
| 1000 | GSFLGRRCPM | 10.000 |
| 107 | TPAGAFLLGW | 10.000 |
| 62 | AARKEFSTTL | 9.000 |
| 522 | YAIYNEDKLM | 9.000 |
| 865 | QAQEQEVAGF | 9.000 |
| 749 | KQIEVAEKEM | 8.000 |
| 764 | LSHKKEEDLL | 7.500 |
| 428 | KVPRKDLIVM | 6.000 |
| 545 | KNKCGLTPLL | 6.000 |
| 945 | EPRASPGTPS | 6.000 |
| 492 | QCQEDECVLM | 6.000 |
| 83 | RALPGSLPAF | 6.000 |
| 1061 | APKCRPGTLC | 6.000 |
| 126 | VPRPQAAPAT | 6.000 |
| 1021 | DSNRETHQAF | 5.000 |
| 339 | LSHKVIQCVF | 5.000 |
| 624 | SSHHVICEL | 5.000 |
| 266 | GSLSVFQLHL | 5.000 |
| 104 | QSATPAGAFL | 5.000 |
| 687 | ASAGNGDDGL | 5.000 |
| 80 | SSSRALPGSL | 5.000 |
| 593 | GSASIVNLLL | 5.000 |
| 348 | FAKKKNVDKW | 4.500 |
| 411 | HVRREDLDKL | 4.500 |
| 982 | KSVCDSSGWI | 4.000 |
| 128 | RPQAAPATSA | 4.000 |
| 1065 | RPGTLCHTDT | 4.000 |
| 633 | LLSDYKEKQM | 4.000 |
| 529 | KLMAKALLLY | 4.000 |
| 253 | GPQEQPSEEA | 4.000 |
| 645 | ISSENSNPVI | 4.000 |
| 315 | AARLSGLNSI | 3.600 |
| 11 | QATFAAATGL | 3.000 |
| 559 | EQKQEVVKFL | 3.000 |
| 1106 | SAGGVGPTTL | 3.000 |
| 161 | LTRAFQVVHL | 3.000 |

TABLE XXI-continued

| Pos | 1234567890 | Score |
|---|---|---|
| 1060 | LAPKCRPGTL | 3.000 |
| 914 | RSQIGDPGGV | 3.000 |
| 152 | DAACLRAQGL | 3.000 |
| 958 | LASGARAAAL | 3.000 |
| 89 | LPAFADLPRS | 3.000 |
| 15 | AAATGLWAAL | 3.000 |
| 105 | SATPAGAFLL | 3.000 |
| 847 | ASVQQLCYKW | 2.500 |
| 388 | GSGKSNVGTW | 2.500 |
| 887 | ASVQQLCYKW | 2.500 |
| 533 | KALLLYGADI | 2.400 |
| 810 | SVKEKLLKTI | 2.400 |
| 634 | LSDYKEKQML | 2.250 |
| 179 | AGCPPSRNSY | 2.000 |
| 275 | LIQCIPNLSY | 2.000 |
| 138 | TPSRDPSPPC | 2.000 |
| 817 | KTIQLNEEAL | 2.000 |
| 318 | LSGLNSIMQI | 2.000 |
| 364 | EGYGHSFLIM | 2.000 |
| 675 | NPVGLPENLT | 2.000 |
| 983 | SVCDSSGWIL | 2.000 |
| 1051 | LGQDDRAGVL | 2.000 |
| 144 | SPPCHQRRDA | 2.000 |
| 916 | QIGDPGGVPL | 2.000 |
| 361 | CLSEGYGHSF | 2.000 |
| 45 | LPCCNLEKGS | 2.000 |
| 34 | DPVTWRKEPA | 2.000 |
| 885 | AQASVQQLCY | 2.000 |
| 8 | LPTQATFAAA | 2.000 |
| 516 | GNTALHYAIY | 2.000 |
| 461 | GNSEVVQLLL | 2.000 |
| 923 | VPLSEGGTAA | 2.000 |
| 830 | KVAGFSLRQL | 2.000 |
| 612 | DLSGQTAREY | 2.000 |
| 628 | HVICELLSDY | 2.000 |
| 206 | LPGAPGRSSS | 2.000 |
| 282 | LSYPLVLRHI | 2.000 |
| 845 | AQASVQQLCY | 2.000 |

TABLE XXI-continued

| Pos | 1234567890 | Score |
|---|---|---|
| 197 | QGLEAASANL | 2.000 |
| 604 | QNVDVSSQDL | 2.000 |
| 434 | LIVMLRDTDM | 2.000 |
| 235 | PPAHQRLLFL | 2.000 |
| 1013 | SPAMRLKSDS | 2.000 |
| 992 | LPVPTFSSGS | 2.000 |
| 688 | SAGNGDDGLI | 1.800 |
| 506 | GADGNIQDEY | 1.800 |
| 324 | IMQIKEFEEL | 1.500 |
| 777 | SMLREEIAKL | 1.500 |

Tables XXII-XLIX:

TABLE XXII

| Pos | 123456789 | score |
|---|---|---|
| colspan="3" | V1A-A1-9mers:251P5G2  Each peptide is a portion of SEQ ID NO: 3; each start position is specified, the length of peptide is 9 amino acids, and the end position for each peptide is the start position plus eight. | |
| 131 | PVSSSLIFY | 19 |
| 243 | TSSTLPWAY | 19 |
| 148 | QINLHVSKY | 18 |
| 196 | IQELQEILV | 18 |
| 65 | LNFQNDFKY | 17 |
| 227 | PVSFSVGMY | 17 |
| 29 | LDLRPERTY | 16 |
| 32 | RPERTYLPV | 16 |
| 183 | QIMLFSSVY | 16 |
| 205 | PSQPQPLPK | 16 |
| 21 | ASSPFLLFL | 15 |
| 70 | DFKYEASFY | 15 |
| 72 | KYEASFYLR | 15 |
| 20 | SASSPFLLF | 14 |
| 193 | MTLIQELQE | 14 |
| 116 | STIFTFHLF | 13 |
| 175 | LFRDVFLKQ | 13 |
| 212 | PKDLCRGKS | 13 |
| 28 | FLDLRPERT | 12 |

TABLE XXII-continued

| Pos | 123456789 | score |
|---|---|---|
| 51 | LLTMVFLSP | 12 |
| 219 | KSHQHILLP | 12 |
| 245 | STLPWAYDR | 12 |
| 23 | SPFLLFLDL | 11 |
| 45 | LIHMVVLLT | 11 |
| 61 | LFESLNFQN | 11 |
| 153 | VSKYCSLFP | 11 |
| 163 | NSIIRGLFF | 11 |
| 176 | FRDVFLKQI | 11 |
| 199 | LQEILVPSQ | 11 |
| 68 | QNDFKYEAS | 10 |
| 87 | SICTTCLLG | 10 |
| 119 | FTFHLFSWS | 10 |
| 128 | LSFPVSSSL | 10 |
| 143 | SSNVTQINL | 10 |
| 171 | FTLSLFRDV | 10 |
| 209 | QPLPKDLCR | 10 |
| 236 | KMDFIISTS | 10 |
| 241 | ISTSSTLPW | 10 |
| 10 | ASQPTLFSF | 9 |
| 13 | PTLFSFFSA | 9 |
| 90 | TTCLLGMLQ | 9 |
| 103 | SPSISWLVR | 9 |
| 106 | ISWLVRFKW | 9 |
| 133 | SSSLIFYTV | 9 |
| 139 | YTVASSNVT | 9 |

V2A-HLA-A1-9mers:251P5G2
Each peptide is a portion of SEQ ID NO: 5; each start position is specified, the length of peptide is 9 amino acids, and the end position for each peptide is the start position plus eight.

| Pos | 123456789 | score |
|---|---|---|
| 3 | ASQPTLCSF | 9 |
| 6 | PTLCSFFSA | 9 |
| 2 | LASQPTLCS | 7 |
| 1 | VLASQPTLC | 6 |
| 7 | TLCSFFSAS | 4 |
| 9 | CSFFSASSP | 4 |

TABLE XXII-continued

V2A-HLA-A1-9mers:251P5G2
Each peptide is a portion of SEQ ID NO: 5; each start position is specified, the length of peptide is 9 amino acids, and the end position for each peptide is the start position plus eight.

| Pos | 123456789 | score |
|---|---|---|
| 3 | ASQPTLCSF | 9 |
| 6 | PTLCSFFSA | 9 |
| 2 | LASQPTLCS | 7 |
| 1 | VLASQPTLC | 6 |
| 7 | TLCSFFSAS | 4 |
| 9 | CSFFSASSP | 4 |

V3A-HLA-A1-9mers:251P5G2
Each peptide is a portion of SEQ ID NO: 7; each start position is specified, the length of peptide is 9 amino acids, and the end position for each peptide is the start position plus eight.

| Pos | 123456789 | score |
|---|---|---|
| 7 | IRDLSICTT | 10 |
| 1 | FYLRRVIRD | 6 |
| 4 | RRVIRDLSI | 6 |
| 2 | YLRRVIRDL | 5 |
| 6 | VIRDLSICT | 5 |

V4A-HLA-A1-9mers:251P5G2
Each peptide is a portion of SEQ ID NO: 9; each start position is specified, the length of peptide is 9 amino acids, and the end position for each peptide is the start position plus eight.

| Pos | 123456789 | score |
|---|---|---|
| 7 | LLDMLQVVN | 12 |
| 1 | SICTTCLLD | 10 |
| 4 | TTCLLDMLQ | 8 |
| 3 | CTTCLLDML | 7 |
| 2 | ICTTCLLDM | 6 |
| 5 | TCLLDMLQV | 6 |

TABLE XXII-continued

| Pos | 123456789 | score |
|---|---|---|
| | V12A-HLA-9mers:251P5G2 Each peptide is a portion of SEQ ID NO: 25; each start position is specified, the length of peptide is 9 amino acids, and the end position for each peptide is the start position plus eight. | |
| 8 | LIMLFSSVY | 16 |
| 5 | ISWLIMLFS | 10 |
| 3 | PSISWLIML | 9 |
| 2 | SPSISWLIM | 8 |

TABLE XXIII

| Pos | 123456789 | score |
|---|---|---|
| | V1A-HLA-A0201-9mers:251P5G2 Each peptide is a portion of SEQ ID NO: 3; each start position is specified, the length of peptide is 9 amino acids, and the end position for each peptide is the start position plus eight. | |
| 44 | ALIHMVVLL | 30 |
| 92 | CLLGMLQVV | 28 |
| 191 | YMMTLIQEL | 28 |
| 224 | ILLPVSFSV | 28 |
| 78 | YLRRVIRVL | 26 |
| 194 | TLIQELQEI | 26 |
| 37 | YLPVCHVAL | 25 |
| 165 | IIRGLFFTL | 25 |
| 101 | NISPSISWL | 24 |
| 47 | HMVVLLTMV | 23 |
| 85 | VLSICTTCL | 23 |
| 158 | SLFPINSII | 23 |
| 195 | LIQELQEIL | 23 |
| 239 | FIISTSSTL | 23 |
| 164 | SIIRGLFFT | 22 |
| 7 | LVLASQPTL | 21 |
| 30 | DLRPERTYL | 21 |
| 161 | PINSIIRGL | 21 |
| 21 | ASSPFLLFL | 20 |
| 35 | RTYLPVCHV | 20 |
| 185 | MLFSSVYMM | 20 |

TABLE XXIII-continued

| Pos | 123456789 | score |
|---|---|---|
| 43 | VALIHMVVL | 19 |
| 45 | LIHMVVLLT | 19 |
| 49 | VVLLTMVFL | 19 |
| 53 | TMVFLSPQL | 19 |
| 56 | FLSPQLFES | 19 |
| 135 | SLIFYTVAS | 19 |
| 60 | QLFESLNFQ | 18 |
| 89 | CTTCLLGML | 18 |
| 127 | SLSFPVSSS | 18 |
| 136 | LIFYTVASS | 18 |
| 171 | FTLSLFRDV | 18 |
| 233 | GMYKMDFII | 18 |
| 26 | LLFLDLRPE | 17 |
| 50 | VLLTMVFLS | 17 |
| 77 | FYLRRVIRV | 17 |
| 94 | LGMLQVVNI | 17 |
| 128 | LSFPVSSSL | 17 |
| 141 | VASSNVTQI | 17 |
| 157 | CSLFPINSI | 17 |
| 167 | RGLFFTLSL | 17 |
| 174 | SLFRDVFLK | 17 |
| 184 | IMLFSSVYM | 17 |
| 220 | SHQHILLPV | 17 |
| 3 | FISKLVLAS | 16 |
| 38 | LPVCHVALI | 16 |
| 41 | CHVALIHMV | 16 |
| 42 | HVALIHMVV | 16 |
| 86 | LSICTTCLL | 16 |
| 95 | GMLQVVNIS | 16 |
| 182 | KQIMLFSSV | 16 |
| 203 | LVPSQPQPL | 16 |
| 6 | KLVLASQPT | 15 |
| 23 | SPFLLFLDL | 15 |
| 28 | FLDLRPERT | 15 |
| 57 | LSPQLFESL | 15 |
| 74 | EASFYLRRV | 15 |
| 80 | RRVIRVLSI | 15 |
| 91 | TCLLGMLQV | 15 |
| 93 | LLGMLQVVN | 15 |

TABLE XXIII-continued

| Pos | 123456789 | score |
|---|---|---|
| 98 | QVVNISPSI | 15 |
| 105 | SISWLVRFK | 15 |
| 133 | SSSLIFYTV | 15 |
| 148 | QINLHVSKY | 15 |
| 151 | LHVSKYCSL | 15 |
| 154 | SKYCSLFPI | 15 |
| 168 | GLFFTLSLF | 15 |
| 173 | LSLFRDVFL | 15 |
| 178 | DVFLKQIML | 15 |
| 198 | ELQEILVPS | 15 |
| 202 | ILVPSQPQP | 15 |
| 223 | HILLPVSFS | 15 |
| 235 | YKMDFIIST | 15 |
| 242 | STSSTLPWA | 15 |
| 247 | LPWAYDRGV | 15 |
| 25 | FLLFLDLRP | 14 |
| 46 | IHMVVLLTM | 14 |
| 51 | LLTMVFLSP | 14 |
| 71 | FLYEASFYL | 14 |
| 82 | VIRVLSICT | 14 |
| 122 | HLFSWSLSF | 14 |
| 145 | NVTQINLHV | 14 |
| 187 | FSSVYMMTL | 14 |
| 236 | KMDFIISTS | 14 |

V2A-HLA-A0201-9mers:251P5G2
Each peptide is a portion of SEQ ID NO: 5; each start position is specified, the length of peptide is 9 amino acids, and the end position for each peptide is the start position plus eight.

| Pos | 123456789 | score |
|---|---|---|
| 1 | VLASQPTLC | 13 |
| 7 | TLCSFFSAS | 12 |
| 2 | LASQPTLCS | 10 |
| 3 | ASQPTLCSF | 10 |
| 6 | PTLCSFFSA | 9 |
| 8 | LCSFFSASS | 6 |

TABLE XXIII-continued

V3A-HLA-A0201-9mers:251P5G2
Each peptide is a portion of SEQ ID NO: 7; each start position is specified, the length of peptide is 9 amino acids, and the end position for each peptide is the start position plus eight.

| Pos | 123456789 | score |
|---|---|---|
| 2 | YLRRVIRDL | 26 |
| 9 | DLSICTTCL | 21 |
| 6 | VIRDLSICT | 15 |
| 7 | IRDLSICTT | 12 |

V4A-HLA-A0201-9mers:251P5G2
Each peptide is a portion of SEQ ID NO: 9; each start position is specified, the length of peptide is 9 amino acids, and the end position for each peptide is the start position plus eight.

| Pos | 123456789 | score |
|---|---|---|
| 6 | CLLDMLQVV | 27 |
| 3 | CTTCLLDML | 18 |
| 8 | LDMLQVVNI | 17 |
| 7 | LLDMLQVVN | 15 |
| 9 | DMLQVVNIS | 14 |
| 5 | TCLLDMLQV | 13 |

V12A-HLA-A0201-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 7 | WLIMLFSSV | 25 |
| 4 | SISWLIMLF | 15 |
| 3 | PSISWLIML | 13 |
| 8 | LIMLFSSVY | 12 |

V12B-HLA-A0201-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 777 | MLREEIAKL | 30 |
| 548 | GLTPLLLGV | 29 |
| 802 | KILEEIESV | 29 |
| 18 | GLWAALTTV | 28 |
| 599 | LLLEQNVDV | 28 |

TABLE XXIII-continued

| Pos | 123456789 | score |
|---|---|---|
| 261 | ALGVGSLSV | 27 |
| 273 | HLIQCIPNL | 27 |
| 566 | FLIKKKANL | 26 |
| 111 | FLLGWERVV | 25 |
| 334 | KLHSLSHKV | 25 |
| 467 | LLLDRRCQL | 25 |
| 533 | ALLLYGADI | 25 |
| 266 | SLSVFQLHL | 24 |
| 528 | KLMAKALLL | 24 |
| 285 | LVLRHIPEI | 23 |
| 312 | ATAARLSGL | 23 |
| 946 | RASPGTPSL | 23 |
| 197 | GLEAASANL | 22 |
| 242 | FLPRAPQAV | 22 |
| 305 | ILGLELPAT | 22 |
| 327 | KEFEELVKL | 22 |
| 378 | KISGLIQEM | 22 |
| 15 | AATGLWAAL | 21 |
| 286 | VLRHIPEIL | 21 |
| 300 | ETGGGILGL | 21 |
| 315 | ARLSGLNSI | 21 |
| 371 | IMKETSTKI | 21 |
| 652 | VITILNIKL | 21 |
| 654 | TILNIKLPL | 21 |
| 770 | DLLRENSML | 21 |
| 781 | EIAKLRLEL | 21 |
| 784 | KLRLELDET | 21 |
| 1098 | SLPHFHVSA | 21 |
| 5 | ILLPTQATF | 20 |
| 83 | ALPGSLPAF | 20 |
| 159 | GLTRAFQVV | 20 |
| 277 | CIPNLSYPL | 20 |
| 325 | QIKEFEELV | 20 |
| 369 | FLIMKETST | 20 |
| 586 | ILAVCCGSA | 20 |
| 588 | AVCCGSASI | 20 |
| 840 | LAQHAQASV | 20 |
| 880 | LAQHAQASV | 20 |

TABLE XXIII-continued

| Pos | 123456789 | score |
|---|---|---|
| 14 | AAATGLWAA | 19 |
| 35 | VTWRKEPAV | 19 |
| 68 | TTLTGHSAL | 19 |
| 70 | LTGHSALSL | 19 |
| 104 | SATPAGAFL | 19 |
| 304 | GILGLELPA | 19 |
| 309 | ELPATAARL | 19 |
| 411 | VRREDLDKL | 19 |
| 432 | DLIVMLRDT | 19 |
| 457 | SANGNSEVV | 19 |
| 498 | VLMLLEHGA | 19 |
| 521 | YAIYNEDKL | 19 |
| 555 | GVHEQKQEV | 19 |
| 576 | ALDRYGRTA | 19 |
| 655 | ILNIKLPLK | 19 |
| 687 | SAGNGDDGL | 19 |
| 742 | ILTNKQKQI | 19 |
| 809 | SVKEKLLKT | 19 |
| 817 | TIQLNEEAL | 19 |
| 904 | QAQEQGAAL | 19 |
| 956 | RLASGARAA | 19 |
| 965 | ALPPPTGKN | 19 |
| 4 | HILLPTQAT | 18 |
| 11 | ATFAAATGL | 18 |
| 105 | ATPAGAFLL | 18 |
| 450 | RTALHLASA | 18 |
| 456 | ASANGNSEV | 18 |
| 477 | VLDNKKRTA | 18 |
| 485 | ALIKAVQCQ | 18 |
| 551 | PLLLGVHEQ | 18 |
| 584 | ALILAVCCG | 18 |
| 592 | GSASIVNLL | 18 |
| 595 | SIVNLLLEQ | 18 |
| 624 | SHHHVICEL | 18 |
| 656 | LNIKLPLKV | 18 |
| 659 | KLPLKVEEE | 18 |
| 830 | VAGFSLRQL | 18 |
| 843 | HAQASVQQL | 18 |
| 870 | VAGFSLRQL | 18 |

TABLE XXIII-continued

| Pos | 123456789 | score |
|---|---|---|
| 883 | HAQASVQQL | 18 |
| 916 | IGDPGGVPL | 18 |
| 953 | SLVRLASGA | 18 |
| 1112 | TTLGSNREI | 18 |
| 86 | GSLPAFADL | 17 |
| 117 | RVVQRRLEV | 17 |
| 152 | AACLRAQGL | 17 |
| 161 | TRAFQVVHL | 17 |
| 259 | EEALGVGSL | 17 |
| 316 | RLSGLNSIM | 17 |
| 330 | EELVKLHSL | 17 |
| 337 | SLSHKVIQC | 17 |
| 374 | ETSTKISGL | 17 |
| 385 | EMGSGKSNV | 17 |
| 403 | AFMEPRYHV | 17 |
| 427 | KVPRKDLIV | 17 |
| 459 | NGNSEVVQL | 17 |
| 460 | GNSEVVQLL | 17 |
| 493 | QEDECVLML | 17 |
| 529 | LMAKALLLY | 17 |
| 535 | LLYGADIES | 17 |
| 581 | GRTALILAV | 17 |
| 593 | SASIVNLLL | 17 |
| 620 | YAVSSHHHV | 17 |
| 648 | NSNPVITIL | 17 |
| 677 | GLPENLTNG | 17 |
| 813 | KLLKTIQLN | 17 |
| 914 | SQIGDPGGV | 17 |
| 939 | HLPPREPRA | 17 |
| 990 | ILPVPTFSS | 17 |
| 6 | LLPTQATFA | 16 |
| 62 | ARKEFSTTL | 16 |
| 75 | ALSLSSSRA | 16 |
| 110 | AFLLGWERV | 16 |
| 200 | AASANLPGA | 16 |
| 217 | LRYRSGPSV | 16 |
| 235 | PAHQRLLFL | 16 |
| 240 | LLFLPRAPQ | 16 |

TABLE XXIII-continued

| Pos | 123456789 | score |
|---|---|---|
| 270 | FQLHLIQCI | 16 |
| 280 | NLSYPLVLR | 16 |
| 307 | GLELPATAA | 16 |
| 318 | SGLNSIMQI | 16 |
| 338 | LSHKVIQCV | 16 |
| 500 | MLLEHGADG | 16 |
| 518 | ALHYAIYNE | 16 |
| 544 | KNKCGLTPL | 16 |
| 545 | NKCGLTPLL | 16 |
| 552 | LLLGVHEQK | 16 |
| 569 | KKKANLNAL | 16 |
| 591 | CGSASIVNL | 16 |
| 628 | VICELLSDY | 16 |
| 632 | LLSDYKEKQ | 16 |
| 694 | GLIPQRKSR | 16 |
| 806 | EIESVKEKL | 16 |
| 819 | QLNEEALTK | 16 |
| 827 | KTKVAGFSL | 16 |
| 911 | ALRSQIGDP | 16 |
| 923 | PLSEGGTAA | 16 |
| 985 | DSSGWILPV | 16 |
| 1050 | LGQDDRAGV | 16 |
| 1058 | VLAPKCRPG | 16 |
| 1089 | TLPHRDTTT | 16 |
| 1106 | AGGVGPTTL | 16 |
| 47 | CNLEKGSWL | 15 |
| 54 | WLSFPGTAA | 15 |
| 76 | LSLSSSRAL | 15 |
| 80 | SSRALPGSL | 15 |
| 82 | RALPGSLPA | 15 |
| 122 | RLEVPRPQA | 15 |
| 129 | QAAPATSAT | 15 |
| 168 | HLAPTAPDG | 15 |
| 264 | VGSLSVFQL | 15 |
| 293 | ILKFSEKET | 15 |
| 302 | GGGILGLEL | 15 |
| 306 | LGLELPATA | 15 |
| 345 | CVFAKKKNV | 15 |
| 370 | LIMKETSTK | 15 |

TABLE XXIII-continued

| Pos | 123456789 | score |
|---|---|---|
| 381 | GLIQEMGSG | 15 |
| 415 | DLDKLHRAA | 15 |
| 474 | QLNVLDNKK | 15 |
| 478 | LDNKKRTAL | 15 |
| 482 | KRTALIKAV | 15 |
| 531 | AKALLLYGA | 15 |
| 534 | LLLYGADIE | 15 |
| 559 | QKQEVVKFL | 15 |
| 600 | LLEQNVDVS | 15 |
| 611 | DLSGQTARE | 15 |
| 621 | AVSSHHHVI | 15 |
| 644 | ISSENSNPV | 15 |
| 728 | QLSEEQNTG | 15 |
| 753 | AEKEMNSEL | 15 |
| 755 | KEMNSELSL | 15 |
| 762 | SLSHKKEED | 15 |
| 799 | RENKILEEI | 15 |
| 834 | SLRQLGLAQ | 15 |
| 850 | QLCYKWNHT | 15 |
| 874 | SLRQLGLAQ | 15 |
| 957 | LASGARAAA | 15 |
| 958 | ASGARAAAL | 15 |
| 982 | SVCDSSGWI | 15 |
| 1027 | QAFRDKDDL | 15 |
| 1096 | TTSLPHFHV | 15 |
| 1104 | VSAGGVGPT | 15 |
| 1105 | SAGGVGPTT | 15 |
| 43 | VLPCCNLEK | 14 |
| 77 | SLSSSRALP | 14 |
| 112 | LLGWERVVQ | 14 |
| 155 | LRAQGLTRA | 14 |
| 162 | RAFQVVHLA | 14 |
| 232 | AEPPAHQRL | 14 |
| 256 | QPSEEALGV | 14 |
| 267 | LSVFQLHLI | 14 |
| 278 | IPNLSYPLV | 14 |
| 282 | SYPLVLRHI | 14 |
| 324 | MQIKEFEEL | 14 |

TABLE XXIII-continued

| Pos | 123456789 | score |
|---|---|---|
| 360 | CLSEGYGHS | 14 |
| 420 | HRAAWWGKV | 14 |
| 429 | PRKDLIVML | 14 |
| 452 | ALHLASANG | 14 |
| 470 | DRRCQLNVL | 14 |
| 501 | LLEHGADGN | 14 |
| 522 | AIYNEDKLM | 14 |
| 553 | LLGVHEQKQ | 14 |
| 577 | LDRYGRTAL | 14 |
| 578 | DRYGRTALI | 14 |
| 597 | VNLLLEQNV | 14 |
| 604 | NVDVSSQDL | 14 |
| 660 | LPLKVEEEI | 14 |
| 668 | IKKHGSNPV | 14 |
| 670 | KHGSNPVGL | 14 |
| 734 | NTGISQDEI | 14 |
| 771 | LLRENSMLR | 14 |
| 810 | VKEKLLKTI | 14 |
| 816 | KTIQLNEEA | 14 |
| 824 | ALTKTKVAG | 14 |
| 839 | GLAQHAQAS | 14 |
| 879 | GLAQHAQAS | 14 |
| 890 | QLCYKWGHT | 14 |
| 932 | GDQGPGTHL | 14 |
| 947 | ASPGTPSLV | 14 |
| 949 | PGTPSLVRL | 14 |
| 950 | GTPSLVRLA | 14 |
| 1088 | TTLPHRDTT | 14 |
| 1113 | TLGSNREIT | 14 |

TABLE XXV

| Pos | 123456789 | score |
|---|---|---|
| | V1A-HLA-A0203-9mers:251P5G2 | |
| | No results found. V2A-HLA-A0203-9mers:251P5G2 | |
| | No results found. V3A-HLA-A0203-9mers:251P5G2 | |
| | No results found. | |

TABLE XXV-continued

| Pos | 123456789 | score |
|---|---|---|
| | V4A-HLA-A0202-9mers:251P5G2 | |
| | No results found. | |
| | V12A-HLA-A0203-9mers:251P5G2 | |
| | No results found. | |
| | V12B-HLA-A0203-9mers:251P5G2 | |
| | No results found. | |

TABLE XXIV

| Pos | 123456789 | score |
|---|---|---|
| | V1A-HLA-A0202-9mers:251P5G2 | |
| | No results found. | |
| | V2A-HLA-A0202-9mers:251P5G2 | |
| | No results found. | |
| | V3A-HLA-A0202-9mers:251P5G2 | |
| | No results found. | |
| | V4A-HLA-A0202-9mers:251P5G2 | |
| | No results found. | |
| | V12A-HLA-A0202-9mers:251P5G2 | |
| | No results found. | |
| | V12B-HLA-A0202-9mers:251P5G2 | |
| | No results found. | |

TABLE XXVI

| Pos | 123456789 | score |
|---|---|---|
| | V1A-HLA-A3-9mers:251P5G2 Each peptide is a portion of SEQ ID NO: 3; each start position is specified, the length of peptide is 9 amino acids, and the end position for each peptide is the start position plus eight. | |
| 81 | RVIRVLSIC | 24 |
| 174 | SLFRDVFLK | 24 |
| 183 | QIMLFSSVY | 24 |
| 39 | PVCHVALIH | 21 |
| 64 | SLNFQNDFK | 21 |
| 78 | YLRRVIRVL | 21 |
| 84 | RVLSICTTC | 21 |
| 44 | ALIHMVVLL | 20 |

TABLE XXVI-continued

| Pos | 123456789 | score |
|---|---|---|
| 48 | MVVLLTMVF | 20 |
| 147 | TQINLHVSK | 20 |
| 148 | QINLHVSKY | 20 |
| 172 | TLSLFRDVF | 20 |
| 224 | ILLPVSFSV | 20 |
| 105 | SISWLVRFK | 19 |
| 122 | HLFSWSLSF | 19 |
| 135 | SLIFYTVAS | 19 |
| 140 | TVASSNVTQ | 19 |
| 165 | IIRGLFFTL | 19 |
| 7 | LVLASQPTL | 18 |
| 30 | DLRPERTYL | 18 |
| 92 | CLLGMLQVV | 18 |
| 93 | LLGMLQVVN | 18 |
| 189 | SVYMMTLIQ | 18 |
| 202 | ILVPSQPQP | 18 |
| 214 | DLCRGKSHQ | 18 |
| 227 | PVSFSVGMY | 18 |
| 239 | FIISTSSTL | 18 |
| 8 | VLASQPTLF | 17 |
| 42 | HVALIHMVV | 17 |
| 49 | VVLLTMVFL | 17 |
| 76 | SFYLRRVIR | 17 |
| 152 | HVSKYCSLF | 17 |
| 158 | SLFPINSII | 17 |
| 164 | SIIRGLFFT | 17 |
| 168 | GLFFTLSLF | 17 |
| 205 | PSQPQPLPK | 17 |
| 222 | QHILLPVSF | 17 |
| 225 | LLPVSFSVG | 17 |
| 51 | LLTMVFLSP | 16 |
| 54 | MVFLSPQLF | 16 |
| 107 | SWLVRFKWK | 16 |
| 109 | LVRFKWKST | 16 |
| 127 | SLSFPVSSS | 16 |
| 131 | PVSSSLIFY | 16 |
| 163 | NSIIRGLFF | 16 |
| 213 | KDLCRGKSH | 16 |
| 231 | SVGMYKMDF | 16 |

TABLE XXVI-continued

| Pos | 123456789 | score |
|---|---|---|
| 25 | FLLFLDLRP | 15 |
| 29 | LDLRPERTY | 15 |
| 37 | YLPVCHVAL | 15 |
| 98 | QVVNISPSI | 15 |
| 99 | VVNISPSIS | 15 |
| 101 | NISPSISWL | 15 |
| 137 | IFYTVASSN | 15 |
| 198 | ELQEILVPS | 15 |
| 209 | QPLPKDLCR | 15 |
| 228 | VSFSVGMYK | 15 |
| 6 | KLVLASQPT | 14 |
| 14 | TLFSFFSAS | 14 |
| 28 | FLDLRPERT | 14 |
| 180 | FLKQIMLFS | 14 |
| 200 | QEILVPSQP | 14 |
| 223 | HILLPVSFS | 14 |
| 56 | FLSPQLFES | 13 |
| 60 | QLFESLNFQ | 13 |
| 70 | DFKYEASFY | 13 |
| 96 | MLQVVNISP | 13 |
| 103 | SPSISWLVR | 13 |
| 108 | WLVRFKWKS | 13 |
| 136 | LIFYTVASS | 13 |
| 145 | NVTQINLHV | 13 |
| 178 | DVFLKQIML | 13 |
| 194 | TLIQELQEI | 13 |
| 215 | LCRGKSHQH | 13 |
| 245 | STLPWAYDR | 13 |
| 3 | FISKLVLAS | 12 |
| 5 | SKLVLASQP | 12 |
| 10 | ASQPTLFSF | 12 |
| 45 | LIHMVVLLT | 12 |
| 50 | VLLTMVFLS | 12 |
| 80 | RRVIRVLSI | 12 |
| 85 | VLSICTTCL | 12 |
| 87 | SICTTCLLG | 12 |
| 113 | KWKSTIFTF | 12 |
| 211 | LPKDLCRGK | 12 |

TABLE XXVI-continued

| Pos | 123456789 | score |
|---|---|---|
| 26 | LLFLDLRPE | 11 |
| 43 | VALIHMVVL | 11 |
| 82 | VIRVLSICT | 11 |
| 91 | TCLLGMLQV | 11 |
| 104 | PSISWLVRF | 11 |
| 111 | RFKWKSTIF | 11 |
| 117 | TIFTFHLFS | 11 |
| 167 | RGLFFTLSL | 11 |
| 182 | KQIMLFSSV | 11 |
| 185 | MLFSSVYMM | 11 |
| 197 | QELQEILVP | 11 |
| 203 | LVPSQPQPL | 11 |
| 240 | IISTSSTLP | 11 |

V3A-HLA-A3-
9mers:251P5G2
Each peptide is a portion of SEQ ID NO: 7; each start position is specified, the length of peptide is 9 amino acids, and the end position for each peptide is the start position plus eight.

| Pos | 123456789 | score |
|---|---|---|
| 5 | RVIRDLSIC | 23 |
| 2 | YLRRVIRDL | 17 |
| 4 | RRVIRDLSI | 12 |
| 6 | VIRDLSICT | 12 |
| 9 | DLSICTTCL | 12 |
| 8 | RDLSICTTC | 11 |

V4A-HLA-V3-
9mers:251P5G2
Each peptide is a portion of SEQ ID NO: 9; each start position is specified, the length of peptide is 9 amino acids, and the end position for each peptide is the start position plus eight.

| Pos | 123456789 | score |
|---|---|---|
| 7 | LLDMLQVVN | 18 |
| 6 | CLLDMLQVV | 17 |
| 1 | SICTTCLLD | 12 |
| 5 | TCLLDMLQV | 9 |

TABLE XXVI-continued

V12A-HLA-A3-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 9 | LIMLFSSVY | 22 |
| 8 | WLIMLFSSV | 18 |
| 5 | SISWLIMLF | 14 |

V12B-HLA-A3-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 819 | QLNEEALTK | 33 |
| 803 | ILEEIESVK | 30 |
| 154 | CLRAQGLTR | 29 |
| 410 | HVRREDLDK | 29 |
| 5 | ILLPTQATF | 28 |
| 552 | LLLGVHEQK | 28 |
| 341 | KVIQCVFAK | 27 |
| 370 | LIMKETSTK | 25 |
| 382 | LIQEMGSGK | 25 |
| 436 | MLRDTDMNK | 25 |
| 655 | ILNIKLPLK | 24 |
| 43 | VLPCCNLEK | 23 |
| 576 | ALDRYGRTA | 23 |
| 651 | PVITILNIK | 23 |
| 694 | GLIPQRKSR | 23 |
| 695 | LIPQRKSRK | 23 |
| 1010 | DVSPAMRLK | 23 |
| 342 | VIQCVFAKK | 22 |
| 474 | QLNVLDNKK | 22 |
| 528 | KLMAKALLL | 22 |
| 533 | ALLLYGADI | 22 |
| 631 | ELLSDYKEK | 22 |
| 332 | LVKLHSLSH | 21 |
| 563 | VVKFLIKKK | 21 |
| 661 | PLKVEEEIK | 21 |
| 834 | SLRQLGLAQ | 21 |
| 874 | SLRQLGLAQ | 21 |
| 956 | RLASGARAA | 21 |
| 1103 | HVSAGGVGP | 21 |
| 83 | ALPGSLPAF | 20 |
| 117 | RVVQRRLEV | 20 |
| 261 | ALGVGSLSV | 20 |
| 319 | GLNSIMQIK | 20 |
| 418 | KLHRAAWWG | 20 |
| 427 | KVPRKDLIV | 20 |
| 480 | NKKRTALIK | 20 |
| 562 | EVVKFLIKK | 20 |
| 588 | AVCCGSASI | 20 |
| 681 | NLTNGASAG | 20 |
| 786 | RLELDETKH | 20 |
| 953 | SLVRLASGA | 20 |
| 954 | LVRLASGAR | 20 |
| 964 | AALPPPTGK | 20 |
| 1001 | FLGRRCPMF | 20 |
| 56 | SFPGTAARK | 19 |
| 112 | LLGWERVVQ | 19 |
| 118 | VVQRRLEVP | 19 |
| 165 | QVVHLAPTA | 19 |
| 216 | ALRYRSGPS | 19 |
| 316 | RLSGLNSIM | 19 |
| 326 | IKEFEELVK | 19 |
| 467 | LLLDRRCQL | 19 |
| 500 | MLLEHGADG | 19 |
| 770 | DLLRENSML | 19 |
| 771 | LLRENSMLR | 19 |
| 829 | KVAGFSLRQ | 19 |
| 915 | QIGDPGGVP | 19 |
| 31 | RADPVTWRK | 18 |
| 42 | AVLPCCNLE | 18 |
| 111 | FLLGWERVV | 18 |
| 122 | RLEVPRPQA | 18 |
| 239 | RLLFLPRAP | 18 |
| 249 | AVSGPQEQP | 18 |
| 280 | NLSYPLVLR | 18 |

TABLE XXVI-continued

| Pos | 123456789 | score |
|---|---|---|
| 291 | PEILKFSEK | 18 |
| 309 | ELPATAARL | 18 |
| 557 | HEQKQEVVK | 18 |
| 618 | REYAVSSHH | 18 |
| 627 | HVICELLSD | 18 |
| 628 | VICELLSDY | 18 |
| 663 | KVEEEIKKH | 18 |
| 824 | ALTKTKVAG | 18 |
| 923 | PLSEGGTAA | 18 |
| 971 | GKNGRSPTK | 18 |
| 1062 | KCRPGTLCH | 18 |
| 18 | GLWAALTTV | 17 |
| 75 | ALSLSSSRA | 17 |
| 124 | EVPRPQAAP | 17 |
| 159 | GLTRAFQVV | 17 |
| 160 | LTRAFQVVH | 17 |
| 168 | HLAPTAPDG | 17 |
| 188 | RLTHVRCAQ | 17 |
| 203 | ANLPGAPGR | 17 |
| 218 | RYRSGPSVS | 17 |
| 288 | RHIPEILKF | 17 |
| 369 | FLIMKETST | 17 |
| 452 | ALHLASANG | 17 |
| 463 | EVVQLLLDR | 17 |
| 534 | LLLYGADIE | 17 |
| 566 | FLIKKKANL | 17 |
| 584 | ALILAVCCG | 17 |
| 598 | NLLLEQNVD | 17 |
| 599 | LLLEQNVDV | 17 |
| 621 | AVSSHHHVI | 17 |
| 728 | QLSEEQNTG | 17 |
| 740 | DEILTNKQK | 17 |
| 742 | ILTNKQKQI | 17 |
| 776 | SMLREEIAK | 17 |
| 777 | MLREEIAKL | 17 |
| 784 | KLRLELDET | 17 |
| 785 | LRLELDETK | 17 |
| 809 | SVKEKLLKT | 17 |
| 911 | ALRSQIGDP | 17 |

TABLE XXVI-continued

| Pos | 123456789 | score |
|---|---|---|
| 965 | ALPPPTGKN | 17 |
| 1054 | DRAGVLAPK | 17 |
| 1089 | TLPHRDTTT | 17 |
| 1098 | SLPHFHVSA | 17 |
| 87 | SLPAFADLP | 16 |
| 211 | RSSSCALRY | 16 |
| 307 | GLELPATAA | 16 |
| 347 | FAKKKNVDK | 16 |
| 381 | GLIQEMGSG | 16 |
| 423 | AWWGKVPRK | 16 |
| 434 | IVMLRDTDM | 16 |
| 466 | QLLLDRRCQ | 16 |
| 477 | VLDNKKRTA | 16 |
| 485 | ALIKAVQCQ | 16 |
| 522 | AIYNEDKLM | 16 |
| 535 | LLYGADIES | 16 |
| 548 | GLTPLLLGV | 16 |
| 561 | QEVVKFLIK | 16 |
| 586 | ILAVCCGSA | 16 |
| 596 | IVNLLLEQN | 16 |
| 747 | QKQIEVAEK | 16 |
| 797 | QLRENKILE | 16 |
| 802 | KILEEIESV | 16 |
| 821 | NEEALTKTK | 16 |
| 869 | EVAGFSLRQ | 16 |
| 973 | NGRSPTKQK | 16 |
| 989 | WILPVPTFS | 16 |
| 1108 | GVGPTTLGS | 16 |

TABLE XXVII

| Pos | 123456789 | score |
|---|---|---|

V1A-HLA-A26-
9mers:251P5G2
Each peptide is a portion of
SEQ ID NO: 3; each start
position is specified, the
length of peptide is 9 amino
acids, and the end position
for each peptide is the start
position plus eight.

| Pos | 123456789 | score |
|---|---|---|
| 178 | DVFLKQIML | 28 |
| 101 | NISPSISWL | 26 |

TABLE XXVII-continued

| Pos | 123456789 | score |
|---|---|---|
| 116 | STIFTFHLF | 26 |
| 131 | PVSSSLIFY | 26 |
| 148 | QINLHVSKY | 26 |
| 227 | PVSFSVGMY | 26 |
| 165 | IIRGLFFTL | 25 |
| 168 | GLFFTLSLF | 25 |
| 185 | MLFSSVYMM | 25 |
| 30 | DLRPERTYL | 24 |
| 54 | MVFLSPQLF | 24 |
| 70 | DFKYEASFY | 24 |
| 89 | CTTCLLGML | 24 |
| 161 | PINSIIRGL | 24 |
| 44 | ALIHMVVLL | 23 |
| 49 | VVLLTMVFL | 23 |
| 179 | VFLKQIMLF | 23 |
| 48 | MVVLLTMVF | 22 |
| 122 | HLFSWSLSF | 22 |
| 152 | HVSKYCSLF | 22 |
| 203 | LVPSQPQPL | 22 |
| 239 | FIISTSSTL | 22 |
| 8 | VLASQPTLF | 21 |
| 183 | QIMLFSSVY | 21 |
| 195 | LIQELQEIL | 21 |
| 198 | ELQEILVPS | 21 |
| 231 | SVGMYKMDF | 21 |
| 7 | LVLASQPTL | 20 |
| 17 | SFFSASSPF | 20 |
| 78 | YLRRVIRVL | 20 |
| 37 | YLPVCHVAL | 19 |
| 104 | PSISWLVRF | 19 |
| 229 | SFSVGMYKM | 19 |
| 111 | RFKWKSTIF | 18 |
| 119 | FTFHLFSWS | 18 |
| 136 | LFIYTVASS | 18 |
| 172 | TLSLFRDVF | 18 |
| 3 | FISKLVLAS | 17 |
| 10 | ASQPTLFSF | 17 |
| 11 | SQPTLFSFF | 17 |

TABLE XXVII-continued

| Pos | 123456789 | score |
|---|---|---|
| 14 | TLFSFFSAS | 17 |
| 60 | QLFESLNFQ | 17 |
| 81 | RVIRVLSIC | 17 |
| 194 | TLIQELQEI | 17 |
| 201 | EILVPSQPQ | 17 |
| 238 | DFIISTSST | 17 |
| 13 | PTLFSFFSA | 16 |
| 18 | FFSASSPFL | 16 |
| 56 | FLSPQLFES | 16 |
| 57 | LSPQLFESL | 16 |
| 63 | ESLNFQNDF | 16 |
| 85 | VLSICTTCL | 16 |
| 113 | KWKSTIFTF | 16 |
| 164 | SIIRGLFFT | 16 |
| 171 | FTLSLFRDV | 16 |
| 214 | DLCRGKSHQ | 16 |
| 242 | STSSTLPWA | 16 |
| 2 | PFISKLVLA | 15 |
| 20 | SASSPFLLF | 15 |
| 23 | SPFLLFLDL | 15 |
| 35 | RTYLPVCHV | 15 |
| 52 | LTMVFLSPQ | 15 |
| 69 | NDFKYEASF | 15 |
| 92 | CLLGMLQVV | 15 |
| 105 | SISWLVRFK | 15 |
| 120 | TFHLFSWSL | 15 |
| 151 | LHVSKYCSL | 15 |
| 191 | YMMTLIQEL | 15 |
| 210 | PLPKDLCRG | 15 |
| 222 | QHILLPVSF | 15 |
| 223 | HILLPVSFS | 15 |
| 225 | LLPVSFSVG | 15 |
| 21 | ASSPFLLFL | 14 |
| 26 | LLFLDLRPE | 14 |
| 45 | LIHMVVLLT | 14 |
| 65 | LNFQNDFKY | 14 |
| 127 | SLSFPVSSS | 14 |
| 128 | LSFPVSSSL | 14 |
| 140 | TVASSNVTQ | 14 |

TABLE XXVII-continued

| Pos | 123456789 | score |
|---|---|---|
| 146 | VTQINLHVS | 14 |
| 174 | SLFRDVFLK | 14 |
| 180 | FLKQIMLFS | 14 |
| 246 | TLPWAYDRG | 14 |
| 40 | VCHVALIHM | 13 |
| 43 | VALIHMVVL | 13 |
| 51 | LLTMVFLSP | 13 |
| 88 | ICTTCLLGM | 13 |
| 158 | SLFPINSII | 13 |
| 186 | LFSSVYMMT | 13 |
| 187 | FSSVYMMTL | 13 |
| 202 | ILVPSQPQP | 13 |

V2A-HLA-A26-9mers:251P5G2
Each peptide is a portion of SEQ ID NO: 5; each start position is specified, the length of peptide is 9 amino acids, and the end position for each peptide is the start position plus eight.

| Pos | 123456789 | score |
|---|---|---|
| 3 | ASQPTLCSF | 17 |
| 6 | PTLCSFFSA | 16 |
| 7 | TLCSFFSAS | 15 |
| 4 | SQPTLCSFF | 13 |
| 1 | VLASQPTLC | 11 |

V3A-HLA-A26-9mers:251P5G2
Each peptide is a portion of SEQ ID NO: 7; each start position is specified, the length of peptide is 9 amino acids, and the end position for each peptide is the start position plus eight.

| Pos | 123456789 | score |
|---|---|---|
| 9 | DLSICTTCL | 22 |
| 2 | YLRRVIRDL | 20 |
| 5 | RVIRDLSIC | 17 |
| 6 | VIRDLSICT | 12 |

V12A-HLA-A26-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 5 | SISWLIMLF | 26 |
| 9 | LIMLFSSVY | 21 |

TABLE XXVII-continued

| Pos | 123456789 | score |
|---|---|---|
| 8 | WLIMLFSSV | 17 |
| 4 | PSISWLIML | 16 |
| 2 | ISPSISWLI | 2 |

V12B-HLA-A26-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 1094 | DTTTSLPHF | 33 |
| 300 | ETGGGILGL | 31 |
| 374 | ETSTKISGL | 31 |
| 83 | ALPGSLPAF | 28 |
| 628 | VICELLSDY | 28 |
| 781 | EIAKLRLEL | 28 |
| 825 | LTKTKVAGF | 28 |
| 378 | KISGLIQEM | 27 |
| 516 | NTALHYAIY | 26 |
| 806 | EIESVKEKL | 26 |
| 273 | HLIQCIPNL | 25 |
| 309 | ELPATAARL | 25 |
| 312 | ATAARLSGL | 25 |
| 558 | AQKQEVVKF | 24 |
| 724 | DTQKQLSEE | 24 |
| 770 | DLLRENSML | 24 |
| 777 | MLREEIAKL | 24 |
| 994 | PTFSSGSFL | 23 |
| 463 | EVVQLLLDR | 22 |
| 562 | EVVKFLIKK | 22 |
| 566 | FLIKKKANL | 22 |
| 751 | EVAEKEMNS | 22 |
| 1010 | DVSPAMRLK | 22 |
| 5 | ILLPTQATF | 21 |
| 11 | ATFAAATGL | 21 |
| 604 | NVDVSSQDL | 21 |
| 1024 | ETHQAFRDK | 21 |
| 68 | TTLTGHSAL | 20 |
| 70 | LTGHSALSL | 20 |
| 259 | EEALGVGSL | 20 |
| 277 | CIPNLSYPL | 20 |

TABLE XXVII-continued

| Pos | 123456789 | score |
|---|---|---|
| 316 | RLSGLNSIM | 20 |
| 330 | EELVKLHSL | 20 |
| 357 | DDFCLSEGY | 20 |
| 432 | DLIVMLRDT | 20 |
| 631 | ELLSDYKEK | 20 |
| 652 | VITILNIKL | 20 |
| 667 | EIKKHGSNP | 20 |
| 827 | KTKVAGFSL | 20 |
| 869 | EVAGFSLRQ | 20 |
| 1001 | FLGRRCPMF | 20 |
| 1072 | DTPPHRNAD | 20 |
| 105 | ATPAGAFLL | 19 |
| 124 | EVPRPQAAP | 19 |
| 288 | RHIPEILKF | 19 |
| 328 | EFEELVKLH | 19 |
| 401 | DSAFMEPRY | 19 |
| 470 | DRRCQLNVL | 19 |
| 494 | EDECVLMLL | 19 |
| 606 | DVSSQDLSG | 19 |
| 611 | DLSGQTARE | 19 |
| 749 | QIEVAEKEM | 19 |
| 791 | ETKHQNQLR | 19 |
| 809 | SVKEKLLKT | 19 |
| 817 | TIQLNEEAL | 19 |
| 1080 | DTPPHRHTT | 19 |
| 93 | DLPRSCPES | 18 |
| 197 | GLEAASANL | 18 |
| 262 | LGVGSLSVF | 18 |
| 292 | EILKFSEKE | 18 |
| 321 | NSIMQIKEF | 18 |
| 327 | KEFEELVKL | 18 |
| 341 | KVIQCVFAK | 18 |
| 415 | DLDKLHRAA | 18 |
| 434 | IVMLRDTDM | 18 |
| 467 | LLLDRRCQL | 18 |
| 522 | AIYNEDKLM | 18 |
| 540 | DIESKNKCG | 18 |
| 654 | TILNIKLPL | 18 |
| 741 | EILTNKQKQ | 18 |
| 788 | ELDETKHQN | 18 |
| 65 | EFSTTLTGH | 17 |
| 266 | SLSVFQLHL | 17 |
| 289 | HIPEILKFS | 17 |
| 331 | ELVKLHSLS | 17 |
| 429 | PRKDLIVML | 17 |
| 439 | DTDMNKRDK | 17 |
| 450 | RTALHLASA | 17 |
| 513 | EYGNTALHY | 17 |
| 528 | KLMAKALLL | 17 |
| 563 | VVKFLIKKK | 17 |
| 627 | HVICELLSD | 17 |
| 663 | KVEEEIKKH | 17 |
| 711 | DTENEEYHS | 17 |
| 802 | KILEEIESV | 17 |
| 865 | AQEQEVAGF | 17 |
| 949 | PGTPSLVRL | 17 |
| 950 | GTPSLVRLA | 17 |
| 988 | GWILPVPTF | 17 |
| 1030 | RDKDDLPFF | 17 |
| 8 | PTQATFAAA | 16 |
| 161 | TRAFQVVHL | 16 |
| 285 | LVLRHIPEI | 16 |
| 286 | VLRHIPEIL | 16 |
| 324 | MQIKEFEEL | 16 |
| 342 | VIQCVFAKK | 16 |
| 381 | GLIQEMGSG | 16 |
| 394 | GTWGDYDDS | 16 |
| 464 | VVQLLLDRR | 16 |
| 485 | ALIKAVQCQ | 16 |
| 493 | QEDECVLML | 16 |
| 497 | CVLMLLEHG | 16 |
| 509 | NIQDEYGNT | 16 |
| 526 | EDKLMAKAL | 16 |
| 529 | LMAKALLLY | 16 |
| 548 | GLTPLLLGV | 16 |
| 549 | LTPLLLGVH | 16 |
| 582 | RTALILAVC | 16 |

TABLE XXVII-continued

| Pos | 123456789 | score |
|---|---|---|
| 595 | SIVNLLLEQ | 16 |
| 596 | IVNLLLEQN | 16 |
| 615 | QTAREYAVS | 16 |
| 651 | PVITILNIK | 16 |
| 653 | ITILNIKLP | 16 |
| 677 | GLPENLTNG | 16 |
| 721 | EQNDTQKQL | 16 |
| 760 | ELSLSHKKE | 16 |
| 790 | DETKHQNQL | 16 |
| 805 | EEIESVKEK | 16 |
| 812 | EKLLKTIQL | 16 |
| 1000 | SFLGRRCPM | 16 |
| 1034 | DLPFFKTQQ | 16 |
| 1049 | DLGQDDRAG | 16 |

TABLE XXVIII

| Pos | 123456789 | score |
|---|---|---|
| \multicolumn{3}{l}{V1A-HLA-B0702-9mers:251P5G2 Each peptide is a portion of SEQ ID NO: 3; each start position is specified, the length of peptide is 9 amino acids, and the end position for each peptide is the start position plus eight.} | | |
| 1 | MPFISKLVL | 23 |
| 23 | SPFLLFLDL | 23 |
| 207 | QPQPLPKDL | 21 |
| 32 | RPERTYLPV | 20 |
| 21 | ASSPFLLFL | 18 |
| 38 | LPVCHVALI | 18 |
| 130 | FPVSSSLIF | 18 |
| 226 | LPVSFSVGM | 18 |
| 247 | LPWAYDRGV | 17 |
| 165 | IIRGLFFTL | 16 |
| 204 | VPSQPQPLP | 16 |
| 18 | FFSASSPFL | 15 |
| 30 | DLRPERTYL | 15 |
| 44 | ALIHMVVLL | 15 |
| 103 | SPSISWLVR | 15 |
| 20 | SASSPFLLF | 14 |

TABLE XXVIII-continued

| Pos | 123456789 | score |
|---|---|---|
| 85 | VLSICTTCL | 14 |
| 167 | RGLFFTLSL | 14 |
| 37 | YLPVCHVAL | 13 |
| 43 | VALIHMVVL | 13 |
| 49 | VVLLTMVFL | 13 |
| 78 | YLRRVIRVL | 13 |
| 101 | NISPSISWL | 13 |
| 173 | LSLFRDVFL | 13 |
| 209 | QPLPKDLCR | 13 |
| 7 | LVLASQPTL | 12 |
| 115 | KSTIFTFHL | 12 |
| 187 | FSSVYMMTL | 12 |
| 218 | GKSHQHILL | 12 |
| 12 | QPTLFSFFS | 11 |
| 19 | FSASSPFLL | 11 |
| 35 | RTYLPVCHV | 11 |
| 53 | TMVFLSPQL | 11 |
| 57 | LSPQLFESL | 11 |
| 86 | LSICTTCLL | 11 |
| 128 | LSFPVSSSL | 11 |
| 191 | YMMTLIQEL | 11 |
| 203 | LVPSQPQPL | 11 |
| 217 | RGKSHQHIL | 11 |
| \multicolumn{3}{l}{V2A-HLA-B0702-9mers:251P5G2 Each peptide is a portion of SEQ ID NO: 5; each start position is specified, the length of peptide is 9 amino acids, and the end position for each peptide is the start position plus eight.} | | |
| 5 | QPTLCSFFS | 11 |
| 3 | ASQPTLCSF | 9 |
| 2 | LASQPTLCS | 8 |
| 4 | SQPTLCSFF | 7 |
| 6 | PTLCSFFSA | 7 |

TABLE XXVIII-continued

Pos | 123456789 | score
---|---|---

V3A-HLA-B0702-9mers:251P5G2
Each peptide is a portion of SEQ ID NO: 7; each start position is specified, the length of peptide is 9 amino acids, and the end position for each peptide is the start position plus eight.

| Pos | 123456789 | score |
|---|---|---|
| 9 | DLSICTTCL | 14 |
| 2 | YLRRVIRDL | 12 |
| 4 | RRVIRDLSI | 9 |
| 6 | VIRDLSICT | 8 |
| 7 | IRDLSICTT | 8 |

V4A-B0702-9mers:251P5G2
Each peptide is a portion of SEQ ID NO: 9; each start position is specified, the length of peptide is 9 amino acids, and the end position for each peptide is the start position plus eight.

| Pos | 123456789 | score |
|---|---|---|
| 3 | CTTCLLDML | 10 |
| 8 | LDMLQVVNI | 10 |
| 2 | ICTTCLLDM | 9 |
| 5 | TCLLDMLQV | 8 |
| 6 | CLLDMLQVV | 7 |
| 7 | LLDMLQVVN | 4 |

V12A-HLA-B0702-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 3 | SPSISWLIM | 20 |
| 4 | PSISWLIML | 10 |

V12B-HLA-B0702-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 228 | APSPAEPPA | 23 |
| 170 | APTAPDGGA | 22 |
| 181 | PPSRNSYRL | 22 |
| 233 | EPPAHQRLL | 22 |
| 674 | NPVGLPENL | 22 |
| 1060 | APKCRPGTL | 22 |
| 1082 | PPHRHTTTL | 22 |
| 125 | VPRPQAAPA | 21 |
| 28 | NPSRADPVT | 20 |
| 234 | PPAHQRLLF | 20 |
| 256 | QPSEEALGV | 20 |
| 428 | VPRKDLIVM | 20 |
| 84 | LPGSLPAFA | 19 |
| 208 | APGRSSSCA | 19 |
| 1006 | CPMFDVSPA | 19 |
| 7 | LPTQATFAA | 18 |
| 243 | LPRAPQAVS | 18 |
| 278 | IPNLSYPLV | 18 |
| 650 | NPVITILNI | 18 |
| 98 | CPESEQSAT | 17 |
| 144 | PPCHQRRDA | 17 |
| 660 | LPLKVEEEI | 17 |
| 678 | LPENLTNGA | 17 |
| 916 | IGDPGGVPL | 17 |
| 922 | VPLSEGGTA | 17 |
| 932 | GDQGPGTHL | 17 |
| 941 | PPREPRASP | 17 |
| 948 | SPGTPSLVR | 17 |
| 1073 | TPPHRNADT | 17 |
| 1081 | TPPHRHTTT | 17 |
| 15 | AATGLWAAL | 16 |
| 106 | TPAGAFLLG | 16 |
| 141 | DPSPPCHQR | 16 |
| 205 | LPGAPGRSS | 16 |
| 300 | ETGGGILGL | 16 |
| 781 | EIAKLRLEL | 16 |
| 946 | RASPGTPSL | 16 |
| 951 | TPSLVRLAS | 16 |
| 958 | ASGARAAAL | 16 |
| 993 | VPTFSSGSF | 16 |
| 36 | TWRKEPAVL | 15 |
| 131 | APATSATPS | 15 |
| 173 | APDGGAGCP | 15 |
| 230 | SPAEPPAHQ | 15 |

TABLE XXVIII-continued

| Pos | 123456789 | score |
|---|---|---|
| 528 | KLMAKALLL | 15 |
| 577 | LDRYGRTAL | 15 |
| 591 | CGSASIVNL | 15 |
| 918 | DPGGVPLSE | 15 |
| 11 | ATFAAATGL | 14 |
| 54 | WLSFPGTAA | 14 |
| 88 | LPAFADLPR | 14 |
| 104 | SATPAGAFL | 14 |
| 161 | TRAFQVVHL | 14 |
| 222 | GPSVSSAPS | 14 |
| 246 | APQAVSGPQ | 14 |
| 266 | SLSVFQLHL | 14 |
| 302 | GGGILGLEL | 14 |
| 312 | ATAARLSGL | 14 |
| 406 | EPRYHVRRE | 14 |
| 425 | WGKVPRKDL | 14 |
| 445 | RDKQKRTAL | 14 |
| 478 | LDNKKRTAL | 14 |
| 493 | QEDECVLML | 14 |
| 541 | IESKNKCGL | 14 |
| 545 | NKCGLTPLL | 14 |
| 546 | KCGLTPLLL | 14 |
| 579 | RYGRTALIL | 14 |
| 593 | SASIVNLLL | 14 |
| 670 | KHGSNPVGL | 14 |
| 755 | KEMNSELSL | 14 |
| 832 | GFSLRQLGL | 14 |
| 872 | GFSLRQLGL | 14 |
| 944 | EPRASPGTP | 14 |
| 1091 | PHRDTTTSL | 14 |
| 1106 | AGGVGPTTL | 14 |
| 41 | PAVLPCCNL | 13 |
| 62 | ARKEFSTTL | 13 |
| 70 | LTGHSALSL | 13 |
| 80 | SSRALPGSL | 13 |
| 86 | GSLPAFADL | 13 |
| 105 | ATPAGAFLL | 13 |
| 127 | RPQAAPATS | 13 |
| 137 | TPSRDPSPP | 13 |
| 147 | HQRRDAACL | 13 |
| 209 | PGRSSSCAL | 13 |
| 232 | AEPPAHQRL | 13 |
| 235 | PAHQRLLFL | 13 |
| 259 | EEALGVGSL | 13 |
| 264 | VGSLSVFQL | 13 |
| 279 | PNLSYPLVL | 13 |
| 309 | ELPATAARL | 13 |
| 327 | KEFEELVKL | 13 |
| 374 | ETSTKISGL | 13 |
| 403 | AFMEPRYHV | 13 |
| 447 | KQKRTALHL | 13 |
| 459 | NGNSEVVQL | 13 |
| 460 | GNSEVVQLL | 13 |
| 470 | DRRCQLNVL | 13 |
| 544 | KNKCGLTPL | 13 |
| 550 | TPLLLGVHE | 13 |
| 569 | KKKANLNAL | 13 |
| 647 | ENSNPVITI | 13 |
| 654 | TILNIKLPL | 13 |
| 777 | MLREEIAKL | 13 |
| 779 | REEIAKLRL | 13 |
| 807 | IESVKEKLL | 13 |
| 904 | QAQEQGAAL | 13 |
| 935 | GPGTHLPPR | 13 |
| 949 | PGTPSLVRL | 13 |
| 957 | LASGARAAA | 13 |
| 985 | DSSGWILPV | 13 |
| 1009 | FDVSPAMRL | 13 |
| 40 | EPAVLPCCN | 12 |
| 61 | AARKEFSTT | 12 |
| 83 | ALPGSLPAF | 12 |
| 94 | LPRSCPESE | 12 |
| 115 | WERVVQRRL | 12 |
| 122 | RLEVPRPQA | 12 |
| 128 | PQAAPATSA | 12 |
| 152 | AACLRAQGL | 12 |
| 197 | GLEAASANL | 12 |

TABLE XXVIII-continued

| Pos | 123456789 | score |
|---|---|---|
| 200 | AASANLPGA | 12 |
| 254 | QEQPSEEAL | 12 |
| 286 | VLRHIPEIL | 12 |
| 298 | EKETGGGIL | 12 |
| 324 | MQIKEFEEL | 12 |
| 362 | SEGYGHSFL | 12 |
| 408 | RYHVRREDL | 12 |
| 411 | VRREDLDKL | 12 |
| 429 | PRKDLIVML | 12 |
| 461 | NSEVVQLLL | 12 |
| 511 | QDEYGNTAL | 12 |
| 526 | EDKLMAKAL | 12 |
| 559 | QKQEVVKFL | 12 |
| 566 | FLIKKKANL | 12 |
| 592 | GSASIVNLL | 12 |
| 648 | NSNPVITIL | 12 |
| 703 | KPENQQFPD | 12 |
| 753 | AEKEMNSEL | 12 |
| 812 | EKLLKTIQL | 12 |
| 827 | KTKVAGFSL | 12 |
| 843 | HAQASVQQL | 12 |
| 867 | EQEVAGFSL | 12 |
| 883 | HAQASVQQL | 12 |
| 966 | LPPPTGKNG | 12 |
| 968 | PPTGKNGRS | 12 |
| 976 | SPTKQKSVC | 12 |
| 983 | VCDSSGWIL | 12 |
| 991 | LPVPTFSSG | 12 |
| 994 | PTFSSGSFL | 12 |
| 1032 | KDDLPFFKT | 12 |
| 1043 | SPRHTKDLG | 12 |
| 1051 | GQDDRAGVL | 12 |
| 1064 | RPGTLCHTD | 12 |
| 1079 | ADTPPHRHT | 12 |
| 1090 | LPHRDTTTS | 12 |
| 1099 | LPHFHVSAG | 12 |
| 4 | HILLPTQAT | 11 |
| 13 | FAAATGLWA | 11 |
| 33 | DPVTWRKEP | 11 |

TABLE XXVIII-continued

| Pos | 123456789 | score |
|---|---|---|
| 47 | CNLEKGSWL | 11 |
| 57 | FPGTAARKE | 11 |
| 68 | TTLTGHSAL | 11 |
| 76 | LSLSSSRAL | 11 |
| 82 | RALPGSLPA | 11 |
| 102 | EQSATPAGA | 11 |
| 103 | QSATPAGAF | 11 |
| 149 | RRDAACLRA | 11 |
| 156 | RAQGLTRAF | 11 |
| 261 | ALGVGSLSV | 11 |
| 273 | HLIQCIPNL | 11 |
| 277 | CIPNLSYPL | 11 |
| 283 | YPLVLRHIP | 11 |
| 290 | IPEILKFSE | 11 |
| 304 | GILGLELPA | 11 |
| 307 | GLELPATAA | 11 |
| 310 | LPATAARLS | 11 |
| 316 | PLSGLNSIM | 11 |
| 330 | EELVKLHSL | 11 |
| 378 | KISGLIQEM | 11 |
| 467 | LLLDRRCQL | 11 |
| 491 | QCQEDECVL | 11 |
| 494 | EDECVLMLL | 11 |
| 527 | DKLMAKALL | 11 |
| 604 | NVDVSSQDL | 11 |
| 621 | AVSSHHHVI | 11 |
| 634 | SDYKEKQML | 11 |
| 687 | SAGNGDDGL | 11 |
| 696 | IPQRKSRKP | 11 |
| 709 | FPDTENEEY | 11 |
| 721 | EQNDTQKQL | 11 |
| 763 | LSHKKEEDL | 11 |
| 764 | SHKKEEDLL | 11 |
| 790 | DETKHQNQL | 11 |
| 806 | EIESVKEKL | 11 |
| 817 | TIQLNEEAL | 11 |
| 830 | VAGFSLRQL | 11 |
| 870 | VAGFSLRQL | 11 |

TABLE XXVIII-continued

| Pos | 123456789 | score |
|---|---|---|
| 923 | PLSEGGTAA | 11 |
| 930 | AAGDQGPGT | 11 |
| 940 | LPPREPRAS | 11 |
| 962 | RAAALPPPT | 11 |
| 988 | GWILPVPTF | 11 |
| 1003 | GRRCPMFDV | 11 |
| 1012 | SPAMRLKSD | 11 |
| 1029 | FRDKDDLPF | 11 |
| 1035 | LPFFKTQQS | 11 |
| 1042 | QSPRHTKDL | 11 |
| 1096 | TTSLPHFHV | 11 |
| 1104 | VSAGGVGPT | 11 |
| 1105 | SAGGVGPTT | 11 |
| 1110 | GPTTLGSNR | 11 |

TABLE XXIX

| Pos | 123456789 | score |
|---|---|---|
| \multicolumn{3}{l}{V1A-HLA-B08-9mers:251P5G2 Each peptide is a portion of SEQ ID NO: 3; each start position is specified, the length of peptide is 9 amino acids, and the end position for each peptide is the start position plus eight.} | | |
| 111 | RFKWKSTIF | 26 |
| 78 | YLRRVIRVL | 23 |
| 30 | DLRPERTYL | 22 |
| 165 | IIRGLFFTL | 21 |
| 178 | DVFLKQIML | 21 |
| 151 | LHVSKYCSL | 20 |
| 217 | RGKSHQHIL | 20 |
| 23 | SPFLLFLDL | 19 |
| 37 | YLPVCHVAL | 19 |
| 173 | LSLFRDVFL | 19 |
| 44 | ALIHMVVLL | 18 |
| 232 | VGMYKMDFI | 18 |
| 85 | VLSICTTCL | 17 |
| 109 | LVRFKWKST | 17 |
| 113 | KWKSTIFTF | 17 |
| 180 | FLKQIMLFS | 17 |

TABLE XXIX-continued

| Pos | 123456789 | score |
|---|---|---|
| 207 | QPQPLPKDL | 17 |
| 1 | MPFISKLVL | 16 |
| 28 | FLDLRPERT | 16 |
| 43 | VALIHMVVL | 16 |
| 195 | LIQELQEIL | 16 |
| 209 | QPLPKDLCR | 16 |
| 211 | LPKDLCRGK | 16 |
| 215 | LCRGKSHQH | 16 |
| 80 | RRVIRVLSI | 15 |
| 101 | NISPSISWL | 15 |
| 158 | SLFPINSII | 15 |
| 161 | PINSIIRGL | 15 |
| 239 | FIISTSSTL | 15 |
| 163 | NSIIRGLFF | 14 |
| 8 | VLASQPTLF | 13 |
| 38 | LPVCHVALI | 13 |
| 49 | VVLLTMVFL | 13 |
| 71 | FKYEASFYL | 13 |
| 122 | HLFSWSLSF | 13 |
| 130 | FPVSSSLIF | 13 |
| 143 | SSNVTQINL | 13 |
| 168 | GLFFTLSLF | 13 |
| 172 | TLSLFRDVF | 13 |
| 194 | TLIQELQEI | 13 |
| 4 | ISKLVLASQ | 12 |
| 20 | SASSPFLLF | 12 |
| 76 | SFYLRRVIR | 12 |
| 82 | VIRVLSICT | 12 |
| 107 | SWLVRFKWK | 12 |
| 141 | VASSNVTQI | 12 |
| 153 | VSKYCSLFP | 12 |
| 187 | FSSVYMMTL | 12 |
| 191 | YMMTLIQEL | 12 |

TABLE XXIX-continued

| Pos | 123456789 | score |
|---|---|---|
| | V2A-HLA-B08-9mers:251P5G2 Each peptide is a portion of SEQ ID NO: 5; each start position is specified, the length of peptide is 9 amino acids, and the end position for each peptide is the start position plus eight. | |
| 4 | SQPTLCSFF | 8 |
| 1 | VLASQPTLC | 7 |
| 5 | QPTLCSFFS | 7 |
| 7 | TLCSFFSAS | 7 |
| 3 | ASQPTLCSF | 6 |
| 2 | LASQPTLCS | 4 |
| | V3A-HLA-B08-9mers:251P5G2 Each peptide is a portion of SEQ ID NO: 7; each start position is specified, the length of peptide is 9 amino acids, and the end position for each peptide is the start position plus eight. | |
| 2 | YLRRVIRDL | 23 |
| 9 | DLSICTTCL | 16 |
| 4 | RRVIRDLSI | 14 |
| 6 | VIRDLSICT | 11 |
| | V4A-HLA-B08-9mers:251P5G2 Each peptide is a portion of SEQ ID NO: 9; each start position is specified, the length of peptide is 9 amino acids, and the end position for each peptide is the start position plus eight. | |
| 3 | CTTCLLDML | 10 |
| 8 | LDMLQVVNI | 9 |
| 7 | LLDMLQVVN | 7 |
| 1 | SICTTCLLD | 6 |
| 6 | CLLDMLQVV | 6 |
| | V12A-HLA-B08-9mers:251P5G2 Each peptide is a portion of SEQ ID NO: 25; each start position is specified, the length of peptide is 9 amino acids, and the end position for each peptide is the start position plus eight. | |
| 5 | SISWLIMLF | 13 |
| 4 | PSISWLIML | 10 |
| 3 | SPSISWLIM | 8 |

TABLE XXIX-continued

| Pos | 123456789 | score |
|---|---|---|
| 2 | ISPSISWLI | 7 |
| 8 | WLIMLFSSV | 6 |
| | V12B-HLA-B08-9mers:251P5G2 Each peptide is a portion of SEQ ID NO: 25; each start position is specified, the length of peptide is 9 amino acids, and the end position for each peptide is the start position plus eight. | |
| 1060 | APKCRPGTL | 34 |
| 445 | RDKQKRTAL | 31 |
| 347 | FAKKKNVDK | 27 |
| 566 | FLIKKKANL | 27 |
| 825 | LTKTKVAGF | 27 |
| 528 | KLMAKALLL | 26 |
| 526 | EDKLMAKAL | 25 |
| 777 | MLREEIAKL | 25 |
| 467 | LLLDRRCQL | 24 |
| 479 | DNKKRTALI | 24 |
| 567 | LIKKKANLN | 24 |
| 742 | ILTNKQKQI | 24 |
| 753 | AEKEMNSEL | 24 |
| 782 | IAKLRLELD | 24 |
| 809 | SVKEKLLKT | 24 |
| 152 | AACLRAQGL | 23 |
| 286 | VLRHIPEIL | 23 |
| 330 | EELVKLHSL | 23 |
| 374 | ETSTKISGL | 23 |
| 807 | IESVKEKLL | 23 |
| 812 | EKLLKTIQL | 23 |
| 47 | CNLEKGSWL | 22 |
| 62 | ARKEFSTTL | 22 |
| 235 | PAHQRLLFL | 22 |
| 425 | WGKVPRKDL | 22 |
| 429 | PRKDLIVML | 22 |
| 542 | ESKNKCGLT | 22 |
| 635 | DYKEKQMLK | 22 |
| 764 | SHKKEEDLL | 22 |
| 216 | ALRYRSGPS | 21 |
| 353 | VDKWDDFCL | 21 |

TABLE XXIX-continued

| Pos | 123456789 | score |
|---|---|---|
| 478 | LDNKKRTAL | 21 |
| 569 | KKKANLNAL | 21 |
| 744 | TNKQKQIEV | 21 |
| 827 | KTKVAGFSL | 21 |
| 977 | PTKQKSVCD | 21 |
| 1001 | FLGRRCPMF | 21 |
| 297 | SEKETGGGI | 20 |
| 447 | KQKRTALHL | 20 |
| 544 | KNKCGLTPL | 20 |
| 558 | EQKQEVVKF | 20 |
| 763 | LSHKKEEDL | 20 |
| 832 | GFSLRQLGL | 20 |
| 872 | GFSLRQLGL | 20 |
| 266 | SLSVFQLHL | 19 |
| 293 | ILKFSEKET | 19 |
| 337 | SLSHKVIQC | 19 |
| 339 | SHKVIQCVF | 19 |
| 371 | IMKETSTKI | 19 |
| 408 | RYHVRREDL | 19 |
| 411 | VRREDLDKL | 19 |
| 659 | KLPLKVEEE | 19 |
| 698 | QRKSRKPEN | 19 |
| 701 | SRKPENQQF | 19 |
| 762 | SLSHKKEED | 19 |
| 958 | ASGARAAAL | 19 |
| 1051 | GQDDRAGVL | 19 |
| 80 | SSRALPGSL | 18 |
| 233 | EPPAHQRLL | 18 |
| 273 | HLIQCIPNL | 18 |
| 309 | ELPATAARL | 18 |
| 312 | ATAARLSGL | 18 |
| 577 | LDRYGRTAL | 18 |
| 115 | WERVVQRRL | 17 |
| 147 | HQRRDAACL | 17 |
| 197 | GLEAASANL | 17 |
| 209 | PGRSSSCAL | 17 |
| 369 | FLIMKETST | 17 |
| 443 | NKRDKQKRT | 17 |
| 477 | VLDNKKRTA | 17 |

TABLE XXIX-continued

| Pos | 123456789 | score |
|---|---|---|
| 593 | SASIVNLLL | 17 |
| 655 | ILNIKLPLK | 17 |
| 661 | PLKVEEEIK | 17 |
| 696 | IPQRKSRKP | 17 |
| 770 | DLLRENSML | 17 |
| 781 | EIAKLRLEL | 17 |
| 823 | EALTKTKVA | 17 |
| 850 | QLCYKWNHT | 17 |
| 890 | QLCYKWGHT | 17 |
| 904 | QAQEQGAAL | 17 |
| 968 | PPTGKNGRS | 17 |
| 1012 | SPAMRLKSD | 17 |
| 1014 | AMRLKSDSN | 17 |
| 1021 | SNRETHQAF | 17 |
| 1058 | VLAPKCRPG | 17 |
| 36 | TWRKEPAVL | 16 |
| 49 | LEKGSWLSF | 16 |
| 104 | SATPAGAFL | 16 |
| 181 | PPSRNSYRL | 16 |
| 325 | QIKEFEELV | 16 |
| 351 | KNVDKWDDF | 16 |
| 406 | EPRYHVRRE | 16 |
| 470 | DRRCQLNVL | 16 |
| 540 | DIESKNKCG | 16 |
| 641 | MLKISSENS | 16 |
| 652 | VITILNIKL | 16 |
| 657 | NIKLPLKVE | 16 |
| 667 | EIKKHGSNP | 16 |
| 674 | NPVGLPENL | 16 |
| 687 | SAGNGDDGL | 16 |
| 806 | EIESVKEKL | 16 |
| 814 | LLKTIQLNE | 16 |
| 817 | TIQLNEEAL | 16 |
| 843 | HAQASVQQL | 16 |
| 883 | HAQASVQQL | 16 |
| 1016 | RLKSDSNRE | 16 |
| 1028 | AFRDKDDLP | 16 |
| 1030 | RDKDDLPFF | 16 |

TABLE XXIX-continued

| Pos | 123456789 | score |
|---|---|---|
| 1035 | LPFFKTQQS | 16 |
| 1082 | PPHRHTTTL | 16 |
| 1091 | PHRDTTTSL | 16 |

TABLE XXX

| Pos | 123456789 | score |
|---|---|---|
| V1A-HLA-B1510-9mers:251P5G2 Each peptide is a portion of SEQ ID NO: 3; each start position is specified, the length of peptide is 9 amino acids, and the end position for each peptide is the start position plus eight. | | |
| 46 | IHMVVLLTM | 20 |
| 151 | LHVSKYCSL | 20 |
| 222 | QHILLPVSF | 19 |
| 78 | YLRRVIRVL | 16 |
| 37 | YLPVCHVAL | 15 |
| 43 | VALIHMVVL | 15 |
| 101 | NISPSISWL | 14 |
| 165 | IIRGLFFTL | 14 |
| 187 | FSSVYMMTL | 14 |
| 1 | MPFISKLVL | 13 |
| 21 | ASSPFLLFL | 13 |
| 30 | DLRPERTYL | 13 |
| 44 | ALIHMVVLL | 13 |
| 49 | VVLLTMVFL | 13 |
| 161 | PINSIIRGL | 13 |
| 191 | YMMTLIQEL | 13 |
| 207 | QPQPLPKDL | 13 |
| 7 | LVLASQPTL | 12 |
| 18 | FFSASSPFL | 12 |
| 19 | FSASSPFLL | 12 |
| 53 | TMVFLSPQL | 12 |
| 128 | LSFPVSSSL | 12 |
| 173 | LSLFRDVFL | 12 |
| 218 | GKSHQHILL | 12 |
| 41 | CHVALIHMV | 11 |
| 57 | LSPQLFESL | 11 |
| 71 | FKYEASFYL | 11 |

TABLE XXX-continued

| Pos | 123456789 | score |
|---|---|---|
| 85 | VLSICTTCL | 11 |
| 120 | TFHLFSWSL | 11 |
| 143 | SSNVTQINL | 11 |
| 172 | TLSLFRDVF | 11 |
| 195 | LIQELQEIL | 11 |
| 203 | LVPSQPQPL | 11 |
| 239 | FIISTSSTL | 11 |
| 23 | SPFLLFLDL | 10 |
| 86 | LSICTTCLL | 10 |
| 89 | CTTCLLGML | 10 |
| 104 | PSISWLVRF | 10 |
| 115 | KSTIFTFHL | 10 |
| 121 | FHLFSWSLS | 10 |
| 162 | INSIIRGLF | 10 |
| 167 | RGLFFTLSL | 10 |
| 178 | DVFLKQIML | 10 |
| 184 | IMLFSSVYM | 10 |
| 217 | RGKSHQHIL | 10 |
| 220 | SHQHILLPV | 10 |
| 229 | SFSVGMYKM | 10 |
| V2A-B1510-9mers:251P5G2 Each peptide is a portion of SEQ ID NO: 5; each start position is specified, the length of peptide is 9 amino acids, and the end position for each peptide is the start position plus eight. | | |
| 3 | ASQPTLCSF | 8 |
| 4 | SQPTLCSFF | 6 |
| V3A-HLA-B1510-9mers:251P5G2 Each peptide is a portion of SEQ ID NO: 7; each start position is specified, the length of peptide is 9 amino acids, and the end position for each peptide is the start position plus eight. | | |
| 2 | YLRRVIRDL | 14 |
| 9 | DLSICTTCL | 11 |

TABLE XXX-continued

Pos | 123456789 | score
---|---|---
 | V4A-HLA-B1510-9mers:251P5G2 Each peptide is a portion of SEQ ID NO: 9; each start position is specified, the length of peptide is 9 amino acids, and the end position for each peptide is the start position plus eight. | 
3 | CTTCLLDML | 10
2 | ICTTCLLDM | 8
7 | LLDMLQVVN | 4
 | V12A-HLA-B1510-9mers:251P5G2 Each peptide is a portion of SEQ ID NO: 25; each start position is specified, the length of peptide is 9 amino acids, and the end position for each peptide is the start position plus eight. | 
1 | ISPSISWL | 16
4 | PSISWLIML | 10
5 | SISWLIMLF | 8
3 | SPSISWLIM | 7
 | V12B-HLA-B1510-9mers:251P5G2 Each peptide is a portion of SEQ ID NO: 25; each start position is specified, the length of peptide is 9 amino acids, and the end position for each peptide is the start position plus eight. | 
670 | KHGSNPVGL | 24
624 | SHHHVICEL | 22
190 | THVRCAQGL | 21
625 | HHHVICELL | 21
764 | SHKKEEDLL | 21
1091 | PHRDTTTSL | 21
288 | RHIPEILKF | 19
339 | SHKVIQCVF | 19
916 | IGDPGGVPL | 17
541 | IESKNKCGL | 16
949 | PGTPSLVRL | 16
36 | TWRKEPAVL | 15
115 | WERVVQRRL | 15
161 | TRAFQVVHL | 15
781 | EIAKLRLEL | 15
938 | THLPPREPR | 15
946 | RASPGTPSL | 15

TABLE XXX-continued

Pos | 123456789 | score
---|---|---
181 | PPSRNSYRL | 14
232 | AEPPAHQRL | 14
259 | EEALGVGSL | 14
300 | ETGGGILGL | 14
429 | PRKDLIVML | 14
460 | GNSEVVQLL | 14
556 | VHEQKQEVV | 14
591 | CGSASIVNL | 14
779 | REEIAKLRL | 14
807 | IESVKEKLL | 14
842 | QHAQASVQQ | 14
882 | QHAQASVQQ | 14
1051 | GQDDRAGVL | 14
1106 | AGGVGPTTL | 14
68 | TTLTGHSAL | 13
76 | LSLSSSRAL | 13
86 | GSLPAFADL | 13
233 | EPPAHQRLL | 13
254 | QEQPSEEAL | 13
273 | HLIQCIPNL | 13
279 | PNLSYPLVL | 13
298 | EKETGGGIL | 13
309 | ELPATAARL | 13
327 | KEFEELVKL | 13
335 | LHSLSHKVI | 13
366 | GHSFLIMKE | 13
374 | ETSTKISGL | 13
425 | WGKVPRKDL | 13
445 | RDKQKRTAL | 13
459 | NGNSEVVQL | 13
478 | LDNKKRTAL | 13
491 | QCQEDECVL | 13
511 | QDEYGNTAL | 13
577 | LDRYGRTAL | 13
592 | GSASIVNLL | 13
648 | NSNPVITIL | 13
717 | YHSDEQNDT | 13
793 | KHQNQLREN | 13

TABLE XXX-continued

| Pos | 123456789 | score |
|---|---|---|
| 806 | EIESVKEKL | 13 |
| 817 | TIQLNEEAL | 13 |
| 867 | EQEVAGFSL | 13 |
| 932 | GDQGPGTHL | 13 |
| 1009 | FDVSPAMRL | 13 |
| 1069 | CHTDTPPHR | 13 |
| 15 | AATGLWAAL | 12 |
| 62 | ARKEFSTTL | 12 |
| 72 | GHSALSLSS | 12 |
| 104 | SATPAGAFL | 12 |
| 197 | GLEAASANL | 12 |
| 264 | VGSLSVFQL | 12 |
| 266 | SLSVFQLHL | 12 |
| 302 | GGGILGLEL | 12 |
| 324 | MQIKEFEEL | 12 |
| 330 | EELVKLHSL | 12 |
| 408 | RYHVRREDL | 12 |
| 461 | NSEVVQLLL | 12 |
| 467 | LLLDRRCQL | 12 |
| 470 | DRRCQLNVL | 12 |
| 493 | QEDECVLML | 12 |
| 494 | EDECVLMLL | 12 |
| 521 | YAIYNEDKL | 12 |
| 526 | EDKLMAKAL | 12 |
| 545 | NKCGLTPLL | 12 |
| 559 | QKQEVVKFL | 12 |
| 566 | FLIKKKANL | 12 |
| 569 | KKKANLNAL | 12 |
| 634 | SDYKEKQML | 12 |
| 654 | TILNIKLPL | 12 |
| 674 | NPVGLPENL | 12 |
| 721 | EQNDTQKQL | 12 |
| 753 | AEKEMNSEL | 12 |
| 777 | MLREEIAKL | 12 |
| 830 | VAGFSLRQL | 12 |
| 832 | GFSLRQLGL | 12 |
| 870 | VAGFSLRQL | 12 |
| 872 | GFSLRQLGL | 12 |
| 896 | GHTEKTEQQ | 12 |

TABLE XXX-continued

| Pos | 123456789 | score |
|---|---|---|
| 904 | QAQEQGAAL | 12 |
| 1025 | THQAFRDKD | 12 |
| 1060 | APKCRPGTL | 12 |
| 1102 | FHVSAGGVG | 12 |
| 3 | QHILLPTQA | 11 |
| 5 | ILLPTQATF | 11 |
| 41 | PAVLPCCNL | 11 |
| 47 | CNLEKGSWL | 11 |
| 80 | SSRALPGSL | 11 |
| 105 | ATPAGAFLL | 11 |
| 146 | CHQRRDAAC | 11 |
| 167 | VHLAPTAPD | 11 |
| 209 | PGRSSSCAL | 11 |
| 235 | PAHQRLLFL | 11 |
| 286 | VLRHIPEIL | 11 |
| 312 | ATAARLSGL | 11 |
| 362 | SEGYGHSFL | 11 |
| 409 | YHVRREDLD | 11 |
| 411 | VRREDLDKL | 11 |
| 503 | EHGADGNIQ | 11 |
| 519 | LHYAIYNED | 11 |
| 527 | DKLMAKALL | 11 |
| 544 | KNKCGLTPL | 11 |
| 546 | KCGLTPLLL | 11 |
| 558 | EQKQEVVKF | 11 |
| 593 | SASIVNLLL | 11 |
| 604 | NVDVSSQDL | 11 |
| 687 | SAGNGDDGL | 11 |
| 735 | TGISQDEIL | 11 |
| 763 | LSHKKEEDL | 11 |
| 790 | DETKHQNQL | 11 |
| 812 | EKLLKTIQL | 11 |
| 827 | KTKVAGFSL | 11 |
| 843 | HAQASVQQL | 11 |
| 856 | NHTEKTEQQ | 11 |
| 883 | HAQASVQQL | 11 |
| 958 | ASGARAAAL | 11 |
| 988 | GWILPVPTF | 11 |

TABLE XXX-continued

| Pos | 123456789 | score |
|---|---|---|
| 1027 | QAFRDKDDL | 11 |
| 1045 | RHTKDLGQD | 11 |
| 1082 | PPHRHTTTL | 11 |
| 1085 | RHTTTLPHR | 11 |

TABLE XXXI

| Pos | 123456789 | score |
|---|---|---|
| \multicolumn{3}{l}{V1A-HLA-B2705-9mers:251P5G2 Each peptide is a portion of SEQ ID NO: 3; each start position is specified, the length of peptide is 9 amino acids, and the end position for each peptide is the start position plus eight.} | | |
| 80 | RRVIRVLSI | 24 |
| 110 | VRFKWKSTI | 24 |
| 34 | ERTYLPVCH | 20 |
| 216 | CRGKSHQHI | 19 |
| 83 | IRVLSICTT | 18 |
| 111 | RFKWKSTIF | 18 |
| 128 | LSFPVSSSL | 18 |
| 167 | RGLFFTLSL | 18 |
| 168 | GLFFTLSLF | 18 |
| 176 | FRDVFLKQI | 18 |
| 178 | DVFLKQIML | 18 |
| 179 | VFLKQIMLF | 18 |
| 1 | MPFISKLVL | 17 |
| 7 | LVLASQPTL | 17 |
| 59 | PQLFESLNF | 17 |
| 69 | NDFKYEASF | 17 |
| 23 | SPFLLFLDL | 16 |
| 65 | LNFQNDFKY | 16 |
| 101 | NISPSISWL | 16 |
| 104 | PSISWLVRF | 16 |
| 113 | KWKSTIFTF | 16 |
| 122 | HLFSWSLSF | 16 |
| 169 | LFFTLSLFR | 16 |
| 209 | QPLPKDLCR | 16 |
| 217 | RGKSHQHIL | 16 |
| 222 | QHILLPVSF | 16 |

TABLE XXXI-continued

| Pos | 123456789 | score |
|---|---|---|
| 17 | SFFSASSPF | 15 |
| 27 | LFLDLRPER | 15 |
| 44 | ALIHMVVLL | 15 |
| 48 | MVVLLTMVF | 15 |
| 53 | TMVFLSPQL | 15 |
| 54 | MVFLSPQLF | 15 |
| 63 | ESLNFQNDF | 15 |
| 78 | YLRRVIRVL | 15 |
| 143 | SSNVTQINL | 15 |
| 147 | TQINLHVSK | 15 |
| 165 | IIRGLFFTL | 15 |
| 177 | RDVFLKQIM | 15 |
| 191 | YMMTLIQEL | 15 |
| 228 | VSFSVGMYK | 15 |
| 239 | FIISTSSTL | 15 |
| 245 | STLPWAYDR | 15 |
| 10 | ASQPTLFSF | 14 |
| 21 | ASSPFLLFL | 14 |
| 24 | PFLLFLDLR | 14 |
| 30 | DLRPERTYL | 14 |
| 43 | VALIHMVVL | 14 |
| 49 | VVLLTMVFL | 14 |
| 57 | LSPQLFESL | 14 |
| 71 | FKYEASFYL | 14 |
| 72 | KYEASFYLR | 14 |
| 76 | SFYLRRVIR | 14 |
| 120 | TFHLFSWSL | 14 |
| 130 | FPVSSSLIF | 14 |
| 157 | CSLFPINSI | 14 |
| 161 | PINSIIRGL | 14 |
| 166 | IRGLFFTLS | 14 |
| 173 | LSLFRDVFL | 14 |
| 174 | SLFRDVFLK | 14 |
| 184 | IMLFSSVYM | 14 |
| 185 | MLFSSVYMM | 14 |
| 195 | LIQELQEIL | 14 |
| 218 | GKSHQHILL | 14 |
| 233 | GMYKMDFII | 14 |
| 18 | FFSASSPFL | 13 |

TABLE XXXI-continued

| Pos | 123456789 | score |
|---|---|---|
| 46 | IHMVVLLTM | 13 |
| 73 | YEASFYLRR | 13 |
| 103 | SPSISWLVR | 13 |
| 144 | SNVTQINLH | 13 |
| 148 | QINLHVSKY | 13 |
| 151 | LHVSKYCSL | 13 |
| 152 | HVSKYCSLF | 13 |
| 158 | SLFPINSII | 13 |
| 163 | NSIIRGLFF | 13 |
| 194 | TLIQELQEI | 13 |
| 213 | KDLCRGKSH | 13 |
| 215 | LCRGKSHQH | 13 |
| 229 | SFSVGMYKM | 13 |
| 8 | VLASQPTLF | 12 |
| 11 | SQPTLFSFF | 12 |
| 20 | SASSPFLLF | 12 |
| 29 | LDLRPERTY | 12 |
| 31 | LRPERTYLP | 12 |
| 75 | ASFYLRRVI | 12 |
| 79 | LRRVIRVLS | 12 |
| 85 | VLSICTTCL | 12 |
| 86 | LSICTTCLL | 12 |
| 89 | CTTCLLGML | 12 |
| 105 | SISWLVRFK | 12 |
| 107 | SWLVRFKWK | 12 |
| 115 | KSTIFTFHL | 12 |
| 116 | STIFTFHLF | 12 |
| 159 | LFPINSIIR | 12 |
| 162 | INSIIRGLF | 12 |
| 172 | TLSLFRDVF | 12 |
| 183 | QIMLFSSVY | 12 |
| 187 | FSSVYMMTL | 12 |
| 205 | PSQPQPLPK | 12 |
| 207 | QPQPLPKDL | 12 |
| 231 | SVGMYKMDF | 12 |
| 19 | FSASSPFLL | 11 |
| 37 | YLPVCHVAL | 11 |
| 39 | PVCHVALIH | 11 |

TABLE XXXI-continued

| Pos | 123456789 | score |
|---|---|---|
| 64 | SLNFQNDFK | 11 |
| 70 | DFKYEASFY | 11 |
| 88 | ICTTCLLGM | 11 |
| 94 | LGMLQVVNI | 11 |
| 98 | QVVNISPSI | 11 |
| 114 | WKSTIFTFH | 11 |
| 131 | PVSSSLIFY | 11 |
| 211 | LPKDLCRGK | 11 |
| 226 | LPVSFSVGM | 11 |

V2A-B2705-
9mers:251P5G2
Each peptide is a portion of SEQ ID NO: 5; each start position is specified, the length of peptide is 9 amino acids, and the end position for each peptide is the start position plus eight.

| Pos | 123456789 | score |
|---|---|---|
| 3 | ASQPTLCSF | 14 |
| 4 | SQPTLCSFF | 12 |
| 9 | CSFFSASSP | 7 |

V3A-HLA-B2705-
9mers:251P5G2
Each peptide is a portion of SEQ ID NO: 7; each start position is specified, the length of peptide is 9 amino acids, and the end position for each peptide is the start position plus eight.

| Pos | 123456789 | score |
|---|---|---|
| 4 | RRVIRDLSI | 24 |
| 7 | IRDLSICTT | 17 |
| 2 | YLRRVIRDL | 14 |
| 9 | DLSICTTCL | 12 |
| 3 | LRRVIRDLS | 11 |

V4A-HLA-B2705-
9mers:251P5G2
Each peptide is a portion of SEQ ID NO: 9; each start position is specified, the length of peptide is 9 amino acids, and the end position for each peptide is the start position plus eight.

| Pos | 123456789 | score |
|---|---|---|
| 3 | CTTCLLDML | 12 |
| 2 | ICTTCLLDM | 11 |
| 8 | LDMLQVVNI | 11 |
| 9 | DMLQVVNIS | 7 |
| 5 | TCLLDMLQV | 5 |
| 7 | LLDMLQVVN | 5 |

V12A-HLA-B2705-

TABLE XXXI-continued

| Pos | 123456789 | score |
|---|---|---|
| 9mers:251P5G2 Each peptide is a portion of SEQ ID NO: 25; each start position is specified, the length of peptide is 9 amino acids, and the end position for each peptide is the start position plus eight. | | |
| 5 | SISWLIMLF | 15 |
| 4 | PSISWLIML | 14 |
| 9 | LIMLFSSVY | 12 |
| 2 | ISPSISWLI | 10 |
| 3 | SPSISWLIM | 10 |
| V12B-HLA-B2705-9mers:251P5G2 Each peptide is a portion of SEQ ID NO: 25; each start position is specified, the length of peptide is 9 amino acids, and the end position for each peptide is the start position plus eight. | | |
| 1015 | MRLKSDSNR | 29 |
| 62 | ARKEFSTTL | 26 |
| 785 | LRLELDETK | 26 |
| 210 | GRSSSCALR | 25 |
| 429 | PRKDLIVML | 25 |
| 1054 | DRAGVLAPK | 25 |
| 30 | SRADPVTWR | 24 |
| 288 | RHIPEILKF | 24 |
| 315 | ARLSGLNSI | 24 |
| 411 | VRREDLDKL | 24 |
| 412 | RREDLDKLH | 24 |
| 701 | SRKPENQQF | 24 |
| 835 | LRQLGLAQH | 24 |
| 875 | LRQLGLAQH | 24 |
| 1029 | FRDKDDLPF | 24 |
| 437 | LRDTDMNKR | 23 |
| 470 | DRRCQLNVL | 23 |
| 778 | LREEIAKLR | 23 |
| 1022 | NRETHQAFR | 23 |
| 161 | TRAFQVVHL | 22 |
| 287 | LRHIPEILK | 22 |
| 617 | AREYAVSSH | 22 |
| 139 | SRDPSPPCH | 21 |
| 148 | QRRDAACLR | 21 |

TABLE XXXI-continued

| Pos | 123456789 | score |
|---|---|---|
| 327 | KEFEELVKL | 21 |
| 578 | DRYGRTALI | 21 |
| 691 | GDDGLIPQR | 21 |
| 109 | GAFLLGWER | 20 |
| 183 | SRNSYRLTH | 20 |
| 273 | HLIQCIPNL | 20 |
| 988 | GWILPVPTF | 20 |
| 31 | RADPVTWRK | 19 |
| 155 | LRAQGLTRA | 19 |
| 445 | RDKQKRTAL | 19 |
| 471 | RRCQLNVLD | 19 |
| 566 | FLIKKKANL | 19 |
| 946 | RASPGTPSL | 19 |
| 1076 | HRNADTPPH | 19 |
| 1084 | HRHTTTLPH | 19 |
| 5 | ILLPTQATF | 18 |
| 121 | RRLEVPRPQ | 18 |
| 203 | ANLPGAPGR | 18 |
| 300 | ETGGGILGL | 18 |
| 423 | AWWGKVPRK | 18 |
| 430 | RKDLIVMLR | 18 |
| 581 | GRTALILAV | 18 |
| 610 | QDLSGQTAR | 18 |
| 777 | MLREEIAKL | 18 |
| 779 | REEIAKLRL | 18 |
| 932 | GDQGPGTHL | 18 |
| 971 | GKNGRSPTK | 18 |
| 11 | ATFAAATGL | 17 |
| 55 | LSFPGTAAR | 17 |
| 86 | GSLPAFADL | 17 |
| 114 | GWERVVQRR | 17 |
| 149 | RRDAACLRA | 17 |
| 156 | RAQGLTRAF | 17 |
| 176 | GGAGCPPSR | 17 |
| 197 | GLEAASANL | 17 |
| 238 | QRLLFLPRA | 17 |
| 262 | LGVGSLSVF | 17 |
| 316 | RLSGLNSIM | 17 |
| 341 | KVIQCVFAK | 17 |

TABLE XXXI-continued

| Pos | 123456789 | score |
|---|---|---|
| 378 | KISGLIQEM | 17 |
| 413 | REDLDKLHR | 17 |
| 538 | GADIESKNK | 17 |
| 544 | KNKCGLTPL | 17 |
| 558 | EQKQEVVKF | 17 |
| 562 | EVVKFLIKK | 17 |
| 591 | CGSASIVNL | 17 |
| 618 | REYAVSSHH | 17 |
| 648 | NSNPVITIL | 17 |
| 663 | KVEEEIKKH | 17 |
| 694 | GLIPQRKSR | 17 |
| 738 | SQDEILTNK | 17 |
| 786 | RLELDETKH | 17 |
| 832 | GFSLRQLGL | 17 |
| 872 | GFSLRQLGL | 17 |
| 905 | AQEQGAALR | 17 |
| 964 | AALPPPTGK | 17 |
| 974 | GRSPTKQKS | 17 |
| 1110 | GPTTLGSNR | 17 |
| 56 | SFPGTAARK | 16 |
| 74 | SALSLSSSR | 16 |
| 83 | ALPGSLPAF | 16 |
| 120 | QRRLEVPRP | 16 |
| 211 | RSSSCALRY | 16 |
| 219 | YRSGPSVSS | 16 |
| 281 | LSYPLVLRH | 16 |
| 291 | PEILKFSEK | 16 |
| 302 | GGGILGLEL | 16 |
| 321 | NSIMQIKEF | 16 |
| 324 | MQIKEFEEL | 16 |
| 444 | KRDKQKRTA | 16 |
| 460 | GNSEVVQLL | 16 |
| 463 | EVVQLLLDR | 16 |
| 473 | CQLNVLDNK | 16 |
| 482 | KRTALIKAV | 16 |
| 552 | LLLGVHEQK | 16 |
| 563 | VVKFLIKKK | 16 |
| 579 | RYGRTALIL | 16 |

TABLE XXXI-continued

| Pos | 123456789 | score |
|---|---|---|
| 592 | GSASIVNLL | 16 |
| 634 | SDYKEKQML | 16 |
| 662 | LKVEEEIKK | 16 |
| 674 | NPVGLPENL | 16 |
| 695 | LIPQRKSRK | 16 |
| 719 | SDEQNDTQK | 16 |
| 759 | SELSLSHKK | 16 |
| 790 | DETKHQNQL | 16 |
| 798 | LRENKILEE | 16 |
| 805 | EEIESVKEK | 16 |
| 808 | ESVKEKLLK | 16 |
| 812 | EKLLKTIQL | 16 |
| 865 | AQEQEVAGF | 16 |
| 949 | PGTPSLVRL | 16 |
| 955 | VRLASGARA | 16 |
| 1004 | RRCPMFDVS | 16 |
| 1009 | FDVSPAMRL | 16 |
| 1030 | RDKDDLPFF | 16 |
| 1085 | RHTTTLPHR | 16 |
| 1106 | AGGVGPTTL | 16 |
| 15 | AATGLWAAL | 15 |
| 36 | TWRKEPAVL | 15 |
| 41 | PAVLPCCNL | 15 |
| 47 | CNLEKGSWL | 15 |
| 49 | LEKGSWLSF | 15 |
| 68 | TTLTGHSAL | 15 |
| 115 | WERVVQRRL | 15 |
| 179 | GCPPSRNSY | 15 |
| 217 | LRYRSGPSV | 15 |
| 259 | EEALGVGSL | 15 |
| 330 | EELVKLHSL | 15 |
| 333 | VKLHSLSHK | 15 |
| 347 | FAKKKNVDK | 15 |
| 370 | LIMKETSTK | 15 |
| 374 | ETSTKISGL | 15 |
| 397 | GDYDDSAFM | 15 |
| 422 | AAWWGKVPR | 15 |
| 464 | VVQLLLDRR | 15 |
| 474 | QLNVLDNKK | 15 |

TABLE XXXI-continued

| Pos | 123456789 | score |
|---|---|---|
| 475 | LNVLDNKKR | 15 |
| 478 | LDNKKRTAL | 15 |
| 511 | QDEYGNTAL | 15 |
| 528 | KLMAKALLL | 15 |
| 571 | KANLNALDR | 15 |
| 624 | SHHHVICEL | 15 |
| 635 | DYKEKQMLK | 15 |
| 651 | PVITILNIK | 15 |
| 652 | VITILNIKL | 15 |
| 654 | TILNIKLPL | 15 |
| 740 | DEILTNKQK | 15 |
| 753 | AEKEMNSEL | 15 |
| 755 | KEMNSELSL | 15 |
| 770 | DLLRENSML | 15 |
| 781 | EIAKLRLEL | 15 |
| 794 | HQNQLRENK | 15 |
| 799 | RENKILEEI | 15 |
| 803 | ILEEIESVK | 15 |
| 819 | QLNEEALTK | 15 |
| 846 | ASVQQLCYK | 15 |
| 886 | ASVQQLCYK | 15 |
| 892 | CYKWGHTEK | 15 |
| 916 | IGDPGGVPL | 15 |
| 935 | GPGTHLPPR | 15 |
| 994 | PTFSSGSFL | 15 |
| 1047 | TKDLGQDDR | 15 |
| 1051 | GQDDRAGVL | 15 |
| 1077 | RNADTPPHR | 15 |
| 23 | LTTVSNPSR | 14 |
| 37 | WRKEPAVLP | 14 |
| 70 | LTGHSALSL | 14 |
| 76 | LSLSSSRAL | 14 |
| 105 | ATPAGAFLL | 14 |
| 113 | LGWERVVQR | 14 |
| 126 | PRPQAAPAT | 14 |
| 181 | PPSRNSYRL | 14 |
| 185 | NSYRLTHVR | 14 |

TABLE XXXI-continued

V12B-HLA-B2705-
9mers:251P5G2
Each peptide is a portion of
SEQ ID NO: 25; each start
position is specified, the
length of peptide is 9 amino
acids, and the end position
for each peptide is the start
position plus eight.

| Pos | 123456789 | score |
|---|---|---|
| 1015 | MRLKSDSNR | 29 |
| 62 | ARKEFSTTL | 26 |
| 785 | LRLELDETK | 26 |
| 210 | GRSSSCALR | 25 |
| 429 | PRKDLIVML | 25 |
| 1054 | DRAGVLAPK | 25 |
| 30 | SRADPVTWR | 24 |
| 288 | RHIPEILKF | 24 |
| 315 | ARLSGLNSI | 24 |
| 411 | VRREDLDKL | 24 |
| 412 | RREDLDKLH | 24 |
| 701 | SRKPENQQF | 24 |
| 835 | LRQLGLAQH | 24 |
| 875 | LRQLGLAQH | 24 |
| 1029 | FRDKDDLPF | 24 |
| 437 | LRDTDMNKR | 23 |
| 470 | DRRCQLNVL | 23 |
| 778 | LREEIAKLR | 23 |
| 1022 | NRETHQAFR | 23 |
| 161 | TRAFQVVHL | 22 |
| 287 | LRHIPEILK | 22 |
| 617 | AREYAVSSH | 22 |
| 139 | SRDPSPPCH | 21 |
| 148 | QRRDAACLR | 21 |
| 327 | KEFEELVKL | 21 |
| 578 | DRYGRTALI | 21 |
| 691 | GDDGLIPQR | 21 |
| 109 | GAFLLGWER | 20 |
| 183 | SRNSYRLTH | 20 |
| 273 | HLIQCIPNL | 20 |
| 988 | GWILPVPTF | 20 |
| 31 | RADPVTWRK | 19 |
| 155 | LRAQGLTRA | 19 |
| 445 | RDKQKRTAL | 19 |

TABLE XXXI-continued

| Pos | 123456789 | score |
|---|---|---|
| 471 | RRCQLNVLD | 19 |
| 566 | FLIKKKANL | 19 |
| 946 | RASPGTPSL | 19 |
| 1076 | HRNADTPPH | 19 |
| 1084 | HRHTTTLPH | 19 |
| 5 | ILLPTQATF | 18 |
| 121 | RRLEVPRPQ | 18 |
| 203 | ANLPGAPGR | 18 |
| 300 | ETGGGILGL | 18 |
| 423 | AWWGKVPRK | 18 |
| 430 | RKDLIVMLR | 18 |
| 581 | GRTALILAV | 18 |
| 610 | QDLSGQTAR | 18 |
| 777 | MLREEIAKL | 18 |
| 779 | REEIAKLRL | 18 |
| 932 | GDQGPGTHL | 18 |
| 971 | GKNGRSPTK | 18 |
| 11 | ATFAAATGL | 17 |
| 55 | LSFPGTAAR | 17 |
| 86 | GSLPAFADL | 17 |
| 114 | GWERVVQRR | 17 |
| 149 | RRDAACLRA | 17 |
| 156 | RAQGLTRAF | 17 |
| 176 | GGAGCPPSR | 17 |
| 197 | GLEAASANL | 17 |
| 238 | QRLLFLPRA | 17 |
| 262 | LGVGSLSVF | 17 |
| 316 | RLSGLNSIM | 17 |
| 341 | KVIQCVFAK | 17 |
| 378 | KISGLIQEM | 17 |
| 413 | REDLDKLHR | 17 |
| 538 | GADIESKNK | 17 |
| 544 | KNKCGLTPL | 17 |
| 558 | EQKQEVVKF | 17 |
| 562 | EVVKFLIKK | 17 |
| 591 | CGSASIVNL | 17 |
| 618 | REYAVSSHH | 17 |
| 648 | NSNPVITIL | 17 |

TABLE XXXI-continued

| Pos | 123456789 | score |
|---|---|---|
| 663 | KVEEEIKKH | 17 |
| 694 | GLIPQRKSR | 17 |
| 738 | SQDEILTNK | 17 |
| 786 | RLELDETKH | 17 |
| 832 | GFSLRQLGL | 17 |
| 872 | GFSLRQLGL | 17 |
| 905 | AQEQGAALR | 17 |
| 964 | AALPPPTGK | 17 |
| 974 | GRSPTKQKS | 17 |
| 1110 | GPTTLGSNR | 17 |
| 56 | SFPGTAARK | 16 |
| 74 | SALSLSSSR | 16 |
| 83 | ALPGSLPAF | 16 |
| 120 | QRRLEVPRP | 16 |
| 211 | RSSSCALRY | 16 |
| 219 | YRSGPSVSS | 16 |
| 281 | LSYPLVLRH | 16 |
| 291 | PEILKFSEK | 16 |
| 302 | GGGILGLEL | 16 |
| 321 | NSIMQIKEF | 16 |
| 324 | MQIKEFEEL | 16 |
| 444 | KRDKQKRTA | 16 |
| 460 | GNSEVVQLL | 16 |
| 463 | EVVQLLLDR | 16 |
| 473 | CQLNVLDNK | 16 |
| 482 | KRTALIKAV | 16 |
| 552 | LLLGVHEQK | 16 |
| 563 | VVKFLIKKK | 16 |
| 579 | RYGRTALIL | 16 |
| 592 | GSASIVNLL | 16 |
| 634 | SDYKEKQML | 16 |
| 662 | LKVEEEIKK | 16 |
| 674 | NPVGLPENL | 16 |
| 695 | LIPQRKSRK | 16 |
| 719 | SDEQNDTQK | 16 |
| 759 | SELSLSHKK | 16 |
| 790 | DETKHQNQL | 16 |
| 798 | LRENKILEE | 16 |
| 805 | EEIESVKEK | 16 |

TABLE XXXI-continued

| Pos | 123456789 | score |
|---|---|---|
| 808 | ESVKEKLLK | 16 |
| 812 | EKLLKTIQL | 16 |
| 865 | AQEQEVAGF | 16 |
| 949 | PGTPSLVRL | 16 |
| 955 | VRLASGARA | 16 |
| 1004 | RRCPMFDVS | 16 |
| 1009 | FDVSPAMRL | 16 |
| 1030 | RDKDDLPFF | 16 |
| 1085 | RHTTTLPHR | 16 |
| 1106 | AGGVGPTTL | 16 |
| 15 | AATGLWAAL | 15 |
| 36 | TWRKEPAVL | 15 |
| 41 | PAVLPCCNL | 15 |
| 47 | CNLEKGSWL | 15 |
| 49 | LEKGSWLSF | 15 |
| 68 | TTLTGHSAL | 15 |
| 115 | WERVVQRRL | 15 |
| 179 | GCPPSRNSY | 15 |
| 217 | LRYRSGPSV | 15 |
| 259 | EEALGVGSL | 15 |
| 330 | EELVKLHSL | 15 |
| 333 | VKLHSLSHK | 15 |
| 347 | FAKKKNVDK | 15 |
| 370 | LIMKETSTK | 15 |
| 374 | ETSTKISGL | 15 |
| 397 | GDYDDSAFM | 15 |
| 422 | AAWWGKVPR | 15 |
| 464 | VVQLLLDRR | 15 |
| 474 | QLNVLDNKK | 15 |
| 475 | LNVLDNKKR | 15 |
| 478 | LDNKKRTAL | 15 |
| 511 | QDEYGNTAL | 15 |
| 528 | KLMAKALLL | 15 |
| 571 | KANLNALDR | 15 |
| 624 | SHHHVICEL | 15 |
| 635 | DYKEKQMLK | 15 |
| 651 | PVITILNIK | 15 |
| 652 | VITILNIKL | 15 |

TABLE XXXI-continued

| Pos | 123456789 | score |
|---|---|---|
| 654 | TILNIKLPL | 15 |
| 740 | DEILTNKQK | 15 |
| 753 | AEKEMNSEL | 15 |
| 755 | KEMNSELSL | 15 |
| 770 | DLLRENSML | 15 |
| 781 | EIAKLRLEL | 15 |
| 794 | HQNQLRENK | 15 |
| 799 | RENKILEEI | 15 |
| 803 | ILEEIESVK | 15 |
| 819 | QLNEEALTK | 15 |
| 846 | ASVQQLCYK | 15 |
| 886 | ASVQQLCYK | 15 |
| 892 | CYKWGHTEK | 15 |
| 916 | IGDPGGVPL | 15 |
| 935 | GPGTHLPPR | 15 |
| 994 | PTFSSGSFL | 15 |
| 1047 | TKDLGQDDR | 15 |
| 1051 | GQDDRAGVL | 15 |
| 1077 | RNADTPPHR | 15 |
| 23 | LTTVSNPSR | 14 |
| 37 | WRKEPAVLP | 14 |
| 70 | LTGHSALSL | 14 |
| 76 | LSLSSSRAL | 14 |
| 105 | ATPAGAFLL | 14 |
| 113 | LGWERVVQR | 14 |
| 126 | PRPQAAPAT | 14 |
| 181 | PPSRNSYRL | 14 |
| 185 | NSYRLTHVR | 14 |
| 231 | PAEPPAHQR | 14 |
| 232 | AEPPAHQRL | 14 |
| 235 | PAHQRLLFL | 14 |
| 244 | PRAPQAVSG | 14 |
| 264 | VGSLSVFQL | 14 |
| 265 | GSLSVFQLH | 14 |
| 279 | PNLSYPLVL | 14 |
| 308 | LELPATAAR | 14 |
| 309 | ELPATAARL | 14 |
| 318 | SGLNSIMQI | 14 |
| 319 | GLNSIMQIK | 14 |

TABLE XXXI-continued

| Pos | 123456789 | score |
|---|---|---|
| 326 | IKEFEELVK | 14 |
| 339 | SHKVIQCVF | 14 |
| 342 | VIQCVFAKK | 14 |
| 343 | IQCVFAKKK | 14 |
| 351 | KNVDKWDDF | 14 |
| 407 | PRYHVRRED | 14 |
| 408 | RYHVRREDL | 14 |
| 436 | MLRDTDMNK | 14 |
| 441 | DMNKRDKQK | 14 |
| 447 | KQKRTALHL | 14 |
| 449 | KRTALHLAS | 14 |
| 459 | NGNSEVVQL | 14 |
| 461 | NSEVVQLLL | 14 |
| 521 | YAIYNEDKL | 14 |
| 527 | DKLMAKALL | 14 |
| 536 | LYGADIESK | 14 |
| 541 | IESKNKCGL | 14 |
| 545 | NKCGLTPLL | 14 |
| 546 | KCGLTPLLL | 14 |
| 557 | HEQKQEVVK | 14 |
| 569 | KKKANLNAL | 14 |
| 572 | ANLNALDRY | 14 |
| 577 | LDRYGRTAL | 14 |
| 629 | ICELLSDYK | 14 |
| 655 | ILNIKLPLK | 14 |
| 692 | DDGLIPQRK | 14 |
| 747 | QKQIEVAEK | 14 |
| 758 | NSELSLSHK | 14 |
| 765 | HKKEEDLLR | 14 |
| 772 | LRENSMLRE | 14 |
| 776 | SMLREEIAK | 14 |
| 796 | NQLRENKIL | 14 |
| 806 | EIESVKEKL | 14 |
| 828 | TKVAGFSLR | 14 |
| 849 | QQLCYKWNH | 14 |
| 868 | QEVAGFSLR | 14 |
| 931 | AGDQGPGTH | 14 |
| 938 | THLPPREPR | 14 |

TABLE XXXI-continued

| Pos | 123456789 | score |
|---|---|---|
| 948 | SPGTPSLVR | 14 |
| 967 | PPPTGKNGR | 14 |
| 996 | FSSGSFLGR | 14 |
| 1003 | GRRCPMFDV | 14 |
| 1007 | PMFDVSPAM | 14 |
| 1027 | QAFRDKDDL | 14 |
| 1038 | FKTQQSPRH | 14 |
| 1062 | KCRPGTLCH | 14 |
| 1093 | RDTTTSLPH | 14 |

TABLE XXXII

| Pos | 123456789 | score |
|---|---|---|
| V1A-HLA-B2709-9mers:251P5G2 Each peptide is a portion of SEQ ID NO: 3; each start position is specified, the length of peptide is 9 amino acids, and the end position for each peptide is the start position plus eight. | | |
| 80 | RRVIRVLSI | 25 |
| 110 | VRFKWKSTI | 20 |
| 176 | FRDVFLKQI | 19 |
| 216 | CRGKSHQHI | 18 |
| 167 | RGLFFTLSL | 17 |
| 35 | RTYLPVCHV | 15 |
| 217 | RGKSHQHIL | 15 |
| 44 | ALIHMVVLL | 14 |
| 1 | MPFISKLVL | 13 |
| 7 | LVLASQPTL | 13 |
| 21 | ASSPFLLFL | 13 |
| 23 | SPFLLFLDL | 13 |
| 32 | RPERTYLPV | 13 |
| 43 | VALIHMVVL | 13 |
| 49 | VVLLTMVFL | 13 |
| 53 | TMVFLSPQL | 13 |
| 115 | KSTIFTFHL | 13 |
| 128 | LSFPVSSSL | 13 |
| 168 | GLFFTLSLF | 13 |
| 173 | LSLFRDVFL | 13 |
| 177 | RDVFLKQIM | 13 |

TABLE XXXII-continued

| Pos | 123456789 | score |
|---|---|---|
| 185 | MLFSSVYMM | 13 |
| 218 | GKSHQHILL | 13 |
| 233 | GMYKMDFII | 13 |
| 34 | ERTYLPVCH | 12 |
| 59 | PQLFESLNF | 12 |
| 71 | FKYEASFYL | 12 |
| 77 | FYLRRVIRV | 12 |
| 79 | LRRVIRVLS | 12 |
| 83 | IRVLSICTT | 12 |
| 91 | TCLLGMLQV | 12 |
| 104 | PSISWLVRF | 12 |
| 111 | RFKWKSTIF | 12 |
| 122 | HLFSWSLSF | 12 |
| 151 | LHVSKYCSL | 12 |
| 158 | SLFPINSII | 12 |
| 161 | PINSIIRGL | 12 |
| 178 | DVFLKQIML | 12 |
| 184 | IMLFSSVYM | 12 |
| 224 | ILLPVSFSV | 12 |
| 239 | FIISTSSTL | 12 |

V2A-B2709-9mers:251P5G2
Each peptide is a portion of SEQ ID NO: 5; each start position is specified, the length of peptide is 9 amino acids, and the end position for each peptide is the start position plus eight.

| Pos | 123456789 | score |
|---|---|---|
| 3 | ASQPTLCSF | 10 |
| 4 | SQPTLCSFF | 8 |

V3A-B2709-9mers:251P5G2
Each peptide is a portion of SEQ ID NO: 7; each start position is specified, the length of peptide is 9 amino acids, and the end position for each peptide is the start position plus eight.

| Pos | 123456789 | score |
|---|---|---|
| 4 | RRVIRDLSI | 24 |
| 3 | LRRVIRDLS | 11 |
| 7 | IRDLSICTT | 11 |

TABLE XXXII-continued

V4A-HLA-B2709-9mers:251P5G2
Each peptide is a portion of SEQ ID NO: 9; each start position is specified, the length of peptide is 9 amino acids, and the end position for each peptide is the start position plus eight.

| Pos | 123456789 | score |
|---|---|---|
| 5 | TCLLDMLQV | 13 |
| 2 | ICTTCLLDM | 11 |
| 3 | CTTCLLDML | 11 |
| 8 | LDMLQVVNI | 11 |
| 6 | CLLDMLQVV | 10 |

V12A-HLA-B2709-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 4 | PSISWLIML | 12 |
| 2 | ISPSISWLI | 11 |
| 3 | SPSISWLIM | 9 |
| 8 | WLIMLFSSV | 9 |
| 5 | SISWLIMLF | 8 |

V12B-B2709-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 581 | GRTALILAV | 23 |
| 161 | TRAFQVVHL | 22 |
| 315 | ARLSGLNSI | 22 |
| 62 | ARKEFSTTL | 21 |
| 217 | LRYRSGPSV | 21 |
| 411 | VRREDLDKL | 21 |
| 429 | PRKDLIVML | 21 |
| 482 | KRTALIKAV | 21 |
| 1003 | GRRCPMFDV | 21 |
| 470 | DRRCQLNVL | 20 |
| 578 | DRYGRTALI | 20 |
| 701 | SRKPENQQF | 20 |
| 1029 | FRDKDDLPF | 20 |
| 420 | HRAAWWGKV | 18 |

TABLE XXXII-continued

| Pos | 123456789 | score |
|---|---|---|
| 86 | GSLPAFADL | 16 |
| 121 | RRLEVPRPQ | 16 |
| 149 | RRDAACLRA | 16 |
| 579 | RYGRTALIL | 16 |
| 592 | GSASIVNLL | 16 |
| 779 | REEIAKLRL | 16 |
| 946 | RASPGTPSL | 16 |
| 288 | RHIPEILKF | 15 |
| 327 | HEFEELVKL | 15 |
| 471 | RRCQLNVLD | 15 |
| 1004 | RRCPMFDVS | 15 |
| 11 | ATFAAATGL | 14 |
| 117 | RVVQRRLEV | 14 |
| 197 | GLEAASANL | 14 |
| 210 | GRSSSCALR | 14 |
| 238 | QRLLFLPRA | 14 |
| 279 | PNLSYPLVL | 14 |
| 302 | GGGILGLEL | 14 |
| 397 | GDYDDSAFM | 14 |
| 408 | RYHVRREDL | 14 |
| 412 | RREDLDKLH | 14 |
| 445 | RDKQKRTAL | 14 |
| 447 | KQKRTALHL | 14 |
| 449 | KRTALHLAS | 14 |
| 459 | NGNSEVVQL | 14 |
| 460 | GNSEVVQLL | 14 |
| 528 | KLMAKALLL | 14 |
| 548 | GLTPLLLGV | 14 |
| 654 | TILNIKLPL | 14 |
| 670 | KHGSNPVGL | 14 |
| 832 | GFSLRQLGL | 14 |
| 872 | GFSLRQLGL | 14 |
| 949 | PGTPSLVRL | 14 |
| 974 | GRSPTKQKS | 14 |
| 988 | GWILPVPTF | 14 |
| 1009 | FDVSPAMRL | 14 |
| 1030 | RDKDDLPFF | 14 |
| 1051 | GQDDRAGVL | 14 |

TABLE XXXII-continued

| Pos | 123456789 | score |
|---|---|---|
| 76 | LSLSSSRAL | 13 |
| 120 | QRRLEVPRP | 13 |
| 187 | YRLTHVRCA | 13 |
| 232 | AEPPAHQRL | 13 |
| 244 | PRAPQAVSG | 13 |
| 273 | HLIQCIPNL | 13 |
| 426 | GKVPRKDLI | 13 |
| 467 | LLLDRRCQL | 13 |
| 515 | GNTALHYAI | 13 |
| 546 | KCGLTPLLL | 13 |
| 614 | GQTAREYAV | 13 |
| 755 | KEMNSELSL | 13 |
| 799 | RENKILEEI | 13 |
| 812 | EKLLKTIQL | 13 |
| 916 | IGDPGGVPL | 13 |
| 932 | GDQGPGTHL | 13 |
| 955 | VRLASGARA | 13 |
| 994 | PTFSSGSFL | 13 |
| 1015 | MRLKSDSNR | 13 |
| 1027 | QAFRDKDDL | 13 |
| 5 | ILLPTQATF | 12 |
| 15 | AATGLWAAL | 12 |
| 37 | WRKEPAVLP | 12 |
| 41 | PAVLPCCNL | 12 |
| 47 | CNLEKGSWL | 12 |
| 68 | TTLTGHSAL | 12 |
| 70 | LTGHSALSL | 12 |
| 104 | SATPAGAFL | 12 |
| 105 | ATPAGAFLL | 12 |
| 110 | AFLLGWERV | 12 |
| 126 | PRPQAAPAT | 12 |
| 139 | SRDPSPPCH | 12 |
| 147 | HQRRDAACL | 12 |
| 152 | AACLRAQGL | 12 |
| 156 | RAQGLTRAF | 12 |
| 158 | QGLTRAFQV | 12 |
| 159 | GLTRAFQVV | 12 |
| 181 | PPSRNSYRL | 12 |
| 183 | SRNSYRLTH | 12 |

TABLE XXXII-continued

| Pos | 123456789 | score |
|---|---|---|
| 184 | RNSYRLTHV | 12 |
| 190 | THVRCAQGL | 12 |
| 264 | VGSLSVFQL | 12 |
| 309 | ELPATAARL | 12 |
| 316 | RLSGLNSIM | 12 |
| 330 | EELVKLHSL | 12 |
| 364 | GYGHSFLIM | 12 |
| 407 | PRYHVRRED | 12 |
| 444 | KRDKQKRTA | 12 |
| 493 | QEDECVLML | 12 |
| 527 | DKLMAKALL | 12 |
| 544 | KNKCGLTPL | 12 |
| 566 | FLIKKKANL | 12 |
| 569 | KKKANLNAL | 12 |
| 591 | CGSASIVNL | 12 |
| 617 | AREYAVSSH | 12 |
| 634 | SDYKEKQML | 12 |
| 674 | NPVGLPENL | 12 |
| 698 | QRKSRKPEN | 12 |
| 735 | TGISQDEIL | 12 |
| 770 | DLLRENSML | 12 |
| 772 | LRENSMLRE | 12 |
| 778 | LREEIAKLR | 12 |
| 785 | LRLELDETK | 12 |
| 790 | DETKHQNQL | 12 |
| 796 | NQLRENKIL | 12 |
| 802 | KILEEIESV | 12 |
| 827 | KTKVAGFSL | 12 |
| 843 | HAQASVQQL | 12 |
| 883 | HAQASVQQL | 12 |
| 942 | PREPRASPG | 12 |
| 958 | ASGARAAAL | 12 |
| 961 | ARAAALPPP | 12 |
| 975 | RSPTKQKSV | 12 |
| 1076 | HRNADTPPH | 12 |
| 18 | GLWAALTTV | 11 |
| 30 | SRADPVTWR | 11 |
| 115 | WERVVQRRL | 11 |

TABLE XXXII-continued

| Pos | 123456789 | score |
|---|---|---|
| 116 | ERVVQRRLE | 11 |
| 148 | QRRDAACLR | 11 |
| 155 | LRAQGLTRA | 11 |
| 192 | VRCAQGLEA | 11 |
| 209 | PGRSSSCAL | 11 |
| 219 | YRSGPSVSS | 11 |
| 235 | PAHQRLLFL | 11 |
| 254 | QEQPSEEAL | 11 |
| 259 | EEALGVGSL | 11 |
| 266 | SLSVFQLHL | 11 |
| 277 | CIPNLSYPL | 11 |
| 285 | LVLRHIPEI | 11 |
| 286 | VLRHIPEIL | 11 |
| 300 | ETGGGILGL | 11 |
| 312 | ATAARLSGL | 11 |
| 318 | SGLNSIMQI | 11 |
| 324 | MQIKEFEEL | 11 |
| 334 | KLHSLSHKV | 11 |
| 345 | CVFAKKKNV | 11 |
| 351 | KNVDKWDDF | 11 |
| 353 | VDKWDDFCL | 11 |
| 427 | KVPRKDLIV | 11 |
| 437 | LRDTDMNKR | 11 |
| 461 | NSEVVQLLL | 11 |
| 491 | QCQEDECVL | 11 |
| 521 | YAIYNEDKL | 11 |
| 522 | AIYNEDKLM | 11 |
| 526 | EDKLMAKAL | 11 |
| 533 | ALLLYGADI | 11 |
| 541 | IESKNKCGL | 11 |
| 545 | NKCGLTPLL | 11 |
| 555 | GVHEQKQEV | 11 |
| 559 | QKQEVVKFL | 11 |
| 593 | SASIVNLLL | 11 |
| 597 | VNLLLEQNV | 11 |
| 599 | LLLEQNVDV | 11 |
| 625 | HHHVICELL | 11 |
| 648 | NSNPVITIL | 11 |
| 650 | NPVITILNI | 11 |

TABLE XXXII-continued

| Pos | 123456789 | score |
|---|---|---|
| 652 | VITILNIKL | 11 |
| 721 | EQNDTQKQL | 11 |
| 742 | ILTNKQKQI | 11 |
| 753 | AEKEMNSEL | 11 |
| 781 | EIAKLRLEL | 11 |
| 798 | LRENKILEE | 11 |
| 806 | EIESVKEKL | 11 |
| 807 | IESVKEKLL | 11 |
| 830 | VAGFSLRQL | 11 |
| 835 | LRQLGLAQH | 11 |
| 870 | VAGFSLRQL | 11 |
| 875 | LRQLGLAQH | 11 |
| 912 | LRSQIGDPG | 11 |
| 945 | PRASPGTPS | 11 |
| 983 | VCDSSGWIL | 11 |
| 1007 | PMFDVSPAM | 11 |
| 1044 | PRHTKDLGQ | 11 |
| 1060 | APKCRPGTL | 11 |
| 1084 | HRHTTTLPH | 11 |
| 1106 | AGGVGPTTL | 11 |

TABLE XXXIII

| Pos | 123456789 | score |
|---|---|---|
| V1A-HLA-B4402-9mers:251P5G2 Each peptide is a portion of SEQ ID NO: 3; each start position is specified, the length of peptide is 9 amino acids, and the end position for each peptide is the start position plus eight. | | |
| 21 | ASSPFLLFL | 19 |
| 44 | ALIHMVVLL | 19 |
| 101 | NISPSISWL | 18 |
| 10 | ASQPTLFSF | 17 |
| 116 | STIFTFHLF | 17 |
| 23 | SPFLLFLDL | 16 |
| 75 | ASFYLRRVI | 16 |
| 78 | YLRRVIRVL | 16 |
| 163 | NSIIRGLFF | 16 |
| 197 | QELQEILVP | 16 |

TABLE XXXIII-continued

| Pos | 123456789 | score |
|---|---|---|
| 200 | QEILVPSQP | 16 |
| 207 | QPQPLPKDL | 16 |
| 222 | QHILLPVSF | 16 |
| 20 | SASSPFLLF | 15 |
| 54 | MVFLSPQLF | 15 |
| 63 | ESLNFQNDF | 15 |
| 86 | LSICTTCLL | 15 |
| 104 | PSISWLVRF | 15 |
| 113 | KWKSTIFTF | 15 |
| 128 | LSFPVSSSL | 15 |
| 158 | SLFPINSII | 15 |
| 161 | PINSIIRGL | 15 |
| 179 | VFLKQIMLF | 15 |
| 191 | YMMTLIQEL | 15 |
| 243 | TSSTLPWAY | 15 |
| 1 | MPFISKLVL | 14 |
| 11 | SQPTLFSFF | 14 |
| 29 | LDLRPERTY | 14 |
| 30 | DLRPERTYL | 14 |
| 37 | YLPVCHVAL | 14 |
| 62 | FESLNFQND | 14 |
| 65 | LNFQNDFKY | 14 |
| 100 | VNISPSISW | 14 |
| 162 | INSIIRGLF | 14 |
| 168 | GLFFTLSLF | 14 |
| 172 | TLSLFRDVF | 14 |
| 178 | DVFLKQIML | 14 |
| 239 | FIISTSSTL | 14 |
| 17 | SFFSASSPF | 13 |
| 33 | PERTYLPVC | 13 |
| 43 | VALIHMVVL | 13 |
| 48 | MVVLLTMVF | 13 |
| 49 | VVLLTMVFL | 13 |
| 69 | NDFKYEASF | 13 |
| 106 | ISWLVRFKW | 13 |
| 122 | HLFSWSLSF | 13 |
| 131 | PVSSSLIFY | 13 |
| 148 | QINLHVSKY | 13 |

TABLE XXXIII-continued

| Pos | 123456789 | score |
|---|---|---|
| 157 | CSLFPINSI | 13 |
| 165 | IIRGLFFTL | 13 |
| 167 | RGLFFTLSL | 13 |
| 173 | LSLFRDVFL | 13 |
| 176 | FRDVFLKQI | 13 |
| 183 | QIMLFSSVY | 13 |
| 218 | GKSHQHILL | 13 |
| 7 | LVLASQPTL | 12 |
| 8 | VLASQPTLF | 12 |
| 19 | FSASSPFLL | 12 |
| 57 | LSPQLFESL | 12 |
| 59 | PQLFESLNF | 12 |
| 85 | VLSICTTCL | 12 |
| 94 | LGMLQVVNI | 12 |
| 115 | KSTIFTFHL | 12 |
| 141 | VASSNVTQI | 12 |
| 143 | SSNVTQINL | 12 |
| 152 | HVSKYCSLF | 12 |
| 187 | FSSVYMMTL | 12 |
| 194 | TLIQELQEI | 12 |
| 203 | LVPSQPQPL | 12 |
| 227 | PVSFSVGMY | 12 |
| 241 | ISTSSTLPW | 12 |
| 18 | FFSASSPFL | 11 |
| 53 | TMVFLSPQL | 11 |
| 70 | DFKYEASFY | 11 |
| 73 | YEASFYLRR | 11 |
| 80 | RRVIRVLSI | 11 |
| 89 | CTTCLLGML | 11 |
| 110 | VRFKWKSTI | 11 |
| 118 | IFTFHLFSW | 11 |
| 120 | TFHLFSWSL | 11 |
| 129 | SFPVSSSLI | 11 |
| 130 | FPVSSSLIF | 11 |
| 217 | RGKSHQHIL | 11 |
| 231 | SVGMYKMDF | 11 |
| 38 | LPVCHVALI | 10 |
| 71 | FKYEASFYL | 10 |
| 98 | QVVNISPSI | 10 |

TABLE XXXIII-continued

| Pos | 123456789 | score |
|---|---|---|
| 111 | RFKWKSTIF | 10 |
| 151 | LHVSKYCSL | 10 |
| 154 | SKYCSLFPI | 10 |
| 188 | SSVYMMTLI | 10 |
| 195 | LIQELQEIL | 10 |
| 232 | VGMYKMDFI | 9 |

V2A-B4402-9mers:251P5G2
Each peptide is a portion of SEQ ID NO: 5; each start position is specified, the length of peptide is 9 amino acids, and the end position for each peptide is the start position plus eight.

| 3 | ASQPTLCSF | 17 |
| 4 | SQPTLCSFF | 13 |

V3A-HLA-B4402-9mers:251P5G2
Each peptide is a portion of SEQ ID NO: 7; each start position is specified, the length of peptide is 9 amino acids, and the end position for each peptide is the start position plus eight.

| 2 | YLRRVIRDL | 15 |
| 9 | DLSICTTCL | 12 |
| 4 | RRVIRDLSI | 10 |

V4A-HLA-B4402-9mers:251P5G2
Each peptide is a portion of SEQ ID NO: 9; each start position is specified, the length of peptide is 9 amino acids, and the end position for each peptide is the start position plus eight.

| 8 | LDMLQVVNI | 12 |
| 3 | CTTCLLDML | 11 |
| 1 | SICTTCLLD | 4 |
| 5 | TCLLDMLQV | 4 |
| 6 | CLLDMLQVV | 4 |

V12A-HLA-B4402-9mers:251P5G2
Each peptide is a portion of SEQ ID NO: 25; each start position is specified, the length of peptide is 9 amino acids, and the end position for each peptide is the start position plus eight.

| 1 | ISPSISWL | 16 |
| 5 | SISWLIMLF | 16 |

TABLE XXXIII-continued

| Pos | 123456789 | score |
|---|---|---|
| 4 | PSISWLIML | 15 |
| 9 | LIMLFSSVY | 13 |
| 2 | ISPSISWLI | 11 |

V12B-HLA-B4402-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 232 | AEPPAHQRL | 27 |
| 327 | KEFEELVKL | 26 |
| 254 | QEQPSEEAL | 25 |
| 330 | EELVKLHSL | 25 |
| 259 | EEALGVGSL | 24 |
| 755 | KEMNSELSL | 24 |
| 807 | IESVKEKLL | 24 |
| 493 | QEDECVLML | 23 |
| 753 | AEKEMNSEL | 23 |
| 49 | LEKGSWLSF | 22 |
| 541 | IESKNKCGL | 22 |
| 790 | DETKHQNQL | 22 |
| 115 | WERVVQRRL | 21 |
| 288 | RHIPEILKF | 21 |
| 362 | SEGYGHSFL | 21 |
| 779 | REEIAKLRL | 21 |
| 799 | RENKILEEI | 20 |
| 297 | SEKETGGGI | 19 |
| 321 | NSIMQIKEF | 19 |
| 502 | LEHGADGNI | 19 |
| 83 | ALPGSLPAF | 18 |
| 526 | EDKLMAKAL | 18 |
| 780 | EEIAKLRLE | 18 |
| 805 | EEIESVKEK | 18 |
| 123 | LEVPRPQAA | 17 |
| 300 | ETGGGILGL | 17 |
| 308 | LELPATAAR | 17 |
| 374 | ETSTKISGL | 17 |
| 648 | NSNPVITIL | 17 |
| 740 | DEILTNKQK | 17 |
| 812 | EKLLKTIQL | 17 |

TABLE XXXIII-continued

| Pos | 123456789 | score |
|---|---|---|
| 958 | ASGARAAAL | 17 |
| 11 | ATFAAATGL | 16 |
| 15 | AATGLWAAL | 16 |
| 64 | KEFSTTLTG | 16 |
| 105 | ATPAGAFLL | 16 |
| 152 | AACLRAQGL | 16 |
| 179 | GCPPSRNSY | 16 |
| 273 | HLIQCIPNL | 16 |
| 348 | AKKKNVDKW | 16 |
| 569 | KKKANLNAL | 16 |
| 572 | ANLNALDRY | 16 |
| 721 | EQNDTQKQL | 16 |
| 988 | GWILPVPTF | 16 |
| 1060 | APKCRPGTL | 16 |
| 5 | ILLPTQATF | 15 |
| 86 | GSLPAFADL | 15 |
| 156 | RAQGLTRAF | 15 |
| 233 | EPPAHQRLL | 15 |
| 291 | PEILKFSEK | 15 |
| 312 | ATAARLSGL | 15 |
| 318 | SGLNSIMQI | 15 |
| 429 | PRKDLIVML | 15 |
| 467 | LLLDRRCQL | 15 |
| 506 | ADGNIQDEY | 15 |
| 513 | EYGNTALHY | 15 |
| 521 | YAIYNEDKL | 15 |
| 528 | KLMAKALLL | 15 |
| 546 | KCGLTPLLL | 15 |
| 558 | EQKQEVVKF | 15 |
| 591 | CGSASIVNL | 15 |
| 647 | ENSNPVITI | 15 |
| 666 | EEIKKHGSN | 15 |
| 701 | SRKPENQQF | 15 |
| 768 | EEDLLRENS | 15 |
| 787 | LELDETKHQ | 15 |
| 796 | NQLRENKIL | 15 |
| 821 | NEEALTKTK | 15 |
| 916 | IGDPGGVPL | 15 |

TABLE XXXIII-continued

| Pos | 123456789 | score |
|---|---|---|
| 946 | RASPGTPSL | 15 |
| 949 | PGTPSLVRL | 15 |
| 1042 | QSPRHTKDL | 15 |
| 1051 | GQDDRAGVL | 15 |
| 1106 | AGGVGPTTL | 15 |
| 62 | ARKEFSTTL | 14 |
| 68 | TTLTGHSAL | 14 |
| 76 | LSLSSSRAL | 14 |
| 101 | SEQSATPAG | 14 |
| 103 | QSATPAGAF | 14 |
| 104 | SATPAGAFL | 14 |
| 264 | VGSLSVFQL | 14 |
| 279 | PNLSYPLVL | 14 |
| 299 | KETGGGILG | 14 |
| 309 | ELPATAARL | 14 |
| 315 | ARLSGLNSI | 14 |
| 324 | MQIKEFEEL | 14 |
| 384 | QEMGSGKSN | 14 |
| 388 | SGKSNVGTW | 14 |
| 416 | LDKLHRAAW | 14 |
| 447 | KQKRTALHL | 14 |
| 459 | NGNSEVVQL | 14 |
| 462 | SEVVQLLLD | 14 |
| 494 | EDECVLMLL | 14 |
| 512 | DEYGNTALH | 14 |
| 545 | NKCGLTPLL | 14 |
| 592 | GSASIVNLL | 14 |
| 593 | SASIVNLLL | 14 |
| 621 | AVSSHHHVI | 14 |
| 624 | SHHHVICEL | 14 |
| 637 | KEKQMLKIS | 14 |
| 646 | SENSNPVIT | 14 |
| 654 | TILNIKLPL | 14 |
| 670 | KHGSNPVGL | 14 |
| 731 | EEQNTGISQ | 14 |
| 759 | SELSLSHKK | 14 |
| 767 | KEEDLLREN | 14 |
| 777 | MLREEIAKL | 14 |
| 781 | EIAKLRLEL | 14 |
| 817 | TIQLNEEAL | 14 |
| 822 | EEALTKTKV | 14 |
| 832 | GFSLRQLGL | 14 |
| 865 | AQEQEVAGF | 14 |
| 872 | GFSLRQLGL | 14 |
| 29 | PSRADPVTW | 13 |
| 39 | KEPAVLPCC | 13 |
| 58 | PGTAARKEF | 13 |
| 181 | PPSRNSYRL | 13 |
| 198 | LEAASANLP | 13 |
| 211 | RSSSCALRY | 13 |
| 234 | PPAHQRLLF | 13 |
| 235 | PAHQRLLFL | 13 |
| 262 | LGVGSLSVF | 13 |
| 266 | SLSVFQLHL | 13 |
| 282 | SYPLVLRHI | 13 |
| 285 | LVLRHIPEI | 13 |
| 298 | EKETGGGIL | 13 |
| 335 | LHSLSHKVI | 13 |
| 339 | SHKVIQCVF | 13 |
| 396 | WGDYDDSAF | 13 |
| 405 | MEPRYHVRR | 13 |
| 413 | REDLDKLHR | 13 |
| 417 | DKLHRAAWW | 13 |
| 425 | WGKVPRKDL | 13 |
| 426 | GKVPRKDLI | 13 |
| 445 | RDKQKRTAL | 13 |
| 460 | GNSEVVQLL | 13 |
| 461 | NSEVVQLLL | 13 |
| 470 | DRRCQLNVL | 13 |
| 478 | LDNKKRTAL | 13 |
| 525 | NEDKLMAKA | 13 |
| 529 | LMAKALLLY | 13 |
| 533 | ALLLYGADI | 13 |
| 559 | QKQEVVKFL | 13 |
| 566 | FLIKKKANL | 13 |
| 577 | LDRYGRTAL | 13 |
| 579 | RYGRTALIL | 13 |

TABLE XXXIII-continued

| Pos | 123456789 | score |
|---|---|---|
| 630 | CELLSDYKE | 13 |
| 650 | NPVITILNI | 13 |
| 664 | VEEEIKKHG | 13 |
| 665 | EEEIKKHGS | 13 |
| 674 | NPVGLPENL | 13 |
| 679 | PENLTNGAS | 13 |
| 688 | AGNGDDGLI | 13 |
| 715 | EEYHSDEQN | 13 |
| 720 | DEQNDTQKQ | 13 |
| 730 | SEEQNTGIS | 13 |
| 735 | TGISQDEIL | 13 |
| 806 | EIESVKEKL | 13 |
| 830 | VAGFSLRQL | 13 |
| 858 | TEKTEQQAQ | 13 |
| 870 | VAGFSLRQL | 13 |
| 898 | TEKTEQQAQ | 13 |
| 906 | QEQGAALRS | 13 |
| 925 | SEGGTAAGD | 13 |
| 1021 | SNRETHQAF | 13 |
| 1027 | QAFRDKDDL | 13 |
| 1082 | PPHRHTTTL | 13 |

TABLE XXXIV

| Pos | 123456789 | score |
|---|---|---|
| | V1A-HLA-B5101-9mers:251P5G2 Each peptide is a portion of SEQ ID NO: 3; each start position is specified, the length of peptide is 9 amino acids, and the end position for each peptide is the start position plus eight. | |
| 38 | LPVCHVALI | 24 |
| 141 | VASSNVTQI | 24 |
| 247 | LPWAYDRGV | 24 |
| 1 | MPFISKLVL | 23 |
| 43 | VALIHMVVL | 23 |
| 74 | EASFYLRRV | 22 |
| 94 | LGMLQVVNI | 21 |
| 32 | RPERTYLPV | 20 |
| 23 | SPFLLFLDL | 19 |

TABLE XXXIV-continued

| Pos | 123456789 | score |
|---|---|---|
| 207 | QPQPLPKDL | 18 |
| 232 | VGMYKMDFI | 18 |
| 92 | CLLGMLQVV | 16 |
| 154 | SKYCSLFPI | 16 |
| 233 | GMYKMDFII | 16 |
| 35 | RTYLPVCHV | 15 |
| 75 | ASFYLRRVI | 15 |
| 77 | FYLRRVIRV | 15 |
| 78 | YLRRVIRVL | 15 |
| 103 | SPSISWLVR | 15 |
| 110 | VRFKWKSTI | 15 |
| 160 | FPINSIIRG | 15 |
| 167 | RGLFFTLSL | 15 |
| 7 | LVLASQPTL | 14 |
| 157 | CSLFPINSI | 14 |
| 209 | QPLPKDLCR | 14 |
| 211 | LPKDLCRGK | 14 |
| 224 | ILLPVSFSV | 14 |
| 9 | LASQPTLFS | 13 |
| 71 | FKYEASFYL | 13 |
| 80 | RRVIRVLSI | 13 |
| 130 | FPVSSSLIF | 13 |
| 171 | FTLSLFRDV | 13 |
| 176 | FRDVFLKQI | 13 |
| 178 | DVFLKQIML | 13 |
| 216 | CRGKSHQHI | 13 |
| 226 | LPVSFSVGM | 13 |
| 20 | SASSPFLLF | 12 |
| 91 | TCLLGMLQV | 12 |
| 129 | SFPVSSSLI | 12 |
| 145 | NVTQINLHV | 12 |
| 158 | SLFPINSII | 12 |
| 165 | IIRGLFFTL | 12 |
| 188 | SSVYMMTLI | 12 |
| 194 | TLIQELQEI | 12 |
| 217 | RGKSHQHIL | 12 |
| 30 | DLRPERTYL | 11 |
| 42 | HVALIHMVV | 11 |
| 49 | VVLLTMVFL | 11 |

TABLE XXXIV-continued

| Pos | 123456789 | score |
|---|---|---|
| 102 | ISPSISWLV | 11 |
| 128 | LSFPVSSSL | 11 |
| 133 | SSSLIFYTV | 11 |
| 173 | LSLFRDVFL | 11 |
| 196 | IQELQEILV | 11 |
| 204 | VPSQPQPLP | 11 |

V2A-B5101-9mers:251P5G2
Each peptide is a portion of SEQ ID NO: 5; each start position is specified, the length of peptide is 9 amino acids, and the end position for each peptide is the start position plus eight.

| Pos | 123456789 | score |
|---|---|---|
| 2 | LASQPTLCS | 13 |
| 5 | QPTLCSFFS | 10 |

V3A-HLA-B5101-9mers
Each peptide is a portion of SEQ ID NO: 7; each start position is specified, the length of peptide is 9 amino acids, and the end position for each peptide is the start position plus eight.

| Pos | 123456789 | score |
|---|---|---|
| 2 | YLRRVIRDL | 12 |
| 4 | RRVIRDLSI | 11 |
| 9 | DLSICTTCL | 11 |
| 1 | FYLRRVIRD | 7 |
| 7 | IRDLSICTT | 6 |

V4A-HLA-B5101-9mers:251P5G2
Each peptide is a portion of SEQ ID NO: 9; each start position is specified, the length of peptide is 9 amino acids, and the end position for each peptide is the start position plus eight.

| Pos | 123456789 | score |
|---|---|---|
| 6 | CLLDMLQVV | 16 |
| 8 | LDMLQVVNI | 15 |
| 5 | TCLLDMLQV | 12 |
| 9 | DMLQVVNIS | 11 |
| 3 | CTTCLLDML | 7 |

TABLE XXXIV-continued

V12A-HLA-B5101-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 2 | ISPSISWLI | 13 |
| 3 | SPSISWLIM | 12 |
| 8 | WLIMLFSSV | 9 |
| 4 | PSISWLIML | 8 |
| 9 | LIMLFSSVY | 5 |
| 6 | ISWLIMLFS | 4 |
| 7 | SWLIMLFSS | 4 |
| 5 | SISWLIMLF | 1 |

V12B-B5101-9mers:251P5G2
Each peptide is a portion of SEQ ID NO: 25; each start position is specified, the length of peptide is 9 amino acids, and the end position for each peptide is the start position plus eight.

| Pos | 123456789 | score |
|---|---|---|
| 660 | LPLKVEEEI | 27 |
| 650 | NPVITILNI | 24 |
| 256 | QPSEEALGV | 22 |
| 457 | SANGNSEVV | 22 |
| 620 | YAVSSHHHV | 22 |
| 278 | IPNLSYPLV | 21 |
| 363 | EGYGHSFLI | 21 |
| 318 | SGLNSIMQI | 20 |
| 521 | YAIYNEDKL | 20 |
| 593 | SASIVNLLL | 20 |
| 830 | VAGFSLRQL | 20 |
| 840 | LAQHAQASV | 20 |
| 843 | HAQASVQQL | 20 |
| 870 | VAGFSLRQL | 20 |
| 880 | LAQHAQASV | 20 |
| 883 | HAQASVQQL | 20 |
| 233 | EPPAHQRLL | 19 |
| 578 | DRYGRTALI | 19 |
| 674 | NPVGLPENL | 19 |
| 918 | DPGGVPLSE | 19 |
| 1060 | APKCRPGTL | 19 |

TABLE XXXIV-continued

| Pos | 123456789 | score |
|---|---|---|
| 1082 | PPHRHTTTL | 19 |
| 158 | QGLTRAFQV | 18 |
| 235 | PAHQRLLFL | 18 |
| 371 | IMKETSTKI | 18 |
| 823 | EALTKTKVA | 18 |
| 904 | QAQEQGAAL | 18 |
| 15 | AATGLWAAL | 17 |
| 152 | AACLRAQGL | 17 |
| 181 | PPSRNSYRL | 17 |
| 335 | LHSLSHKVI | 17 |
| 428 | VPRKDLIVM | 17 |
| 688 | AGNGDDGLI | 17 |
| 908 | QGAALRSQI | 17 |
| 1027 | QAFRDKDDL | 17 |
| 1050 | LGQDDRAGV | 17 |
| 1112 | TTLGSNREI | 17 |
| 21 | AALTTVSNP | 16 |
| 33 | DPVTWRKEP | 16 |
| 41 | PAVLPCCNL | 16 |
| 57 | FPGTAARKE | 16 |
| 104 | SATPAGAFL | 16 |
| 111 | FLLGWERVV | 16 |
| 243 | LPRAPQAVS | 16 |
| 264 | VGSLSVFQL | 16 |
| 282 | SYPLVLRHI | 16 |
| 459 | NGNSEVVQL | 16 |
| 484 | TALIKAVQC | 16 |
| 517 | TALHYAIYN | 16 |
| 591 | CGSASIVNL | 16 |
| 599 | LLLEQNVDV | 16 |
| 616 | TAREYAVSS | 16 |
| 636 | YKEKQMLKI | 16 |
| 687 | SAGNGDDGL | 16 |
| 696 | IPQRKSRKP | 16 |
| 729 | LSEEQNTGI | 16 |
| 810 | VKEKLLKTI | 16 |
| 946 | RASPGTPSL | 16 |
| 949 | PGTPSLVRL | 16 |

TABLE XXXIV-continued

| Pos | 123456789 | score |
|---|---|---|
| 1106 | AGGVGPTTL | 16 |
| 44 | LPCCNLEKG | 15 |
| 130 | AAPATSATP | 15 |
| 162 | RAFQVVHLA | 15 |
| 169 | LAPTAPDGG | 15 |
| 217 | LRYRSGPSV | 15 |
| 260 | EALGVGSLS | 15 |
| 285 | LVLRHIPEI | 15 |
| 306 | LGLELPATA | 15 |
| 310 | LPATAARLS | 15 |
| 347 | FAKKKNVDK | 15 |
| 470 | DRRCQLNVL | 15 |
| 479 | DNKKRTALI | 15 |
| 550 | TPLLLGVHE | 15 |
| 575 | NALDRYGRT | 15 |
| 583 | TALILAVCC | 15 |
| 645 | SSENSNPVI | 15 |
| 647 | ENSNPVITI | 15 |
| 656 | LNIKLPLKV | 15 |
| 693 | DGLIPQRKS | 15 |
| 916 | IGDPGGVPL | 15 |
| 922 | VPLSEGGTA | 15 |
| 940 | LPPREPRAS | 15 |
| 944 | EPRASPGTP | 15 |
| 948 | SPGTPSLVR | 15 |
| 966 | LPPPTGKNG | 15 |
| 985 | DSSGWILPV | 15 |
| 1081 | TPPHRHTTT | 15 |
| 1090 | LPHRDTTTS | 15 |
| 1105 | SAGGVGPTT | 15 |
| 13 | FAAATGLWA | 14 |
| 18 | GLWAALTTV | 14 |
| 28 | NPSRADPVT | 14 |
| 61 | AARKEFSTT | 14 |
| 89 | PAFADLPRS | 14 |
| 106 | TPAGAFLLG | 14 |
| 113 | LGWERVVQR | 14 |
| 127 | RPQAAPATS | 14 |
| 131 | APATSATPS | 14 |

TABLE XXXIV-continued

| Pos | 123456789 | score |
|-----|-----------|-------|
| 141 | DPSPPCHQR | 14 |
| 151 | DAACLRAQG | 14 |
| 205 | LPGAPGRSS | 14 |
| 230 | SPAEPPAHQ | 14 |
| 262 | LGVGSLSVF | 14 |
| 270 | FQLHLIQCI | 14 |
| 279 | PNLSYPLVL | 14 |
| 283 | YPLVLRHIP | 14 |
| 315 | ARLSGLNSI | 14 |
| 338 | LSHKVIQCV | 14 |
| 406 | EPRYHVRRE | 14 |
| 421 | RAAWWGKVP | 14 |
| 451 | TALHLASAN | 14 |
| 455 | LASANGNSE | 14 |
| 530 | MAKALLLYG | 14 |
| 742 | ILTNKQKQI | 14 |
| 910 | AALRSQIGD | 14 |
| 951 | TPSLVRLAS | 14 |
| 964 | AALPPPTGK | 14 |
| 968 | PPTGKNGRS | 14 |
| 976 | SPTKQKSVC | 14 |
| 991 | LPVPTFSSG | 14 |
| 1035 | LPFFKTQQS | 14 |
| 1059 | LAPKCRPGT | 14 |
| 1078 | NADTPPHRH | 14 |
| 1099 | LPHFHVSAG | 14 |
| 10 | QATFAAATG | 13 |
| 17 | TGLWAALTT | 13 |
| 31 | RADPVTWRK | 13 |
| 82 | RALPGSLPA | 13 |
| 84 | LPGSLPAFA | 13 |
| 88 | LPAFADLPR | 13 |
| 94 | LPRSCPESE | 13 |
| 107 | PAGAFLLGW | 13 |
| 143 | SPPCHQRRD | 13 |
| 172 | TAPDGGAGC | 13 |
| 209 | PGRSSSCAL | 13 |
| 215 | CALRYRSGP | 13 |

TABLE XXXIV-continued

| Pos | 123456789 | score |
|-----|-----------|-------|
| 245 | RAPQAVSGP | 13 |
| 246 | APQAVSGPQ | 13 |
| 252 | GPQEQPSEE | 13 |
| 267 | LSVFQLHLI | 13 |
| 297 | SEKETGGGI | 13 |
| 302 | GGGILGLEL | 13 |
| 327 | KEFEELVKL | 13 |
| 386 | MGSGKSNVG | 13 |
| 402 | SAFMEPRYH | 13 |
| 425 | WGKVPRKDL | 13 |
| 502 | LEHGADGNI | 13 |
| 533 | ALLLYGADI | 13 |
| 556 | VHEQKQEVV | 13 |
| 559 | QKQEVVKFL | 13 |
| 621 | AVSSHHHVI | 13 |
| 644 | ISSENSNPV | 13 |
| 676 | VGLPENLTN | 13 |
| 678 | LPENLTNGA | 13 |
| 709 | FPDTENEEY | 13 |
| 735 | TGISQDEIL | 13 |
| 752 | VAEKEMNSE | 13 |
| 770 | DLLRENSML | 13 |
| 782 | IAKLRLELD | 13 |
| 795 | QNQLRENKI | 13 |
| 802 | KILEEIESV | 13 |
| 864 | QAQEQEVAG | 13 |
| 957 | LASGARAAA | 13 |
| 960 | GARAAALPP | 13 |
| 963 | AAALPPPTG | 13 |
| 967 | PPPTGKNGR | 13 |
| 1055 | RAGVLAPKC | 13 |
| 1064 | PPGTLCHTD | 13 |
| 1073 | TPPHRNADT | 13 |
| 1074 | PPHRNADTP | 13 |

TABLE XXXV

| Pos | 1234567890 | score |
|---|---|---|
| | V1A-HLA-A0201-10mers:251P5G2 Each peptide is a portion of SEQ ID NO: 3; each start position is specified, the length of peptide is 10 amino acids, and the end position for each peptide is the start position plus nine. | |
| 37 | YLPVCHVALI | 26 |
| 93 | LLGMLQVVNI | 26 |
| 56 | FLSPQLFESL | 25 |
| 6 | KLVLASQPTL | 24 |
| 164 | SIIRGLFFTL | 24 |
| 202 | ILVPSQPQPL | 24 |
| 43 | VALIHMVVLL | 23 |
| 44 | ALIHMVVLLT | 23 |
| 127 | SLSFPVSSSL | 23 |
| 150 | NLHVSKYCSL | 22 |
| 172 | TLSLFRDVFL | 22 |
| 194 | TLIQELQEIL | 22 |
| 195 | LIQELQEILV | 22 |
| 223 | HILLPVSFSV | 22 |
| 20 | SASSPFLLFL | 21 |
| 45 | LIHMVVLLTM | 21 |
| 85 | VLSICTTCLL | 21 |
| 135 | SLIFYTVASS | 21 |
| 246 | TLPWAYDRGV | 21 |
| 87 | SICTTCLLGM | 20 |
| 101 | NISPSISWLV | 20 |
| 184 | IMLFSSVYMM | 20 |
| 193 | MTLIQELQEI | 20 |
| 82 | VIRVLSICTT | 19 |
| 225 | LLPVSFSVGM | 19 |
| 42 | HVALIHMVVL | 18 |
| 52 | LTMVFLSPQL | 18 |
| 73 | YEASFYLRRV | 18 |
| 119 | FTFHLFSWSL | 18 |
| 140 | TVASSNVTQI | 18 |
| 160 | FPINSIIRGL | 18 |
| 190 | VYMMTLIQEL | 18 |
| 3 | FISKLVLASQ | 17 |
| 36 | TYLPVCHVAL | 17 |

TABLE XXXV-continued

| Pos | 1234567890 | score |
|---|---|---|
| 46 | IHMVVLLTMV | 17 |
| 76 | SFYLRRVIRV | 17 |
| 77 | FYLRRVIRVL | 17 |
| 79 | LRRVIRVLSI | 17 |
| 100 | VNISPSISWL | 17 |
| 156 | YCSLFPINSI | 17 |
| 25 | FLLFLDLRPE | 16 |
| 26 | LLFLDLRPER | 16 |
| 40 | VCHVALIHMV | 16 |
| 48 | MVVLLTMVFL | 16 |
| 50 | VLLTMVFLSP | 16 |
| 84 | RVLSICTTCL | 16 |
| 91 | TCLLGMLQVV | 16 |
| 92 | CLLGMLQVVN | 16 |
| 174 | SLFRDVFLKQ | 16 |
| 180 | FLKQIMLFSS | 16 |
| 198 | ELQEILVPSQ | 16 |
| 219 | KSHQHILLPV | 16 |
| 224 | ILLPVSFSVG | 16 |
| 14 | TLFSFFSASS | 15 |
| 31 | LRPERTYLPV | 15 |
| 51 | LLTMVFLSPQ | 15 |
| 88 | ICTTCLLGML | 15 |
| 90 | TTCLLGMLQV | 15 |
| 108 | WLVRFKWKST | 15 |
| 109 | LVRFKWKSTI | 15 |
| 117 | TIFTFHLFSW | 15 |
| 122 | HLFSWSLSFP | 15 |
| 158 | SLFPINSIIR | 15 |
| 166 | IRGLFFTLSL | 15 |
| 183 | QIMLFSSVYM | 15 |
| 185 | MLFSSVYMMT | 15 |
| 8 | VLASQPTLFS | 14 |
| 17 | SFFSASSPFL | 14 |
| 29 | LDLRPERTYL | 14 |
| 64 | SLNFQNDFKY | 14 |
| 78 | YLRRVIRVLS | 14 |
| 96 | MLQVVNISPS | 14 |

TABLE XXXV-continued

| Pos | 1234567890 | score |
|---|---|---|
| 132 | VSSSLIFYTV | 14 |
| 175 | LFRDVFLKQI | 14 |
| 181 | LKQIMLFSSV | 14 |
| 186 | LFSSVYMMTL | 14 |
| 231 | SVGMYKMDFI | 14 |
| 28 | FLDLRPERTY | 13 |
| 60 | QLFESLNFQN | 13 |
| 95 | GMLQVVNISP | 13 |
| 97 | LQVVNISPSI | 13 |
| 128 | LSFPVSSSLI | 13 |
| 137 | IFYTVASSNV | 13 |
| 144 | SNVTQINLHV | 13 |
| 238 | DFIISTSSTL | 13 |
| 9 | LASQPTLFSF | 12 |
| 22 | SSPFLLFLDL | 12 |
| 30 | DLRPERTYLP | 12 |
| 105 | SISWLVRFKW | 12 |
| 123 | LFSWSLSFPV | 12 |
| 136 | LIFYTVASSN | 12 |
| 142 | ASSNVTQINL | 12 |
| 165 | IIRGLFFTLS | 12 |
| 168 | GLFFTLSLFR | 12 |
| 215 | LCRGKSHQHI | 12 |

V2A-A0201-10mers:251P5G2
Each peptide is a portion of SEQ ID NO: 5; each start position is specified, the length of peptide is 10 amino acids, and the end position for each peptide is the start position plus nine.

| Pos | 1234567890 | score |
|---|---|---|
| 2 | VLASQPTLCS | 14 |
| 8 | TLCSFFSASS | 14 |
| 3 | LASQPTLCSF | 12 |
| 1 | LVLASQPTLC | 8 |

V3A-A0201-10mers:251P5G2
Each peptide is a portion of SEQ ID NO: 7; each start position is specified, the length of peptide is 10 amino acids, and the end position for each peptide is the start position plus nine.

| Pos | 1234567890 | score |
|---|---|---|
| 7 | VIRDLSICTT | 20 |
| 10 | DLSICTTCLL | 19 |

TABLE XXXV-continued

| Pos | 1234567890 | score |
|---|---|---|
| 2 | FYLRRVIRDL | 17 |
| 4 | LRRVIRDLSI | 13 |
| 3 | YLRRVIRDLS | 12 |
| 9 | RDLSICTTCL | 12 |
| 6 | RVIRDLSICT | 10 |

V4A-A0201-10mers:251P5G2
Each peptide is a portion of SEQ ID NO: 9; each start position is specified, the length of peptide is 10 amino acids, and the end position for each peptide is the start position plus nine.

| Pos | 1234567890 | score |
|---|---|---|
| 8 | LLDMLQVVNI | 26 |
| 2 | SICTTCLLDM | 19 |
| 6 | TCLLDMLQVV | 16 |
| 3 | ICTTCLLDML | 15 |
| 5 | TTCLLDMLQV | 15 |
| 7 | CLLDMLQVVN | 15 |

V12A-HLA-A0201-9mers:251P5G2
Each peptide is a portion of SEQ ID NO: 25; each start position is specified, the length of peptide is 10 amino acids, and the end position for each peptide is the start position plus nine.

| Pos | 1234567890 | score |
|---|---|---|
| 2 | NISPSISWLI | 18 |
| 10 | LIMLFSSVYM | 17 |
| 4 | SPSISWLIML | 16 |
| 8 | SWLIMLFSSV | 16 |
| 9 | WLIMLFSSVY | 12 |
| 6 | SISWLIMLFS | 11 |
| 7 |ISWLIMLFSS | 9 |

V12B-HLA-A0201-10mers:251P5G2
Each peptide is a portion of SEQ ID NO: 25; each start position is specified, the length of peptide is 10 amino acids, and the end position for each peptide is the start position plus nine.

| Pos | 1234567890 | score |
|---|---|---|
| 777 | SMLREEIAKL | 30 |
| 840 | GLAQHAQASV | 27 |
| 880 | GLAQHAQASV | 27 |
| 338 | SLSHKVIQCV | 26 |
| 656 | ILNIKLPLKV | 26 |

TABLE XXXV-continued

| Pos | 1234567890 | score |
|---|---|---|
| 267 | SLSVFQLHLI | 25 |
| 70 | TLTGHSALSL | 24 |
| 217 | ALRYRSGPSV | 24 |
| 599 | NLLLEQNVDV | 24 |
| 76 | ALSLSSSRAL | 23 |
| 305 | GILGLELPAT | 23 |
| 469 | LLDRRCQLNV | 23 |
| 577 | ALDRYGRTAL | 23 |
| 820 | QLNEEALTKT | 23 |
| 830 | KVAGFSLRQL | 23 |
| 161 | LTRAFQVVHL | 22 |
| 285 | PLVLRHIPEI | 22 |
| 324 | IMQIKEFEEL | 22 |
| 467 | QLLLDRRCQL | 22 |
| 478 | VLDNKKRTAL | 22 |
| 763 | SLSHKKEEDL | 22 |
| 1050 | DLGQDDRAGV | 22 |
| 15 | AAATGLWAAL | 21 |
| 315 | AARLSGLNSI | 21 |
| 371 | LIMKETSTKI | 21 |
| 536 | LLYGADIESK | 21 |
| 660 | KLPLKVEEEI | 21 |
| 729 | QLSEEQNTGI | 21 |
| 916 | QIGDPGGVPL | 21 |
| 958 | LASGARAAAL | 21 |
| 1059 | VLAPKCRPGT | 21 |
| 6 | ILLPTQATFA | 20 |
| 84 | ALPGSLPAFA | 20 |
| 306 | ILGLELPATA | 20 |
| 411 | HVRREDLDKL | 20 |
| 600 | LLLEQNVDVS | 20 |
| 644 | KISSENSNPV | 20 |
| 810 | SVKEKLLKTI | 20 |
| 1106 | SAGGVGPTTL | 20 |
| 264 | GVGSLSVFQL | 19 |
| 273 | LHLIQCIPNL | 19 |
| 278 | CIPNLSYPLV | 19 |
| 502 | LLEHGADGNI | 19 |
| 654 | ITILNIKLPL | 19 |

TABLE XXXV-continued

| Pos | 1234567890 | score |
|---|---|---|
| 678 | GLPENLTNGA | 19 |
| 744 | LTNKQKQIEV | 19 |
| 798 | QLRENKILEE | 19 |
| 870 | EVAGFSLRQL | 19 |
| 957 | RLASGARAAA | 19 |
| 18 | TGLWAALTTV | 18 |
| 36 | VTWRKEPAVL | 18 |
| 62 | AARKEFSTTL | 18 |
| 113 | LLGWERVVQR | 18 |
| 155 | CLRAQGLTRA | 18 |
| 241 | LLFLPRAPQA | 18 |
| 261 | EALGVGSLSV | 18 |
| 286 | LVLRHIPEIL | 18 |
| 300 | KETGGGILGL | 18 |
| 309 | LELPATAARL | 18 |
| 327 | IKEFEELVKL | 18 |
| 335 | KLHSLSHKVI | 18 |
| 403 | SAFMEPRYHV | 18 |
| 456 | LASANGNSEV | 18 |
| 459 | ANGNSEVVQL | 18 |
| 548 | CGLTPLLLGV | 18 |
| 553 | LLLGVHEQKQ | 18 |
| 581 | YGRTALILAV | 18 |
| 586 | LILAVCCGSA | 18 |
| 588 | LAVCCGSASI | 18 |
| 624 | SSHHHVICEL | 18 |
| 802 | NKILEEIESV | 18 |
| 815 | LLKTIQLNEE | 18 |
| 817 | KTIQLNEEAL | 18 |
| 825 | ALTKTKVAGF | 18 |
| 835 | SLRQLGLAQH | 18 |
| 875 | SLRQLGLAQH | 18 |
| 949 | SPGTPSLVRL | 18 |
| 1060 | LAPKCRPGTL | 18 |
| 7 | LLPTQATFAA | 17 |
| 44 | VLPCCNLEKG | 17 |
| 105 | SATPAGAFLL | 17 |
| 112 | FLLGWERVVQ | 17 |

TABLE XXXV-continued

| Pos | 1234567890 | score |
|---|---|---|
| 184 | SRNSYRLTHV | 17 |
| 190 | LTHVRCAQGL | 17 |
| 242 | LFLPRAPQAV | 17 |
| 259 | SEEALGVGSL | 17 |
| 282 | LSYPLVLRHI | 17 |
| 330 | FEELVKLHSL | 17 |
| 429 | VPRKDLIVML | 17 |
| 470 | LDRRCQLNVL | 17 |
| 529 | KLMAKALLLY | 17 |
| 530 | LMAKALLLYG | 17 |
| 533 | KALLLYGADI | 17 |
| 541 | DIESKNKCGL | 17 |
| 544 | SKNKCGLTPL | 17 |
| 556 | GVHEQKQEVV | 17 |
| 569 | IKKKANLNAL | 17 |
| 597 | IVNLLLEQNV | 17 |
| 647 | SENSNPVITI | 17 |
| 687 | ASAGNGDDGL | 17 |
| 804 | ILEEIESVKE | 17 |
| 983 | SVCDSSGWIL | 17 |
| 1099 | SLPHFHVSAG | 17 |
| 14 | FAAATGLWAA | 16 |
| 68 | STTLTGHSAL | 16 |
| 110 | GAFLLGWERV | 16 |
| 152 | DAACLRAQGL | 16 |
| 197 | QGLEAASANL | 16 |
| 262 | ALGVGSLSVF | 16 |
| 334 | VKLHSLSHKV | 16 |
| 490 | AVQCQEDECV | 16 |
| 494 | QEDECVLMLL | 16 |
| 510 | NIQDEYGNTA | 16 |
| 523 | AIYNEDKLMA | 16 |
| 549 | GLTPLLLGVH | 16 |
| 589 | AVCCGSASIV | 16 |
| 591 | CCGSASIVNL | 16 |
| 633 | LLSDYKEKQM | 16 |
| 670 | KKHGSNPVGL | 16 |
| 737 | GISQDEILTN | 16 |
| 753 | VAEKEMNSEL | 16 |

TABLE XXXV-continued

| Pos | 1234567890 | score |
|---|---|---|
| 858 | QLGLAQHAQA | 16 |
| 843 | QHAQASVQQL | 16 |
| 878 | QLGLAQHAQA | 16 |
| 883 | QHAQASVQQL | 16 |
| 947 | RASPGTPSLV | 16 |
| 169 | HLAPTAPDGG | 15 |
| 277 | QCIPNLSYPL | 15 |
| 302 | TGGGILGLEL | 15 |
| 312 | PATAARLSGL | 15 |
| 361 | CLSEGYGHSF | 15 |
| 370 | FLIMKETSTK | 15 |
| 374 | KETSTKISGL | 15 |
| 455 | HLASANGNSE | 15 |
| 460 | NGNSEVVQLL | 15 |
| 468 | LLLDRRCQLN | 15 |
| 482 | KKRTALIKAV | 15 |
| 493 | CQEDECVLML | 15 |
| 501 | MLLEHGADGN | 15 |
| 511 | IQDEYGNTAL | 15 |
| 535 | LLLYGADIES | 15 |
| 566 | KFLIKKKANL | 15 |
| 585 | ALILAVCCGS | 15 |
| 587 | ILAVCCGSAS | 15 |
| 592 | CGSASIVNLL | 15 |
| 601 | LLEQNVDVSS | 15 |
| 621 | YAVSSHHHVI | 15 |
| 650 | SNPVITILNI | 15 |
| 652 | PVITILNIKL | 15 |
| 655 | TILNIKLPLK | 15 |
| 668 | EIKKHGSNPV | 15 |
| 695 | GLIPQRKSRK | 15 |
| 772 | LLRENSMLRE | 15 |
| 799 | LRENKILEEI | 15 |
| 832 | AGFSLRQLGL | 15 |
| 872 | AGFSLRQLGL | 15 |
| 904 | QQAQEQGAAL | 15 |
| 985 | CDSSGWILPV | 15 |
| 1017 | RLKSDSNRET | 15 |

TABLE XXXV-continued

| Pos | 1234567890 | score |
|---|---|---|
| 5 | HILLPTQATF | 14 |
| 23 | ALTTVSNPSR | 14 |
| 27 | VSNPSRADPV | 14 |
| 80 | SSSRALPGSL | 14 |
| 83 | RALPGSLPAF | 14 |
| 104 | QSATPAGAFL | 14 |
| 111 | AFLLGWERVV | 14 |
| 123 | RLEVPRPQAA | 14 |
| 195 | CAQGLEAASA | 14 |
| 205 | NLPGAPGRSS | 14 |
| 220 | YRSGPSVSSA | 14 |
| 233 | AEPPAHQRLL | 14 |
| 235 | PPAHQRLLFL | 14 |
| 266 | GSLSVFQLHL | 14 |
| 279 | IPNLSYPLVL | 14 |
| 281 | NLSYPLVLRH | 14 |
| 318 | LSGLNSIMQI | 14 |
| 320 | GLNSIMQIKE | 14 |
| 353 | NVDKWDDFCL | 14 |
| 382 | GLIQEMGSGK | 14 |
| 383 | LIQEMGSGKS | 14 |
| 395 | GTWGDYDDSA | 14 |
| 420 | LHRAAWWGKV | 14 |
| 427 | GKVPRKDLIV | 14 |
| 434 | LIVMLRDTDM | 14 |
| 437 | MLRDTDMNKR | 14 |
| 453 | ALHLASANGN | 14 |
| 457 | ASANGNSEVV | 14 |
| 461 | GNSEVVQLLL | 14 |
| 486 | ALIKAVQCQE | 14 |
| 500 | LMLLEHGADG | 14 |
| 519 | ALHYAIYNED | 14 |
| 521 | HYAIYNEDKL | 14 |
| 534 | ALLLYGADIE | 14 |
| 555 | LGVHEQKQEV | 14 |
| 567 | FLIKKKANLN | 14 |
| 568 | LIKKKANLNA | 14 |
| 593 | GSASIVNLLL | 14 |
| 596 | SIVNLLLEQN | 14 |

TABLE XXXV-continued

| Pos | 1234567890 | score |
|---|---|---|
| 614 | SGQTAREYAV | 14 |
| 688 | SAGNGDDGLI | 14 |
| 735 | NTGISQDEIL | 14 |
| 742 | EILTNKQKQI | 14 |
| 779 | LREEIAKLRL | 14 |
| 784 | AKLRLELDET | 14 |
| 814 | KLLKTIQLNE | 14 |
| 818 | TIQLNEEALT | 14 |
| 867 | QEQEVAGFSL | 14 |
| 930 | TAAGDQGPGT | 14 |
| 975 | GRSPTKQKSV | 14 |
| 990 | WILPVPTFSS | 14 |
| 991 | ILPVPTFSSG | 14 |
| 1089 | TTLPHRDTTT | 14 |
| 1091 | LPHRDTTTSL | 14 |

V2A-HLA-A0202-10mers:251P5G2

No results found.

TABLE XXXVI

| Pos | 123456789 | score |
|---|---|---|

V1A-HLA-A0202-10mers:251P5G2

No results found.
V3A-HLA-A0202-10mers:251P5G2

No results found.
V4A-HLA-A0202-10mers:251P5G2

No results found.
V12A-HLA-A0202-10mers:251P5G2

No results found.
V12B-HLA-A0202-10mers:251P5G2

No results found.

TABLE XXXVII

| Pos | 123456789 | score |
|---|---|---|

V1A-HLA-A0203-10mers:251P5G2

No results found.

V2A-HLA-A0203-10mers:251P5G2

No results found.

TABLE XXXVII-continued

| Pos | 123456789 | score |
|---|---|---|
| \multicolumn{3}{c}{V3A-HLA-A0203-10mers:251P5G2} |||

No results found.

V4A-HLA-A0203-10mers:251P5G2

No results found.

V12A-HLA-A0203-10mers:251P5G2

No results found.

V12B-A0203-10mers:251P5G2
Each peptide is a portion of SEQ ID NO: 25; each start position is specified, the length of peptide is 10 amino acids, and the end position for each peptide is the start position plus nine.

| Pos | 123456789 | score |
|---|---|---|
| 8 | LPTQATFAAA | 27 |
| 957 | RLASGARAAA | 27 |
| 7 | LLPTQATFAA | 19 |
| 14 | FAAATGLWAA | 19 |
| 54 | SWLSFPGTAA | 19 |
| 123 | RLEVPRPQAA | 19 |
| 145 | PPCHQRRDAA | 19 |
| 193 | VRCAQGLEAA | 19 |
| 307 | LGLELPATAA | 19 |
| 415 | EDLDKLHRAA | 19 |
| 903 | EQQAQEQGAA | 19 |
| 923 | VPLSEGGTAA | 19 |
| 956 | VRLASGARAA | 19 |
| 84 | ALPGSLPAFA | 18 |
| 102 | SEQSATPAGA | 18 |
| 125 | EVPRPQAAPA | 18 |
| 195 | CAQGLEAASA | 18 |
| 306 | ILGLELPATA | 18 |
| 450 | KRTALHLASA | 18 |
| 525 | YNEDKLMAKA | 18 |
| 680 | PENLTNGASA | 18 |
| 838 | QLGLAQHAQA | 18 |
| 878 | QLGLAQHAQA | 18 |
| 955 | LVRLASGARA | 18 |
| 9 | PTQATFAAAT | 17 |
| 15 | AAATGLWAAL | 17 |

TABLE XXXVII-continued

| Pos | 123456789 | score |
|---|---|---|
| 55 | WLSFPGTAAR | 17 |
| 124 | LEVPRPQAAP | 17 |
| 146 | PCHQRRDAAC | 17 |
| 194 | RCAQGLEAAS | 17 |
| 308 | GLELPATAAR | 17 |
| 416 | DLDKLHRAAW | 17 |
| 904 | QQAQEQGAAL | 17 |
| 924 | PLSEGGTAAG | 17 |
| 958 | LASGARAAAL | 17 |

TABLE XXXVIII

| Pos | 1234567890 | score |
|---|---|---|
| \multicolumn{3}{c}{V1A-HLA-A3-10mers:251P5G2} |||

Each peptide is a portion of SEQ ID NO: 3; each start position is specified, the length of peptide is 10 amino acids, and the end position for each peptide is the start position plus nine.

| Pos | 1234567890 | score |
|---|---|---|
| 224 | ILLPVSFSVG | 24 |
| 227 | PVSFSVGMYK | 24 |
| 92 | CLLGMLQVVN | 22 |
| 28 | FLDLRPERTY | 21 |
| 78 | YLRRVIRVLS | 21 |
| 7 | LVLASQPTLF | 20 |
| 42 | HVALIHMVVL | 20 |
| 81 | RVIRVLSICT | 20 |
| 109 | LVRFKWKSTI | 20 |
| 210 | PLPKDLCRGK | 20 |
| 214 | DLCRGKSHQH | 20 |
| 44 | ALIHMVVLLT | 19 |
| 135 | SLIFYTVASS | 19 |
| 164 | SIIRGLFFTL | 19 |
| 182 | KQIMLFSSVY | 19 |
| 6 | KLVLASQPTL | 18 |
| 158 | SLFPINSIIR | 18 |
| 189 | SVYMMTLIQE | 18 |
| 50 | VLLTMVFLSP | 17 |
| 64 | SLNFQNDFKY | 17 |
| 84 | RVLSICTTCL | 17 |

TABLE XXXVIII-continued

| Pos | 1234567890 | score |
|---|---|---|
| 98 | QVVNISPSIS | 17 |
| 146 | VTQINLHVSK | 17 |
| 168 | GLFFTLSLFR | 17 |
| 174 | SLFRDVFLKQ | 17 |
| 26 | LLFLDLRPER | 16 |
| 30 | DLRPERTYLP | 16 |
| 60 | QLFESLNFQN | 16 |
| 127 | SLSFPVSSSL | 16 |
| 136 | LIFYTVASSN | 16 |
| 165 | IIRGLFFTLS | 16 |
| 178 | DVFLKQIMLF | 16 |
| 202 | ILVPSQPQPL | 16 |
| 14 | TLFSFFSASS | 15 |
| 45 | LIHMVVLLTM | 15 |
| 48 | MVVLLTMVFL | 15 |
| 56 | FLSPQLFESL | 15 |
| 82 | VIRVLSICTT | 15 |
| 108 | WLVRFKWKST | 15 |
| 140 | TVASSNVTQI | 15 |
| 172 | TLSLFRDVFL | 15 |
| 183 | QIMLFSSVYM | 15 |
| 8 | VLASQPTLFS | 14 |
| 54 | MVFLSPQLFE | 14 |
| 93 | LLGMLQVVNI | 14 |
| 106 | ISWLVRFKWK | 14 |
| 145 | NVTQINLHVS | 14 |
| 161 | PINSIIRGLF | 14 |
| 204 | VPSQPQPLPK | 14 |
| 225 | LLPVSFSVGM | 14 |
| 3 | FISKLVLASQ | 13 |
| 4 | ISKLVLASQP | 13 |
| 10 | ASQPTLFSFF | 13 |
| 35 | RTYLPVCHVA | 13 |
| 37 | YLPVCHVALI | 13 |
| 49 | VVLLTMVFLS | 13 |
| 51 | LLTMVFLSPQ | 13 |
| 63 | ESLNFQNDFK | 13 |
| 96 | MLQVVNISPS | 13 |
| 99 | VVNISPSISW | 13 |

TABLE XXXVIII-continued

| Pos | 1234567890 | score |
|---|---|---|
| 102 | ISPSISWLVR | 13 |
| 104 | PSISWLVRFK | 13 |
| 122 | HLFSWSLSFP | 13 |
| 147 | TQINLHVSKY | 13 |
| 152 | HVSKYCSLFP | 13 |
| 162 | INSIIRGLFF | 13 |
| 167 | RGLFFTLSLF | 13 |
| 180 | FLKQIMLFSS | 13 |
| 194 | TLIQELQEIL | 13 |
| 198 | ELQEILVPSQ | 13 |
| 201 | EILVPSQPQP | 13 |
| 223 | HILLPVSFSV | 13 |
| 240 | IISTSSTLPW | 13 |
| 25 | FLLFLDLRPE | 12 |
| 33 | PERTYLPVCH | 12 |
| 69 | NDFKYEASFY | 12 |
| 72 | KYEASFYLRR | 12 |
| 75 | ASFYLRRVIR | 12 |
| 87 | SICTTCLLGM | 12 |
| 150 | NLHVSKYCSL | 12 |
| 173 | LSLFRDVFLK | 12 |
| 185 | MLFSSVYMMT | 12 |
| 221 | HQHILLPVSF | 12 |
| 239 | FIISTSSTLP | 12 |
| 32 | RPERTYLPVC | 11 |
| 68 | QNDFKYEASF | 11 |
| 85 | VLSICTTCLL | 11 |
| 101 | NISPSISWLV | 11 |
| 121 | FHLFSWSLSF | 11 |
| 148 | QINLHVSKYC | 11 |
| 171 | FTLSLFRDVF | 11 |
| 231 | SVGMYKMDFI | 11 |
| 238 | DFIISTSSTL | 11 |

TABLE XXXVIII-continued

Pos　　1234567890　　score

V2A-A3-
10mers:251P5G2
Each peptide is a portion of SEQ ID NO: 5; each start position is specified, the length of peptide is 10 amino acids, and the end position for each peptide is the start position plus nine.

| Pos | Peptide | score |
|---|---|---|
| 1 | LVLASQPTLC | 16 |
| 8 | TLCSFFSASS | 15 |
| 2 | VLASQPTLCS | 14 |
| 4 | ASQPTLCSFF | 13 |
| 9 | LCSFFSASSP | 8 |
| 10 | CSFFSASSPF | 7 |

V3A-A3-
10mers:251P5G2
Each peptide is a portion of SEQ ID NO: 7; each start position is specified, the length of peptide is 10 amino acids, and the end position for each peptide is the start position plus nine.

| Pos | Peptide | score |
|---|---|---|
| 6 | RVIRDLSICT | 20 |
| 3 | YLRRVIRDLS | 17 |
| 7 | VIRDLSICTT | 16 |
| 10 | DLSICTTCLL | 11 |
| 4 | LRRVIRDLSI | 8 |
| 5 | RRVIRDLSIC | 8 |
| 8 | IRDLSICTTC | 8 |

V4A-A3-
10mers:251P5G2
Each peptide is a portion of SEQ ID NO: 9; each start position is specified, the length of peptide is 10 amino acids, and the end position for each peptide is the start position plus nine.

| Pos | Peptide | score |
|---|---|---|
| 7 | CLLDMLQVVN | 21 |
| 8 | LLDMLQVVNI | 14 |
| 2 | SICTTCLLDM | 12 |

V12A-HLA-A3-
10mers:251P5G2
Each peptide is a portion of SEQ ID NO: 25; each start position is specified, the length of peptide is 10 amino acids, and the end position for each peptide is the start position plus nine.

| Pos | Peptide | score |
|---|---|---|
| 9 | WLIMLFSSVY | 26 |
| 10 | LIMLFSSVYM | 13 |
| 6 | SISWLIMLFS | 12 |

TABLE XXXVIII-continued

Pos　　1234567890　　score

V12B-HLA-A3-
10mers:251P5G2
Each peptide is a portion of SEQ ID NO: 25; each start position is specified, the length of peptide is 10 amino acids, and the end position for each peptide is the start position plus nine.

| Pos | Peptide | score |
|---|---|---|
| 43 | AVLPCCNLEK | 31 |
| 785 | KLRLELDETK | 31 |
| 803 | KILEEIESVK | 31 |
| 370 | FLIMKETSTK | 30 |
| 326 | QIKEFEELVK | 29 |
| 342 | KVIQCVFAKK | 29 |
| 382 | GLIQEMGSGK | 29 |
| 695 | GLIPQRKSRK | 29 |
| 536 | LLYGADIESK | 28 |
| 419 | KLHRAAWWGK | 26 |
| 552 | PLLGVHEQK | 26 |
| 160 | GLTRAFQVVH | 25 |
| 333 | LVKLHSLSHK | 25 |
| 819 | IQLNEEALTK | 25 |
| 262 | ALGVGSLSVF | 24 |
| 529 | KLMAKALLLY | 24 |
| 835 | SLRQLGLAQH | 24 |
| 875 | SLRQLGLAQH | 24 |
| 112 | FLLGWERVVQ | 23 |
| 287 | VLRHIPELIK | 23 |
| 5 | HILLPTQATF | 22 |
| 154 | ACLRAQGLTR | 22 |
| 549 | GLTPLLLGVH | 22 |
| 628 | HVICELLSDY | 22 |
| 6 | ILLPTQATFA | 21 |
| 113 | LLGWERVVQR | 21 |
| 119 | VVQRRLEVPR | 21 |
| 217 | ALRYRSGPSV | 21 |
| 306 | ILGLELPATA | 21 |
| 343 | VIQCVFAKKK | 21 |
| 612 | DLSGQTAREY | 21 |
| 655 | TILNIKLPLK | 21 |
| 662 | PLKVEEEIKK | 21 |

TABLE XXXVIII-continued

| Pos | 1234567890 | score |
|---|---|---|
| 778 | MLREEIAKLR | 21 |
| 70 | TLTGHSALSL | 20 |
| 88 | SLPAFADLPR | 20 |
| 189 | RLTHVRCAQG | 20 |
| 240 | RLLFLPRAPQ | 20 |
| 243 | FLPRAPQAVS | 20 |
| 361 | CLSEGYGHSF | 20 |
| 428 | KVPRKDLIVM | 20 |
| 523 | AIYNEDKLMA | 20 |
| 563 | EVVKFLIKKK | 20 |
| 587 | ILAVCCGSAS | 20 |
| 771 | DLLRENSMLR | 20 |
| 825 | ALTKTKVAGF | 20 |
| 954 | SLVRLASGAR | 20 |
| 955 | LVRLASGARA | 20 |
| 957 | RLASGARAAA | 20 |
| 23 | ALTTVSNPSR | 19 |
| 49 | NLEKGSWLSF | 19 |
| 56 | LSFPGTAARK | 19 |
| 84 | ALPGSLPAFA | 19 |
| 125 | EVPRPQAAPA | 19 |
| 192 | HVRCAQGLEA | 19 |
| 275 | LIQCIPNLSY | 19 |
| 308 | GLELPATAAR | 19 |
| 332 | ELVKLHSLSH | 19 |
| 467 | QLLLDRRCQL | 19 |
| 486 | ALIKAVQCQE | 19 |
| 534 | ALLLYGADIE | 19 |
| 577 | ALDRYGRTAL | 19 |
| 589 | AVCCGSASIV | 19 |
| 629 | VICELLSDYK | 19 |
| 798 | QLRENKILEE | 19 |
| 830 | KVAGFSLRQL | 19 |
| 838 | QLGLAQHAQA | 19 |
| 878 | QLGLAQHAQA | 19 |
| 891 | QLCYKWGHTE | 19 |
| 912 | ALRSQIGDPG | 19 |
| 922 | GVPLSEGGTA | 19 |
| 966 | ALPPPTGKNG | 19 |

TABLE XXXVIII-continued

| Pos | 1234567890 | score |
|---|---|---|
| 973 | KNGRSPTLQK | 19 |
| 55 | WLSFPGTAAR | 18 |
| 118 | RVVQRRLEVP | 18 |
| 433 | DLIVMLRDTD | 18 |
| 437 | MLRDTDMNKR | 18 |
| 513 | DEYGNTALHY | 18 |
| 557 | VHEQKQEVVK | 18 |
| 676 | PVGLPENLTN | 18 |
| 814 | KLLKTIQLNE | 18 |
| 916 | QIGDPGGVPL | 18 |
| 1040 | KTQQSPRHTK | 18 |
| 1054 | DDRAGVLAPK | 18 |
| 19 | GLWAALTTVS | 17 |
| 78 | SLSSSRALPG | 17 |
| 205 | NLPGAPGRSS | 17 |
| 241 | LLFLPRAPQA | 17 |
| 281 | NLSYPLVLRH | 17 |
| 294 | ILKFSEKETG | 17 |
| 317 | RLSGLNSIMQ | 17 |
| 335 | KLHSLSHKVI | 17 |
| 453 | ALHLASANGN | 17 |
| 477 | NVLDNKKRTA | 17 |
| 480 | DNKKRTALIK | 17 |
| 574 | NLNALDRYGR | 17 |
| 585 | ALILAVCCGS | 17 |
| 599 | NLLLEQNVDV | 17 |
| 600 | LLLEQNVDVS | 17 |
| 622 | AVSSHHHVIC | 17 |
| 656 | ILNIKLPLKV | 17 |
| 747 | KQKQIEVAEK | 17 |
| 772 | LLRENSMLRE | 17 |
| 804 | ILEEIESVKE | 17 |
| 810 | SVKEKLLKTI | 17 |
| 964 | AAALPPPTGK | 17 |
| 991 | ILPVPTFSSG | 17 |
| 993 | PVPTFSSGSF | 17 |
| 1011 | DVSPAMRLKS | 17 |
| 1031 | RDKDDLPFFK | 17 |

TABLE XXXVIII-continued

| Pos | 1234567890 | score |
|---|---|---|
| 94 | DLPRSCPESE | 16 |
| 123 | RLEVPRPQAA | 16 |
| 155 | CLRAQGLTRA | 16 |
| 183 | PSRNSYRLTH | 16 |
| 286 | LVLRHIPEIL | 16 |
| 291 | IPEILKFSEK | 16 |
| 346 | CVFAKKKNVD | 16 |
| 410 | YHVRREDLDK | 16 |
| 411 | HVRREDLDKL | 16 |
| 436 | VMLRDTDMNK | 16 |
| 455 | HLASANGNSE | 16 |
| 469 | LLDRRCQLNV | 16 |
| 475 | QLNVLDNKKR | 16 |
| 484 | RTALIKAVQC | 16 |
| 501 | MLLEHGADGN | 16 |
| 510 | NIQDEYGNTA | 16 |
| 520 | LHYAIYNEDK | 16 |
| 561 | KQEVVKFLIK | 16 |
| 567 | FLIKKKANLN | 16 |
| 601 | LLEQNVDVSS | 16 |
| 635 | SDYKEKQMLK | 16 |
| 740 | QDEILTNKQK | 16 |
| 840 | GLAQHAQASV | 16 |
| 851 | QLCYKWNHTE | 16 |
| 870 | EVAGFSLRQL | 16 |
| 880 | GLAQHAQASV | 16 |
| 948 | ASPGTPSLVR | 16 |
| 971 | TGKNGRSPTK | 16 |
| 1109 | GVGPTTLGSN | 16 |
| 26 | TVSNPSRADP | 15 |
| 76 | ALSLSSSRAL | 15 |
| 166 | QVVHLAPTAP | 15 |
| 169 | HLAPTAPDGG | 15 |
| 179 | AGCPPSRNSY | 15 |
| 198 | GLEAASANLP | 15 |
| 218 | LRYRSGPSVS | 15 |
| 250 | AVSGPQEQPS | 15 |
| 310 | ELPATAARLS | 15 |
| 347 | VFAKKKNVDK | 15 |

TABLE XXXVIII-continued

| Pos | 1234567890 | score |
|---|---|---|
| 416 | DLDKLHRAAW | 15 |
| 439 | RDTDMNKRDK | 15 |
| 473 | RCQLNVLDNK | 15 |
| 524 | IYNEDKLMAK | 15 |
| 556 | GVHEQKQEVV | 15 |
| 571 | KKANLNALDR | 15 |
| 586 | LILAVCCGSA | 15 |
| 616 | QTAREYAVSS | 15 |
| 719 | HSDEQNDTQK | 15 |
| 737 | GISQDEILTN | 15 |
| 787 | RLELDETKHQ | 15 |
| 794 | KHQNQLRENK | 15 |
| 808 | IESVKEKLLK | 15 |
| 821 | LNEEALTKTK | 15 |
| 852 | LCYKWNHTEK | 15 |
| 892 | LCYKWGHTEK | 15 |
| 924 | PLSEGGTAAG | 15 |
| 940 | HLPPREPRAS | 15 |
| 983 | SVCDSSGWIL | 15 |
| 990 | WILPVPTFSS | 15 |
| 1002 | FLGRRCPMFD | 15 |
| 1017 | RLKSDSNRET | 15 |
| 1059 | VLAPKCRPGT | 15 |
| 1090 | TLPHRDTTTS | 15 |
| 1099 | SLPHFHVSAG | 15 |

TABLE XXXIX

| Pos | 1234567890 | score |
|---|---|---|
| \multicolumn{3}{c}{V1A-HLA-A26-10mers:251P5G2 Each peptide is a portion of SEQ ID NO: 3; each start position is specified, the length of peptide is 10 amino acids, and the end position for each peptide is the start position plus nine.} | | |
| 178 | DVFLKQIMLF | 33 |
| 42 | HVALIHMVVL | 24 |
| 164 | SIIRGLFFTL | 24 |
| 39 | PVCHVALIHM | 23 |
| 48 | MVVLLTMVFL | 23 |

TABLE XXXIX-continued

| Pos | 1234567890 | score |
|---|---|---|
| 56 | FLSPQLFESL | 23 |
| 87 | SICTTCLLGM | 23 |
| 238 | DFIISTSSTL | 23 |
| 45 | LIHMVVLLTM | 22 |
| 198 | ELQEILVPSQ | 22 |
| 242 | STSSTLPWAY | 22 |
| 70 | DFKYEASFYL | 21 |
| 119 | FTFHLFSWSL | 21 |
| 150 | NLHVSKYCSL | 21 |
| 161 | PINSIIRGLF | 21 |
| 171 | FTLSLFRDVF | 21 |
| 7 | LVLASQPTLF | 20 |
| 52 | LTMVFLSPQL | 20 |
| 186 | LFSSVYMMTL | 20 |
| 28 | FLDLRPERTY | 19 |
| 64 | SLNFQNDFKY | 19 |
| 84 | RVLSICTTCL | 19 |
| 183 | QIMLFSSVYM | 19 |
| 194 | TLIQELQEIL | 19 |
| 202 | ILVPSQPQPL | 19 |
| 225 | LLPVSFSVGM | 19 |
| 17 | SFFSASSPFL | 18 |
| 127 | SLSFPVSSSL | 18 |
| 147 | TQINLHVSKY | 18 |
| 201 | EILVPSQPQP | 18 |
| 3 | FISKLVLASQ | 17 |
| 6 | KLVLASQPTL | 17 |
| 10 | ASQPTLFSFF | 17 |
| 117 | TIFTFHLFSW | 17 |
| 129 | SFPVSSSLIF | 17 |
| 140 | TVASSNVTQI | 17 |
| 172 | TLSLFRDVFL | 17 |
| 185 | MLFSSVYMMT | 17 |
| 245 | STLPWAYDRG | 17 |
| 9 | LASQPTLFSF | 16 |
| 13 | PTLFSFFSAS | 16 |
| 19 | FSASSPFLLF | 16 |
| 30 | DLRPERTYLP | 16 |

TABLE XXXIX-continued

| Pos | 1234567890 | score |
|---|---|---|
| 85 | VLSICTTCLL | 16 |
| 100 | VNISPSISWL | 16 |
| 103 | SPSISWLVRF | 16 |
| 122 | HLFSWSLSFP | 16 |
| 135 | SLIFYTVASS | 16 |
| 165 | IIRGLFFTLS | 16 |
| 193 | MTLIQELQEI | 16 |
| 226 | LPVSFSVGMY | 16 |
| 228 | VSFSVGMYKM | 16 |

V2A-A26-
10mers:251P5G2
Each peptide is a portion of
SEQ ID NO: 5; each start
position is specified, the
length of peptide is 10 amino
acids, and the end position
for each peptide is the start
position plus nine.

| 3 | LASQPTLCSF | 16 |
|---|---|---|
| 7 | PTLCSFFSAS | 16 |
| 4 | ASQPTLCSFF | 13 |
| 10 | CSFFSASSPF | 13 |
| 8 | TLCSFFSASS | 11 |
| 1 | LVLASQPTLC | 10 |
| 2 | VLASQPTLCS | 10 |

V3A-A26-
10mers:251P5G2
Each peptide is a portion of
SEQ ID NO: 7; each start
position is specified, the
length of peptide is 10 amino
acids, and the end position
for each peptide is the start
position plus nine.

| 10 | DLSICTTCLL | 22 |
|---|---|---|
| 7 | VIRDLSICTT | 15 |
| 2 | FYLRRVIRDL | 12 |
| 6 | RVIRDLSICT | 12 |
| 1 | SFYLRRVIRD | 11 |

V4A-HLA-A26-
10mers:251P5G2
Each peptide is a portion of
SEQ ID NO: 9; each start
position is specified, the
length of peptide is 10 amino
acids, and the end position
for each peptide is the start
position plus nine.

| 2 | SICTTCLLDM | 22 |
|---|---|---|
| 5 | TTCLLDMLQV | 15 |
| 8 | LLDMLQVVNI | 15 |

TABLE XXXIX-continued

| Pos | 1234567890 | score |
|---|---|---|
| 3 | ICTTCLLDML | 13 |
| 4 | CTTCLLDMLQ | 11 |
| 7 | CLLDMLQVVN | 10 |

V12A-HLA-A26-10mers:251P5G2
Each peptide is a portion of SEQ ID NO: 25; each start position is specified, the length of peptide is 10 amino acids, and the end position for each peptide is the start position plus nine.

| Pos | 1234567890 | score |
|---|---|---|
| 9 | WLIMLFSSVY | 21 |
| 10 | LIMLFSSVYM | 19 |
| 5 | PSISWLIMLF | 18 |
| 6 | SISWLIMLFS | 14 |
| 4 | SPSISWLIML | 13 |
| 2 | NISPSISWLI | 12 |
| 3 | ISPSISWLIM | 10 |

V12B-HLA-A26-10mers:251P5G2
Each peptide is a portion of SEQ ID NO: 25; each start position is specified, the length of peptide is 10 amino acids, and the end position for each peptide is the start position plus nine.

| Pos | 1234567890 | score |
|---|---|---|
| 870 | EVAGFSLRQL | 32 |
| 612 | DLSGQTAREY | 27 |
| 628 | HVICELLSDY | 27 |
| 541 | DIESKNKCGL | 26 |
| 830 | KVAGFSLRQL | 26 |
| 807 | EIESVKEKLL | 25 |
| 825 | ALTKTKVAGF | 25 |
| 161 | LTRAFQVVHL | 24 |
| 264 | GVGSLSVFQL | 24 |
| 752 | EVAEKEMNSE | 24 |
| 262 | ALGVGSLSVF | 23 |
| 411 | HVRREDLDKL | 23 |
| 428 | KVPRKDLIVM | 23 |
| 607 | DVSSQDLSGQ | 23 |
| 301 | ETGGGILGLE | 22 |
| 464 | EVVQLLLDRR | 22 |
| 529 | KLMAKALLLY | 22 |
| 563 | EVVKFLIKKK | 22 |
| 782 | EIAKLRLELD | 22 |
| 817 | KTIQLNEEAL | 22 |
| 993 | PVPTFSSGSF | 22 |
| 5 | HILLPTQATF | 21 |
| 275 | LIQCIPNLSY | 21 |
| 361 | CLSEGYGHSF | 21 |
| 652 | PVITILNIKL | 21 |
| 712 | DTENEEYHSD | 21 |
| 49 | NLEKGSWLSF | 20 |
| 68 | STTLTGHSAL | 20 |
| 190 | LTHVRCAQGL | 20 |
| 353 | NVDKWDDFCL | 20 |
| 364 | EGYGHSFLIM | 20 |
| 559 | EQKQEVVKFL | 20 |
| 654 | ITILNIKLPL | 20 |
| 916 | QIGDPGGVPL | 20 |
| 1001 | SFLGRRCPMF | 20 |
| 1073 | DTPPHRNADT | 20 |
| 36 | VTWRKEPAVL | 19 |
| 70 | TLTGHSALSL | 19 |
| 342 | KVIQCVFAKK | 19 |
| 513 | DEYGNTALHY | 19 |
| 709 | QFPDTENEEY | 19 |
| 789 | ELDETKHQNQ | 19 |
| 806 | EEIESVKEKL | 19 |
| 983 | SVCDSSGWIL | 19 |
| 1011 | DVSPAMRLKS | 19 |
| 1081 | DTPPHRHTTT | 19 |
| 83 | RALPGSLPAF | 18 |
| 125 | EVPRPQAAPA | 18 |
| 269 | SVFQLHLIQC | 18 |
| 286 | LVLRHIPEIL | 18 |
| 293 | EILKFSEKET | 18 |
| 305 | GILGLELPAT | 18 |
| 401 | DDSAFMEPRY | 18 |
| 416 | DLDKLHRAAW | 18 |
| 434 | LIVMLRDTDM | 18 |
| 440 | DTDMNKRDKQ | 18 |
| 478 | VLDNKKRTAL | 18 |

TABLE XXXIX-continued

| Pos | 1234567890 | score |
|---|---|---|
| 577 | ALDRYGRTAL | 18 |
| 633 | LLSDYKEKQM | 18 |
| 648 | ENSNPVITIL | 18 |
| 668 | EIKKHGSNPV | 18 |
| 725 | DTQKQLSEEQ | 18 |
| 735 | NTGISQDEIL | 18 |
| 792 | ETKHQNQLRE | 18 |
| 865 | QAQEQEVAGF | 18 |
| 1021 | DSNRETHQAF | 18 |
| 1025 | ETHQAFRDKD | 18 |
| 76 | ALSLSSSRAL | 17 |
| 103 | EQSATPAGAF | 17 |
| 152 | DAACLRAQGL | 17 |
| 234 | EPPAHQRLLF | 17 |
| 333 | LVKLHSLSHK | 17 |
| 378 | TKISGLIQEM | 17 |
| 467 | QLLLDRRCQL | 17 |
| 558 | HEQKQEVVKF | 17 |
| 742 | EILTNKQKQI | 17 |
| 781 | EEIAKLRLEL | 17 |
| 810 | SVKEKLLKTI | 17 |
| 1009 | MFDVSPAMRL | 17 |
| 1029 | AFRDKDDLPF | 17 |
| 1030 | FRDKDDLPFF | 17 |
| 1035 | DLPFFKTQQS | 17 |
| 1050 | DLGQDDRAGV | 17 |
| 1109 | GVGPTTLGSN | 17 |
| 41 | EPAVLPCCNL | 16 |
| 94 | DLPRSCPESE | 16 |
| 278 | CIPNLSYPLV | 16 |
| 332 | ELVKLHSLSH | 16 |
| 375 | ETSTKISGLI | 16 |
| 377 | STKISGLIQE | 16 |
| 433 | DLIVMLRDTD | 16 |
| 447 | DKQKRTALHL | 16 |
| 494 | QEDECVLMLL | 16 |
| 527 | EDKLMAKALL | 16 |
| 566 | KFLIKKKANL | 16 |
| 579 | DRYGRTALIL | 16 |
| 632 | ELLSDYKEKQ | 16 |
| 763 | SLSHKKEEDL | 16 |
| 769 | EEDLLRENSM | 16 |
| 770 | EDLLRENSML | 16 |
| 828 | KTKVAGFSLR | 16 |
| 843 | QHAQASVQQL | 16 |
| 883 | QHAQASVQQL | 16 |
| 978 | PTKQKSVCDS | 16 |
| 1094 | RDTTTSLPHF | 16 |
| 1095 | DTTTSLPHFH | 16 |
| 71 | LTGHSALSLS | 15 |
| 106 | ATPAGAFLLG | 15 |
| 118 | RVVQRRLEVP | 15 |
| 172 | PTAPDGGAGC | 15 |
| 288 | LRHIPEILKF | 15 |
| 300 | KETGGGILGL | 15 |
| 310 | ELPATAARLS | 15 |
| 321 | LNSIMQIKEF | 15 |
| 329 | EFEELVKLHS | 15 |
| 374 | KETSTKISGL | 15 |
| 429 | VPRKDLIVML | 15 |
| 516 | GNTALHYAIY | 15 |
| 536 | LLYGADIESK | 15 |
| 569 | IKKKANLNAL | 15 |
| 572 | KANLNALDRY | 15 |
| 591 | CCGSASIVNL | 15 |
| 596 | SIVNLLLEQN | 15 |
| 655 | TILNIKLPLK | 15 |
| 721 | DEQNDTQKQL | 15 |
| 737 | GISQDEILTN | 15 |
| 755 | EKEMNSELSL | 15 |
| 761 | ELSLSHKKEE | 15 |
| 771 | DLLRENSMLR | 15 |
| 772 | LLRENSMLRE | 15 |
| 798 | QLRENKILEE | 15 |
| 820 | QLNEEALTKT | 15 |
| 835 | SLRQLGLAQH | 15 |
| 848 | SVQQLCYKWN | 15 |

TABLE XXXIX-continued

| Pos | 1234567890 | score |
|---|---|---|
| 875 | SLRQLGLAQH | 15 |
| 888 | SVQQLCYKWG | 15 |
| 988 | SGWILPVPTF | 15 |
| 991 | ILPVPTFSSG | 15 |
| 1099 | SLPHFHVSAG | 15 |

TABLE XL

| Pos | 1234567890 | score |
|---|---|---|
| | V1A-HLA-B0702-10mers:251P5G2 Each peptide is a portion of SEQ ID NO: 3; each start position is specified, the length of peptide is 10 amino acids, and the end position for each peptide is the start position plus nine. | |
| 103 | SPSISWLVRF | 20 |
| 160 | FPINSIIRGL | 20 |
| 1 | MPFISKLVLA | 18 |
| 58 | SPQLFESLNF | 18 |
| 12 | QPTLFSFFSA | 17 |
| 20 | SASSPFLLFL | 15 |
| 166 | IRGLFFTLSL | 15 |
| 172 | TLSLFRDVFL | 15 |
| 204 | VPSQPQPLPK | 15 |
| 36 | TYLPVCHVAL | 14 |
| 42 | HVALIHMVVL | 14 |
| 56 | FLSPQLFESL | 14 |
| 142 | ASSNVTQINL | 14 |
| 18 | FFSASSPFLL | 13 |
| 22 | SSPFLLFLDL | 13 |
| 32 | RPERTYLPVC | 13 |
| 43 | VALIHMVVLL | 13 |
| 48 | MVVLLTMVFL | 13 |
| 84 | RVLSICTTCL | 13 |
| 85 | VLSICTTCLL | 13 |
| 114 | WKSTIFTFHL | 13 |
| 202 | ILVPSQPQPL | 13 |
| 6 | KLVLASQPTL | 12 |
| 17 | SFFSASSPFL | 12 |
| 29 | LDLRPERTYL | 12 |

TABLE XL-continued

| Pos | 1234567890 | score |
|---|---|---|
| 38 | LPVCHVALIH | 12 |
| 52 | LTMVFLSPQL | 12 |
| 127 | SLSFPVSSSL | 12 |
| 162 | INSIIRGLFF | 12 |
| 186 | LFSSVYMMTL | 12 |
| 216 | CRGKSHQHIL | 12 |
| 10 | ASQPTLFSFF | 11 |
| 44 | ALIHMVVLLT | 11 |
| 74 | EASFYLRRVI | 11 |
| 77 | FYLRRVIRVL | 11 |
| 79 | LRRVIRVLSI | 11 |
| 88 | ICTTCLLGML | 11 |
| 130 | FPVSSSLIFY | 11 |
| 164 | SIIRGLFFTL | 11 |
| 177 | RDVFLKQIML | 11 |
| 190 | VYMMTLIQEL | 11 |
| 207 | QPQPLPKDLC | 11 |
| 209 | QPLPKDLCRG | 11 |
| 211 | LPKDLCRGKS | 11 |
| 217 | RGKSHQHILL | 11 |
| 226 | LPVSFSVGMY | 11 |
| 19 | FSASSPFLLF | 10 |
| 23 | SPFLLFLDLR | 10 |
| 70 | DFKYEASFYL | 10 |
| 93 | LLGMLQVVNI | 10 |
| 100 | VNISPSISWL | 10 |
| 119 | FTFHLFSWSL | 10 |
| 133 | SSSLIFYTVA | 10 |
| 150 | NLHVSKYCSL | 10 |
| 194 | TLIQELQEIL | 10 |
| 206 | SQPQPLPKDL | 10 |
| 215 | LCRGKSHQHI | 10 |
| 219 | KSHQHILLPV | 10 |
| 238 | DFIISTSSTL | 10 |
| 31 | LRPERTYLPV | 9 |
| 46 | IHMVVLLTMV | 9 |
| 101 | NISPSISWLV | 9 |
| 111 | RFKWKSTIFT | 9 |

TABLE XL-continued

| Pos | 1234567890 | score |
|---|---|---|
| 123 | LFSWSLSFPV | 9 |
| 132 | VSSSLIFYTV | 9 |
| 140 | TVASSNVTQI | 9 |
| 183 | QIMLFSSVYM | 9 |
| 187 | FSSVYMMTLI | 9 |

V3A-B0702-10mers:251P5G2
Each peptide is a portion of SEQ ID NO: 7; each start position is specified, the length of peptide is 10 amino acids, and the end position for each peptide is the start position plus nine.

| Pos | 1234567890 | score |
|---|---|---|
| 9 | RDLSICTTCL | 13 |
| 10 | DLSICTTCLL | 13 |
| 2 | FYLRRVIRDL | 10 |
| 4 | LRRVIRDLSI | 10 |
| 7 | VIRDLSICTT | 8 |
| 6 | RVIRDLSICT | 7 |

V4A-HLA-B0702-10mers:251P5G2
Each peptide is a portion of SEQ ID NO: 9; each start position is specified, the length of peptide is 10 amino acids, and the end position for each peptide is the start position plus nine.

| Pos | 1234567890 | score |
|---|---|---|
| 3 | ICTTCLLDML | 11 |
| 8 | LLDMLQVVNI | 10 |
| 2 | SICTTCLLDM | 8 |
| 5 | TTCLLDMLQV | 8 |
| 6 | TCLLDMLQVV | 7 |

V2A-B0702-10mers:251P5G2
Each peptide is a portion of SEQ ID NO: 5; each start position is specified, the length of peptide is 10 amino acids, and the end position for each peptide is the start position plus nine.

| Pos | 1234567890 | score |
|---|---|---|
| 6 | QPTLCSFFSA | 17 |
| 4 | ASQPTLCSFF | 10 |
| 3 | LASQPTLCSF | 8 |

TABLE XL-continued

V12A-HLA-B0702-10mers:251P5G2
Each peptide is a portion of SEQ ID NO: 25; each start position is specified, the length of peptide is 10 amino acids, and the end position for each peptide is the start position plus nine.

| Pos | 1234567890 | score |
|---|---|---|
| 4 | SPSISWLIML | 22 |
| 2 | NISPSISWLI | 9 |
| 3 | ISPSISWLIM | 9 |
| 10 | LIMLFSSVYM | 9 |
| 8 | SWLIMLFSSV | 7 |
| 5 | PSISWLIMLF | 6 |
| 6 | SISWLIMLFS | 5 |
| 7 | ISWLIMLFSS | 1 |
| 9 | WLIMLFSSVY | 1 |

V12B-HLA-B0702-10mers:251P5G2
Each peptide is a portion of SEQ ID NO: 25; each start position is specified, the length of peptide is 10 amino acids, and the end position for each peptide is the start position plus nine.

| Pos | 1234567890 | score |
|---|---|---|
| 429 | VPRKDLIVML | 25 |
| 209 | APGRSSSCAL | 24 |
| 235 | PPAHQRLLFL | 24 |
| 279 | IPNLSYPLVL | 24 |
| 949 | SPGTPSLVRL | 23 |
| 41 | EPAVLPCCNL | 22 |
| 1082 | TPPHRHTTTL | 22 |
| 1091 | LPHRDTTTSL | 22 |
| 126 | VPRPQAAPAT | 21 |
| 234 | EPPAHQRLLF | 21 |
| 994 | VPTFSSGSFL | 21 |
| 181 | CPPSRNSYRL | 20 |
| 8 | LPTQATFAAA | 19 |
| 128 | RPQAAPATSA | 19 |
| 704 | KPENQQFPDT | 19 |
| 1007 | CPMFDVSPAM | 19 |
| 1065 | RPGTLCHTDT | 19 |
| 58 | FPGTAARKEF | 18 |
| 145 | PPCHQRRDAA | 18 |
| 182 | PPSRNSYRLT | 18 |

TABLE XL-continued

| Pos | 1234567890 | score |
|---|---|---|
| 675 | NPVGLPENLT | 18 |
| 923 | VPLSEGGTAA | 18 |
| 34 | DPVTWRKEPA | 17 |
| 144 | SPPCHQRRDA | 17 |
| 229 | APSPAEPPAH | 17 |
| 62 | AARKEFSTTL | 16 |
| 161 | LTRAFQVVHL | 16 |
| 174 | APDGGAGCPP | 16 |
| 253 | GPQEQPSEEA | 16 |
| 445 | KRDKQKRTAL | 16 |
| 459 | ANGNSEVVQL | 16 |
| 577 | ALDRYGRTAL | 16 |
| 945 | EPRASPGTPS | 16 |
| 958 | LASGARAAAL | 16 |
| 15 | AAATGLWAAL | 15 |
| 76 | ALSLSSSRAL | 15 |
| 107 | TPAGAFLLGW | 15 |
| 132 | APATSATPSR | 15 |
| 244 | LPRAPQAVSG | 15 |
| 300 | KETGGGILGL | 15 |
| 302 | TGGGILGLEL | 15 |
| 670 | KKHGSNPVGL | 15 |
| 687 | ASAGNGDDGL | 15 |
| 781 | EEIAKLRLEL | 15 |
| 29 | NPSRADPVTW | 14 |
| 70 | TLTGHSALSL | 14 |
| 86 | PGSLPAFADL | 14 |
| 138 | TPSRDPSPPC | 14 |
| 171 | APTAPDGGAG | 14 |
| 247 | APQAVSGPQE | 14 |
| 311 | LPATAARLSG | 14 |
| 407 | EPRYHVRRED | 14 |
| 461 | GNSEVVQLLL | 14 |
| 478 | VLDNKKRTAL | 14 |
| 511 | IQDEYGNTAL | 14 |
| 546 | NKCGLTPLLL | 14 |
| 579 | DRYGRTALIL | 14 |
| 592 | CGSASIVNLL | 14 |

TABLE XL-continued

| Pos | 1234567890 | score |
|---|---|---|
| 648 | ENSNPVITIL | 14 |
| 654 | ITILNIKLPL | 14 |
| 830 | KVAGFSLRQL | 14 |
| 832 | AGFSLRQLGL | 14 |
| 870 | EVAGFSLRQL | 14 |
| 872 | AGFSLRQLGL | 14 |
| 916 | QIGDPGGVPL | 14 |
| 932 | AGDQGPGTHL | 14 |
| 1042 | QQSPRHTKDL | 14 |
| 1044 | SPRHTKDLGQ | 14 |
| 1106 | SAGGVGPTTL | 14 |
| 104 | QSATPAGAFL | 13 |
| 142 | DPSPPCHQRR | 13 |
| 206 | LPGAPGRSSS | 13 |
| 223 | GPSVSSAPSP | 13 |
| 233 | AEPPAHQRLL | 13 |
| 257 | QPSEEALGVG | 13 |
| 327 | IKEFEELVKL | 13 |
| 362 | LSEGYGHSFL | 13 |
| 425 | WWGKVPRKDL | 13 |
| 447 | DKQKRTALHL | 13 |
| 470 | LDRRCQLNVL | 13 |
| 493 | CQEDECVLML | 13 |
| 526 | NEDKLMAKAL | 13 |
| 544 | SKNKCGLTPL | 13 |
| 545 | KNKCGLTPLL | 13 |
| 559 | EQKQEVVKFL | 13 |
| 569 | IKKKANLNAL | 13 |
| 591 | CCGSASIVNL | 13 |
| 593 | GSASIVNLLL | 13 |
| 697 | IPQRKSRKPE | 13 |
| 755 | EKEMNSELSL | 13 |
| 904 | QQAQEQGAAL | 13 |
| 919 | DPGGVPLSEG | 13 |
| 942 | PRREPRASPG | 13 |
| 946 | PRASPGTPSL | 13 |
| 952 | TPSLVRLASG | 13 |
| 977 | SPTKQKSVCD | 13 |
| 1029 | AFRDKDDLPF | 13 |

TABLE XL-continued

| Pos | 1234567890 | score |
|---|---|---|
| 1061 | APKCRPGTLC | 13 |
| 36 | VTWRKEPAVL | 12 |
| 80 | SSSRALPGSL | 12 |
| 84 | ALPGSLPAFA | 12 |
| 85 | LPGSLPAFAD | 12 |
| 89 | LPAFADLPRS | 12 |
| 95 | LPRSCPESEQ | 12 |
| 259 | SEEALGVGSL | 12 |
| 264 | GVGSLSVFQL | 12 |
| 266 | GSLSVFQLHL | 12 |
| 277 | QCIPNLSYPL | 12 |
| 291 | IPEILKFSEK | 12 |
| 309 | LELPATAARL | 12 |
| 324 | IMQIKEFEEL | 12 |
| 353 | NVDKWDDFCL | 12 |
| 364 | EGYGHSFLIM | 12 |
| 387 | MGSGKSNVGT | 12 |
| 411 | HVRREDLDKL | 12 |
| 527 | EDKLMAKALL | 12 |
| 528 | DKLMAKALLL | 12 |
| 566 | KFLIKKKANL | 12 |
| 763 | SLSHKKEEDL | 12 |
| 779 | LREEIAKLRL | 12 |
| 812 | KEKLLKTIQL | 12 |
| 817 | KTIQLNEEAL | 12 |
| 843 | QHAQASVQQL | 12 |
| 883 | QHAQASVQQL | 12 |
| 936 | GPGTHLPPRE | 12 |
| 941 | LPPREPRASP | 12 |
| 962 | ARAAALPPPT | 12 |
| 969 | PPTGKNGRSP | 12 |
| 1075 | PPHRNADTPP | 12 |
| 1083 | PPHRHTTTLP | 12 |

TABLE XLI

| Pos | 123456789 | score |
|---|---|---|
| V1A-HLA-B08-10mers:251P5G2 | | |
| No results found. | | |

TABLE XLI-continued

| Pos | 123456789 | score |
|---|---|---|
| V2A-HLA-B08-10mers:251P5G2 | | |
| No results found. | | |
| V3A-HLA-B08-10mers:251P5G2 | | |
| No results found. | | |
| V4A-HLA-B08-10mers:251P5G2 | | |
| No results found. | | |
| V12A-HLA-B08-10mers:251P5G2 | | |
| No results found. | | |
| V12B-HLA-B08-10mers:251P5G2 | | |
| No results found. | | |

TABLE XLII

| Pos | 123456789 | score |
|---|---|---|
| V1A-HLA-B1510-10mers:251P5G2 | | |
| No results found. | | |
| V2A-HLA-B1510-10mers:251P5G2 | | |
| No results found. | | |
| V3A-HLA-B1510-10mers:251P5G2 | | |
| No results found. | | |
| V4A-HLA-B1510-10mers:251P5G2 | | |
| No results found. | | |
| V12A-HLA-B1510-10mers:251P5G2 | | |
| No results found. | | |
| V12B-HLA-B1510-10mers:251P5G2 | | |
| No results found. | | |

TABLE XLIII

| Pos | 123456789 | score |
|---|---|---|
| V1A-HLA-B2705-10mers:251P5G2 | | |
| No results found. | | |
| V2A-HLA-B2705-10mers:251P5G2 | | |
| No results found. | | |
| V3A-HLA-B2705-10mers:251P5G2 | | |
| No results found. | | |
| V4A-HLA-B2705-10mers:251P5G2 | | |
| No results found. | | |
| V12A-HLA-B2705-10mers:251P5G2 | | |
| No results found. | | |

TABLE XLIII-continued

| Pos | 123456789 | score |
|---|---|---|
| V12B-HLA-B2705-10mers:251P5G2 | | |
| No results found. | | |

TABLE XLIV

V1A-HLA-B2709-10mers:251P5G2

| Pos | 123456789 | score |
|---|---|---|
| No results found. | | |

V2A-HLA-B2709-10mers:251P5G2

| Pos | 123456789 | score |
|---|---|---|
| No results found. | | |

V3A-HLA-B2709-10mers:251P5G2

| Pos | 123456789 | score |
|---|---|---|
| No results found. | | |

V4A-HLA-B2709-10mers:251P5G2

| Pos | 123456789 | score |
|---|---|---|
| No results found. | | |

V12A-HLA-B2709-10mers:251P5G2

| Pos | 123456789 | score |
|---|---|---|
| No results found. | | |

V12B-HLA-B2709-10mers:251P5G2

| Pos | 123456789 | score |
|---|---|---|
| No results found. | | |

TABLE XLV

V1A-HLA-B4402-10mers:251P5G2
Each peptide is a portion of SEQ ID NO: 3; each start position is specified, the length of peptide is 10 amino acids, and the end position for each peptide is the start position plus nine.

| Pos | 1234567890 | score |
|---|---|---|
| 62 | FESLNFQNDF | 23 |
| 160 | FPINSIIRGL | 18 |
| 10 | ASQPTLFSFF | 17 |
| 36 | TYLPVCHVAL | 17 |
| 77 | FYLRRVIRVL | 17 |
| 164 | SIIRGLFFTL | 17 |
| 178 | DVFLKQIMLF | 17 |
| 100 | VNISPSISWL | 16 |
| 142 | ASSNVTQINL | 16 |
| 147 | TQINLHVSKY | 16 |

TABLE XLV-continued

| Pos | | score |
|---|---|---|
| 56 | FLSPQLFESL | 15 |
| 182 | KQIMLFSSVY | 15 |
| 206 | SQPQPLPKDL | 15 |
| 242 | STSSTLPWAY | 15 |
| 20 | SASSPFLLFL | 14 |
| 22 | SSPFLLFLDL | 14 |
| 28 | FLDLRPERTY | 14 |
| 43 | VALIHMVVLL | 14 |
| 69 | NDFKYEASFY | 14 |
| 74 | EASFYLRRVI | 14 |
| 103 | SPSISWLVRF | 14 |
| 105 | SISWLVRFKW | 14 |
| 112 | FKWKSTIFTF | 14 |
| 115 | KSTIFTFHLF | 14 |
| 117 | TIFTFHLFSW | 14 |
| 128 | LSFPVSSSLI | 14 |
| 156 | YCSLFPINSI | 14 |
| 190 | VYMMTLIQEL | 14 |
| 200 | QEILVPSQPQ | 14 |
| 202 | ILVPSQPQPL | 14 |
| 238 | DFIISTSSTL | 14 |
| 240 | IISTSSTLPW | 14 |
| 6 | KLVLASQPTL | 13 |
| 7 | LVLASQPTLF | 13 |
| 17 | SFFSASSPFL | 13 |
| 18 | FFSASSPFLL | 13 |
| 19 | FSASSPFLLF | 13 |
| 29 | LDLRPERTYL | 13 |
| 33 | PERTYLPVCH | 13 |
| 42 | HVALIHMVVL | 13 |
| 58 | SPQLFESLNF | 13 |
| 85 | VLSICTTCLL | 13 |
| 114 | WKSTIFTFHL | 13 |
| 129 | SFPVSSSLIF | 13 |
| 166 | IRGLFFTLSL | 13 |
| 167 | RGLFFTLSLF | 13 |
| 171 | FTLSLFRDVF | 13 |
| 172 | TLSLFRDVFL | 13 |
| 175 | LFRDVFLKQI | 13 |

TABLE XLV-continued

| | | |
|---|---|---|
| 194 | TLIQELQEIL | 13 |
| 197 | QELQEILVPS | 13 |
| 9 | LASQPTLFSF | 12 |
| 16 | FSFFSASSPF | 12 |
| 47 | HMVVLLTMVF | 12 |
| 48 | MVVLLTMVFL | 12 |
| 52 | LTMVFLSPQL | 12 |
| 53 | TMVFLSPQLF | 12 |
| 64 | SLNFQNDFKY | 12 |
| 73 | YEASFYLRRV | 12 |
| 84 | RVLSICTTCL | 12 |
| 88 | ICTTCLLGML | 12 |
| 110 | VRFKWKSTIF | 12 |
| 119 | FTFHLFSWSL | 12 |
| 121 | FHLFSWSLSF | 12 |
| 127 | SLSFPVSSSL | 12 |
| 130 | FPVSSSLIFY | 12 |
| 161 | PINSIIRGLF | 12 |
| 162 | INSIIRGLFF | 12 |
| 186 | LFSSVYMMTL | 12 |
| 217 | RGKSHQHILL | 12 |
| 221 | HQHILLPVSF | 12 |
| 37 | YLPVCHVALI | 11 |
| 68 | QNDFKYEASF | 11 |
| 99 | VVNISPSISW | 11 |
| 150 | NLHVSKYCSL | 11 |
| 151 | LHVSKYCSLF | 11 |
| 177 | RDVFLKQIML | 11 |
| 216 | CRGKSHQHIL | 11 |
| 226 | LPVSFSVGMY | 11 |
| 230 | FSVGMYKMDF | 11 |

V2A-B4402-10mers:251P5G2
Each peptide is a portion of SEQ ID NO: 5; each start position is specified, the length of peptide is 10 amino acids, and the end position for each peptide is the start position plus nine.

| Pos | 1234567890 | score |
|---|---|---|
| 4 | ASQPTLCSFF | 16 |
| 3 | LASQPTLCSF | 12 |
| 10 | CSFFSASSPF | 12 |

V3A-B4402-10mers:251P5G2
Each peptide is a portion of SEQ ID NO: 7; each start position is specified, the length of peptide is 10 amino acids, and the end position for each peptide is the start position plus nine.

| Pos | 1234567890 | score |
|---|---|---|
| 2 | FYLRRVIRDL | 16 |
| 10 | DLSICTTCLL | 13 |
| 9 | RDLSICTTCL | 12 |
| 4 | LRRVIRDLSI | 9 |

V4A-HLA-B4402-10mers:251P5G2
Each peptide is a portion of SEQ ID NO: 9; each start position is specified, the length of peptide is 10 amino acids, and the end position for each peptide is the start position plus nine.

| Pos | 1234567890 | score |
|---|---|---|
| 3 | ICTTCLLDML | 12 |
| 8 | LLDMLQVVNI | 11 |
| 1 | LSICTTCLLD | 5 |

V12A-HLA-B4402-10mers
Each peptide is a portion of SEQ ID NO: 25; each start position is specified, the length of peptide is 10 amino acids, and the end position for each peptide is the start position plus nine.

| Pos | 1234567890 | score |
|---|---|---|
| 5 | PSISWLIMLF | 17 |
| 2 | NISPSISWLI | 14 |
| 4 | SPSISWLIML | 14 |
| 9 | WLIMLFSSVY | 14 |

V12B-HLA-B4402-10mers:251P5G2
Each peptide is a portion of SEQ ID NO: 25; each start position is specified, the length of peptide is 10 amino acids, and the end position for each peptide is the start position plus nine.

| Pos | 1234567890 | score |
|---|---|---|
| 233 | AEPPAHQRLL | 29 |
| 526 | NEDKLMAKAL | 27 |
| 781 | EEIAKLRLEL | 27 |
| 300 | KETGGGILGL | 26 |
| 806 | EEIESVKEKL | 26 |
| 309 | LELPATAARL | 25 |
| 812 | KEKLLKTIQL | 25 |
| 374 | KETSTKISGL | 24 |
| 721 | DEQNDTQKQL | 24 |
| 330 | FEELVKLHSL | 23 |
| 494 | QEDECVLMLL | 23 |
| 513 | DEYGNTALHY | 23 |
| 558 | HEQKQEVVKF | 23 |

TABLE XLV-continued

| | | |
|---|---|---|
| 259 | SEEALGVGSL | 22 |
| 647 | SENSNPVITI | 22 |
| 298 | SEKETGGGIL | 21 |
| 363 | SEGYGHSFLI | 20 |
| 867 | QEQEVAGFSL | 20 |
| 774 | RENSMLREEI | 19 |
| 76 | ALSLSSSRAL | 18 |
| 179 | AGCPPSRNSY | 18 |
| 577 | ALDRYGRTAL | 18 |
| 12 | ATFAAATGLW | 17 |
| 83 | RALPGSLPAF | 17 |
| 328 | KEFEELVKLH | 17 |
| 459 | ANGNSEVVQL | 17 |
| 648 | ENSNPVITIL | 17 |
| 732 | EEQNTGISQD | 17 |
| 777 | SMLREEIAKL | 17 |
| 823 | EEALTKTKVA | 17 |
| 1042 | QQSPRHTKDL | 17 |
| 15 | AAATGLWAAL | 16 |
| 29 | NPSRADPVTW | 16 |
| 103 | EQSATPAGAF | 16 |
| 105 | SATPAGAFLL | 16 |
| 209 | APGRSSSCAL | 16 |
| 234 | EPPAHQRLLF | 16 |
| 277 | QCIPNLSYPL | 16 |
| 321 | LNSIMQIKEF | 16 |
| 652 | PVITILNIKL | 16 |
| 817 | KTIQLNEEAL | 16 |
| 832 | AGFSLRQLGL | 16 |
| 870 | EVAGFSLRQL | 16 |
| 872 | AGFSLRQLGL | 16 |
| 124 | LEVPRPQAAP | 15 |
| 262 | ALGVGSLSVF | 15 |
| 288 | LRHIPEILKF | 15 |
| 292 | PEILKFSEKE | 15 |
| 445 | KRDKQKRTAL | 15 |
| 478 | VLDNKKRTAL | 15 |
| 529 | KLMAKALLLY | 15 |
| 546 | NKCGLTPLLL | 15 |

TABLE XLV-continued

| | | |
|---|---|---|
| 559 | EQKQEVVKFL | 15 |
| 654 | ITILNIKLPL | 15 |
| 667 | EEIKKHGSNP | 15 |
| 741 | DEILTNKQKQ | 15 |
| 742 | EILTNKQKQI | 15 |
| 756 | KEMNSELSLS | 15 |
| 760 | SELSLSHKKE | 15 |
| 769 | EEDLLRENSM | 15 |
| 807 | EIESVKEKLL | 15 |
| 830 | KVAGFSLRQL | 15 |
| 958 | LASGARAAAL | 15 |
| 1029 | AFRDKDDLPF | 15 |
| 58 | FPGTAARKEF | 14 |
| 62 | AARKEFSTTL | 14 |
| 65 | KEFSTTLTGH | 14 |
| 68 | STTLTGHSAL | 14 |
| 80 | SSSRALPGSL | 14 |
| 156 | LRAQGLTRAF | 14 |
| 255 | QEQPSEEALG | 14 |
| 260 | EEALGVGSLS | 14 |
| 273 | LHLIQCIPNL | 14 |
| 279 | IPNLSYPLVL | 14 |
| 315 | AARLSGLNSI | 14 |
| 331 | EELVKLHSLS | 14 |
| 406 | MEPRYHVRRE | 14 |
| 414 | REDLDKLHRA | 14 |
| 416 | DLDKLHRAAW | 14 |
| 429 | VPRKDLIVML | 14 |
| 467 | QLLLDRRCQL | 14 |
| 470 | LDRRCQLNVL | 14 |
| 527 | EDKLMAKALL | 14 |
| 528 | DKLMAKALLL | 14 |
| 569 | IKKKANLNAL | 14 |
| 591 | CCGSASIVNL | 14 |
| 592 | CGSASIVNLL | 14 |
| 612 | DLSGQTAREY | 14 |
| 624 | SSHHVICEL | 14 |
| 628 | HVICELLSDY | 14 |
| 631 | CELLSDYKEK | 14 |
| 650 | SNPVITILNI | 14 |

TABLE XLV-continued

| | | |
|---|---|---|
| 670 | KKHGSNPVGL | 14 |
| 687 | ASAGNGDDGL | 14 |
| 754 | AEKEMNSELS | 14 |
| 770 | EDLLRENSML | 14 |
| 788 | LELDETKHQN | 14 |
| 825 | ALTKTKVAGF | 14 |
| 845 | AQASVQQLCY | 14 |
| 847 | ASVQQLCYKW | 14 |
| 885 | AQASVQQLCY | 14 |
| 887 | ASVQQLCYKW | 14 |
| 932 | AGDQGPGTHL | 14 |
| 944 | REPRASPGTP | 14 |
| 949 | SPGTPSLVRL | 14 |
| 1106 | SAGGVGPTTL | 14 |

TABLE XLVI

| Pos | 123456789 | score |
|---|---|---|
| V1A-HLA-B5101-10mers:251P5G2 | | |
| No results found. | | |
| V2A-HLA-B5101-10mers:251P5G2 | | |
| No results found. | | |
| V3A-HLA-B5101-10mers:251P5G2 | | |
| No results found. | | |
| V4A-HLA-B5101-10mers:251P5G2 | | |
| No results found. | | |
| V12A-HLA-B5101-10mers:251P5G2 | | |
| No results found. | | |
| V12B-HLA-B5101-10mers:251P5G2 | | |
| No results found. | | |

TABLE XLVII-V12A

| Pos | 123456789012345 | score |
|---|---|---|
| HLA-DRBI0101-15mers:251P5G2 Each peptide is a portion of SEQ ID NO: 25; each start position is specified, the length of peptide is 15 amino acids, and the end position for each peptide is the start position plus fourteen. | | |
| 1 | MLQVVNISPSISWL | 33 |
| 2 | MLQVVNISPSISWLI | 29 |
| 11 | SISWLIMLFSSVYMM | 27 |
| 9 | SPSISWLIMLFSSVY | 24 |
| 12 | ISWLIMLFSSVYMMT | 23 |
| 13 | SWLIMLFSSVYMMTL | 23 |

TABLE XLVII-V12A-continued

| Pos | 123456789012345 | score |
|---|---|---|
| 5 | VVNISPSISWLIMLF | 22 |
| 3 | LQVVNISPSISWLIM | 18 |
| 14 | WLIMLFSSVYMMTLI | 17 |
| 10 | PSISWLIMLFSSVYM | 15 |
| 6 | VNISPSISWLIMLFS | 14 |
| DRB1-0101-15mers:251P5G2 Each peptide is a portion of SEQ ID NO: 25; each start position is specified, the length of peptide is 15 amino acids, and the end position for each peptide is the start position plus fourteen. | | |
| 169 | AFQVVHLAPTAPDGG | 32 |
| 40 | PVTWRKEPAVLPCCN | 30 |
| 386 | SGLIQEMGSGKSNVG | 30 |
| 644 | EKQMLKISSENSNPV | 30 |
| 656 | NPVITILNIKPLKV | 29 |
| 10 | HILLPTQATFAAATG | 28 |
| 567 | QEVVKFLIKKKANLN | 28 |
| 993 | SGWILPVPTFSSGSF | 28 |
| 57 | KGSWLSFPGTAARKE | 27 |
| 428 | AAWWGKVPRKDLIVM | 27 |
| 437 | KDLIVMLRDTDMNKR | 27 |
| 501 | DECVLMLLEHGADGN | 27 |
| 529 | IYNEDKLMAKALLLY | 27 |
| 659 | ITILNIKLPLKVEEE | 27 |
| 958 | PSLVRLASGARAAAL | 27 |
| 6 | KSHQHILLPTQATFA | 26 |
| 16 | QATFAAATGLWAALT | 26 |
| 84 | LSSSRALPGSLPAFA | 26 |
| 94 | LPAFADLPRSCPESE | 26 |
| 155 | RRDAACLRAQGLTRA | 26 |
| 158 | AACLRAQGLTRAFQV | 26 |
| 195 | LTHVRCAQGLEAASA | 26 |
| 220 | SCALRYRSGPSVSSA | 26 |
| 222 | ALRYRSGPSVSSAPS | 26 |
| 332 | IKEFEELVKLHSLSH | 26 |
| 374 | SFLIMKETSTKISGL | 26 |
| 600 | ASIVNLLLEQNVDVS | 26 |
| 671 | EEEIKKHGSNPVGLP | 26 |
| 925 | PGGVPLSEGGTAAGD | 26 |
| 992 | SSGWILPVPTFSSGS | 26 |
| 1012 | CPMFDVSPAMRLKSD | 26 |

TABLE XLVII-V12A-continued

| Pos | 123456789012345 | score |
|---|---|---|
| 9 | QHILLPTQATFAAAT | 25 |
| 70 | KEFSTTLTGHSALSL | 25 |
| 73 | STTLTGHSALSLSSS | 25 |
| 118 | LLGWERVVQRRLEVP | 25 |
| 198 | VRCAQGLEAASANLP | 25 |
| 208 | SANLPGAPGRSSSCA | 25 |
| 244 | QRLLFLPRAPQAVSG | 25 |
| 286 | NLSYPLVLRHIPEIL | 25 |
| 310 | GILGLELPATAARLS | 25 |
| 313 | GLELPATAARLSGLN | 25 |
| 335 | FEELVKLHSLSHKVI | 25 |
| 338 | LVKLHSLSHKVIQCV | 25 |
| 536 | MAKALLLYGADIESK | 25 |
| 830 | ALTKTKVAGFSLRQL | 25 |
| 919 | RSQIGDPGGVPLSEG | 25 |
| 23 | TGLWAALTTVSNPSR | 24 |
| 69 | RKEFSTTLTGHSALS | 24 |
| 79 | HSALSLSSSRALPGS | 24 |
| 128 | RLEVPRPQAAPATSA | 24 |
| 201 | AQGLEAASANLPGAP | 24 |
| 245 | RLLFLPRAPQAVSGP | 24 |
| 267 | ALGVGSLSVFQLHLI | 24 |
| 281 | IQCIPNLSYPLVLRH | 24 |
| 317 | PATAARLSGLNSIMQ | 24 |
| 346 | HKVIQCVFAKKKNVD | 24 |
| 364 | DFCLSEGYGHSFLIM | 24 |
| 375 | FLIMKETSTKISGLI | 24 |
| 513 | DGNIQDEYGNTALHY | 24 |
| 590 | ALILAVCCGSASIVN | 24 |
| 592 | ILAVCCGSASIVNLL | 24 |
| 612 | DVSSQDLSGQTAREY | 24 |
| 681 | PVGLPENLTNGASAG | 24 |
| 699 | DPLIPQRKSRKPENQ | 24 |
| 815 | SVKEKLLKTIQLNEE | 24 |
| 915 | GAALRSQIGDPGGVP | 24 |
| 940 | QGPGTHLPPREPRAS | 24 |
| 943 | GTHLPPREPRASPGT | 24 |
| 986 | QKSVCDSSGWILPVP | 24 |
| 1104 | SLPHFHVSAGGVGPT | 24 |
| 22 | ATGLWAALTTVSNPS | 23 |
| 103 | SCPESEQSATPAGAF | 23 |
| 309 | GGILGLELPATAARL | 23 |
| 493 | IKAVQCQEDECVLML | 23 |
| 615 | SQDLSGQTAREYAVS | 23 |
| 655 | SNPVITILNIKLPLK | 23 |
| 810 | LEEIESVKEKLLKTI | 23 |
| 957 | TPSLVRLASGARAAA | 23 |
| 1038 | KDDLPFFKTQQSPRH | 23 |
| 1041 | LPFFKTQQSPRHTKD | 23 |
| 1093 | TTTLPHRDTTTSLPH | 23 |
| 78 | GHSALSLSSSRALPG | 22 |
| 87 | SRALPGSLPAFADLP | 22 |
| 126 | QRRLEVPRPQAAPAT | 22 |
| 190 | RNSYRLTHVRCAQGL | 22 |
| 277 | QLHLIQCIPNLSYPL | 22 |
| 289 | YPLVLRHIPEILKFS | 22 |
| 305 | KETGGGILGLELPAT | 22 |
| 320 | AARLSGLNSIMQIKE | 22 |
| 362 | WDDFCLSEGYGHSFL | 22 |
| 524 | ALHYAIYNEDKLMAK | 22 |
| 549 | SKNKCGLTPLLLGVH | 22 |
| 559 | LLGVEHQKQEVVKFL | 22 |
| 589 | TALILAVCCGSASIV | 22 |
| 603 | VNLLLEQNVDVSSQD | 22 |
| 632 | HHVICELLSDYKEKQ | 22 |
| 647 | MLKISSENSNPVITI | 22 |
| 807 | NKILEEIESVKEKLL | 22 |
| 842 | RQLGLAQHAQASVQQ | 22 |
| 870 | QAQEQEVAGFSLRQL | 22 |
| 882 | RQLGLAQHAQASVQQ | 22 |
| 996 | ILPVPTFSSGSFLGR | 22 |
| 1109 | HVSAGGVGPTTLGSN | 22 |
| 14 | PTQATFAAATGLWAA | 21 |
| 264 | SEEALGVGSLSVFQL | 21 |
| 569 | VVKFLIKKKANLNAL | 21 |
| 607 | LEQNVDVSSQDLSGQ | 20 |
| 757 | EVAEKEMNSELSLSH | 21 |

TABLE XLVII-V12A-continued

| Pos | 123456789012345 | score |
|---|---|---|
| 804 | LRENKILEEIESVKE | 21 |
| 828 | EEALTKTKVAGFSLR | 21 |
| 60 | WLSFPGTAARKEFST | 20 |
| 114 | AGAFLLGWERVVQRR | 20 |
| 225 | YRSGPSVSSAPSPAE | 20 |
| 256 | VSGPQEQPSEEALGV | 20 |
| 300 | LKFSEKETGGGILGL | 20 |
| 306 | ETGGGILGLELPATA | 20 |
| 327 | NSIMQIKEFEELVKL | 20 |
| 372 | GHSFLIMKETSTKIS | 20 |
| 639 | LSDYKEKQMLKISSE | 20 |
| 733 | KQLSEEQNTGISQDE | 20 |
| 1011 | RCPMFDVSPAMRLKS | 20 |
| 1032 | HQAFRDKDDLPFFKT | 20 |
| 1106 | PHFHVSAGGVGPTTL | 20 |
| 65 | GTAARKEFSTTLTGH | 19 |
| 123 | RVVQRRLEVPRPQAA | 19 |
| 241 | PAHQRLLFLPRAPQA | 19 |
| 259 | PQEQPSEEALGVGSL | 19 |
| 273 | LSVFQLHLIQCIPNL | 19 |
| 299 | ILKFSEKETGGGILG | 19 |
| 414 | RYHVRREDLDKLHRA | 19 |
| 456 | RTALHLASANGNSEV | 19 |
| 478 | RCQLNVLDNKKRTAL | 19 |
| 504 | VLMLLEHGADGNIQD | 19 |
| 863 | HTEKTEQQAQEQEVA | 15 |
| 866 | KTEQQAQEQEVAGFS | 15 |
| 903 | HTEKTEQQAQEQGAA | 15 |
| 906 | KTEQQAQEQGAALRS | 15 |
| 908 | EQQAQEQGAALRSQI | 15 |
| 927 | GVPLSEGGTAAGDQG | 15 |
| 936 | AAGDQGPGTHLPPRE | 15 |
| 949 | REPRASPGTPSLVRL | 15 |
| 980 | GRSPTKQKSVCDSSG | 15 |
| 985 | KQKSVCDSSGWILPV | 15 |
| 1010 | RRCPMFDVSPAMRLK | 15 |
| 1023 | LKSDSNRETHQAFRD | 15 |
| 1045 | KTQQSPRHTKDLGQD | 15 |

TABLE XLVII-V12A-continued

| Pos | 123456789012345 | score |
|---|---|---|
| 1058 | QDDRAGVLAPKCRPG | 15 |
| 1059 | DDRAGVLAPKCRPGT | 15 |
| 1085 | ADTPPHRHTTTLPHR | 15 |
| 1086 | DTPPHRHTTTLPHRD | 15 |
| 1094 | TTLPHRDTTTSLPHF | 15 |

TABLE XLVIII-V12A

HLA-DRB10301-15mers:251P5G2
Each peptide is a portion of SEQ ID NO: 25; each start position is specified, the length of peptide is 15 amino acids, and the end position for each peptide is the start position plus fourteen.

| Pos | 123456789012345 | score |
|---|---|---|
| 1 | MLQVVNISPSISWL | 22 |
| 12 | ISWLIMLFSSVYMMT | 20 |
| 13 | SWLIMLFSSVYMMTL | 13 |
| 14 | WLIMLFSSVYMMTLI | 13 |
| 2 | MLQVVNISPSISWLI | 12 |
| 5 | VVNISPSISWLIMLF | 12 |
| 8 | ISPSISWLIMLFSSV | 12 |
| 3 | LQVVNISPSISWLIM | 11 |
| 4 | QVVNISPSISWLIML | 11 |
| 9 | SPSISWLIMLFSSVY | 11 |
| 15 | LIMLFSSVYMMTLIQ | 11 |
| 470 | VVQLLLDRRCQLVNL | 37 |
| 635 | ICELLSDYKEKQMLK | 30 |
| 1020 | AMRLKSDSNRETHQA | 29 |
| 8 | HQHILLPTQATFAAA | 28 |
| 569 | VVKFLIKKKANLNAL | 27 |
| 655 | SNPVITILNIKPLK | 27 |
| 810 | LEEIESVKEKLLKTI | 27 |
| 1053 | TKDLGQDDRAGVLAP | 27 |
| 278 | LHLIQCIPNLSYPLV | 26 |
| 481 | LNVLDNKKRTALIKA | 26 |
| 580 | LNALDRYGRTALILA | 26 |
| 544 | GADIESKNKCGLTPL | 25 |
| 766 | ELSLSHKKEEDLLRE | 25 |
| 724 | HSDEQNDTQKQLSEE | 24 |
| 439 | LIVMLRDTDMNKRDK | 23 |
| 712 | NQQFPDTENEEYHSD | 23 |

TABLE XLVIII-V12A-continued

HLA-DRBI0301-15mers:251P5G2
Each peptide is a portion of SEQ ID NO: 25; each start position is specified, the length of peptide is 15 amino acids, and the end position for each peptide is the start position plus fourteen.

| Pos | 123456789012345 | score |
|---|---|---|
| 780 | ENSMLREEIAKLRLE | 23 |
| 740 | NTGISQDEILTNKQK | 22 |
| 790 | KLRLELDETKHQNQL | 22 |
| 73 | STTLTGHSALSLSSS | 21 |
| 79 | HSALSLSSSRALPGS | 21 |
| 432 | GKVPRKDLIVMLRDT | 21 |
| 828 | EEALTKTKVAGFSLR | 21 |
| 46 | EPAVLPCCNLEKGSW | 20 |
| 52 | CCNLEKGSWLSFPGT | 20 |
| 115 | GAFLLGWERVVQRRL | 20 |
| 243 | HQRLLFLPRAPQAVS | 20 |
| 267 | ALGVGSLSVFQLHLI | 20 |
| 289 | YPLVLRHIPEILKFS | 20 |
| 329 | IMQIKEFEELVKLHS | 20 |
| 414 | RYHVRREDLDKLHRA | 20 |
| 501 | DECVLMLLEHGADGN | 20 |
| 532 | EDKLMAKALLLYGAD | 20 |
| 556 | TPLLLGVHEQKQEVV | 20 |
| 600 | ASIVNLLLEQNVDVS | 20 |
| 602 | IVNLLLEQNVDVSSQ | 20 |
| 631 | HHHVICELLSDYKEK | 20 |
| 661 | ILNIKLPLKVEEEIK | 20 |
| 817 | KEKLLKTIQLNEEAL | 20 |
| 821 | LKTIQLNEEALTKTK | 20 |
| 919 | RSQIGDPGGVPLSEG | 20 |
| 38 | ADPVTWRKEPAVLPC | 19 |
| 265 | EEALGVGSLSVFQLH | 19 |
| 290 | PLVLRHIPEILKFSE | 19 |
| 296 | IPEILKFSEKETGGG | 19 |
| 327 | NSIMQIKEFEELVKL | 19 |
| 354 | AKKKNVDKWDDFCLS | 19 |
| 364 | DFCLSEGYGHSFLIM | 19 |
| 480 | QLNVLDNKKRTALIK | 19 |
| 571 | KFLIKKKANLNALDR | 19 |
| 645 | KQMLKISSENSNPVI | 19 |
| 665 | KLPLKVEEEIKKHGS | 19 |

TABLE XLVIII-V12A-continued

HLA-DRBI0301-15mers:251P5G2
Each peptide is a portion of SEQ ID NO: 25; each start position is specified, the length of peptide is 15 amino acids, and the end position for each peptide is the start position plus fourteen.

| Pos | 123456789012345 | score |
|---|---|---|
| 679 | SNPVGLPENLTNGAS | 19 |
| 720 | NEEYHSDEQNDTQKQ | 19 |
| 745 | QDEILTNKQKQIEVA | 19 |
| 806 | ENKILEEIESVKEKL | 19 |
| 833 | KTKVAGFSLRQLGLA | 19 |
| 873 | EQEVAGFSLRQLGLA | 19 |
| 960 | LVRLASGARAAALPP | 19 |
| 986 | QKSVCDSSGWILPVP | 19 |
| 996 | ILPVPTFSSGSFLGR | 19 |
| 1014 | MFDVSPAMRLKSDSN | 19 |
| 26 | WAALTTVSNPSRADP | 18 |
| 29 | LTTVSNPSRADPVTW | 18 |
| 122 | ERVVQRRLEVPRPQA | 18 |
| 163 | AQGLTRAFQVVHLAP | 18 |
| 246 | LLFLPRAPQAVSGPQ | 18 |
| 269 | GVGSLSVFQLHLIQC | 18 |
| 293 | LRHIPEILKFSEKET | 18 |
| 297 | PEILKFSEKETGGGI | 18 |
| 323 | LSGLNSIMQIKEFEE | 18 |
| 349 | IQCVFAKKKNVDKWD | 18 |
| 356 | KKNVDKWDDFCLSEG | 18 |
| 419 | REDLDKLHRAAWWGK | 18 |
| 436 | RKDLIVMLRDTDMNK | 18 |
| 445 | DTDMNKRDKQKRTAL | 18 |
| 446 | TDMNKRDKQKRTALH | 18 |
| 472 | QLLLDRRCQLNVLDN | 18 |
| 479 | CQLNVLDNKKRTALI | 18 |
| 530 | YNEDKLMAKALLLYG | 18 |
| 559 | LLGVHEQKQEVVKFL | 18 |
| 567 | QEVVKFLIKKKANLN | 18 |
| 608 | EQNVDVSSQDLSGQT | 18 |
| 615 | SQDLSGQTAREYAVS | 18 |
| 698 | DDGLIPQRKSRKPEN | 18 |
| 711 | ENQQFPDTENEEYHS | 18 |
| 746 | DEILTNKQKQIEVAE | 18 |

TABLE XLVIII-V12A-continued

HLA-DRBI0301-15mers:251P5G2

Each peptide is a portion of SEQ ID NO: 25; each start position is specified, the length of peptide is 15 amino acids, and the end position for each peptide is the start position plus fourteen.

| Pos | 123456789012345 | score |
|---|---|---|
| 773 | KEEDLLRENSMLREE | 18 |
| 1004 | SGSFLGRRCPMFDVS | 18 |
| 1032 | HQAFRDKDDLPFFKT | 18 |
| 1033 | QAFRDKDDLPFFKTQ | 18 |
| 1054 | KDLGQDDRAGVLAPK | 18 |
| 1094 | TTLPHRDTTTSLPHF | 18 |

TABLE XLIX-V12A

HLA-DR1-0410-15mers:251P5G2

No results found.

DR-0401-15mers:251P5G2

Each peptide is a portion of SEQ ID NO: 25; each start position is specified, the length of peptide is 15 amino acids, and the end position for each peptide is the start position plus fourteen.

| Pos | Peptide | Score |
|---|---|---|
| 23 | TGLWAALTTVSNPSR | 28 |
| 118 | LLGWERVVQRRLEVP | 28 |
| 428 | AAWWGKVPRKDLIVM | 28 |
| 720 | NEEYHSDEQNDTQKQ | 28 |
| 22 | ATGLWAALTTVSNPS | 26 |
| 243 | HQRLLFLPRAPQAVS | 26 |
| 246 | LLFLPRAPQAVSGPQ | 26 |
| 320 | AARLSGLNSIMQIKE | 26 |
| 338 | LVKLHSLSHKVIQCV | 26 |
| 374 | SFLIMKETSTKISGL | 26 |
| 470 | VVQLLLDRRCQLNVL | 26 |
| 602 | IVNLLLEQNVDVSSQ | 26 |
| 632 | HHVICELLSDYKEKQ | 26 |
| 644 | EKQMLKISSENSNPV | 26 |
| 647 | MLKISSENSNPVITI | 26 |
| 655 | SNPVITILNIKLPLK | 26 |
| 732 | QKQLSEEQNTGISQD | 26 |
| 790 | KLRLELDETKHQNQL | 26 |
| 841 | LRQLGLAQHAQASVQ | 26 |
| 881 | LRQLGLAQHAQASVQ | 26 |
| 993 | SGWILPVPTFSSGSF | 26 |
| 1014 | MFDVSPAMRLKSDSN | 26 |
| 1020 | AMRLKSDSNRETHQA | 26 |
| 1038 | KDDLPFFKTQQSPRH | 26 |
| 1053 | TKDLGQDDRAGVLAP | 26 |
| 16 | QATFAAATGLWAALT | 22 |
| 57 | KGSWLSFPGTAARKE | 22 |
| 69 | RKEFSTTLTGHSALS | 22 |
| 94 | LPAFADLPRSCPESE | 22 |
| 167 | TRAFQVVHLAPTAPD | 22 |
| 222 | ALRYRSGPSVSSAPS | 22 |
| 286 | NLSYPLVLRHIPEIL | 22 |
| 332 | IKEFEELVKLHSLSH | 22 |
| 527 | YAIYNEDKLMAKALL | 22 |
| 540 | LLLYGADIESKNKCG | 22 |
| 623 | AREYAVSSHHHVICE | 22 |
| 856 | QLCYKWNHTEKTEQQ | 22 |
| 896 | QLCYKWGHTEKTEQQ | 22 |
| 10 | HILLPTQATFAAATG | 20 |
| 26 | WAALTTVSNPSRADP | 20 |
| 46 | EPAVLPCCNLEKGSW | 20 |
| 79 | HSALSLSSSRALPGS | 20 |
| 115 | GAFLLGWERVVQRRL | 20 |
| 163 | AQGLTRAFQVVHLAP | 20 |
| 170 | FQVVHLAPTAPDGGA | 20 |
| 195 | LTHVRCAQGLEAASA | 20 |
| 208 | SANLPGAPGRSSSCA | 20 |
| 228 | GPSVSSAPSPAEPPA | 20 |
| 267 | ALGVGSLSVFQLHLI | 20 |
| 270 | VGSLSVFQLHLIQCI | 20 |
| 275 | VFQLHLIQCIPNLSY | 20 |
| 278 | LHLIQCIPNLSYPLV | 20 |
| 281 | IQCIPNLSYPLVLRH | 20 |
| 290 | PLVLRHIPEILKFSE | 20 |
| 296 | IPEILKFSEKETGGG | 20 |
| 308 | GGGILGLELPATAAR | 20 |
| 309 | GGILGLELPATAARL | 20 |
| 323 | LSGLNSIMQIKEFEE | 20 |
| 329 | IMQIKEFEELVKLHS | 20 |
| 335 | FEELVKLHSLSHKVI | 20 |
| 346 | HKVIQCVFAKKKNVD | 20 |
| 375 | FLIMKETSTKISGLI | 20 |

TABLE XLIX-V12A-continued

| | | |
|---|---|---|
| 382 | STKISGLIQEMGSGK | 20 |
| 385 | ISGLIQEMGSGKSNV | 20 |
| 386 | SGLIQEMGSGKSNVG | 20 |
| 414 | RYHVRREDLDKLHRA | 20 |
| 419 | REDLDKLHRAAWWGK | 20 |
| 422 | LDKLHRAAWWGKVPR | 20 |
| 437 | KDLIVMLRDTDMNKR | 20 |
| 439 | LIVMLRDTDMNKRDK | 20 |
| 456 | RTALHLASANGNSEV | 20 |
| 478 | RCQLNVLDNKKRTAL | 20 |
| 489 | RTALIKAVQCQEDEC | 20 |
| 501 | DECVLMLLEHGADGN | 20 |
| 502 | ECVLMLLEHGADGNI | 20 |
| 513 | DGNIQDEYGNTALHY | 20 |
| 526 | HYAIYNEDKLMAKAL | 20 |
| 539 | ALLLYGADIESKNKC | 20 |
| 555 | LTPLLLGVHEQKQEV | 20 |
| 556 | TLPPPGVHEQKQEVV | 20 |
| 559 | LLGVHEQKQEVVKFL | 20 |
| 566 | KQEVVKFLIKKKANL | 20 |
| 567 | QEVVKFLIKKKANLN | 20 |
| 577 | KANLNALDRYGRTAL | 20 |
| 580 | LNALDRYGRTALILA | 20 |
| 588 | RTALILAVCCGSASI | 20 |
| 589 | TALILAVCCGSASIV | 20 |
| 599 | SASIVNLLLEQNVDV | 20 |
| 600 | ASIVNLLLEQNVDVS | 20 |
| 608 | EQNVDVSSQDLSGQT | 20 |
| 635 | ICELLSDYKEKQMLK | 20 |
| 658 | VITILNIKLPLKVEE | 20 |
| 665 | KLPLKVEEEIKKHGS | 20 |
| 671 | EEEIKKHGSNPVGLP | 20 |
| 679 | SNPVGLPENLTNGAS | 20 |
| 681 | PVGLPENLTNGASAG | 20 |
| 685 | PENLTNGASAGNGDD | 20 |
| 740 | NTGISQDEILTNKQK | 20 |
| 745 | QDEILTNKQKQIEVA | 20 |
| 753 | QKQIEVAEKEMNSEL | 20 |
| 760 | EKEMNSELSLSHKKE | 20 |

TABLE XLIX-V12A-continued

| | | |
|---|---|---|
| 774 | EEDLLRENSMLREEI | 20 |
| 780 | ENSMLREEIAKLRLE | 20 |
| 788 | IAKLRLELDETKHQN | 20 |
| 792 | RLELDETKHQNQLRE | 20 |
| 806 | ENKILEEIESVKEKL | 20 |
| 807 | NKILEEIESVKEKLL | 20 |
| 810 | LEEIESVKEKLLKTI | 20 |
| 823 | TIQLNEEALTKTKVA | 20 |
| 833 | KTKVAGFSLRQLGLA | 20 |
| 843 | QLGLAQHAQASVQQL | 20 |
| 851 | QASVQQLCYKWNHTE | 20 |
| 873 | EQEVAGFSLRQLGLA | 20 |
| 883 | QLGLAQHAQASVQQL | 20 |
| 957 | TPSLVRLASGARAAA | 20 |
| 958 | PSLVRLASGARAAAL | 20 |
| 960 | LVRLASGARAAALPP | 20 |
| 996 | ILPVPTFSSGSFLGR | 20 |
| 7 | SHQHILLPTQATFAA | 18 |
| 65 | GTAARKEFSTTLTGH | 18 |
| 66 | TAARKEFSTTLTGHS | 18 |
| 75 | TLTGHSALSLSSSRA | 18 |
| 78 | GHSALSLSSSRALPG | 18 |
| 125 | VQRRLEVPRPQAAPA | 18 |
| 160 | CLRAQGLTRAFQVVH | 18 |
| 200 | CAQGLEAASANLPGA | 18 |
| 216 | GRSSSCALRYRSGPS | 18 |
| 225 | YRSGPSVSSAPSPAE | 18 |
| 236 | SPAEPPAHQRLLFLP | 18 |
| 249 | LPRAPQAVSGPQEQP | 18 |
| 264 | SEEALGVGSLSVFQL | 18 |
| 269 | GVGSLSVFQLHLIQC | 18 |
| 400 | GTWGDYDDSAFMEPR | 18 |
| 406 | DDSAFMEPRYHVRRE | 18 |
| 411 | MEPRYHVRREDLDKL | 18 |
| 446 | TDMNKRDKQKRTALH | 18 |
| 452 | DKQKRTALHLASANG | 18 |
| 464 | ANGNSEVQLLLDRR | 18 |
| 469 | EVVQLLLDRRCQLNV | 18 |
| 518 | DEYGNTALHYAIYNE | 18 |
| 523 | TALHYAIYNEDKLMA | 18 |

TABLE XLIX-V12A-continued

| | | |
|---|---|---|
| 541 | LLYGADIESKNKCGL | 18 |
| 596 | CCGSASIVNLLLEQN | 18 |
| 607 | LEQNVDVSSQDLSGQ | 18 |
| 611 | VDVSSQDLSGQTARE | 18 |
| 638 | LLSDYKEKQMLKISS | 18 |
| 652 | SENSNPVITILNIKL | 18 |
| 682 | VGLPENLTNGASAGN | 18 |
| 696 | NGDDGLIPQRKSRKP | 18 |
| 721 | EEYHSDEQNDTQKQL | 18 |
| 724 | HSDEQNDTQKQLSEE | 18 |
| 737 | EEQNTGISQDEILTN | 18 |
| 742 | GISQDEILTNKQKQI | 18 |
| 743 | ISQDEILTNKQKQIE | 18 |
| 756 | IEVAEKEMNSELSLS | 18 |
| 771 | HKKEEDLLRENSMLR | 18 |
| 815 | SVKEKLLKTIQLNEE | 18 |
| 824 | IQLNEEALTKTKVAG | 18 |
| 835 | KVAGFSLRQLGLAQH | 18 |
| 840 | SLRQLGLAQHAQASV | 18 |
| 859 | YKWNHTEKTEQQAQE | 18 |
| 875 | EVAGFSLRQLGLAQH | 18 |
| 880 | SLRQLGLAQHAQASV | 18 |
| 899 | YKWGHTEKTEQQAQE | 18 |
| 911 | AQEQGAALRSQIGDP | 18 |
| 954 | SPGTPSLVRLASGAR | 18 |
| 985 | KQKSVCDSSGWILPV | 18 |
| 1010 | RRCPMFDVSPAMRLK | 18 |
| 1017 | VSPAMRLKSDSNRET | 18 |
| 1068 | KCRPGTLCHTDTPPH | 18 |
| 1090 | HRHTTTLPHRDTTTS | 18 |
| 1094 | TTLPHRDTTTSLPHF | 18 |
| 1099 | RDTTTSLPHFHVSAG | 18 |
| 350 | QCVFAKKKNVDKWDD | 17 |
| 40 | PVTWRKEPAVLPCCN | 16 |
| 114 | AGAFLLGWERVVQRR | 16 |
| 190 | RNSYRLTHVRCAQGL | 16 |
| 273 | LSVFQLHLIQCIPNL | 16 |
| 359 | VDKWDDFCLSEGYGH | 16 |
| 368 | SEGYGHSFLIMKETS | 16 |
| 372 | GHSFLIMKETSTKIS | 16 |
| 517 | QDEYGNTALHYAIYN | 16 |
| 524 | ALHYAIYNEDKLMAK | 16 |
| 583 | LDRYGRTALILAVCC | 16 |
| 712 | NQQFPDTENEEYHSD | 16 |
| 858 | CYKWNHTEKTEQQAQ | 16 |
| 898 | CYKWGHTEKTEQQAQ | 16 |
| 992 | SSGWILPVPTFSSGS | 16 |
| 1012 | CPMFDVSPAMRLKSD | 16 |
| 1040 | DLPFFKTQQSPRHTK | 16 |
| 1041 | LPFFKTQQSPRHTKD | 16 |
| 373 | HSFLIMKETSTKISG | 15 |
| 438 | DLIVMLRDTDMNKRD | 15 |
| 472 | QLLLDRRCQLNVLDN | 15 |
| 481 | LNVLDNKKRTALIKA | 15 |
| 571 | KFLIKKKANLNALDR | 15 |
| 1062 | AGVLAPKCRPGTLCH | 15 |
| 1093 | TTTLPHRDTTTSLPH | 15 |
| 8 | HQHILLPTQATFAAA | 14 |
| 9 | QHILLPTQATFAAAT | 14 |
| 29 | LTTVSNPSRADPVTW | 14 |
| 58 | GSWLSFPGTAARKEF | 14 |
| 73 | STTLTGHSALSLSSS | 14 |
| 87 | SRALPGSLPAFADLP | 14 |
| 91 | PGSLPAFADLPRSCP | 14 |
| 116 | AFLLGWERVVQRRLE | 14 |
| 126 | QRRLEVPRPQAAPAT | 14 |
| 128 | RLEVPRPQAAPATSA | 14 |
| 158 | AACLRAQGLTRAFQV | 14 |
| 169 | AFQVVHLAPTAPDGG | 14 |
| 192 | SYRLTHVRCAQGLEA | 14 |
| 201 | AQGLEAASANLPGAP | 14 |
| 244 | QRLLFLPRAPQAVSG | 14 |
| 253 | PQAVSGPQEQPSEEA | 14 |
| 272 | SLSVFQLHLIQCIPN | 14 |
| 277 | QLHLIQCIPNLSYPL | 14 |
| 289 | YPLVLRHIPEILKFS | 14 |
| 293 | LRHIPEILKFSEKET | 14 |
| 311 | ILGLELPATAARLSG | 14 |
| 313 | GLELPATAARLSGLN | 14 |

TABLE XLIX-V12A-continued

| | | |
|---|---|---|
| 326 | LNSIMQIKEFEELVK | 14 |
| 336 | EELVKLHSLSHVKIQ | 14 |
| 345 | SHKVIQCVFAKKKNV | 14 |
| 356 | KKNVDKWDDFCLSEG | 14 |
| 389 | IQEMGSGKSNVGTWG | 14 |
| 436 | RKDLIVMLRDTDMNK | 14 |
| 458 | ALHLASANGNSEVVQ | 14 |
| 467 | NSEVVQLLLDRRCQL | 14 |
| 468 | SEVVQLLLDRRCQLN | 14 |
| 480 | QLNVDNKKRTALIK | 14 |
| 490 | TALIKAVQCQEDECV | 14 |
| 493 | IKAVQCQEDECVLML | 14 |
| 503 | CVLMLLEHGADGNIQ | 14 |
| 504 | VLMLLEHGADGNIQD | 14 |
| 505 | LMLLEHGADGNIQDE | 14 |
| 522 | NTALHYAIYNEDKLM | 14 |
| 533 | DKLMAKALLLYGADI | 14 |
| 538 | KALLLYGADIESKNK | 14 |
| 552 | KCGLTPLLLGVHEQK | 14 |
| 557 | PLLLGVHEQKQEVVK | 14 |
| 590 | ALILAVCCGSASIVN | 14 |
| 592 | ILAVCCGSASIVNLL | 14 |
| 603 | VNLLLEQNVDVSSQD | 14 |
| 604 | NLLLEQNVDVSSQDL | 14 |
| 610 | NVDVSSQDLSGQTAR | 14 |
| 625 | EYAVSSHHHVICELL | 14 |
| 631 | HHHVICELLSDYKEK | 14 |
| 636 | CELLSDYKEKQMLKI | 14 |
| 645 | KQMLKISSENSNPVI | 14 |
| 656 | NPVITILNIKLPLKV | 14 |
| 667 | PLKVEEEIKKHGSNP | 14 |
| 698 | DDGLIPQRKSRKPEN | 14 |
| 781 | NSMLREEIAKLRLEL | 14 |
| 785 | REEIAKLRLELDETK | 14 |
| 817 | KEKLLKTIQLNEEAL | 14 |
| 818 | EKLLKTIQLNEEALT | 14 |
| 821 | LKTIQLNEEALTKTK | 14 |
| 838 | GFSLRQLGLAQHAQA | 14 |
| 878 | GFSLRQLGLAQHAQA | 14 |

TABLE XLIX-V12A-continued

| | | |
|---|---|---|
| 891 | QASVQQLCYKWGHTE | 14 |
| 919 | RSQIGDPGGVPLSEG | 14 |
| 925 | PGGVPLSEGGTAAGD | 14 |
| 927 | GVPLSEGGTAAGDQG | 14 |
| 986 | QKSVCDSSGWILPVP | 14 |
| 1011 | RCPMFDVSPAMRLKS | 14 |
| 1071 | PGTLCHTDTPPHRNA | 14 |
| 1102 | TTSLPHFHVSAGGVG | 14 |
| 1107 | HFHVSAGGVGPTTLG | 14 |
| 1112 | AGGVGPTTLGSNREI | 14 |

HLA-DRB1-15mers:251P5G2
Each peptide is a portion of SEQ ID NO: 25; each start position is specified, the length of peptide is 15 amino acids, and the end position for each peptide is the start position plus fourteen.

| | | |
|---|---|---|
| 1 | MLQVVNISPSISWL | 21 |
| 2 | MLQVVNISPSISWLI | 19 |
| 9 | SPSISWLIMLFSSVY | 18 |
| 11 | SISWLIMLFSSVYMM | 16 |
| 12 | ISWLIMLFSSVYMMT | 13 |
| 10 | PSISWLIMLFSSVYM | 12 |
| 15 | LIMLFSSVYMMTLIQ | 9 |

DRB1-1101-15mers:251P5G2
Each peptide is a portion of SEQ ID NO: 25; each start position is specified, the length of peptide is 15 amino acids, and the end position for each peptide is the start position plus fourteen.

| | | |
|---|---|---|
| 332 | IKEFEELVKLHSLSH | 32 |
| 286 | NLSYPLVLRHIPEIL | 31 |
| 94 | LPAFADLPRSCPESE | 30 |
| 567 | QEVVKFLIKKKANLN | 27 |
| 428 | AAWWGKVPRKDLIVM | 24 |
| 166 | LTRAFQVVHLAPTAP | 23 |
| 954 | SPGTPSLVRLASGAR | 22 |
| 118 | LLGWERVVQRRLEVP | 21 |
| 338 | LVKLHSLSHKVIQCV | 21 |
| 371 | YGHSFLIMKETSTKI | 21 |
| 436 | RKDLIVMLRDTDMNK | 21 |
| 480 | QLNVDNKKRTALIK | 21 |
| 656 | NPVITILNIKLPLKV | 21 |
| 1002 | FSSGSFLGRRCPMFD | 21 |
| 1014 | MFDVSPAMRLKSDSN | 21 |
| 29 | LTTVSNPSRADPVTW | 20 |
| 125 | VQRRLEVPRPQAAPA | 20 |

TABLE XLIX-V12A-continued

| | | |
|---|---|---|
| 192 | SYRLTHVRCAQGLEA | 20 |
| 243 | HQRLLFLPRAPQAVS | 20 |
| 293 | LRHIPEILKFSEKET | 20 |
| 297 | PEILKFSEKETGGGI | 20 |
| 419 | REDLDKLHRAAWWGK | 20 |
| 502 | ECVLMLLEHGADGNI | 20 |
| 526 | HYAIYNEDKLMAKAL | 20 |
| 577 | KANLNALDRYGRTAL | 20 |
| 641 | DYKEKQMLKISSENS | 20 |
| 667 | PLKVEEEIKKHGSNP | 20 |
| 668 | LKVEEEIKKHGSNPV | 20 |
| 771 | HKKEEDLLRENSMLR | 20 |
| 841 | LRQLGLAQHAQASVQ | 20 |
| 881 | LRQLGLAQHAQASVQ | 20 |
| 960 | LVRLASGARAAALPP | 20 |
| 386 | SGLIQEMGSGKSNVG | 19 |
| 623 | AREYAVSSHHHVICE | 19 |
| 169 | AFQVVHLAPTAPDGG | 18 |
| 382 | STKISGLIQEMGSGK | 18 |
| 501 | DECVLMLLEHGADGN | 18 |
| 569 | VVKFLIKKKANLNAL | 18 |
| 589 | TALILAVCCGSASIV | 18 |
| 644 | EKQMLKISSENSNPV | 18 |
| 858 | CYKWNHTEKTEQQAQ | 18 |
| 891 | QASVQQLCYKWGHTE | 18 |
| 898 | CYKWGHTEKTEQQAQ | 18 |
| 992 | SSGWILPVPTFSSGS | 18 |
| 993 | SGWILPVPTFSSGSF | 18 |
| 1105 | LPHFHVSAGGVGPTT | 18 |
| 40 | PVTWRKEPAVLPCCN | 17 |
| 119 | LGWERVVQRRLEVPR | 17 |
| 167 | TRAFQVVHLAPTAPD | 17 |
| 190 | RNSYRLTHVRCAQGL | 17 |
| 442 | MLRDTDMNKRDKQKR | 17 |
| 486 | NKKRTALIKAVQCQE | 17 |
| 563 | HEQKQEVVKFLIKKK | 17 |
| 583 | LDRYGRTALILAVCC | 17 |
| 746 | DEILTNKQKQIEVAE | 17 |
| 836 | VAGFSLRQLGLAQHA | 17 |

TABLE XLIX-V12A-continued

| | | |
|---|---|---|
| 876 | VAGFSLRQLGLAQHA | 17 |
| 1090 | HRHTTTLPHRDTTTS | 17 |
| 16 | QATFAAATGLWAALT | 16 |
| 23 | TGLWAALTTVSNPSR | 16 |
| 57 | KGSWLSFPGTAARKE | 16 |
| 62 | SFPGTAARKEFSTTL | 16 |
| 69 | RKEFSTTLTGHSALS | 16 |
| 189 | SRNSYRLTHVRCAQG | 16 |
| 216 | GRSSSCALRYRSGPS | 16 |
| 222 | ALRYRSGPSVSSAPS | 16 |
| 299 | ILKFSEKETGGGILG | 16 |
| 334 | EFEELVKLHSLSHKV | 16 |
| 349 | IQCVFAKKKNVDKWD | 16 |
| 359 | VDKWDDFCLSEGYGH | 16 |
| 372 | GHSFLIMKETSTKIS | 16 |
| 402 | WGDYDDSAFMEPRYH | 16 |
| 408 | SAFMEPRYHVRREDL | 16 |
| 517 | QDEYGNTALHYAIYN | 16 |
| 555 | LTPLLLGVHEQKQEV | 16 |
| 698 | DDGLIPQRKSRKPEN | 16 |
| 782 | SMLREEIAKLRLELD | 16 |
| 1060 | DRAGVLAPKCRPGTL | 16 |
| 1099 | RDTTTSLPHFHVSAG | 16 |
| 36 | SRADPVTWRKEPAVL | 15 |
| 80 | SALSLSSSRALPGSL | 15 |
| 115 | GAFLLGWERVVQRRL | 15 |
| 147 | DPSPPCHQRRDAACL | 15 |
| 287 | LSYPLVLRHIPEILK | 15 |
| 418 | RREDLDKLHRAAWWG | 15 |
| 445 | DTDMNKRDKQKRTAL | 15 |
| 447 | DMNKRDKQKRTALHL | 15 |
| 468 | SEVVQLLLDRRCQLN | 15 |
| 469 | EVVQLLLDRRCQLNV | 15 |
| 530 | YNEDKLMAKALLLYG | 15 |
| 552 | KCGLTPLLLGVHEQK | 15 |
| 568 | EVVKFLIKKKANLNA | 15 |
| 625 | EYAVSSHHHVICELL | 15 |
| 635 | ICELLSDYKEKQMLK | 15 |
| 725 | SDEQNDTQKQLSEEQ | 15 |
| 753 | QKQIEVAEKEMNSEL | 15 |

TABLE XLIX-V12A-continued

| | | |
|---|---|---|
| 763 | MNSELSLSHKKEEDL | 15 |
| 814 | ESVKEKLLKTIQLNE | 15 |
| 825 | QLNEEALTKTKVAGF | 15 |
| 834 | TKVAGFSLRQLGLAQ | 15 |
| 874 | QEVAGFSLRQLGLAQ | 15 |
| 940 | QGPGTHLPPREPRAS | 15 |
| 977 | GKNGRSPTKQKSVCD | 15 |
| 1046 | TQQSPRHTKDLGQDD | 15 |
| 1074 | LCHTDTPPHRNADTP | 15 |

TABLE L

Protein Properties of 251P5G2

| | Bioinformatic Program | Outcome |
|---|---|---|
| ORF | ORF finder | 722-1489 |
| Protein length | | 255aa |
| Transmembrane region | TM Pred | 6TM, N-terminal outside, aa 7-29, 43-62, 82-100, 118-138, 158-176, 180-199 |
| | HMMTop | 6TM, aa 7-29, 38-58, 85-109, 118-142, 169-193, 224-243 |
| | Sosui | 5TM, aa 6-28, 39-61, 86-108, 119-141, 166-188 |
| | TMHMM | 5TM, N terminal inside, aa 7-29, 44-62, 83-102, 117-139, 159-181 |
| Signal Peptide | Signal P | cleavage between aa 129-130 |
| pI | pI/MW tool | pI 9.4 |
| Molecular weight | pI/MW tool | 29.3 kD |
| Localization | PSORT | microbody (peroxisome) 74.8%, mitochondrial inner membrane 71.4%, plasma membrane 65.0%, mitochondrial intermembrane 30.4% |
| | PSORT II | 44.4%: endoplasmic reticulum, 22.2%: mitochondrial, 22.2%: Golgi, 11.1%: nuclear |
| Motifs | Pfam | Vomeronasal organ pheromone receptor family, V1R |
| | Prints | Rhodopsin-like GPCR superfamily signature |
| | Blocks | Iodothyronine deiodinase aa 2-29 |

TABLE LI

Exon compositions of 251P5G2 v.1

| Exon number | Start | End |
|---|---|---|
| 1 | 1 | 2156 |

TABLE LII(a)

Nucleotide sequence of transcript variant 251P5G2 v.12 (SEQ ID NO: 70)

```
gttttttttt ttttttttt tttttttt tattttaagg gattcgttta ataggacttg    60
tggtaagtgg aataatgcca tgcaaaggtc cccatgtcta accaccaggt tctaggcatg   120
tattatggta tatgagaaat gggaattcag gctgcagatg aaatcaaggt tgataaccag   180
ctgactctaa aacaaaaaca ttaacttgaa ttacagattt gggcctaatg taattataag   240
cattcttaaa agtgaaagaa ataataagag aaactgagtg ctgtgatgtg agtcagttaa   300
acttttttt caacttttc tttaggtgat tattttccct taacataaaa tttactttag   360
ctcaactata caaacatgtg agttattgtt atgtaaccat cactcttcat taagaaatgc   420
tttgtaaaaa gtgagccagt ttttcatata cattcttcaa aatacattct caacattata   480
catcaaatta tatatacata catgcacaca tacactatat atatcaagga tttatatgag   540
aggattaatt aagaaaaaaa ttagtggaat aaaaataatg tttatgataa ttttggccat   600
agaatatata atacagatga tgtgaagtac aaaatgtttt ttatacttca tattttgatg   660
tacaaagtat gtttgtcttt gtaattcaga tgattacttt gcacttgtgt tcccatgaaa   720
aatgcctttc atttctaagc tggtattggc atctcagcca acactttct ccttcttttc   780
tgcgtcttct ccttttctgc ttttctgga tctcaggcca gagcgcactt acctaccagt   840
ctgtcatgtg gccctcatcc acatggtggt ccttctcacc atggtgttct tgtctccaca   900
gctctttgaa tcactgaatt ttcagaatga cttcaaatat gaggcatcct tctacctgag   960
gagggtgatc agggtcctct ccatttgtac cacctgcctc ctggacatgc tgcaggtcgt  1020
caacatcagc cccagcattt cctggttgat aatgctgttc tcaagtctct acatgatgac  1080
```

TABLE LII(a)-continued

Nucleotide sequence of transcript variant 251P5G2 v.12 (SEQ ID NO: 70)

```
tctcattcag gaactacagg agatcctggt accttcacag ccccagcctc tacctaagga 1140
tctttgcaga ggcaagagcc atcagcacat cctgctgccg actcaagcaa cttttgctgc 1200
agcaactgga ctatgggctg cactaaccac cgtatcaaat ccaagcagag cagatcctgt 1260
gacctggaga aggagccgg ctgtccttcc ctgctgtaac ctagagaaag gaagctggct 1320
gtccttccct ggcacagctg cacgcaagga attttccacc acgctcaccg ggcacagcgc 1380
gctgagcctc tccagttcgc gggccctccc cggctcgctc ccggctttcg cagacctccc 1440
ccgctcctgc cctgagtccg agcagagcgc aacgccagcc ggcgccttcc tcctgggctg 1500
ggagcgagtg gtgcagcggc ggctcgaagt ccccgggcct caagcagccc ccgcgactag 1560
cgcgacaccc tcgcgggatc cgagtccacc ctgccaccag cgccgggacg ccgcgtgcct 1620
cagagcccaa gggctgaccc gggccttcca ggtggtccat ctcgctccta cggctcccga 1680
cggtggcgct gggtgtcccc catcccgcaa ttcctaccgg ctgacccatg tgcgctgcgc 1740
ccaggggctg gaggctgcca gcgccaacct tcccggcgct ccggggcgga gcagctcctg 1800
cgccctgcgc taccgcagcg gcccttcagt cagctccgcg ccgtccccg cagagccccc 1860
ggcgcaccag cgcctgcttt tccttccccg agcgcctcaa gcagtctctg ggccgcagga 1920
acagccctct gaagaggcgc ttggtgtagg aagcctctca gttttccagt tacacctaat 1980
acagtgtatt ccaaatctaa gttacccact agtacttcgg cacattccag aaattctgaa 2040
attttctgaa aaggaaactg gtggtggaat tctaggctta gaattaccag cgacagctgc 2100
tcgcctctca ggattaaaca gcataatgca aatcaaagag tttgaagaat tggtaaaact 2160
tcacagcttg tcacacaaag tcattcagtg tgtgtttgca aagaaaaaaa atgtagacaa 2220
atgggatgac ttttgtctta gtgagggtta tggacattca ttcttaataa tgaaagaaac 2280
gtcgactaaa atatcaggtt taattcagga gatggggagc ggcaagagca acgtgggcac 2340
ttggggagac tacgacgaca gcgccttcat ggagccgagg taccacctcc gtcgagaaga 2400
tctggacaag ctccacagag ctgcctggtg gggtaaagtc cccagaaagg atctcatcgt 2460
catgctcagg gacactgaca tgaacaagag ggacaagcaa aagaggactg ctctacattt 2520
ggcctctgcc aatggaaatt cagaagtagt acaactcctg ctggacagac gatgtcaact 2580
taacgtcctt gacaacaaaa aaggacagc tctgataaag gccgtacaat gccaggaaga 2640
tgaatgtgtg ttaatgttgc tggaacatgg cgctgatgga aatattcaag atgagtatgg 2700
aaataccgct ctacactatg ctatctacaa tgaagataaa ttaatggcca aagcactgct 2760
cttatatggt gctgatattg aatcaaaaaa caagtgtggc ctcacaccac ttttgcttgg 2820
cgtacatgaa caaaaacagg aagtggtgaa atttttaatc aagaaaaaag ctaatttaaa 2880
tgcacttgat agatatggaa gaactgcccct catacttgct gtatgttgtg gatcagcaag 2940
tatagtcaat cttctacttg agcaaaatgt tgatgtatct tctcaagatc tatctggaca 3000
gacggccaga gagtatgctg tttctagtca tcatcatgta atttgtgaat tactttctga 3060
ctataaagaa aaacagatgc taaaaatctc ttctgaaaac agcaatccag tgataaccat 3120
ccttaatatc aaacttccac tcaaggttga agaagaaata aagaagcatg gaagtaatcc 3180
tgtgggatta ccagaaaacc tgactaatgg tgccagtgct ggcaatggtg atgatggatt 3240
aattccacaa aggaagagca gaaaacctga aatcagcaa tttcctgaca ctgagaatga 3300
agagtatcac agtgacgaac aaaatgatac ccagaaacaa ctttctgaag aacagaacac 3360
```

TABLE LII(a)-continued

Nucleotide sequence of transcript variant 251P5G2 v.12 (SEQ ID NO: 70)

```
tggaatatca caagatgaga ttctgactaa taaacaaaag cagatagaag tggctgaaaa    3420
ggaaatgaat tctgagcttt ctcttagtca taagaaagaa gaagatctct tgcgtgaaaa    3480
cagcatgttg cgggaagaaa ttgccaagct aagactggaa ctagatgaaa caaaacatca    3540
gaaccagcta agggaaaata aaattttgga ggaaattgaa agtgtaaaag aaaaacttct    3600
aaagactata caactgaatg aagaagcatt aacgaaaacc aaggtggctg gtttctcttt    3660
gcgccagctt ggccttgccc agcatgcaca agcctcagtg caacagctgt gctacaaatg    3720
gaaccacaca gagaaaacag agcagcaggc tcaggagcag gaggtggctg gtttctcttt    3780
gcgccagctt ggccttgccc agcatgcaca agcctcagta caacaactgt gctacaaatg    3840
gggccacaca gagaaaacag agcagcaggc tcaggagcag ggagctgcgc tgaggtccca    3900
gataggcgac cctggcgggg tgcccctgag cgaaggggggg acagcagcag gagaccaggg    3960
tccagggacc cacctcccac cgagggaacc tcgagcctcc cctggcaccc ctagcttggt    4020
ccgcctggcc tccggagccc gagctgctgc gcttccccca cccacaggga aaaacggccg    4080
atctccaacc aaacagaaat ctgtgtgtga ctcctctggt tggatactgc cagtccccac    4140
atttttcttcc gggagttttc ttggcagaag gtgcccaatg tttgatgttt cgccagccat    4200
gaggctgaaa agtgacagca atagagaaac acatcaggct ttccgcgaca agatgacct    4260
tcccttcttc aaaactcagc aatctccacg gcacacaaag gacttaggac aagatgaccg    4320
agctggagtc ctcgcccaa aatgcaggcc cggaacactc tgccacacgg acacaccacc    4380
acacagaaat gcggacacac caccacacag acacaccacc acgctgccac acagagacac    4440
caccacatcg ttgccacact ttcatgtgtc agctggcggt gtgggcccca cgactctggg    4500
ctctaataga gaaattactt ag
```

TABLE LIII(a)

Nucleotide sequence alignment of 251P5G2 v.1 (SEQ ID NO: 71) and 251P5G2 v.12 (SEQ ID NO: 72)

```
Score = 2009 bits (1045), Expect = 0.0 Identities = 1047/1048 (99%) Strand = Plus/Plus 251P5G2v.1:    1  gtttttttttttttttttttttttttttttattttaagggattcgtttaataggacttg   60
                  ||||||||||||||||||||||||||||||||||||||||||||||||||||||||||||
251P5G2v.12:   1  gtttttttttttttttttttttttttttttattttaagggattcgtttaataggacttg   60

251P5G2v.1:   61  tggtaagtggaataatgccatgcaaaggtccccatgtctaaccaccaggttctaggcatg  120
                  ||||||||||||||||||||||||||||||||||||||||||||||||||||||||||||
251P5G2v.12:  61  tggtaagtggaataatgccatgcaaaggtccccatgtctaaccaccaggttctaggcatg  120

251P5G2v.1:  121  tattatggtatatgagaaatgggaattcaggctgcagatgaaatcaaggttgataaccag  180
                  ||||||||||||||||||||||||||||||||||||||||||||||||||||||||||||
251P5G2v.12: 121  tattatggtatatgagaaatgggaattcaggctgcagatgaaatcaaggttgataaccag  180

251P5G2v.1:  181  ctgactctaaaacaaaaacattaacttgaattacagatttgggcctaatgtaattataag  240
                  ||||||||||||||||||||||||||||||||||||||||||||||||||||||||||||
251P5G2v.12: 181  ctgactctaaaacaaaaacattaacttgaattacagatttgggcctaatgtaattataag  240

251P5G2v.1:  241  cattcttaaaagtgaaagaaataataagagaaactgagtgctgtgatgtgagtcagttaa  300
                  ||||||||||||||||||||||||||||||||||||||||||||||||||||||||||||
251P5G2v.12: 241  cattcttaaaagtgaaagaaataataagagaaactgagtgctgtgatgtgagtcagttaa  300

251P5G2v.1:  301  acttttttttcaacttttctttaggtgattattttcccttaacataaaatttactttag  360
                  ||||||||||||||||||||||||||||||||||||||||||||||||||||||||||||
251P5G2v.12: 301  acttttttttcaacttttctttaggtgattattttcccttaacataaaatttactttag  360

251P5G2v.1:  361  ctcaactatacaaacatgtgagttattgttatgtaaccatcactcttcattaagaaatgc  420
                  ||||||||||||||||||||||||||||||||||||||||||||||||||||||||||||
251P5G2v.12: 361  ctcaactatacaaacatgtgagttattgttatgtaaccatcactcttcattaagaaatgc  420
```

TABLE LIII(a)-continued

Nucleotide sequence alignment of 251P5G2 v.1 (SEQ ID NO: 71) and 251P5G2 v.12 (SEQ ID NO: 72)

```
251P5G2v.1:   421  tttgtaaaaagtgagccagttttcatatacattcttcaaaatacattctcaacattata  480
                   ||||||||||||||||||||||||||||||||||||||||||||||||||||||||||||
251P5G2v.12:  421  tttgtaaaaagtgagccagttttcatatacattcttcaaaatacattctcaacattata  480

251P5G2v.1:   481  catcaaattatatatacatacatgcacacatacactatatatatcaaggatttatatgag  540
                   ||||||||||||||||||||||||||||||||||||||||||||||||||||||||||||
251P5G2v.12:  481  catcaaattatatatacatacatgcacacatacactatatatatcaaggatttatatgag  540

251P5G2v.1:   541  aggattaattaagaaaaaaattagtggaataaaaataatgtttatgataattttggccat  600
                   ||||||||||||||||||||||||||||||||||||||||||||||||||||||||||||
251P5G2v.12:  541  aggattaattaagaaaaaaattagtggaataaaaataatgtttatgataattttggccat  600

251P5G2v.1:   601  agaatatataatacagatgatgtgaagtacaaaatgttttttatacttcatattttgatg  660
                   ||||||||||||||||||||||||||||||||||||||||||||||||||||||||||||
251P5G2v.12:  601  agaatatataatacagatgatgtgaagtacaaaatgttttttatacttcatattttgatg  660

251P5G2v.1:   661  tacaaagtatgtttgtctttgtaattcagatgattactttgcacttgtgttcccatgaaa  720
                   ||||||||||||||||||||||||||||||||||||||||||||||||||||||||||||
251P5G2v.12:  661  tacaaagtatgtttgtctttgtaattcagatgattactttgcacttgtgttcccatgaaa  720

251P5G2v.1:   721  aatgcctttcatttctaagctggtattggcatctcagccaacacttttctccttcttttc  780
                   ||||||||||||||||||||||||||||||||||||||||||||||||||||||||||||
251P5G2v.12:  721  aatgcctttcatttctaagctggtattggcatctcagccaacacttttctccttcttttc  780

251P5G2v.1:   781  tgcgtcttctccttttctgcttttctggatctcaggccagagcgcacttacctaccagt  840
                   ||||||||||||||||||||||||||||||||||||||||||||||||||||||||||||
251P5G2v.12:  781  tgcgtcttctccttttctgcttttctggatctcaggccagagcgcacttacctaccagt  840

251P5G2v.1:   841  ctgtcatgtggccctcatccacatggtggtccttctccacatggtgttcttgtctccaca  900
                   ||||||||||||||||||||||||||||||||||||||||||||||||||||||||||||
251P5G2v.12:  841  ctgtcatgtggccctcatccacatggtggtccttctccacatggtgttcttgtctccaca  900

251P5G2v.1:   901  gctctttgaatcactgaattttcagaatgacttcaaatatgaggcatctttctacctgag  960
                   ||||||||||||||||||||||||||||||||||||||||||||||||||||||||||||
251P5G2v.12:  901  gctctttgaatcactgaattttcagaatgacttcaaatatgaggcatctttctacctgag  960

251P5G2v.1:   961  gagggtgatcagggtcctctccatttgtaccacctgcctcctgggcatgctgcaggtcgt 1020
                   |||||||||||||||||||||||||||||||||||||||||||||||| |||||||||||
251P5G2v.12:  961  gagggtgatcagggtcctctccatttgtaccacctgcctcctggacatgctgcaggtcgt 1020

251P5G2v.1:  1021  caacatcagccccagcatttcctggttg                                 1048
                   ||||||||||||||||||||||||||||
251P5G2v.12: 1021  caacatcagccccagcatttcctggttg                                 1048
```

Score = 254 bits (132), Expect = 3e-64 Identities = 132/132 (100%) Strand = Plus/Plus

```
251P5G2v.1:  1271  ataatgctgttctcaagtgtctacatgatgactctcattcaggaactacaggagatcctg 1330
                   ||||||||||||||||||||||||||||||||||||||||||||||||||||||||||||
251P5G2v.12: 1049  ataatgctgttctcaagtgtctacatgatgactctcattcaggaactacaggagatcctg 1108

251P5G2v.1:  1331  gtaccttcacagccccagcctctacctaaggatctttgcagaggcaagagccatcagcac 1390
                   ||||||||||||||||||||||||||||||||||||||||||||||||||||||||||||
251P5G2v.12: 1109  gtaccttcacagccccagcctctacctaaggatctttgcagaggcaagagccatcagcac 1168

251P5G2v.1:  1391  atcctgctgccg                                                 1402
                   ||||||||||||
251P5G2v.12: 1169  atcctgctgccg                                                 1180
```

TABLE LIV(a)

Peptide sequences of protein coded by 251P5G2 v.12 (SEQ ID NO: 73)

```
MPFISKLVLA SQPTLFSFFS ASSPFLLFLD LRPERTYLPV CHAVALIHMVV LLTMVFLSPQ    60
LFESLNFQND FKYEASFYLR RVIRVLSICT TCLLDMLQVV NISPSISWLI MNLSSVYMMT   120
LIQELQEILV PSQPQPLPKD LCRGKSHQHI LLPTQATFAA ATGLWAALTT VSNPSRADPV   180
TWRKEPAVLP CCNLEKGSWL SFPGTAARKE FSTTLTGHSA LSLSSSRALP GSLPAFADLP   240
```

TABLE LIV(a)-continued

Peptide sequences of protein coded by 251P5G2 v.12
(SEQ ID NO: 73)

| | | | | | | |
|---|---|---|---|---|---|---|
| RSCPESEQSA | TPAGAFLLGW | ERVVQRRLEV | PRPQAAPATS | ATPSRDPSPP | CHQRRDAACL | 300 |
| RAQGLTRAFQ | VVHLAPTAPD | GGAGCPPSRN | SYRLTHVRCA | QGLEAASANL | PGAPGRSSSC | 360 |
| ALRYRSGPSV | SSAPSPAEPP | AHQRLLFLPR | APQAVSGPQE | QPSEEALGVG | SLSVFQLHLI | 420 |
| QCIPNLSYPL | VLRHIPEILK | FSEKETGGGI | LGLELPATAA | RLSGLNSIMQ | IKEFEELVKL | 480 |
| HSLSHKVIQC | VFAKKKNVDK | WDDFCLSEGY | GHSFLIMKET | STKISGLIQE | MGSGKSNVGT | 540 |
| WGDYDDSAFM | EPRYHVRRED | LDKLHRAAWW | GKVPRKDLIV | MLRDTDMNKR | DKQKRTALHL | 600 |
| ASANGNSEVV | QLLLDRRCQL | NVLDNKKRTA | LIKAVQCQED | ECVLMLLEHG | ADGNIQDEYG | 660 |
| NTALHYAIYN | EDKLMAKALL | LYGADIESKN | KCGLTPLLLG | VHEQKQEVVK | FLIKKKANLN | 720 |
| ALDRYGRTAL | ILAVCCGSAS | IVNLLLEQNV | DVSSQDLSGQ | TAREYAVSSH | HHVICELLSD | 780 |
| YKEKQMLKIS | SENSNPVITI | LNIKLPLKVE | EETKKHGSNP | VGLPENLTNG | ASAGNGDDGL | 840 |
| IPQRKSRKPE | NQQFPDTENE | EYHSDEQNDT | QKQLSEEQNT | GISQDEILTN | KQKQIEVAEK | 900 |
| EMNSELSLSH | KKEEDLLREN | SMLREEIAKL | RLELDETKHQ | NQLRENKILE | EIESVKEKLL | 960 |
| KTIQLNEEAL | TKTKVAGFSL | RQLGLAQHAQ | ASVQQLCYKW | NHTEKTEQQA | QEQFVAGFSL | 1020 |
| RQLGLAQHAQ | ASVQQLCYKW | GHTEKTEQQA | QEQGAALRSQ | IGDPGGVPLS | EGGTAAGDQG | 1080 |
| PGTHLPPREP | RASPGTPSLV | RLASGARAAA | LPPPTGKNGR | SPTKQKSVCD | SSGWILPVPT | 1140 |
| FSSGSFLGRR | CPMFDVSPAM | RLKSDSNRET | HQAFRDKDDL | PFFKTQQSPR | HTKDLGQDDR | 1200 |
| AGVLAPKCRP | GTLCHTDTPP | HRNADTPPHR | HTTTLPHRDT | TSLPHFHVS | AGGVGPTTLG | 1260 |
| SNREIT | | | | | | 1266 |

TABLE LV(a)

Amino acid sequence alignment of 121P1F1 v.1 (SEQ ID NO: 74) and
251P5G2 v.12 (SEQ ID NO: 75)

```
Score = 269 bits (688), Expect = 2e-71 Identities = 152/227 (66%),
Positives = 152/227 (66%), Gaps = 74/227 (32%)
251P5G2v.1:     1 MPFISKLVIASQPTLFSFFSASSPFLLFLDLRPERTYLPVCHVALIHMVVLLTMVFLSPQ    60
                  MPFISKLVIASQPTLFSFFSASSPFLLFLDLRPERTYLPVCHVALIHMVVLLTMVFLSPQ
251P5G2v.12:    1 MPFISKLVIASQPTLFSFFSASSPFLLFLDLRPERTYLPVCHVALIHMVVLLTMVFLSPQ    60

251P5G2v.1:    61 LFESLNFQNDFKYEASFYLRRVIRVLSICTTCLLGMLQVVNISPSISWLVRKFWKSTIFT   120
                  LFESLNFQNDFKYEASFYLRRVIRVLSICTTCLL MLQVVNISPSISWL
251P5G2v.12:   61 LFESLNFQNDFKYEASFYLRRVIRVLSICTTCLLGMLQVVNISPSISWL-----------   109

251P5G2v.1:   121 FHLFSWSLSFPVSSSLIFYTVASSNVTQINLHVSKYCSLFPINSIIRGLFFTLSLFRDVF   180

251P5G2v.12:  109 ------------------------------------------------------------   109

251P5G2v.1:   181 IKQIMLFSSVYMMTLIQELQEILVPSQPQPLPKDLCRGKSHQHILIP                227
                     IMLFSSVYMMTLIQELQEILVPSQPQPLPKDLCRGKSHQHILIP
251P5G2v.12:  110 ---IMLFSSVYMMTLIQELQEILVPSQPQPLPKDLCRGKSHQHILIP                153
```

TABLE LII(b)

Nucleotide sequence of transcript variant 251P5G2 v.13 (SEQ ID NO: 76)

| | | | | |
|---|---|---|---|---|
| atgcctttca | tttctaagct | ggtattggca | tctcagccaa | cacttttctc cttcttttct | 60 |
| gcgtcttctc | cttttctgct | ttttctggat | ctcaggccag | agcgcactta cctaccagtc | 120 |
| tgtcatgtgg | ccctcatcca | catggtggtc | cttctcacca | tggtgttctt gtctccacag | 180 |
| ctcttttgaat | cactgaattt | tcagaatgac | ttcaaatatg | aggcatcttt ctacctgagg | 240 |

TABLE LII(b)-continued

| Nucleotide sequence of transcript variant 251P5G2 v.13 (SEQ ID NO: 76) | |
|---|---|
| agggtgatca gggtcctctc catttgtacc acctgcctcc tggacatgct gcaggtcgtc | 300 |
| aacatcagcc ccagcatttc ctggttgata atgctgttct caagtgtcta catgatgact | 360 |
| ctcattcagg aactacagga gatcctggta ccttcacagc cccagcctct acctaaggat | 420 |
| ctttgcagac gcaagagcca tcagcacatc ctgctgccga ctcaagcaac ttttgctgca | 480 |
| gcaactggac tatgggctgc actaaccacc gtatcaaatc caagcagagc agatcctgtg | 540 |
| acctggagaa aggagccggc tgtccttccc tgctgtaacc tagagaaagg aagctggctg | 600 |
| tccttccctg gcacagctgc acgcaaggaa ttttccacca cgctcaccgg gcacagcgcg | 660 |
| ctgagcctct ccagttcgcg ggccctcccc ggctcgctcc cggctttcgc agacctcccc | 720 |
| cgctcctgcc ctgagtccga gcagagcgca acgccagccg gcgccttcct cctgggctgg | 780 |
| gagcgagtgg tgcagcggcg gctcgaagtc ccccggcctc aagcagcccc cgcgactagc | 840 |
| gcgacaccct cgcgggatcc gagtccaccc tgccaccagc gccgggacgc cgcgtgcctc | 900 |
| agagcccaag ggctgacccg ggccttccag gtggtccatc tcgctcctac ggctcccgac | 960 |
| ggtggcgctg ggtgtccccc atcccgcaat tcctaccggc tgacccatgt gcgctgcgcc | 1020 |
| caggggctgg aggctgccag cgccaacctt cccggcgctc cggggcggag cagctcctgc | 1080 |
| gccctgcgct accgcagcgg cccttcagtc agctccgcgc cgtcccccgc agagcccccg | 1140 |
| gcgcaccagc gcctgctttt ccttccccga gcgcctcaag cagtctctgg gccgcaggaa | 1200 |
| cagccctctg aagaggcgct tggtgtagga agcctctcag ttttccagtt acacctaata | 1260 |
| cagtgtattc caaatctaag ttacccacta gtacttcggc acattccaga aattctgaaa | 1320 |
| ttttctgaaa aggaaactgg tggtggaatt ctaggcttag aattaccagc gacagctgct | 1380 |
| cgcctctcag gattaaacag cataatgcaa atcaaagagt ttgaagaatt ggtaaaactt | 1440 |
| cacagcttgt cacacaaagt cattcagtgt gtgtttgcaa agaaaaaaaa tgtagacaaa | 1500 |
| tgggatgact tttgtcttag tgagggttat ggacattcat tcttaataat gaaagaaacg | 1560 |
| tcgactaaaa tatcaggttt aattcaggag atggggagcg gcaagaccaa cgtgggcact | 1620 |
| tggggagact acgacgacag cgccttcatg gagccgaggt accacgtccg tcgagaagat | 1680 |
| ctggacaagc tccacagagc tgcctggtgg ggtaaagtcc ccagaaagga tctcatcgtc | 1740 |
| atgctcaggg acactgacat gaacaagagg gacaagcaaa agaggactgc tctacatttg | 1800 |
| gcctctgcca atggaaattc agaagtagta caactcctgc tggacagacg atgtcaactt | 1860 |
| aacgtccttg acaacaaaaa aaggacagct ctgataaagg ccgtacaatg ccaggaagat | 1920 |
| gaatgtgtgt taatgttgct ggaacatggc gctgatggaa atattcaaga tgagtatgga | 1980 |
| aataccgctc tacactatgc tatctacaat gaagataaat taatgccaa agcactgctc | 2040 |
| ttatatggtg ctgatattga atcaaaaaac aagtgtggcc tcacaccact tttgcttggc | 2100 |
| gtacatgaac aaaaacagga agtggtgaaa tttttaatca agaaaaaagc taatttaaat | 2160 |
| gcacttgata gatatggaag aactgccctc atacttgctg tatgttgtgg atcagcaagt | 2220 |
| atagtcaatc ttctacttga gcaaaatgtt gatgtatctt ctcaagatct atctggacag | 2280 |
| acggccagag agtatgctgt ttctagtcat catcatgtaa tttgtgaatt actttctgac | 2340 |
| tataaagaaa aacagatgct aaaaatctct tctgaaaaca gcaatccagt gataaccatc | 2400 |
| cttaatatca aacttccact caaggttgaa gaagaaataa agaagcatgg aagtaatcct | 2460 |
| gtgggattac cagaaaacct gactaatggt gccagtgctg gcaatggtga tgatggatta | 2520 |
| attccacaaa ggaagagcag aaaacctgaa aatcagcaat ttcctgacac tgagaatgaa | 2580 |

TABLE LII(b)-continued

Nucleotide sequence of transcript variant 251P5G2 v.13 (SEQ ID NO: 76)

```
gagtatcaca gtgacgaaca aaatgatacc cagaaacaac tttctgaaga acagaacact  2640
ggaatatcac aagatgagat tctgactaat aaacaaaagc agatagaagt ggctgaaaag  2700
gaaatgaatt ctgagctttc tcttagtcat aagaaagaag aagatctctt gcgtgaaaac  2760
agcatgttgc gggaagaaat tgccaagcta agactggaac tagatgaaac aaaacatcag  2820
aaccagctaa gggaaaataa aattttggag gaaattgaaa gtgtaaaaga aaaacttcta  2880
aagactatac aactgaatga agaagcatta acgaaaacca aggtggctgg tttctctttg  2940
cgccagcttg gccttgccca gcatgcacaa gcctcagtgc aacagctgtg ctacaaatgg  3000
aaccacacag agaaaacaga gcagcaggct caggagcagg aggtggctgg tttctctttg  3060
cgccagcttg gccttgccca gcatgcacaa gcctcagtac aacaactgtg ctacaaatgg  3120
ggccacacag agaaaacaga gcagcaggct caggagcagg gagctgcgct gaggtcccag  3180
ataggcgacc ctggcggggt gccctgagc gaagggggga cagcagcagg agaccagggt  3240
ccagggaccc acctcccacc gagggaacct cgagcctccc ctggcacccc tagcttggtc  3300
cgcctggcct ccggagcccg agctgctgcg cttcccccac ccacagggaa aaacggccga  3360
tctccaaca aacagaaatc tgtgtgtgac tcctctggtt ggatactgcc agtcccccaca  3420
ttttcttccg ggagttttct tggcagaagg tgcccaatgt ttgatgtttc gccagccatg  3480
aggctgaaaa gtgacagcaa tagagaaaca catcaggctt ccgcgacaa agatgacctt  3540
cccttcttca aaactcagca atctccacg cacacaaagg acttaggaca agatgaccga  3600
gctggagtgc tcgccccaaa atgcaggccc ggaacactct gccacacgga cacaccacca  3660
cacagaaatg cggacacacc accacacaga cacaccacca cgctgccaca cagagacacc  3720
accacatcgt tgccacactt tcatgtgtca gctggcggtg tgggcccac gactctgggc  3780
tctaatagag aaattactta g
```

TABLE LIII(b)

Nucleotide sequence alignment of 251P5G2 v.1 (SEQ ID NO: 77) and 251P5G2 v.13 (SEQ ID NO: 78)

Score = 623 bits (324), Expect = e-175 Identities = 326/327 (99%) Strand = Plus/Plus

```
Query:   722  atgcctttcatttctaagctggtattggcatctcagccaacacttttctccttcttttct   781
              ||||||||||||||||||||||||||||||||||||||||||||||||||||||||||||
Sbjct:     1  atgcctttcatttctaagctggtattggcatctcagccaacacttttctccttcttttct    60

Query:   782  gcgtcttctccttttctgcttttctggatctcaggccagagcgcacttacctaccagtc   841
              ||||||||||||||||||||||||||||||||||||||||||||||||||||||||||||
Sbjct:    61  gcgtcttctccttttctgcttttctggatctcaggccagagcgcacttacctaccagtc   120

Query:   842  tgtcatgtggccctcatccacatggtggtccttctcaccatggtgttcttgtctccacag   901
              ||||||||||||||||||||||||||||||||||||||||||||||||||||||||||||
Sbjct:   121  tgtcatgtggccctcatccacatggtggtccttctcaccatggtgttcttgtctccacag   180

Query:   902  ctctttgaatcactgaattttcagaatgacttcaaatatgaggcatctttctacctgagg   961
              ||||||||||||||||||||||||||||||||||||||||||||||||||||||||||||
Sbjct:   181  ctctttgaatcactgaattttcagaatgacttcaaatatgaggcatctttctacctgagg   240

Query:   962  agggtgatcagggtcctctccatttgtaccacctgcctcctgggcatgctgcaggtcgtc  1021
              |||||||||||||||| ||||||||||||||||||||||||||||| |||||||||||||
Sbjct:   241  agggtgatcagggtcctctccatttgtaccacctgcctcctggacatgctgcaggtcgtc   300

Query:  1022  aacatcagccccagcatttcctggttg                                  1048
              |||||||||||||||||||||||||||
Sbjct:   301  aacatcagccccagcatttcctggttg                                   327
```

TABLE LIII(b)-continued

Nucleotide sequence alignment of 251P5G2 v.1 (SEQ ID NO: 77) and 251P5G2 v.13 (SEQ ID NO: 78)

```
Score = 254 bits (132), Expect = 3e-64 Identities = 132/132 (100%) Strand = Plus/Plus Query:  1271  ataatgctgttctcaagtgtctacatgatgactctcattcaggaactacaggagatcctg  1330
              ||||||||||||||||||||||||||||||||||||||||||||||||||||||||||||
Sbjct:   328  ataatgctgttctcaagtgtctacatgatgactctcattcaggaactacaggagatcctg   387

Query:  1331  gtaccttcacagccccagcctctacctaaggatctttgcagaggcaagagccatcagcac  1390
              ||||||||||||||||||||||||||||||||||||||||||||||||||||||||||||
Sbjct:   388  gtaccttcacagccccagcctctacctaaggatctttgcagaggcaagagccatcagcac   447

Query:  1391  atcctgctgccg  1402
              ||||||||||||
Sbjct:   448  atcctgctgccg   459
```

TABLE LIV(b)

Peptide sequences of protein coded by 251P5G2 v.13 (SEQ ID NO: 79)

| | | | | | | |
|---|---|---|---|---|---|---|
| MPFISKLVLA | SQPTLFSFFS | ASSPFLLFLD | LRPERTYLPV | CHVALIHMVV | LLTMVFLSPQ | 60 |
| LFESLNFQND | FKYEASFYLR | RVIRVLSICT | TCLLDMLQVV | NISPSISWLI | MLFSSVYMMT | 120 |
| LIQELQEILV | PSQPQPLPKD | LCRGKSHQHI | LLPTQATFAA | ATGLWAALTT | VSNPSRADPV | 180 |
| TWRKEPAVLP | CCNLEKGSWL | SFPGTAARKE | FSTTLTGHSA | LSLSSSRALP | GSLPAFADLP | 240 |
| RSCPESEQSA | TPAFAFLLGW | ERVVQRRLEV | PRPQAAPATS | ATPSRDPSPP | CHQRRDAACL | 300 |
| RAQGLTRAFQ | VVHLAPTAPD | GGAGCPPSRN | SYRLTHVRCA | QGLEAASANL | PGAPGRSSSC | 360 |
| ALRYRSGPSV | SSAPSPAEPP | AHQRLLFLPR | APQAVSGPQE | QPSEEALGVG | SLSVFQLHLI | 420 |
| QCIPNLSYPL | VLRHIPEILK | FSEKETGGGI | LGLELPATAA | RLSGLNSIMQ | IKEFEELVKL | 480 |
| HSLSHKVIQC | VFAKKKNVDK | WDDFCLSEGY | GHSFLIMKET | STKISGLIQE | MGSGKSNVGT | 540 |
| WGDYDDSAFM | EPRYHVRRED | LDKLHRAAWW | GKVPRKDLIV | MLRDTDMNKR | DKQKRTALHL | 600 |
| ASANGNSEVV | QLLLDRRCQL | NVLDNKKRTA | LIKAVQCQED | ECVLMLLEHG | ADGNIQDEYG | 660 |
| NTALHYAIYN | EDKLMAKALL | LYGADIESKN | KCGLTPLLLG | VHEQKQEVVK | FLIKKKANLN | 720 |
| ALDRYGRTAL | ILAVCCGSAS | IVNLLLEQNV | DVSSQDLSGQ | TAREYAVSSH | HHVICELLSD | 780 |
| YKEKQMLKIS | SENSNPVITI | LNIKLPLKVE | EEIKKHGSNP | VGLPENLTNG | ASAGNGDDGL | 840 |
| IPQRKSRKPE | NQQFPDTENE | EYHSDEQNDT | QKQLSEEQNT | GISQDEILTN | KQKQIEVAEK | 900 |
| EMNSELSLSH | KKEEDLLREN | SMLREEIAKL | RLELDETKHQ | NQLRENKILE | EIESVKEKLL | 960 |
| KTIQLNEEAL | TKTKVAGFSL | RQLGLAQHAQ | ASVQQLCYKW | NHTEKTEQQA | QEQFVAGFSL | 1020 |
| RQLGLAQHAQ | ASVQQLCYKW | GHTEKTEQQA | QEQGAALRSQ | IGDPGGVPLS | EGGTAAGDQG | 1080 |
| PGTHLPPREP | RASPGTPSLV | RLASGARAAA | LPPPTGKNGR | SPTKQKSVCD | SSGWILPVPT | 1140 |
| FSSGSFLGRR | CPMFDVSPAM | RLKSDSNRET | HQAFRDKDDL | PFFKTQQSPR | HTKDLGQDDR | 1200 |
| AGVLAPKCRP | GILCHTDTPP | HRNADTPPHR | HTTTLPHRDT | TTSLPHFHVS | AGGVGPTTLG | 1260 |
| SNREIT | | | | | | |

TABLE LV(b)

Amino acid sequence alignment of 121P1F1 v.1 (SEQ ID NO: 80) and 251P5G2 v.13 (SEQ ID NO: 81)

```
Score = 269 bits (688), Expect = 2e-71 Identities = 152/227 (66%), Positives =
152/227 (66%), Gaps = 74/227 (32%)
251P5G2v.1:    1 MPFISKLVLASQPTLFSFFSASSPFLLFLDLRPERTYLPVCHVALIHMVVLLTMVFLSPQ  60
                 MPFISKLVLASQPTLFSFFSASSPFLLFLDLRPERTYLPVCHVALIHMVVLLTMVFLSPQ
```

TABLE LV(b)-continued

Amino acid sequence alignment of 121P1F1 v.1 (SEQ ID NO: 80) and
251P5G2 v.13 (SEQ ID NO: 81)

```
251P5G2v.13:    1 MPFISKLVLASQPTLFSFFSASSPFLLFLDLRPERTYLPVCHVALIHMVVLLTMVFLSPQ   60

251P5G2v.1:    61 LFESLNFQNDFKYEASFYLRRVIRVLSICTTCLLGMLQVVNISPSISWLVRFKWKSTIFT  120
                  LFESLNFQNDFKYEASFYLRRVIRVLSICTTCLL MLQVVNISPSISWL
251P5G2v.13:   61 LFESLNFQNDFKYEASFYLRRVIRVLSICTTCLLDMLQVVNISPSISWL----------  109

251P5G2v.1:   121 FHLFSWSLSFPVSSSLIFYIVASSNVIQINLHVSKYCSLFPTNSIIRGLFFILSLFRDVF  130

251P5G2v.13: 109 ------------------------------------------------------------ 109

251P5G2v.1:   181 LKQIMLFSSVYMMTLIQELQEILVPSQPQPLPKDLCRGKSHQHILLP              227
                     IMLFSSVYMMTLIQELQEILVPSQPQPLPKDLCRGKSHQHILLP
251P5G2v.13: 110 ---IMLFSSVYMMTLIQELQEILVPSQPQPLPKDLCRGKSHQHILLP              153
```

The invention claimed is:

1. An isolated polynucleotide which has the nucleic acid sequence of SEQ ID NO:2.

2. An isolated polynucleotide which has the nucleic acid sequence comprising residues 722 to 1489 of SEQ ID NO:2.

3. A viral vector that comprises the polynucleotide of claim 1.

4. An isolated host cell that contains the vector of claim 3.

5. A process for producing a protein comprising the amino acid sequence of SEQ ID NO:3, comprising culturing a host cell of claim 4 under conditions sufficient for the production of the protein, and recovering the protein from the culture.

* * * * *

SEQUENCE LISTING

<160> NUMBER OF SEQ ID NOS: 83

<210> SEQ ID NO 1
<211> LENGTH: 162
<212> TYPE: DNA
<213> ORGANISM: Homo sapiens

<400> SEQUENCE: 1

```
gatcaccctc ctcaggtaga aagatgcctc atatttgaag tcattctgaa aattcagtga   60
ttcaaagagc tgtggagaca agaacaccat ggtgagaagg accaccatgt ggataagggc  120
cacatgacag actggtaggt aagtgcgctc tggcctgaga tc                      162
```

<210> SEQ ID NO 2
<211> LENGTH: 2156
<212> TYPE: DNA
<213> ORGANISM: Homo sapiens
<220> FEATURE:
<221> NAME/KEY: CDS
<222> LOCATION: (722)...(1489)

<400> SEQUENCE: 2

```
gtttttttt tttttttttt ttttttttt tatttaagg gattcgttta ataggacttg    60
tggtaagtgg aataatgcca tgcaaaggtc cccatgtcta accaccaggt tctaggcatg  120
tattatggta tatgagaaat gggaattcag gctgcagatg aaatcaaggt tgataaccag  180
ctgactctaa acaaaaaaca ttaacttgaa ttacagattt gggcctaatg taattataag  240
cattcttaaa agtgaaagaa ataataagag aaactgagtg ctgtgatgtg agtcagttaa  300
acttttttt caactttttc tttaggtgat tattttccct taacataaaa tttactttag  360
ctcaactata caaacatgtg agttattgtt atgtaaccat cactcttcat taagaaatgc  420
tttgtaaaaa gtgagccagt ttttcatata cattcttcaa aatacattct caacattata  480
catcaaatta tatatacata catgcacaca tacactatat atatcaagga tttatatgag  540
aggattaatt aagaaaaaaa ttagtggaat aaaaataatg tttatgataa ttttggccat  600
agaatatata atacagatga tgtgaagtac aaaatgtttt ttatacttca tattttgatg  660
tacaaagtat gtttgtcttt gtaattcaga tgattacttt gcacttgtgt tcccatgaaa  720
a atg cct ttc att tct aag ctg gta ttg gca tct cag cca aca ctt ttc  769
  Met Pro Phe Ile Ser Lys Leu Val Leu Ala Ser Gln Pro Thr Leu Phe
  1               5                  10                  15
```

-continued

| | |
|---|---|
| tcc ttc ttt tct gcg tct tct cct ttt ctg ctt ttt ctg gat ctc agg<br>Ser Phe Phe Ser Ala Ser Ser Pro Phe Leu Leu Phe Leu Asp Leu Arg<br>     20                        25                     30 | 817 |
| cca gag cgc act tac cta cca gtc tgt cat gtg gcc ctc atc cac atg<br>Pro Glu Arg Thr Tyr Leu Pro Val Cys His Val Ala Leu Ile His Met<br>    35                       40                    45 | 865 |
| gtg gtc ctt ctc acc atg gtg ttc ttg tct cca cag ctc ttt gaa tca<br>Val Val Leu Leu Thr Met Val Phe Leu Ser Pro Gln Leu Phe Glu Ser<br>50                     55                    60 | 913 |
| ctg aat ttt cag aat gac ttc aaa tat gag gca tct ttc tac ctg agg<br>Leu Asn Phe Gln Asn Asp Phe Lys Tyr Glu Ala Ser Phe Tyr Leu Arg<br>65                     70                    75                    80 | 961 |
| agg gtg atc agg gtc ctc tcc att tgt acc acc tgc ctc ctg ggc atg<br>Arg Val Ile Arg Val Leu Ser Ile Cys Thr Thr Cys Leu Leu Gly Met<br>                   85                    90                    95 | 1009 |
| ctg cag gtc gtc aac atc agc ccc agc att tcc tgg ttg gtg agg ttt<br>Leu Gln Val Val Asn Ile Ser Pro Ser Ile Ser Trp Leu Val Arg Phe<br>         100                     105                110 | 1057 |
| aaa tgg aaa tcc aca att ttt acc ttc cat ttg ttc tca tgg tct ctc<br>Lys Trp Lys Ser Thr Ile Phe Thr Phe His Leu Phe Ser Trp Ser Leu<br>       115                   120                  125 | 1105 |
| agt ttt cct gtt agt agt agc ctg atc ttt tac act gtg gct tct tcc<br>Ser Phe Pro Val Ser Ser Ser Leu Ile Phe Tyr Thr Val Ala Ser Ser<br>130                   135                   140 | 1153 |
| aat gtg acc cag atc aat ttg cat gtc agt aaa tac tgt tca ctt ttc<br>Asn Val Thr Gln Ile Asn Leu His Val Ser Lys Tyr Cys Ser Leu Phe<br>145                  150                 155                160 | 1201 |
| cca ata aac tcc ata atc aga gga ctg ttt ttc act ctg tca tta ttc<br>Pro Ile Asn Ser Ile Ile Arg Gly Leu Phe Phe Thr Leu Ser Leu Phe<br>                 165                   170                175 | 1249 |
| aga gat gtt ttt ctt aaa caa ata atg ctg ttc tca agt gtc tac atg<br>Arg Asp Val Phe Leu Lys Gln Ile Met Leu Phe Ser Ser Val Tyr Met<br>         180                     185                190 | 1297 |
| atg act ctc att cag gaa cta cag gag atc ctg gta cct tca cag ccc<br>Met Thr Leu Ile Gln Glu Leu Gln Glu Ile Leu Val Pro Ser Gln Pro<br>     195                     200                205 | 1345 |
| cag cct cta cct aag gat ctt tgc aga ggc aag agc cat cag cac atc<br>Gln Pro Leu Pro Lys Asp Leu Cys Arg Gly Lys Ser His Gln His Ile<br>210                   215                   220 | 1393 |
| ctg ctg ccg gtg agt ttc tcg gtg ggc atg tac aag atg gac ttc atc<br>Leu Leu Pro Val Ser Phe Ser Val Gly Met Tyr Lys Met Asp Phe Ile<br>225                  230                   235                240 | 1441 |
| atc tca acc tcc tca aca ttg cca tgg gca tat gac cgt ggt gtc tag<br>Ile Ser Thr Ser Ser Thr Leu Pro Trp Ala Tyr Asp Arg Gly Val *<br>                 245                   250                255 | 1489 |
| aggctagtgg gcagtgtcta taccattgtc aggttttggg tgctactgag atctgataaa | 1549 |
| agggtaatca atgtgatgta aactataaga caaatgttta aaggttaatt tgtatgaatc | 1609 |
| ctgtcatgag ttaaattatt cagagtgttc attatagaga ataatccaaa gttaaaataa | 1669 |
| ttggataatt tatttgtatg taggataaaa gtagtaggag attgcttctt gaagatttaa | 1729 |
| aattatattg agtgtaatta tttgcattaa ataattttta aatgttttga atagcaagta | 1789 |
| ttgatataat taaactttcg aataacttag tgctttgcct ttattcctaa tgtttatatg | 1849 |
| gaagcatgtg gtcaatgttt gatgcattac agctctgagc ggtccttctg tattaggtgg | 1909 |
| tcatcattta tatacttctc cataaaagat taaggacctg gaaatgtaag atacatgaag | 1969 |
| aaaatctaag tggagaggct gtttgtggtt aagtgataac agtgttgtaa gcgatgcatg | 2029 |
| aggtaggtgt tcagtgcata tcctctgcat tttattaata aacactgtaa aatttagaag | 2089 |

```
aaaattgttt caccaaatgc acataaaact aataaaatag agtggatttt gatatgtccc    2149
tcgtgcc                                                              2156

<210> SEQ ID NO 3
<211> LENGTH: 255
<212> TYPE: PRT
<213> ORGANISM: Homo sapiens

<400> SEQUENCE: 3

Met Pro Phe Ile Ser Lys Leu Val Leu Ala Ser Gln Pro Thr Leu Phe
 1               5                  10                  15

Ser Phe Phe Ser Ala Ser Ser Pro Phe Leu Leu Phe Leu Asp Leu Arg
                20                  25                  30

Pro Glu Arg Thr Tyr Leu Pro Val Cys His Val Ala Leu Ile His Met
            35                  40                  45

Val Val Leu Leu Thr Met Val Phe Leu Ser Pro Gln Leu Phe Glu Ser
50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Gly Met
                85                  90                  95

Leu Gln Val Asn Ile Ser Pro Ser Ile Ser Trp Leu Val Arg Phe
            100                 105                 110

Lys Trp Lys Ser Thr Ile Phe Thr Phe His Leu Phe Ser Trp Ser Leu
        115                 120                 125

Ser Phe Pro Val Ser Ser Ser Leu Ile Phe Tyr Thr Val Ala Ser Ser
    130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
        195                 200                 205

Gln Pro Leu Pro Lys Asp Leu Cys Arg Gly Lys Ser His Gln His Ile
    210                 215                 220

Leu Leu Pro Val Ser Phe Ser Val Gly Met Tyr Lys Met Asp Phe Ile
225                 230                 235                 240

Ile Ser Thr Ser Ser Thr Leu Pro Trp Ala Tyr Asp Arg Gly Val
                245                 250                 255

<210> SEQ ID NO 4
<211> LENGTH: 2156
<212> TYPE: DNA
<213> ORGANISM: Homo sapiens
<220> FEATURE:
<221> NAME/KEY: CDS
<222> LOCATION: (722)...(1489)

<400> SEQUENCE: 4
gttttttttt tttttttttt tttttttttt tattttaagg gattcgttta ataggacttg    60
tggtaagtgg aataatgcca tgcaaaggtc cccatgtcta accaccaggt tctaggcatg   120
tattatggta tatgagaaat gggaattcag gctgcagatg aaatcaaggt tgataaccag   180
ctgactctaa aacaaaaaca ttaacttgaa ttacagattt gggcctaatg taattataag   240
```

-continued

```
cattcttaaa agtgaaagaa ataataagag aaactgagtg ctgtgatgtg agtcagttaa    300 acttttttt caactttttc tttaggtgat tattttccct taacataaaa tttactttag    360
ctcaactata caaacatgtg agttattgtt atgtaaccat cactcttcat taagaaatgc    420
tttgtaaaaa gtgagccagt ttttcatata cattcttcaa aatacattct caacattata    480
catcaaatta tatatacata catgcacaca tacactatat atatcaagga tttatatgag    540
aggattaatt aagaaaaaaa ttagtggaat aaaaataatg tttatgataa ttttggccat    600
agaatatata atacagatga tgtgaagtac aaaatgtttt ttatacttca tattttgatg    660
tacaaagtat gtttgtcttt gtaattcaga tgattacttt gcacttgtgt tcccatgaaa    720
```

| | | | | | | | | | | | | | | | |
|---|---|---|---|---|---|---|---|---|---|---|---|---|---|---|---|
| a atg | cct | ttc | att | tct | aag | ctg | gta | ttg | gca | tct | cag | cca | aca | ctt | tgc | 769 |
| Met | Pro | Phe | Ile | Ser | Lys | Leu | Val | Leu | Ala | Ser | Gln | Pro | Thr | Leu | Cys | |
| 1 | | | 5 | | | | | 10 | | | | | 15 | | | |

```
tcc ttc ttt tct gcg tct tct cct ttt ctg ctt ttt ctg gat ctc agg    817
Ser Phe Phe Ser Ala Ser Ser Pro Phe Leu Leu Phe Leu Asp Leu Arg
            20                  25                  30 cca gag cgc act tac cta cca gtc tgt cat gtg gcc ctc atc cac atg    865
Pro Glu Arg Thr Tyr Leu Pro Val Cys His Val Ala Leu Ile His Met
        35                  40                  45 gtg gtc ctt ctc acc atg gtg ttc ttg tct cca cag ctc ttt gaa tca    913
Val Val Leu Leu Thr Met Val Phe Leu Ser Pro Gln Leu Phe Glu Ser
    50                  55                  60 ctg aat ttt cag aat gac ttc aaa tat gag gca tct ttc tac ctg agg    961
Leu Asn Phe Gln Asn Asp Phe Lys Tyr Glu Ala Ser Phe Tyr Leu Arg
65                  70                  75                  80 agg gtg atc agg gtc ctc tcc att tgt acc acc tgc ctc ctg ggc atg   1009
Arg Val Ile Arg Val Leu Ser Ile Cys Thr Thr Cys Leu Leu Gly Met
                85                  90                  95 ctg cag gtc gtc aac atc agc ccc agc att tcc tgg ttg gtg agg ttt   1057
Leu Gln Val Val Asn Ile Ser Pro Ser Ile Ser Trp Leu Val Arg Phe
            100                 105                 110 aaa tgg aaa tcc aca att ttt acc ttc cat ttg ttc tca tgg tct ctc   1105
Lys Trp Lys Ser Thr Ile Phe Thr Phe His Leu Phe Ser Trp Ser Leu
        115                 120                 125 agt ttt cct gtt agt agt agc ctg atc ttt tac act gtg gct tct tcc   1153
Ser Phe Pro Val Ser Ser Ser Leu Ile Phe Tyr Thr Val Ala Ser Ser
    130                 135                 140 aat gtg acc cag atc aat ttg cat gtc agt aaa tac tgt tca ctt ttc   1201
Asn Val Thr Gln Ile Asn Leu His Val Ser Lys Tyr Cys Ser Leu Phe
145                 150                 155                 160 cca ata aac tcc ata atc aga gga ctg ttt ttc act ctg tca tta ttc   1249
Pro Ile Asn Ser Ile Ile Arg Gly Leu Phe Phe Thr Leu Ser Leu Phe
                165                 170                 175 aga gat gtt ttt ctt aaa caa ata atg ctg ttc tca agt gtc tac atg   1297
Arg Asp Val Phe Leu Lys Gln Ile Met Leu Phe Ser Ser Val Tyr Met
            180                 185                 190 atg act ctc att cag gaa cta cag gag atc ctg gta cct tca cag ccc   1345
Met Thr Leu Ile Gln Glu Leu Gln Glu Ile Leu Val Pro Ser Gln Pro
        195                 200                 205 cag cct cta cct aag gat ctt tgc aga ggc aag agc cat cag cac atc   1393
Gln Pro Leu Pro Lys Asp Leu Cys Arg Gly Lys Ser His Gln His Ile
    210                 215                 220 ctg ctg ccg gtg agt ttc tcg gtg ggc atg tac aag atg gac ttc atc   1441
Leu Leu Pro Val Ser Phe Ser Val Gly Met Tyr Lys Met Asp Phe Ile
225                 230                 235                 240 atc tca acc tcc tca aca ttg cca tgg gca tat gac cgt ggt gtc tag   1489
Ile Ser Thr Ser Ser Thr Leu Pro Trp Ala Tyr Asp Arg Gly Val  *
```

```
                          245              250              255
aggctagtgg gcagtgtcta taccattgtc aggttttttgg tgctactgag atctgataaa  1549
agggtaatca atgtgatgta aactataaga caaatgttta aaaggttaat tgtatgaatc  1609
ctgtcatgag ttaaattatt cagagtgttc attatagaga ataatccaaa gttaaaataa  1669
ttggataatt tatttgtatg taggataaaa gtagtaggag attgcttctt gaagatttaa  1729
aattatattg agtgtaatta tttgcattaa ataattttta aatgttttga atagcaagta  1789
ttgatataat taaactttcg aataacttag tgctttgcct ttattcctaa tgtttatatg  1849
gaagcatgtg gtcaatgttt gatgcattac agctctgagc ggtccttctg tattaggtgg  1909
tcatcattta tacttctc cataaaagat taaggacctg gaaatgtaag atacatgaag  1969
aaaatctaag tggagaggct gtttgtggtt aagtgataac agtgttgtaa gcgatgcatg  2029
aggtaggtgt tcagtgcata tcctctgcat tttattaata aacactgtaa aatttagaag  2089
aaaattgttt caccaaatgc acataaaact aataaaatag agtggatttt gatatgtccc  2149
tcgtgcc                                                            2156
```

<210> SEQ ID NO 5
<211> LENGTH: 255
<212> TYPE: PRT
<213> ORGANISM: Homo sapiens

<400> SEQUENCE: 5

```
Met Pro Phe Ile Ser Lys Leu Val Leu Ala Ser Gln Pro Thr Leu Cys
  1               5                  10                  15

Ser Phe Phe Ser Ala Ser Ser Pro Phe Leu Leu Phe Leu Asp Leu Arg
                 20                  25                  30

Pro Glu Arg Thr Tyr Leu Pro Val Cys His Val Ala Leu Ile His Met
             35                  40                  45

Val Val Leu Leu Thr Met Val Phe Leu Ser Pro Gln Leu Phe Glu Ser
         50                  55                  60

Leu Asn Phe Gln Asn Asp Phe Lys Tyr Glu Ala Ser Phe Tyr Leu Arg
 65                  70                  75                  80

Arg Val Ile Arg Val Leu Ser Ile Cys Thr Thr Cys Leu Leu Gly Met
                 85                  90                  95

Leu Gln Val Val Asn Ile Ser Pro Ser Ile Ser Trp Leu Val Arg Phe
            100                 105                 110

Lys Trp Lys Ser Thr Ile Phe Thr Phe His Leu Phe Ser Trp Ser Leu
            115                 120                 125

Ser Phe Pro Val Ser Ser Ser Leu Ile Phe Tyr Thr Val Ala Ser Ser
        130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
        195                 200                 205

Gln Pro Leu Pro Lys Asp Leu Cys Arg Gly Lys Ser His Gln His Ile
    210                 215                 220

Leu Leu Pro Val Ser Phe Ser Val Gly Met Tyr Lys Met Asp Phe Ile
225                 230                 235                 240
```

```
Ile Ser Thr Ser Ser Thr Leu Pro Trp Ala Tyr Asp Arg Gly Val
                245                 250                 255

<210> SEQ ID NO 6
<211> LENGTH: 2156
<212> TYPE: DNA
<213> ORGANISM: Homo sapiens
<220> FEATURE:
<221> NAME/KEY: CDS
<222> LOCATION: (722)...(1489)

<400> SEQUENCE: 6 gtttttttt  ttttttttt  tttttttttt  tattttaagg  gattcgttta  ataggacttg     60
tggtaagtgg  aataatgcca  tgcaaaggtc  cccatgtcta  accaccaggt  tctaggcatg    120
tattatggta  tatgagaaat  gggaattcag  gctgcagatg  aaatcaaggt  tgataaccag    180
ctgactctaa  aacaaaaaca  ttaacttgaa  ttacagattt  gggcctaatg  taattataag    240
cattcttaaa  agtgaaagaa  ataataagag  aaactgagtg  ctgtgatgtg  agtcagttaa    300
actttttttt  caacttttc   tttaggtgat  tattttccct  taacataaaa  tttactttag    360
ctcaactata  caaacatgtg  agttattgtt  atgtaaccat  cactcttcat  taagaaatgc    420
tttgtaaaaa  gtgagccagt  ttttcatata  cattcttcaa  aatacattct  caacattata    480
catcaaatta  tatatacata  catgcacaca  tacactatat  atcaagga   tttatatgag    540 aggattaatt  aagaaaaaa   ttagtggaat  aaaaataatg  tttatgataa  ttttggccat    600
agaatatata  atacagatga  tgtgaagtac  aaaatgtttt  ttatacttca  tattttgatg    660
tacaaagtat  gtttgtcttt  gtaattcaga  tgattacttt  gcacttgtgt  tcccatgaaa    720 a atg cct ttc att tct aag ctg gta ttg gca tct cag cca aca ctt ttc        769
  Met Pro Phe Ile Ser Lys Leu Val Leu Ala Ser Gln Pro Thr Leu Phe
   1               5                  10                  15 tcc ttc ttt tct gcg tct tct cct ttt ctg ctt ttt ctg gat ctc agg         817
Ser Phe Phe Ser Ala Ser Ser Pro Phe Leu Leu Phe Leu Asp Leu Arg
            20                  25                  30 cca gag cgc act tac cta cca gtc tgt cat gtg gcc ctc atc cac atg         865
Pro Glu Arg Thr Tyr Leu Pro Val Cys His Val Ala Leu Ile His Met
        35                  40                  45 gtg gtc ctt ctc acc atg gtg ttc ttg tct cca cag ctc ttt gaa tca         913
Val Val Leu Leu Thr Met Val Phe Leu Ser Pro Gln Leu Phe Glu Ser
    50                  55                  60 ctg aat ttt cag aat gac ttc aaa tat gag gca tct ttc tac ctg agg         961
Leu Asn Phe Gln Asn Asp Phe Lys Tyr Glu Ala Ser Phe Tyr Leu Arg
65                  70                  75                  80 agg gtg atc agg gac ctc tcc att tgt acc acc tgc ctc ctg ggc atg        1009
Arg Val Ile Arg Asp Leu Ser Ile Cys Thr Thr Cys Leu Leu Gly Met
                85                  90                  95 ctg cag gtc gtc aac atc agc ccc agc att tcc tgg ttg gtg agg ttt        1057
Leu Gln Val Val Asn Ile Ser Pro Ser Ile Ser Trp Leu Val Arg Phe
            100                 105                 110 aaa tgg aaa tcc aca att ttt acc ttc cat ttg ttc tca tgg tct ctc        1105
Lys Trp Lys Ser Thr Ile Phe Thr Phe His Leu Phe Ser Trp Ser Leu
        115                 120                 125 agt ttt cct gtt agt agt agc ctg atc ttt tac act gtg gct tct tcc        1153
Ser Phe Pro Val Ser Ser Ser Leu Ile Phe Tyr Thr Val Ala Ser Ser
    130                 135                 140 aat gtg acc cag atc aat ttg cat gtc agt aaa tac tgt tca ctt ttc        1201
Asn Val Thr Gln Ile Asn Leu His Val Ser Lys Tyr Cys Ser Leu Phe
145                 150                 155                 160 cca ata aac tcc ata atc aga gga ctg ttt ttc act ctg tca tta ttc        1249
```

```
Pro Ile Asn Ser Ile Ile Arg Gly Leu Phe Phe Thr Leu Ser Leu Phe
                165                 170                 175 aga gat gtt ttt ctt aaa caa ata atg ctg ttc tca agt gtc tac atg      1297
Arg Asp Val Phe Leu Lys Gln Ile Met Leu Phe Ser Ser Val Tyr Met
            180                 185                 190 atg act ctc att cag gaa cta cag gag atc ctg gta cct tca cag ccc      1345
Met Thr Leu Ile Gln Glu Leu Gln Glu Ile Leu Val Pro Ser Gln Pro
        195                 200                 205 cag cct cta cct aag gat ctt tgc aga ggc aag agc cat cag cac atc      1393
Gln Pro Leu Pro Lys Asp Leu Cys Arg Gly Lys Ser His Gln His Ile
    210                 215                 220 ctg ctg ccg gtg agt ttc tcg gtg ggc atg tac aag atg gac ttc atc      1441
Leu Leu Pro Val Ser Phe Ser Val Gly Met Tyr Lys Met Asp Phe Ile
225                 230                 235                 240 atc tca acc tcc tca aca ttg cca tgg gca tat gac cgt ggt gtc tag      1489
Ile Ser Thr Ser Ser Thr Leu Pro Trp Ala Tyr Asp Arg Gly Val  *
                245                 250                 255 aggctagtgg gcagtgtcta taccattgtc aggtttttgg tgctactgag atctgataaa     1549
agggtaatca atgtgatgta aactataaga caaatgttta aaaggttaat tgtatgaatc     1609
ctgtcatgag ttaaattatt cagagtgttc attatagaga ataatccaaa gttaaaataa     1669
ttggataatt tatttgtatg taggataaaa gtagtaggag attgcttctt gaagatttaa     1729
aattatattg agtgtaatta tttgcattaa ataattttta aatgttttga atagcaagta     1789
ttgatataat taaactttcg aataacttag tgctttgcct ttattcctaa tgtttatatg     1849
gaagcatgtg gtcaatgttt gatgcattac agctctgagc ggtccttctg tattaggtgg     1909
tcatcattta tatacttctc cataaaagat taaggacctg gaaatgtaag atacatgaag     1969
aaaatctaag tggagaggct gtttgtggtt aagtgataac agtgttgtaa gcgatgcatg     2029
aggtaggtgt tcagtgcata tcctctgcat tttattaata aacactgtaa aatttagaag     2089
aaaattgttt caccaaatgc acataaaact aataaaatag agtggatttt gatatgtccc     2149
tcgtgcc                                                              2156
```

<210> SEQ ID NO 7
<211> LENGTH: 255
<212> TYPE: PRT
<213> ORGANISM: Homo sapiens

<400> SEQUENCE: 7

```
Met Pro Phe Ile Ser Lys Leu Val Leu Ala Ser Gln Pro Thr Leu Phe
 1               5                  10                  15

Ser Phe Phe Ser Ala Ser Ser Pro Phe Leu Leu Phe Leu Asp Leu Arg
            20                  25                  30

Pro Glu Arg Thr Tyr Leu Pro Val Cys His Val Ala Leu Ile His Met
        35                  40                  45

Val Val Leu Leu Thr Met Val Phe Leu Ser Pro Gln Leu Phe Glu Ser
    50                  55                  60

Leu Asn Phe Gln Asn Asp Phe Lys Tyr Glu Ala Ser Phe Tyr Leu Arg
65                  70                  75                  80

Arg Val Ile Arg Asp Leu Ser Ile Cys Thr Thr Cys Leu Leu Gly Met
                85                  90                  95

Leu Gln Val Val Asn Ile Ser Pro Ser Ile Ser Trp Leu Val Arg Phe
            100                 105                 110

Lys Trp Lys Ser Thr Ile Phe Thr Phe His Leu Phe Ser Trp Ser Leu
        115                 120                 125
```

```
Ser Phe Pro Val Ser Ser Leu Ile Phe Tyr Thr Val Ala Ser Ser
    130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
                195                 200                 205

Gln Pro Leu Pro Lys Asp Leu Cys Arg Gly Lys Ser His Gln His Ile
    210                 215                 220

Leu Leu Pro Val Ser Phe Ser Val Gly Met Tyr Lys Met Asp Phe Ile
225                 230                 235                 240

Ile Ser Thr Ser Ser Thr Leu Pro Trp Ala Tyr Asp Arg Gly Val
                245                 250                 255

<210> SEQ ID NO 8
<211> LENGTH: 2156
<212> TYPE: DNA
<213> ORGANISM: Homo sapiens
<220> FEATURE:
<221> NAME/KEY: CDS
<222> LOCATION: (722)...(1489)

<400> SEQUENCE: 8
gttttttttt tttttttttt tttttttttt tattttaagg gattcgttta ataggacttg      60
tggtaagtgg aataatgcca tgcaaaggtc cccatgtcta accaccaggt tctaggcatg     120
tattatggta tatgagaaat gggaattcag gctgcagatg aaatcaaggt tgataaccag     180
ctgactctaa aacaaaaaca ttaacttgaa ttacagattt gggcctaatg taattataag     240
cattcttaaa agtgaaagaa ataataagag aaactgagtg ctgtgatgtg agtcagttaa     300
actttttttt caacttttttc tttaggtgat tattttccct taacataaaa tttactttag     360
ctcaactata caaacatgtg agttattgtt atgtaaccat cactcttcat taagaaatgc     420
tttgtaaaaa gtgagccagt ttttcatata cattcttcaa aatacattct caacattata     480
catcaaatta tatatacata catgcacaca tacactatat atatcaagga tttatatgag     540
aggattaatt aagaaaaaaa ttagtggaat aaaaataatg tttatgataa ttttggccat     600
agaatatata atacagatga tgtgaagtac aaaatgtttt ttatacttca tattttgatg     660
tacaaagtat gtttgtcttt gtaattcaga tgattacttt gcacttgtgt tcccatgaaa     720 a atg cct ttc att tct aag ctg gta ttg gca tct cag cca aca ctt ttc     769
  Met Pro Phe Ile Ser Lys Leu Val Leu Ala Ser Gln Pro Thr Leu Phe
    1               5                  10                  15 tcc ttc ttt tct gcg tct tct cct ttt ctg ctt ttt ctg gat ctc agg       817
Ser Phe Phe Ser Ala Ser Ser Pro Phe Leu Leu Phe Leu Asp Leu Arg
                20                  25                  30 cca gag cgc act tac cta cca gtc tgt cat gtg gcc ctc atc cac atg       865
Pro Glu Arg Thr Tyr Leu Pro Val Cys His Val Ala Leu Ile His Met
            35                  40                  45 gtg gtc ctt ctc acc atg gtg ttc ttg tct cca cag ctc ttt gaa tca       913
Val Val Leu Leu Thr Met Val Phe Leu Ser Pro Gln Leu Phe Glu Ser
    50                  55                  60 ctg aat ttt cag aat gac ttc aaa tat gag gca tct ttc tac ctg agg       961
Leu Asn Phe Gln Asn Asp Phe Lys Tyr Glu Ala Ser Phe Tyr Leu Arg
 65                  70                  75                  80
```

```
agg gtg atc agg gtc ctc tcc att tgt acc acc tgc ctc ctg gac atg      1009
Arg Val Ile Arg Val Leu Ser Ile Cys Thr Thr Cys Leu Leu Asp Met
            85                  90                  95 ctg cag gtc gtc aac atc agc ccc agc att tcc tgg ttg gtg agg ttt      1057
Leu Gln Val Val Asn Ile Ser Pro Ser Ile Ser Trp Leu Val Arg Phe
            100                 105                 110 aaa tgg aaa tcc aca att ttt acc ttc cat ttg ttc tca tgg tct ctc      1105
Lys Trp Lys Ser Thr Ile Phe Thr Phe His Leu Phe Ser Trp Ser Leu
            115                 120                 125 agt ttt cct gtt agt agt agc ctg atc ttt tac act gtg gct tct tcc      1153
Ser Phe Pro Val Ser Ser Ser Leu Ile Phe Tyr Thr Val Ala Ser Ser
        130                 135                 140 aat gtg acc cag atc aat ttg cat gtc agt aaa tac tgt tca ctt ttc      1201
Asn Val Thr Gln Ile Asn Leu His Val Ser Lys Tyr Cys Ser Leu Phe
145                 150                 155                 160 cca ata aac tcc ata atc aga gga ctg ttt ttc act ctg tca tta ttc      1249
Pro Ile Asn Ser Ile Ile Arg Gly Leu Phe Phe Thr Leu Ser Leu Phe
                165                 170                 175 aga gat gtt ttt ctt aaa caa ata atg ctg ttc tca agt gtc tac atg      1297
Arg Asp Val Phe Leu Lys Gln Ile Met Leu Phe Ser Ser Val Tyr Met
            180                 185                 190 atg act ctc att cag gaa cta cag gag atc ctg gta cct tca cag ccc      1345
Met Thr Leu Ile Gln Glu Leu Gln Glu Ile Leu Val Pro Ser Gln Pro
            195                 200                 205 cag cct cta cct aag gat ctt tgc aga ggc aag agc cat cag cac atc      1393
Gln Pro Leu Pro Lys Asp Leu Cys Arg Gly Lys Ser His Gln His Ile
        210                 215                 220 ctg ctg ccg gtg agt ttc tcg gtg ggc atg tac aag atg gac ttc atc      1441
Leu Leu Pro Val Ser Phe Ser Val Gly Met Tyr Lys Met Asp Phe Ile
225                 230                 235                 240 atc tca acc tcc tca aca ttg cca tgg gca tat gac cgt ggt gtc tag      1489
Ile Ser Thr Ser Ser Thr Leu Pro Trp Ala Tyr Asp Arg Gly Val  *
                245                 250                 255 aggctagtgg gcagtgtcta taccattgtc aggttttttgg tgctactgag atctgataaa   1549
agggtaatca atgtgatgta aactataaga caaatgttta aaaggttaat tgtatgaatc   1609
ctgtcatgag ttaaattatt cagagtgttc attatagaga ataatccaaa gttaaaataa   1669
ttggataatt tatttgtatg taggataaaa gtagtaggag attgcttctt gaagatttaa   1729
aattatattg agtgtaatta tttgcattaa aataatttta aatgttttga atagcaagta   1789
ttgatataat taaactttcg aataacttag tgctttgcct ttattcctaa tgtttatatg   1849
gaagcatgtg tcaatgtttt gatgcattac agctctgagc ggtccttctg tattaggtgg   1909
tcatcattta tatacttctc cataaaagat taaggacctg gaaatgtaag atacatgaag   1969
aaaatctaag tggagaggct gtttgtggtt aagtgataac agtgttgtaa gcgatgcatg   2029
aggtaggtgt tcagtgcata tcctctgcat tttattaata aacactgtaa aatttagaag   2089
aaaattgttt caccaaatgc acataaaact aataaaatag agtggatttt gatatgtccc   2149
tcgtgcc                                                              2156
```

<210> SEQ ID NO 9
<211> LENGTH: 255
<212> TYPE: PRT
<213> ORGANISM: Homo sapiens

<400> SEQUENCE: 9

Met Pro Phe Ile Ser Lys Leu Val Leu Ala Ser Gln Pro Thr Leu Phe
1               5                   10                  15

-continued

```
Ser Phe Phe Ser Ala Ser Ser Pro Phe Leu Leu Phe Leu Asp Leu Arg
            20                  25                  30
Pro Glu Arg Thr Tyr Leu Pro Val Cys His Val Ala Leu Ile His Met
        35                  40                  45
Val Val Leu Leu Thr Met Val Phe Leu Ser Pro Gln Leu Phe Glu Ser
    50                  55                  60
Leu Asn Phe Gln Asn Asp Phe Lys Tyr Glu Ala Ser Phe Tyr Leu Arg
65                  70                  75                  80
Arg Val Ile Arg Val Leu Ser Ile Cys Thr Thr Cys Leu Leu Asp Met
                85                  90                  95
Leu Gln Val Val Asn Ile Ser Pro Ser Ile Ser Trp Leu Val Arg Phe
            100                 105                 110
Lys Trp Lys Ser Thr Ile Phe Thr Phe His Leu Phe Ser Trp Ser Leu
        115                 120                 125
Ser Phe Pro Val Ser Ser Ser Leu Ile Phe Tyr Thr Val Ala Ser Ser
    130                 135                 140
Asn Val Thr Gln Ile Asn Leu His Val Ser Lys Tyr Cys Ser Leu Phe
145                 150                 155                 160
Pro Ile Asn Ser Ile Ile Arg Gly Leu Phe Phe Thr Leu Ser Leu Phe
                165                 170                 175
Arg Asp Val Phe Leu Lys Gln Ile Met Leu Phe Ser Ser Val Tyr Met
            180                 185                 190
Met Thr Leu Ile Gln Glu Leu Gln Glu Ile Leu Val Pro Ser Gln Pro
        195                 200                 205
Gln Pro Leu Pro Lys Asp Leu Cys Arg Gly Lys Ser His Gln His Ile
    210                 215                 220
Leu Leu Pro Val Ser Phe Ser Val Gly Met Tyr Lys Met Asp Phe Ile
225                 230                 235                 240
Ile Ser Thr Ser Ser Thr Leu Pro Trp Ala Tyr Asp Arg Gly Val
                245                 250                 255
```

<210> SEQ ID NO 10
<211> LENGTH: 2156
<212> TYPE: DNA
<213> ORGANISM: Homo sapiens
<220> FEATURE:
<221> NAME/KEY: CDS
<222> LOCATION: (722)...(1489)

<400> SEQUENCE: 10

```
gttttttttt tttttttttt tttttttttt tattttaagg gattcgttta ataggacttg      60
tggtaagtgg aataatgcca tgcaaaggtc cccatgtcta accaccaggt tctaggcatg     120
tattatggta tatgagaaat gggaattcag gctgcagatg aaatcaaggt tgataaccag     180
ctgactctaa aacaaaaaca ttaacttgaa ttacagattt gggcctaatg taattataag     240
cattcttaaa agtgaaagaa ataataagag aaactgagtg ctgtgatgtg agtcagttaa     300
acttttttt caactttttc tttaggtgat tatttccct taacataaaa tttactttag       360
ctcaactata caaacatgtg agttattgtt atgtaaccat cactcttcat taagaaatgc     420
tttgtaaaaa gtgagccagt ttttcatata cattcttcaa aatacattct caacattata     480
catcaaatta tatatacata catgcacaca tacactatat atatcaagga tttatatgag     540
aggattaatt aagaaaaaaa ttagtggaat aaaaataatg tttatgataa ttttggccat     600
agaatatata atacagatga tgtgaagtac aaaatgtttt ttatacttca tattttgatg     660
tacaaagtat gtttgtcttt gtaattcaga tgattacttt gcacttgtgt tcccatgaaa     720
```

```
a atg cct ttc att tct aag ctg gta ttg gca tct cag cca aca ctt ttc      769
  Met Pro Phe Ile Ser Lys Leu Val Leu Ala Ser Gln Pro Thr Leu Phe
   1               5                  10                  15 tcc ttc ttt tct gcg tct tct cct ttt ctg ctt ttt ctg gat ctc agg        817
Ser Phe Phe Ser Ala Ser Ser Pro Phe Leu Leu Phe Leu Asp Leu Arg
                20                  25                  30 cca gag cgc act tac cta cca gtc tgt cat gtg gcc ctc atc cac atg        865
Pro Glu Arg Thr Tyr Leu Pro Val Cys His Val Ala Leu Ile His Met
            35                  40                  45 gtg gtc ctt ctc acc atg gtg ttc ttg tct cca cag ctc ttt gaa tca        913
Val Val Leu Leu Thr Met Val Phe Leu Ser Pro Gln Leu Phe Glu Ser
 50                  55                  60 ctg aat ttt cag aat gac ttc aaa tat gag gca tct ttc tac ctg agg        961
Leu Asn Phe Gln Asn Asp Phe Lys Tyr Glu Ala Ser Phe Tyr Leu Arg
 65                  70                  75                  80 agg gtg atc agg gtc ctc tcc att tgt acc acc tgc ctc ctg ggc atg       1009
Arg Val Ile Arg Val Leu Ser Ile Cys Thr Thr Cys Leu Leu Gly Met
                85                  90                  95 ctg cag gtc gtc aac atc agc ccc agc att tcc tgg ttg gtg agg ttt       1057
Leu Gln Val Val Asn Ile Ser Pro Ser Ile Ser Trp Leu Val Arg Phe
            100                 105                 110 aaa tgg aaa tcc aca att ttt acc ttc cat ttg ttc tca tgg tct ctc       1105
Lys Trp Lys Ser Thr Ile Phe Thr Phe His Leu Phe Ser Trp Ser Leu
        115                 120                 125 agt ttt cct gtt agt agt agc ctg atc ttt tac act gtg gct tct tcc       1153
Ser Phe Pro Val Ser Ser Ser Leu Ile Phe Tyr Thr Val Ala Ser Ser
130                 135                 140 aat gtg acc cag atc aat ttg cat gtc agt aaa tac tgt tca ctt ttc       1201
Asn Val Thr Gln Ile Asn Leu His Val Ser Lys Tyr Cys Ser Leu Phe
145                 150                 155                 160 cca ata aac tcc ata atc aga gga ctg ttt ttc act ctg tca tta ttc       1249
Pro Ile Asn Ser Ile Ile Arg Gly Leu Phe Phe Thr Leu Ser Leu Phe
                165                 170                 175 aga gat gtt ttt ctt aaa cag ata atg ctg ttc tca agt gtc tac atg       1297
Arg Asp Val Phe Leu Lys Gln Ile Met Leu Phe Ser Ser Val Tyr Met
            180                 185                 190 atg act ctc att cag gaa cta cag gag atc ctg gta cct tca cag ccc       1345
Met Thr Leu Ile Gln Glu Leu Gln Glu Ile Leu Val Pro Ser Gln Pro
        195                 200                 205 cag cct cta cct aag gat ctt tgc aga ggc aag agc cat cag cac atc       1393
Gln Pro Leu Pro Lys Asp Leu Cys Arg Gly Lys Ser His Gln His Ile
210                 215                 220 ctg ctg ccg gtg agt ttc tcg gtg ggc atg tac aag atg gac ttc atc       1441
Leu Leu Pro Val Ser Phe Ser Val Gly Met Tyr Lys Met Asp Phe Ile
225                 230                 235                 240 atc tca acc tcc tca aca ttg cca tgg gca tat gac cgt ggt gtc tag       1489
Ile Ser Thr Ser Ser Thr Leu Pro Trp Ala Tyr Asp Arg Gly Val *
                245                 250                 255 aggctagtgg gcagtgtcta taccattgtc aggttttttgg tgctactgag atctgataaa   1549
agggtaatca atgtgatgta aactataaga caaatgttta aaaggttaat tgtatgaatc    1609
ctgtcatgag ttaaattatt cagagtgttc attatagaga ataatccaaa gttaaaataa    1669
ttggataatt tatttgtatg taggataaaa gtagtaggag attgcttctt gaagatttaa    1729
aattatattg agtgtaatta tttgcattaa aataatttta aatgttttga atagcaagta    1789
ttgatataat taaactttcg aataacttag tgctttgcct ttattcctaa tgttatatg     1849 gaagcatgtg gtcaatgttt gatgcattac agctctgagc ggtccttctg tattaggtgg    1909
```

```
tcatcattta tatacttctc cataaaagat taaggacctg gaaatgtaag atacatgaag    1969
aaaatctaag tggagaggct gtttgtggtt aagtgataac agtgttgtaa gcgatgcatg    2029
aggtaggtgt tcagtgcata tcctctgcat tttattaata aacactgtaa aatttagaag    2089
aaaattgttt caccaaatgc acataaaact aataaaatag agtggatttt gatatgtccc    2149
tcgtgcc                                                              2156
```

<210> SEQ ID NO 11
<211> LENGTH: 255
<212> TYPE: PRT
<213> ORGANISM: Homo sapiens

<400> SEQUENCE: 11

```
Met Pro Phe Ile Ser Lys Leu Val Leu Ala Ser Gln Pro Thr Leu Phe
 1               5                  10                  15

Ser Phe Phe Ser Ala Ser Ser Pro Phe Leu Leu Phe Leu Asp Leu Arg
            20                  25                  30

Pro Glu Arg Thr Tyr Leu Pro Val Cys His Val Ala Leu Ile His Met
        35                  40                  45

Val Val Leu Leu Thr Met Val Phe Leu Ser Pro Gln Leu Phe Glu Ser
    50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Gly Met
                85                  90                  95

Leu Gln Val Val Asn Ile Ser Pro Ser Ile Ser Trp Leu Val Arg Phe
           100                 105                 110

Lys Trp Lys Ser Thr Ile Phe Thr Phe His Leu Phe Ser Trp Ser Leu
       115                 120                 125

Ser Phe Pro Val Ser Ser Ser Leu Ile Phe Tyr Thr Val Ala Ser Ser
   130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
           180                 185                 190

Met Thr Leu Ile Gln Glu Leu Gln Glu Ile Leu Val Pro Ser Gln Pro
       195                 200                 205

Gln Pro Leu Pro Lys Asp Leu Cys Arg Gly Lys Ser His Gln His Ile
   210                 215                 220

Leu Leu Pro Val Ser Phe Ser Val Gly Met Tyr Lys Met Asp Phe Ile
225                 230                 235                 240

Ile Ser Thr Ser Ser Thr Leu Pro Trp Ala Tyr Asp Arg Gly Val
                245                 250                 255
```

<210> SEQ ID NO 12
<211> LENGTH: 2156
<212> TYPE: DNA
<213> ORGANISM: Homo sapiens
<220> FEATURE:
<221> NAME/KEY: CDS
<222> LOCATION: (722)...(1489)

<400> SEQUENCE: 12

```
gtttttttt ttttttttt tttttttttt tatttaagg gattcgttta ataggacttg      60
```

-continued

```
tggtaagtgg aataatgcca tgcaaaggtc cccatgtcta accaccaggt tctaggcatg    120
tattatggta tatgagaaat gggaattcag gctgcagatg aaatcaaggt tgataaccag    180
ctgactctaa aacaaaaaca ttaacttgaa ttacagattt gggcctaatg taattataag    240
cattcttaaa agtgaaagaa ataataagag aaactgagtg ctgtgatgtg agtcagttaa    300
actttttttt caacttttc tttaggtgat tattttccct taacataaaa tttactttag    360
ctcaactata caaacatgtg agttattgtt atgtaaccat cactcttcat taagaaatgc    420
tttgtaaaaa gtgagccagt ttttcatata cattcttcaa aatacattct caacattata    480
catcaaatta tatatacata catgcacaca tacactatat atatcaagga tttatatgag    540
aggattaatt aagaaaaaaa ttagtggaat aaaaataatg tttatgataa ttttggccat    600
agaatatata atacagatga tgtgaagtac aaaatgtttt ttatacttca tattttgatg    660
tacaaagtat gtttgtcttt gtaattcaga tgattacttt gcacttgtgt tcccatgaaa    720 a atg cct ttc att tct aag ctg gta ttg gca tct cag cca aca ctt ttc    769
  Met Pro Phe Ile Ser Lys Leu Val Leu Ala Ser Gln Pro Thr Leu Phe
    1               5                  10                  15 tcc ttc ttt tct gcg tct tct cct ttt ctg ctt ttt ctg gat ctc agg        817
Ser Phe Phe Ser Ala Ser Ser Pro Phe Leu Leu Phe Leu Asp Leu Arg
                20                  25                  30 cca gag cgc act tac cta cca gtc tgt cat gtg gcc ctc atc cac atg        865
Pro Glu Arg Thr Tyr Leu Pro Val Cys His Val Ala Leu Ile His Met
            35                  40                  45 gtg gtc ctt ctc acc atg gtg ttc ttg tct cca cag ctc ttt gaa tca        913
Val Val Leu Leu Thr Met Val Phe Leu Ser Pro Gln Leu Phe Glu Ser
        50                  55                  60 ctg aat ttt cag aat gac ttc aaa tat gag gca tct ttc tac ctg agg        961
Leu Asn Phe Gln Asn Asp Phe Lys Tyr Glu Ala Ser Phe Tyr Leu Arg
    65                  70                  75                  80 agg gtg atc agg gtc ctc tcc att tgt acc acc tgc ctc ctg ggc atg       1009
Arg Val Ile Arg Val Leu Ser Ile Cys Thr Thr Cys Leu Leu Gly Met
                85                  90                  95 ctg cag gtc gtc aac atc agc ccc agc att tcc tgg ttg gtg agg ttt       1057
Leu Gln Val Val Asn Ile Ser Pro Ser Ile Ser Trp Leu Val Arg Phe
            100                 105                 110 aaa tgg aaa tcc aca att ttt acc ttc cat ttg ttc tca tgg tct ctc       1105
Lys Trp Lys Ser Thr Ile Phe Thr Phe His Leu Phe Ser Trp Ser Leu
        115                 120                 125 agt ttt cct gtt agt agt agc ctg atc ttt tac act gtg gct tct tcc       1153
Ser Phe Pro Val Ser Ser Ser Leu Ile Phe Tyr Thr Val Ala Ser Ser
    130                 135                 140 aat gtg acc cag atc aat ttg cat gtc agt aaa tac tgt tca ctt ttc       1201
Asn Val Thr Gln Ile Asn Leu His Val Ser Lys Tyr Cys Ser Leu Phe
145                 150                 155                 160 cca ata aac tcc ata atc aga gga ctg ttt ttc act ctg tca tta ttc       1249
Pro Ile Asn Ser Ile Ile Arg Gly Leu Phe Phe Thr Leu Ser Leu Phe
                165                 170                 175 aga gat gtt ttt ctt aaa caa ata atg ctg ttc tca agt gtc tac atg       1297
Arg Asp Val Phe Leu Lys Gln Ile Met Leu Phe Ser Ser Val Tyr Met
            180                 185                 190 atg act ctc att cag gaa cta cag gag atc ctg gta cct tca cag ccc       1345
Met Thr Leu Ile Gln Glu Leu Gln Glu Ile Leu Val Pro Ser Gln Pro
        195                 200                 205 cag cct cta cct aag gat ctt tgc aga ggc aag agc cat cag cac atc       1393
Gln Pro Leu Pro Lys Asp Leu Cys Arg Gly Lys Ser His Gln His Ile
    210                 215                 220 ctg ctg ccg gtg agt ttc tcg gtg ggc atg tac aag atg gac ttc atc       1441
```

```
Leu Leu Pro Val Ser Phe Ser Val Gly Met Tyr Lys Met Asp Phe Ile
225                 230                 235                 240 atc tca acc tcc tca acg ttg cca tgg gca tat gac cgt ggt gtc tag      1489
Ile Ser Thr Ser Ser Thr Leu Pro Trp Ala Tyr Asp Arg Gly Val  *
                    245                 250                 255 aggctagtgg gcagtgtcta taccattgtc aggtttttgg tgctactgag atctgataaa    1549
agggtaatca atgtgatgta aactataaga caaatgttta aaaggttaat tgtatgaatc    1609
ctgtcatgag ttaaattatt cagagtgttc attatagaga ataatccaaa gttaaaataa    1669
ttggataatt tatttgtatg taggataaaa gtagtaggag attgcttctt gaagatttaa    1729
aattatattg agtgtaatta tttgcattaa ataattttta aatgttttga atagcaagta    1789
ttgatataat taaactttcg aataacttag tgctttgcct ttattcctaa tgtttatatg    1849
gaagcatgtg gtcaatgttt gatgcattac agctctgagc ggtccttctg tattaggtgg    1909
tcatcattta tatacttctc cataaaagat taaggacctg gaaatgtaag atacatgaag    1969
aaaatctaag tggagaggct gtttgtggtt aagtgataac agtgttgtaa gcgatgcatg    2029
aggtaggtgt tcagtgcata tcctctgcat tttattaata aacactgtaa aatttagaag    2089
aaaattgttt caccaaatgc acataaaact aataaaatag agtggatttt gatatgtccc    2149
tcgtgcc                                                              2156

<210> SEQ ID NO 13
<211> LENGTH: 255
<212> TYPE: PRT
<213> ORGANISM: Homo sapiens

<400> SEQUENCE: 13

Met Pro Phe Ile Ser Lys Leu Val Leu Ala Ser Gln Pro Thr Leu Phe
 1               5                  10                  15

Ser Phe Phe Ser Ala Ser Ser Pro Phe Leu Leu Phe Leu Asp Leu Arg
                20                  25                  30

Pro Glu Arg Thr Tyr Leu Pro Val Cys His Val Ala Leu Ile His Met
            35                  40                  45

Val Val Leu Leu Thr Met Val Phe Leu Ser Pro Gln Leu Phe Glu Ser
        50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Gly Met
                85                  90                  95

Leu Gln Val Val Asn Ile Ser Pro Ser Ile Ser Trp Leu Val Arg Phe
            100                 105                 110

Lys Trp Lys Ser Thr Ile Phe Thr Phe His Leu Phe Ser Trp Ser Leu
        115                 120                 125

Ser Phe Pro Val Ser Ser Leu Ile Phe Tyr Thr Val Ala Ser Ser
    130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
        195                 200                 205

Gln Pro Leu Pro Lys Asp Leu Cys Arg Gly Lys Ser His Gln His Ile
```

```
                    210                 215                 220
Leu Leu Pro Val Ser Phe Ser Val Gly Met Tyr Lys Met Asp Phe Ile
225                 230                 235                 240

Ile Ser Thr Ser Ser Thr Leu Pro Trp Ala Tyr Asp Arg Gly Val
                245                 250                 255

<210> SEQ ID NO 14
<211> LENGTH: 2156
<212> TYPE: DNA
<213> ORGANISM: Homo sapiens
<220> FEATURE:
<221> NAME/KEY: CDS
<222> LOCATION: (722)...(1489)

<400> SEQUENCE: 14 gtttttttt tttttttttt tttttttttt tattttaagg gattcgttta ataggacttg      60
tggtaagtgg aataatgcca tgcaaaggtc cccatgtcta accaccaggt tctaggcatg     120
tattatggta tatgagaaat gggaattcag gctgcagatg aaatcaaggt tgataaccag     180
ctgactctaa aacaaaaaca ttaacttgaa ttacagattt gggcctaatg taattataag     240
cattcttaaa agtgaaagaa ataataagag aaactgagtg ctgtgatgtg agtcagttaa     300 acttttttt caacttttc tttaggtgat tattttccct taacataaaa tttactttag      360
ctcaactata caaacatgtg agttattgtt atgtaaccat cactcttcat taagaaatgc     420
tttgtaaaaa gtgagccagt ttttcatata cattcttcaa aatacattct caacattata     480
catcaaatta tatatacata catgcacaca tacactatat atatcaagga tttatatgag     540
aggattaatt aagaaaaaaa ttagtggaat aaaaataatg tttatgataa ttttggccat     600
agaatatata atacagatga tgtgaagtac aaaatgtttt ttatacttca tattttgatg     660
tacaaagtat gtttgtcttt gtaattcaga tgattacttt gcacttgtgt cccatgaaa      720 a atg cct ttc att tct aag ctg gta ttg gca tct cag cca aca ctt ttc    769
  Met Pro Phe Ile Ser Lys Leu Val Leu Ala Ser Gln Pro Thr Leu Phe
   1               5                  10                  15 tcc ttc ttt tct gcg tct tct cct ttt ctg ctt ttt ctg gat ctc agg      817
Ser Phe Phe Ser Ala Ser Ser Pro Phe Leu Leu Phe Leu Asp Leu Arg
                20                  25                  30 cca gag cgc act tac cta cca gtc tgt cat gtg gcc ctc atc cac atg     865
Pro Glu Arg Thr Tyr Leu Pro Val Cys His Val Ala Leu Ile His Met
            35                  40                  45 gtg gtc ctt ctc acc atg gtg ttc ttg tct cca cag ctc ttt gaa tca     913
Val Val Leu Leu Thr Met Val Phe Leu Ser Pro Gln Leu Phe Glu Ser
     50                  55                  60 ctg aat ttt cag aat gac ttc aaa tat gag gca tct ttc tac ctg agg     961
Leu Asn Phe Gln Asn Asp Phe Lys Tyr Glu Ala Ser Phe Tyr Leu Arg
 65                  70                  75                  80 agg gtg atc agg gtc ctc tcc att tgt acc acc tgc ctc ctg ggc atg    1009
Arg Val Ile Arg Val Leu Ser Ile Cys Thr Thr Cys Leu Leu Gly Met
                 85                  90                  95 ctg cag gtc gtc aac atc agc ccc agc att tcc tgg ttg gtg agg ttt    1057
Leu Gln Val Val Asn Ile Ser Pro Ser Ile Ser Trp Leu Val Arg Phe
            100                 105                 110 aaa tgg aaa tcc aca att ttt acc ttc cat ttg ttc tca tgg tct ctc    1105
Lys Trp Lys Ser Thr Ile Phe Thr Phe His Leu Phe Ser Trp Ser Leu
        115                 120                 125 agt ttt cct gtt agt agt agc ctg atc ttt tac act gtg gct tct tcc    1153
Ser Phe Pro Val Ser Ser Ser Leu Ile Phe Tyr Thr Val Ala Ser Ser
    130                 135                 140
```

```
aat gtg acc cag atc aat ttg cat gtc agt aaa tac tgt tca ctt ttc    1201
Asn Val Thr Gln Ile Asn Leu His Val Ser Lys Tyr Cys Ser Leu Phe
145                 150                 155                 160 cca ata aac tcc ata atc aga gga ctg ttt ttc act ctg tca tta ttc    1249
Pro Ile Asn Ser Ile Ile Arg Gly Leu Phe Phe Thr Leu Ser Leu Phe
                165                 170                 175 aga gat gtt ttt ctt aaa caa ata atg ctg ttc tca agt gtc tac atg    1297
Arg Asp Val Phe Leu Lys Gln Ile Met Leu Phe Ser Ser Val Tyr Met
            180                 185                 190 atg act ctc att cag gaa cta cag gag atc ctg gta cct tca cag ccc    1345
Met Thr Leu Ile Gln Glu Leu Gln Glu Ile Leu Val Pro Ser Gln Pro
        195                 200                 205 cag cct cta cct aag gat ctt tgc aga ggc aag agc cat cag cac atc    1393
Gln Pro Leu Pro Lys Asp Leu Cys Arg Gly Lys Ser His Gln His Ile
    210                 215                 220 ctg ctg ccg gtg agt ttc tcg gtg ggc atg tac aag atg gac ttc atc    1441
Leu Leu Pro Val Ser Phe Ser Val Gly Met Tyr Lys Met Asp Phe Ile
225                 230                 235                 240 atc tca acc tcc tca aca ttg cca tgg gca tat gac cgt ggt gtc tag    1489
Ile Ser Thr Ser Ser Thr Leu Pro Trp Ala Tyr Asp Arg Gly Val *
                245                 250                 255 aggctagtgg gcagtgtcta taccattgtc aggttttttgg tgctactgag atctgataaa    1549
agggtaatca atgtgatgta aactataaga caaatgttta aaaggttaat tgtatgaatc    1609
ctgtcatgag ttaaattatt cagagtgttc attatagaga ataatccaaa gttaaaataa    1669
ttggataatt tatttgtatg taggataaaa gtagtaggag attgcttctt gaagatttaa    1729
aattatattg agtgtaatta tttgcattaa ataattttta aatgttttga atagcaagta    1789
ttgatataat taaactttcg aataacttag tgctttgcct ttattcctaa tgtttatatg    1849
gaagcatgtg gtcaatgttt gatgcattac agctctgagc ggtccttctg tattaggtgg    1909
tcatcattta tgtacttctc cataaaagat taaggacctg gaaatgtaag atacatgaag    1969
aaaatctaag tggagaggct gtttgtggtt aagtgataac agtgttgtaa gcgatgcatg    2029
aggtaggtgt tcagtgcata tcctctgcat tttattaata aacactgtaa aatttagaag    2089
aaaattgttt caccaaatgc acataaaact aataaaatag agtggatttt gatatgtccc    2149
tcgtgcc                                                                2156
```

<210> SEQ ID NO 15
<211> LENGTH: 255
<212> TYPE: PRT
<213> ORGANISM: Homo sapiens

<400> SEQUENCE: 15

```
Met Pro Phe Ile Ser Lys Leu Val Leu Ala Ser Gln Pro Thr Leu Phe
 1               5                  10                  15

Ser Phe Phe Ser Ala Ser Ser Pro Phe Leu Leu Phe Leu Asp Leu Arg
            20                  25                  30

Pro Glu Arg Thr Tyr Leu Pro Val Cys His Val Ala Leu Ile His Met
        35                  40                  45

Val Val Leu Leu Thr Met Val Phe Leu Ser Pro Gln Leu Phe Glu Ser
    50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Gly Met
                85                  90                  95

Leu Gln Val Val Asn Ile Ser Pro Ser Ile Ser Trp Leu Val Arg Phe
```

-continued

```
                    100                 105                 110
Lys Trp Lys Ser Thr Ile Phe Thr Phe His Leu Phe Ser Trp Ser Leu
            115                 120                 125

Ser Phe Pro Val Ser Ser Ser Leu Ile Phe Tyr Thr Val Ala Ser Ser
        130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
        195                 200                 205

Gln Pro Leu Pro Lys Asp Leu Cys Arg Gly Lys Ser His Gln His Ile
    210                 215                 220

Leu Leu Pro Val Ser Phe Ser Val Gly Met Tyr Lys Met Asp Phe Ile
225                 230                 235                 240

Ile Ser Thr Ser Ser Thr Leu Pro Trp Ala Tyr Asp Arg Gly Val
                245                 250                 255
```

<210> SEQ ID NO 16
<211> LENGTH: 2156
<212> TYPE: DNA
<213> ORGANISM: Homo sapiens
<220> FEATURE:
<221> NAME/KEY: CDS
<222> LOCATION: (722)...(1489)

<400> SEQUENCE: 16

```
gtttttttt tttttttttt tttttttttt tattttaagg gattcgttta ataggacttg      60
tggtaagtgg aataatgcca tgcaaaggtc cccatgtcta accaccaggt tctaggcatg     120
tattatggta tatgagaaat gggaattcag gctgcagatg aaatcaaggt tgataaccag     180
ctgactctaa acaaaaaaca ttaacttgaa ttacagattt gggcctaatg taattataag     240
cattcttaaa agtgaaagaa ataataagag aaactgagtg ctgtgatgtg agtcagttaa     300
actttttttt caacttttc tttaggtgat tattttcct taacataaaa tttactttag       360
ctcaactata caaacatgtg agttattgtt atgtaaccat cactcttcat taagaaatgc     420
tttgtaaaaa gtgagccagt ttttcatata cattcttcaa aatacattct caacattata     480
catcaaatta tatatacata catgcacaca tacactatat atatcaagga tttatatgat     540
aggattaatt aagaaaaaaa ttagtggaat aaaaataatg tttatgataa ttttggccat     600
agaatatata atacagatga tgtgaagtac aaaatgtttt ttatacttca tattttgatg    660
tacaaagtat gtttgtcttt gtaattcaga tgattacttt gcacttgtgt tcccatgaaa    720
```

```
a atg cct ttc att tct aag ctg gta ttg gca tct cag cca aca ctt ttc      769
  Met Pro Phe Ile Ser Lys Leu Val Leu Ala Ser Gln Pro Thr Leu Phe
  1               5                  10                  15 tcc ttc ttt tct gcg tct tct cct ttt ctg ctt ttt ctg gat ctc agg        817
Ser Phe Phe Ser Ala Ser Ser Pro Phe Leu Leu Phe Leu Asp Leu Arg
                20                  25                  30 cca gag cgc act tac cta cca gtc tgt cat gtg gcc ctc atc cac atg        865
Pro Glu Arg Thr Tyr Leu Pro Val Cys His Val Ala Leu Ile His Met
            35                  40                  45 gtg gtc ctt ctc acc atg gtg ttc ttg tct cca cag ctc ttt gaa tca        913
Val Val Leu Leu Thr Met Val Phe Leu Ser Pro Gln Leu Phe Glu Ser
        50                  55                  60
```

```
ctg aat ttt cag aat gac ttc aaa tat gag gca tct ttc tac ctg agg     961
Leu Asn Phe Gln Asn Asp Phe Lys Tyr Glu Ala Ser Phe Tyr Leu Arg
 65                  70                  75                  80 agg gtg atc agg gtc ctc tcc att tgt acc acc tgc ctc ctg ggc atg    1009
Arg Val Ile Arg Val Leu Ser Ile Cys Thr Thr Cys Leu Leu Gly Met
             85                  90                  95 ctg cag gtc gtc aac atc agc ccc agc att tcc tgg ttg gtg agg ttt    1057
Leu Gln Val Val Asn Ile Ser Pro Ser Ile Ser Trp Leu Val Arg Phe
         100                 105                 110 aaa tgg aaa tcc aca att ttt acc ttc cat ttg ttc tca tgg tct ctc    1105
Lys Trp Lys Ser Thr Ile Phe Thr Phe His Leu Phe Ser Trp Ser Leu
     115                 120                 125 agt ttt cct gtt agt agt agc ctg atc ttt tac act gtg gct tct tcc    1153
Ser Phe Pro Val Ser Ser Ser Leu Ile Phe Tyr Thr Val Ala Ser Ser
 130                 135                 140 aat gtg acc cag atc aat ttg cat gtc agt aaa tac tgt tca ctt ttc    1201
Asn Val Thr Gln Ile Asn Leu His Val Ser Lys Tyr Cys Ser Leu Phe
145                 150                 155                 160 cca ata aac tcc ata atc aga gga ctg ttt ttc act ctg tca tta ttc    1249
Pro Ile Asn Ser Ile Ile Arg Gly Leu Phe Phe Thr Leu Ser Leu Phe
                165                 170                 175 aga gat gtt ttt ctt aaa caa ata atg ctg ttc tca agt gtc tac atg    1297
Arg Asp Val Phe Leu Lys Gln Ile Met Leu Phe Ser Ser Val Tyr Met
            180                 185                 190 atg act ctc att cag gaa cta cag gag atc ctg gta cct tca cag ccc    1345
Met Thr Leu Ile Gln Glu Leu Gln Glu Ile Leu Val Pro Ser Gln Pro
        195                 200                 205 cag cct cta cct aag gat ctt tgc aga ggc aag agc cat cag cac atc    1393
Gln Pro Leu Pro Lys Asp Leu Cys Arg Gly Lys Ser His Gln His Ile
    210                 215                 220 ctg ctg ccg gtg agt ttc tcg gtg ggc atg tac aag atg gac ttc atc    1441
Leu Leu Pro Val Ser Phe Ser Val Gly Met Tyr Lys Met Asp Phe Ile
225                 230                 235                 240 atc tca acc tcc tca aca ttg cca tgg gca tat gac cgt ggt gtc tag    1489
Ile Ser Thr Ser Ser Thr Leu Pro Trp Ala Tyr Asp Arg Gly Val  *
                245                 250                 255 aggctagtgg gcagtgtcta taccattgtc aggttttttgg tgctactgag atctgataaa  1549
agggtaatca atgtgatgta aactataaga caaatgttta aaaggttaat tgtatgaatc  1609
ctgtcatgag ttaaattatt cagagtgttc attatagaga ataatccaaa gttaaaataa  1669
ttggataatt tatttgtatg taggataaaa gtagtaggag attgcttctt gaagatttaa  1729
aattatattg agtgtaatta tttgcattaa ataattttta aatgttttga atagcaagta  1789
ttgatataat taaactttcg aataacttag tgctttgcct ttattcctaa tgtttatatg  1849
gaagcatgtg gtcaatgttt gatgcattac agctctgagc ggtccttctg tattaggtgg  1909
tcatcattta tatacttctc cataaaagat taaggacctg gaaatgtaag atacatgaag  1969
aaaatctaag tggagaggct gttttgtggtt aagtgataac agtgttgtaa gcgatgcatg  2029
aggtaggtgt tcagtgcata tcctctgcat tttattaata aacactgtaa aatttagaag  2089
aaaattgttt caccaaatgc acataaaact aataaaatag agtggatttt gatatgtccc  2149
tcgtgcc                                                             2156
```

<210> SEQ ID NO 17
<211> LENGTH: 255
<212> TYPE: PRT
<213> ORGANISM: Homo sapiens

<400> SEQUENCE: 17

Met Pro Phe Ile Ser Lys Leu Val Leu Ala Ser Gln Pro Thr Leu Phe
1               5                   10                  15

Ser Phe Phe Ser Ala Ser Ser Pro Phe Leu Leu Phe Leu Asp Leu Arg
            20                  25                  30

Pro Glu Arg Thr Tyr Leu Pro Val Cys His Val Ala Leu Ile His Met
        35                  40                  45

Val Val Leu Leu Thr Met Val Phe Leu Ser Pro Gln Leu Phe Glu Ser
    50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Gly Met
                85                  90                  95

Leu Gln Val Val Asn Ile Ser Pro Ser Ile Ser Trp Leu Val Arg Phe
            100                 105                 110

Lys Trp Lys Ser Thr Ile Phe Thr Phe His Leu Phe Ser Trp Ser Leu
        115                 120                 125

Ser Phe Pro Val Ser Ser Ser Leu Ile Phe Tyr Thr Val Ala Ser Ser
    130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
        195                 200                 205

Gln Pro Leu Pro Lys Asp Leu Cys Arg Gly Lys Ser His Gln His Ile
    210                 215                 220

Leu Leu Pro Val Ser Phe Ser Val Gly Met Tyr Lys Met Asp Phe Ile
225                 230                 235                 240

Ile Ser Thr Ser Ser Thr Leu Pro Trp Ala Tyr Asp Arg Gly Val
                245                 250                 255

<210> SEQ ID NO 18
<211> LENGTH: 2156
<212> TYPE: DNA
<213> ORGANISM: Homo sapiens
<220> FEATURE:
<221> NAME/KEY: CDS
<222> LOCATION: (722)...(1489)

<400> SEQUENCE: 18 gtttttttt ttttttttt ttttttttt tatttaagg gattcgttta ataggacttg      60
tggtaagtgg aataatgcca tgcaaaggtc cccatgtcta accaccaggt tctaggcatg    120
tattatggta tatgagaaat gggaattcag gctgcagatg aaatcaaggt tgataaccag    180
ctgactctaa aacaaaaaca ttaacttgaa ttacagattt gggcctaatg taattataag    240
cattcttaaa agtgaaagaa ataataagag aaactgagtg ctgtgatgtg agtcagttaa    300
actttttttt caactttttc tttaggtgat tattttccct taacataaaa tttactttag    360
ctcaactata caaacatgtg agttattgtt atgtaaccat cactcttcat taagaaatgc    420
tttgtaaaaa gtgagccagt ttttcatata cattcttcaa aatacattct caacattata    480
tatcaaatta tatatacata catgcacaca tacactatat atatcaagga tttatatgag    540

-continued

```
aggattaatt aagaaaaaaa ttagtggaat aaaaataatg tttatgataa ttttggccat    600
agaatatata atacagatga tgtgaagtac aaaatgtttt ttatacttca tattttgatg    660
tacaaagtat gtttgtcttt gtaattcaga tgattacttt gcacttgtgt tcccatgaaa    720
```

| | | | | | | | | | | | | | | | | |
|---|---|---|---|---|---|---|---|---|---|---|---|---|---|---|---|---|
| a atg cct ttc att tct aag ctg gta ttg gca tct cag cca aca ctt ttc | | | | | | | | | | | | | | | | 769 |
| Met Pro Phe Ile Ser Lys Leu Val Leu Ala Ser Gln Pro Thr Leu Phe | | | | | | | | | | | | | | | |
| 1 | | | | 5 | | | | | 10 | | | | | 15 | | |

```
tcc ttc ttt tct gcg tct tct cct ttt ctg ctt ttt ctg gat ctc agg     817
Ser Phe Phe Ser Ala Ser Ser Pro Phe Leu Leu Phe Leu Asp Leu Arg
                20                  25                  30 cca gag cgc act tac cta cca gtc tgt cat gtg gcc ctc atc cac atg     865
Pro Glu Arg Thr Tyr Leu Pro Val Cys His Val Ala Leu Ile His Met
        35                  40                  45 gtg gtc ctt ctc acc atg gtg ttc ttg tct cca cag ctc ttt gaa tca     913
Val Val Leu Leu Thr Met Val Phe Leu Ser Pro Gln Leu Phe Glu Ser
    50                  55                  60 ctg aat ttt cag aat gac ttc aaa tat gag gca tct ttc tac ctg agg     961
Leu Asn Phe Gln Asn Asp Phe Lys Tyr Glu Ala Ser Phe Tyr Leu Arg
65                  70                  75                  80 agg gtg atc agg gtc ctc tcc att tgt acc acc tgc ctc ctg ggc atg    1009
Arg Val Ile Arg Val Leu Ser Ile Cys Thr Thr Cys Leu Leu Gly Met
                85                  90                  95 ctg cag gtc gtc aac atc agc ccc agc att tcc tgg ttg gtg agg ttt    1057
Leu Gln Val Val Asn Ile Ser Pro Ser Ile Ser Trp Leu Val Arg Phe
            100                 105                 110 aaa tgg aaa tcc aca att ttt acc ttc cat ttg ttc tca tgg tct ctc    1105
Lys Trp Lys Ser Thr Ile Phe Thr Phe His Leu Phe Ser Trp Ser Leu
        115                 120                 125 agt ttt cct gtt agt agt agc ctg atc ttt tac act gtg gct tct tcc    1153
Ser Phe Pro Val Ser Ser Ser Leu Ile Phe Tyr Thr Val Ala Ser Ser
    130                 135                 140 aat gtg acc cag atc aat ttg cat gtc agt aaa tac tgt tca ctt ttc    1201
Asn Val Thr Gln Ile Asn Leu His Val Ser Lys Tyr Cys Ser Leu Phe
145                 150                 155                 160 cca ata aac tcc ata atc aga gga ctg ttt ttc act ctg tca tta ttc    1249
Pro Ile Asn Ser Ile Ile Arg Gly Leu Phe Phe Thr Leu Ser Leu Phe
                165                 170                 175 aga gat gtt ttt ctt aaa caa ata atg ctg ttc tca agt gtc tac atg    1297
Arg Asp Val Phe Leu Lys Gln Ile Met Leu Phe Ser Ser Val Tyr Met
            180                 185                 190 atg act ctc att cag gaa cta cag gag atc ctg gta cct tca cag ccc    1345
Met Thr Leu Ile Gln Glu Leu Gln Glu Ile Leu Val Pro Ser Gln Pro
        195                 200                 205 cag cct cta cct aag gat ctt tgc aga ggc aag agc cat cag cac atc    1393
Gln Pro Leu Pro Lys Asp Leu Cys Arg Gly Lys Ser His Gln His Ile
    210                 215                 220 ctg ctg ccg gtg agt ttc tcg gtg ggc atg tac aag atg gac ttc atc    1441
Leu Leu Pro Val Ser Phe Ser Val Gly Met Tyr Lys Met Asp Phe Ile
225                 230                 235                 240 atc tca acc tcc tca aca ttg cca tgg gca tat gac cgt ggt gtc tag    1489
Ile Ser Thr Ser Ser Thr Leu Pro Trp Ala Tyr Asp Arg Gly Val  *
                245                 250                 255 aggctagtgg gcagtgtcta taccattgtc aggttttttgg tgctactgag atctgataaa  1549
agggtaatca atgtgatgta aactataaga caaatgttta aaaggttaat tgtatgaatc   1609
ctgtcatgag ttaaattatt cagagtgttc attatagaga ataatccaaa gttaaaataa   1669
ttggataatt tatttgtatg taggataaaa gtagtaggag attgcttctt gaagatttaa   1729
aattatattg agtgtaatta tttgcattaa ataattttta aatgttttga atagcaagta   1789
```

```
ttgatataat taaactttcg aataacttag tgctttgcct ttattcctaa tgtttatatg   1849
gaagcatgtg gtcaatgttt gatgcattac agctctgagc ggtccttctg tattaggtgg   1909
tcatcattta tatacttctc cataaaagat taaggacctg gaaatgtaag atacatgaag   1969
aaaatctaag tggagaggct gtttgtggtt aagtgataac agtgttgtaa gcgatgcatg   2029
aggtaggtgt tcagtgcata tcctctgcat tttattaata aacactgtaa aatttagaag   2089
aaaattgttt caccaaatgc acataaaact aataaaatag agtggatttt gatatgtccc   2149
tcgtgcc                                                             2156
```

<210> SEQ ID NO 19
<211> LENGTH: 255
<212> TYPE: PRT
<213> ORGANISM: Homo sapiens

<400> SEQUENCE: 19

```
Met Pro Phe Ile Ser Lys Leu Val Leu Ala Ser Gln Pro Thr Leu Phe
 1               5                  10                  15

Ser Phe Phe Ser Ala Ser Ser Pro Phe Leu Leu Phe Leu Asp Leu Arg
                20                  25                  30

Pro Glu Arg Thr Tyr Leu Pro Val Cys His Val Ala Leu Ile His Met
            35                  40                  45

Val Val Leu Leu Thr Met Val Phe Leu Ser Pro Gln Leu Phe Glu Ser
        50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Gly Met
                85                  90                  95

Leu Gln Val Val Asn Ile Ser Pro Ser Ile Ser Trp Leu Val Arg Phe
            100                 105                 110

Lys Trp Lys Ser Thr Ile Phe Thr Phe His Leu Phe Ser Trp Ser Leu
        115                 120                 125

Ser Phe Pro Val Ser Ser Ser Leu Ile Phe Tyr Thr Val Ala Ser Ser
    130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
        195                 200                 205

Gln Pro Leu Pro Lys Asp Leu Cys Arg Gly Lys Ser His Gln His Ile
    210                 215                 220

Leu Leu Pro Val Ser Phe Ser Val Gly Met Tyr Lys Met Asp Phe Ile
225                 230                 235                 240

Ile Ser Thr Ser Ser Thr Leu Pro Trp Ala Tyr Asp Arg Gly Val
                245                 250                 255
```

<210> SEQ ID NO 20
<211> LENGTH: 2156
<212> TYPE: DNA
<213> ORGANISM: Homo sapiens
<220> FEATURE:
<221> NAME/KEY: CDS
<222> LOCATION: (722)...(1489)

<400> SEQUENCE: 20

```
gtttttttttt tttttttttt tttttttttt tattttaagg gattcgttta ataggacttg      60
tggtaagtgg aataatgcca tgcaaaggtc cccatgtcta accaccaggt tctaggcatg     120
tattatggta tatgagaaat gggaattcag gctgcagatg aaatcaaggt tgataaccag     180
ctgactctaa aacaaaaaca ttaacttgaa ttacagattt gggcctaatg taattataag     240
cattcttaaa agtgaaagaa ataataagag aaactgagta ctgtgatgtg agtcagttaa     300
acttttttt caacttttc tttaggtgat tattttccct taacataaaa tttactttag     360
ctcaactata caaacatgtg agttattgtt atgtaaccat cactcttcat taagaaatgc     420
tttgtaaaaa gtgagccagt ttttcatata cattcttcaa aatacattct caacattata     480
catcaaatta tatatacata catgcacaca tacactatat atatcaagga tttatatgag     540
aggattaatt aagaaaaaaa ttagtggaat aaaaataatg tttatgataa ttttggccat     600
agaatatata atacagatga tgtgaagtac aaaatgtttt ttatacttca tattttgatg     660
tacaaagtat gtttgtcttt gtaattcaga tgattacttt gcacttgtgt tcccatgaaa     720
```

|        |        |        |        |        |        |        |        |        |        |        |        |        |        |        |        |
|--------|--------|--------|--------|--------|--------|--------|--------|--------|--------|--------|--------|--------|--------|--------|--------|
| a atg | cct | ttc | att | tct | aag | ctg | gta | ttg | gca | tct | cag | cca | aca | ctt | ttc | 769 |
| Met | Pro | Phe | Ile | Ser | Lys | Leu | Val | Leu | Ala | Ser | Gln | Pro | Thr | Leu | Phe | |
| 1 | | | | 5 | | | | | 10 | | | | | 15 | | |

```
tcc ttc ttt tct gcg tct tct cct ttt ctg ctt ttt ctg gat ctc agg       817
Ser Phe Phe Ser Ala Ser Ser Pro Phe Leu Leu Phe Leu Asp Leu Arg
         20                  25                  30 cca gag cgc act tac cta cca gtc tgt cat gtg gcc ctc atc cac atg       865
Pro Glu Arg Thr Tyr Leu Pro Val Cys His Val Ala Leu Ile His Met
 35                  40                  45 gtg gtc ctt ctc acc atg gtg ttc ttg tct cca cag ctc ttt gaa tca       913
Val Val Leu Leu Thr Met Val Phe Leu Ser Pro Gln Leu Phe Glu Ser
 50                  55                  60 ctg aat ttt cag aat gac ttc aaa tat gag gca tct ttc tac ctg agg       961
Leu Asn Phe Gln Asn Asp Phe Lys Tyr Glu Ala Ser Phe Tyr Leu Arg
 65                  70                  75                  80 agg gtg atc agg gtc ctc tcc att tgt acc acc tgc ctc ctg ggc atg     1009
Arg Val Ile Arg Val Leu Ser Ile Cys Thr Thr Cys Leu Leu Gly Met
                 85                  90                  95 ctg cag gtc gtc aac atc agc ccc agc att tcc tgg ttg gtg agg ttt     1057
Leu Gln Val Val Asn Ile Ser Pro Ser Ile Ser Trp Leu Val Arg Phe
             100                 105                 110 aaa tgg aaa tcc aca att ttt acc ttc cat ttg ttc tca tgg tct ctc     1105
Lys Trp Lys Ser Thr Ile Phe Thr Phe His Leu Phe Ser Trp Ser Leu
         115                 120                 125 agt ttt cct gtt agt agt agc ctg atc ttt tac act gtg gct tct tcc     1153
Ser Phe Pro Val Ser Ser Ser Leu Ile Phe Tyr Thr Val Ala Ser Ser
     130                 135                 140 aat gtg acc cag atc aat ttg cat gtc agt aaa tac tgt tca ctt ttc     1201
Asn Val Thr Gln Ile Asn Leu His Val Ser Lys Tyr Cys Ser Leu Phe
145                 150                 155                 160 cca ata aac tcc ata atc aga gga ctg ttt ttc act ctg tca tta ttc     1249
Pro Ile Asn Ser Ile Ile Arg Gly Leu Phe Phe Thr Leu Ser Leu Phe
                 165                 170                 175 aga gat gtt ttt ctt aaa caa ata atg ctg ttc tca agt gtc tac atg     1297
Arg Asp Val Phe Leu Lys Gln Ile Met Leu Phe Ser Ser Val Tyr Met
             180                 185                 190 atg act ctc att cag gaa cta cag gag atc ctg gta cct tca cag ccc     1345
Met Thr Leu Ile Gln Glu Leu Gln Glu Ile Leu Val Pro Ser Gln Pro
         195                 200                 205
```

```
cag cct cta cct aag gat ctt tgc aga ggc aag agc cat cag cac atc         1393
Gln Pro Leu Pro Lys Asp Leu Cys Arg Gly Lys Ser His Gln His Ile
    210             215                 220 ctg ctg ccg gtg agt ttc tcg gtg ggc atg tac aag atg gac ttc atc         1441
Leu Leu Pro Val Ser Phe Ser Val Gly Met Tyr Lys Met Asp Phe Ile
225                 230                 235                 240 atc tca acc tcc tca aca ttg cca tgg gca tat gac cgt ggt gtc tag         1489
Ile Ser Thr Ser Ser Thr Leu Pro Trp Ala Tyr Asp Arg Gly Val  *
                245                 250                 255 aggctagtgg gcagtgtcta taccattgtc aggtttttgg tgctactgag atctgataaa       1549
agggtaatca atgtgatgta aactataaga caaatgttta aaaggttaat tgtatgaatc       1609
ctgtcatgag ttaaattatt cagagtgttc attatagaga ataatccaaa gttaaaataa       1669
ttggataatt tatttgtatg taggataaaa gtagtaggag attgcttctt gaagatttaa       1729
aattatattg agtgtaatta tttgcattaa ataattttta aatgttttga atagcaagta       1789
ttgatataat taaactttcg aataacttag tgctttgcct ttattcctaa tgtttatatg       1849
gaagcatgtg gtcaatgttt gatgcattac agctctgagc ggtccttctg tattaggtgg       1909
tcatcattta tatacttctc cataaaagat taaggacctg gaaatgtaag atacatgaag       1969
aaaatctaag tggagaggct gtttgtggtt aagtgataac agtgttgtaa gcgatgcatg       2029
aggtaggtgt tcagtgcata tcctctgcat tttattaata aacactgtaa aatttagaag       2089
aaaattgttt caccaaatgc acataaaact aataaaatag agtggatttt gatatgtccc       2149
tcgtgcc                                                                 2156

<210> SEQ ID NO 21
<211> LENGTH: 255
<212> TYPE: PRT
<213> ORGANISM: Homo sapiens

<400> SEQUENCE: 21

Met Pro Phe Ile Ser Lys Leu Val Leu Ala Ser Gln Pro Thr Leu Phe
1               5                   10                  15

Ser Phe Phe Ser Ala Ser Ser Pro Phe Leu Leu Phe Leu Asp Leu Arg
            20                  25                  30

Pro Glu Arg Thr Tyr Leu Pro Val Cys His Val Ala Leu Ile His Met
        35                  40                  45

Val Val Leu Leu Thr Met Val Phe Leu Ser Pro Gln Leu Phe Glu Ser
    50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Gly Met
                85                  90                  95

Leu Gln Val Val Asn Ile Ser Pro Ser Ile Ser Trp Leu Val Arg Phe
            100                 105                 110

Lys Trp Lys Ser Thr Ile Phe Thr Phe His Leu Phe Ser Trp Ser Leu
        115                 120                 125

Ser Phe Pro Val Ser Ser Leu Ile Phe Tyr Thr Val Ala Ser Ser
    130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190
```

```
Met Thr Leu Ile Gln Glu Leu Gln Glu Ile Leu Val Pro Ser Gln Pro
        195                 200                 205
Gln Pro Leu Pro Lys Asp Leu Cys Arg Gly Lys Ser His Gln His Ile
    210                 215                 220
Leu Leu Pro Val Ser Phe Ser Val Gly Met Tyr Lys Met Asp Phe Ile
225                 230                 235                 240
Ile Ser Thr Ser Ser Thr Leu Pro Trp Ala Tyr Asp Arg Gly Val
                245                 250                 255

<210> SEQ ID NO 22
<211> LENGTH: 2156
<212> TYPE: DNA
<213> ORGANISM: Homo sapiens
<220> FEATURE:
<221> NAME/KEY: CDS
<222> LOCATION: (722)...(1489)

<400> SEQUENCE: 22 gtttttttt tttttttttt tttttttttt tattttaagg gattcgttta ataggacttg      60
tggtaagtgg aataatgcca tgcaaaggtc cccatgtcta accaccaggt tctaggcatg     120
tattatggta tatgagaaat gggaattcag gctgcagatg atatcaaggt tgataaccag     180
ctgactctaa aacaaaaaca ttaacttgaa ttacagatttt gggcctaatg taattataag    240
cattcttaaa agtgaaagaa ataataagag aaactgagtg ctgtgatgtg agtcagttaa     300 acttttttttt caacttttttc tttaggtgat tattttccct taacataaaa tttactttag   360
ctcaactata caaacatgtg agttattgtt atgtaaccat cactcttcat taagaaatgc    420
tttgtaaaaa gtgagccagt ttttcatata cattcttcaa aatacattct caacattata    480
catcaaatta tatatacata catgcacaca tacactatat atatcaagga tttatatgag    540
aggattaatt aagaaaaaaa ttagtggaat aaaaataatg tttatgataa ttttggccat    600
agaatatata atacagatga tgtgaagtac aaaatgtttt ttatacttca tattttgatg    660
tacaaagtat gtttgtcttt gtaattcaga tgattacttt gcacttgtgt tcccatgaaa    720 a atg cct ttc att tct aag ctg gta ttg gca tct cag cca aca ctt ttc   769
  Met Pro Phe Ile Ser Lys Leu Val Leu Ala Ser Gln Pro Thr Leu Phe
    1               5                   10                  15 tcc ttc ttt tct gcg tct tct cct ttt ctg ctt ttt ctg gat ctc agg     817
Ser Phe Phe Ser Ala Ser Ser Pro Phe Leu Leu Phe Leu Asp Leu Arg
                20                  25                  30 cca gag cgc act tac cta cca gtc tgt cat gtg gcc ctc atc cac atg     865
Pro Glu Arg Thr Tyr Leu Pro Val Cys His Val Ala Leu Ile His Met
        35                  40                  45 gtg gtc ctt ctc acc atg gtg ttc ttg tct cca cag ctc ttt gaa tca     913
Val Val Leu Leu Thr Met Val Phe Leu Ser Pro Gln Leu Phe Glu Ser
    50                  55                  60 ctg aat ttt cag aat gac ttc aaa tat gag gca tct ttc tac ctg agg     961
Leu Asn Phe Gln Asn Asp Phe Lys Tyr Glu Ala Ser Phe Tyr Leu Arg
65                  70                  75                  80 agg gtg atc agg gtc ctc tcc att tgt acc acc tgc ctc ctg ggc atg    1009
Arg Val Ile Arg Val Leu Ser Ile Cys Thr Thr Cys Leu Leu Gly Met
                85                  90                  95 ctg cag gtc gtc aac atc agc ccc agc att tcc tgg ttg gtg agg ttt    1057
Leu Gln Val Val Asn Ile Ser Pro Ser Ile Ser Trp Leu Val Arg Phe
            100                 105                 110 aaa tgg aaa tcc aca att ttt acc ttc cat ttg ttc tca tgg tct ctc    1105
Lys Trp Lys Ser Thr Ile Phe Thr Phe His Leu Phe Ser Trp Ser Leu
        115                 120                 125
```

| | | | | | | | | | | | | | | | |
|---|---|---|---|---|---|---|---|---|---|---|---|---|---|---|---|
| agt | ttt | cct | gtt | agt | agt | agc | ctg | atc | ttt | tac | act | gtg | gct | tct | tcc | 1153 |
| Ser | Phe | Pro | Val | Ser | Ser | Ser | Leu | Ile | Phe | Tyr | Thr | Val | Ala | Ser | Ser | |
| | | | 130 | | | | | 135 | | | | | 140 | | | | agt ttt cct gtt agt agt agc ctg atc ttt tac act gtg gct tct tcc 1153
Ser Phe Pro Val Ser Ser Ser Leu Ile Phe Tyr Thr Val Ala Ser Ser
        130                 135                 140 aat gtg acc cag atc aat ttg cat gtc agt aaa tac tgt tca ctt ttc 1201
Asn Val Thr Gln Ile Asn Leu His Val Ser Lys Tyr Cys Ser Leu Phe
145                 150                 155                 160 cca ata aac tcc ata atc aga gga ctg ttt ttc act ctg tca tta ttc 1249
Pro Ile Asn Ser Ile Ile Arg Gly Leu Phe Phe Thr Leu Ser Leu Phe
                165                 170                 175 aga gat gtt ttt ctt aaa caa ata atg ctg ttc tca agt gtc tac atg 1297
Arg Asp Val Phe Leu Lys Gln Ile Met Leu Phe Ser Ser Val Tyr Met
            180                 185                 190 atg act ctc att cag gaa cta cag gag atc ctg gta cct tca cag ccc 1345
Met Thr Leu Ile Gln Glu Leu Gln Glu Ile Leu Val Pro Ser Gln Pro
        195                 200                 205 cag cct cta cct aag gat ctt tgc aga ggc aag agc cat cag cac atc 1393
Gln Pro Leu Pro Lys Asp Leu Cys Arg Gly Lys Ser His Gln His Ile
    210                 215                 220 ctg ctg ccg gtg agt ttc tcg gtg ggc atg tac aag atg gac ttc atc 1441
Leu Leu Pro Val Ser Phe Ser Val Gly Met Tyr Lys Met Asp Phe Ile
225                 230                 235                 240 atc tca acc tcc tca aca ttg cca tgg gca tat gac cgt ggt gtc tag 1489
Ile Ser Thr Ser Ser Thr Leu Pro Trp Ala Tyr Asp Arg Gly Val *
                245                 250                 255 aggctagtgg gcagtgtcta taccattgtc aggttttttgg tgctactgag atctgataaa  1549
agggtaatca atgtgatgta aactataaga caaatgttta aaaggttaat tgtatgaatc  1609
ctgtcatgag ttaaattatt cagagtgttc attatagaga ataatccaaa gttaaaataa  1669
ttggataatt tatttgtatg taggataaaa gtagtaggga attgcttctt gaagatttaa  1729
aattatattg agtgtaatta tttgcattaa ataattttta aatgttttga atagcaagta  1789
ttgatataat taaactttcg aataacttag tgctttgcct ttattcctaa tgtttatatg  1849
gaagcatgtg gtcaatgttt gatgcattac agctctgagc ggtccttctg tattaggtgg  1909
tcatcattta tatacttctc cataaaagat taaggacctg gaaatgtaag atacatgaag  1969
aaaatctaag tggagaggct gtttgtggtt aagtgataac agtgttgtaa gcgatgcatg  2029
aggtaggtgt tcagtgcata tcctctgcat tttattaata aacactgtaa aatttagaag  2089
aaaattgttt caccaaatgc acataaaact aataaaatag agtggatttt gatatgtccc  2149
tcgtgcc  2156

<210> SEQ ID NO 23
<211> LENGTH: 255
<212> TYPE: PRT
<213> ORGANISM: Homo sapiens

<400> SEQUENCE: 23

Met Pro Phe Ile Ser Lys Leu Val Leu Ala Ser Gln Pro Thr Leu Phe
1               5                   10                  15

Ser Phe Pro Ser Ala Ser Ser Pro Phe Leu Leu Phe Leu Asp Leu Arg
            20                  25                  30

Pro Glu Arg Thr Tyr Leu Pro Val Cys His Val Ala Leu Ile His Met
        35                  40                  45

Val Val Leu Leu Thr Met Val Phe Leu Ser Pro Gln Leu Phe Glu Ser
    50                  55                  60

Leu Asn Phe Gln Asn Asp Phe Lys Tyr Glu Ala Ser Phe Tyr Leu Arg
65                  70                  75                  80

```
Arg Val Ile Arg Val Leu Ser Ile Cys Thr Thr Cys Leu Leu Gly Met
                85                  90                  95
Leu Gln Val Val Asn Ile Ser Pro Ser Ile Ser Trp Leu Val Arg Phe
            100                 105                 110
Lys Trp Lys Ser Thr Ile Phe Thr Phe His Leu Phe Ser Trp Ser Leu
        115                 120                 125
Ser Phe Pro Val Ser Ser Leu Ile Phe Tyr Thr Val Ala Ser Ser
    130                 135                 140
Asn Val Thr Gln Ile Asn Leu His Val Ser Lys Tyr Cys Ser Leu Phe
145                 150                 155                 160
Pro Ile Asn Ser Ile Ile Arg Gly Leu Phe Phe Thr Leu Ser Leu Phe
                165                 170                 175
Arg Asp Val Phe Leu Lys Gln Ile Met Leu Phe Ser Ser Val Tyr Met
            180                 185                 190
Met Thr Leu Ile Gln Glu Leu Gln Glu Ile Leu Val Pro Ser Gln Pro
        195                 200                 205
Gln Pro Leu Pro Lys Asp Leu Cys Arg Gly Lys Ser His Gln His Ile
    210                 215                 220
Leu Leu Pro Val Ser Phe Ser Val Gly Met Tyr Lys Met Asp Phe Ile
225                 230                 235                 240
Ile Ser Thr Ser Ser Thr Leu Pro Trp Ala Tyr Asp Arg Gly Val
                245                 250                 255

<210> SEQ ID NO 24
<211> LENGTH: 4522
<212> TYPE: DNA
<213> ORGANISM: Homo sapiens
<220> FEATURE:
<221> NAME/KEY: CDS
<222> LOCATION: (722)...(4522)

<400> SEQUENCE: 24 gtttttttt tttttttttt tttttttttt tatttaaagg gattcgttta ataggacttg      60
tggtaagtgg aataatgcca tgcaaaggtc cccatgtcta accaccaggt tctaggcatg    120
tattatggta tatgagaaat gggaattcag gctgcagatg aaatcaaggt tgataaccag    180
ctgactctaa aacaaaaaca ttaacttgaa ttacagattt gggcctaatg taattataag    240
cattcttaaa agtgaaagaa ataataagag aaactgagtg ctgtgatgtg agtcagttaa    300
acttttttt caacttttc tttaggtgat tatttttccct taacataaaa tttacttag     360
ctcaactata caaacatgtg agttattgtt atgtaaccat cactcttcat taagaaatgc    420
tttgtaaaaa gtgagccagt ttttcatata cattcttcaa aatacattct caacattata    480
catcaaatta tatatacata catgcacaca tacactatat atatcaagga tttatatgag    540
aggattaatt aagaaaaaaa ttagtggaat aaaaataatg tttatgataa ttttggccat    600
agaatatata atacagatga tgtgaagtac aaaatgtttt ttatacttca tattttgatg    660
tacaaagtat gtttgtcttt gtaattcaga tgattacttt gcacttgtgt tcccatgaaa    720 a atg cct ttc att tct aag ctg gta ttg gca tct cag cca aca ctt ttc    769
  Met Pro Phe Ile Ser Lys Leu Val Leu Ala Ser Gln Pro Thr Leu Phe
  1               5                   10                  15 tcc ttc ttt tct gcg tct tct cct ttt ctg ctt ttt ctg gat ctc agg    817
Ser Phe Phe Ser Ala Ser Ser Pro Phe Leu Leu Phe Leu Asp Leu Arg
            20                  25                  30 cca gag cgc act tac cta cca gtc tgt cat gtg gcc ctc atc cac atg    865
Pro Glu Arg Thr Tyr Leu Pro Val Cys His Val Ala Leu Ile His Met
```

-continued

```
         35                  40                  45
gtg gtc ctt ctc acc atg gtg ttc ttg tct cca cag ctc ttt gaa tca        913
Val Val Leu Leu Thr Met Val Phe Leu Ser Pro Gln Leu Phe Glu Ser
         50                  55                  60 ctg aat ttt cag aat gac ttc aaa tat gag gca tct ttc tac ctg agg        961
Leu Asn Phe Gln Asn Asp Phe Lys Tyr Glu Ala Ser Phe Tyr Leu Arg
65                  70                  75                  80 agg gtg atc agg gtc ctc tcc att tgt acc acc tgc ctc ctg gac atg       1009
Arg Val Ile Arg Val Leu Ser Ile Cys Thr Thr Cys Leu Leu Asp Met
                85                  90                  95 ctg cag gtc gtc aac atc agc ccc agc att tcc tgg ttg ata atg ctg       1057
Leu Gln Val Val Asn Ile Ser Pro Ser Ile Ser Trp Leu Ile Met Leu
            100                 105                 110 ttc tca agt gtc tac atg atg act ctc att cag gaa cta cag gag atc       1105
Phe Ser Ser Val Tyr Met Met Thr Leu Ile Gln Glu Leu Gln Glu Ile
        115                 120                 125 ctg gta cct tca cag ccc cag cct cta cct aag gat ctt tgc aga ggc       1153
Leu Val Pro Ser Gln Pro Gln Pro Leu Pro Lys Asp Leu Cys Arg Gly
    130                 135                 140 aag agc cat cag cac atc ctg ctg ccg act caa gca act ttt gct gca       1201
Lys Ser His Gln His Ile Leu Leu Pro Thr Gln Ala Thr Phe Ala Ala
145                 150                 155                 160 gca act gga cta tgg gct gca cta acc acc gta tca aat cca agc aga       1249
Ala Thr Gly Leu Trp Ala Ala Leu Thr Thr Val Ser Asn Pro Ser Arg
                165                 170                 175 gca gat cct gtg acc tgg aga aag gag ccg gct gtc ctt ccc tgc tgt       1297
Ala Asp Pro Val Thr Trp Arg Lys Glu Pro Ala Val Leu Pro Cys Cys
            180                 185                 190 aac cta gag aaa gga agc tgg ctg tcc ttc cct ggc aca gct gca cgc       1345
Asn Leu Glu Lys Gly Ser Trp Leu Ser Phe Pro Gly Thr Ala Ala Arg
        195                 200                 205 aag gaa ttt tcc acc acg ctc acc ggg cac agc gcg ctg agc ctc tcc       1393
Lys Glu Phe Ser Thr Thr Leu Thr Gly His Ser Ala Leu Ser Leu Ser
    210                 215                 220 agt tcg cgg gcc ctc ccc ggc tcg ctc ccg gct ttc gca gac ctc ccc       1441
Ser Ser Arg Ala Leu Pro Gly Ser Leu Pro Ala Phe Ala Asp Leu Pro
225                 230                 235                 240 cgc tcc tgc cct gag tcc gag cag agc gca acg cca gcc ggc gcc ttc       1489
Arg Ser Cys Pro Glu Ser Glu Gln Ser Ala Thr Pro Ala Gly Ala Phe
                245                 250                 255 ctc ctg ggc tgg gag cga gtg gtg cag cgg cgg ctc gaa gtc ccc cgg       1537
Leu Leu Gly Trp Glu Arg Val Val Gln Arg Arg Leu Glu Val Pro Arg
            260                 265                 270 cct caa gca gcc ccc gcg act agc gcg aca ccc tcg cgg gat ccg agt       1585
Pro Gln Ala Ala Pro Ala Thr Ser Ala Thr Pro Ser Arg Asp Pro Ser
        275                 280                 285 cca ccc tgc cac cag cgc cgg gac gcc gcg tgc ctc aga gcc caa ggg       1633
Pro Pro Cys His Gln Arg Arg Asp Ala Ala Cys Leu Arg Ala Gln Gly
    290                 295                 300 ctg acc cgg gcc ttc cag gtg gtc cat ctc gct cct acg gct ccc gac       1681
Leu Thr Arg Ala Phe Gln Val Val His Leu Ala Pro Thr Ala Pro Asp
305                 310                 315                 320 ggt ggc gct ggg tgt ccc cca tcc cgc aat tcc tac cgg ctg acc cat       1729
Gly Gly Ala Gly Cys Pro Pro Ser Arg Asn Ser Tyr Arg Leu Thr His
                325                 330                 335 gtg cgc tgc gcc cag ggg ctg gag gct gcc agc gcc aac ctt ccc ggc       1777
Val Arg Cys Ala Gln Gly Leu Glu Ala Ala Ser Ala Asn Leu Pro Gly
            340                 345                 350 gct ccg ggg cgg agc agc tcc tgc gcc ctg cgc tac cgc agc ggc cct       1825
```

```
                Ala Pro Gly Arg Ser Ser Ser Cys Ala Leu Arg Tyr Arg Ser Gly Pro
                            355                 360                 365 tca gtc agc tcc gcg ccg tcc ccc gca gag ccc ccg gcg cac cag cgc        1873
Ser Val Ser Ser Ala Pro Ser Pro Ala Glu Pro Pro Ala His Gln Arg
    370                 375                 380 ctg ctt ttc ctt ccc cga gcg cct caa gca gtc tct ggg ccg cag gaa        1921
Leu Leu Phe Leu Pro Arg Ala Pro Gln Ala Val Ser Gly Pro Gln Glu
385                 390                 395                 400 cag ccc tct gaa gag gcg ctt ggt gta gga agc ctc tca gtt ttc cag        1969
Gln Pro Ser Glu Glu Ala Leu Gly Val Gly Ser Leu Ser Val Phe Gln
                405                 410                 415 tta cac cta ata cag tgt att cca aat cta agt tac cca cta gta ctt        2017
Leu His Leu Ile Gln Cys Ile Pro Asn Leu Ser Tyr Pro Leu Val Leu
            420                 425                 430 cgg cac att cca gaa att ctg aaa ttt tct gaa aag gaa act ggt ggt        2065
Arg His Ile Pro Glu Ile Leu Lys Phe Ser Glu Lys Glu Thr Gly Gly
        435                 440                 445 gga att cta ggc tta gaa tta cca gcg aca gct gct cgc ctc tca gga        2113
Gly Ile Leu Gly Leu Glu Leu Pro Ala Thr Ala Ala Arg Leu Ser Gly
    450                 455                 460 tta aac agc ata atg caa atc aaa gag ttt gaa gaa ttg gta aaa ctt        2161
Leu Asn Ser Ile Met Gln Ile Lys Glu Phe Glu Glu Leu Val Lys Leu
465                 470                 475                 480 cac agc ttg tca cac aaa gtc att cag tgt gtg ttt gca aag aaa aaa        2209
His Ser Leu Ser His Lys Val Ile Gln Cys Val Phe Ala Lys Lys Lys
                485                 490                 495 aat gta gac aaa tgg gat gac ttt tgt ctt agt gag ggt tat gga cat        2257
Asn Val Asp Lys Trp Asp Asp Phe Cys Leu Ser Glu Gly Tyr Gly His
            500                 505                 510 tca ttc tta ata atg aaa gaa acg tcg act aaa ata tca ggt tta att        2305
Ser Phe Leu Ile Met Lys Glu Thr Ser Thr Lys Ile Ser Gly Leu Ile
        515                 520                 525 cag gag atg ggg agc ggc aag agc aac gtg ggc act tgg gga gac tac        2353
Gln Glu Met Gly Ser Gly Lys Ser Asn Val Gly Thr Trp Gly Asp Tyr
    530                 535                 540 gac gac agc gcc ttc atg gag ccg agg tac cac gtc cgt cga gaa gat        2401
Asp Asp Ser Ala Phe Met Glu Pro Arg Tyr His Val Arg Arg Glu Asp
545                 550                 555                 560 ctg gac aag ctc cac aga gct gcc tgg tgg ggt aaa gtc ccc aga aag        2449
Leu Asp Lys Leu His Arg Ala Ala Trp Trp Gly Lys Val Pro Arg Lys
                565                 570                 575 gat ctc atc gtc atg ctc agg gac act gac atg aac aag agg gac aag        2497
Asp Leu Ile Val Met Leu Arg Asp Thr Asp Met Asn Lys Arg Asp Lys
            580                 585                 590 caa aag agg act gct cta cat ttg gcc tct gcc aat gga aat tca gaa        2545
Gln Lys Arg Thr Ala Leu His Leu Ala Ser Ala Asn Gly Asn Ser Glu
        595                 600                 605 gta gta caa ctc ctg ctg gac aga cga tgt caa ctt aac gtc ctt gac        2593
Val Val Gln Leu Leu Leu Asp Arg Arg Cys Gln Leu Asn Val Leu Asp
    610                 615                 620 aac aaa aaa agg aca gct ctg ata aag gcc gta caa tgc agg aa gat        2641
Asn Lys Lys Arg Thr Ala Leu Ile Lys Ala Val Gln Cys Gln Glu Asp
625                 630                 635                 640 gaa tgt gtg tta atg ttg ctg gaa cat ggc gct gat gga aat att caa        2689
Glu Cys Val Leu Met Leu Leu Glu His Gly Ala Asp Gly Asn Ile Gln
                645                 650                 655 gat gag tat gga aat acc gct cta cac tat gct atc tac aat gaa gat        2737
Asp Glu Tyr Gly Asn Thr Ala Leu His Tyr Ala Ile Tyr Asn Glu Asp
            660                 665                 670
```

```
aaa tta atg gcc aaa gca ctg ctc tta tat ggt gct gat att gaa tca    2785
Lys Leu Met Ala Lys Ala Leu Leu Leu Tyr Gly Ala Asp Ile Glu Ser
            675                 680                 685 aaa aac aag tgt ggc ctc aca cca ctt ttg ctt ggc gta cat gaa caa    2833
Lys Asn Lys Cys Gly Leu Thr Pro Leu Leu Leu Gly Val His Glu Gln
        690                 695                 700 aaa cag gaa gtg gtg aaa ttt tta atc aag aaa aaa gct aat tta aat    2881
Lys Gln Glu Val Val Lys Phe Leu Ile Lys Lys Lys Ala Asn Leu Asn
705                 710                 715                 720 gca ctt gat aga tat gga aga act gcc ctc ata ctt gct gta tgt tgt    2929
Ala Leu Asp Arg Tyr Gly Arg Thr Ala Leu Ile Leu Ala Val Cys Cys
                725                 730                 735 gga tca gca agt ata gtc aat ctt cta ctt gag caa aat gtt gat gta    2977
Gly Ser Ala Ser Ile Val Asn Leu Leu Leu Glu Gln Asn Val Asp Val
            740                 745                 750 tct tct caa gat cta tct gga cag acg gcc aga gag tat gct gtt tct    3025
Ser Ser Gln Asp Leu Ser Gly Gln Thr Ala Arg Glu Tyr Ala Val Ser
        755                 760                 765 agt cat cat cat gta att tgt gaa tta ctt tct gac tat aaa gaa aaa    3073
Ser His His His Val Ile Cys Glu Leu Leu Ser Asp Tyr Lys Glu Lys
770                 775                 780 cag atg cta aaa atc tct tct gaa aac agc aat cca gtg ata acc atc    3121
Gln Met Leu Lys Ile Ser Ser Glu Asn Ser Asn Pro Val Ile Thr Ile
785                 790                 795                 800 ctt aat atc aaa ctt cca ctc aag gtt gaa gaa gaa ata aag aag cat    3169
Leu Asn Ile Lys Leu Pro Leu Lys Val Glu Glu Glu Ile Lys Lys His
                805                 810                 815 gga agt aat cct gtg gga tta cca gaa aac ctg act aat ggt gcc agt    3217
Gly Ser Asn Pro Val Gly Leu Pro Glu Asn Leu Thr Asn Gly Ala Ser
            820                 825                 830 gct ggc aat ggt gat gat gga tta att cca caa agg aag agc aga aaa    3265
Ala Gly Asn Gly Asp Asp Gly Leu Ile Pro Gln Arg Lys Ser Arg Lys
        835                 840                 845 cct gaa aat cag caa ttt cct gac act gag aat gaa gag tat cac agt    3313
Pro Glu Asn Gln Gln Phe Pro Asp Thr Glu Asn Glu Glu Tyr His Ser
850                 855                 860 gac gaa caa aat gat acc cag aaa caa ctt tct gaa gaa cag aac act    3361
Asp Glu Gln Asn Asp Thr Gln Lys Gln Leu Ser Glu Glu Gln Asn Thr
865                 870                 875                 880 gga ata tca caa gat gag att ctg act aat aaa caa aag cag ata gaa    3409
Gly Ile Ser Gln Asp Glu Ile Leu Thr Asn Lys Gln Lys Gln Ile Glu
                885                 890                 895 gtg gct gaa aag gaa atg aat tct gag ctt tct ctt agt cat aag aaa    3457
Val Ala Glu Lys Glu Met Asn Ser Glu Leu Ser Leu Ser His Lys Lys
            900                 905                 910 gaa gaa gat ctc ttg cgt gaa aac agc atg ttg cgg gaa gaa att gcc    3505
Glu Glu Asp Leu Leu Arg Glu Asn Ser Met Leu Arg Glu Glu Ile Ala
        915                 920                 925 aag cta aga ctg gaa cta gat gaa aca aaa cat cag aac cag cta agg    3553
Lys Leu Arg Leu Glu Leu Asp Glu Thr Lys His Gln Asn Gln Leu Arg
930                 935                 940 gaa aat aaa att ttg gag gaa att gaa agt gta aaa gaa aaa ctt cta    3601
Glu Asn Lys Ile Leu Glu Glu Ile Glu Ser Val Lys Glu Lys Leu Leu
945                 950                 955                 960 aag act ata caa ctg aat gaa gaa gca tta acg aaa acc aag gtg gct    3649
Lys Thr Ile Gln Leu Asn Glu Glu Ala Leu Thr Lys Thr Lys Val Ala
                965                 970                 975 ggt ttc tct ttg cgc cag ctt ggc ctt gcc cag cat gca caa gcc tca    3697
Gly Phe Ser Leu Arg Gln Leu Gly Leu Ala Gln His Ala Gln Ala Ser
            980                 985                 990
```

-continued

```
gtg caa cag ctg tgc tac aaa tgg aac cac aca gag aaa aca gag cag      3745
Val Gln Gln Leu Cys Tyr Lys Trp Asn His Thr Glu Lys Thr Glu Gln
    995                 1000                1005 cag gct cag gag cag gag gtg gct ggt ttc tct ttg cgc cag ctt ggc      3793
Gln Ala Gln Glu Gln Glu Val Ala Gly Phe Ser Leu Arg Gln Leu Gly
1010                1015                1020 ctt gcc cag cat gca caa gcc tca gta caa caa ctg tgc tac aaa tgg      3841
Leu Ala Gln His Ala Gln Ala Ser Val Gln Gln Leu Cys Tyr Lys Trp
1025                1030                1035                1040 ggc cac aca gag aaa aca gag cag cag gct cag gag cag gga gct gcg      3889
Gly His Thr Glu Lys Thr Glu Gln Gln Ala Gln Glu Gln Gly Ala Ala
                1045                1050                1055 ctg agg tcc cag ata ggc gac cct ggc ggg gtg ccc ctg agc gaa ggg      3937
Leu Arg Ser Gln Ile Gly Asp Pro Gly Gly Val Pro Leu Ser Glu Gly
                1060                1065                1070 ggg aca gca gca gga gac cag ggt cca ggg acc cac ctc cca ccg agg      3985
Gly Thr Ala Ala Gly Asp Gln Gly Pro Gly Thr His Leu Pro Pro Arg
            1075                1080                1085 gaa cct cga gcc tcc cct ggc acc cct agc ttg gtc cgc ctg gcc tcc      4033
Glu Pro Arg Ala Ser Pro Gly Thr Pro Ser Leu Val Arg Leu Ala Ser
        1090                1095                1100 gga gcc cga gct gct gcg ctt ccc cca ccc aca ggg aaa aac ggc cga      4081
Gly Ala Arg Ala Ala Ala Leu Pro Pro Pro Thr Gly Lys Asn Gly Arg
1105                1110                1115                1120 tct cca acc aaa cag aaa tct gtg tgt gac tcc tct ggt tgg ata ctg      4129
Ser Pro Thr Lys Gln Lys Ser Val Cys Asp Ser Ser Gly Trp Ile Leu
                1125                1130                1135 cca gtc ccc aca ttt tct tcc ggg agt ttt ctt ggc aga agg tgc cca      4177
Pro Val Pro Thr Phe Ser Ser Gly Ser Phe Leu Gly Arg Arg Cys Pro
                1140                1145                1150 atg ttt gat gtt tcg cca gcc atg agg ctg aaa agt gac agc aat aga      4225
Met Phe Asp Val Ser Pro Ala Met Arg Leu Lys Ser Asp Ser Asn Arg
            1155                1160                1165 gaa aca cat cag gct ttc cgc gac aaa gat gac ctt ccc ttc ttc aaa      4273
Glu Thr His Gln Ala Phe Arg Asp Lys Asp Asp Leu Pro Phe Phe Lys
        1170                1175                1180 act cag caa tct cca cgg cac aca aag gac tta gga caa gat gac cga      4321
Thr Gln Gln Ser Pro Arg His Thr Lys Asp Leu Gly Gln Asp Asp Arg
1185                1190                1195                1200 gct gga gtg ctc gcc cca aaa tgc agg ccc gga aca ctc tgc cac acg      4369
Ala Gly Val Leu Ala Pro Lys Cys Arg Pro Gly Thr Leu Cys His Thr
                1205                1210                1215 gac aca cca cca cac aga aat gcg gac aca cca cca cac aga cac acc      4417
Asp Thr Pro Pro His Arg Asn Ala Asp Thr Pro Pro His Arg His Thr
                1220                1225                1230 acc acg ctg cca cac aga gac acc acc aca tcg ttg cca cac ttt cat      4465
Thr Thr Leu Pro His Arg Asp Thr Thr Thr Ser Leu Pro His Phe His
            1235                1240                1245 gtg tca gct ggc ggt gtg ggc ccc acg act ctg ggc tct aat aga gaa      4513
Val Ser Ala Gly Gly Val Gly Pro Thr Thr Leu Gly Ser Asn Arg Glu
        1250                1255                1260 att act tag                                                          4522
Ile Thr *
1265
```

<210> SEQ ID NO 25
<211> LENGTH: 1266
<212> TYPE: PRT
<213> ORGANISM: Homo sapiens -continued

```
<400> SEQUENCE: 25

Met Pro Phe Ile Ser Lys Leu Val Leu Ala Ser Gln Pro Thr Leu Phe
1               5                   10                  15

Ser Phe Phe Ser Ala Ser Ser Pro Phe Leu Leu Phe Leu Asp Leu Arg
            20                  25                  30

Pro Glu Arg Thr Tyr Leu Pro Val Cys His Val Ala Leu Ile His Met
        35                  40                  45

Val Val Leu Leu Thr Met Val Phe Leu Ser Pro Gln Leu Phe Glu Ser
    50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Asp Met
                85                  90                  95

Leu Gln Val Val Asn Ile Ser Pro Ser Ile Ser Trp Leu Ile Met Leu
            100                 105                 110

Phe Ser Ser Val Tyr Met Met Thr Leu Ile Gln Glu Leu Gln Glu Ile
        115                 120                 125

Leu Val Pro Ser Gln Pro Gln Pro Leu Pro Lys Asp Leu Cys Arg Gly
    130                 135                 140

Lys Ser His Gln His Ile Leu Leu Pro Thr Gln Ala Thr Phe Ala Ala
145                 150                 155                 160

Ala Thr Gly Leu Trp Ala Ala Leu Thr Thr Val Ser Asn Pro Ser Arg
                165                 170                 175

Ala Asp Pro Val Thr Trp Arg Lys Glu Pro Ala Val Leu Pro Cys Cys
            180                 185                 190

Asn Leu Glu Lys Gly Ser Trp Leu Ser Phe Pro Gly Thr Ala Ala Arg
        195                 200                 205

Lys Glu Phe Ser Thr Thr Leu Thr Gly His Ser Ala Leu Ser Leu Ser
    210                 215                 220

Ser Ser Arg Ala Leu Pro Gly Ser Leu Pro Ala Phe Ala Asp Leu Pro
225                 230                 235                 240

Arg Ser Cys Pro Glu Ser Glu Gln Ser Ala Thr Pro Ala Gly Ala Phe
                245                 250                 255

Leu Leu Gly Trp Glu Arg Val Val Gln Arg Arg Leu Glu Val Pro Arg
            260                 265                 270

Pro Gln Ala Ala Pro Ala Thr Ser Ala Thr Pro Ser Arg Asp Pro Ser
        275                 280                 285

Pro Pro Cys His Gln Arg Arg Asp Ala Ala Cys Leu Arg Ala Gln Gly
    290                 295                 300

Leu Thr Arg Ala Phe Gln Val Val His Leu Ala Pro Thr Ala Pro Asp
305                 310                 315                 320

Gly Gly Ala Gly Cys Pro Pro Ser Arg Asn Ser Tyr Arg Leu Thr His
                325                 330                 335

Val Arg Cys Ala Gln Gly Leu Glu Ala Ala Ser Ala Asn Leu Pro Gly
            340                 345                 350

Ala Pro Gly Arg Ser Ser Cys Ala Leu Arg Tyr Arg Ser Gly Pro
        355                 360                 365

Ser Val Ser Ser Ala Pro Ser Pro Ala Glu Pro Ala His Gln Arg
    370                 375                 380

Leu Leu Phe Leu Pro Arg Ala Pro Gln Ala Val Ser Gly Pro Gln Glu
385                 390                 395                 400

Gln Pro Ser Glu Glu Ala Leu Gly Val Gly Ser Leu Ser Val Phe Gln
                405                 410                 415
```

```
Leu His Leu Ile Gln Cys Ile Pro Asn Leu Ser Tyr Pro Leu Val Leu
            420                 425                 430

Arg His Ile Pro Glu Ile Leu Lys Phe Ser Glu Lys Glu Thr Gly Gly
            435                 440                 445

Gly Ile Leu Gly Leu Glu Leu Pro Ala Thr Ala Ala Arg Leu Ser Gly
            450                 455                 460

Leu Asn Ser Ile Met Gln Ile Lys Glu Phe Glu Glu Leu Val Lys Leu
465                 470                 475                 480

His Ser Leu Ser His Lys Val Ile Gln Cys Val Phe Ala Lys Lys Lys
            485                 490                 495

Asn Val Asp Lys Trp Asp Asp Phe Cys Leu Ser Glu Gly Tyr Gly His
            500                 505                 510

Ser Phe Leu Ile Met Lys Glu Thr Ser Thr Lys Ile Ser Gly Leu Ile
            515                 520                 525

Gln Glu Met Gly Ser Gly Lys Ser Asn Val Gly Thr Trp Gly Asp Tyr
            530                 535                 540

Asp Asp Ser Ala Phe Met Glu Pro Arg Tyr His Val Arg Arg Glu Asp
545                 550                 555                 560

Leu Asp Lys Leu His Arg Ala Ala Trp Trp Gly Lys Val Pro Arg Lys
            565                 570                 575

Asp Leu Ile Val Met Leu Arg Asp Thr Asp Met Asn Lys Arg Asp Lys
            580                 585                 590

Gln Lys Arg Thr Ala Leu His Leu Ala Ser Ala Asn Gly Asn Ser Glu
            595                 600                 605

Val Val Gln Leu Leu Leu Asp Arg Arg Cys Gln Leu Asn Val Leu Asp
            610                 615                 620

Asn Lys Lys Arg Thr Ala Leu Ile Lys Ala Val Gln Cys Gln Glu Asp
625                 630                 635                 640

Glu Cys Val Leu Met Leu Leu Glu His Gly Ala Asp Gly Asn Ile Gln
            645                 650                 655

Asp Glu Tyr Gly Asn Thr Ala Leu His Tyr Ala Ile Tyr Asn Glu Asp
            660                 665                 670

Lys Leu Met Ala Lys Ala Leu Leu Tyr Gly Ala Asp Ile Glu Ser
            675                 680                 685

Lys Asn Lys Cys Gly Leu Thr Pro Leu Leu Gly Val His Glu Gln
            690                 695                 700

Lys Gln Glu Val Val Lys Phe Leu Ile Lys Lys Ala Asn Leu Asn
705                 710                 715                 720

Ala Leu Asp Arg Tyr Gly Arg Thr Ala Leu Ile Leu Ala Val Cys Cys
            725                 730                 735

Gly Ser Ala Ser Ile Val Asn Leu Leu Leu Glu Gln Asn Val Asp Val
            740                 745                 750

Ser Ser Gln Asp Leu Ser Gly Gln Thr Ala Arg Glu Tyr Ala Val Ser
            755                 760                 765

Ser His His His Val Ile Cys Glu Leu Leu Ser Asp Tyr Lys Glu Lys
            770                 775                 780

Gln Met Leu Lys Ile Ser Ser Glu Asn Ser Asn Pro Val Ile Thr Ile
785                 790                 795                 800

Leu Asn Ile Lys Leu Pro Leu Lys Val Glu Glu Ile Lys Lys His
            805                 810                 815

Gly Ser Asn Pro Val Gly Leu Pro Glu Asn Leu Thr Asn Gly Ala Ser
            820                 825                 830
```

-continued

```
Ala Gly Asn Gly Asp Asp Gly Leu Ile Pro Gln Arg Lys Ser Arg Lys
            835                 840                 845

Pro Glu Asn Gln Gln Phe Pro Asp Thr Glu Asn Glu Glu Tyr His Ser
    850                 855                 860

Asp Glu Gln Asn Asp Thr Gln Lys Gln Leu Ser Glu Glu Gln Asn Thr
865                 870                 875                 880

Gly Ile Ser Gln Asp Glu Ile Leu Thr Asn Lys Gln Lys Gln Ile Glu
                885                 890                 895

Val Ala Glu Lys Glu Met Asn Ser Glu Leu Ser Leu Ser His Lys Lys
            900                 905                 910

Glu Glu Asp Leu Leu Arg Glu Asn Ser Met Leu Arg Glu Glu Ile Ala
            915                 920                 925

Lys Leu Arg Leu Glu Leu Asp Glu Thr Lys His Gln Asn Gln Leu Arg
        930                 935                 940

Glu Asn Lys Ile Leu Glu Glu Ile Glu Ser Val Lys Glu Lys Leu Leu
945                 950                 955                 960

Lys Thr Ile Gln Leu Asn Glu Glu Ala Leu Thr Lys Thr Lys Val Ala
                965                 970                 975

Gly Phe Ser Leu Arg Gln Leu Gly Leu Ala Gln His Ala Gln Ala Ser
            980                 985                 990

Val Gln Gln Leu Cys Tyr Lys Trp Asn His Thr Glu Lys Thr Glu Gln
        995                1000                1005

Gln Ala Gln Glu Gln Glu Val Ala Gly Phe Ser Leu Arg Gln Leu Gly
    1010                1015                1020

Leu Ala Gln His Ala Gln Ala Ser Val Gln Gln Leu Cys Tyr Lys Trp
1025                1030                1035                1040

Gly His Thr Glu Lys Thr Glu Gln Gln Ala Gln Glu Gln Gly Ala Ala
                1045                1050                1055

Leu Arg Ser Gln Ile Gly Asp Pro Gly Gly Val Pro Leu Ser Glu Gly
            1060                1065                1070

Gly Thr Ala Ala Gly Asp Gln Gly Pro Gly Thr His Leu Pro Pro Arg
            1075                1080                1085

Glu Pro Arg Ala Ser Pro Gly Thr Pro Ser Leu Val Arg Leu Ala Ser
    1090                1095                1100

Gly Ala Arg Ala Ala Ala Leu Pro Pro Thr Gly Lys Asn Gly Arg
1105                1110                1115                1120

Ser Pro Thr Lys Gln Lys Ser Val Cys Asp Ser Ser Gly Trp Ile Leu
            1125                1130                1135

Pro Val Pro Thr Phe Ser Ser Gly Ser Phe Leu Gly Arg Arg Cys Pro
        1140                1145                1150

Met Phe Asp Val Ser Pro Ala Met Arg Leu Lys Ser Asp Ser Asn Arg
            1155                1160                1165

Glu Thr His Gln Ala Phe Arg Asp Lys Asp Leu Pro Phe Phe Lys
    1170                1175                1180

Thr Gln Gln Ser Pro Arg His Thr Lys Asp Leu Gly Gln Asp Asp Arg
1185                1190                1195                1200

Ala Gly Val Leu Ala Pro Lys Cys Arg Pro Gly Thr Leu Cys His Thr
                1205                1210                1215

Asp Thr Pro Pro His Arg Asn Ala Asp Thr Pro Pro His Arg His Thr
            1220                1225                1230

Thr Thr Leu Pro His Arg Asp Thr Thr Thr Ser Leu Pro His Phe His
            1235                1240                1245

Val Ser Ala Gly Gly Val Gly Pro Thr Thr Leu Gly Ser Asn Arg Glu
```

```
                      1250                    1255                   1260
Ile Thr
1265

<210> SEQ ID NO 26
<211> LENGTH: 3801
<212> TYPE: DNA
<213> ORGANISM: Homo sapiens
<220> FEATURE:
<221> NAME/KEY: CDS
<222> LOCATION: (1)...(3801)

<400> SEQUENCE: 26 atg cct ttc att tct aag ctg gta ttg gca tct cag cca aca ctt ttc        48
Met Pro Phe Ile Ser Lys Leu Val Leu Ala Ser Gln Pro Thr Leu Phe
1               5                   10                  15 tcc ttc ttt tct gcg tct tct cct ttt ctg ctt ttt ctg gat ctc agg        96
Ser Phe Phe Ser Ala Ser Ser Pro Phe Leu Leu Phe Leu Asp Leu Arg
            20                  25                  30 cca gag cgc act tac cta cca gtc tgt cat gtg gcc ctc atc cac atg       144
Pro Glu Arg Thr Tyr Leu Pro Val Cys His Val Ala Leu Ile His Met
        35                  40                  45 gtg gtc ctt ctc acc atg gtg ttc ttg tct cca cag ctc ttt gaa tca       192
Val Val Leu Leu Thr Met Val Phe Leu Ser Pro Gln Leu Phe Glu Ser
    50                  55                  60 ctg aat ttt cag aat gac ttc aaa tat gag gca tct ttc tac ctg agg       240
Leu Asn Phe Gln Asn Asp Phe Lys Tyr Glu Ala Ser Phe Tyr Leu Arg
65                  70                  75                  80 agg gtg atc agg gtc ctc tcc att tgt acc acc tgc ctc ctg gac atg       288
Arg Val Ile Arg Val Leu Ser Ile Cys Thr Thr Cys Leu Leu Asp Met
                85                  90                  95 ctg cag gtc gtc aac atc agc ccc agc att tcc tgg ttg ata atg ctg       336
Leu Gln Val Val Asn Ile Ser Pro Ser Ile Ser Trp Leu Ile Met Leu
            100                 105                 110 ttc tca agt gtc tac atg atg act ctc att cag gaa cta cag gag atc       384
Phe Ser Ser Val Tyr Met Met Thr Leu Ile Gln Glu Leu Gln Glu Ile
        115                 120                 125 ctg gta cct tca cag ccc cag cct cta cct aag gat ctt tgc aga ggc       432
Leu Val Pro Ser Gln Pro Gln Pro Leu Pro Lys Asp Leu Cys Arg Gly
    130                 135                 140 aag agc cat cag cac atc ctg ctg ccg act caa gca act ttt gct gca       480
Lys Ser His Gln His Ile Leu Leu Pro Thr Gln Ala Thr Phe Ala Ala
145                 150                 155                 160 gca act gga cta tgg gct gca cta acc acc gta tca aat cca agc aga       528
Ala Thr Gly Leu Trp Ala Ala Leu Thr Thr Val Ser Asn Pro Ser Arg
                165                 170                 175 gca gat cct gtg acc tgg aga aag gag ccg gct gtc ctt ccc tgc tgt       576
Ala Asp Pro Val Thr Trp Arg Lys Glu Pro Ala Val Leu Pro Cys Cys
            180                 185                 190 aac cta gag aaa gga agc tgg ctg tcc ttc cct ggc aca gct gca cgc       624
Asn Leu Glu Lys Gly Ser Trp Leu Ser Phe Pro Gly Thr Ala Ala Arg
        195                 200                 205 aag gaa ttt tcc acc acg ctc acc ggg cac agc gcg ctg agc ctc tcc       672
Lys Glu Phe Ser Thr Thr Leu Thr Gly His Ser Ala Leu Ser Leu Ser
    210                 215                 220 agt tcg cgg gcc ctc ccc ggc tcg ctc ccg gct ttc gca gac ctc ccc       720
Ser Ser Arg Ala Leu Pro Gly Ser Leu Pro Ala Phe Ala Asp Leu Pro
225                 230                 235                 240 cgc tcc tgc cct gag tcc gag cag agc gca acg cca gcc ggc gcc ttc       768
Arg Ser Cys Pro Glu Ser Glu Gln Ser Ala Thr Pro Ala Gly Ala Phe
                245                 250                 255
```

```
ctc ctg ggc tgg gag cga gtg gtg cag cgg cgg ctc gaa gtc ccc cgg       816
Leu Leu Gly Trp Glu Arg Val Val Gln Arg Arg Leu Glu Val Pro Arg
        260                 265                 270 cct caa gca gcc ccc gcg act agc gcg aca ccc tcg cgg gat ccg agt       864
Pro Gln Ala Ala Pro Ala Thr Ser Ala Thr Pro Ser Arg Asp Pro Ser
    275                 280                 285 cca ccc tgc cac cag cgc cgg gac gcc gcg tgc ctc aga gcc caa ggg       912
Pro Pro Cys His Gln Arg Arg Asp Ala Ala Cys Leu Arg Ala Gln Gly
290                 295                 300 ctg acc cgg gcc ttc cag gtg gtc cat ctc gct cct acg gct ccc gac       960
Leu Thr Arg Ala Phe Gln Val Val His Leu Ala Pro Thr Ala Pro Asp
305                 310                 315                 320 ggt ggc gct ggg tgt ccc cca tcc cgc aat tcc tac cgg ctg acc cat      1008
Gly Gly Ala Gly Cys Pro Pro Ser Arg Asn Ser Tyr Arg Leu Thr His
            325                 330                 335 gtg cgc tgc gcc cag ggg ctg gag gct gcc agc gcc aac ctt ccc ggc      1056
Val Arg Cys Ala Gln Gly Leu Glu Ala Ala Ser Ala Asn Leu Pro Gly
        340                 345                 350 gct ccg ggg cgg agc agc tcc tgc gcc ctg cgc tac cgc agc ggc cct      1104
Ala Pro Gly Arg Ser Ser Ser Cys Ala Leu Arg Tyr Arg Ser Gly Pro
    355                 360                 365 tca gtc agc tcc gcg ccg tcc ccc gca gag ccc ccg gcg cac cag cgc      1152
Ser Val Ser Ser Ala Pro Ser Pro Ala Glu Pro Pro Ala His Gln Arg
370                 375                 380 ctg ctt ttc ctt ccc cga gcg cct caa gca gtc tct ggg ccg cag gaa      1200
Leu Leu Phe Leu Pro Arg Ala Pro Gln Ala Val Ser Gly Pro Gln Glu
385                 390                 395                 400 cag ccc tct gaa gag gcg ctt ggt gta gga agc ctc tca gtt ttc cag      1248
Gln Pro Ser Glu Glu Ala Leu Gly Val Gly Ser Leu Ser Val Phe Gln
            405                 410                 415 tta cac cta ata cag tgt att cca aat cta agt tac cca cta gta ctt      1296
Leu His Leu Ile Gln Cys Ile Pro Asn Leu Ser Tyr Pro Leu Val Leu
        420                 425                 430 cgg cac att cca gaa att ctg aaa ttt tct gaa aag gaa act ggt ggt      1344
Arg His Ile Pro Glu Ile Leu Lys Phe Ser Glu Lys Glu Thr Gly Gly
    435                 440                 445 gga att cta ggc tta gaa tta cca gcg aca gct gct cgc ctc tca gga      1392
Gly Ile Leu Gly Leu Glu Leu Pro Ala Thr Ala Ala Arg Leu Ser Gly
450                 455                 460 tta aac agc ata atg caa atc aaa gag ttt gaa gaa ttg gta aaa ctt      1440
Leu Asn Ser Ile Met Gln Ile Lys Glu Phe Glu Glu Leu Val Lys Leu
465                 470                 475                 480 cac agc ttg tca cac aaa gtc att cag tgt gtg ttt gca aag aaa aaa      1488
His Ser Leu Ser His Lys Val Ile Gln Cys Val Phe Ala Lys Lys Lys
            485                 490                 495 aat gta gac aaa tgg gat gac ttt tgt ctt agt gag ggt tat gga cat      1536
Asn Val Asp Lys Trp Asp Asp Phe Cys Leu Ser Glu Gly Tyr Gly His
        500                 505                 510 tca ttc tta ata atg aaa gaa acg tcg act aaa ata tca ggt tta att      1584
Ser Phe Leu Ile Met Lys Glu Thr Ser Thr Lys Ile Ser Gly Leu Ile
    515                 520                 525 cag gag atg ggg agc ggc aag agc aac gtg gga act tgg gga gac tac      1632
Gln Glu Met Gly Ser Gly Lys Ser Asn Val Gly Thr Trp Gly Asp Tyr
530                 535                 540 gac gac agc gcc ttc atg gag ccg agg tac cac gtc cgt cga gaa gat      1680
Asp Asp Ser Ala Phe Met Glu Pro Arg Tyr His Val Arg Arg Glu Asp
545                 550                 555                 560 ctg gac aag ctc cac aga gct gcc tgg tgg ggt aaa gtc ccc aga aag      1728
Leu Asp Lys Leu His Arg Ala Ala Trp Trp Gly Lys Val Pro Arg Lys
```

-continued

```
                  565                 570                 575
gat ctc atc gtc atg ctc agg gac act gac atg aac aag agg gac aag    1776
Asp Leu Ile Val Met Leu Arg Asp Thr Asp Met Asn Lys Arg Asp Lys
            580                 585                 590 caa aag agg act gct cta cat ttg gcc tct gcc aat gga aat tca gaa    1824
Gln Lys Arg Thr Ala Leu His Leu Ala Ser Ala Asn Gly Asn Ser Glu
        595                 600                 605 gta gta caa ctc ctg ctg gac aga cga tgt caa ctt aac gtc ctt gac    1872
Val Val Gln Leu Leu Leu Asp Arg Arg Cys Gln Leu Asn Val Leu Asp
    610                 615                 620 aac aaa aaa agg aca gct ctg ata aag gcc gta caa tgc cag gaa gat    1920
Asn Lys Lys Arg Thr Ala Leu Ile Lys Ala Val Gln Cys Gln Glu Asp
625                 630                 635                 640 gaa tgt gtg tta atg ttg ctg gaa cat ggc gct gat gga aat att caa    1968
Glu Cys Val Leu Met Leu Leu Glu His Gly Ala Asp Gly Asn Ile Gln
            645                 650                 655 gat gag tat gga aat acc gct cta cac tat gct atc tac aat gaa gat    2016
Asp Glu Tyr Gly Asn Thr Ala Leu His Tyr Ala Ile Tyr Asn Glu Asp
        660                 665                 670 aaa tta atg gcc aaa gca ctg ctc tta tat ggt gct gat att gaa tca    2064
Lys Leu Met Ala Lys Ala Leu Leu Leu Tyr Gly Ala Asp Ile Glu Ser
    675                 680                 685 aaa aac aag tgt ggc ctc aca cca ctt ttg ctt ggc gta cat gaa caa    2112
Lys Asn Lys Cys Gly Leu Thr Pro Leu Leu Leu Gly Val His Glu Gln
690                 695                 700 aaa cag gaa gtg gtg aaa ttt tta atc aag aaa aaa gct aat tta aat    2160
Lys Gln Glu Val Val Lys Phe Leu Ile Lys Lys Lys Ala Asn Leu Asn
705                 710                 715                 720 gca ctt gat aga tat gga aga act gcc ctc ata ctt gct gta tgt tgt    2208
Ala Leu Asp Arg Tyr Gly Arg Thr Ala Leu Ile Leu Ala Val Cys Cys
            725                 730                 735 gga tca gca agt ata gtc aat ctt cta ctt gag caa aat gtt gat gta    2256
Gly Ser Ala Ser Ile Val Asn Leu Leu Leu Glu Gln Asn Val Asp Val
        740                 745                 750 tct tct caa gat cta tct gga cag acg gcc aga gag tat gct gtt tct    2304
Ser Ser Gln Asp Leu Ser Gly Gln Thr Ala Arg Glu Tyr Ala Val Ser
    755                 760                 765 agt cat cat cat gta att tgt gaa tta ctt tct gac tat aaa gaa aaa    2352
Ser His His His Val Ile Cys Glu Leu Leu Ser Asp Tyr Lys Glu Lys
770                 775                 780 cag atg cta aaa atc tct tct gaa aac agc aat cca gtg ata acc atc    2400
Gln Met Leu Lys Ile Ser Ser Glu Asn Ser Asn Pro Val Ile Thr Ile
            785                 790                 795                 800 ctt aat atc aaa ctt cca ctc aag gtt gaa gaa gaa ata aag aag cat    2448
Leu Asn Ile Lys Leu Pro Leu Lys Val Glu Glu Glu Ile Lys Lys His
        805                 810                 815 gga agt aat cct gtg gga tta cca gaa aac ctg act aat ggt gcc agt    2496
Gly Ser Asn Pro Val Gly Leu Pro Glu Asn Leu Thr Asn Gly Ala Ser
    820                 825                 830 gct ggc aat ggt gat gat gga tta att cca caa agg aag agc aga aaa    2544
Ala Gly Asn Gly Asp Asp Gly Leu Ile Pro Gln Arg Lys Ser Arg Lys
835                 840                 845 cct gaa aat cag caa ttt cct gac act gag aat gaa gag tat cac agt    2592
Pro Glu Asn Gln Gln Phe Pro Asp Thr Glu Asn Glu Glu Tyr His Ser
            850                 855                 860 gac gaa caa aat gat acc cag aaa caa ctt tct gaa gaa cag aac act    2640
Asp Glu Gln Asn Asp Thr Gln Lys Gln Leu Ser Glu Glu Gln Asn Thr
        865                 870                 875                 880 gga ata tca caa gat gag att ctg act aat aaa caa aag cag ata gaa    2688
Gly Ile Ser Gln Asp Glu Ile Leu Thr Asn Lys Gln Lys Gln Ile Glu
```

```
Gly Ile Ser Gln Asp Glu Ile Leu Thr Asn Lys Gln Lys Gln Ile Glu
                885                 890                 895 gtg gct gaa aag gaa atg aat tct gag ctt tct ctt agt cat aag aaa      2736
Val Ala Glu Lys Glu Met Asn Ser Glu Leu Ser Leu Ser His Lys Lys
            900                 905                 910 gaa gaa gat ctc ttg cgt gaa aac agc atg ttg cgg gaa gaa att gcc      2784
Glu Glu Asp Leu Leu Arg Glu Asn Ser Met Leu Arg Glu Glu Ile Ala
            915                 920                 925 aag cta aga ctg gaa cta gat gaa aca aaa cat cag aac cag cta agg      2832
Lys Leu Arg Leu Glu Leu Asp Glu Thr Lys His Gln Asn Gln Leu Arg
            930                 935                 940 gaa aat aaa att ttg gag gaa att gaa agt gta aaa gaa aaa ctt cta      2880
Glu Asn Lys Ile Leu Glu Glu Ile Glu Ser Val Lys Glu Lys Leu Leu
945                 950                 955                 960 aag act ata caa ctg aat gaa gaa gca tta acg aaa acc aag gtg gct      2928
Lys Thr Ile Gln Leu Asn Glu Glu Ala Leu Thr Lys Thr Lys Val Ala
                965                 970                 975 ggt ttc tct ttg cgc cag ctt ggc ctt gcc cag cat gca caa gcc tca      2976
Gly Phe Ser Leu Arg Gln Leu Gly Leu Ala Gln His Ala Gln Ala Ser
                980                 985                 990 gtg caa cag ctg tgc tac aaa tgg aac cac aca gag aaa aca gag cag      3024
Val Gln Gln Leu Cys Tyr Lys Trp Asn His Thr Glu Lys Thr Glu Gln
                995                 1000                1005 cag gct cag gag cag gag gtg gct ggt ttc tct ttg cgc cag ctt ggc      3072
Gln Ala Gln Glu Gln Glu Val Ala Gly Phe Ser Leu Arg Gln Leu Gly
    1010                1015                1020 ctt gcc cag cat gca caa gcc tca gta caa caa ctg tgc tac aaa tgg      3120
Leu Ala Gln His Ala Gln Ala Ser Val Gln Gln Leu Cys Tyr Lys Trp
1025                1030                1035                1040 ggc cac aca gag aaa aca gag cag cag gct cag gag cag gga gct gcg      3168
Gly His Thr Glu Lys Thr Glu Gln Gln Ala Gln Glu Gln Gly Ala Ala
                1045                1050                1055 ctg agg tcc cag ata ggc gac cct ggc ggg gtg ccc ctg agc gaa ggg      3216
Leu Arg Ser Gln Ile Gly Asp Pro Gly Gly Val Pro Leu Ser Glu Gly
                1060                1065                1070 ggg aca gca gca gga gac cag ggt cca ggg acc cac ctc cca ccg agg      3264
Gly Thr Ala Ala Gly Asp Gln Gly Pro Gly Thr His Leu Pro Pro Arg
                1075                1080                1085 gaa cct cga gcc tcc cct ggc acc cct agc ttg gtc cgc ctg gcc tcc      3312
Glu Pro Arg Ala Ser Pro Gly Thr Pro Ser Leu Val Arg Leu Ala Ser
                1090                1095                1100 gga gcc cga gct gct gcg ctt ccc cca ccc aca ggg aaa aac ggc cga      3360
Gly Ala Arg Ala Ala Ala Leu Pro Pro Pro Thr Gly Lys Asn Gly Arg
1105                1110                1115                1120 tct cca acc aaa cag aaa tct gtg tgt gac tcc tct ggt tgg ata ctg      3408
Ser Pro Thr Lys Gln Lys Ser Val Cys Asp Ser Ser Gly Trp Ile Leu
                1125                1130                1135 cca gtc ccc aca ttt tct tcc ggg agt ttt ctt ggc aga agg tgc cca      3456
Pro Val Pro Thr Phe Ser Ser Gly Ser Phe Leu Gly Arg Arg Cys Pro
                1140                1145                1150 atg ttt gat gtt tcg cca gcc atg agg ctg aaa agt gac agc aat aga      3504
Met Phe Asp Val Ser Pro Ala Met Arg Leu Lys Ser Asp Ser Asn Arg
                1155                1160                1165 gaa aca cat cag gct ttc cgc gac aaa gat gac ctt ccc ttc ttc aaa      3552
Glu Thr His Gln Ala Phe Arg Asp Lys Asp Asp Leu Pro Phe Phe Lys
            1170                1175                1180 act cag caa tct cca cgg cac aca aag gac tta gga caa gat gac cga      3600
Thr Gln Gln Ser Pro Arg His Thr Lys Asp Leu Gly Gln Asp Asp Arg
1185                1190                1195                1200
```

```
gct gga gtg ctc gcc cca aaa tgc agg ccc gga aca ctc tgc cac acg      3648
Ala Gly Val Leu Ala Pro Lys Cys Arg Pro Gly Thr Leu Cys His Thr
                1205                1210                1215 gac aca cca cca cac aga aat gcg gac aca cca cca cac aga cac acc      3696
Asp Thr Pro Pro His Arg Asn Ala Asp Thr Pro Pro His Arg His Thr
                1220                1225                1230 acc acg ctg cca cac aga gac acc acc aca tcg ttg cca cac ttt cat      3744
Thr Thr Leu Pro His Arg Asp Thr Thr Thr Ser Leu Pro His Phe His
                1235                1240                1245 gtg tca gct ggc ggt gtg ggc ccc acg act ctg ggc tct aat aga gaa      3792
Val Ser Ala Gly Gly Val Gly Pro Thr Thr Leu Gly Ser Asn Arg Glu
                1250                1255                1260 att act tag                                                          3801
Ile Thr  *
1265
```

<210> SEQ ID NO 27
<211> LENGTH: 1266
<212> TYPE: PRT
<213> ORGANISM: Homo sapiens

<400> SEQUENCE: 27

```
Met Pro Phe Ile Ser Lys Leu Val Leu Ala Ser Gln Pro Thr Leu Phe
 1               5                  10                  15

Ser Phe Phe Ser Ala Ser Ser Pro Phe Leu Leu Phe Leu Asp Leu Arg
             20                  25                  30

Pro Glu Arg Thr Tyr Leu Pro Val Cys His Val Ala Leu Ile His Met
         35                  40                  45

Val Val Leu Leu Thr Met Val Phe Leu Ser Pro Gln Leu Phe Glu Ser
     50                  55                  60

Leu Asn Phe Gln Asn Asp Phe Lys Tyr Glu Ala Ser Phe Tyr Leu Arg
 65                  70                  75                  80

Arg Val Ile Arg Val Leu Ser Ile Cys Thr Thr Cys Leu Leu Asp Met
                 85                  90                  95

Leu Gln Val Val Asn Ile Ser Pro Ser Ile Ser Trp Leu Ile Met Leu
            100                 105                 110

Phe Ser Ser Val Tyr Met Met Thr Leu Ile Gln Glu Leu Gln Glu Ile
        115                 120                 125

Leu Val Pro Ser Gln Pro Gln Pro Leu Pro Lys Asp Leu Cys Arg Gly
    130                 135                 140

Lys Ser His Gln His Ile Leu Leu Pro Thr Gln Ala Thr Phe Ala Ala
145                 150                 155                 160

Ala Thr Gly Leu Trp Ala Ala Leu Thr Thr Val Ser Asn Pro Ser Arg
                165                 170                 175

Ala Asp Pro Val Thr Trp Arg Lys Glu Pro Ala Val Leu Pro Cys Cys
            180                 185                 190

Asn Leu Glu Lys Gly Ser Trp Leu Ser Phe Pro Gly Thr Ala Ala Arg
        195                 200                 205

Lys Glu Phe Ser Thr Thr Leu Thr Gly His Ser Ala Leu Ser Leu Ser
    210                 215                 220

Ser Ser Arg Ala Leu Pro Gly Ser Leu Pro Ala Phe Ala Asp Leu Pro
225                 230                 235                 240

Arg Ser Cys Pro Glu Ser Glu Gln Ser Ala Thr Pro Ala Gly Ala Phe
                245                 250                 255

Leu Leu Gly Trp Glu Arg Val Val Gln Arg Arg Leu Glu Val Pro Arg
            260                 265                 270
```

-continued

```
Pro Gln Ala Ala Pro Ala Thr Ser Ala Thr Pro Ser Arg Asp Pro Ser
        275                 280                 285

Pro Pro Cys His Gln Arg Arg Asp Ala Ala Cys Leu Arg Ala Gln Gly
        290                 295                 300

Leu Thr Arg Ala Phe Gln Val Val His Leu Ala Pro Thr Ala Pro Asp
305                 310                 315                 320

Gly Gly Ala Gly Cys Pro Pro Ser Arg Asn Ser Tyr Arg Leu Thr His
                325                 330                 335

Val Arg Cys Ala Gln Gly Leu Glu Ala Ala Ser Ala Asn Leu Pro Gly
            340                 345                 350

Ala Pro Gly Arg Ser Ser Cys Ala Leu Arg Tyr Arg Ser Gly Pro
                355                 360                 365

Ser Val Ser Ser Ala Pro Ser Pro Ala Glu Pro Pro Ala His Gln Arg
        370                 375                 380

Leu Leu Phe Leu Pro Arg Ala Pro Gln Ala Val Ser Gly Pro Gln Glu
385                 390                 395                 400

Gln Pro Ser Glu Glu Ala Leu Gly Val Gly Ser Leu Ser Val Phe Gln
                405                 410                 415

Leu His Leu Ile Gln Cys Ile Pro Asn Leu Ser Tyr Pro Leu Val Leu
            420                 425                 430

Arg His Ile Pro Glu Ile Leu Lys Phe Ser Glu Lys Glu Thr Gly Gly
                435                 440                 445

Gly Ile Leu Gly Leu Glu Leu Pro Ala Thr Ala Ala Arg Leu Ser Gly
        450                 455                 460

Leu Asn Ser Ile Met Gln Ile Lys Glu Phe Glu Glu Leu Val Lys Leu
465                 470                 475                 480

His Ser Leu Ser His Lys Val Ile Gln Cys Val Phe Ala Lys Lys Lys
                485                 490                 495

Asn Val Asp Lys Trp Asp Asp Phe Cys Leu Ser Glu Gly Tyr Gly His
                500                 505                 510

Ser Phe Leu Ile Met Lys Glu Thr Ser Thr Lys Ile Ser Gly Leu Ile
        515                 520                 525

Gln Glu Met Gly Ser Gly Lys Ser Asn Val Gly Thr Trp Gly Asp Tyr
530                 535                 540

Asp Asp Ser Ala Phe Met Glu Pro Arg Tyr His Val Arg Arg Glu Asp
545                 550                 555                 560

Leu Asp Lys Leu His Arg Ala Ala Trp Trp Gly Lys Val Pro Arg Lys
                565                 570                 575

Asp Leu Ile Val Met Leu Arg Asp Thr Asp Met Asn Lys Arg Asp Lys
                580                 585                 590

Gln Lys Arg Thr Ala Leu His Leu Ala Ser Ala Asn Gly Asn Ser Glu
        595                 600                 605

Val Val Gln Leu Leu Leu Asp Arg Arg Cys Gln Leu Asn Val Leu Asp
610                 615                 620

Asn Lys Lys Arg Thr Ala Leu Ile Lys Ala Val Gln Cys Gln Glu Asp
625                 630                 635                 640

Glu Cys Val Leu Met Leu Leu Glu His Gly Ala Asp Gly Asn Ile Gln
                645                 650                 655

Asp Glu Tyr Gly Asn Thr Ala Leu His Tyr Ala Ile Tyr Asn Glu Asp
                660                 665                 670

Lys Leu Met Ala Lys Ala Leu Leu Leu Tyr Gly Ala Asp Ile Glu Ser
        675                 680                 685

Lys Asn Lys Cys Gly Leu Thr Pro Leu Leu Leu Gly Val His Glu Gln
```

```
            690                 695                 700
Lys Gln Glu Val Val Lys Phe Leu Ile Lys Lys Ala Asn Leu Asn
705                 710                 715                 720

Ala Leu Asp Arg Tyr Gly Arg Thr Ala Leu Ile Leu Ala Val Cys Cys
                725                 730                 735

Gly Ser Ala Ser Ile Val Asn Leu Leu Leu Glu Gln Asn Val Asp Val
                740                 745                 750

Ser Ser Gln Asp Leu Ser Gly Gln Thr Ala Arg Glu Tyr Ala Val Ser
                755                 760                 765

Ser His His His Val Ile Cys Glu Leu Ser Asp Tyr Lys Glu Lys
770                 775                 780

Gln Met Leu Lys Ile Ser Ser Glu Asn Ser Asn Pro Val Ile Thr Ile
785                 790                 795                 800

Leu Asn Ile Lys Leu Pro Leu Lys Val Glu Glu Ile Lys Lys His
                805                 810                 815

Gly Ser Asn Pro Val Gly Leu Pro Glu Asn Leu Thr Asn Gly Ala Ser
                820                 825                 830

Ala Gly Asn Gly Asp Asp Gly Leu Ile Pro Gln Arg Lys Ser Arg Lys
                835                 840                 845

Pro Glu Asn Gln Gln Phe Pro Asp Thr Glu Asn Glu Glu Tyr His Ser
850                 855                 860

Asp Glu Gln Asn Asp Thr Gln Lys Gln Leu Ser Glu Gln Asn Thr
865                 870                 875                 880

Gly Ile Ser Gln Asp Glu Ile Leu Thr Asn Lys Gln Lys Gln Ile Glu
                885                 890                 895

Val Ala Glu Lys Glu Met Asn Ser Glu Leu Ser Leu Ser His Lys Lys
                900                 905                 910

Glu Glu Asp Leu Leu Arg Glu Asn Ser Met Leu Arg Glu Glu Ile Ala
                915                 920                 925

Lys Leu Arg Leu Glu Leu Asp Glu Thr Lys His Gln Asn Gln Leu Arg
                930                 935                 940

Glu Asn Lys Ile Leu Glu Glu Ile Glu Ser Val Lys Glu Lys Leu Leu
945                 950                 955                 960

Lys Thr Ile Gln Leu Asn Glu Glu Ala Leu Thr Lys Thr Lys Val Ala
                965                 970                 975

Gly Phe Ser Leu Arg Gln Leu Gly Leu Ala Gln His Ala Gln Ala Ser
                980                 985                 990

Val Gln Gln Leu Cys Tyr Lys Trp Asn His Thr Glu Lys Thr Glu Gln
                995                 1000                1005

Gln Ala Gln Glu Gln Glu Val Ala Gly Phe Ser Leu Arg Gln Leu Gly
                1010                1015                1020

Leu Ala Gln His Ala Gln Ala Ser Val Gln Gln Leu Cys Tyr Lys Trp
1025                1030                1035                1040

Gly His Thr Glu Lys Thr Glu Gln Gln Ala Gln Gln Gly Ala Ala
                1045                1050                1055

Leu Arg Ser Gln Ile Gly Asp Pro Gly Gly Val Pro Leu Ser Glu Gly
                1060                1065                1070

Gly Thr Ala Ala Gly Asp Gln Gly Pro Gly Thr His Leu Pro Pro Arg
                1075                1080                1085

Glu Pro Arg Ala Ser Pro Gly Thr Pro Ser Leu Val Arg Leu Ala Ser
                1090                1095                1100

Gly Ala Arg Ala Ala Ala Leu Pro Pro Pro Thr Gly Lys Asn Gly Arg
1105                1110                1115                1120
```

-continued

```
Ser Pro Thr Lys Gln Lys Ser Val Cys Asp Ser Ser Gly Trp Ile Leu
                1125                1130                1135

Pro Val Pro Thr Phe Ser Ser Gly Ser Phe Leu Gly Arg Arg Cys Pro
            1140                1145                1150

Met Phe Asp Val Ser Pro Ala Met Arg Leu Lys Ser Asp Ser Asn Arg
            1155                1160                1165

Glu Thr His Gln Ala Phe Arg Asp Lys Asp Leu Pro Phe Phe Lys
        1170                1175                1180

Thr Gln Gln Ser Pro Arg His Thr Lys Asp Leu Gly Gln Asp Asp Arg
1185                1190                1195                1200

Ala Gly Val Leu Ala Pro Lys Cys Arg Pro Gly Thr Leu Cys His Thr
                1205                1210                1215

Asp Thr Pro Pro His Arg Asn Ala Asp Thr Pro Pro His Arg His Thr
            1220                1225                1230

Thr Thr Leu Pro His Arg Asp Thr Thr Thr Ser Leu Pro His Phe His
            1235                1240                1245

Val Ser Ala Gly Gly Val Gly Pro Thr Thr Leu Gly Ser Asn Arg Glu
1250                1255                1260

Ile Thr
1265

<210> SEQ ID NO 28
<211> LENGTH: 255
<212> TYPE: PRT
<213> ORGANISM: Homo sapiens

<400> SEQUENCE: 28

Met Pro Phe Ile Ser Lys Leu Val Leu Ala Ser Gln Pro Thr Leu Phe
1               5                   10                  15

Ser Phe Phe Ser Ala Ser Ser Pro Phe Leu Leu Phe Leu Asp Leu Arg
            20                  25                  30

Pro Glu Arg Thr Tyr Leu Pro Val Cys His Val Ala Leu Ile His Met
        35                  40                  45

Val Val Leu Leu Thr Met Val Phe Leu Ser Pro Gln Leu Phe Glu Ser
50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Gly Met
                85                  90                  95

Leu Gln Val Val Asn Ile Ser Pro Ser Ile Ser Trp Leu Val Arg Phe
            100                 105                 110

Lys Trp Lys Ser Thr Ile Phe Thr Phe His Leu Phe Ser Trp Ser Leu
        115                 120                 125

Ser Phe Pro Val Ser Ser Leu Ile Phe Tyr Thr Val Ala Ser Ser
    130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
        195                 200                 205

Gln Pro Leu Pro Lys Asp Leu Cys Arg Gly Lys Ser His Gln His Ile
```

```
                210                 215                 220
Leu Leu Pro Val Ser Phe Ser Val Gly Met Tyr Lys Met Asp Phe Ile
225                 230                 235                 240

Ile Ser Thr Ser Ser Thr Leu Pro Trp Ala Tyr Asp Arg Gly Val
                245                 250                 255

<210> SEQ ID NO 29
<211> LENGTH: 255
<212> TYPE: PRT
<213> ORGANISM: Homo sapiens

<400> SEQUENCE: 29

Met Pro Phe Ile Ser Lys Leu Val Leu Ala Ser Gln Pro Thr Leu Cys
1               5                   10                  15

Ser Phe Phe Ser Ala Ser Ser Pro Phe Leu Leu Phe Leu Asp Leu Arg
                20                  25                  30

Pro Glu Arg Thr Tyr Leu Pro Val Cys His Val Ala Leu Ile His Met
            35                  40                  45

Val Val Leu Leu Thr Met Val Phe Leu Ser Pro Gln Leu Phe Glu Ser
        50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Gly Met
                85                  90                  95

Leu Gln Val Val Asn Ile Ser Pro Ser Ile Ser Trp Leu Val Arg Phe
            100                 105                 110

Lys Trp Lys Ser Thr Ile Phe Thr Phe His Leu Phe Ser Trp Ser Leu
        115                 120                 125

Ser Phe Pro Val Ser Ser Leu Ile Phe Tyr Thr Val Ala Ser Ser
130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
        195                 200                 205

Gln Pro Leu Pro Lys Asp Leu Cys Arg Gly Lys Ser His Gln His Ile
    210                 215                 220

Leu Leu Pro Val Ser Phe Ser Val Gly Met Tyr Lys Met Asp Phe Ile
225                 230                 235                 240

Ile Ser Thr Ser Ser Thr Leu Pro Trp Ala Tyr Asp Arg Gly Val
                245                 250                 255

<210> SEQ ID NO 30
<211> LENGTH: 255
<212> TYPE: PRT
<213> ORGANISM: Homo sapiens

<400> SEQUENCE: 30

Met Pro Phe Ile Ser Lys Leu Val Leu Ala Ser Gln Pro Thr Leu Phe
1               5                   10                  15

Ser Phe Phe Ser Ala Ser Ser Pro Phe Leu Leu Phe Leu Asp Leu Arg
                20                  25                  30

Pro Glu Arg Thr Tyr Leu Pro Val Cys His Val Ala Leu Ile His Met
```

```
            35                  40                  45
Val Val Leu Leu Thr Met Val Phe Leu Ser Pro Gln Leu Phe Glu Ser
 50                  55                  60

Leu Asn Phe Gln Asn Asp Phe Lys Tyr Glu Ala Ser Phe Tyr Leu Arg
 65                  70                  75                  80

Arg Val Ile Arg Asp Leu Ser Ile Cys Thr Cys Leu Leu Gly Met
                 85                  90                  95

Leu Gln Val Val Asn Ile Ser Pro Ser Ile Ser Trp Leu Val Arg Phe
                100                 105                 110

Lys Trp Lys Ser Thr Ile Phe Thr Phe His Leu Phe Ser Trp Ser Leu
                115                 120                 125

Ser Phe Pro Val Ser Ser Leu Ile Phe Tyr Thr Val Ala Ser Ser
            130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
                180                 185                 190

Met Thr Leu Ile Gln Glu Leu Gln Glu Ile Leu Val Pro Ser Gln Pro
            195                 200                 205

Gln Pro Leu Pro Lys Asp Leu Cys Arg Gly Lys Ser His Gln His Ile
            210                 215                 220

Leu Leu Pro Val Ser Phe Ser Val Gly Met Tyr Lys Met Asp Phe Ile
225                 230                 235                 240

Ile Ser Thr Ser Ser Thr Leu Pro Trp Ala Tyr Asp Arg Gly Val
                245                 250                 255

<210> SEQ ID NO 31
<211> LENGTH: 255
<212> TYPE: PRT
<213> ORGANISM: Homo sapiens

<400> SEQUENCE: 31

Met Pro Phe Ile Ser Lys Leu Val Leu Ala Ser Gln Pro Thr Leu Phe
 1               5                  10                  15

Ser Phe Phe Ser Ala Ser Ser Pro Phe Leu Leu Phe Leu Asp Leu Arg
                20                  25                  30

Pro Glu Arg Thr Tyr Leu Pro Val Cys His Val Ala Leu Ile His Met
                35                  40                  45

Val Val Leu Leu Thr Met Val Phe Leu Ser Pro Gln Leu Phe Glu Ser
 50                  55                  60

Leu Asn Phe Gln Asn Asp Phe Lys Tyr Glu Ala Ser Phe Tyr Leu Arg
 65                  70                  75                  80

Arg Val Ile Arg Val Leu Ser Ile Cys Thr Thr Cys Leu Leu Asp Met
                 85                  90                  95

Leu Gln Val Val Asn Ile Ser Pro Ser Ile Ser Trp Leu Val Arg Phe
                100                 105                 110

Lys Trp Lys Ser Thr Ile Phe Thr Phe His Leu Phe Ser Trp Ser Leu
                115                 120                 125

Ser Phe Pro Val Ser Ser Ser Leu Ile Phe Tyr Thr Val Ala Ser Ser
            130                 135                 140

Asn Val Thr Gln Ile Asn Leu His Val Ser Lys Tyr Cys Ser Leu Phe
145                 150                 155                 160
```

-continued

```
Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
        195                 200                 205

Gln Pro Leu Pro Lys Asp Leu Cys Arg Gly Lys Ser His Gln His Ile
    210                 215                 220

Leu Leu Pro Val Ser Phe Ser Val Gly Met Tyr Lys Met Asp Phe Ile
225                 230                 235                 240

Ile Ser Thr Ser Ser Thr Leu Pro Trp Ala Tyr Asp Arg Gly Val
                245                 250                 255

<210> SEQ ID NO 32
<211> LENGTH: 1266
<212> TYPE: PRT
<213> ORGANISM: Homo sapiens

<400> SEQUENCE: 32

Met Pro Phe Ile Ser Lys Leu Val Leu Ala Ser Gln Pro Thr Leu Phe
  1               5                  10                  15

Ser Phe Phe Ser Ala Ser Ser Pro Phe Leu Leu Phe Leu Asp Leu Arg
                 20                  25                  30

Pro Glu Arg Thr Tyr Leu Pro Val Cys His Val Ala Leu Ile His Met
             35                  40                  45

Val Val Leu Leu Thr Met Val Phe Leu Ser Pro Gln Leu Phe Glu Ser
         50                  55                  60

Leu Asn Phe Gln Asn Asp Phe Lys Tyr Glu Ala Ser Phe Tyr Leu Arg
 65                  70                  75                  80

Arg Val Ile Arg Val Leu Ser Ile Cys Thr Thr Cys Leu Leu Asp Met
                 85                  90                  95

Leu Gln Val Val Asn Ile Ser Pro Ser Ile Ser Trp Leu Ile Met Leu
                100                 105                 110

Phe Ser Ser Val Tyr Met Met Thr Leu Ile Gln Glu Leu Gln Glu Ile
            115                 120                 125

Leu Val Pro Ser Gln Pro Gln Pro Leu Pro Lys Asp Leu Cys Arg Gly
        130                 135                 140

Lys Ser His Gln His Ile Leu Leu Pro Thr Gln Ala Thr Phe Ala Ala
145                 150                 155                 160

Ala Thr Gly Leu Trp Ala Ala Leu Thr Thr Val Ser Asn Pro Ser Arg
                165                 170                 175

Ala Asp Pro Val Thr Trp Arg Lys Glu Pro Ala Val Leu Pro Cys Cys
            180                 185                 190

Asn Leu Glu Lys Gly Ser Trp Leu Ser Phe Pro Gly Thr Ala Ala Arg
        195                 200                 205

Lys Glu Phe Ser Thr Thr Leu Thr Gly His Ser Ala Leu Ser Leu Ser
    210                 215                 220

Ser Ser Arg Ala Leu Pro Gly Ser Leu Pro Ala Phe Ala Asp Leu Pro
225                 230                 235                 240

Arg Ser Cys Pro Glu Ser Glu Gln Ser Ala Thr Pro Ala Gly Ala Phe
                245                 250                 255

Leu Leu Gly Trp Glu Arg Val Val Gln Arg Arg Leu Glu Val Pro Arg
            260                 265                 270

Pro Gln Ala Ala Pro Ala Thr Ser Ala Thr Pro Ser Arg Asp Pro Ser
        275                 280                 285
```

-continued

```
Pro Pro Cys His Gln Arg Arg Asp Ala Ala Cys Leu Arg Ala Gln Gly
    290                 295                 300

Leu Thr Arg Ala Phe Gln Val Val His Leu Ala Pro Thr Ala Pro Asp
305                 310                 315                 320

Gly Gly Ala Gly Cys Pro Pro Ser Arg Asn Ser Tyr Arg Leu Thr His
                325                 330                 335

Val Arg Cys Ala Gln Gly Leu Glu Ala Ala Ser Ala Asn Leu Pro Gly
            340                 345                 350

Ala Pro Gly Arg Ser Ser Ser Cys Ala Leu Arg Tyr Arg Ser Gly Pro
        355                 360                 365

Ser Val Ser Ser Ala Pro Ser Pro Ala Glu Pro Pro Ala His Gln Arg
    370                 375                 380

Leu Leu Phe Leu Pro Arg Ala Pro Gln Ala Val Ser Gly Pro Gln Glu
385                 390                 395                 400

Gln Pro Ser Glu Glu Ala Leu Gly Val Gly Ser Leu Ser Val Phe Gln
                405                 410                 415

Leu His Leu Ile Gln Cys Ile Pro Asn Leu Ser Tyr Pro Leu Val Leu
            420                 425                 430

Arg His Ile Pro Glu Ile Leu Lys Phe Ser Glu Lys Glu Thr Gly Gly
        435                 440                 445

Gly Ile Leu Gly Leu Glu Leu Pro Ala Thr Ala Ala Arg Leu Ser Gly
    450                 455                 460

Leu Asn Ser Ile Met Gln Ile Lys Glu Phe Glu Glu Leu Val Lys Leu
465                 470                 475                 480

His Ser Leu Ser His Lys Val Ile Gln Cys Val Phe Ala Lys Lys Lys
                485                 490                 495

Asn Val Asp Lys Trp Asp Asp Phe Cys Leu Ser Glu Gly Tyr Gly His
            500                 505                 510

Ser Phe Leu Ile Met Lys Glu Thr Ser Thr Lys Ile Ser Gly Leu Ile
        515                 520                 525

Gln Glu Met Gly Ser Gly Lys Ser Asn Val Gly Thr Trp Gly Asp Tyr
    530                 535                 540

Asp Asp Ser Ala Phe Met Glu Pro Arg Tyr His Val Arg Arg Glu Asp
545                 550                 555                 560

Leu Asp Lys Leu His Arg Ala Ala Trp Trp Gly Lys Val Pro Arg Lys
                565                 570                 575

Asp Leu Ile Val Met Leu Arg Asp Thr Asp Met Asn Lys Arg Asp Lys
            580                 585                 590

Gln Lys Arg Thr Ala Leu His Leu Ala Ser Ala Asn Gly Asn Ser Glu
        595                 600                 605

Val Val Gln Leu Leu Leu Asp Arg Arg Cys Gln Leu Asn Val Leu Asp
    610                 615                 620

Asn Lys Lys Arg Thr Ala Leu Ile Lys Ala Val Gln Cys Gln Glu Asp
625                 630                 635                 640

Glu Cys Val Leu Met Leu Leu Glu His Gly Ala Asp Gly Asn Ile Gln
                645                 650                 655

Asp Glu Tyr Gly Asn Thr Ala Leu His Tyr Ala Ile Tyr Asn Glu Asp
            660                 665                 670

Lys Leu Met Ala Lys Ala Leu Leu Leu Tyr Gly Ala Asp Ile Glu Ser
        675                 680                 685

Lys Asn Lys Cys Gly Leu Thr Pro Leu Leu Leu Gly Val His Glu Gln
    690                 695                 700
```

-continued

```
Lys Gln Glu Val Val Lys Phe Leu Ile Lys Lys Ala Asn Leu Asn
705                 710                 715                 720

Ala Leu Asp Arg Tyr Gly Arg Thr Ala Leu Ile Leu Ala Val Cys Cys
            725                 730                 735

Gly Ser Ala Ser Ile Val Asn Leu Leu Leu Glu Gln Asn Val Asp Val
            740                 745                 750

Ser Ser Gln Asp Leu Ser Gly Gln Thr Ala Arg Glu Tyr Ala Val Ser
        755                 760                 765

Ser His His His Val Ile Cys Glu Leu Leu Ser Asp Tyr Lys Glu Lys
    770                 775                 780

Gln Met Leu Lys Ile Ser Ser Glu Asn Ser Asn Pro Val Ile Thr Ile
785                 790                 795                 800

Leu Asn Ile Lys Leu Pro Leu Lys Val Glu Glu Ile Lys Lys His
                805                 810                 815

Gly Ser Asn Pro Val Gly Leu Pro Glu Asn Leu Thr Asn Gly Ala Ser
            820                 825                 830

Ala Gly Asn Gly Asp Asp Gly Leu Ile Pro Gln Arg Lys Ser Arg Lys
            835                 840                 845

Pro Glu Asn Gln Gln Phe Pro Asp Thr Glu Asn Glu Glu Tyr His Ser
        850                 855                 860

Asp Glu Gln Asn Asp Thr Gln Lys Gln Leu Ser Glu Glu Gln Asn Thr
865                 870                 875                 880

Gly Ile Ser Gln Asp Glu Ile Leu Thr Asn Lys Gln Lys Gln Ile Glu
            885                 890                 895

Val Ala Glu Lys Glu Met Asn Ser Glu Leu Ser Leu Ser His Lys Lys
            900                 905                 910

Glu Glu Asp Leu Leu Arg Glu Asn Ser Met Leu Arg Glu Glu Ile Ala
        915                 920                 925

Lys Leu Arg Leu Glu Leu Asp Glu Thr Lys His Gln Asn Gln Leu Arg
        930                 935                 940

Glu Asn Lys Ile Leu Glu Glu Ile Glu Ser Val Lys Glu Lys Leu Leu
945                 950                 955                 960

Lys Thr Ile Gln Leu Asn Glu Glu Ala Leu Thr Lys Thr Lys Val Ala
            965                 970                 975

Gly Phe Ser Leu Arg Gln Leu Gly Leu Ala Gln His Ala Gln Ala Ser
            980                 985                 990

Val Gln Gln Leu Cys Tyr Lys Trp Asn His Thr Glu Lys Thr Glu Gln
        995                 1000                1005

Gln Ala Gln Glu Gln Glu Val Ala Gly Phe Ser Leu Arg Gln Leu Gly
        1010                1015                1020

Leu Ala Gln His Ala Gln Ala Ser Val Gln Gln Leu Cys Tyr Lys Trp
1025                1030                1035                1040

Gly His Thr Glu Lys Thr Glu Gln Gln Ala Gln Glu Gln Gly Ala Ala
            1045                1050                1055

Leu Arg Ser Gln Ile Gly Asp Pro Gly Gly Val Pro Leu Ser Glu Gly
        1060                1065                1070

Gly Thr Ala Ala Gly Asp Gln Gly Pro Gly Thr His Leu Pro Pro Arg
            1075                1080                1085

Glu Pro Arg Ala Ser Pro Gly Thr Pro Ser Leu Val Arg Leu Ala Ser
        1090                1095                1100

Gly Ala Arg Ala Ala Ala Leu Pro Pro Thr Gly Lys Asn Gly Arg
1105                1110                1115                1120

Ser Pro Thr Lys Gln Lys Ser Val Cys Asp Ser Ser Gly Trp Ile Leu
```

```
                       1125              1130              1135
Pro Val Pro Thr Phe Ser Ser Gly Ser Phe Leu Gly Arg Arg Cys Pro
                1140              1145              1150
Met Phe Asp Val Ser Pro Ala Met Arg Leu Lys Ser Asp Ser Asn Arg
                1155              1160              1165
Glu Thr His Gln Ala Phe Arg Asp Lys Asp Leu Pro Phe Phe Lys
            1170              1175              1180
Thr Gln Gln Ser Pro Arg His Thr Lys Asp Leu Gly Gln Asp Asp Arg
1185              1190              1195              1200
Ala Gly Val Leu Ala Pro Lys Cys Arg Pro Gly Thr Leu Cys His Thr
                1205              1210              1215
Asp Thr Pro Pro His Arg Asn Ala Asp Thr Pro Pro His Arg His Thr
                1220              1225              1230
Thr Thr Leu Pro His Arg Asp Thr Thr Thr Ser Leu Pro His Phe His
                1235              1240              1245
Val Ser Ala Gly Gly Val Gly Pro Thr Thr Leu Gly Ser Asn Arg Glu
                1250              1255              1260
Ile Thr
1265

<210> SEQ ID NO 33
<211> LENGTH: 228
<212> TYPE: PRT
<213> ORGANISM: Homo sapiens

<400> SEQUENCE: 33

Phe Leu Leu Phe Leu Asp Leu Arg Pro Glu Arg Thr Tyr Leu Pro Val
1               5                   10                  15
Cys His Val Ala Leu Ile His Met Val Val Leu Thr Met Val Phe
                20                  25                  30
Leu Ser Pro Gln Leu Phe Glu Ser Leu Asn Phe Gln Asn Asp Phe Lys
                35                  40                  45
Tyr Glu Ala Ser Phe Tyr Leu Arg Arg Val Ile Arg Val Leu Ser Ile
            50                  55                  60
Cys Thr Thr Cys Leu Leu Gly Met Leu Gln Val Val Asn Ile Ser Pro
65                  70                  75                  80
Ser Ile Ser Trp Leu Val Arg Phe Lys Trp Lys Ser Thr Ile Phe Thr
                85                  90                  95
Phe His Leu Phe Ser Trp Ser Leu Ser Phe Pro Val Ser Ser Ser Leu
                100                 105                 110
Ile Phe Tyr Thr Val Ala Ser Ser Asn Val Thr Gln Ile Asn Leu His
                115                 120                 125
Val Ser Lys Tyr Cys Ser Leu Phe Pro Ile Asn Ser Ile Ile Arg Gly
            130                 135                 140
Leu Phe Phe Thr Leu Ser Leu Phe Arg Asp Val Phe Leu Lys Gln Ile
145                 150                 155                 160
Met Leu Phe Ser Ser Val Tyr Met Met Thr Leu Ile Gln Glu Leu Gln
                165                 170                 175
Glu Ile Leu Val Pro Ser Gln Pro Gln Pro Leu Pro Lys Asp Leu Cys
                180                 185                 190
Arg Gly Lys Ser His Gln His Ile Leu Leu Pro Val Ser Phe Ser Val
            195                 200                 205
Gly Met Tyr Lys Met Asp Phe Ile Ile Ser Thr Ser Ser Thr Leu Pro
            210                 215                 220
```

```
Trp Ala Tyr Asp
225

<210> SEQ ID NO 34
<211> LENGTH: 234
<212> TYPE: PRT
<213> ORGANISM: Homo sapiens

<400> SEQUENCE: 34

Phe Tyr Ile Phe Ile Ile Leu Gly His Arg Pro Lys Pro Met Asp Leu
  1               5                  10                  15

Ile Ser Cys Gln Gln Thr Phe Ile His Ile Met Leu Phe Phe Thr Ala
             20                  25                  30

Gly Asp Ile Leu His Thr Asp Ile Phe Glu Ser Met Asn Ile Glu Asn
         35                  40                  45

Asp Phe Lys Cys Lys Thr Thr Phe Tyr Ile Cys Arg Val Met Arg Gly
 50                  55                  60

Leu Ser Ile Cys Thr Thr Cys Leu Leu Ser Val Phe Gln Ala Val Thr
 65                  70                  75                  80

Ile Ser Pro Asn Thr Ser Leu Leu Ala Lys Phe Lys His Lys Leu Lys
                 85                  90                  95

Lys Tyr Thr Ile Asn Ala Phe Phe Tyr Ile Trp Ser Phe Asn Leu Ser
            100                 105                 110

Phe Ser Ser Asn Leu Ile Phe Tyr Val Gly Ala Tyr Thr Asn Val Ser
        115                 120                 125

Glu Thr Asn Gln Met Lys Val Thr Lys Tyr Cys Ser Leu Phe Pro Met
130                 135                 140

Asn Tyr Ile Ile Arg Gly Leu Ile Leu Thr Val Thr Thr Ser Arg Asp
145                 150                 155                 160

Val Phe Leu Val Gly Val Met Leu Ile Thr Ser Thr Tyr Met Val Ile
                165                 170                 175

Ile Leu Phe Arg His Gln Arg Gln Cys Lys His Leu His Ser Ile Arg
            180                 185                 190

His Leu Arg Ala Ser Pro Glu Lys Lys Ala Thr Gln Thr Ile Leu Leu
        195                 200                 205

Leu Val Val Phe Phe Val Val Met Tyr Trp Val Asp Phe Ile Ile Ser
210                 215                 220

Ser Thr Ser Val Leu Leu Trp Met Tyr Asp
225                 230

<210> SEQ ID NO 35
<211> LENGTH: 1213
<212> TYPE: PRT
<213> ORGANISM: Homo sapiens

<400> SEQUENCE: 35

Met Val Phe Leu Ser Pro Gln Leu Phe Glu Ser Leu Asn Phe Gln Asn
  1               5                  10                  15

Asp Phe Lys Tyr Glu Ala Ser Phe Tyr Leu Arg Arg Val Ile Arg Val
             20                  25                  30

Leu Ser Ile Cys Thr Thr Cys Leu Leu Asp Met Leu Gln Val Val Asn
             35                  40                  45

Ile Ser Pro Ser Ile Ser Trp Leu Ile Met Leu Phe Ser Ser Val Tyr
             50                  55                  60

Met Met Thr Leu Ile Gln Glu Leu Gln Glu Ile Leu Val Pro Ser Gln
 65                  70                  75                  80
```

```
Pro Gln Pro Leu Pro Lys Asp Leu Cys Arg Gly Lys Ser His Gln His
                 85                  90                  95
Ile Leu Leu Pro Thr Gln Ala Thr Phe Ala Ala Ala Thr Gly Leu Trp
            100                 105                 110
Ala Ala Leu Thr Thr Val Ser Asn Pro Ser Arg Ala Asp Pro Val Thr
            115                 120                 125
Trp Arg Lys Glu Pro Ala Val Leu Pro Cys Cys Asn Leu Glu Lys Gly
        130                 135                 140
Ser Trp Leu Ser Phe Pro Gly Thr Ala Arg Lys Glu Phe Ser Thr
145                 150                 155                 160
Thr Leu Thr Gly His Ser Ala Leu Ser Leu Ser Ser Arg Ala Leu
                165                 170                 175
Pro Gly Ser Leu Pro Ala Phe Ala Asp Leu Pro Arg Ser Cys Pro Glu
            180                 185                 190
Ser Glu Gln Ser Ala Thr Pro Ala Gly Ala Phe Leu Leu Gly Trp Glu
            195                 200                 205
Arg Val Val Gln Arg Leu Glu Val Pro Arg Pro Gln Ala Ala Pro
        210                 215                 220
Ala Thr Ser Ala Thr Pro Ser Arg Asp Pro Ser Pro Cys His Gln
225                 230                 235                 240
Arg Arg Asp Ala Ala Cys Leu Arg Ala Gln Gly Leu Thr Arg Ala Phe
                245                 250                 255
Gln Val Val His Leu Ala Pro Thr Ala Pro Asp Gly Gly Ala Gly Cys
            260                 265                 270
Pro Pro Ser Arg Asn Ser Tyr Arg Leu Thr His Val Arg Cys Ala Gln
        275                 280                 285
Gly Leu Glu Ala Ala Ser Ala Asn Leu Pro Gly Ala Pro Gly Arg Ser
        290                 295                 300
Ser Ser Cys Ala Leu Arg Tyr Arg Ser Gly Pro Ser Val Ser Ser Ala
305                 310                 315                 320
Pro Ser Pro Ala Glu Pro Ala His Gln Arg Leu Leu Phe Leu Pro
            325                 330                 335
Arg Ala Pro Gln Ala Val Ser Gly Pro Gln Gln Pro Ser Glu Glu
        340                 345                 350
Ala Leu Gly Val Gly Ser Leu Ser Val Phe Gln Leu His Leu Ile Gln
        355                 360                 365
Cys Ile Pro Asn Leu Ser Tyr Pro Leu Val Leu Arg His Ile Pro Glu
370                 375                 380
Ile Leu Lys Phe Ser Glu Lys Glu Thr Gly Gly Gly Ile Leu Gly Leu
385                 390                 395                 400
Glu Leu Pro Ala Thr Ala Ala Arg Leu Ser Gly Leu Asn Ser Ile Met
                405                 410                 415
Gln Ile Lys Glu Phe Glu Glu Leu Val Lys Leu His Ser Leu Ser His
            420                 425                 430
Lys Val Ile Gln Cys Val Phe Ala Lys Lys Asn Val Asp Lys Trp
        435                 440                 445
Asp Asp Phe Cys Leu Ser Glu Gly Tyr Gly His Ser Phe Leu Ile Met
        450                 455                 460
Lys Glu Thr Ser Thr Lys Ile Ser Gly Leu Ile Gln Glu Met Gly Ser
465                 470                 475                 480
Gly Lys Ser Asn Val Gly Thr Trp Gly Asp Tyr Asp Asp Ser Ala Phe
                485                 490                 495
Met Glu Pro Arg Tyr His Val Arg Arg Glu Asp Leu Asp Lys Leu His
```

-continued

```
                500                 505                 510
Arg Ala Ala Trp Trp Gly Lys Val Pro Arg Lys Asp Leu Ile Val Met
        515                 520                 525

Leu Arg Asp Thr Asp Met Asn Lys Arg Asp Lys Gln Lys Arg Thr Ala
    530                 535                 540

Leu His Leu Ala Ser Ala Asn Gly Asn Ser Glu Val Val Gln Leu Leu
545                 550                 555                 560

Leu Asp Arg Arg Cys Gln Leu Asn Val Leu Asp Asn Lys Lys Arg Thr
                565                 570                 575

Ala Leu Ile Lys Ala Val Gln Cys Gln Glu Asp Glu Cys Val Leu Met
            580                 585                 590

Leu Leu Glu His Gly Ala Asp Gly Asn Ile Gln Asp Glu Tyr Gly Asn
        595                 600                 605

Thr Ala Leu His Tyr Ala Ile Tyr Asn Glu Asp Lys Leu Met Ala Lys
    610                 615                 620

Ala Leu Leu Leu Tyr Gly Ala Asp Ile Glu Ser Lys Asn Lys Cys Gly
625                 630                 635                 640

Leu Thr Pro Leu Leu Leu Gly Val His Glu Gln Lys Gln Glu Val Val
                645                 650                 655

Lys Phe Leu Ile Lys Lys Lys Ala Asn Leu Asn Ala Leu Asp Arg Tyr
            660                 665                 670

Gly Arg Thr Ala Leu Ile Leu Ala Val Cys Cys Gly Ser Ala Ser Ile
        675                 680                 685

Val Asn Leu Leu Leu Glu Gln Asn Val Asp Val Ser Ser Gln Asp Leu
    690                 695                 700

Ser Gly Gln Thr Ala Arg Glu Tyr Ala Val Ser Ser His His His Val
705                 710                 715                 720

Ile Cys Glu Leu Leu Ser Asp Tyr Lys Glu Lys Gln Met Leu Lys Ile
                725                 730                 735

Ser Ser Glu Asn Ser Asn Pro Val Ile Thr Ile Leu Asn Ile Lys Leu
            740                 745                 750

Pro Leu Lys Val Glu Glu Ile Lys Lys His Gly Ser Asn Pro Val
        755                 760                 765

Gly Leu Pro Glu Asn Leu Thr Asn Gly Ala Ser Ala Gly Asn Gly Asp
    770                 775                 780

Asp Gly Leu Ile Pro Gln Arg Lys Ser Arg Lys Pro Glu Asn Gln Gln
785                 790                 795                 800

Phe Pro Asp Thr Glu Asn Glu Glu Tyr His Ser Asp Glu Gln Asn Asp
                805                 810                 815

Thr Gln Lys Gln Leu Ser Glu Glu Gln Asn Thr Gly Ile Ser Gln Asp
            820                 825                 830

Glu Ile Leu Thr Asn Lys Gln Lys Gln Ile Glu Val Ala Glu Lys Glu
        835                 840                 845

Met Asn Ser Glu Leu Ser Leu Ser His Lys Lys Glu Glu Asp Leu Leu
    850                 855                 860

Arg Glu Asn Ser Met Leu Arg Glu Glu Ile Ala Lys Leu Arg Leu Glu
865                 870                 875                 880

Leu Asp Glu Thr Lys His Gln Asn Gln Leu Arg Glu Asn Lys Ile Leu
                885                 890                 895

Glu Glu Ile Glu Ser Val Lys Glu Lys Leu Leu Lys Thr Ile Gln Leu
            900                 905                 910

Asn Glu Glu Ala Leu Thr Lys Thr Lys Val Ala Gly Phe Ser Leu Arg
        915                 920                 925
```

```
Gln Leu Gly Leu Ala Gln His Ala Gln Ala Ser Val Gln Gln Leu Cys
            930                 935                 940

Tyr Lys Trp Asn His Thr Glu Lys Thr Glu Gln Gln Ala Gln Glu Gln
945                 950                 955                 960

Glu Val Ala Gly Phe Ser Leu Arg Gln Leu Gly Leu Ala Gln His Ala
                965                 970                 975

Gln Ala Ser Val Gln Gln Leu Cys Tyr Lys Trp Gly His Thr Glu Lys
            980                 985                 990

Thr Glu Gln Gln Ala Gln Glu Gln Gly Ala Ala Leu Arg Ser Gln Ile
        995                 1000                1005

Gly Asp Pro Gly Gly Val Pro Leu Ser Glu Gly Gly Thr Ala Ala Gly
    1010                1015                1020

Asp Gln Gly Pro Gly Thr His Leu Pro Pro Arg Glu Pro Arg Ala Ser
1025                1030                1035                1040

Pro Gly Thr Pro Ser Leu Val Arg Leu Ala Ser Gly Ala Arg Ala Ala
                1045                1050                1055

Ala Leu Pro Pro Pro Thr Gly Lys Asn Gly Arg Ser Pro Thr Lys Gln
            1060                1065                1070

Lys Ser Val Cys Asp Ser Ser Gly Trp Ile Leu Pro Val Pro Thr Phe
        1075                1080                1085

Ser Ser Gly Ser Phe Leu Gly Arg Arg Cys Pro Met Phe Asp Val Ser
    1090                1095                1100

Pro Ala Met Arg Leu Lys Ser Asp Ser Asn Arg Glu Thr His Gln Ala
1105                1110                1115                1120

Phe Arg Asp Lys Asp Asp Leu Pro Phe Phe Lys Thr Gln Gln Ser Pro
                1125                1130                1135

Arg His Thr Lys Asp Leu Gly Gln Asp Asp Arg Ala Gly Val Leu Ala
            1140                1145                1150

Pro Lys Cys Arg Pro Gly Thr Leu Cys His Thr Asp Thr Pro Pro His
        1155                1160                1165

Arg Asn Ala Asp Thr Pro Pro His Arg His Thr Thr Leu Pro His
    1170                1175                1180

Arg Asp Thr Thr Thr Ser Leu Pro His Phe His Val Ser Ala Gly Gly
1185                1190                1195                1200

Val Gly Pro Thr Thr Leu Gly Ser Asn Arg Glu Ile Thr
                1205                1210

<210> SEQ ID NO 36
<211> LENGTH: 1213
<212> TYPE: PRT
<213> ORGANISM: Homo sapiens

<400> SEQUENCE: 36

Met Val Phe Leu Ser Pro Gln Leu Phe Glu Ser Leu Asn Phe Gln Asn
  1               5                  10                  15

Asp Phe Lys Tyr Glu Ala Ser Phe Tyr Leu Arg Arg Val Ile Arg Val
                20                  25                  30

Leu Ser Ile Cys Thr Thr Cys Leu Leu Asp Met Leu Gln Val Val Asn
            35                  40                  45

Ile Ser Pro Ser Ile Ser Trp Leu Ile Met Leu Phe Ser Ser Val Tyr
        50                  55                  60

Met Met Thr Leu Ile Gln Glu Leu Gln Glu Ile Leu Val Pro Ser Gln
65                  70                  75                  80

Pro Gln Pro Leu Pro Lys Asp Leu Cys Arg Gly Lys Ser His Gln His
```

-continued

```
                85                  90                  95
Ile Leu Leu Pro Thr Gln Ala Thr Phe Ala Ala Thr Gly Leu Trp
            100                 105                 110

Ala Ala Leu Thr Thr Val Ser Asn Pro Ser Arg Ala Asp Pro Val Thr
            115                 120                 125

Trp Arg Lys Glu Pro Ala Val Leu Pro Cys Cys Asn Leu Glu Lys Gly
        130                 135                 140

Ser Trp Leu Ser Phe Pro Gly Thr Ala Arg Lys Glu Phe Ser Thr
145                 150                 155                 160

Thr Leu Thr Gly His Ser Ala Leu Ser Leu Ser Ser Arg Ala Leu
                165                 170                 175

Pro Gly Ser Leu Pro Ala Phe Ala Asp Leu Pro Arg Ser Cys Pro Glu
            180                 185                 190

Ser Glu Gln Ser Ala Thr Pro Ala Gly Ala Phe Leu Leu Gly Trp Glu
                195                 200                 205

Arg Val Val Gln Arg Arg Leu Glu Val Pro Arg Pro Gln Ala Ala Pro
        210                 215                 220

Ala Thr Ser Ala Thr Pro Ser Arg Asp Pro Ser Pro Cys His Gln
225                 230                 235                 240

Arg Arg Asp Ala Ala Cys Leu Arg Ala Gln Gly Leu Thr Arg Ala Phe
            245                 250                 255

Gln Val Val His Leu Ala Pro Thr Ala Pro Asp Gly Gly Ala Gly Cys
                260                 265                 270

Pro Pro Ser Arg Asn Ser Tyr Arg Leu Thr His Val Arg Cys Ala Gln
            275                 280                 285

Gly Leu Glu Ala Ala Ser Ala Asn Leu Pro Gly Ala Pro Gly Arg Ser
        290                 295                 300

Ser Ser Cys Ala Leu Arg Tyr Arg Ser Gly Pro Ser Val Ser Ser Ala
305                 310                 315                 320

Pro Ser Pro Ala Glu Pro Pro Ala His Gln Arg Leu Leu Phe Leu Pro
            325                 330                 335

Arg Ala Pro Gln Ala Val Ser Gly Pro Gln Glu Gln Pro Ser Glu Glu
            340                 345                 350

Ala Leu Gly Val Gly Ser Leu Ser Val Phe Gln Leu His Leu Ile Gln
            355                 360                 365

Cys Ile Pro Asn Leu Ser Tyr Pro Leu Val Leu Arg His Ile Pro Glu
        370                 375                 380

Ile Leu Lys Phe Ser Glu Lys Glu Thr Gly Gly Gly Ile Leu Gly Leu
385                 390                 395                 400

Glu Leu Pro Ala Thr Ala Ala Arg Leu Ser Gly Leu Asn Ser Ile Met
            405                 410                 415

Gln Ile Lys Glu Phe Glu Glu Leu Val Lys Leu His Ser Leu Ser His
            420                 425                 430

Lys Val Ile Gln Cys Val Phe Ala Lys Lys Asn Val Asp Lys Trp
        435                 440                 445

Asp Asp Phe Cys Leu Ser Glu Gly Tyr Gly His Ser Phe Leu Ile Met
450                 455                 460

Lys Glu Thr Ser Thr Lys Ile Ser Gly Leu Ile Gln Glu Met Gly Ser
465                 470                 475                 480

Gly Lys Ser Asn Val Gly Thr Trp Gly Asp Tyr Asp Ser Ala Phe
                485                 490                 495

Met Glu Pro Arg Tyr His Val Arg Arg Glu Asp Leu Asp Lys Leu His
            500                 505                 510
```

-continued

```
Arg Ala Ala Trp Trp Gly Lys Val Pro Arg Lys Asp Leu Ile Val Met
        515                 520                 525
Leu Arg Asp Thr Asp Met Asn Lys Arg Asp Lys Gln Lys Arg Thr Ala
    530                 535                 540
Leu His Leu Ala Ser Ala Asn Gly Asn Ser Glu Val Val Gln Leu Leu
545                 550                 555                 560
Leu Asp Arg Arg Cys Gln Leu Asn Val Leu Asp Asn Lys Lys Arg Thr
                565                 570                 575
Ala Leu Ile Lys Ala Val Gln Cys Gln Glu Asp Glu Cys Val Leu Met
            580                 585                 590
Leu Leu Glu His Gly Ala Asp Gly Asn Ile Gln Asp Glu Tyr Gly Asn
        595                 600                 605
Thr Ala Leu His Tyr Ala Ile Tyr Asn Glu Asp Lys Leu Met Ala Lys
    610                 615                 620
Ala Leu Leu Leu Tyr Gly Ala Asp Ile Glu Ser Lys Asn Lys Cys Gly
625                 630                 635                 640
Leu Thr Pro Leu Leu Leu Gly Val His Glu Gln Lys Gln Glu Val Val
                645                 650                 655
Lys Phe Leu Ile Lys Lys Ala Asn Leu Asn Ala Leu Asp Arg Tyr
            660                 665                 670
Gly Arg Thr Ala Leu Ile Leu Ala Val Cys Cys Gly Ser Ala Ser Ile
        675                 680                 685
Val Asn Leu Leu Leu Glu Gln Asn Val Asp Val Ser Ser Gln Asp Leu
    690                 695                 700
Ser Gly Gln Thr Ala Arg Glu Tyr Ala Val Ser Ser His His His Val
705                 710                 715                 720
Ile Cys Glu Leu Leu Ser Asp Tyr Lys Glu Lys Gln Met Leu Lys Ile
                725                 730                 735
Ser Ser Glu Asn Ser Asn Pro Val Ile Thr Ile Leu Asn Ile Lys Leu
            740                 745                 750
Pro Leu Lys Val Glu Glu Ile Lys Lys His Gly Ser Asn Pro Val
        755                 760                 765
Gly Leu Pro Glu Asn Leu Thr Asn Gly Ala Ser Ala Gly Asn Gly Asp
    770                 775                 780
Asp Gly Leu Ile Pro Gln Arg Lys Ser Arg Lys Pro Glu Asn Gln Gln
785                 790                 795                 800
Phe Pro Asp Thr Glu Asn Glu Glu Tyr His Ser Asp Glu Gln Asn Asp
                805                 810                 815
Thr Gln Lys Gln Leu Ser Glu Glu Gln Asn Thr Gly Ile Ser Gln Asp
            820                 825                 830
Glu Ile Leu Thr Asn Lys Gln Lys Gln Ile Glu Val Ala Glu Lys Glu
        835                 840                 845
Met Asn Ser Glu Leu Ser Leu Ser His Lys Lys Glu Glu Asp Leu Leu
    850                 855                 860
Arg Glu Asn Ser Met Leu Arg Glu Glu Ile Ala Lys Leu Arg Leu Glu
865                 870                 875                 880
Leu Asp Glu Thr Lys His Gln Asn Gln Leu Arg Glu Asn Lys Ile Leu
                885                 890                 895
Glu Glu Ile Glu Ser Val Lys Glu Lys Leu Leu Lys Thr Ile Gln Leu
            900                 905                 910
Asn Glu Glu Ala Leu Thr Lys Thr Lys Val Ala Gly Phe Ser Leu Arg
        915                 920                 925
```

```
Gln Leu Gly Leu Ala Gln His Ala Gln Ala Ser Val Gln Gln Leu Cys
    930                 935                 940

Tyr Lys Trp Asn His Thr Glu Lys Thr Glu Gln Gln Ala Gln Glu Gln
945                 950                 955                 960

Glu Val Ala Gly Phe Ser Leu Arg Gln Leu Gly Leu Ala Gln His Ala
                965                 970                 975

Gln Ala Ser Val Gln Gln Leu Cys Tyr Lys Trp Gly His Thr Glu Lys
            980                 985                 990

Thr Glu Gln Gln Ala Gln Glu Gln Gly Ala Ala Leu Arg Ser Gln Ile
        995                 1000                1005

Gly Asp Pro Gly Gly Val Pro Leu Ser Glu Gly Gly Thr Ala Ala Gly
    1010                1015                1020

Asp Gln Gly Pro Gly Thr His Leu Pro Pro Arg Glu Pro Arg Ala Ser
1025                1030                1035                1040

Pro Gly Thr Pro Ser Leu Val Arg Leu Ala Ser Gly Ala Arg Ala Ala
                1045                1050                1055

Ala Leu Pro Pro Pro Thr Gly Lys Asn Gly Arg Ser Pro Thr Lys Gln
            1060                1065                1070

Lys Ser Val Cys Asp Ser Ser Gly Trp Ile Leu Pro Val Pro Thr Phe
        1075                1080                1085

Ser Ser Gly Ser Phe Leu Gly Arg Arg Cys Pro Met Phe Asp Val Ser
    1090                1095                1100

Pro Ala Met Arg Leu Lys Ser Asp Ser Asn Arg Glu Thr His Gln Ala
1105                1110                1115                1120

Phe Arg Asp Lys Asp Leu Pro Phe Phe Lys Thr Gln Gln Ser Pro
                1125                1130                1135

Arg His Thr Lys Asp Leu Gly Gln Asp Asp Arg Ala Gly Val Leu Ala
            1140                1145                1150

Pro Lys Cys Arg Pro Gly Thr Leu Cys His Thr Asp Thr Pro Pro His
        1155                1160                1165

Arg Asn Ala Asp Thr Pro Pro His Arg His Thr Thr Leu Pro His
    1170                1175                1180

Arg Asp Thr Thr Thr Ser Leu Pro His Phe His Val Ser Ala Gly Gly
1185                1190                1195                1200

Val Gly Pro Thr Thr Leu Gly Ser Asn Arg Glu Ile Thr
                1205                1210

<210> SEQ ID NO 37
<211> LENGTH: 14
<212> TYPE: PRT
<213> ORGANISM: Tetanus toxoid

<400> SEQUENCE: 37

Gln Tyr Ile Lys Ala Asn Ser Lys Phe Ile Gly Ile Thr Glu
1               5                   10

<210> SEQ ID NO 38
<211> LENGTH: 21
<212> TYPE: PRT
<213> ORGANISM: Plasmodium falciparum

<400> SEQUENCE: 38

Asp Ile Glu Lys Lys Ile Ala Lys Met Glu Lys Ala Ser Ser Val Phe
1               5                   10                  15

Asn Val Val Asn Ser
            20
```

```
<210> SEQ ID NO 39
<211> LENGTH: 16
<212> TYPE: PRT
<213> ORGANISM: Strepcococcus

<400> SEQUENCE: 39

Gly Ala Val Asp Ser Ile Leu Gly Gly Val Ala Thr Tyr Gly Ala Ala
 1               5                  10                  15

<210> SEQ ID NO 40
<211> LENGTH: 13
<212> TYPE: PRT
<213> ORGANISM: Artificial Sequence
<220> FEATURE:
<223> OTHER INFORMATION: Pan DR-binding epitope
<220> FEATURE:
<221> NAME/KEY: VARIANT
<222> LOCATION: 3
<223> OTHER INFORMATION: Xaa = cyclohexylalanine, phenylalanine, or
      tyrosine
<220> FEATURE:
<221> NAME/KEY: VARIANT
<222> LOCATION: 1, 13
<223> OTHER INFORMATION: Xaa = D-alanine or L-alanine

<400> SEQUENCE: 40

Xaa Lys Xaa Val Ala Ala Trp Thr Leu Lys Ala Ala Xaa
 1               5                  10

<210> SEQ ID NO 41
<211> LENGTH: 14
<212> TYPE: DNA
<213> ORGANISM: Artificial Sequence
<220> FEATURE:
<223> OTHER INFORMATION: Primer

<400> SEQUENCE: 41
ttttgatcaa gctt                                                         14

<210> SEQ ID NO 42
<211> LENGTH: 42
<212> TYPE: DNA
<213> ORGANISM: Artificial Sequence
<220> FEATURE:
<223> OTHER INFORMATION: Primer

<400> SEQUENCE: 42
ctaatacgac tcactatagg gctcgagcgg ccgcccgggc ag                           42

<210> SEQ ID NO 43
<211> LENGTH: 12
<212> TYPE: DNA
<213> ORGANISM: Artificial Sequence
<220> FEATURE:
<223> OTHER INFORMATION: Primer

<400> SEQUENCE: 43
gatcctgccc gg                                                           12

<210> SEQ ID NO 44
<211> LENGTH: 40
<212> TYPE: DNA
<213> ORGANISM: Artificial Sequence
<220> FEATURE:
<223> OTHER INFORMATION: Primer

<400> SEQUENCE: 44
```

-continued

```
gtaatacgac tcactatagg gcagcgtggt cgcggccgag                    40
```

<210> SEQ ID NO 45
<211> LENGTH: 10
<212> TYPE: DNA
<213> ORGANISM: Artificial Sequence
<220> FEATURE:
<223> OTHER INFORMATION: Primer

<400> SEQUENCE: 45

```
gatcctcggc                                                      10
```

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46

```
ctaatacgac tcactatagg gc                                        22
```

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47

```
tcgagcggcc gcccgggcag ga                                        22
```

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48

```
agcgtggtcg cggccgagga                                           20
```

<210> SEQ ID NO 49
<211> LENGTH: 25
<212> TYPE: DNA
<213> ORGANISM: Artificial Sequence
<220> FEATURE:
<223> OTHER INFORMATION: Primer

<400> SEQUENCE: 49

```
atatcgccgc gctcgtcgtc gacaa                                     25
```

<210> SEQ ID NO 50
<211> LENGTH: 26
<212> TYPE: DNA
<213> ORGANISM: Artificial Sequence
<220> FEATURE:
<223> OTHER INFORMATION: Primer

<400> SEQUENCE: 50

```
agccacacgc agctcattgt agaagg                                    26
```

<210> SEQ ID NO 51
<211> LENGTH: 23
<212> TYPE: DNA
<213> ORGANISM: Artificial Sequence -continued

```
<220> FEATURE:
<223> OTHER INFORMATION: RT-PCR Primer

<400> SEQUENCE: 51
agtgattcaa agagctgtgg aga                                              23

<210> SEQ ID NO 52
<211> LENGTH: 22
<212> TYPE: DNA
<213> ORGANISM: Artificial Sequence
<220> FEATURE:
<223> OTHER INFORMATION: RT-PCR Primer

<400> SEQUENCE: 52
ggccagagcg cacttaccta cc                                               22

<210> SEQ ID NO 53
<211> LENGTH: 24
<212> TYPE: DNA
<213> ORGANISM: Artificial Sequence
<220> FEATURE:
<223> OTHER INFORMATION: Epitope Tag

<400> SEQUENCE: 53
gattacaagg atgacgacga taag                                             24

<210> SEQ ID NO 54
<211> LENGTH: 4
<212> TYPE: PRT
<213> ORGANISM: Homo sapiens

<400> SEQUENCE: 54

Asn Val Thr Gln
 1

<210> SEQ ID NO 55
<211> LENGTH: 6
<212> TYPE: PRT
<213> ORGANISM: Homo sapiens

<400> SEQUENCE: 55

Gly Leu Phe Phe Thr Leu
 1               5

<210> SEQ ID NO 56
<211> LENGTH: 22
<212> TYPE: PRT
<213> ORGANISM: Homo sapiens

<400> SEQUENCE: 56

Leu Arg Pro Glu Arg Thr Tyr Leu Pro Val Cys His Val Ala Leu Ile
 1               5                  10                  15

His Met Val Val Leu Leu
                20

<210> SEQ ID NO 57
<211> LENGTH: 255
<212> TYPE: PRT
<213> ORGANISM: Homo sapiens

<400> SEQUENCE: 57

Met Pro Phe Ile Ser Lys Leu Val Leu Ala Ser Gln Pro Thr Leu Phe
 1               5                  10                  15

Ser Phe Phe Ser Ala Ser Ser Pro Phe Leu Leu Phe Leu Asp Leu Arg
```

```
                    20                  25                  30
Pro Glu Arg Thr Tyr Leu Pro Val Cys His Val Ala Leu Ile His Met
                35                  40                  45
Val Val Leu Leu Thr Met Val Phe Leu Ser Pro Gln Leu Phe Glu Ser
 50                  55                  60
Leu Asn Phe Gln Asn Asp Phe Lys Tyr Glu Ala Ser Phe Tyr Leu Arg
 65                  70                  75                  80
Arg Val Ile Arg Val Leu Ser Ile Cys Thr Thr Cys Leu Leu Gly Met
                 85                  90                  95
Leu Gln Val Val Asn Ile Ser Pro Ser Ile Ser Trp Leu Val Arg Phe
                100                 105                 110
Lys Trp Lys Ser Thr Ile Phe Thr Phe His Leu Phe Ser Trp Ser Leu
                115                 120                 125
Ser Phe Pro Val Ser Ser Leu Ile Phe Tyr Thr Val Ala Ser Ser
                130                 135                 140
Asn Val Thr Gln Ile Asn Leu His Val Ser Lys Tyr Cys Ser Leu Phe
145                 150                 155                 160
Pro Ile Asn Ser Ile Ile Arg Gly Leu Phe Phe Thr Leu Ser Leu Phe
                165                 170                 175
Arg Asp Val Phe Leu Lys Gln Ile Met Leu Phe Ser Ser Val Tyr Met
                180                 185                 190
Met Thr Leu Ile Gln Glu Leu Gln Glu Ile Leu Val Pro Ser Gln Pro
                195                 200                 205
Gln Pro Leu Pro Lys Asp Leu Cys Arg Gly Lys Ser His Gln His Ile
                210                 215                 220
Leu Leu Pro Val Ser Phe Ser Val Gly Met Tyr Lys Met Asp Phe Ile
225                 230                 235                 240
Ile Ser Thr Ser Ser Thr Leu Pro Trp Ala Tyr Asp Arg Gly Val
                245                 250                 255
```

<210> SEQ ID NO 58
<211> LENGTH: 17
<212> TYPE: PRT
<213> ORGANISM: Homo sapiens

<400> SEQUENCE: 58

```
Val Leu Ala Ser Gln Pro Thr Leu Cys Ser Phe Phe Ser Ala Ser Ser
 1               5                  10                  15
Pro
```

<210> SEQ ID NO 59
<211> LENGTH: 19
<212> TYPE: PRT
<213> ORGANISM: Homo sapiens

<400> SEQUENCE: 59

```
Leu Val Leu Ala Ser Gln Pro Thr Leu Cys Ser Phe Phe Ser Ala Ser
 1               5                  10                  15
Ser Pro Phe
```

<210> SEQ ID NO 60
<211> LENGTH: 17
<212> TYPE: PRT
<213> ORGANISM: Homo sapiens

<400> SEQUENCE: 60

```
Phe Tyr Leu Arg Arg Val Ile Arg Asp Leu Ser Ile Cys Thr Thr Cys
```

```
<210> SEQ ID NO 61
<211> LENGTH: 19
<212> TYPE: PRT
<213> ORGANISM: Homo sapiens

<400> SEQUENCE: 61

Ser Phe Tyr Leu Arg Arg Val Ile Arg Asp Leu Ser Ile Cys Thr Thr
1               5                   10                  15

Cys Leu Leu

<210> SEQ ID NO 62
<211> LENGTH: 17
<212> TYPE: PRT
<213> ORGANISM: Homo sapiens

<400> SEQUENCE: 62

Ser Ile Cys Thr Thr Cys Leu Leu Asp Met Leu Gln Val Val Asn Ile
1               5                   10                  15

Ser

<210> SEQ ID NO 63
<211> LENGTH: 19
<212> TYPE: PRT
<213> ORGANISM: Homo sapiens

<400> SEQUENCE: 63

Leu Ser Ile Cys Thr Thr Cys Leu Leu Asp Met Leu Gln Val Val Asn
1               5                   10                  15

Ile Ser Pro

<210> SEQ ID NO 64
<211> LENGTH: 16
<212> TYPE: PRT
<213> ORGANISM: Homo sapiens

<400> SEQUENCE: 64

Ile Ser Pro Ser Ile Ser Trp Leu Ile Met Leu Phe Ser Ser Val Tyr
1               5                   10                  15

<210> SEQ ID NO 65
<211> LENGTH: 18
<212> TYPE: PRT
<213> ORGANISM: Homo sapiens

<400> SEQUENCE: 65

Asn Ile Ser Pro Ser Ile Ser Trp Leu Ile Met Leu Phe Ser Ser Val
1               5                   10                  15

Tyr Met

<210> SEQ ID NO 66
<211> LENGTH: 28
<212> TYPE: PRT
<213> ORGANISM: Homo sapiens

<400> SEQUENCE: 66

Met Leu Gln Val Val Asn Ile Ser Pro Ser Ile Ser Trp Leu Ile Met
1               5                   10                  15

Leu Phe Ser Ser Val Tyr Met Met Thr Leu Ile Gln
```

<210> SEQ ID NO 67
<211> LENGTH: 1121
<212> TYPE: PRT
<213> ORGANISM: Homo sapiens

<400> SEQUENCE: 67

```
Ser His Gln His Ile Leu Leu Pro Thr Gln Ala Thr Phe Ala Ala Ala
  1               5                  10                  15

Thr Gly Leu Trp Ala Ala Leu Thr Thr Val Ser Asn Pro Ser Arg Ala
                 20                  25                  30

Asp Pro Val Thr Trp Arg Lys Glu Pro Ala Val Leu Pro Cys Cys Asn
             35                  40                  45

Leu Glu Lys Gly Ser Trp Leu Ser Phe Pro Gly Thr Ala Ala Arg Lys
         50                  55                  60

Glu Phe Ser Thr Thr Leu Thr Gly His Ser Ala Leu Ser Leu Ser Ser
 65                  70                  75                  80

Ser Arg Ala Leu Pro Gly Ser Leu Pro Ala Phe Ala Asp Leu Pro Arg
                 85                  90                  95

Ser Cys Pro Glu Ser Glu Gln Ser Ala Thr Pro Ala Gly Ala Phe Leu
            100                 105                 110

Leu Gly Trp Glu Arg Val Val Gln Arg Leu Glu Val Pro Arg Pro
        115                 120                 125

Gln Ala Ala Pro Ala Thr Ser Ala Thr Pro Ser Arg Asp Pro Ser Pro
130                 135                 140

Pro Cys His Gln Arg Arg Asp Ala Ala Cys Leu Arg Ala Gln Gly Leu
145                 150                 155                 160

Thr Arg Ala Phe Gln Val Val His Leu Ala Pro Thr Ala Pro Asp Gly
                165                 170                 175

Gly Ala Gly Cys Pro Pro Ser Arg Asn Ser Tyr Arg Leu Thr His Val
            180                 185                 190

Arg Cys Ala Gln Gly Leu Glu Ala Ala Ser Ala Asn Leu Pro Gly Ala
        195                 200                 205

Pro Gly Arg Ser Ser Ser Cys Ala Leu Arg Tyr Arg Ser Gly Pro Ser
    210                 215                 220

Val Ser Ser Ala Pro Ser Pro Ala Glu Pro Pro Ala His Gln Arg Leu
225                 230                 235                 240

Leu Phe Leu Pro Arg Ala Pro Gln Ala Val Ser Gly Pro Gln Glu Gln
                245                 250                 255

Pro Ser Glu Glu Ala Leu Gly Val Gly Ser Leu Ser Val Phe Gln Leu
            260                 265                 270

His Leu Ile Gln Cys Ile Pro Asn Leu Ser Tyr Pro Leu Val Leu Arg
        275                 280                 285

His Ile Pro Glu Ile Leu Lys Phe Ser Glu Lys Glu Thr Gly Gly Gly
    290                 295                 300

Ile Leu Gly Leu Glu Leu Pro Ala Thr Ala Ala Arg Leu Ser Gly Leu
305                 310                 315                 320

Asn Ser Ile Met Gln Ile Lys Glu Phe Glu Glu Leu Val Lys Leu His
                325                 330                 335

Ser Leu Ser His Lys Val Ile Gln Cys Val Phe Ala Lys Lys Lys Asn
            340                 345                 350

Val Asp Lys Trp Asp Asp Phe Cys Leu Ser Glu Gly Tyr Gly His Ser
        355                 360                 365
```

-continued

Phe Leu Ile Met Lys Glu Thr Ser Thr Lys Ile Ser Gly Leu Ile Gln
        370                 375                 380

Glu Met Gly Ser Gly Lys Ser Asn Val Gly Thr Trp Gly Asp Tyr Asp
385                 390                 395                 400

Asp Ser Ala Phe Met Glu Pro Arg Tyr His Val Arg Arg Glu Asp Leu
                405                 410                 415

Asp Lys Leu His Arg Ala Ala Trp Trp Gly Lys Val Pro Arg Lys Asp
            420                 425                 430

Leu Ile Val Met Leu Arg Asp Thr Asp Met Asn Lys Arg Asp Lys Gln
            435                 440                 445

Lys Arg Thr Ala Leu His Leu Ala Ser Ala Asn Gly Asn Ser Glu Val
450                 455                 460

Val Gln Leu Leu Leu Asp Arg Arg Cys Gln Leu Asn Val Leu Asp Asn
465                 470                 475                 480

Lys Lys Arg Thr Ala Leu Ile Lys Ala Val Gln Cys Gln Glu Asp Glu
                485                 490                 495

Cys Val Leu Met Leu Leu Glu His Gly Ala Asp Gly Asn Ile Gln Asp
                500                 505                 510

Glu Tyr Gly Asn Thr Ala Leu His Tyr Ala Ile Tyr Asn Glu Asp Lys
            515                 520                 525

Leu Met Ala Lys Ala Leu Leu Leu Tyr Gly Ala Asp Ile Glu Ser Lys
530                 535                 540

Asn Lys Cys Gly Leu Thr Pro Leu Leu Leu Gly Val His Glu Gln Lys
545                 550                 555                 560

Gln Glu Val Val Lys Phe Leu Ile Lys Lys Ala Asn Leu Asn Ala
                565                 570                 575

Leu Asp Arg Tyr Gly Arg Thr Ala Leu Ile Leu Ala Val Cys Cys Gly
            580                 585                 590

Ser Ala Ser Ile Val Asn Leu Leu Leu Glu Gln Asn Val Asp Val Ser
            595                 600                 605

Ser Gln Asp Leu Ser Gly Gln Thr Ala Arg Glu Tyr Ala Val Ser Ser
            610                 615                 620

His His His Val Ile Cys Glu Leu Leu Ser Asp Tyr Lys Glu Lys Gln
625                 630                 635                 640

Met Leu Lys Ile Ser Ser Glu Asn Ser Asn Pro Val Ile Thr Ile Leu
                645                 650                 655

Asn Ile Lys Leu Pro Leu Lys Val Glu Glu Glu Ile Lys Lys His Gly
                660                 665                 670

Ser Asn Pro Val Gly Leu Pro Glu Asn Leu Thr Asn Gly Ala Ser Ala
        675                 680                 685

Gly Asn Gly Asp Asp Gly Leu Ile Pro Gln Arg Lys Ser Arg Lys Pro
        690                 695                 700

Glu Asn Gln Gln Phe Pro Asp Thr Glu Asn Glu Glu Tyr His Ser Asp
705                 710                 715                 720

Glu Gln Asn Asp Thr Gln Lys Gln Leu Ser Glu Glu Gln Asn Thr Gly
                725                 730                 735

Ile Ser Gln Asp Glu Ile Leu Thr Asn Lys Gln Lys Gln Ile Glu Val
                740                 745                 750

Ala Glu Lys Glu Met Asn Ser Glu Leu Ser Leu Ser His Lys Lys Glu
            755                 760                 765

Glu Asp Leu Leu Arg Glu Asn Ser Met Leu Arg Glu Glu Ile Ala Lys
        770                 775                 780

Leu Arg Leu Glu Leu Asp Glu Thr Lys His Gln Asn Gln Leu Arg Glu

```
            785                 790                 795                 800

Asn Lys Ile Leu Glu Glu Ile Glu Ser Val Lys Glu Lys Leu Leu Lys
                805                 810                 815

Thr Ile Gln Leu Asn Glu Glu Ala Leu Thr Lys Thr Lys Val Ala Gly
            820                 825                 830

Phe Ser Leu Arg Gln Leu Gly Leu Ala Gln His Ala Gln Ala Ser Val
        835                 840                 845

Gln Gln Leu Cys Tyr Lys Trp Asn His Thr Glu Lys Thr Glu Gln Gln
    850                 855                 860

Ala Gln Glu Gln Glu Val Ala Gly Phe Ser Leu Arg Gln Leu Gly Leu
865                 870                 875                 880

Ala Gln His Ala Gln Ala Ser Val Gln Gln Leu Cys Tyr Lys Trp Gly
                885                 890                 895

His Thr Glu Lys Thr Glu Gln Gln Ala Gln Glu Gln Gly Ala Ala Leu
            900                 905                 910

Arg Ser Gln Ile Gly Asp Pro Gly Gly Val Pro Leu Ser Glu Gly Gly
        915                 920                 925

Thr Ala Ala Gly Asp Gln Gly Pro Gly Thr His Leu Pro Pro Arg Glu
    930                 935                 940

Pro Arg Ala Ser Pro Gly Thr Pro Ser Leu Val Arg Leu Ala Ser Gly
945                 950                 955                 960

Ala Arg Ala Ala Leu Pro Pro Pro Thr Gly Lys Asn Gly Arg Ser
                965                 970                 975

Pro Thr Lys Gln Lys Ser Val Cys Asp Ser Ser Gly Trp Ile Leu Pro
            980                 985                 990

Val Pro Thr Phe Ser Ser Gly Ser Phe Leu Gly Arg Arg Cys Pro Met
        995                 1000                1005

Phe Asp Val Ser Pro Ala Met Arg Leu Lys Ser Asp Ser Asn Arg Glu
    1010                1015                1020

Thr His Gln Ala Phe Arg Asp Lys Asp Leu Pro Phe Phe Lys Thr
1025                1030                1035                1040

Gln Gln Ser Pro Arg His Thr Lys Asp Leu Gly Gln Asp Asp Arg Ala
                1045                1050                1055

Gly Val Leu Ala Pro Lys Cys Arg Pro Gly Thr Leu Cys His Thr Asp
            1060                1065                1070

Thr Pro Pro His Arg Asn Ala Asp Thr Pro His Arg His Thr Thr
        1075                1080                1085

Thr Leu Pro His Arg Asp Thr Thr Thr Ser Leu Pro His Phe His Val
    1090                1095                1100

Ser Ala Gly Gly Val Gly Pro Thr Thr Leu Gly Ser Asn Arg Glu Ile
1105                1110                1115                1120

Thr

<210> SEQ ID NO 68
<211> LENGTH: 1122
<212> TYPE: PRT
<213> ORGANISM: Homo sapiens

<400> SEQUENCE: 68

Lys Ser His Gln His Ile Leu Leu Pro Thr Gln Ala Thr Phe Ala Ala
 1               5                  10                  15

Ala Thr Gly Leu Trp Ala Ala Leu Thr Thr Val Ser Asn Pro Ser Arg
            20                  25                  30

Ala Asp Pro Val Thr Trp Arg Lys Glu Pro Ala Val Leu Pro Cys Cys
```

-continued

```
                35                  40                  45
Asn Leu Glu Lys Gly Ser Trp Leu Ser Phe Pro Gly Thr Ala Ala Arg
 50                  55                  60

Lys Glu Phe Ser Thr Thr Leu Thr Gly His Ser Ala Leu Ser Leu Ser
 65                  70                  75                  80

Ser Ser Arg Ala Leu Pro Gly Ser Leu Pro Ala Phe Ala Asp Leu Pro
                 85                  90                  95

Arg Ser Cys Pro Glu Ser Glu Gln Ser Ala Thr Pro Ala Gly Ala Phe
                100                 105                 110

Leu Leu Gly Trp Glu Arg Val Val Gln Arg Arg Leu Glu Val Pro Arg
                115                 120                 125

Pro Gln Ala Ala Pro Ala Thr Ser Ala Thr Pro Ser Arg Asp Pro Ser
130                 135                 140

Pro Pro Cys His Gln Arg Arg Asp Ala Ala Cys Leu Arg Ala Gln Gly
145                 150                 155                 160

Leu Thr Arg Ala Phe Gln Val Val His Leu Ala Pro Thr Ala Pro Asp
                165                 170                 175

Gly Gly Ala Gly Cys Pro Pro Ser Arg Asn Ser Tyr Arg Leu Thr His
                180                 185                 190

Val Arg Cys Ala Gln Gly Leu Glu Ala Ala Ser Ala Asn Leu Pro Gly
                195                 200                 205

Ala Pro Gly Arg Ser Ser Cys Ala Leu Arg Tyr Arg Ser Gly Pro
210                 215                 220

Ser Val Ser Ser Ala Pro Ser Pro Ala Glu Pro Pro Ala His Gln Arg
225                 230                 235                 240

Leu Leu Phe Leu Pro Arg Ala Pro Gln Ala Val Ser Gly Pro Gln Glu
                245                 250                 255

Gln Pro Ser Glu Glu Ala Leu Gly Val Gly Ser Leu Ser Val Phe Gln
                260                 265                 270

Leu His Leu Ile Gln Cys Ile Pro Asn Leu Ser Tyr Pro Leu Val Leu
                275                 280                 285

Arg His Ile Pro Glu Ile Leu Lys Phe Ser Glu Lys Glu Thr Gly Gly
                290                 295                 300

Gly Ile Leu Gly Leu Glu Leu Pro Ala Thr Ala Ala Arg Leu Ser Gly
305                 310                 315                 320

Leu Asn Ser Ile Met Gln Ile Lys Glu Phe Glu Leu Val Lys Leu
                325                 330                 335

His Ser Leu Ser His Lys Val Ile Gln Cys Val Phe Ala Lys Lys Lys
                340                 345                 350

Asn Val Asp Lys Trp Asp Asp Phe Cys Leu Ser Glu Gly Tyr Gly His
                355                 360                 365

Ser Phe Leu Ile Met Lys Glu Thr Ser Thr Lys Ile Ser Gly Leu Ile
                370                 375                 380

Gln Glu Met Gly Ser Gly Lys Ser Asn Val Gly Thr Trp Gly Asp Tyr
385                 390                 395                 400

Asp Asp Ser Ala Phe Met Glu Pro Arg Tyr His Val Arg Arg Glu Asp
                405                 410                 415

Leu Asp Lys Leu His Arg Ala Ala Trp Trp Gly Lys Val Pro Arg Lys
                420                 425                 430

Asp Leu Ile Val Met Leu Arg Asp Thr Asp Met Asn Lys Arg Asp Lys
                435                 440                 445

Gln Lys Arg Thr Ala Leu His Leu Ala Ser Ala Asn Gly Asn Ser Glu
450                 455                 460
```

```
Val Val Gln Leu Leu Leu Asp Arg Arg Cys Gln Leu Asn Val Leu Asp
465                 470                 475                 480

Asn Lys Lys Arg Thr Ala Leu Ile Lys Ala Val Gln Cys Gln Glu Asp
                485                 490                 495

Glu Cys Val Leu Met Leu Leu Glu His Gly Ala Asp Gly Asn Ile Gln
                500                 505                 510

Asp Glu Tyr Gly Asn Thr Ala Leu His Tyr Ala Ile Tyr Asn Glu Asp
                515                 520                 525

Lys Leu Met Ala Lys Ala Leu Leu Leu Tyr Gly Ala Asp Ile Glu Ser
530                 535                 540

Lys Asn Lys Cys Gly Leu Thr Pro Leu Leu Leu Gly Val His Glu Gln
545                 550                 555                 560

Lys Gln Glu Val Val Lys Phe Leu Ile Lys Lys Ala Asn Leu Asn
                565                 570                 575

Ala Leu Asp Arg Tyr Gly Arg Thr Ala Leu Ile Leu Ala Val Cys Cys
                580                 585                 590

Gly Ser Ala Ser Ile Val Asn Leu Leu Leu Glu Gln Asn Val Asp Val
                595                 600                 605

Ser Ser Gln Asp Leu Ser Gly Gln Thr Ala Arg Glu Tyr Ala Val Ser
610                 615                 620

Ser His His His Val Ile Cys Glu Leu Leu Ser Asp Tyr Lys Glu Lys
625                 630                 635                 640

Gln Met Leu Lys Ile Ser Ser Glu Asn Ser Asn Pro Val Ile Thr Ile
                645                 650                 655

Leu Asn Ile Lys Leu Pro Leu Lys Val Glu Glu Ile Lys Lys His
                660                 665                 670

Gly Ser Asn Pro Val Gly Leu Pro Glu Asn Leu Thr Asn Gly Ala Ser
                675                 680                 685

Ala Gly Asn Gly Asp Asp Gly Leu Ile Pro Gln Arg Lys Ser Arg Lys
                690                 695                 700

Pro Glu Asn Gln Gln Phe Pro Asp Thr Glu Asn Glu Glu Tyr His Ser
705                 710                 715                 720

Asp Glu Gln Asn Asp Thr Gln Lys Gln Leu Ser Glu Glu Gln Asn Thr
                725                 730                 735

Gly Ile Ser Gln Asp Glu Ile Leu Thr Asn Lys Gln Lys Gln Ile Glu
                740                 745                 750

Val Ala Glu Lys Glu Met Asn Ser Glu Leu Ser Leu Ser His Lys Lys
                755                 760                 765

Glu Glu Asp Leu Leu Arg Glu Asn Ser Met Leu Arg Glu Glu Ile Ala
770                 775                 780

Lys Leu Arg Leu Glu Leu Asp Glu Thr Lys His Gln Asn Gln Leu Arg
785                 790                 795                 800

Glu Asn Lys Ile Leu Glu Glu Ile Glu Ser Val Lys Glu Lys Leu Leu
                805                 810                 815

Lys Thr Ile Gln Leu Asn Glu Glu Ala Leu Thr Lys Thr Lys Val Ala
                820                 825                 830

Gly Phe Ser Leu Arg Gln Leu Gly Leu Ala Gln His Ala Gln Ala Ser
                835                 840                 845

Val Gln Gln Leu Cys Tyr Lys Trp Asn His Thr Glu Lys Thr Glu Gln
                850                 855                 860

Gln Ala Gln Glu Gln Glu Val Ala Gly Phe Ser Leu Arg Gln Leu Gly
865                 870                 875                 880
```

-continued

```
Leu Ala Gln His Ala Gln Ala Ser Val Gln Gln Leu Cys Tyr Lys Trp
            885                 890                 895

Gly His Thr Glu Lys Thr Glu Gln Gln Ala Gln Glu Gln Gly Ala Ala
            900                 905                 910

Leu Arg Ser Gln Ile Gly Asp Pro Gly Gly Val Pro Leu Ser Glu Gly
            915                 920                 925

Gly Thr Ala Ala Gly Asp Gln Gly Pro Gly Thr His Leu Pro Pro Arg
    930                 935                 940

Glu Pro Arg Ala Ser Pro Gly Thr Pro Ser Leu Val Arg Leu Ala Ser
945                 950                 955                 960

Gly Ala Arg Ala Ala Leu Pro Pro Thr Gly Lys Asn Gly Arg
                965                 970                 975

Ser Pro Thr Lys Gln Lys Ser Val Cys Asp Ser Ser Gly Trp Ile Leu
            980                 985                 990

Pro Val Pro Thr Phe Ser Ser Gly Ser Phe Leu Gly Arg Arg Cys Pro
            995                 1000                1005

Met Phe Asp Val Ser Pro Ala Met Arg Leu Lys Ser Asp Ser Asn Arg
            1010                1015                1020

Glu Thr His Gln Ala Phe Arg Asp Lys Asp Leu Pro Phe Phe Lys
1025                1030                1035                1040

Thr Gln Gln Ser Pro Arg His Thr Lys Asp Leu Gly Gln Asp Asp Arg
            1045                1050                1055

Ala Gly Val Leu Ala Pro Lys Cys Arg Pro Gly Thr Leu Cys His Thr
            1060                1065                1070

Asp Thr Pro Pro His Arg Asn Ala Asp Thr Pro His Arg His Thr
            1075                1080                1085

Thr Thr Leu Pro His Arg Asp Thr Thr Thr Ser Leu Pro His Phe His
            1090                1095                1100

Val Ser Ala Gly Gly Val Gly Pro Thr Thr Leu Gly Ser Asn Arg Glu
1105                1110                1115                1120

Ile Thr

<210> SEQ ID NO 69
<211> LENGTH: 1127
<212> TYPE: PRT
<213> ORGANISM: Homo sapiens

<400> SEQUENCE: 69

Asp Leu Cys Arg Gly Lys Ser His Gln His Ile Leu Leu Pro Thr Gln
1               5                   10                  15

Ala Thr Phe Ala Ala Ala Thr Gly Leu Trp Ala Ala Leu Thr Thr Val
            20                  25                  30

Ser Asn Pro Ser Arg Ala Asp Pro Val Thr Trp Arg Lys Glu Pro Ala
            35                  40                  45

Val Leu Pro Cys Cys Asn Leu Glu Lys Gly Ser Trp Leu Ser Phe Pro
            50                  55                  60

Gly Thr Ala Ala Arg Lys Glu Phe Ser Thr Thr Leu Thr Gly His Ser
65                  70                  75                  80

Ala Leu Ser Leu Ser Ser Ser Arg Ala Leu Pro Gly Ser Leu Pro Ala
            85                  90                  95

Phe Ala Asp Leu Pro Arg Ser Cys Pro Glu Ser Glu Gln Ser Ala Thr
            100                 105                 110

Pro Ala Gly Ala Phe Leu Leu Gly Trp Glu Arg Val Val Gln Arg Arg
            115                 120                 125
```

-continued

```
Leu Glu Val Pro Arg Pro Gln Ala Ala Pro Ala Thr Ser Ala Thr Pro
    130                 135                 140

Ser Arg Asp Pro Ser Pro Pro Cys His Gln Arg Arg Asp Ala Ala Cys
145                 150                 155                 160

Leu Arg Ala Gln Gly Leu Thr Arg Ala Phe Gln Val Val His Leu Ala
                165                 170                 175

Pro Thr Ala Pro Asp Gly Gly Ala Gly Cys Pro Pro Ser Arg Asn Ser
            180                 185                 190

Tyr Arg Leu Thr His Val Arg Cys Ala Gln Gly Leu Glu Ala Ala Ser
        195                 200                 205

Ala Asn Leu Pro Gly Ala Pro Gly Arg Ser Ser Cys Ala Leu Arg
    210                 215                 220

Tyr Arg Ser Gly Pro Ser Val Ser Ser Ala Pro Ser Pro Ala Glu Pro
225                 230                 235                 240

Pro Ala His Gln Arg Leu Leu Phe Leu Pro Arg Ala Pro Gln Ala Val
                245                 250                 255

Ser Gly Pro Gln Glu Gln Pro Ser Glu Glu Ala Leu Gly Val Gly Ser
            260                 265                 270

Leu Ser Val Phe Gln Leu His Leu Ile Gln Cys Ile Pro Asn Leu Ser
        275                 280                 285

Tyr Pro Leu Val Leu Arg His Ile Pro Glu Ile Leu Lys Phe Ser Glu
    290                 295                 300

Lys Glu Thr Gly Gly Gly Ile Leu Gly Leu Glu Leu Pro Ala Thr Ala
305                 310                 315                 320

Ala Arg Leu Ser Gly Leu Asn Ser Ile Met Gln Ile Lys Glu Phe Glu
                325                 330                 335

Glu Leu Val Lys Leu His Ser Leu Ser His Lys Val Ile Gln Cys Val
            340                 345                 350

Phe Ala Lys Lys Lys Asn Val Asp Lys Trp Asp Asp Phe Cys Leu Ser
        355                 360                 365

Glu Gly Tyr Gly His Ser Phe Leu Ile Met Lys Glu Thr Ser Thr Lys
    370                 375                 380

Ile Ser Gly Leu Ile Gln Glu Met Gly Ser Gly Lys Ser Asn Val Gly
385                 390                 395                 400

Thr Trp Gly Asp Tyr Asp Asp Ser Ala Phe Met Glu Pro Arg Tyr His
                405                 410                 415

Val Arg Arg Glu Asp Leu Asp Lys Leu His Arg Ala Ala Trp Trp Gly
            420                 425                 430

Lys Val Pro Arg Lys Asp Leu Ile Val Met Leu Arg Asp Thr Asp Met
        435                 440                 445

Asn Lys Arg Asp Lys Gln Lys Arg Thr Ala Leu His Leu Ala Ser Ala
    450                 455                 460

Asn Gly Asn Ser Glu Val Val Gln Leu Leu Leu Asp Arg Arg Cys Gln
465                 470                 475                 480

Leu Asn Val Leu Asp Asn Lys Lys Arg Thr Ala Leu Ile Lys Ala Val
                485                 490                 495

Gln Cys Gln Glu Asp Glu Cys Val Leu Met Leu Leu Glu His Gly Ala
            500                 505                 510

Asp Gly Asn Ile Gln Asp Glu Tyr Gly Asn Thr Ala Leu His Tyr Ala
        515                 520                 525

Ile Tyr Asn Glu Asp Lys Leu Met Ala Lys Ala Leu Leu Leu Tyr Gly
    530                 535                 540

Ala Asp Ile Glu Ser Lys Asn Lys Cys Gly Leu Thr Pro Leu Leu Leu
```

-continued

```
            545                 550                 555                 560
        Gly Val His Glu Gln Lys Gln Glu Val Val Lys Phe Leu Ile Lys Lys
                        565                 570                 575
        Lys Ala Asn Leu Asn Ala Leu Asp Arg Tyr Gly Arg Thr Ala Leu Ile
                    580                 585                 590
        Leu Ala Val Cys Cys Gly Ser Ala Ser Ile Val Asn Leu Leu Leu Glu
                    595                 600                 605
        Gln Asn Val Asp Val Ser Ser Gln Asp Leu Ser Gly Gln Thr Ala Arg
                    610                 615                 620
        Glu Tyr Ala Val Ser Ser His His Val Ile Cys Glu Leu Leu Ser
        625                 630                 635                 640
        Asp Tyr Lys Glu Lys Gln Met Leu Lys Ile Ser Ser Glu Asn Ser Asn
                        645                 650                 655
        Pro Val Ile Thr Ile Leu Asn Ile Lys Leu Pro Leu Lys Val Glu Glu
                    660                 665                 670
        Glu Ile Lys Lys His Gly Ser Asn Pro Val Gly Leu Pro Glu Asn Leu
                    675                 680                 685
        Thr Asn Gly Ala Ser Ala Gly Asn Gly Asp Asp Gly Leu Ile Pro Gln
                690                 695                 700
        Arg Lys Ser Arg Lys Pro Glu Asn Gln Gln Phe Pro Asp Thr Glu Asn
        705                 710                 715                 720
        Glu Glu Tyr His Ser Asp Gln Asn Asp Thr Gln Lys Gln Leu Ser
                        725                 730                 735
        Glu Glu Gln Asn Thr Gly Ile Ser Gln Asp Glu Ile Leu Thr Asn Lys
                    740                 745                 750
        Gln Lys Gln Ile Glu Val Ala Glu Lys Glu Met Asn Ser Glu Leu Ser
                    755                 760                 765
        Leu Ser His Lys Lys Glu Glu Asp Leu Leu Arg Glu Asn Ser Met Leu
                    770                 775                 780
        Arg Glu Glu Ile Ala Lys Leu Arg Leu Glu Leu Asp Glu Thr Lys His
        785                 790                 795                 800
        Gln Asn Gln Leu Arg Glu Asn Lys Ile Leu Glu Glu Ile Glu Ser Val
                        805                 810                 815
        Lys Glu Lys Leu Leu Lys Thr Ile Gln Leu Asn Glu Glu Ala Leu Thr
                    820                 825                 830
        Lys Thr Lys Val Ala Gly Phe Ser Leu Arg Gln Leu Gly Leu Ala Gln
                    835                 840                 845
        His Ala Gln Ala Ser Val Gln Gln Leu Cys Tyr Lys Trp Asn His Thr
                    850                 855                 860
        Glu Lys Thr Glu Gln Gln Ala Gln Glu Gln Val Ala Gly Phe Ser
        865                 870                 875                 880
        Leu Arg Gln Leu Gly Leu Ala Gln His Ala Gln Ala Ser Val Gln Gln
                        885                 890                 895
        Leu Cys Tyr Lys Trp Gly His Thr Glu Lys Thr Glu Gln Gln Ala Gln
                    900                 905                 910
        Glu Gln Gly Ala Ala Leu Arg Ser Gln Ile Gly Asp Pro Gly Gly Val
                    915                 920                 925
        Pro Leu Ser Glu Gly Gly Thr Ala Ala Gly Asp Gln Gly Pro Gly Thr
                    930                 935                 940
        His Leu Pro Pro Arg Glu Pro Arg Ala Ser Pro Gly Thr Pro Ser Leu
        945                 950                 955                 960
        Val Arg Leu Ala Ser Gly Ala Arg Ala Ala Ala Leu Pro Pro Pro Thr
                        965                 970                 975
```

-continued

```
Gly Lys Asn Gly Arg Ser Pro Thr Lys Gln Lys Ser Val Cys Asp Ser
                980                 985                 990
Ser Gly Trp Ile Leu Pro Val Pro Thr Phe Ser Gly Ser Phe Leu
            995                 1000                1005
Gly Arg Arg Cys Pro Met Phe Asp Val Ser Pro Ala Met Arg Leu Lys
        1010                1015                1020
Ser Asp Ser Asn Arg Glu Thr His Gln Ala Phe Arg Asp Lys Asp Asp
1025                1030                1035                1040
Leu Pro Phe Phe Lys Thr Gln Gln Ser Pro Arg His Thr Lys Asp Leu
            1045                1050                1055
Gly Gln Asp Asp Arg Ala Gly Val Leu Ala Pro Lys Cys Arg Pro Gly
        1060                1065                1070
Thr Leu Cys His Thr Asp Thr Pro Pro His Arg Asn Ala Asp Thr Pro
            1075                1080                1085
Pro His Arg His Thr Thr Thr Leu Pro His Arg Asp Thr Thr Thr Ser
        1090                1095                1100
Leu Pro His Phe His Val Ser Ala Gly Gly Val Gly Pro Thr Thr Leu
1105                1110                1115                1120
Gly Ser Asn Arg Glu Ile Thr
            1125

<210> SEQ ID NO 70
<211> LENGTH: 4522
<212> TYPE: DNA
<213> ORGANISM: Homo sapiens

<400> SEQUENCE: 70 gtttttttt  ttttttttt  tttttttttt  tattttaagg  gattcgttta  ataggacttg       60
tggtaagtgg  aataatgcca  tgcaaaggtc  cccatgtcta  accaccaggt  tctaggcatg     120
tattatggta  tatgagaaat  gggaattcag  gctgcagatg  aaatcaaggt  tgataaccag     180
ctgactctaa  aacaaaaaca  ttaacttgaa  ttacagattt  gggcctaatg  taattataag     240
cattcttaaa  agtgaaagaa  ataataagag  aaactgagtg  ctgtgatgtg  agtcagttaa     300
acttttttt  caacttttc  tttaggtgat  tatttccct  taacataaaa  tttactttag        360
ctcaactata  caaacatgtg  agttattgtt  atgtaaccat  cactcttcat  taagaaatgc     420
tttgtaaaaa  gtgagccagt  ttttcatata  cattcttcaa  aatacattct  caacattata     480
catcaaatta  tatatacata  catgcacaca  tacactatat  atatcaagga  tttatatgag    540
aggattaatt  aagaaaaaaa  ttagtggaat  aaaaataatg  tttatgataa  ttttggccat     600
agaatatata  atacagatga  tgtgaagtac  aaaatgtttt  ttatacttca  tattttgatg    660
tacaaagtat  gtttgtcttt  gtaattcaga  tgattacttt  gcacttgtgt  tcccatgaaa     720
aatgcctttc  atttctaagc  tggtattggc  atctcagcca  acacttttct  ccttctttc     780
tgcgtcttct  cctttttctgc  tttttctgga  tctcaggcca  gagcgcactt  acctaccagt    840
ctgtcatgtg  gccctcatcc  acatggtggt  ccttctcacc  atggtgttct  tgtctccaca     900
gctctttgaa  tcactgaatt  ttcagaatga  cttcaaatat  gaggcatctt  tctacctgag    960
gagggtgatc  agggtcctct  ccatttgtac  cacctgcctc  ctggacatgc  tgcaggtcgt   1020
caacatcagc  cccagcattt  cctggttgat  aatgctgttc  tcaagtgtct  acatgatgac   1080
tctcattcag  gaactacagg  agatcctggt  accttcacag  ccccagcctc  tacctaagga   1140
tctttgcaga  ggcaagagcc  atcagcacat  cctgctgccg  actcaagcaa  cttttgctgc   1200
```

```
agcaactgga ctatgggctg cactaaccac cgtatcaaat ccaagcagag cagatcctgt    1260
gacctggaga aaggagccgg ctgtccttcc ctgctgtaac ctagagaaag gaagctggct    1320
gtccttccct ggcacagctg cacgcaagga attttccacc acgctcaccg ggcacagcgc    1380
gctgagcctc tccagttcgc gggccctccc cggctcgctc ccggctttcg cagacctccc    1440
ccgctcctgc cctgagtccg agcagagcgc aacgccagcc ggcgccttcc tcctgggctg    1500
ggagcgagtg gtgcagcggc ggctcgaagt cccccggcct caagcagccc ccgcgactag    1560
cgcgacaccc tcgcgggatc cgagtccacc ctgccaccag cgccgggacg ccgcgtgcct    1620
cagagcccaa gggctgaccc gggccttcca ggtggtccat ctcgctccta cggctcccga    1680
cggtggcgct gggtgtcccc catcccgcaa ttcctaccgg ctgacccatg tgcgctgcgc    1740
ccaggggctg gaggctgcca cgccaacct tcccggcgct ccggggcgga gcagctcctg    1800
cgccctgcgc taccgcagcg gcccttcagt cagctccgcg ccgtccccg cagagccccc    1860 ggcgcaccag cgcctgcttt tccttccccg agcgcctcaa gcagtctctg ggccgcagga    1920
acagccctct gaagaggcgc ttggtgtagg aagcctctca gttttccagt tacacctaat    1980
acagtgtatt ccaaatctaa gttacccact agtacttcgg cacattccag aaattctgaa    2040
attttctgaa aaggaaactg gtggtggaat tctaggctta gaattaccag cgacagctgc    2100
tcgcctctca ggattaaaca gcataatgca aatcaaagag tttgaagaat tggtaaaact    2160
tcacagcttg tcacacaaag tcattcagtg tgtgtttgca aagaaaaaaa atgtagacaa    2220
atgggatgac ttttgtctta gtgagggtta tggacattca ttcttaataa tgaaagaaac    2280
gtcgactaaa atatcaggtt taattcagga gatggggagc ggcaagagca acgtgggcac    2340
ttggggagac tacgacgaca gcgccttcat ggagccgagg taccacgtcc gtcgagaaga    2400
tctggacaag ctccacagag ctgcctggtg gggtaaagtc cccagaaagg atctcatcgt    2460
catgctcagg gacactgaca tgaacaagag ggacaagcaa aagaggactg ctctacattt    2520
ggcctctgcc aatggaaatt cagaagtagt acaactcctg ctggacagac gatgtcaact    2580
taacgtcctt gacaacaaaa aaaggacagc tctgataaag gccgtacaat gccaggaaga    2640
tgaatgtgtg ttaatgttgc tggaacatgg cgctgatgga atattcaag atgagtatgg    2700 aaataccgct ctacactatg ctatctacaa tgaagataaa ttaatggcca aagcactgct    2760
cttatatggt gctgatattg aatcaaaaaa caagtgtggc ctcacaccac tttgcttgg    2820 cgtacatgaa caaaaacagg aagtggtgaa atttttaatc aagaaaaaag ctaatttaaa    2880
tgcacttgat agatatggaa gaactgccct catacttgct gtatgttgtg gatcagcaag    2940
tatagtcaat cttctacttg agcaaaatgt tgatgtatct tctcaagatc tatctggaca    3000
gacggccaga gagtatgctg tttctagtca tcatcatgta atttgtgaat tactttctga    3060
ctataaagaa aaacagatgc taaaaatctc ttctgaaaac agcaatccag tgataaccat    3120
ccttaatatc aaacttccac tcaaggttga agaagaaata aagaagcatg gaagtaatcc    3180
tgtgggatta ccagaaaacc tgactaatgg tgccagtgct ggcaatggtg atgatggatt    3240
aattccacaa aggaagagca gaaaacctga aaatcagcaa tttcctgaca ctgagaatga    3300
agagtatcac agtgacgaac aaaatgatac ccagaaacaa ctttctgaag aacagaacac    3360
tggaatatca caagatgaga ttctgactaa taaacaaaag cagatagaag tggctgaaaa    3420
ggaaatgaat tctgagcttt ctcttagtca taagaaagaa gaagatctct tgcgtgaaaa    3480
cagcatgttg cggaagaaa ttgccaagct aagactggaa ctagatgaaa caaaacatca    3540
gaaccagcta agggaaaata aaattttgga ggaaattgaa agtgtaaaag aaaaacttct    3600
```

| | |
|---|---|
| aaagactata caactgaatg aagaagcatt aacgaaaacc aaggtggctg gtttctcttt | 3660 |
| gcgccagctt ggccttgccc agcatgcaca agcctcagtg caacagctgt gctacaaatg | 3720 |
| gaaccacaca gagaaaacag agcagcaggc tcaggagcag gaggtggctg gtttctcttt | 3780 |
| gcgccagctt ggccttgccc agcatgcaca agcctcagta caacaactgt gctacaaatg | 3840 |
| gggccacaca gagaaaacag agcagcaggc tcaggagcag ggagctgcgc tgaggtccca | 3900 |
| gataggcgac cctggcgggg tgcccctgag cgaagggggg acagcagcag gagaccaggg | 3960 |
| tccagggacc cacctcccac cgagggaacc tcgagcctcc cctggcaccc ctagcttggt | 4020 |
| ccgcctggcc tccggagccc gagctgctgc gcttccccca cccacaggga aaacggccg | 4080 |
| atctccaacc aaacagaaat ctgtgtgtga ctcctctggt tggatactgc cagtccccac | 4140 |
| attttcttcc gggagttttc ttggcagaag gtgcccaatg tttgatgttt cgccagccat | 4200 |
| gaggctgaaa agtgacagca atagagaaac acatcaggct ttccgcgaca agatgacct | 4260 |
| tcccttcttc aaaactcagc aatctccacg gcacacaaag gacttaggac aagatgaccg | 4320 |
| agctggagtg ctcgccccaa aatgcaggcc cggaacactc tgccacacgg acacaccacc | 4380 |
| acacagaaat gcggacacac caccacacag acacaccacc acgctgccac acagagacac | 4440 |
| caccacatcg ttgccacact ttcatgtgtc agctggcggt gtgggcccca cgactctggg | 4500 |
| ctctaataga gaaattactt ag | 4522 |

<210> SEQ ID NO 71
<211> LENGTH: 1180
<212> TYPE: DNA
<213> ORGANISM: Homo sapiens

<400> SEQUENCE: 71

| | |
|---|---|
| gtttttttt tttttttttt tttttttttt tattttaagg gattcgttta ataggacttg | 60 |
| tggtaagtgg aataatgcca tgcaaaggtc cccatgtcta accaccaggt tctaggcatg | 120 |
| tattatggta tatgagaaat gggaattcag gctgcagatg aaatcaaggt tgataaccag | 180 |
| ctgactctaa aacaaaaaca ttaacttgaa ttacagattt gggcctaatg taattataag | 240 |
| cattcttaaa agtgaaagaa ataataagag aaactgagtg ctgtgatgtg agtcagttaa | 300 |
| acttttttt caacttttc tttaggtgat tattttccct taacataaaa tttactttag | 360 |
| ctcaactata caaacatgtg agttattgtt atgtaaccat cactcttcat taagaaatgc | 420 |
| tttgtaaaaa gtgagccagt ttttcatata cattcttcaa aatacattct caacattata | 480 |
| catcaaatta tatatacata catgcacaca tacactatat atatcaagga tttatatgag | 540 |
| aggattaatt aagaaaaaaa ttagtggaat aaaaataatg tttatgataa ttttggccat | 600 |
| agaatatata atacagatga tgtgaagtac aaaatgtttt ttatacttca tattttgatg | 660 |
| tacaaagtat gtttgtcttt gtaattcaga tgattacttt gcacttgtgt tcccatgaaa | 720 |
| aatgcctttc atttctaagc tggtattggc atctcagcca acacttttct ccttctttc | 780 |
| tgcgtcttct ccttttctgc ttttttctgga tctcaggcca gagcgcactt acctaccagt | 840 |
| ctgtcatgtg gccctcatcc acatggtggt ccttctcacc atggtgttct tgtctccaca | 900 |
| gctctttgaa tcactgaatt ttcagaatga cttcaaatat gaggcatctt tctacctgag | 960 |
| gagggtgatc agggtcctct ccatttgtac cacctgcctc ctgggcatgc tgcaggtcgt | 1020 |
| caacatcagc cccagcattt cctggttgat aatgctgttc tcaagtgtct acatgatgac | 1080 |
| tctcattcag gaactacagg agatcctggt accttcacag ccccagcctc tacctaagga | 1140 |

```
tctttgcaga ggcaagagcc atcagcacat cctgctgccg            1180
```

<210> SEQ ID NO 72
<211> LENGTH: 1180
<212> TYPE: DNA
<213> ORGANISM: Homo sapiens

<400> SEQUENCE: 72

```
gttttttttt tttttttttt tttttttttt tattttaagg gattcgttta ataggacttg     60
tggtaagtgg aataatgcca tgcaaaggtc cccatgtcta accaccaggt tctaggcatg    120
tattatggta tatgagaaat gggaattcag gctgcagatg aaatcaaggt tgataaccag    180
ctgactctaa aacaaaaaca ttaacttgaa ttacagattt gggcctaatg taattataag    240
cattcttaaa agtgaaagaa ataataagag aaactgagtg ctgtgatgtg agtcagttaa    300
acttttttt caacttttc tttaggtgat tattttccct taacataaaa tttactttag    360
ctcaactata caaacatgtg agttattgtt atgtaaccat cactcttcat taagaaatgc    420
tttgtaaaaa gtgagccagt ttttcatata cattcttcaa aatacattct caacattata    480
catcaaatta tatatacata catgcacaca tacactatat atatcaagga tttatatgag    540
aggattaatt aagaaaaaaa ttagtggaat aaaaataatg tttatgataa ttttggccat    600
agaatatata atacagatga tgtgaagtac aaaatgtttt ttatacttca tattttgatg    660
tacaaagtat gtttgtcttt gtaattcaga tgattacttt gcacttgtgt tcccatgaaa    720
aatgcctttc atttctaagc tggtattggc atctcagcca acactttcct ccttctttc    780
tgcgtcttct ccttttctgc ttttctgga tctcaggcca gagcgcactt acctaccagt    840
ctgtcatgtg gccctcatcc acatggtggt ccttctcacc atggtgttct tgtctccaca    900
gctctttgaa tcactgaatt ttcagaatga cttcaaatat gaggcatctt tctacctgag    960
gagggtgatc agggtcctct ccatttgtac cacctgcctc ctggacatgc tgcaggtcgt   1020
caacatcagc cccagcattt cctggttgat aatgctgttc tcaagtgtct acatgatgac   1080
tctcattcag gaactacagg agatcctggt accttcacag ccccagcctc tacctaagga   1140
tctttgcaga ggcaagagcc atcagcacat cctgctgccg                         1180
```

<210> SEQ ID NO 73
<211> LENGTH: 1266
<212> TYPE: PRT
<213> ORGANISM: Homo sapiens

<400> SEQUENCE: 73

```
Met Pro Phe Ile Ser Lys Leu Val Leu Ala Ser Gln Pro Thr Leu Phe
 1               5                   10                  15

Ser Phe Phe Ser Ala Ser Ser Pro Phe Leu Leu Phe Leu Asp Leu Arg
            20                  25                  30

Pro Glu Arg Thr Tyr Leu Pro Val Cys His Val Ala Leu Ile His Met
        35                  40                  45

Val Val Leu Leu Thr Met Val Phe Leu Ser Pro Gln Leu Phe Glu Ser
    50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Asp Met
                85                  90                  95

Leu Gln Val Val Asn Ile Ser Pro Ser Ile Ser Trp Leu Ile Met Leu
            100                 105                 110
```

-continued

```
Phe Ser Ser Val Tyr Met Met Thr Leu Ile Gln Glu Leu Gln Glu Ile
        115                 120                 125

Leu Val Pro Ser Gln Pro Gln Pro Leu Pro Lys Asp Leu Cys Arg Gly
    130                 135                 140

Lys Ser His Gln His Ile Leu Leu Pro Thr Gln Ala Thr Phe Ala Ala
145                 150                 155                 160

Ala Thr Gly Leu Trp Ala Ala Leu Thr Thr Val Ser Asn Pro Ser Arg
                165                 170                 175

Ala Asp Pro Val Thr Trp Arg Lys Glu Pro Ala Val Leu Pro Cys Cys
            180                 185                 190

Asn Leu Glu Lys Gly Ser Trp Leu Ser Phe Pro Gly Thr Ala Ala Arg
        195                 200                 205

Lys Glu Phe Ser Thr Thr Leu Thr Gly His Ser Ala Leu Ser Leu Ser
    210                 215                 220

Ser Ser Arg Ala Leu Pro Gly Ser Leu Pro Ala Phe Ala Asp Leu Pro
225                 230                 235                 240

Arg Ser Cys Pro Glu Ser Gln Ser Ala Thr Pro Ala Gly Ala Phe
                245                 250                 255

Leu Leu Gly Trp Glu Arg Val Val Gln Arg Arg Leu Glu Val Pro Arg
                260                 265                 270

Pro Gln Ala Ala Pro Ala Thr Ser Ala Thr Pro Ser Arg Asp Pro Ser
        275                 280                 285

Pro Pro Cys His Gln Arg Arg Asp Ala Ala Cys Leu Arg Ala Gln Gly
        290                 295                 300

Leu Thr Arg Ala Phe Gln Val Val His Leu Ala Pro Thr Ala Pro Asp
305                 310                 315                 320

Gly Gly Ala Gly Cys Pro Pro Ser Arg Asn Ser Tyr Arg Leu Thr His
                325                 330                 335

Val Arg Cys Ala Gln Gly Leu Glu Ala Ala Ser Ala Asn Leu Pro Gly
            340                 345                 350

Ala Pro Gly Arg Ser Ser Cys Ala Leu Arg Tyr Arg Ser Gly Pro
        355                 360                 365

Ser Val Ser Ser Ala Pro Ser Pro Ala Glu Pro Ala His Gln Arg
    370                 375                 380

Leu Leu Phe Leu Pro Arg Ala Pro Gln Ala Val Ser Gly Pro Gln Glu
385                 390                 395                 400

Gln Pro Ser Glu Glu Ala Leu Gly Val Gly Ser Leu Ser Val Phe Gln
                405                 410                 415

Leu His Leu Ile Gln Cys Ile Pro Asn Leu Ser Tyr Pro Leu Val Leu
            420                 425                 430

Arg His Ile Pro Glu Ile Leu Lys Phe Ser Glu Lys Glu Thr Gly Gly
        435                 440                 445

Gly Ile Leu Gly Leu Glu Leu Pro Ala Thr Ala Arg Leu Ser Gly
    450                 455                 460

Leu Asn Ser Ile Met Gln Ile Lys Glu Phe Glu Leu Val Lys Leu
465                 470                 475                 480

His Ser Leu Ser His Lys Val Ile Gln Cys Val Phe Ala Lys Lys Lys
                485                 490                 495

Asn Val Asp Lys Trp Asp Asp Phe Cys Leu Ser Glu Gly Tyr Gly His
            500                 505                 510

Ser Phe Leu Ile Met Lys Glu Thr Ser Thr Lys Ile Ser Gly Leu Ile
        515                 520                 525

Gln Glu Met Gly Ser Gly Lys Ser Asn Val Gly Thr Trp Gly Asp Tyr
```

-continued

```
            530                 535                 540
Asp Asp Ser Ala Phe Met Glu Pro Arg Tyr His Val Arg Arg Glu Asp
545                 550                 555                 560

Leu Asp Lys Leu His Arg Ala Ala Trp Trp Gly Lys Val Pro Arg Lys
                565                 570                 575

Asp Leu Ile Val Met Leu Arg Asp Thr Asp Met Asn Lys Arg Asp Lys
                580                 585                 590

Gln Lys Arg Thr Ala Leu His Leu Ala Ser Ala Asn Gly Asn Ser Glu
            595                 600                 605

Val Val Gln Leu Leu Leu Asp Arg Arg Cys Gln Leu Asn Val Leu Asp
610                 615                 620

Asn Lys Lys Arg Thr Ala Leu Ile Lys Ala Val Gln Cys Gln Glu Asp
625                 630                 635                 640

Glu Cys Val Leu Met Leu Leu Glu His Gly Ala Asp Gly Asn Ile Gln
                645                 650                 655

Asp Glu Tyr Gly Asn Thr Ala Leu His Tyr Ala Ile Tyr Asn Glu Asp
                660                 665                 670

Lys Leu Met Ala Lys Ala Leu Leu Leu Tyr Gly Ala Asp Ile Glu Ser
            675                 680                 685

Lys Asn Lys Cys Gly Leu Thr Pro Leu Leu Leu Gly Val His Glu Gln
            690                 695                 700

Lys Gln Glu Val Val Lys Phe Leu Ile Lys Lys Ala Asn Leu Asn
705                 710                 715                 720

Ala Leu Asp Arg Tyr Gly Arg Thr Ala Leu Ile Leu Ala Val Cys Cys
                725                 730                 735

Gly Ser Ala Ser Ile Val Asn Leu Leu Leu Glu Gln Asn Val Asp Val
                740                 745                 750

Ser Ser Gln Asp Leu Ser Gly Gln Thr Ala Arg Glu Tyr Ala Val Ser
            755                 760                 765

Ser His His His Val Ile Cys Glu Leu Leu Ser Asp Tyr Lys Glu Lys
            770                 775                 780

Gln Met Leu Lys Ile Ser Ser Glu Asn Ser Asn Pro Val Ile Thr Ile
785                 790                 795                 800

Leu Asn Ile Lys Leu Pro Leu Lys Val Glu Glu Ile Lys Lys His
                805                 810                 815

Gly Ser Asn Pro Val Gly Leu Pro Glu Asn Leu Thr Asn Gly Ala Ser
                820                 825                 830

Ala Gly Asn Gly Asp Asp Gly Leu Ile Pro Gln Arg Lys Ser Arg Lys
            835                 840                 845

Pro Glu Asn Gln Gln Phe Pro Asp Thr Glu Asn Glu Glu Tyr His Ser
            850                 855                 860

Asp Glu Gln Asn Asp Thr Gln Lys Gln Leu Ser Glu Glu Gln Asn Thr
865                 870                 875                 880

Gly Ile Ser Gln Asp Glu Ile Leu Thr Asn Lys Gln Lys Gln Ile Glu
                885                 890                 895

Val Ala Glu Lys Glu Met Asn Ser Glu Leu Ser Leu Ser His Lys Lys
            900                 905                 910

Glu Glu Asp Leu Leu Arg Glu Asn Ser Met Leu Arg Glu Glu Ile Ala
            915                 920                 925

Lys Leu Arg Leu Glu Leu Asp Glu Thr Lys His Gln Asn Gln Leu Arg
            930                 935                 940

Glu Asn Lys Ile Leu Glu Glu Ile Glu Ser Val Lys Glu Lys Leu Leu
945                 950                 955                 960
```

```
Lys Thr Ile Gln Leu Asn Glu Glu Ala Leu Thr Lys Thr Lys Val Ala
                965                 970                 975

Gly Phe Ser Leu Arg Gln Leu Gly Leu Ala Gln His Ala Gln Ala Ser
            980                 985                 990

Val Gln Gln Leu Cys Tyr Lys Trp Asn His Thr Glu Lys Thr Glu Gln
        995                 1000                1005

Gln Ala Gln Glu Gln Val Ala Gly Phe Ser Leu Arg Gln Leu Gly
    1010                1015                1020

Leu Ala Gln His Ala Gln Ala Ser Val Gln Gln Leu Cys Tyr Lys Trp
1025                1030                1035                1040

Gly His Thr Glu Lys Thr Glu Gln Gln Ala Gln Glu Gln Gly Ala Ala
                1045                1050                1055

Leu Arg Ser Gln Ile Gly Asp Pro Gly Gly Val Pro Leu Ser Glu Gly
                1060                1065                1070

Gly Thr Ala Ala Gly Asp Gln Gly Pro Gly Thr His Leu Pro Pro Arg
            1075                1080                1085

Glu Pro Arg Ala Ser Pro Gly Thr Pro Ser Leu Val Arg Leu Ala Ser
    1090                1095                1100

Gly Ala Arg Ala Ala Ala Leu Pro Pro Pro Thr Gly Lys Asn Gly Arg
1105                1110                1115                1120

Ser Pro Thr Lys Gln Lys Ser Val Cys Asp Ser Ser Gly Trp Ile Leu
                1125                1130                1135

Pro Val Pro Thr Phe Ser Ser Gly Ser Phe Leu Gly Arg Arg Cys Pro
            1140                1145                1150

Met Phe Asp Val Ser Pro Ala Met Arg Leu Lys Ser Asp Ser Asn Arg
            1155                1160                1165

Glu Thr His Gln Ala Phe Arg Asp Lys Asp Asp Leu Pro Phe Phe Lys
    1170                1175                1180

Thr Gln Gln Ser Pro Arg His Thr Lys Asp Leu Gly Gln Asp Asp Arg
1185                1190                1195                1200

Ala Gly Val Leu Ala Pro Lys Cys Arg Pro Gly Thr Leu Cys His Thr
            1205                1210                1215

Asp Thr Pro Pro His Arg Asn Ala Asp Thr Pro Pro His Arg His Thr
            1220                1225                1230

Thr Thr Leu Pro His Arg Asp Thr Thr Thr Ser Leu Pro His Phe His
            1235                1240                1245

Val Ser Ala Gly Gly Val Gly Pro Thr Thr Leu Gly Ser Asn Arg Glu
            1250                1255                1260

Ile Thr
1265

<210> SEQ ID NO 74
<211> LENGTH: 227
<212> TYPE: PRT
<213> ORGANISM: Homo sapiens

<400> SEQUENCE: 74

Met Pro Phe Ile Ser Lys Leu Val Leu Ala Ser Gln Pro Thr Leu Phe
  1               5                  10                  15

Ser Phe Phe Ser Ala Ser Ser Pro Phe Leu Leu Phe Leu Asp Leu Arg
                20                  25                  30

Pro Glu Arg Thr Tyr Leu Pro Val Cys His Val Ala Leu Ile His Met
            35                  40                  45

Val Val Leu Leu Thr Met Val Phe Leu Ser Pro Gln Leu Phe Glu Ser
```

```
                50                 55                 60
Leu Asn Phe Gln Asn Asp Phe Lys Tyr Glu Ala Ser Phe Tyr Leu Arg
 65                  70                  75                  80

Arg Val Ile Arg Val Leu Ser Ile Cys Thr Thr Cys Leu Leu Gly Met
                 85                  90                  95

Leu Gln Val Val Asn Ile Ser Pro Ser Ile Ser Trp Leu Val Arg Phe
            100                 105                 110

Lys Trp Lys Ser Thr Ile Phe Thr Phe His Leu Phe Ser Trp Ser Leu
            115                 120                 125

Ser Phe Pro Val Ser Ser Leu Ile Phe Tyr Thr Val Ala Ser Ser
        130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
        195                 200                 205

Gln Pro Leu Pro Lys Asp Leu Cys Arg Gly Lys Ser His Gln His Ile
    210                 215                 220

Leu Leu Pro
225

<210> SEQ ID NO 75
<211> LENGTH: 153
<212> TYPE: PRT
<213> ORGANISM: Homo sapiens

<400> SEQUENCE: 75

Met Pro Phe Ile Ser Lys Leu Val Leu Ala Ser Gln Pro Thr Leu Phe
  1               5                  10                  15

Ser Phe Phe Ser Ala Ser Ser Pro Phe Leu Leu Phe Leu Asp Leu Arg
             20                  25                  30

Pro Glu Arg Thr Tyr Leu Pro Val Cys His Val Ala Leu Ile His Met
         35                  40                  45

Val Val Leu Leu Thr Met Val Phe Leu Ser Pro Gln Leu Phe Glu Ser
     50                  55                  60

Leu Asn Phe Gln Asn Asp Phe Lys Tyr Glu Ala Ser Phe Tyr Leu Arg
 65                  70                  75                  80

Arg Val Ile Arg Val Leu Ser Ile Cys Thr Thr Cys Leu Leu Asp Met
                 85                  90                  95

Leu Gln Val Val Asn Ile Ser Pro Ser Ile Ser Trp Leu Ile Met Leu
            100                 105                 110

Phe Ser Ser Val Tyr Met Met Thr Leu Ile Gln Glu Leu Gln Glu Ile
            115                 120                 125

Leu Val Pro Ser Gln Pro Gln Pro Leu Pro Lys Asp Leu Cys Arg Gly
        130                 135                 140

Lys Ser His Gln His Ile Leu Leu Pro
145                 150

<210> SEQ ID NO 76
<211> LENGTH: 3801
<212> TYPE: DNA
<213> ORGANISM: Homo sapiens
```

<400> SEQUENCE: 76

```
atgcctttca tttctaagct ggtattggca tctcagccaa cacttttctc cttcttttct        60
gcgtcttctc ctttttctgct tttttctggat ctcaggccag agcgcactta cctaccagtc      120
tgtcatgtgg ccctcatcca catggtggtc cttctcacca tggtgttctt gtctccacag       180
ctctttgaat cactgaattt tcagaatgac ttcaaatatg aggcatcttt ctacctgagg       240
agggtgatca gggtcctctc catttgtacc acctgcctcc tggacatgct gcaggtcgtc       300
aacatcagcc ccagcatttc ctggttgata atgctgttct caagtgtcta catgatgact       360
ctcattcagg aactacagga gatcctggta ccttcacagc cccagcctct acctaaggat       420
ctttgcagag gcaagagcca tcagcacatc ctgctgccga ctcaagcaac ttttgctgca       480
gcaactggac tatgggctgc actaaccacc gtatcaaatc aagcagagc agatcctgtg       540
acctggagaa aggagccggc tgtccttccc tgctgtaacc tagagaaagg aagctggctg      600
tccttccctg gcacagctgc acgcaaggaa ttttccacca cgctcaccgg gcacagcgcg      660
ctgagcctct ccagttcgcg ggccctcccc ggctcgctcc cggctttcgc agacctcccc      720
cgctcctgcc ctgagtccga gcagagcgca acgccagccg gcgccttcct cctgggctgg      780
gagcgagtgg tgcagcggcg gctcgaagtc ccccggcctc aagcagcccc cgcgactagc      840
gcgacaccct cgcgggatcc gagtccaccc tgccaccagc gccgggacgc cgcgtgcctc      900
agagcccaag ggctgacccg ggccttccag gtggtccatc tcgctcctac ggctcccgac       960
ggtggcgctg ggtgtccccc atcccgcaat tcctaccggc tgacccatgt gcgctgcgcc      1020
caggggctgg aggctgccag cgccaacctt cccggcgctc cggggcggag cagctcctgc      1080
gccctgcgct accgcagcgg ccctcagtc agctccgcgc cgtcccccgc agagcccccg      1140
gcgcaccagc gcctgctttt ccttccccga gcgcctcaag cagtctctgg gccgcaggaa      1200
cagccctctg aagaggcgct tggtgtagga agcctctcag tttccagtt acacctaata       1260
cagtgtattc caaatctaag ttacccacta gtacttcggc acattccaga aattctgaaa      1320
ttttctgaaa aggaaactgg tggtggaatt ctaggcttag aattaccagc gacagctgct      1380
cgcctctcag gattaaacag cataatgcaa atcaaagagt ttgaagaatt ggtaaaactt      1440
cacagcttgt cacacaaagt cattcagtgt gtgtttgcaa agaaaaaaaa tgtagacaaa      1500
tgggatgact tttgtcttag tgagggttat ggacattcat tcttaataat gaaagaaacg      1560
tcgactaaaa tatcaggttt aattcaggag atggggagcg gcaagagcaa cgtgggcact      1620
tggggagact acgacgacag cgccttcatg gagccgaggt accacgtccg tcgagaagat      1680
ctggacaagc tccacagagc tgcctggtgg ggtaaagtcc ccagaaagga tctcatcgtc      1740
atgctcaggg acactgacat gaacaagagg gacaagcaaa agaggactgc tctacatttg      1800
gcctctgcca atggaaattc agaagtagta caactcctgc tggacagacg atgtcaactt      1860
aacgtccttg acaacaaaaa aggacagct ctgataaagg ccgtacaatg ccaggaagat       1920
gaatgtgtgt taatgttgct ggaacatggc gctgatggaa atattcaaga tgagtatgga      1980
aataccgctc tacactatgc tatctacaat gaagataaat taatggccaa agcactgctc      2040
ttatatggtg ctgatattga atcaaaaaac aagtgtggcc tcacaccact tttgcttggc      2100
gtacatgaac aaaaacagga agtggtgaaa tttttaatca agaaaaagc taattaaat       2160
gcacttgata gatatggaag aactgccctc atacttgctg tatgttgtgg atcagcaagt      2220
atagtcaatc ttctacttga gcaaaatgtt gatgtatctt ctcaagatct atctggacag      2280
acggccagag agtatgctgt ttctagtcat catcatgtaa tttgtgaatt actttctgac      2340
```

| | |
|---|---|
| tataaagaaa aacagatgct aaaaatctct tctgaaaaca gcaatccagt gataaccatc | 2400 |
| cttaatatca aacttccact caaggttgaa gaagaaataa agaagcatgg aagtaatcct | 2460 |
| gtgggattac cagaaaacct gactaatggt gccagtgctg gcaatggtga tgatggatta | 2520 |
| attccacaaa ggaagagcag aaaacctgaa aatcagcaat ttcctgacac tgagaatgaa | 2580 |
| gagtatcaca gtgacgaaca aaatgatacc cagaaacaac tttctgaaga acagaacact | 2640 |
| ggaatatcac aagatgagat tctgactaat aaacaaaagc agatagaagt ggctgaaaag | 2700 |
| gaaatgaatt ctgagctttc tcttagtcat aagaaagaag aagatctctt gcgtgaaaac | 2760 |
| agcatgttgc gggaagaaat tgccaagcta agactggaac tagatgaaac aaaacatcag | 2820 |
| aaccagctaa gggaaaataa aattttggag gaaattgaaa gtgtaaaaga aaaacttcta | 2880 |
| aagactatac aactgaatga agaagcatta acgaaaacca aggtggctgg tttctctttg | 2940 |
| cgccagcttg gccttgccca gcatgcacaa gcctcagtgc aacagctgtg ctacaaatgg | 3000 |
| aaccacacag agaaaacaga gcagcaggct caggagcagg aggtggctgg tttctctttg | 3060 |
| cgccagcttg gccttgccca gcatgcacaa gcctcagtac aacaactgtg ctacaaatgg | 3120 |
| ggccacacag agaaaacaga gcagcaggct caggagcagg agctgcgct gaggtcccag | 3180 |
| ataggcgacc ctggcggggt gcccctgagc gaagggggga cagcagcagg agaccagggt | 3240 |
| ccagggaccc acctcccacc gagggaacct cgagcctccc ctggcacccc tagcttggtc | 3300 |
| cgcctggcct ccggagcccg agctgctgcg cttcccccac ccacagggaa aaacggccga | 3360 |
| tctccaacca aacagaaatc tgtgtgtgac tcctctggtt ggatactgcc agtccccaca | 3420 |
| ttttcttccg ggagttttct tggcagaagg tgcccaatgt tgatgtttc gccagccatg | 3480 |
| aggctgaaaa gtgacagcaa tagagaaaca catcaggctt ccgcgacaa agatgacctt | 3540 |
| cccttcttca aaactcagca atctccacgg cacacaaagg acttaggaca agatgaccga | 3600 |
| gctggagtgc tcgcccccaaa atgcaggccc ggaacactct gccacacgga cacaccacca | 3660 |
| cacagaaatg cggacacacc accacacaga cacaccacca cgctgccaca cagagacacc | 3720 |
| accacatcgt tgccacactt tcatgtgtca gctggcggtg tgggccccac gactctgggc | 3780 |
| tctaatagag aaattactta g | 3801 |

<210> SEQ ID NO 77
<211> LENGTH: 459
<212> TYPE: DNA
<213> ORGANISM: Homo sapiens

<400> SEQUENCE: 77

| | |
|---|---|
| atgccttca tttctaagct ggtattggca tctcagccaa cacttttctc cttcttttct | 60 |
| gcgtcttctc ctttctgct ttttctggat ctcaggccag agcgcactta cctaccagtc | 120 |
| tgtcatgtgg ccctcatcca catggtggtc cttctcacca tggtgttctt gtctccacag | 180 |
| ctctttgaat cactgaattt tcagaatgac ttcaaatatg aggcatcttt ctacctgagg | 240 |
| agggtgatca gggtcctctc catttgtacc acctgcctcc tgggcatgct gcaggtcgtc | 300 |
| aacatcagcc ccagcatttc ctggttgata atgctgttct caagtgtcta catgatgact | 360 |
| ctcattcagg aactacagga gatcctggta ccttcacagc cccagcctct acctaaggat | 420 |
| ctttgcagag gcaagagcca tcagcacatc ctgctgccg | 459 |

<210> SEQ ID NO 78
<211> LENGTH: 459
<212> TYPE: DNA

<213> ORGANISM: Homo sapiens

<400> SEQUENCE: 78

```
atgcctttca tttctaagct ggtattggca tctcagccaa cacttttctc cttcttttct      60
gcgtcttctc cttttctgct ttttctggat ctcaggccag agcgcactta cctaccagtc     120
tgtcatgtgg ccctcatcca catggtggtc cttctcacca tggtgttctt gtctccacag     180
ctctttgaat cactgaattt tcagaatgac ttcaaatatg aggcatcttt ctacctgagg     240
agggtgatca gggtcctctc catttgtacc acctgcctcc tggacatgct gcaggtcgtc     300
aacatcagcc ccagcatttc tggttgata atgctgttct caagtgtcta catgatgact     360
ctcattcagg aactacagga gatcctggta ccttcacagc cccagcctct acctaaggat     420
ctttgcagag gcaagagcca tcagcacatc ctgctgccg                           459
```

<210> SEQ ID NO 79
<211> LENGTH: 1266
<212> TYPE: PRT
<213> ORGANISM: Homo sapiens

<400> SEQUENCE: 79

```
Met Pro Phe Ile Ser Lys Leu Val Leu Ala Ser Gln Pro Thr Leu Phe
  1               5                  10                  15

Ser Phe Phe Ser Ala Ser Ser Pro Phe Leu Leu Phe Leu Asp Leu Arg
             20                  25                  30

Pro Glu Arg Thr Tyr Leu Pro Val Cys His Val Ala Leu Ile His Met
         35                  40                  45

Val Val Leu Leu Thr Met Val Phe Leu Ser Pro Gln Leu Phe Glu Ser
     50                  55                  60

Leu Asn Phe Gln Asn Asp Phe Lys Tyr Glu Ala Ser Phe Tyr Leu Arg
 65                  70                  75                  80

Arg Val Ile Arg Val Leu Ser Ile Cys Thr Thr Cys Leu Leu Asp Met
                 85                  90                  95

Leu Gln Val Val Asn Ile Ser Pro Ser Ile Ser Trp Leu Ile Met Leu
            100                 105                 110

Phe Ser Ser Val Tyr Met Met Thr Leu Ile Gln Glu Leu Gln Glu Ile
        115                 120                 125

Leu Val Pro Ser Gln Pro Gln Pro Leu Pro Lys Asp Leu Cys Arg Gly
    130                 135                 140

Lys Ser His Gln His Ile Leu Leu Pro Thr Gln Ala Thr Phe Ala Ala
145                 150                 155                 160

Ala Thr Gly Leu Trp Ala Ala Leu Thr Thr Val Ser Asn Pro Ser Arg
                165                 170                 175

Ala Asp Pro Val Thr Trp Arg Lys Glu Pro Ala Val Leu Pro Cys Cys
            180                 185                 190

Asn Leu Glu Lys Gly Ser Trp Leu Ser Phe Pro Gly Thr Ala Ala Arg
        195                 200                 205

Lys Glu Phe Ser Thr Thr Leu Thr Gly His Ser Ala Leu Ser Leu Ser
    210                 215                 220

Ser Ser Arg Ala Leu Pro Gly Ser Leu Pro Ala Phe Ala Asp Leu Pro
225                 230                 235                 240

Arg Ser Cys Pro Glu Ser Glu Gln Ser Ala Thr Pro Ala Gly Ala Phe
                245                 250                 255

Leu Leu Gly Trp Glu Arg Val Val Gln Arg Arg Leu Glu Val Pro Arg
            260                 265                 270
```

-continued

```
Pro Gln Ala Ala Pro Ala Thr Ser Ala Thr Pro Ser Arg Asp Pro Ser
    275                 280                 285

Pro Pro Cys His Gln Arg Arg Asp Ala Ala Cys Leu Arg Ala Gln Gly
    290                 295                 300

Leu Thr Arg Ala Phe Gln Val Val His Leu Ala Pro Thr Ala Pro Asp
305                 310                 315                 320

Gly Gly Ala Gly Cys Pro Pro Ser Arg Asn Ser Tyr Arg Leu Thr His
                325                 330                 335

Val Arg Cys Ala Gln Gly Leu Glu Ala Ala Ser Ala Asn Leu Pro Gly
            340                 345                 350

Ala Pro Gly Arg Ser Ser Cys Ala Leu Arg Tyr Arg Ser Gly Pro
            355                 360                 365

Ser Val Ser Ser Ala Pro Ser Pro Ala Glu Pro Pro Ala His Gln Arg
    370                 375                 380

Leu Leu Phe Leu Pro Arg Ala Pro Gln Ala Val Ser Gly Pro Gln Glu
385                 390                 395                 400

Gln Pro Ser Glu Glu Ala Leu Gly Val Gly Ser Leu Ser Val Phe Gln
                405                 410                 415

Leu His Leu Ile Gln Cys Ile Pro Asn Leu Ser Tyr Pro Leu Val Leu
            420                 425                 430

Arg His Ile Pro Glu Ile Leu Lys Phe Ser Glu Lys Glu Thr Gly Gly
            435                 440                 445

Gly Ile Leu Gly Leu Glu Leu Pro Ala Thr Ala Ala Arg Leu Ser Gly
    450                 455                 460

Leu Asn Ser Ile Met Gln Ile Lys Glu Phe Glu Glu Leu Val Lys Leu
465                 470                 475                 480

His Ser Leu Ser His Lys Val Ile Gln Cys Val Phe Ala Lys Lys Lys
                485                 490                 495

Asn Val Asp Lys Trp Asp Asp Phe Cys Leu Ser Glu Gly Tyr Gly His
            500                 505                 510

Ser Phe Leu Ile Met Lys Glu Thr Ser Thr Lys Ile Ser Gly Leu Ile
    515                 520                 525

Gln Glu Met Gly Ser Gly Lys Ser Asn Val Gly Thr Trp Gly Asp Tyr
530                 535                 540

Asp Asp Ser Ala Phe Met Glu Pro Arg Tyr His Val Arg Arg Glu Asp
545                 550                 555                 560

Leu Asp Lys Leu His Arg Ala Ala Trp Trp Gly Lys Val Pro Arg Lys
                565                 570                 575

Asp Leu Ile Val Met Leu Arg Asp Thr Asp Met Asn Lys Arg Asp Lys
            580                 585                 590

Gln Lys Arg Thr Ala Leu His Leu Ala Ser Ala Asn Gly Asn Ser Glu
    595                 600                 605

Val Val Gln Leu Leu Leu Asp Arg Arg Cys Gln Leu Asn Val Leu Asp
610                 615                 620

Asn Lys Lys Arg Thr Ala Leu Ile Lys Ala Val Gln Cys Gln Glu Asp
625                 630                 635                 640

Glu Cys Val Leu Met Leu Leu Glu His Gly Ala Asp Gly Asn Ile Gln
                645                 650                 655

Asp Glu Tyr Gly Asn Thr Ala Leu His Tyr Ala Ile Tyr Asn Glu Asp
            660                 665                 670

Lys Leu Met Ala Lys Ala Leu Leu Leu Tyr Gly Ala Asp Ile Glu Ser
    675                 680                 685

Lys Asn Lys Cys Gly Leu Thr Pro Leu Leu Leu Gly Val His Glu Gln
```

-continued

```
            690             695             700
Lys Gln Glu Val Val Lys Phe Leu Ile Lys Lys Ala Asn Leu Asn
705                 710                 715                 720

Ala Leu Asp Arg Tyr Gly Arg Thr Ala Leu Ile Leu Ala Val Cys Cys
                725                 730                 735

Gly Ser Ala Ser Ile Val Asn Leu Leu Leu Glu Gln Asn Val Asp Val
                740                 745                 750

Ser Ser Gln Asp Leu Ser Gly Gln Thr Ala Arg Glu Tyr Ala Val Ser
            755                 760                 765

Ser His His His Val Ile Cys Glu Leu Ser Asp Tyr Lys Glu Lys
770                 775                 780

Gln Met Leu Lys Ile Ser Ser Glu Asn Ser Asn Pro Val Ile Thr Ile
785                 790                 795                 800

Leu Asn Ile Lys Leu Pro Leu Lys Val Glu Glu Ile Lys Lys His
                805                 810                 815

Gly Ser Asn Pro Val Gly Leu Pro Glu Asn Leu Thr Asn Gly Ala Ser
                820                 825                 830

Ala Gly Asn Gly Asp Asp Gly Leu Ile Pro Gln Arg Lys Ser Arg Lys
                835                 840                 845

Pro Glu Asn Gln Gln Phe Pro Asp Thr Glu Asn Glu Glu Tyr His Ser
850                 855                 860

Asp Glu Gln Asn Asp Thr Gln Lys Gln Leu Ser Glu Gln Asn Thr
865                 870                 875                 880

Gly Ile Ser Gln Asp Glu Ile Leu Thr Asn Lys Gln Lys Gln Ile Glu
                885                 890                 895

Val Ala Glu Lys Glu Met Asn Ser Glu Leu Ser Leu Ser His Lys Lys
                900                 905                 910

Glu Glu Asp Leu Leu Arg Glu Asn Ser Met Leu Arg Glu Glu Ile Ala
                915                 920                 925

Lys Leu Arg Leu Glu Leu Asp Glu Thr Lys His Gln Asn Gln Leu Arg
                930                 935                 940

Glu Asn Lys Ile Leu Glu Glu Ile Glu Ser Val Lys Glu Lys Leu Leu
945                 950                 955                 960

Lys Thr Ile Gln Leu Asn Glu Glu Ala Leu Thr Lys Thr Lys Val Ala
                965                 970                 975

Gly Phe Ser Leu Arg Gln Leu Gly Leu Ala Gln His Ala Gln Ala Ser
                980                 985                 990

Val Gln Gln Leu Cys Tyr Lys Trp Asn His Thr Glu Lys Thr Glu Gln
                995                 1000                1005

Gln Ala Gln Glu Gln Glu Val Ala Gly Phe Ser Leu Arg Gln Leu Gly
1010                1015                1020

Leu Ala Gln His Ala Gln Ala Ser Val Gln Gln Leu Cys Tyr Lys Trp
1025                1030                1035                1040

Gly His Thr Glu Lys Thr Glu Gln Gln Ala Gln Gln Gly Ala Ala
                1045                1050                1055

Leu Arg Ser Gln Ile Gly Asp Pro Gly Gly Val Pro Leu Ser Glu Gly
                1060                1065                1070

Gly Thr Ala Ala Gly Asp Gln Gly Pro Gly Thr His Leu Pro Pro Arg
            1075                1080                1085

Glu Pro Arg Ala Ser Pro Gly Thr Pro Ser Leu Val Arg Leu Ala Ser
            1090                1095                1100

Gly Ala Arg Ala Ala Ala Leu Pro Pro Pro Thr Gly Lys Asn Gly Arg
1105                1110                1115                1120
```

Ser Pro Thr Lys Gln Lys Ser Val Cys Asp Ser Ser Gly Trp Ile Leu
            1125                1130                1135

Pro Val Pro Thr Phe Ser Ser Gly Ser Phe Leu Gly Arg Arg Cys Pro
            1140                1145                1150

Met Phe Asp Val Ser Pro Ala Met Arg Leu Lys Ser Asp Ser Asn Arg
            1155                1160                1165

Glu Thr His Gln Ala Phe Arg Asp Lys Asp Leu Pro Phe Phe Lys
        1170                1175                1180

Thr Gln Gln Ser Pro Arg His Thr Lys Asp Leu Gly Gln Asp Arg
1185                1190                1195                1200

Ala Gly Val Leu Ala Pro Lys Cys Arg Pro Gly Thr Leu Cys His Thr
            1205                1210                1215

Asp Thr Pro Pro His Arg Asn Ala Asp Thr Pro Pro His Arg His Thr
            1220                1225                1230

Thr Thr Leu Pro His Arg Asp Thr Thr Thr Ser Leu Pro His Phe His
            1235                1240                1245

Val Ser Ala Gly Gly Val Gly Pro Thr Thr Leu Gly Ser Asn Arg Glu
            1250                1255                1260

Ile Thr
1265

<210> SEQ ID NO 80
<211> LENGTH: 227
<212> TYPE: PRT
<213> ORGANISM: Homo sapiens

<400> SEQUENCE: 80

Met Pro Phe Ile Ser Lys Leu Val Leu Ala Ser Gln Pro Thr Leu Phe
1               5                   10                  15

Ser Phe Phe Ser Ala Ser Ser Pro Phe Leu Leu Phe Leu Asp Leu Arg
            20                  25                  30

Pro Glu Arg Thr Tyr Leu Pro Val Cys His Val Ala Leu Ile His Met
        35                  40                  45

Val Val Leu Leu Thr Met Val Phe Leu Ser Pro Gln Leu Phe Glu Ser
    50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Gly Met
                85                  90                  95

Leu Gln Val Val Asn Ile Ser Pro Ser Ile Ser Trp Leu Val Arg Phe
            100                 105                 110

Lys Trp Lys Ser Thr Ile Phe Thr Phe His Leu Phe Ser Trp Ser Leu
        115                 120                 125

Ser Phe Pro Val Ser Ser Ser Leu Ile Phe Tyr Thr Val Ala Ser Ser
    130                 135                 140

Asn Val Thr Gln Ile Asn Leu His Val Ser Lys Tyr Cys Ser Leu Phe
145                 150                 155                 160

Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
            180                 185                 190

Met Thr Leu Ile Gln Glu Leu Gln Glu Ile Leu Val Pro Ser Gln Pro
        195                 200                 205

Gln Pro Leu Pro Lys Asp Leu Cys Arg Gly Lys Ser His Gln His Ile

```
            210                 215                 220
Leu Leu Pro
225

<210> SEQ ID NO 81
<211> LENGTH: 153
<212> TYPE: PRT
<213> ORGANISM: Homo sapiens

<400> SEQUENCE: 81

Met Pro Phe Ile Ser Lys Leu Val Leu Ala Ser Gln Pro Thr Leu Phe
  1               5                  10                  15

Ser Phe Phe Ser Ala Ser Ser Pro Phe Leu Leu Phe Leu Asp Leu Arg
                 20                  25                  30

Pro Glu Arg Thr Tyr Leu Pro Val Cys His Val Ala Leu Ile His Met
             35                  40                  45

Val Val Leu Leu Thr Met Val Phe Leu Ser Pro Gln Leu Phe Glu Ser
         50                  55                  60

Leu Asn Phe Gln Asn Asp Phe Lys Tyr Glu Ala Ser Phe Tyr Leu Arg
 65                  70                  75                  80

Arg Val Ile Arg Val Leu Ser Ile Cys Thr Thr Cys Leu Leu Asp Met
                 85                  90                  95

Leu Gln Val Val Asn Ile Ser Pro Ser Ile Ser Trp Leu Ile Met Leu
                100                 105                 110

Phe Ser Ser Val Tyr Met Met Thr Leu Ile Gln Glu Leu Gln Glu Ile
            115                 120                 125

Leu Val Pro Ser Gln Pro Gln Pro Leu Pro Lys Asp Leu Cys Arg Gly
        130                 135                 140

Lys Ser His Gln His Ile Leu Leu Pro
145                 150

<210> SEQ ID NO 82
<211> LENGTH: 255
<212> TYPE: PRT
<213> ORGANISM: Homo sapiens

<400> SEQUENCE: 82

Met Pro Phe Ile Ser Lys Leu Val Leu Ala Ser Gln Pro Thr Leu Phe
  1               5                  10                  15

Ser Phe Phe Ser Ala Ser Ser Pro Phe Leu Leu Phe Leu Asp Leu Arg
                 20                  25                  30

Pro Glu Arg Thr Tyr Leu Pro Val Cys His Val Ala Leu Ile His Met
             35                  40                  45

Val Val Leu Leu Thr Met Val Phe Leu Ser Pro Gln Leu Phe Glu Ser
         50                  55                  60

Leu Asn Phe Gln Asn Asp Phe Lys Tyr Glu Ala Ser Phe Tyr Leu Arg
 65                  70                  75                  80

Arg Val Ile Arg Val Leu Ser Ile Cys Thr Thr Cys Leu Leu Gly Met
                 85                  90                  95

Leu Gln Val Val Asn Ile Ser Pro Ser Ile Ser Trp Leu Val Arg Phe
                100                 105                 110

Lys Trp Lys Ser Thr Ile Phe Thr Phe His Leu Phe Ser Trp Ser Leu
            115                 120                 125

Ser Phe Pro Val Ser Ser Leu Ile Phe Tyr Thr Val Ala Ser Ser
        130                 135                 140

Asn Val Thr Gln Ile Asn Leu His Val Ser Lys Tyr Cys Ser Leu Phe
```

```
                145                 150                 155                 160
Pro Ile Asn Ser Ile Ile Arg Gly Leu Phe Phe Thr Leu Ser Leu Phe
                165                 170                 175

Arg Asp Val Phe Leu Lys Gln Ile Met Leu Phe Ser Ser Val Tyr Met
                180                 185                 190

Met Thr Leu Ile Gln Glu Leu Gln Glu Ile Leu Val Pro Ser Gln Pro
                195                 200                 205

Gln Pro Leu Pro Lys Asp Leu Cys Arg Gly Lys Ser His Gln His Ile
                210                 215                 220

Leu Leu Pro Val Ser Phe Ser Val Gly Met Tyr Lys Met Asp Phe Ile
225                 230                 235                 240

Ile Ser Thr Ser Thr Leu Pro Trp Ala Tyr Asp Arg Gly Val
                245                 250                 255

<210> SEQ ID NO 83
<211> LENGTH: 1140
<212> TYPE: PRT
<213> ORGANISM: Homo sapiens

<400> SEQUENCE: 83

Met Pro Phe Ile Ser Lys Leu Val Leu Ala Ser Gln Pro Thr Leu Phe
1               5                   10                  15

Ser Phe Phe Ser Ala Ser Ser Pro Phe Leu Leu Phe Leu Asp Leu Arg
                20                  25                  30

Pro Glu Arg Thr Tyr Leu Pro Val Cys His Val Ala Leu Ile His Met
                35                  40                  45

Val Val Leu Leu Thr Met Val Phe Leu Ser Pro Gln Leu Phe Glu Ser
                50                  55                  60

Leu Asn Phe Gln Asn Asp Phe Lys Tyr Glu Ala Ser Phe Tyr Leu Arg
65                  70                  75                  80

Arg Val Ile Arg Val Leu Ser Ile Cys Thr Thr Cys Leu Leu Asp Met
                85                  90                  95

Leu Gln Val Val Asn Ile Ser Pro Ser Ile Ser Trp Leu Ile Met Leu
                100                 105                 110

Phe Ser Ser Val Tyr Met Met Thr Leu Ile Gln Glu Leu Gln Glu Ile
                115                 120                 125

Leu Val Pro Ser Gln Pro Gln Pro Leu Pro Lys Asp Leu Cys Arg Gly
                130                 135                 140

Lys Ser His Gln His Ile Leu Leu Pro Thr Gln Ala Thr Phe Ala Ala
145                 150                 155                 160

Ala Thr Gly Leu Trp Ala Ala Leu Thr Thr Val Ser Asn Pro Ser Arg
                165                 170                 175

Ala Asp Pro Val Thr Trp Arg Lys Glu Pro Ala Val Leu Pro Cys Cys
                180                 185                 190

Asn Leu Glu Lys Gly Ser Trp Leu Ser Phe Pro Gly Thr Ala Ala Arg
                195                 200                 205

Lys Glu Phe Ser Thr Thr Leu Thr Gly His Ser Ala Leu Ser Leu Ser
                210                 215                 220

Ser Ser Arg Ala Leu Pro Gly Ser Leu Pro Ala Phe Ala Asp Leu Pro
225                 230                 235                 240

Arg Ser Cys Pro Glu Ser Glu Gln Ser Ala Thr Pro Ala Gly Ala Phe
                245                 250                 255

Leu Leu Gly Trp Glu Arg Val Val Gln Arg Arg Leu Glu Val Pro Arg
                260                 265                 270
```

```
Pro Gln Ala Ala Pro Ala Thr Ser Ala Thr Pro Ser Arg Asp Pro Ser
        275                 280                 285

Pro Pro Cys His Gln Arg Arg Asp Ala Ala Cys Leu Arg Ala Gln Gly
        290                 295                 300

Leu Thr Arg Ala Phe Gln Val Val His Leu Ala Pro Thr Ala Pro Asp
305                 310                 315                 320

Gly Gly Ala Gly Cys Pro Pro Ser Arg Asn Ser Tyr Arg Leu Thr His
                325                 330                 335

Val Arg Cys Ala Gln Gly Leu Glu Ala Ala Ser Ala Asn Leu Pro Gly
            340                 345                 350

Ala Pro Gly Arg Ser Ser Ser Cys Ala Leu Arg Tyr Arg Ser Gly Pro
                355                 360                 365

Ser Val Ser Ser Ala Pro Ser Pro Ala Glu Pro Pro Ala His Gln Arg
        370                 375                 380

Leu Leu Phe Leu Pro Arg Ala Pro Gln Ala Val Ser Gly Pro Gln Glu
385                 390                 395                 400

Gln Pro Ser Glu Glu Ala Leu Gly Val Gly Ser Leu Ser Val Phe Gln
                405                 410                 415

Leu His Leu Ile Gln Cys Ile Pro Asn Leu Ser Tyr Pro Leu Val Leu
            420                 425                 430

Arg His Ile Pro Glu Ile Leu Lys Phe Ser Glu Lys Glu Thr Gly Gly
            435                 440                 445

Gly Ile Leu Gly Leu Glu Leu Pro Ala Thr Ala Ala Arg Leu Ser Gly
        450                 455                 460

Leu Asn Ser Ile Met Gln Ile Lys Glu Phe Glu Glu Leu Val Lys Leu
465                 470                 475                 480

His Ser Leu Ser His Lys Val Ile Gln Cys Val Phe Ala Lys Lys Lys
                485                 490                 495

Asn Val Asp Lys Trp Asp Asp Phe Cys Leu Ser Glu Gly Tyr Gly His
                500                 505                 510

Ser Phe Leu Ile Met Lys Glu Thr Ser Thr Lys Ile Ser Gly Leu Ile
        515                 520                 525

Gln Glu Met Gly Ser Gly Lys Ser Asn Val Gly Thr Trp Gly Asp Tyr
530                 535                 540

Asp Asp Ser Ala Phe Met Glu Pro Arg Tyr His Val Arg Arg Glu Asp
545                 550                 555                 560

Leu Asp Lys Leu His Arg Ala Ala Trp Trp Gly Lys Val Pro Arg Lys
                565                 570                 575

Asp Leu Ile Val Met Leu Arg Asp Thr Asp Met Asn Lys Arg Asp Lys
            580                 585                 590

Gln Lys Arg Thr Ala Leu His Leu Ala Ser Ala Asn Gly Asn Ser Glu
        595                 600                 605

Val Val Gln Leu Leu Leu Asp Arg Arg Cys Gln Leu Asn Val Leu Asp
610                 615                 620

Asn Lys Lys Arg Thr Ala Leu Ile Lys Ala Val Gln Cys Gln Glu Asp
625                 630                 635                 640

Glu Cys Val Leu Met Leu Leu Glu His Gly Ala Asp Gly Asn Ile Gln
                645                 650                 655

Asp Glu Tyr Gly Asn Thr Ala Leu His Tyr Ala Ile Tyr Asn Glu Asp
            660                 665                 670

Lys Leu Met Ala Lys Ala Leu Leu Leu Tyr Gly Ala Asp Ile Glu Ser
            675                 680                 685

Lys Asn Lys Cys Gly Leu Thr Pro Leu Leu Leu Gly Val His Glu Gln
```

-continued

```
            690                 695                 700
Lys Gln Glu Val Val Lys Phe Leu Ile Lys Lys Ala Asn Leu Asn
705                 710                 715                 720

Ala Leu Asp Arg Tyr Gly Arg Thr Ala Leu Ile Leu Ala Val Cys Cys
                725                 730                 735

Gly Ser Ala Ser Ile Val Asn Leu Leu Leu Glu Gln Asn Val Asp Val
                740                 745                 750

Ser Ser Gln Asp Leu Ser Gly Gln Thr Ala Arg Glu Tyr Ala Val Ser
                755                 760                 765

Ser His His His Val Ile Cys Glu Leu Leu Ser Asp Tyr Lys Glu Lys
            770                 775                 780

Gln Met Leu Lys Ile Ser Ser Glu Asn Ser Asn Pro Val Ile Thr Ile
785                 790                 795                 800

Leu Asn Ile Lys Leu Pro Leu Lys Val Glu Glu Ile Lys Lys His
                805                 810                 815

Gly Ser Asn Pro Val Gly Leu Pro Glu Asn Leu Thr Asn Gly Ala Ser
                820                 825                 830

Ala Gly Asn Gly Asp Asp Gly Leu Ile Pro Gln Arg Lys Ser Arg Lys
            835                 840                 845

Pro Glu Asn Gln Gln Phe Pro Asp Thr Glu Asn Glu Glu Tyr His Ser
    850                 855                 860

Asp Glu Gln Asn Asp Thr Gln Lys Gln Leu Ser Glu Gln Asn Thr
865                 870                 875                 880

Gly Ile Ser Gln Asp Glu Ile Leu Thr Asn Lys Gln Lys Gln Ile Glu
                885                 890                 895

Val Ala Glu Lys Glu Met Asn Ser Glu Leu Ser Leu Ser His Lys Lys
            900                 905                 910

Glu Glu Asp Leu Leu Arg Glu Asn Ser Met Leu Arg Glu Glu Ile Ala
            915                 920                 925

Lys Leu Arg Leu Glu Leu Asp Glu Thr Lys His Gln Asn Gln Leu Arg
            930                 935                 940

Glu Asn Lys Ile Leu Glu Glu Ile Glu Ser Val Lys Glu Lys Leu Leu
945                 950                 955                 960

Lys Thr Ile Gln Leu Asn Glu Glu Ala Leu Thr Lys Thr Lys Val Ala
                965                 970                 975

Gly Phe Ser Leu Arg Gln Leu Gly Leu Ala Gln His Ala Gln Ala Ser
            980                 985                 990

Val Gln Gln Leu Cys Tyr Lys Trp Asn His Thr Glu Lys Thr Glu Gln
            995                 1000                1005

Gln Ala Gln Glu Gln Glu Val Ala Gly Phe Ser Leu Arg Gln Leu Gly
    1010                1015                1020

Leu Ala Gln His Ala Gln Ala Ser Val Gln Gln Leu Cys Tyr Lys Trp
1025                1030                1035                1040

Gly His Thr Glu Lys Thr Glu Gln Gln Ala Gln Glu Gln Gly Ala Ala
                1045                1050                1055

Leu Arg Ser Gln Ile Gly Asp Pro Gly Gly Val Pro Leu Ser Glu Gly
                1060                1065                1070

Gly Thr Ala Ala Gly Asp Gln Gly Pro Gly Thr His Leu Pro Pro Arg
            1075                1080                1085

Glu Pro Arg Ala Ser Pro Gly Thr Pro Ser Leu Val Arg Leu Ala Ser
    1090                1095                1100

Gly Ala Arg Ala Ala Ala Leu Pro Pro Pro Thr Gly Lys Asn Gly Arg
1105                1110                1115                1120
```

-continued

```
Ser Pro Thr Lys Gln Lys Ser Val Cys Asp Ser Ser Gly Trp Ile Leu
            1125                1130                1135
Pro Val Pro Thr
            1140
```